(12) United States Patent
Feige

(10) Patent No.: US 7,166,707 B2
(45) Date of Patent: Jan. 23, 2007

(54) MODIFIED PEPTIDES AS THERAPEUTIC AGENTS

(75) Inventor: Ulrich Feige, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 631 days.

(21) Appl. No.: 10/609,217

(22) Filed: Jun. 27, 2003

(65) Prior Publication Data
US 2004/0044188 A1   Mar. 4, 2004

Related U.S. Application Data

(62) Division of application No. 09/428,082, filed on Oct. 22, 1999, now Pat. No. 6,660,843.

(60) Provisional application No. 60/105,371, filed on Oct. 23, 1998.

(51) Int. Cl.
 *C07K 1/00* (2006.01)
(52) U.S. Cl. ............... 530/397.1; 530/350; 530/391.1
(58) Field of Classification Search ............ 530/397.1, 530/350, 391.1
See application file for complete search history.

(56) References Cited

U.S. PATENT DOCUMENTS

| | | | |
|---|---|---|---|
| 5,098,833 A | 3/1992 | Lasky et al. |
| 5,116,964 A | 5/1992 | Capon et al. |
| 5,216,131 A | 6/1993 | Lasky et al. |
| 5,223,409 A | 6/1993 | Ladner et al. |
| 5,225,538 A | 7/1993 | Capon et al. |
| 5,229,490 A | 7/1993 | Tam |
| 5,336,603 A | 8/1994 | Capon et al. |
| 5,338,665 A | 8/1994 | Schatz et al. |
| 5,376,367 A | 12/1994 | Williams et al. |
| 5,428,130 A | 6/1995 | Capon et al. |
| 5,432,018 A | 7/1995 | Dower et al. |
| 5,455,165 A | 10/1995 | Capon et al. |
| 5,480,981 A | 1/1996 | Goodwin et al. |
| 5,498,530 A | 3/1996 | Schatz et al. |
| 5,514,582 A | 5/1996 | Capon et al. |
| 5,547,933 A | 8/1996 | Lin |
| 5,565,335 A | 10/1996 | Capon et al. |
| 5,608,035 A | 3/1997 | Yanofsky et al. |
| 5,618,698 A | 4/1997 | Lin |
| 5,621,080 A | 4/1997 | Lin |
| 5,714,147 A | 2/1998 | Capon et al. |
| 5,726,290 A | 3/1998 | Bodary et al. |
| 5,733,731 A | 3/1998 | Schatz et al. |
| 5,739,277 A | 4/1998 | Presta et al. |
| 5,756,349 A | 5/1998 | Lin |
| 5,767,234 A | 6/1998 | Yanofsky et al. |
| 5,773,569 A | 6/1998 | Wrighton et al. |
| 5,786,331 A | 7/1998 | Barrett et al. |
| 5,792,451 A | 8/1998 | Sarubbi et al. |
| 5,840,844 A | 11/1998 | Lasky et al. |
| 5,869,451 A | 2/1999 | Dower et al. |
| 5,869,452 A | 2/1999 | Ng et al. |
| 5,877,151 A | 3/1999 | Pereira |
| 5,880,096 A | 3/1999 | Barrett et al. |
| 5,922,545 A | 7/1999 | Mattheakis et al. |
| 5,932,546 A | 8/1999 | Barrett et al. |
| 5,985,599 A | 11/1999 | McKenzie et al. |
| 6,117,655 A | 9/2000 | Capon et al. |

FOREIGN PATENT DOCUMENTS

| | | |
|---|---|---|
| EP | 0 173 494 | 3/1986 |
| EP | 0 325 224 | 7/1989 |
| EP | 0 526 452 B1 | 2/1993 |
| EP | 0 585 287 | 3/1994 |
| EP | 0 148 605 | 12/1998 |
| EP | 0 911 393 | 4/1999 |
| EP | 0 714 912 | 5/1999 |
| EP | 1 029 870 A2 | 8/2000 |
| WO | WO 94/07921 | 4/1994 |
| WO | WO 95/09917 | 4/1995 |
| WO | WO 95/14714 | 6/1995 |
| WO | WO 96/05309 | 2/1996 |
| WO | WO 96/11214 | 4/1996 |

(Continued)

OTHER PUBLICATIONS

Adey et al. (1996), 'Identification of calmodulin-binding peptide consensus sequences from a phage-displayed random peptide library', *Gene* 169:133-134.

(Continued)

*Primary Examiner*—Sheela J. Huff
(74) *Attorney, Agent, or Firm*—Timothy J. Gaul

(57) ABSTRACT

The present invention concerns fusion of Fc domains with biologically active peptides and a process for preparing pharmaceutical agents using biologically active peptides. In this invention, pharmacologically active compounds are prepared by a process comprising:

a) selecting at least one peptide that modulates the activity of a protein of interest; and b) preparing a pharmacologic agent comprising an Fc domain covalently linked to at least one amino acid of the selected peptide.

Linkage to the vehicle increases the half-life of the peptide, which otherwise would be quickly degraded in vivo. The preferred vehicle is an Fc domain. The peptide is preferably selected by phage display, *E. coli* display, ribosome display, RNA-peptide screening, or chemical-peptide screening.

11 Claims, 37 Drawing Sheets

FOREIGN PATENT DOCUMENTS

| | | |
|---|---|---|
| WO | WO 96/11953 | 4/1996 |
| WO | WO 96/17942 | 6/1996 |
| WO | WO 96/18412 | 6/1996 |
| WO | WO 96/23899 | 8/1996 |
| WO | WO 96/30057 | 10/1996 |
| WO | WO 96/32478 | 10/1996 |
| WO | WO 96/40772 | 12/1996 |
| WO | WO 96/40987 | 12/1996 |
| WO | WO 97/00270 | 1/1997 |
| WO | WO 97/08203 | 3/1997 |
| WO | WO 97/08553 | 3/1997 |
| WO | WO 97/23614 | 7/1997 |
| WO | WO 97/28828 | 8/1997 |
| WO | WO 97/31019 | 8/1997 |
| WO | WO 97/34631 | 9/1997 |
| WO | WO 97/35969 | 10/1997 |
| WO | WO 97/40070 | 10/1997 |
| WO | WO 97/44453 | 11/1997 |
| WO | WO 98/09985 | 3/1998 |
| WO | WO 98/10795 | 3/1998 |
| WO | WO 98/15833 | 4/1998 |
| WO | WO 98/24477 | 6/1998 |
| WO | WO 98/28427 | 7/1998 |
| WO | WO 98/31820 | 7/1998 |
| WO | WO 98/33812 | 8/1998 |
| WO | WO 98/46257 | 10/1998 |
| WO | WO 98/53842 | 12/1998 |
| WO | WO 98/55620 | 12/1998 |
| WO | WO 99/05302 | 2/1999 |
| WO | WO 99/14244 | 3/1999 |
| WO | WO 99/17789 | 4/1999 |
| WO | WO 99/18243 | 4/1999 |
| WO | WO 99/18781 | 4/1999 |
| WO | WO 99/24462 | 5/1999 |
| WO | WO 00/09560 | 2/2000 |
| WO | WO 00/24782 | 5/2000 |
| WO | WO 01/02440 | 1/2001 |
| WO | WO 2004/002417 | 1/2004 |
| WO | WO 2004/002424 | 1/2004 |

OTHER PUBLICATIONS

Adey et al. (1997), 'Isolation of peptides from phage-displayed random peptide libraries that interact with the talin-binding domain of vinculin', Biochem. J. 324:523-528.

Ahern et al. (1990), 'Special Report: The Peptide-Oligonucleotide Partnership', The Scientist 4 (19):24-25.

Akeson et al. (1996), 'AF12198, a Novel Low Molecular Weight Antagonist, Selectively Binds the Human Type I Interleukin (IL)-1 Receptor and Blocks in vivo Responses to IL-1', J. Biol. Chem. 271:30517-30523.

Ball et al. (1997), 'Cell-cycle arrest and inhibition of Cdk4 activity by small peptides based on the carboxy-terminal domain of p21$^{WAF1}$', Current Biology 7:71-80.

Becker et al. (1989), "Expression of a Hybrid Immunoglobulin- T Cell Receptor Protein in Transgenic Mice," Cell 58: 911-921.

Bernard et al. (1980), "Nucleotide dequence of immunoglobulin heavy chain joining segments between translocated $V_H$ and μ constant region genes," Proc. Natl. Acad. Sci. USA 77(6): 3630-3634.

Bhatnagar et al. (1996), 'Structure-Activity Relationships of Novel Hematoregulatory Peptides', J. Med. Chem. 39:3814-3819.

Böttger et al. (1996), 'Identification of novel mdm2 binding peptides by phage display', Oncogene 13:2141-2147.

Böttger et al. (1997), 'Molecular Characterization of the hdm2-p53 Interaction', J. Mol. Biol. 269:744-756.

Boulianne et al. (1984), "Production of functional chimaeric Mousem/human antibody," Nature 312: 643-646.

Brocks et al. (1997), "A TNF receptor antagonistic scFv, which is not secreted in mammalian cells, is expressed as a soluble mono- and bivalent scFv derivative in insect cells," Immunotechnology 3(3):173-184.

Burstein et al. (1988), 'Thymic Humoral Factory γ2: Purification and Amino Acid Sequence of an Immunoregulatory Peptide from Calf Thymus', Biochemistry 27:4066-4071.

Capon et al. (1989), 'Designing CD4 Immunoadhesins for AIDS Therapy', Nature 337:525-531.

Chamow et al. (1996), "Immunoadhesins: principles and applications," Tibtech. 14:52-60.

Chirinos-Rojas et al. (1998), 'A Peptidomimetic Antagonist of TNF-α-Mediated Cytotoxicity Identified from a Phage-Displayed Random Peptide Library', Journal of Immunology 161:5621-5626.

Cooper et al. (1987), 'Purification and characterization of a peptide from amyloid-rich pancreases of type 2 diabetic patients', PNAS 84:8628-8632.

Cortese et al. (1996), 'Selection of biologically active peptides by phage display of random peptide libraries', Current Opinion in Biotechnology 7:616-621.

Couet et al. (1997), 'Identification of Peptide and Protein Ligands for the Caveolin-scaffolding Domain', The Journal of Biological Chemistry 272 (10):6525-6533.

Couet et al. (1997), 'Interaction of a Receptor Tyrosine Kinase, EGF-R, with Caveolins', The Journal of Biological Chemistry vol. 272 (48):30429-30438.

Cuthbertson et al. (1997), 'Design of Low Molecular Weight Hematoregulatory Agents from the Structure-Activity Relationship of a Dimeric Pentapeptide', J. Med. Chem 40:2876-2882.

Cwirla et al. (1997), 'Peptide Agonist of the Thrombopoietin Receptor', Science 276:1696-1699.

Dedman et al. (1993), 'Selection of Targeted Bilogical Modifiers from a Bacteriophage Library of Random Peptides', The Journal of Biological Chemistry 268 (31):23025-23030.

Devlin et al. (1990), 'Random Peptide Libraries: A Source of Specific Protein Binding Molecules', Science 249:404-406.

Duncan et al. (1988), 'Localization of the binding site for the human high-affinity Fc receptor on IgG', Nature 332:563-564.

Dyson et al. (1995), 'Selection of peptide inhibitors of interactions involved in complex protein assemblies: Association of the core and surface antigens of hepatitis B virus', Proc. Natl. Acad. Sci. USA 92:2194-2198.

Fahraeus et al. (1996), 'Inhibition of pRb phosphorylation and cell-cycle progression by a 20-residue peptide derived from p16$^{CDKN2}$/INK4A', Current Biology 6:84-91.

Fairbrother et al. (1998), 'Novel Peptides Selected to Bind Vascular Endothelial Growth Factor Target the Receptor-Binding Site', Biochemistry 37:17754-17764.

Fisher et al. (1996), 'Treatment of septic shock with the tumor necrosis factor receptor: Fc fusion protein', N. Eng. J. Med. 334(26):1697-1702.

Francis, Gillian E. (1992), 'Protein modification and fusion proteins', Focus on Growth 3:4-11.

Fukumoto et al. (1998), 'Peptide mimics of the CTLA4-binding domain stimulate T-cell proliferation', Nature Biotechnology, 16:267-270.

Gan et al. (1988), 'Echistatin', JBC 263:19827-19832.

Garber et al. (2001), "A new synthetic class A amphipathic peptide analogue protects mice from diet-induced atherosclerosis", J. Lipid Research 42: 545-552.

Gascoigne et al. (1987), "Secretion of a chimeric T-cell receptor-immunoglobulin protein," Proc. Natl. Acad. Sci. USA 84: 2936-2940.

Ghetie et al. (1997), 'Increasing the serum persistence of an IgG fragment by random mutagenesis', Nature Biotechnology 15:637-640.

Gibbs et al. (1994), 'Farnesyltransferase Inhibitors: Ras Research Yields a Potential Cancer Therapeutic', Cell 77:175-178.

Gibbs et al. (1994), 'Pharmaceutical Research in Molecular Oncology', Cell 79:193-198.

Goodson et al. (1994), 'High-affinity urokinase receptor antagonists identified with bacteriophase peptide display', Proc. Natl. Acad. Sci. USA 91:7129-7133.

Harvill et al. (1995), 'An IgG3-IL2 fusion protein activates complement, binds FcγRI, generates LAK activity and shows enhanced binding to the high affinity IL-2R', *Immunotech.* 1:95-105.

Herz et al. (1997), "Molecular Approaches to Receptors as Targets for Drug Discovery", *J. of Receptor & Signal Transduction Research* 17(5):671-776.

Hong et al. (1995), 'Protein ligands of the human adenovirus type 2 outer capsid identified by biopanning of a phage-displayed peptide library on separate domains of wild-type and mutant penton capsomers', *The EMBO Journal* 14:4714-4727.

Hughes, David (1998), 'Therapeutic antibodies make a comeback', *Drug Discovery Today* 3(10):439-442.

Inagaki-Ohara et al. (1996), 'Effects of a Nonapeptide Thymic Hormone on Intestinal Intraepithelial Lymphocytes in Mice Following Administration of 5-Fluorouracil[1]', *Cellular Immunology* 17:30-40.

Inglot, Anna D. (1997), 'Classification of Cytokines According to the Receptor Code', *Archivum Immunologies et Therapine Experimentalis* 45:353-357.

Ishikawa et al (1998), 'GD1β-replica peptides functionally mimic GD1α, an adhesion molecule of metastatic tumor cells, and suppress the tumor metastasis', *FEBS* 441:20-24.

Jefferies, D. (1998), 'Selection of Novel Ligands from Phage Display Libraries: An Alternative Approach to Drug and Vaccine Discovery?', *Parasitology Today* 14(5):202-206.

Jefferis et al. (1990), 'Molecular Definition of Interaction Sites on Human IgG for Fc Receptors (huFcγ R)', *Molecular Immunology* 27(12):1237-1240.

Jefferis et al. (1995), Recognition sites on human IgG for Fcγ receptors: the role of glycosylation, *Immunology Letters* 44:111-117.

Johnson et al. (1998), "Identification of a 13 amino acid peptide mimetic of erythropoietin and description of amino acids critical for the mimetic activity of EMP1," *Biochemistry* 37(11):3699-3710.

Jones et al. (1998), 'Stromal Expression of Jagged I Promotes Colony Formation by Fetal Hematopoietic Progenitor Cells', *Blood* 92(5):1505-1511.

Junghans, R.P. (1997), Finally! The Brambell Receptor (FcRB), *Immunologic Research* 16(1):29-57.

Kay et al. (1998), 'From peptides to drugs via phage display', *DDT* 3(8):370-378.

Kemp et al. (1981), "Direct Immunoassay for detecting Escherichia coli colonies that contain polypeptides encoded by cloned DNA segments," *Proc. Natl. Acad. Sci. USA* 78(7):4520-4524.

King et al. (1991), 'Modulation of Bone Marrow Stromal Cell Production of Colony Stimulating Activity by the Synthetic Peptide', *Exp. Hematol.* 19:481.

King et al. (1995), 'Hematoregulatory Peptide, SK&F Induced Stromal Cell Production of KC Enhances CFU-GM Growth and Effector Cell Function', *Blood* 86(1):309a.

Kitamura et al. (1993), 'Adrenomedullin: A Novel Hypotensive Peptide Isolated from Human Pheochromocytoma', *BBRC* 192:553-560.

Kluczyk et al. (1997), 'Immunomodulatory Activity of Oligopeptides Related to Interleukin 1 Receptor Antagonist Sequence', *Archivum Immunologiac et Therapiae Experimentalis* 45:427-433.

Knapp et al. (1989), "Towards a better definition of human leucocyte surface molecules," *Immunology Today* 10(8):253-258.

Koivunen et al. (1999), 'Tumor targeting with a selective gelatinase inhibitor', *Nature Biotech.* 17:768-774.

Kraft et al. (1999), 'Definition of an Unexpected Ligand Recognition Motif for αvβ6 Integrin', *Journal of Biological Chemistry* 274(4):1979-1985.

Kreeger, Karen Young (1998), 'Immunological Applications Top List of Peptide-Synthesis Services', *The Scientist* 10(13):19-20.

Laerum et al. (1988), 'The Dimer of Hemoregulatory Peptide (HP5B) Stimulates Mouse and Human Myelopoiesis in vitro', *Exp. Hemat.* 16:274-280.

Linse et al. (1997), 'A Region of Vitamin K-dependent Protein S That Binds to C4b Binding Protein (C4BP) Identified Using Bacteriophage Peptide Display Libraries', *The Journal of Biological Chemistry* 272(23):14658-14665.

Linsley et al. (1991), 'CTLA-4 is a Second Receptor for the B Cell Activation Antigen B7', *J. Exp. Med.* 174:561-569.

Livnah et al. (1996), 'Functional Mimicry of a Protein Hormone by a Peptide Agonist: The EPO Receptor Complex at 2.8 Å', *Science* 273:464-471.

Loetscher et al. (1993), "Efficacy of a chimeric TNFR-IgG fusion protein to inhibit TNF activity in animal models of septic shock," *Elsevier Science Publishers* pp. 455-462.

Lowman, H.B. (1997), 'Bacteriophage display and discovery of peptide leads for drug development', *Annu. Rev. Biophys. Biomol. Struct.* 26:401-24.

Mariuzza et al. (1989), "Secretion of a Homodimeric $V_aC_K$ t-cell Receptor-Immunoglobulin Chimeric Protein," *J. Biological Chemistry* 24(13):7310-7316.

Martens et al. (1995), 'Peptides which bind to E-selectin and block neutrophil adhesion', *The Journal of Biological Chemistry* 270(36):21129-21136.

Maurer et al. (1997), 'Autodisplay: One-Component System for Efficient Surface Display and Release of Soluble Recombinant Proteins from escherichia coli', *ournal of Bacteriology* 179(3):794-80.

McGregor, Duncan (1996), 'Selection of proteins and peptides from libraries displayed on filamentous bacteriophage', *Molecular Biotechnology* 6:155-162.

Moodie et al. (1994), 'The 3Rs of Llife: Ras, Raf and Growth Regulation', *TIG* 10(2):44-48.

Morikis et al. (1998), 'Solution structure of Compstatin, a potent complement inhibitor', *Protein Science* 7:619-627.

Morrison (1985), "Transfectomas Provide Novel Chimeric Antibodies," *Science* 229:1202-1207.

Morrison et al. (1984), "Chimeric human antibody molecules: Mouse anigen-binding domains with human constant region domains," *Proc. Natl. Acad. Sci. USA* 81:6851-6855.

Munro (1984), "Uses of chimaeric antibodies," *Nature* 312:597-.

Naranda et al. (Jun. 1999), "Activation of erythropoietin receptor in the absence of hormone by a peptide that binds to a domain different from the hormone binding site," *Proc. Natl. Acad. Sci. USA* 96:7569-7574.

Neuberger et al. (1984), "Recombinant antibodies prossessing novel effector functions," *Nature* 312:604-608.

Nishi et al. (1996), 'Tight-binding inhibitory sequences against $pp60^{c-src}$ identified using a random 15-amino-acid peptide library', *FEBS* 399:237-240.

Pasquaimi et al. (1996), 'Organ targeting *in vivo* using phage display peptide libraries', *Nature* 380:364-366.

Paukovits et al. (1984), 'Structural Investigations on a Peptide Regulating Hemopoiesis in vitro and in vivo', *Hoppe-Seylers Z Physiol. Chem* 364:303-311.

Pawson et al. (1993), 'SH2 and SH3 Domains', *Current Biology* 3(7):434-442.

Pierce et al. (1995), 'Identification of cyclized calmodulin antagonists from a phage display random peptide library', *Molecular Diversity* 1:259-265.

Piette et al. (1997), Mdm2: keeping p53 under control, *Oncogene* 15:1001-1010.

Powis,, Garth (1991), Signalling targets for anticancer drug development, *TiPS* 12:188-194.

Rickles et al. (1994), 'Identification of Src, Fyn, Lyn, PI3K and Abl SH3 domain ligands using phage display libraries', *The EMBO Journal* 13(23):5598-5604.

Rodriguez-Viciana et al. (1994), 'Phosphatidylinositol-3-OH kinase as a direct target of Ras', *Nature* 370:527-532.

Sahu et al. (1996), 'Inhibition of Human Complement by a C3-Binding Peptide Isolated from a Phage-Displayed Random Peptide Library[1]', *The Journal of Immunology* 157:884-891.

Sarmay et al. (1992), 'Mapping and Comparison of the Interaction Sites on the Fc Region of IgG Responsible for Triggering Antibody Dependent Cellular Cytotoxicity (ADCC) Through Different Types of Human Fcγ Receptor', *Molecular Immunology* 29(5):633-639.

Scott et al. (1990) 'Searching for Peptide Ligands with an Epitope Library', *Science* 249:386-390.

Sharon et al. (1984), "Expression of a $V_HC_K$ chimaeric protein in mouse myeloma cells," *Nature* 309:364-367.

Siemion et al. (1991), 'The Evidence on the Possible Interleukin-1α Tuftsin Competition', *Archivum Immunologiae et Therapiae Experimentalis* 39:605-611.

Sparks et al. (1994), 'Identification and Characterization of Src SH3 Ligands from Phage-displayed Random Peptide Libraries', *The Journal of Biological Chemistry* 269(39):23853-23856.

Sparks et al. (1996), 'Distinct ligand preferences of Src homology 3 domains from Src, Yes, Abl, Cortactin, p53bp2, PLCγ, Crk, and Grb2', *Proc. Natl. Acad. Sci. USA* 93:1540-1544.

Stauffer et al. (1997), 'Inhibition of Lyn Function in Mast Cell Activation by SH3 Domain Binding Peptides', *Biochemistry* 36:9388-9394.

Takasaki et al. (1997), 'Structure-based design and characterization of exocyclic peptidomimetics that inhibit TNFα binding to its receptor', *Nature Biotechnology* 15:1266-1270.

Traunecker et al. (1986), "A novel approach for preparing anti-T cell Receptor constant region antibodies," *Eur. J. Immunol.* 16: 851-853.

Traunecker et al. (1988), "Soluble CD4 molecules neutralize human immunodeficiency virus type 1," *Nature* 331:84-86.

Traunecker et al. (1989), "Highly efficient neutralization of HIV with recombinant CD4-immunoglobulin molecules," *Nature* 339: 68-70.

Van Zee et al. (1996), 'Protection Against Lethal *Escherichia coli* Bacteremia in Baboons (*Papio anubis*) by Pretreatment with a 55-kDa TNF Receptor (CD120a)-Ig Fusion Protein,Ro 45-2081', *J. Immunol.* 156:2221-2230.

Wells et al. (1992), 'Rapid evolution of peptide and protein binding properties *in vivo*', *Current Opinion of Biotechnology* 3:355-362.

Whitty et al. (1996), 'Small molecule cytokine mimetics', *Chemistry & Biology* 6:R107-R118.

Wieczorek et al. (1994), 'The Immunomodulatory Activity of Tetra- and Tripeptides of Tufsin-Kentsin Group', *Peptides* 15(2):215-221.

Wieczorek et al. (1997), 'A Hexapeptide VTKFYF from C-Terminal Part of Interleukin-1 Receptor Antagonist, an Inhibitor of IL-1—IL-1 Receptor Interaction', *Polish Journal of Pharmacology* 49:107-117.

Williams et al. (1986), "Production of antibody-tagged enzymes by myeloma cells: application to DNA polymerate I Klenow fragment," *Gene* 43:319-324.

Wilson et al. (1998), 'Phage display: applications, innovations, and issues in phage and host biology', *Can. J. Microbiol.* 44:313-329.

Wrighton et al. (1996), 'Small Peptides as Potent Mimetics of the Protein Hormone Erythropoietin', *Science* 273:458-463.

Wrighton et al. (1997), 'Increased potency of an erythropoietin peptide mimetic through covalent dimerization', *Nature Biotechnology* 15:1261-1265.

Yanofsky et al. (1996), 'High Affinity type 1 interleukin I receptor antagonists discovered by screening recombinant peptide libraries', *PNAS* 93:7381-7386.

Yoshida et al. (1984), 'The Activity of Synthetic analogs of Serum Thymic Factor (FTS) to Convert Mouse Pre-T Cells into Thy-1 Positive Cells', *Int. J. Immunopharmac.* 6(2):141-146.

Yu et al. (1994), 'Structural Basis for the Binding of Proline-Rich Peptides to SH3 Domains', *Cell* 76:933-945.

Zheng et al. (1995), 'Administration of Noncytolytic IL-10/Fc in Murine Models of Lipopolysaccharide-Induced Septic Shock and Allogeneic Islet Transplantation', *J. Immunol.* 154:5590-5600.

Abuchowski et al. (1981), "Soluble Polymer Enzyme Adducts," *Enzymes as Drugs:* Chapter 13, Hocenberg and Roberts, eds., Wiley-Interscience, New York, NY, pp. 367-383.

Adjei et al. (1990), "Pulmonary Delivery of Peptide Drugs: Effect of Particle Size on Bioavailability of Leuprolide Acetate in Healthy Male Volunteers," *Pharmaceutical Research* 7(6):565-569.

Adjei et al. (1990), "Bioavailability of leuprolide following intratracheal administration to beagle dogs," *International Journal of Pharmaceutics* 61:135-144.

Braquet et al.(1989), "Effect of Endothelin-1 on Blood Pressure and Bronchopulmonary System of the Guinea Pig," *Journal of Cardiovascular Pharmacology*, 13 (Suppl.5):S143-S146.

Clackson et al. (1995) "A Hot Spot of Binding Energy in a Hormone-Receptor Interface," *Science* 267:383-386.

Creighton (1983), *Thomas E., Proteins: Structures and Molecular Principles*, W.H. Freeman and Company, New York, pp. 70-86.

Davis et al. (1985), "Preparation and Characterization of Antibodies with Specificity for the Amino-terminal Tetrapeptide Sequence of the Platelet-Derived Connective Tissue Activating Peptide-III," *Biochemistry International* 10:395-404.

Debs et al. (1988), "Lung-Specific Delivery of Cytokines Induces Sustained Pulmonary and Systemic Immunomodulation in Rats," *The Journal of Immunology* 140:3482-3488.

Ellison et al.(1982), "The nucleotide sequence of a human immunoglobulin Cγ1 gene," *Nucleic Acids Research* 10:4071-4079.

Erickson et al. (1976), The Proteins, 3$^{rd}$ ed., 2: Chapter 3, Solid-Phase Peptide Synthesis, Neurath et al., eds., Academic Press, New York, pp. 255-527.

Finn et al., The Proteins, 3$^{rd}$ ed., 2: Chapter 2, Solid-Phase Peptide Synthesis, Neurath et al., eds., Academic Press, New York, pp. 105-253 (1976).

Love et al. (1989), "Recombinant Antibodies Possessing Novel Effector Functions," *Methods in Enzymalogy* 178:515-527.

Merrifield, R.B. (1963), "Solid Phase Peptide Synthesis," *Journal of the American Chemical Society* 85:2149-2154.

Ravin et al. (1990), "Preformulation," *Remington Pharmaceutical Sciences*, 18$^{th}$ ed., Chapter 75: Preformulation, pp. 1435-1712.

Roberts et al. (1997), "RNA-peptide fusions for the in vitro selection of peptides and proteins," *Proceedings from the National Academy of Sciences USA* 94:12297-12302.

Smith et al. (1989), "Pulmonary Deposition and Clearance of Aerosolized Alpha-1-Proteinase Inhibitor Administered to Dogs and to Sheep," *Journal of Clinical Investigation* 84:1145-1154.

Stewart et al. (1969), *Solid Phase Peptide Synthesis:* Table of Contents and Indexes only, W.H. Freeman and Company, San Francisco.

Wells et al., (1996) "Hematopoietic Receptor Complexes," *Annual Review of Biochemistry* 65:609-634.

Wrighton et al. (1996), "Small Peptides as Potent Mimetics of the Protein Hormone Erythropoietin," *Science* 273:458-463.

Abstract # 4261. Blood, vol. 106, Issue 11, Nov. 16, 2005. Title: Pharmacokinetics and Pharmacodynamics of CNTO 528, a Novel Erythropoietin Receptor Agonist in Normal and Anemic Rats. Authors: Peter Bugelski et al. p. 1 of 1.

Abstract #4283. Blood, vol. 106, Issue 11, Nov. 16, 2005. Title: A Phase 1, Single and Fractionated, Ascending Dose Study Evaluating the Safety, Pharmacokinetics, Pharmacodynamics and Immunogenicity of an Erythropoietic Mimetic Antibody Fusion Protein, CNTO528 in Healthy Male Subjects. Authors: K.L. Franson et al. p. 1 of 1.

Russel et al, Introduction to phage biology and phage display. In *A Practical Approach*; Oxford University Press; 2004: 1-26.

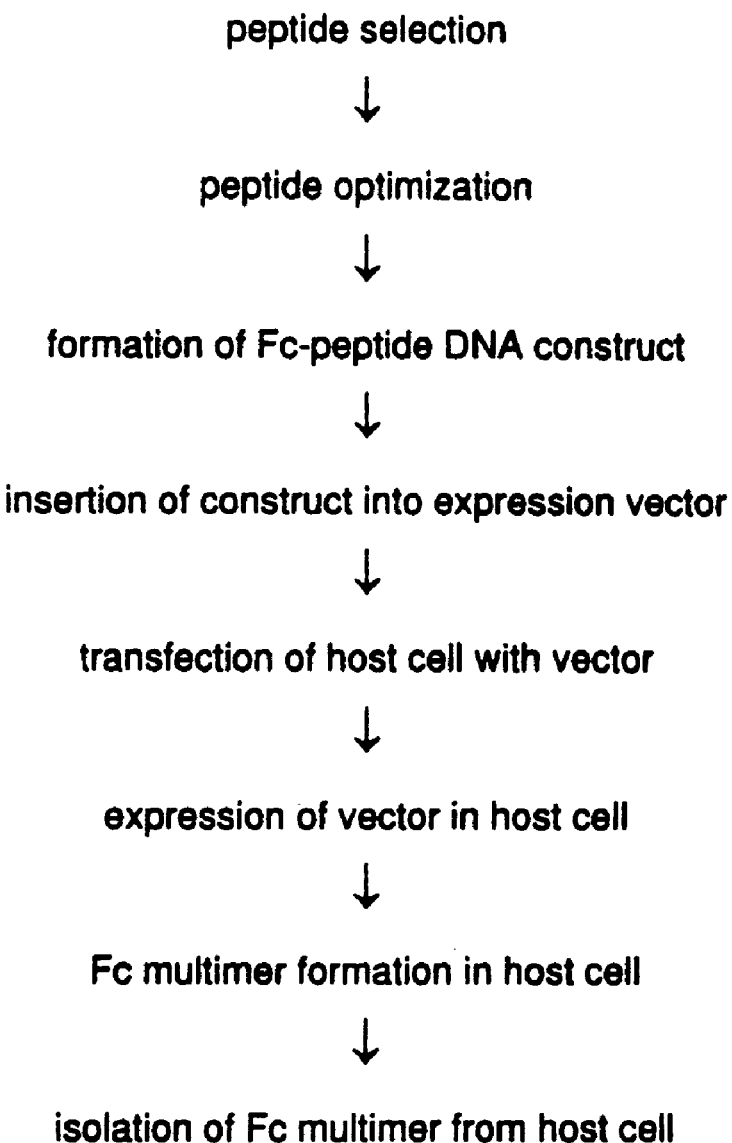

FIG. 2A  FIG. 2B  FIG. 2C
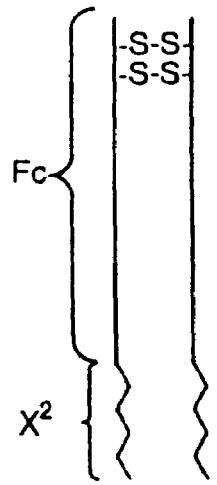 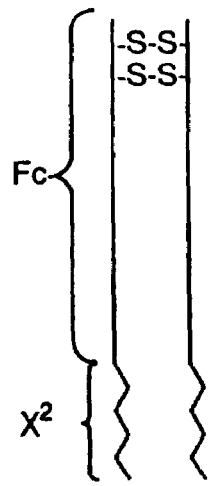 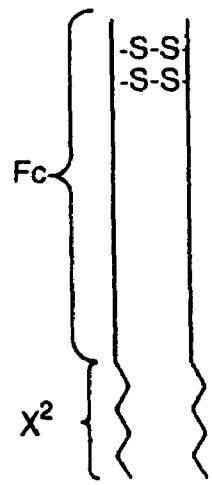
FIG. 2D  FIG. 2E  FIG. 2F
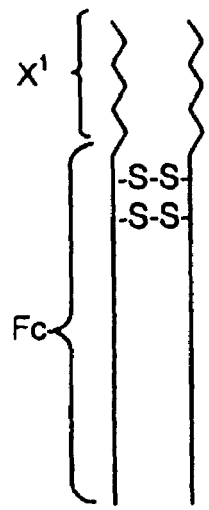 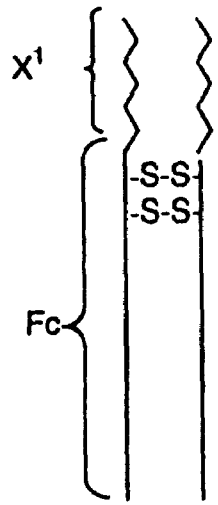 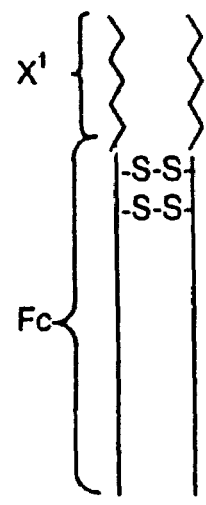

FIG. 4

```
      ATGGACAAAACTCACACATGTCCACCTTGTCCAGCTCCGGAACTCCTGGGGGGACCGTCA
    1 ------+---------+---------+---------+---------+---------+  60
      TACCTGTTTTGAGTGTGTACAGGTGGAACAGGTCGAGGCCTTGAGGACCCCCCTGGCAGT a     M  D  K  T  H  T  C  P  P  C  P  A  P  E  L  L  G  G  P  S  -

GTCTTCCTCTTCCCCCCAAAACCCAAGGACACCCTCATGATCTCCCGGACCCCTGAGGTC
   61 ------+---------+---------+---------+---------+---------+ 120
      CAGAAGGAGAAGGGGGGTTTTGGGTTCCTGTGGGAGTACTAGAGGGCCTGGGGACTCCAG a     V  F  L  P  P  P  K  P  K  D  T  L  M  I  S  R  T  P  E  V  -

ACATGCGTGGTGGTGGACGTGAGCCACGAAGACCCTGAGGTCAAGTTCAACTGGTACGTG
  121 ------+---------+---------+---------+---------+---------+ 180
      TGTACGCACCACCACCTGCACTCGGTGCTTCTGGGACTCCAGTTCAAGTTGACCATGCAC a     T  C  V  V  V  D  V  S  H  E  D  P  E  V  K  F  N  W  Y  V  -

GACGGCGTGGAGGTGCATAATGCCAAGACAAAGCCGCGGGAGGAGCAGTACAACAGCACG
  181 ------+---------+---------+---------+---------+---------+ 240
      CTGCCGCACCTCCACGTATTACGGTTCTGTTTCGGCGCCCTCCTCGTCATGTTGTCGTGC a     D  G  V  E  V  H  N  A  K  T  K  P  R  E  E  Q  Y  N  S  T  -

TACCGTGTGGTCAGCGTCCTCACCGTCCTGCACCAGGACTGGCTGAATGGCAAGGAGTAC
  241 ------+---------+---------+---------+---------+---------+ 300
      ATGGCACACCAGTCGCAGGAGTGGCAGGACGTGGTCCTGACCGACTTACCGTTCCTCATG a     Y  R  V  V  S  V  L  T  V  L  H  Q  D  W  L  N  G  K  E  Y  -

AAGTGCAAGGTCTCCAACAAAGCCCTCCCAGCCCCCATCGAGAAAACCATCTCCAAAGCC
  301 ------+---------+---------+---------+---------+---------+ 360
      TTCACGTTCCAGAGGTTGTTTCGGGAGGGTCGGGGGTAGCTCTTTTGGTAGAGGTTTCGG a     K  C  K  V  S  N  K  A  L  P  A  P  I  E  K  T  I  S  K  A  -

AAAGGGCAGCCCCGAGAACCACAGGTGTACACCCTGCCCCCATCCCGGGATGAGCTGACC
  361 ------+---------+---------+---------+---------+---------+ 420
      TTTCCCGTCGGGGCTCTTGGTGTCCACATGTGGGACGGGGGTAGGGCCCTACTCGACTGG a     K  G  Q  P  R  E  P  Q  V  Y  T  L  P  P  S  R  D  E  L  T  -

AAGAACCAGGTCAGCCTGACCTGCCTGGTCAAAGGCTTCTATCCCAGCGACATCGCCGTG
  421 ------+---------+---------+---------+---------+---------+ 480
      TTCTTGGTCCAGTCGGACTGGACGGACCAGTTTCCGAAGATAGGGTCGCTGTAGCGGCAC a     K  N  Q  V  S  L  T  C  L  V  K  G  F  Y  P  S  D  I  A  V  -

GAGTGGGAGAGCAATGGGCAGCCGGAGAACAACTACAAGACCACGCCTCCCGTGCTGGAC
  481 ------+---------+---------+---------+---------+---------+ 540
      CTCACCCTCTCGTTACCCGTCGGCCTCTTGTTGATGTTCTGGTGCGGAGGGCACGACCTG a     E  W  E  S  N  G  Q  P  E  N  N  Y  K  T  T  P  P  V  L  D  -

TCCGACGGCTCCTTCTTCCTCTACAGCAAGCTCACCGTGGACAAGAGCAGGTGGCAGCAG
  541 ------+---------+---------+---------+---------+---------+ 600
      AGGCTGCCGAGGAAGAAGGAGATGTCGTTCGAGTGGCACCTGTTCTCGTCCACCGTCGTC a     S  D  G  S  F  F  L  Y  S  K  L  T  V  D  K  S  R  W  Q  Q  -

GGGAACGTCTTCTCATGCTCCGTGATGCATGAGGCTCTGCACAACCACTACACGCAGAAG
  601 ------+---------+---------+---------+---------+---------+ 660
      CCCTTGCAGAAGAGTACGAGGCACTACGTACTCCGAGACGTGTTGGTGATGTGCGTCTTC a     G  N  V  F  S  C  S  V  M  H  E  A  L  H  N  H  Y  T  Q  K  -

AGCCTCTCCCTGTCTCCGGGTAAA
  661 ---------+---------+---- 684
      TCGGAGAGGGACAGAGGCCCATTT
```

FIG. 7

```
     XbaI
     |
     TCTAGATTTGTTTTAACTAATTAAAGGAGGAATAACATATGGACAAAACTCACACATGTC
  1  ----------+---------+---------+---------+---------+---------+  60
     AGATCTAAACAAAATTGATTAATTTCCTCCTTATTGTATACCTGTTTTGAGTGTGTACAG
c                                              M  D  K  T  H  T  C  P -

CACCTTGTCCAGCTCCGGAACTCCTGGGGGGACCGTCAGTCTTCCTCTTCCCCCCAAAAC
 61  ----------+---------+---------+---------+---------+---------+  120
     GTGGAACAGGTCGAGGCCTTGAGGACCCCCCTGGCAGTCAGAAGGAGAAGGGGGGTTTTG
c     P  C  P  A  P  E  L  L  G  G  P  S  V  F  L  P  P  P  K  P -

CCAAGGACACCCTCATGATCTCCCGGACCCCTGAGGTCACATGCGTGGTGGTGGACGTGA
121  ----------+---------+---------+---------+---------+---------+  180
     GGTTCCTGTGGGAGTACTAGAGGGCCTGGGGACTCCAGTGTACGCACCACCACCTGCACT
c     K  D  T  L  M  I  S  R  T  P  E  V  T  C  V  V  V  D  V  S -

GCCACGAAGACCCTGAGGTCAAGTTCAACTGGTACGTGGACGGCGTGGAGGTGCATAATG
181  ----------+---------+---------+---------+---------+---------+  240
     CGGTGCTTCTGGGACTCCAGTTCAAGTTGACCATGCACCTGCCGCACCTCCACGTATTAC
c     H  E  D  P  E  V  K  F  N  W  Y  V  D  G  V  E  V  H  N  A -

CCAAGACAAAGCCGCGGGAGGAGCAGTACAACAGCACGTACCGTGTGGTCAGCGTCCTCA
241  ----------+---------+---------+---------+---------+---------+  300
     GGTTCTGTTTCGGCGCCCTCCTCGTCATGTTGTCGTGCATGGCACACCAGTCGCAGGAGT
c     K  T  K  P  R  E  E  Q  Y  N  S  T  Y  R  V  V  S  V  L  T -

CCGTCCTGCACCAGGACTGGCTGAATGGCAAGGAGTACAAGTGCAAGGTCTCCAACAAAG
301  ----------+---------+---------+---------+---------+---------+  360
     GGCAGGACGTGGTCCTGACCGACTTACCGTTCCTCATGTTCACGTTCCAGAGGTTGTTTC
c     V  L  H  Q  D  W  L  N  G  K  E  Y  K  C  K  V  S  N  K  A -

CCCTCCCAGCCCCCATCGAGAAAACCATCTCCAAAGCCAAAGGGCAGCCCCGAGAACCAC
361  ----------+---------+---------+---------+---------+---------+  420
     GGGAGGGTCGGGGGTAGCTCTTTTGGTAGAGGTTTCGGTTTCCCGTCGGGGCTCTTGGTG
c     L  P  A  P  I  E  K  T  I  S  K  A  K  G  Q  P  R  E  P  Q -

AGGTGTACACCCTGCCCCCATCCCGGGATGAGCTGACCAAGAACCAGGTCAGCCTGACCT
421  ----------+---------+---------+---------+---------+---------+  480
     TCCACATGTGGGACGGGGGTAGGGCCCTACTCGACTGGTTCTTGGTCCAGTCGGACTGGA
c     V  Y  T  L  P  P  S  R  D  E  L  T  K  N  Q  V  S  L  T  C -

GCCTGGTCAAAGGCTTCTATCCCAGCGACATCGCCGTGGAGTGGGAGAGCAATGGGCAGC
481  ----------+---------+---------+---------+---------+---------+  540
     CGGACCAGTTTCCGAAGATAGGGTCGCTGTAGCGGCACCTCACCCTCTCGTTACCCGTCG
c     L  V  K  G  F  Y  P  S  D  I  A  V  E  W  E  S  N  G  Q  P -

CGGAGAACAACTACAAGACCACGCCTCCCGTGCTGGACTCCGACGGCTCCTTCTTCCTCT
541  ----------+---------+---------+---------+---------+---------+  600
     GCCTCTTGTTGATGTTCTGGTGCGGAGGGCACGACCTGAGGCTGCCGAGGAAGAAGGAGA
c     E  N  N  Y  K  T  T  P  P  V  L  D  S  D  G  S  F  F  L  Y -

ACAGCAAGCTCACCGTGGACAAGAGCAGGTGGCAGCAGGGGAACGTCTTCTCATGCTCCG
601  ----------+---------+---------+---------+---------+---------+  660
     TGTCGTTCGAGTGGCACCTGTTCTCGTCCACCGTCGTCCCCTTGCAGAAGAGTACGAGGC
c     S  K  L  T  V  D  K  S  R  W  Q  Q  G  N  V  F  S  C  S  V -

TGATGCATGAGGCTCTGCACAACCACTACACGCAGAAGAGCCTCTCCCTGTCTCCGGGTA
661  ----------+---------+---------+---------+---------+---------+  720
     ACTACGTACTCCGAGACGTGTTGGTGATGTGCGTCTTCTCGGAGAGGGACAGAGGCCCAT
c     M  H  E  A  L  H  N  H  Y  T  Q  K  S  L  S  L  S  P  G  K -

AAGGTGGAGGTGGTGGTATCGAAGGTCCGACTCTGCGTCAGTGGCTGGCTGCTCGTGCTT
721  ----------+---------+---------+---------+---------+---------+  780
     TTCCACCTCCACCACCATAGCTTCCAGGCTGAGACGCAGTCACCGACCGACGAGCACGAA
c     G  G  G  G  I  E  G  P  T  L  R  Q  W  L  A  A  R  A  * -

BamHI
     |
     AATCTCGAGGATCC
781  ----------+----  794
     TTAGAGCTCCTAGG
```

FIG. 8

```
       XbaI
         |
      TCTAGATTTGTTTTAACTAATTAAAGGAGGAATAACATATGGACAAAACTCACACATGTC
    1 ----------+----------+----------+----------+----------+----------+  60
      AGATCTAAACAAAATTGATTAATTTCCTCCTTATTGTATACCTGTTTTGAGTGTGTACAG
    c                                     M  D  K  T  H  T  C  P -

CACCTTGTCCAGCTCCGGAACTCCTGGGGGGACCGTCAGTCTTCCTCTTCCCCCCAAAAC
   61 ----------+----------+----------+----------+----------+----------+ 120
      GTGGAACAGGTCGAGGCCTTGAGGACCCCCCTGGCAGTCAGAAGGAGAAGGGGGGTTTTG
    c   P  C  P  A  P  E  L  L  G  G  P  S  V  F  L  F  P  P  K  P -

CCAAGGACACCCTCATGATCTCCCGGACCCCTGAGGTCACATGCGTGGTGGTGGACGTGA
  121 ----------+----------+----------+----------+----------+----------+ 180
      GGTTCCTGTGGGAGTACTAGAGGGCCTGGGGACTCCAGTGTACGCACCACCACCTGCACT
    c   K  D  T  L  M  I  S  R  T  P  E  V  T  C  V  V  V  D  V  S -

GCCACGAAGACCCTGAGGTCAAGTTCAACTGGTACGTGGACGGCGTGGAGGTGCATAATG
  181 ----------+----------+----------+----------+----------+----------+ 240
      CGGTGCTTCTGGGACTCCAGTTCAAGTTGACCATGCACCTGCCGCACCTCCACGTATTAC
    c   H  E  D  P  E  V  K  F  N  W  Y  V  D  G  V  E  V  H  N  A -

CCAAGACAAAGCCGCGGGAGGAGCAGTACAACAGCACGTACCGTGTGGTCAGCGTCCTCA
  241 ----------+----------+----------+----------+----------+----------+ 300
      GGTTCTGTTTCGGCGCCCTCCTCGTCATGTTGTCGTGCATGGCACACCAGTCGCAGGAGT
    c   K  T  K  P  R  E  E  Q  Y  N  S  T  Y  R  V  V  S  V  L  T -

CCGTCCTGCACCAGGACTGGCTGAATGGCAAGGAGTACAAGTGCAAGGTCTCCAACAAAG
  301 ----------+----------+----------+----------+----------+----------+ 360
      GGCAGGACGTGGTCCTGACCGACTTACCGTTCCTCATGTTCACGTTCCAGAGGTTGTTTC
    c   V  L  H  Q  D  W  L  N  G  K  E  Y  K  C  K  V  S  N  K  A -

CCCTCCCAGCCCCCATCGAGAAAACCATCTCCAAAGCCAAAGGGCAGCCCCGAGAACCAC
  361 ----------+----------+----------+----------+----------+----------+ 420
      GGGAGGGTCGGGGGTAGCTCTTTTGGTAGAGGTTTCGGTTTCCCGTCGGGGCTCTTGGTG
    c   L  P  A  P  I  E  K  T  I  S  K  A  K  G  Q  P  R  E  P  Q -

AGGTGTACACCCTGCCCCCATCCCGGGATGAGCTGACCAAGAACCAGGTCAGCCTGACCT
  421 ----------+----------+----------+----------+----------+----------+ 480
      TCCACATGTGGGACGGGGGTAGGGCCCTACTCGACTGGTTCTTGGTCCAGTCGGACTGGA
    c   V  Y  T  L  P  P  S  R  D  E  L  T  K  N  Q  V  S  L  T  C -

GCCTGGTCAAAGGCTTCTATCCCAGCGACATCGCCGTGGAGTGGGAGAGCAATGGGCAGC
  481 ----------+----------+----------+----------+----------+----------+ 540
      CGGACCAGTTTCCGAAGATAGGGTCGCTGTAGCGGCACCTCACCCTCTCGTTACCCGTCG
    c   L  V  K  G  F  Y  P  S  D  I  A  V  E  W  E  S  N  G  Q  P -

CGGAGAACAACTACAAGACCACGCCTCCCGTGCTGGACTCCGACGGCTCCTTCTTCCTCT
  541 ----------+----------+----------+----------+----------+----------+ 600
      GCCTCTTGTTGATGTTCTGGTGCGGAGGGCACGACCTGAGGCTGCCGAGGAAGAAGGAGA
    c   E  N  N  Y  K  T  T  P  P  V  L  D  S  D  G  S  F  F  L  Y -

ACAGCAAGCTCACCGTGGACAAGAGCAGGTGGCAGCAGGGGAACGTCTTCTCATGCTCCG
  601 ----------+----------+----------+----------+----------+----------+ 660
      TGTCGTTCGAGTGGCACCTGTTCTCGTCCACCGTCGTCCCCTTGCAGAAGAGTACGAGGC
    c   S  K  L  T  V  D  K  S  R  W  Q  Q  G  N  V  F  S  C  S  V -

TGATGCATGAGGCTCTGCACAACCACTACACGCAGAAGAGCCTCTCCCTGTCTCCGGGTA
  661 ----------+----------+----------+----------+----------+----------+ 720
      ACTACGTACTCCGAGACGTGTTGGTGATGTGCGTCTTCTCGGAGAGGGACAGAGGCCCAT
    c   M  H  E  A  L  H  N  H  Y  T  Q  K  S  L  S  L  S  P  G  K -

AAGGTGGAGGTGGTGGTATCGAAGGTCCGACTCTGCGTCAGTGGCTGGCTGCTCGTGCTG
  721 ----------+----------+----------+----------+----------+----------+ 780
      TTCCACCTCCACCACCATAGCTTCCAGGCTGAGACGCAGTCACCGACCGACGAGCACGAC
    c   G  G  G  G  I  E  G  P  T  L  R  Q  W  L  A  A  R  A  G -

GTGGTGGAGGTGGCGGCGGAGGTATTGAGGGCCCAACCCTTCGCCAATGGCTTGCAGCAC
  781 ----------+----------+----------+----------+----------+----------+ 840
      CACCACCTCCACCGCCGCCTCCATAACTCCCGGGTTGGGAAGCGGTTACCGAACGTCGTG
    c   G  G  G  G  G  G  I  E  G  P  T  L  R  Q  W  L  A  A  R -

BamHI
                |
      GCGCATAATCTCGAGGATCCG
  841 ----------+----------+- 861
      CGCGTATTAGAGCTCCTAGGC
                         c            A  *  -
```

FIG. 9

```
XbaI
 |
 TCTAGATTTGTTTTAACTAATTAAAGGAGGAATAACATATGATCGAAGGTCCGACTCTGC
1 ----------+---------+---------+---------+---------+---------+ 60
 AGATCTAAACAAAATTGATTAATTTCCTCCTTATTGTATACTAGCTTCCAGGCTGAGACG
                                 M  I  E  G  P  T  L  R -

GTCAGTGGCTGGCTGCTCGTGCTGGCGGTGGTGGCGGAGGGGGTGGCATTGAGGGCCCAA
61 ----------+---------+---------+---------+---------+---------+ 120
 CAGTCACCGACCGACGAGCACGACCGCCACCACCGCCTCCCCCACCGTAACTCCCGGGTT
  Q  W  L  A  A  R  A  G  G  G  G  G  G  I  E  G  P  T -

CCCTTCGCCAATGGCTTGCAGCACGCGCAGGGGGAGGCGGTGGGGACAAAACTCACACAT
121 ----------+---------+---------+---------+---------+---------+ 180
 GGGAAGCGGTTACCGAACGTCGTGCGCGTCCCCCTCCGCCACCCCTGTTTTGAGTGTGTA
  L  R  Q  W  L  A  A  R  A  G  G  G  G  D  K  T  H  T  C -

GTCCACCTTGCCCAGCACCTGAACTCCTGGGGGGACCGTCAGTTTTCCTCTTCCCCCCAA
181 ----------+---------+---------+---------+---------+---------+ 240
 CAGGTGGAACGGGTCGTGGACTTGAGGACCCCCCTGGCAGTCAAAAGGAGAAGGGGGGTT
  P  P  C  P  A  P  E  L  L  G  G  P  S  V  F  L  F  P  P  K -

AACCCAAGGACACCCTCATGATCTCCCGGACCCCTGAGGTCACATGCGTGGTGGTGGACG
241 ----------+---------+---------+---------+---------+---------+ 300
 TTGGGTTCCTGTGGGAGTACTAGAGGGCCTGGGGACTCCAGTGTACGCACCACCACCTGC
  P  K  D  T  L  M  I  S  R  T  P  E  V  T  C  V  V  V  D  V -

TGAGCCACGAAGACCCTGAGGTCAAGTTCAACTGGTACGTGGACGGCGTGGAGGTGCATA
301 ----------+---------+---------+---------+---------+---------+ 360
 ACTCGGTGCTTCTGGGACTCCAGTTCAAGTTGACCATGCACCTGCCGCACCTCCACGTAT
  S  H  E  D  P  E  V  K  F  N  W  Y  V  D  G  V  E  V  H  N -

ATGCCAAGACAAAGCCGCGGGAGGAGCAGTACAACAGCACGTACCGTGTGGTCAGCGTCC
361 ----------+---------+---------+---------+---------+---------+ 420
 TACGGTTCTGTTTCGGCGCCCTCCTCGTCATGTTGTCGTGCATGGCACACCAGTCGCAGG
  A  K  T  K  P  R  E  E  Q  Y  N  S  T  Y  R  V  V  S  V  L -

TCACCGTCCTGCACCAGGACTGGCTGAATGGCAAGGAGTACAAGTGCAAGGTCTCCAACA
421 ----------+---------+---------+---------+---------+---------+ 480
 AGTGGCAGGACGTGGTCCTGACCGACTTACCGTTCCTCATGTTCACGTTCCAGAGGTTGT
  T  V  L  H  Q  D  W  L  N  G  K  E  Y  K  C  K  V  S  N  K -

AAGCCCTCCCAGCCCCCATCGAGAAAACCATCTCCAAAGCCAAAGGGCAGCCCCGAGAAC
481 ----------+---------+---------+---------+---------+---------+ 540
 TTCGGGAGGGTCGGGGGTAGCTCTTTTGGTAGAGGTTTCGGTTTCCCGTCGGGGCTCTTG
  A  L  P  A  P  I  E  K  T  I  S  K  A  K  G  Q  P  R  E  P -

CACAGGTGTACACCCTGCCCCCATCCCGGGATGAGCTGACCAAGAACCAGGTCAGCCTGA
541 ----------+---------+---------+---------+---------+---------+ 600
 GTGTCCACATGTGGGACGGGGGTAGGGCCCTACTCGACTGGTTCTTGGTCCAGTCGGACT
  Q  V  Y  T  L  P  P  S  R  D  E  L  T  K  N  Q  V  S  L  T -

CCTGCCTGGTCAAAGGCTTCTATCCCAGCGACATCGCCGTGGAGTGGGAGAGCAATGGGC
601 ----------+---------+---------+---------+---------+---------+ 660
 GGACGGACCAGTTTCCGAAGATAGGGTCGCTGTAGCGGCACCTCACCCTCTCGTTACCCG
  C  L  V  K  G  F  Y  P  S  D  I  A  V  E  W  E  S  N  G  Q -

AGCCGGAGAACAACTACAAGACCACGCCTCCCGTGCTGGACTCCGACGGCTCCTTCTTCC
661 ----------+---------+---------+---------+---------+---------+ 720
 TCGGCCTCTTGTTGATGTTCTGGTGCGGAGGGCACGACCTGAGGCTGCCGAGGAAGAAGG
  P  E  N  N  Y  K  T  T  P  P  V  L  D  S  D  G  S  F  F  L -

TCTACAGCAAGCTCACCGTGGACAAGAGCAGGTGGCAGCAGGGGAACGTCTTCTCATGCT
721 ----------+---------+---------+---------+---------+---------+ 780
 AGATGTCGTTCGAGTGGCACCTGTTCTCGTCCACCGTCGTCCCCTTGCAGAAGAGTACGA
  Y  S  K  L  T  V  D  K  S  R  W  Q  Q  G  N  V  F  S  C  S -

CCGTGATGCATGAGGCTCTGCACAACCACTACACGCAGAAGAGCCTCTCCCTGTCTCCGG
781 ----------+---------+---------+---------+---------+---------+ 840
 GGCACTACGTACTCCGAGACGTGTTGGTGATGTGCGTCTTCTCGGAGAGGGACAGAGGCC
  V  M  H  E  A  L  H  N  H  Y  T  Q  K  S  L  S  L  S  P  G -

BamHI
       |
  GTAAATAATGGATCC
841 ----------+----- 855
  CATTTATTACCTAGG
     K  *
```

FIG. 10

```
    XbaI
     |
    TCTAGATTTGTTTTAACTAATTAAAGGAGGAATAACATATGATCGAAGGTCCGACTCTGC
  1 ----------+---------+---------+---------+---------+---------+  60
    AGATCTAAACAAAATTGATTAATTTCCTCCTTATTGTATACTAGCTTCCAGGCTGAGACG
c                                       M  I  E  G  P  T  L  R -

GTCAGTGGCTGGCTGCTCGTGCTGGTGGAGGCGGTGGGGACAAAACTCACACATGTCCAC
 61 ----------+---------+---------+---------+---------+---------+ 120
    CAGTCACCGACCGACGAGCACGACCACCTCCGCCACCCCTGTTTTGAGTGTGTACAGGTG
c    Q  W  L  A  A  R  A  G  G  G  G  D  K  T  H  T  C  P  P -

CTTGCCCAGCACCTGAACTCCTGGGGGGACCGTCAGTTTTCCTCTTCCCCCCAAAACCCA
121 ----------+---------+---------+---------+---------+---------+ 180
    GAACGGGTCGTGGACTTGAGGACCCCCCTGGCAGTCAAAAGGAGAAGGGGGGTTTTGGGT
c    C  P  A  P  E  L  L  G  G  P  S  V  F  L  F  P  P  K  P  K -

AGGACACCCTCATGATCTCCCGGACCCCTGAGGTCACATGCGTGGTGGTGGACGTGAGCC
181 ----------+---------+---------+---------+---------+---------+ 240
    TCCTGTGGGAGTACTAGAGGGCCTGGGGACTCCAGTGTACGCACCACCACCTGCACTCGG
c     D  T  L  M  I  S  R  T  P  E  V  T  C  V  V  V  D  V  S  H -

ACGAAGACCCTGAGGTCAAGTTCAACTGGTACGTGGACGGCGTGGAGGTGCATAATGCCA
241 ----------+---------+---------+---------+---------+---------+ 300
    TGCTTCTGGGACTCCAGTTCAAGTTGACCATGCACCTGCCGCACCTCCACGTATTACGGT
c     E  D  P  E  V  K  F  N  W  Y  V  D  G  V  E  V  H  N  A  K -

AGACAAAGCCGCGGGAGGAGCAGTACAACAGCACGTACCGTGTGGTCAGCGTCCTCACCG
301 ----------+---------+---------+---------+---------+---------+ 360
    TCTGTTTCGGCGCCCTCCTCGTCATGTTGTCGTGCATGGCACACCAGTCGCAGGAGTGGC
c     T  K  P  R  E  E  Q  Y  N  S  T  Y  R  V  V  S  V  L  T  V -

TCCTGCACCAGGACTGGCTGAATGGCAAGGAGTACAAGTGCAAGGTCTCCAACAAAGCCC
361 ----------+---------+---------+---------+---------+---------+ 420
    AGGACGTGGTCCTGACCGACTTACCGTTCCTCATGTTCACGTTCCAGAGGTTGTTTCGGG
c     L  H  Q  D  W  L  N  G  K  E  Y  K  C  K  V  S  N  K  A  L -

TCCCAGCCCCCATCGAGAAAACCATCTCCAAAGCCAAAGGGCAGCCCCGAGAACCACAGG
421 ----------+---------+---------+---------+---------+---------+ 480
    AGGGTCGGGGGTAGCTCTTTTGGTAGAGGTTTCGGTTTCCCGTCGGGGCTCTTGGTGTCC
c     P  A  P  I  E  K  T  I  S  K  A  K  G  Q  P  R  E  P  Q  V -

TGTACACCCTGCCCCCATCCCGGGATGAGCTGACCAAGAACCAGGTCAGCCTGACCTGCC
481 ----------+---------+---------+---------+---------+---------+ 540
    ACATGTGGGACGGGGGTAGGGCCCTACTCGACTGGTTCTTGGTCCAGTCGGACTGGACGG
c     Y  T  L  P  P  S  R  D  E  L  T  K  N  Q  V  S  L  T  C  L -

TGGTCAAAGGCTTCTATCCCAGCGACATCGCCGTGGAGTGGGAGAGCAATGGGCAGCCGG
541 ----------+---------+---------+---------+---------+---------+ 600
    ACCAGTTTCCGAAGATAGGGTCGCTGTAGCGGCACCTCACCCTCTCGTTACCCGTCGGCC
c     V  K  G  F  Y  P  S  D  I  A  V  E  W  E  S  N  G  Q  P  E -

AGAACAACTACAAGACCACGCCTCCCGTGCTGGACTCCGACGGCTCCTTCTTCCTCTACA
601 ----------+---------+---------+---------+---------+---------+ 660
    TCTTGTTGATGTTCTGGTGCGGAGGGCACGACCTGAGGCTGCCGAGGAAGAAGGAGATGT
c     N  N  Y  K  T  T  P  P  V  L  D  S  D  G  S  F  F  L  Y  S -

GCAAGCTCACCGTGGACAAGAGCAGGTGGCAGCAGGGGAACGTCTTCTCATGCTCCGTGA
661 ----------+---------+---------+---------+---------+---------+ 720
    CGTTCGAGTGGCACCTGTTCTCGTCCACCGTCGTCCCCTTGCAGAAGAGTACGAGGCACT
c     K  L  T  V  D  K  S  R  W  Q  Q  G  N  V  F  S  C  S  V  M -

TGCATGAGGCTCTGCACAACCACTACACGCAGAAGAGCCTCTCCCTGTCTCCGGGTAAAT
721 ----------+---------+---------+---------+---------+---------+ 780
    ACGTACTCCGAGACGTGTTGGTGATGTGCGTCTTCTCGGAGAGGGACAGAGGCCCATTTA
c     H  E  A  L  H  N  H  Y  T  Q  K  S  L  S  L  S  P  G  K  * -

BamHI
     |
    AATGGATCC
781 --------- 789
    TTACCTAGG
```

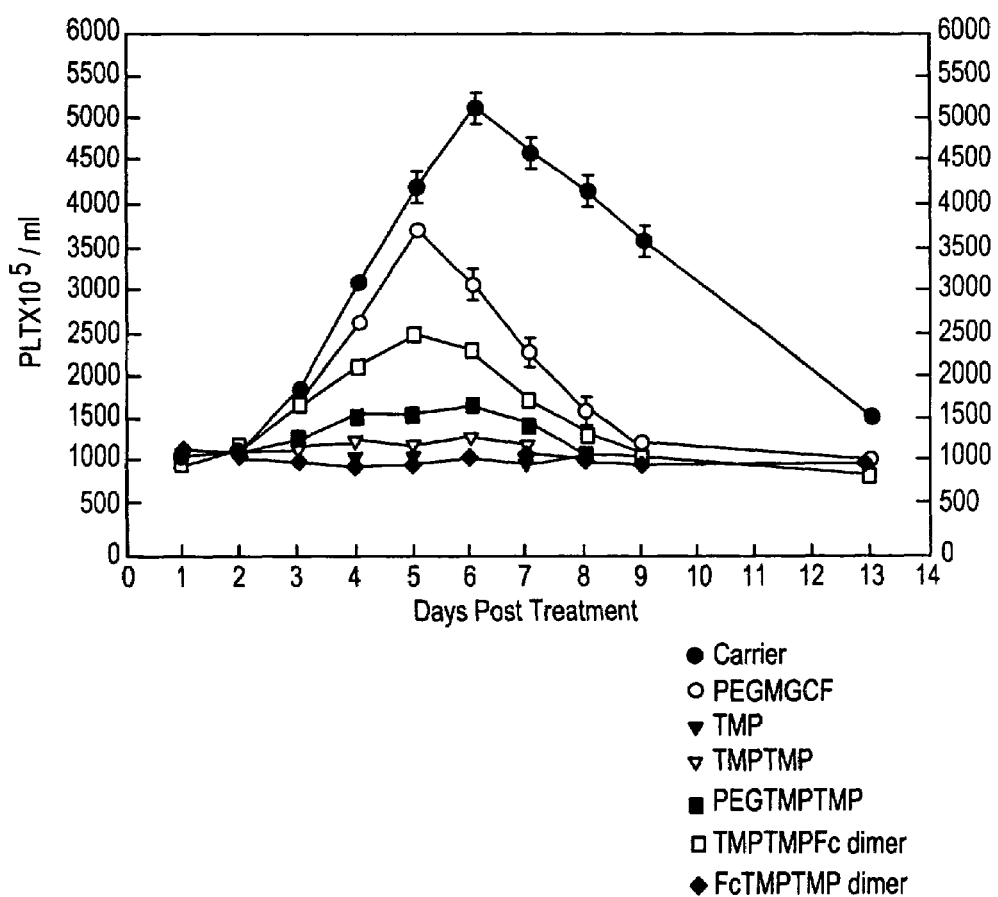

FIG. 13

```
     XbaI
      |
     TCTAGATTTGTTTTAACTAATTAAAGGAGGAATAACATATGGACAAAACTCACACATGTC
  1  ------+---------+---------+---------+---------+---------+  60
     AGATCTAAACAAAATTGATTAATTTCCTCCTTATTGTATACCTGTTTTGAGTGTGTACAG
c                                          M  D  K  T  H  T  C  P -

CACCTTGTCCAGCTCCGGAACTCCTGGGGGGACCGTCAGTCTTCCTCTTCCCCCCAAAAC
 61  ------+---------+---------+---------+---------+---------+ 120
     GTGGAACAGGTCGAGGCCTTGAGGACCCCCCTGGCAGTCAGAAGGAGAAGGGGGGTTTTG
c       P  C  P  A  P  E  L  L  G  G  P  S  V  F  L  F  P  P  K  P -

CCAAGGACACCCTCATGATCTCCCGGACCCCTGAGGTCACATGCGTGGTGGTGGACGTGA
121  ------+---------+---------+---------+---------+---------+ 180
     GGTTCCTGTGGGAGTACTAGAGGGCCTGGGGACTCCAGTGTACGCACCACCACCTGCACT
c       K  D  T  L  M  I  S  R  T  P  E  V  T  C  V  V  V  D  V  S -

GCCACGAAGACCCTGAGGTCAAGTTCAACTGGTACGTGGACGGCGTGGAGGTGCATAATG
181  ------+---------+---------+---------+---------+---------+ 240
     CGGTGCTTCTGGGACTCCAGTTCAAGTTGACCATGCACCTGCCGCACCTCCACGTATTAC
c       H  E  D  P  E  V  K  F  N  W  Y  V  D  G  V  E  V  H  N  A -

CCAAGACAAAGCCGCGGGAGGAGCAGTACAACAGCACGTACCGTGTGGTCAGCGTCCTCA
241  ------+---------+---------+---------+---------+---------+ 300
     GGTTCTGTTTCGGCGCCCTCCTCGTCATGTTGTCGTGCATGGCACACCAGTCGCAGGAGT
c       K  T  K  P  R  E  E  Q  Y  N  S  T  Y  R  V  V  S  V  L  T -

CCGTCCTGCACCAGGACTGGCTGAATGGCAAGGAGTACAAGTGCAAGGTCTCCAACAAAG
301  ------+---------+---------+---------+---------+---------+ 360
     GGCAGGACGTGGTCCTGACCGACTTACCGTTCCTCATGTTCACGTTCCAGAGGTTGTTTC
c       V  L  H  Q  D  W  L  N  G  K  E  Y  K  C  K  V  S  N  K  A -

CCCTCCCAGCCCCCATCGAGAAAACCATCTCCAAAGCCAAAGGGCAGCCCCGAGAACCAC
361  ------+---------+---------+---------+---------+---------+ 420
     GGGAGGGTCGGGGGTAGCTCTTTTGGTAGAGGTTTCGGTTTCCCGTCGGGGCTCTTGGTG
c       L  P  A  P  I  E  K  T  I  S  K  A  K  G  Q  P  R  E  P  Q -

AGGTGTACACCCTGCCCCCATCCCGGGATGAGCTGACCAAGAACCAGGTCAGCCTGACCT
421  ------+---------+---------+---------+---------+---------+ 480
     TCCACATGTGGGACGGGGGTAGGGCCCTACTCGACTGGTTCTTGGTCCAGTCGGACTGGA
c       V  Y  T  L  P  P  S  R  D  E  L  T  K  N  Q  V  S  L  T  C -

GCCTGGTCAAAGGCTTCTATCCCAGCGACATCGCCGTGGAGTGGGAGAGCAATGGGCAGC
481  ------+---------+---------+---------+---------+---------+ 540
     CGGACCAGTTTCCGAAGATAGGGTCGCTGTAGCGGCACCTCACCCTCTCGTTACCCGTCG
c       L  V  K  G  F  Y  P  S  D  I  A  V  E  W  E  S  N  G  Q  P -

CGGAGAACAACTACAAGACCACGCCTCCCGTGCTGGACTCCGACGGCTCCTTCTTCCTCT
541  ------+---------+---------+---------+---------+---------+ 600
     GCCTCTTGTTGATGTTCTGGTGCGGAGGGCACGACCTGAGGCTGCCGAGGAAGAAGGAGA
c       E  N  N  Y  K  T  T  P  P  V  L  D  S  D  G  S  F  F  L  Y -

ACAGCAAGCTCACCGTGGACAAGAGCAGGTGGCAGCAGGGGAACGTCTTCTCATGCTCCG
601  ------+---------+---------+---------+---------+---------+ 660
     TGTCGTTCGAGTGGCACCTGTTCTCGTCCACCGTCGTCCCCTTGCAGAAGAGTACGAGGC
c       S  K  L  T  V  D  K  S  R  W  Q  Q  G  N  V  F  S  C  S  V -

TGATGCATGAGGCTCTGCACAACCACTACACGCAGAAGAGCCTCTCCCTGTCTCCGGGTA
661  ------+---------+---------+---------+---------+---------+ 720
     ACTACGTACTCCGAGACGTGTTGGTGATGTGCGTCTTCTCGGAGAGGGACAGAGGCCCAT
c       M  H  E  A  L  H  N  H  Y  T  Q  K  S  L  S  L  S  P  G  K -

AAGGTGGAGGTGGTGGTGGAGGTACTTACTCTTGCCACTTCGGCCCGCTGACTTGGGTTT
721  ------+---------+---------+---------+---------+---------+ 780
     TTCCACCTCCACCACCACCTCCATGAATGAGAACGGTGAAGCCGGGCGACTGAACCCAAA
c       G  G  G  G  G  G  T  Y  S  C  H  F  G  P  L  T  W  V  C -

BamHI
             |
     GCAAACCGCAGGGTGGTTAATCTCGTGGATCC
781  ------+---------+---------+-- 812
     CGTTTGGCGTCCCACCAATTAGAGCACCTAGG
c       K  P  Q  G  G  *
```

FIG. 14

```
     XbaI
       |
     TCTAGATTTGTTTTAACTAATTAAAGGAGGAATAACATATGGGAGGTACTTACTCTTGCC
  1  ----------+----------+----------+----------+----------+----------+  60
     AGATCTAAACAAAATTGATTAATTTCCTCCTTATTGTATACCCTCCATGAATGAGAACGG
c                                            M  G  G  T  Y  S  C  H  -

ACTTCGGCCCGCTGACTTGGGTATGTAAGCCACAAGGGGGTGGGGGAGGCGGGGGGGACA
 61  ----------+----------+----------+----------+----------+----------+ 120
     TGAAGCCGGGCGACTGAACCCATACATTCGGTGTTCCCCCACCCCCTCCGCCCCCCCTGT
c      F  G  P  L  T  W  V  C  K  P  Q  G  G  G  G  G  G  D  K  -

AAACTCACACATGTCCACCTTGCCCAGCACCTGAACTCCTGGGGGGACCGTCAGTTTTCC
121  ----------+----------+----------+----------+----------+----------+ 180
     TTTGAGTGTGTACAGGTGGAACGGGTCGTGGACTTGAGGACCCCCCTGGCAGTCAAAAGG
c      T  H  T  C  P  P  C  P  A  P  E  L  L  G  G  P  S  V  F  L  -

TCTTCCCCCCAAAACCCAAGGACACCCTCATGATCTCCCGGACCCCTGAGGTCACATGCG
181  ----------+----------+----------+----------+----------+----------+ 240
     AGAAGGGGGGTTTTGGGTTCCTGTGGGAGTACTAGAGGGCCTGGGGACTCCAGTGTACGC
c      F  P  P  K  P  K  D  T  L  M  I  S  R  T  P  E  V  T  C  V  -

TGGTGGTGGACGTGAGCCACGAAGACCCTGAGGTCAAGTTCAACTGGTACGTGGACGGCG
241  ----------+----------+----------+----------+----------+----------+ 300
     ACCACCACCTGCACTCGGTGCTTCTGGGACTCCAGTTCAAGTTGACCATGCACCTGCCGC
c      V  V  D  V  S  H  E  D  P  E  V  K  F  N  W  Y  V  D  G  V  -

TGGAGGTGCATAATGCCAAGACAAAGCCGCGGGAGGAGCAGTACAACAGCACGTACCGTG
301  ----------+----------+----------+----------+----------+----------+ 360
     ACCTCCACGTATTACGGTTCTGTTTCGGCGCCCTCCTCGTCATGTTGTCGTGCATGGCAC
c      E  V  H  N  A  K  T  K  P  R  E  E  Q  Y  N  S  T  Y  R  V  -

TGGTCAGCGTCCTCACCGTCCTGCACCAGGACTGGCTGAATGGCAAGGAGTACAAGTGCA
361  ----------+----------+----------+----------+----------+----------+ 420
     ACCAGTCGCAGGAGTGGCAGGACGTGGTCCTGACCGACTTACCGTTCCTCATGTTCACGT
c      V  S  V  L  T  V  L  H  Q  D  W  L  N  G  K  E  Y  K  C  K  -

AGGTCTCCAACAAAGCCCTCCCAGCCCCCATCGAGAAAACCATCTCCAAAGCCAAAGGGC
421  ----------+----------+----------+----------+----------+----------+ 480
     TCCAGAGGTTGTTTCGGGAGGGTCGGGGGTAGCTCTTTTGGTAGAGGTTTCGGTTTCCCG
c      V  S  N  K  A  L  P  A  P  I  E  K  T  I  S  K  A  K  G  Q  -

AGCCCCGAGAACCACAGGTGTACACCCTGCCCCCATCCCGGGATGAGCTGACCAAGAACC
481  ----------+----------+----------+----------+----------+----------+ 540
     TCGGGGCTCTTGGTGTCCACATGTGGGACGGGGGTAGGGCCCTACTCGACTGGTTCTTGG
c      P  R  E  P  Q  V  Y  T  L  P  P  S  R  D  E  L  T  K  N  Q  -

AGGTCAGCCTGACCTGCCTGGTCAAAGGCTTCTATCCCAGCGACATCGCCGTGGAGTGGG
541  ----------+----------+----------+----------+----------+----------+ 600
     TCCAGTCGGACTGGACGGACCAGTTTCCGAAGATAGGGTCGCTGTAGCGGCACCTCACCC
c      V  S  L  T  C  L  V  K  G  F  Y  P  S  D  I  A  V  E  W  E  -

AGAGCAATGGGCAGCCGGAGAACAACTACAAGACCACGCCTCCCGTGCTGGACTCCGACG
601  ----------+----------+----------+----------+----------+----------+ 660
     TCTCGTTACCCGTCGGCCTCTTGTTGATGTTCTGGTGCGGAGGGCACGACCTGAGGCTGC
c      S  N  G  Q  P  E  N  N  Y  K  T  T  P  P  V  L  D  S  D  G  -

GCTCCTTCTTCCTCTACAGCAAGCTCACCGTGGACAAGAGCAGGTGGCAGCAGGGGAACG
661  ----------+----------+----------+----------+----------+----------+ 720
     CGAGGAAGAAGGAGATGTCGTTCGAGTGGCACCTGTTCTCGTCCACCGTCGTCCCCTTGC
c      S  F  F  L  Y  S  K  L  T  V  D  K  S  R  W  Q  Q  G  N  V  -

TCTTCTCATGCTCCGTGATGCATGAGGCTCTGCACAACCACTACACGCAGAAGAGCCTCT
721  ----------+----------+----------+----------+----------+----------+ 780
     AGAAGAGTACGAGGCACTACGTACTCCGAGACGTGTTGGTGATGTGCGTCTTCTCGGAGA
c      F  S  C  S  V  M  H  E  A  L  H  N  H  Y  T  Q  K  S  L  S  -

BamHI
                   |
     CCCTGTCTCCGGGTAAATAATGGATCC
781  ----------+----------+------- 807
     GGGACAGAGGCCCATTTATTACCTAGG
c      L  S  P  G  K  *
```

FIG. 15

```
      XbaI
       |
       TCTAGATTTGAGTTTTAACTTTTAGAAGGAGGAATAAAATATGGGAGGTACTTACTCTTG
   1   --------+---------+---------+---------+---------+---------+  60
       AGATCTAAACTCAAAATTGAAAATCTTCCTCCTTATTTTATACCCTCCATGAATGAGAAC
b                                                  M  G  G  T  Y  S  C  -

CCACTTCGGCCCACTGACTTGGGTTTGCAAACCGCAGGGTGGCGGCGGCGGCGGCGGTGG
  61   --------+---------+---------+---------+---------+---------+ 120
       GGTGAAGCCGGGTGACTGAACCCAAACGTTTGGCGTCCCACCGCCGCCGCCGCCGCCACC
b        H  F  G  P  L  T  W  V  C  K  P  Q  G  G  G  G  G  G  G  -

TACCTATTCCTGTCATTTTGGCCCGCTGACCTGGGTATGTAAGCCACAAGGGGGTGGGGG
 121   --------+---------+---------+---------+---------+---------+ 180
       ATGGATAAGGACAGTAAAACCGGGCGACTGGACCCATACATTCGGTGTTCCCCCACCCCC
b        T  Y  S  C  H  F  G  P  L  T  W  V  C  K  P  Q  G  G  G  G  -

AGGCGGGGGGGACAAAACTCACACATGTCCACCTTGCCCAGCACCTGAACTCCTGGGGGG
 181   --------+---------+---------+---------+---------+---------+ 240
       TCCGCCCCCCCTGTTTTGAGTGTGTACAGGTGGAACGGGTCGTGGACTTGAGGACCCCCC
b        G  G  G  D  K  T  H  T  C  P  P  C  P  A  P  E  L  L  G  G  -

ACCGTCAGTTTTCCTCTTCCCCCCAAAACCCAAGGACACCCTCATGATCTCCCGGACCCC
 241   --------+---------+---------+---------+---------+---------+ 300
       TGGCAGTCAAAAGGAGAAGGGGGGTTTTGGGTTCCTGTGGGAGTACTAGAGGGCCTGGGG
b        P  S  V  F  L  F  P  P  K  P  K  D  T  L  M  I  S  R  T  P  -

TGAGGTCACATGCGTGGTGGTGGACGTGAGCCACGAAGACCCTGAGGTCAAGTTCAACTG
 301   --------+---------+---------+---------+---------+---------+ 360
       ACTCCAGTGTACGCACCACCACCTGCACTCGGTGCTTCTGGGACTCCAGTTCAAGTTGAC
b        E  V  T  C  V  V  V  D  V  S  H  E  D  P  E  V  K  F  N  W  -

GTACGTGGACGGCGTGGAGGTGCATAATGCCAAGACAAAGCCGCGGGAGGAGCAGTACAA
 361   --------+---------+---------+---------+---------+---------+ 420
       CATGCACCTGCCGCACCTCCACGTATTACGGTTCTGTTTCGGCGCCCTCCTCGTCATGTT
b        Y  V  D  G  V  E  V  H  N  A  K  T  K  P  R  E  E  Q  Y  N  -

CAGCACGTACCGTGTGGTCAGCGTCCTCACCGTCCTGCACCAGGACTGGCTGAATGGCAA
 421   --------+---------+---------+---------+---------+---------+ 480
       GTCGTGCATGGCACACCAGTCGCAGGAGTGGCAGGACGTGGTCCTGACCGACTTACCGTT
b        S  T  Y  R  V  V  S  V  L  T  V  L  H  Q  D  W  L  N  G  K  -

GGAGTACAAGTGCAAGGTCTCCAACAAAGCCCTCCCAGCCCCCATCGAGAAAACCATCTC
 481   --------+---------+---------+---------+---------+---------+ 540
       CCTCATGTTCACGTTCCAGAGGTTGTTTCGGGAGGGTCGGGGGTAGCTCTTTTGGTAGAG
b        E  Y  K  C  K  V  S  N  K  A  L  P  A  P  I  E  K  T  I  S  -

CAAAGCCAAAGGGCAGCCCCGAGAACCACAGGTGTACACCCTGCCCCCATCCCGGGATGA
 541   --------+---------+---------+---------+---------+---------+ 600
       GTTTCGGTTTCCCGTCGGGGCTCTTGGTGTCCACATGTGGGACGGGGGTAGGGCCCTACT
b        K  A  K  G  Q  P  R  E  P  Q  V  Y  T  L  P  P  S  R  D  E  -

GCTGACCAAGAACCAGGTCAGCCTGACCTGCCTGGTCAAAGGCTTCTATCCCAGCGACAT
 601   --------+---------+---------+---------+---------+---------+ 660
       CGACTGGTTCTTGGTCCAGTCGGACTGGACGGACCAGTTTCCGAAGATAGGGTCGCTGTA
b        L  T  K  N  Q  V  S  L  T  C  L  V  K  G  F  Y  P  S  D  I  -

CGCCGTGGAGTGGGAGAGCAATGGGCAGCCGGAGAACAACTACAAGACCACGCCTCCCGT
 661   --------+---------+---------+---------+---------+---------+ 720
       GCGGCACCTCACCCTCTCGTTACCCGTCGGCCTCTTGTTGATGTTCTGGTGCGGAGGGCA
b        A  V  E  W  E  S  N  G  Q  P  E  N  N  Y  K  T  T  P  P  V  -

GCTGGACTCCGACGGCTCCTTCTTCCTCTACAGCAAGCTCACCGTGGACAAGAGCAGGTG
 721   --------+---------+---------+---------+---------+---------+ 780
       CGACCTGAGGCTGCCGAGGAAGAAGGAGATGTCGTTCGAGTGGCACCTGTTCTCGTCCAC
b        L  D  S  D  G  S  F  F  L  Y  S  K  L  T  V  D  K  S  R  W  -

GCAGCAGGGGAACGTCTTCTCATGCTCCGTGATGCATGAGGCTCTGCACAACCACTACAC
 781   --------+---------+---------+---------+---------+---------+ 840
       CGTCGTCCCCTTGCAGAAGAGTACGAGGCACTACGTACTCCGAGACGTGTTGGTGATGTG
b        Q  Q  G  N  V  F  S  C  S  V  M  H  E  A  L  H  N  H  Y  T  -

BamHI
                                                        |
       GCAGAAGAGCCTCTCCCTGTCTCCGGGTAAATAATGGATCC
 841   --------+---------+---------+---------+- 881
       CGTCTTCTCGGAGAGGGACAGAGGCCCATTTATTACCTAGG
b        Q  K  S  L  S  L  S  P  G  K  *
```

FIG. 16

```
     XbaI
      |
     TCTAGATTTGTTTTAACTAATTAAAGGAGGAATAACATATGGACAAAACTCACACATGTC
  1  ............+............+............+............+............+............+ 60
     AGATCTAAACAAAATTGATTAATTTCCTCCTTATTGTATACCTGTTTTGAGTGTGTACAG
c                                        M  D  K  T  H  T  C  P -

CACCTTGCCCAGCACCTGAACTCCTGGGGGGACCGTCAGTTTTCCTCTTCCCCCCAAAAC
 61  ............+............+............+............+............+............+ 120
     GTGGAACGGGTCGTGGACTTGAGGACCCCCCTGGCAGTCAAAAGGAGAAGGGGGGTTTTG
c     P  C  P  A  P  E  L  L  G  G  P  S  V  F  L  P  P  P  K  P -

CCAAGGACACCCTCATGATCTCCCGGACCCCTGAGGTCACATGCGTGGTGGTGGACGTGA
121  ............+............+............+............+............+............+ 180
     GGTTCCTGTGGGAGTACTAGAGGGCCTGGGGACTCCAGTGTACGCACCACCACCTGCACT
c     K  D  T  L  M  I  S  R  T  P  E  V  T  C  V  V  V  D  V  S -

GCCACGAAGACCCTGAGGTCAAGTTCAACTGGTACGTGGACGGCGTGGAGGTGCATAATG
181  ............+............+............+............+............+............+ 240
     CGGTGCTTCTGGGACTCCAGTTCAAGTTGACCATGCACCTGCCGCACCTCCACGTATTAC
c     H  E  D  P  E  V  K  F  N  W  Y  V  D  G  V  E  V  H  N  A -

CCAAGACAAAGCCGCGGGAGGAGCAGTACAACAGCACGTACCGTGTGGTCAGCGTCCTCA
241  ............+............+............+............+............+............+ 300
     GGTTCTGTTTCGGCGCCCTCCTCGTCATGTTGTCGTGCATGGCACACCAGTCGCAGGAGT
c     K  T  K  P  R  E  E  Q  Y  N  S  T  Y  R  V  V  S  V  L  T -

CCGTCCTGCACCAGGACTGGCTGAATGGCAAGGAGTACAAGTGCAAGGTCTCCAACAAAG
301  ............+............+............+............+............+............+ 360
     GGCAGGACGTGGTCCTGACCGACTTACCGTTCCTCATGTTCACGTTCCAGAGGTTGTTTC
c     V  L  H  Q  D  W  L  N  G  K  E  Y  K  C  K  V  S  N  K  A -

CCCTCCCAGCCCCCATCGAGAAAACCATCTCCAAAGCCAAAGGGCAGCCCCGAGAACCAC
361  ............+............+............+............+............+............+ 420
     GGGAGGGTCGGGGGTAGCTCTTTTGGTAGAGGTTTCGGTTTCCCGTCGGGGCTCTTGGTG
c     L  P  A  P  I  E  K  T  I  S  K  A  K  G  Q  P  R  E  P  Q -

AGGTGTACACCCTGCCTCCATCCCGGGATGAGCTGACCAAGAACCAGGTCAGCCTGACCT
421  ............+............+............+............+............+............+ 480
     TCCACATGTGGGACGGAGGTAGGGCCCTACTCGACTGGTTCTTGGTCCAGTCGGACTGGA
c     V  Y  T  L  P  P  S  R  D  E  L  T  K  N  Q  V  S  L  T  C -

GCCTGGTCAAAGGCTTCTATCCCAGCGACATCGCCGTGGAGTGGGAGAGCAATGGGCAGC
481  ............+............+............+............+............+............+ 540
     CGGACCAGTTTCCGAAGATAGGGTCGCTGTAGCGGCACCTCACCCTCTCGTTACCCGTCG
c     L  V  K  G  F  Y  P  S  D  I  A  V  E  W  E  S  N  G  Q  P -

CGGAGAACAACTACAAGACCACGCCTCCCGTGCTGGACTCCGACGGCTCCTTCTTCCTCT
541  ............+............+............+............+............+............+ 600
     GCCTCTTGTTGATGTTCTGGTGCGGAGGGCACGACCTGAGGCTGCCGAGGAAGAAGGAGA
c     E  N  N  Y  K  T  T  P  P  V  L  D  S  D  G  S  F  F  L  Y -

ACAGCAAGCTCACCGTGGACAAGAGCAGGTGGCAGCAGGGGAACGTCTTCTCATGCTCCG
601  ............+............+............+............+............+............+ 660
     TGTCGTTCGAGTGGCACCTGTTCTCGTCCACCGTCGTCCCCTTGCAGAAGAGTACGAGGC
c     S  K  L  T  V  D  K  S  R  W  Q  Q  G  N  V  F  S  C  S  V -

TGATGCATGAGGCTCTGCACAACCACTACACGCAGAAGAGCCTCTCCCTGTCTCCGGGTA
661  ............+............+............+............+............+............+ 720
     ACTACGTACTCCGAGACGTGTTGGTGATGTGCGTCTTCTCGGAGAGGGACAGAGGCCCAT
c     M  H  E  A  L  H  N  H  Y  T  Q  K  S  L  S  L  S  P  G  K -

AAGGTGGAGGTGGTGGCGGAGGTACTTACTCTTGCCACTTCGGCCCACTGACTTGGGTTT
721  ............+............+............+............+............+............+ 780
     TTCCACCTCCACCACCGCCTCCATGAATGAGAACGGTGAAGCCGGGTGACTGAACCCAAA
c     G  G  G  G  G  G  T  Y  S  C  H  F  G  P  L  T  W  V  C  -

GCAAACCGCAGGGTGGCGGCGGCGGCGGCGGTGGTACCTATTCCTGTCATTTTGGCCCGC
781  ............+............+............+............+............+............+ 840
     CGTTTGGCGTCCCACCGCCGCCGCCGCCGCCACCATGGATAAGGACAGTAAAACCGGGCG
c     K  P  Q  G  G  G  G  G  G  G  G  T  Y  S  C  H  F  G  P  L -

BamHI
                                            |
     TGACCTGGGTATGTAAGCCACAAGGGGGTTAATCTCGAGGATCC
841  ............+............+............+............ 884
     ACTGGACCCATACATTCGGTGTTCCCCAATTAGAGCTCCTAGG
c     T  W  V  C  K  P  Q  G  G  *
```

FIG. 17A

[AatII sticky end]  5'    GCGTAACGTATGCATGGTCTCC-
(position #4358 in pAMG21)  3' TGCACGCATTGCATACGTACCAGAGG- -CCATGCGAGAGTAGGGAACTGCCAGGCATCAAATAAAACGAAAGGCTCAGTCGAAAGACT-
-GGTACGCTCTCATCCCTTGACGGTCCGTAGTTTATTTTGCTTTCCGAGTCAGCTTTCTGA- -GGGCCTTTCGTTTTATCTGTTGTTTGTCGGTGAACGCTCTCCTGAGTAGGACAAATCCGC-
-CCCGGAAAGCAAAATAGACAACAAACAGCCACTTGCGAGAGGACTCATCCTGTTTAGGCG- -CGGGAGCGGATTTGAACGTTGCGAAGCAACGGCCCGGAGGGTGGCGGGCAGGACGCCCGC-
-GCCCTCGCCTAAACTTGCAACGCTTCGTTGCCGGGCCTCCCACCGCCCGTCCTGCGGGCG- -CATAAACTGCCAGGCATCAAATTAAGCAGAAGGCCATCCTGACGGATGGCCTTTTTGCGT-
-GTATTTGACGGTCCGTAGTTTAATTCGTCTTCCGGTAGGACTGCCTACCGGAAAAACGCA- AatII
-TTCTACAAACTCTTTTGTTTATTTTTCTAAATACATTCAAATATGGACGTCGTACTTAAC-
-AAGATGTTTGAGAAAACAAATAAAAGATTTATGTAAGTTTATACCTGCAGCATGAATTG- -TTTTAAAGTATGGGCAATCAATTGCTCCTGTTAAAATTGCTTTAGAAATACTTTGGCAGC-
-AAAATTTCATACCCGTTAGTTAACGAGGACAATTTTAACGAAATCTTTATGAAACCGTCG- -GGTTTGTTGTATTGAGTTTCATTTGCGCATTGGTTAAATGGAAAGTGACCGTGCGCTTAC-
-CCAAACAACATAACTCAAAGTAAACGCGTAACCAATTTACCTTTCACTGGCACGCGAATG- -TACAGCCTAATATTTTGAAATATCCCAAGAGCTTTTTCCTTCGCATGCCCACGCTAAAC-
-ATGTCGGATTATAAAACTTTATAGGGTTCTCGAAAAAGGAAGCGTACGGGTGCGATTTG- -ATTCTTTTTCTCTTTTGGTTAAATCGTTGTTTGATTTATTATTTGCTATATTTATTTTTC-
-TAAGAAAAGAGAAAACCAATTTAGCAACAAACTAAATAATAAACGATATAAATAAAAAG- -GATAATTATCAACTAGAGAAGGAACAATTAATGGTATGTTCATACACGCATGTAAAAATA-
-CTATTAATAGTTGATCTCTTCCTTGTTAATTACCATACAAGTATGTGCGTACATTTTTAT- -AACTATCTATATAGTTGTCTTTCTCTGAATGTGCAAAACTAAGCATTCCGAAGCCATTAT-
-TTGATAGATATATCAACAGAAAGAGACTTACACGTTTTGATTCGTAAGGCTTCGGTAATA- -TAGCAGTATGAATAGGGAAACTAAACCCAGTGATAAGACCTGATGATTTCGCTTCTTTAA-
-ATCGTCATACTTATCCCTTTGATTTGGGTCACTATTCTGGACTACTAAAGCGAAGAAATT- -TTACATTTGGAGATTTTTTATTTACAGCATTGTTTTCAAATATATTCCAATTAATCGGTG-
-AATGTAAACCTCTAAAAAATAAATGTCGTAACAAAAGTTTATATAAGGTTAATTAGCCAC- -AATGATTGGAGTTAGAATAATCTACTATAGGATCATATTTTATTAAATTAGCGTCATCAT-
-TTACTAACCTCAATCTTATTAGATGATATCCTAGTATAAAATAATTTAATCGCAGTAGTA- -AATATTGCCTCCATTTTTTAGGGTAATTATCCAGAATTGAAATATCAGATTTAACCATAG-
-TTATAACGGAGGTAAAAAATCCCATTAATAGGTCTTAACTTTATAGTCTAAATTGGTATC- -AATGAGGATAAATGATCGCGAGTAAATAATATTCACAATGTACCATTTTAGTCATATCAG-
-TTACTCCTATTTACTAGCGCTCATTTATTATAAGTGTTACATGGTAAAATCAGTATAGTC- -ATAAGCATTGATTAATATCATTATTGCTTCTACAGGCTTTAATTTTATTAATTATTCTGT-
-TATTCGTAACTAATTATAGTAATAACGAAGATGTCCGAAATTAAAATAATTAATAAGACA- -AAGTGTCGTCGGCATTTATGTCTTTCATACCCATCTCTTTATCCTTACCTATTGTTTGTC-
-TTCACAGCAGCCGTAAATACAGAAAGTATGGGTAGAGAAATAGGAATGGATAACAAACAG- -GCAAGTTTTGCGTGTTATATATCATTAAAACGGTAATAGATTGACATTTGATTCTAATAA-
-CGTTCAAAACGCACAATATATAGTAATTTTGCCATTATCTAACTGTAAACTAAGATTATT-

FIG. 17B

```
-ATTGGATTTTTGTCACACTATTATATCGCTTGAAATACAATTGTTTAACATAAGTACCTG-
-TAACCTAAAAACAGTGTGATAATATAGCGAACTTTATGTTAACAAATTGTATTCATGGAC-

-TAGGATCGTACAGGTTTACGCAAGAAAATGGTTTGTTATAGTCGATTAATCGATTTGATT-
-ATCCTAGCATGTCCAAATGCGTTCTTTTACCAAACAATATCAGCTAATTAGCTAAACTAA-

-CTAGATTTGTTTTAACTAATTAAAGGAGGAATAACATATGGTTAACGCGTTGGAATTCGA-
-GATCTAAACAAAATTGATTAATTTCCTCCTTATTGTATACCAATTGCGCAACCTTAAGCT-
                                                         SacII
-GCTCACTAGTGTCGACCTGCAGGGTACCATGGAAGCTTACTCGAGGATCCGCGGAAAGAA-
-CGAGTGATCACAGCTGGACGTCCCATGGTACCTTCGAATGAGCTCCTAGGCGCCTTTCTT-

-GAAGAAGAAGAAGAAAGCCCGAAAGGAAGCTGAGTTGGCTGCTGCCACCGCTGAGCAATA-
-CTTCTTCTTCTTTCGGGCTTTCCTTCGACTCAACCGACGACGGTGGCGACTCGTTAT-

-ACTAGCATAACCCCTTGGGGCCTCTAAACGGGTCTTGAGGGGTTTTTTGCTGAAAGGAGG-
-TGATCGTATTGGGGAACCCCGGAGATTTGCCCAGAACTCCCCAAAAAACGACTTTCCTCC-

-AACCGCTCTTCACGCTCTTCACGC 3'         [SacII sticky end]
-TTGGCGAGAAGTGCGAGAAGTG   5'         (position #5904 in pAMG21)
```

FIG. 19A

NdeI

```
     CATATGGACAAAACTCACACATGTCCACCTTGTCCAGCTCCGGAACTCCTGGGGGGACCG
  1  ------------+---------+---------+---------+---------+---------+ 60
     GTATACCTGTTTTGAGTGTGTACAGGTGGAACAGGTCGAGGCCTTGAGGACCCCCCTGGC
``` a      M   D   K   T   H   T   C   P   P   C   P   A   P   E   L   L   G   G   P   -

```
     TCAGTCTTCCTCTTCCCCCCAAAACCCAAGGACACCCTCATGATCTCCCGGACCCCTGAG
  61 ------------+---------+---------+---------+---------+---------+ 120
     AGTCAGAAGGAGAAGGGGGGTTTTGGGTTCCTGTGGGAGTACTAGAGGGCCTGGGGACTC
``` a      S   V   F   L   F   P   P   K   P   K   D   T   L   M   I   S   R   T   P   E   -

```
     GTCACATGCGTGGTGGTGGACGTGAGCCACGAAGACCCTGAGGTCAAGTTCAACTGGTAC
 121 ------------+---------+---------+---------+---------+---------+ 180
     CAGTGTACGCACCACCACCTGCACTCGGTGCTTCTGGGACTCCAGTTCAAGTTGACCATG
``` a      V   T   C   V   V   V   D   V   S   H   E   D   P   E   V   K   F   N   W   Y   -

```
     GTGGACGGCGTGGAGGTGCATAATGCCAAGACAAAGCCGCGGGAGGAGCAGTACAACAGC
 181 ------------+---------+---------+---------+---------+---------+ 240
     CACCTGCCGCACCTCCACGTATTACGGTTCTGTTTCGGCGCCCTCCTCGTCATGTTGTCG
``` a      V   D   G   V   E   V   H   N   A   K   T   K   P   R   E   E   Q   Y   N   S   -

```
     ACGTACCGTGTGGTCAGCGTCCTCACCGTCCTGCACCAGGACTGGCTGAATGGCAAGGAG
 241 ------------+---------+---------+---------+---------+---------+ 300
     TGCATGGCACACCAGTCGCAGGAGTGGCAGGACGTGGTCCTGACCGACTTACCGTTCCTC
``` a      T   Y   R   V   V   S   V   L   T   V   L   H   Q   D   W   L   N   G   K   E   -

```
     TACAAGTGCAAGGTCTCCAACAAAGCCCTCCCAGCCCCCATCGAGAAAACCATCTCCAAA
 301 ------------+---------+---------+---------+---------+---------+ 360
     ATGTTCACGTTCCAGAGGTTGTTTCGGGAGGGTCGGGGGTAGCTCTTTTGGTAGAGGTTT
``` a      Y   K   C   K   V   S   N   K   A   L   P   A   P   I   E   K   T   I   S   K   -

```
     GCCAAAGGGCAGCCCCGAGAACCACAGGTGTACACCCTGCCCCCATCCCGGGATGAGCTG
 361 ------------+---------+---------+---------+---------+---------+ 420
     CGGTTTCCCGTCGGGGCTCTTGGTGTCCACATGTGGGACGGGGGTAGGGCCCTACTCGAC
``` a      A   K   G   Q   P   R   E   P   Q   V   Y   T   L   P   P   S   R   D   E   L   -

```
     ACCAAGAACCAGGTCAGCCTGACCTGCCTGGTCAAAGGCTTCTATCCCAGCGACATCGCC
 421 ------------+---------+---------+---------+---------+---------+ 480
     TGGTTCTTGGTCCAGTCGGACTGGACGGACCAGTTTCCGAAGATAGGGTCGCTGTAGCGG
``` a      T   K   N   Q   V   S   L   T   C   L   V   K   G   F   Y   P   S   D   I   A   -

```
     GTGGAGTGGGAGAGCAATGGGCAGCCGGAGAACAACTACAAGACCACGCCTCCCGTGCTG
 481 ------------+---------+---------+---------+---------+---------+ 540
     CACCTCACCCTCTCGTTACCCGTCGGCCTCTTGTTGATGTTCTGGTGCGGAGGGCACGAC
``` a      V   E   W   E   S   N   G   Q   P   E   N   N   Y   K   T   T   P   P   V   L   -

```
     GACTCCGACGGCTCCTTCTTCCTCTACAGCAAGCTCACCGTGGACAAGAGCAGGTGGCAG
 541 ------------+---------+---------+---------+---------+---------+ 600
     CTGAGGCTGCCGAGGAAGAAGGAGATGTCGTTCGAGTGGCACCTGTTCTCGTCCACCGTC
``` a      D   S   D   G   S   F   F   L   Y   S   K   L   T   V   D   K   S   R   W   Q   -

FIG. 19B

```
     CAGGGGAACGTCTTCTCATGCTCCGTGATGCATGAGGCTCTGCACAACCACTACACGCAG
601  ------------+---------+---------+---------+---------+---------+  660
     GTCCCCTTGCAGAAGAGTACGAGGCACTACGTACTCCGAGACGTGTTGGTGATGTGCGTC
``` a      Q   G   N   V   F   S   C   S   V   M   H   E   A   L   H   N   H   Y   T   Q   -

```
     AAGAGCCTCTCCCTGTCTCCGGGTAAAGGTGGAGGTGGTGGTGACTTCCTGCCGCACTAC
661  ------------+---------+---------+---------+---------+---------+  720
     TTCTCGGAGAGGGACAGAGGCCCATTTCCACCTCCACCACCACTGAAGGACGGCGTGATG
``` a      K   S   L   S   L   S   P   G   K   G   G   G   G   D   F   L   P   H   Y   -

```
                                          BamHI
                                            |
     AAAAACACCTCTCTGGGTCACCGTCCGTAATGGATCC
721  ------------+---------+--------+------  757
     TTTTTGTGGAGAGACCCAGTGGCAGGCATTACCTAGG
``` a      K   N   T   S   L   G   H   R   P   *

FIG. 20A

```
     NdeI
     |
     CATATGGACTTCCTGCCGCACTACAAAAACACCTCTCTGGGTCACCGTCCGGGTGGAGGC
  1  --------+---------+---------+---------+---------+---------+  60
     GTATACCTGAAGGACGGCGTGATGTTTTTGTGGAGAGACCCAGTGGCAGGCCCACCTCCG a      M  D  F  L  P  H  Y  K  N  T  S  L  G  H  R  P  G  G  G    -

GGTGGGGACAAAACTCACACATGTCCACCTTGCCCAGCACCTGAACTCCTGGGGGGACCG
 61  --------+---------+---------+---------+---------+---------+  120
     CCACCCCTGTTTTGAGTGTGTACAGGTGGAACGGGTCGTGGACTTGAGGACCCCCCTGGC a      G  G  D  K  T  H  T  C  P  P  C  P  A  P  E  L  L  G  G  P  -

TCAGTTTTCCTCTTCCCCCCAAAACCCAAGGACACCCTCATGATCTCCCGGACCCCTGAG
121  --------+---------+---------+---------+---------+---------+  180
     AGTCAAAAGGAGAAGGGGGGTTTTGGGTTCCTGTGGGAGTACTAGAGGGCCTGGGGACTC a      S  V  F  L  F  P  P  K  P  K  D  T  L  M  I  S  R  T  P  E  -

GTCACATGCGTGGTGGTGGACGTGAGCCACGAAGACCCTGAGGTCAAGTTCAACTGGTAC
181  --------+---------+---------+---------+---------+---------+  240
     CAGTGTACGCACCACCACCTGCACTCGGTGCTTCTGGGACTCCAGTTCAAGTTGACCATG a      V  T  C  V  V  V  D  V  S  H  E  D  P  E  V  K  F  N  W  Y  -

GTGGACGGCGTGGAGGTGCATAATGCCAAGACAAAGCCGCGGGAGGAGCAGTACAACAGC
241  --------+---------+---------+---------+---------+---------+  300
     CACCTGCCGCACCTCCACGTATTACGGTTCTGTTTCGGCGCCCTCCTCGTCATGTTGTCG a      V  D  G  V  E  V  H  N  A  K  T  K  P  R  E  E  Q  Y  N  S  -

ACGTACCGTGTGGTCAGCGTCCTCACCGTCCTGCACCAGGACTGGCTGAATGGCAAGGAG
301  --------+---------+---------+---------+---------+---------+  360
     TGCATGGCACACCAGTCGCAGGAGTGGCAGGACGTGGTCCTGACCGACTTACCGTTCCTC a      T  Y  R  V  V  S  V  L  T  V  L  H  Q  D  W  L  N  G  K  E  -

TACAAGTGCAAGGTCTCCAACAAAGCCCTCCCAGCCCCCATCGAGAAAACCATCTCCAAA
361  --------+---------+---------+---------+---------+---------+  420
     ATGTTCACGTTCCAGAGGTTGTTTCGGGAGGGTCGGGGGTAGCTCTTTTGGTAGAGGTTT a      Y  K  C  K  V  S  N  K  A  L  P  A  P  I  E  K  T  I  S  K  -

GCCAAAGGGCAGCCCCGAGAACCACAGGTGTACACCCTGCCCCCATCCCGGGATGAGCTG
421  --------+---------+---------+---------+---------+---------+  480
     CGGTTTCCCGTCGGGGCTCTTGGTGTCCACATGTGGGACGGGGGTAGGGCCCTACTCGAC a      A  K  G  Q  P  R  E  P  Q  V  Y  T  L  P  P  S  R  D  E  L  -

ACCAAGAACCAGGTCAGCCTGACCTGCCTGGTCAAAGGCTTCTATCCCAGCGACATCGCC
481  --------+---------+---------+---------+---------+---------+  540
     TGGTTCTTGGTCCAGTCGGACTGGACGGACCAGTTTCCGAAGATAGGGTCGCTGTAGCGG a      T  K  N  Q  V  S  L  T  C  L  V  K  G  F  Y  P  S  D  I  A  -

GTGGAGTGGGAGAGCAATGGGCAGCCGGAGAACAACTACAAGACCACGCCTCCCGTGCTG
541  --------+---------+---------+---------+---------+---------+  600
     CACCTCACCCTCTCGTTACCCGTCGGCCTCTTGTTGATGTTCTGGTGCGGAGGGCACGAC a      V  E  W  E  S  N  G  Q  P  E  N  N  Y  K  T  T  P  P  V  L  -
```

FIG. 20B

```
        GACTCCGACGGCTCCTTCTTCCTCTACAGCAAGCTCACCGTGGACAAGAGCAGGTGGCAG
    601 --------+---------+---------+---------+---------+---------+ 660
        CTGAGGCTGCCGAGGAAGAAGGAGATGTCGTTCGAGTGGCACCTGTTCTCGTCCACCGTC a        D   S   D   G   S   F   F   L   Y   S   K   L   T   V   D   K   S   R   W   Q   -

CAGGGGAACGTCTTCTCATGCTCCGTGATGCATGAGGCTCTGCACAACCACTACACGCAG
    661 --------+---------+---------+---------+---------+---------+ 720
        GTCCCCTTGCAGAAGAGTACGAGGCACTACGTACTCCGAGACGTGTTGGTGATGTGCGTC a        Q   G   N   V   F   S   C   S   V   M   H   E   A   L   H   N   H   Y   T   Q   -

BamHI
                                           |
        AAGAGCCTCTCCCTGTCTCCGGGTAAATAATGGATCCGCGG
    721 --------+---------+---------+---------+-- 761
        TTCTCGGAGAGGGACAGAGGCCCATTTATTACCTAGGCGCC a        K   S   L   S   L   S   P   G   K   *
```

FIG. 21A

```
    NdeI
    |
    CATATGGACAAAACTCACACATGTCCACCTTGTCCAGCTCCGGAACTCCTGGGGGGACCG
  1 ----------+---------+---------+---------+---------+---------+ 60
    GTATACCTGTTTTGAGTGTGTACAGGTGGAACAGGTCGAGGCCTTGAGGACCCCCCTGGC a       M  D  K  T  H  T  C  P  P  C  P  A  P  E  L  L  G  G  P  -

TCAGTCTTCCTCTTCCCCCCAAAACCCAAGGACACCCTCATGATCTCCCGGACCCCTGAG
 61 ----------+---------+---------+---------+---------+---------+ 120
    AGTCAGAAGGAGAAGGGGGGTTTTGGGTTCCTGTGGGAGTACTAGAGGGCCTGGGGACTC a       S  V  F  L  F  P  P  K  P  K  D  T  L  M  I  S  R  T  P  E  -

GTCACATGCGTGGTGGTGGACGTGAGCCACGAAGACCCTGAGGTCAAGTTCAACTGGTAC
121 ----------+---------+---------+---------+---------+---------+ 180
    CAGTGTACGCACCACCACCTGCACTCGGTGCTTCTGGGACTCCAGTTCAAGTTGACCATG a       V  T  C  V  V  V  D  V  S  H  E  D  P  E  V  K  F  N  W  Y  -

GTGGACGGCGTGGAGGTGCATAATGCCAAGACAAAGCCGCGGGAGGAGCAGTACAACAGC
181 ----------+---------+---------+---------+---------+---------+ 240
    CACCTGCCGCACCTCCACGTATTACGGTTCTGTTTCGGCGCCCTCCTCGTCATGTTGTCG a       V  D  G  V  E  V  H  N  A  K  T  K  P  R  E  E  Q  Y  N  S  -

ACGTACCGTGTGGTCAGCGTCCTCACCGTCCTGCACCAGGACTGGCTGAATGGCAAGGAG
241 ----------+---------+---------+---------+---------+---------+ 300
    TGCATGGCACACCAGTCGCAGGAGTGGCAGGACGTGGTCCTGACCGACTTACCGTTCCTC a       T  Y  R  V  V  S  V  L  T  V  L  H  Q  D  W  L  N  G  K  E  -

TACAAGTGCAAGGTCTCCAACAAAGCCCTCCCAGCCCCCATCGAGAAAACCATCTCCAAA
301 ----------+---------+---------+---------+---------+---------+ 360
    ATGTTCACGTTCCAGAGGTTGTTTCGGGAGGGTCGGGGGTAGCTCTTTTGGTAGAGGTTT a       Y  K  C  K  V  S  N  K  A  L  P  A  P  I  E  K  T  I  S  K  -

GCCAAAGGGCAGCCCCGAGAACCACAGGTGTACACCCTGCCCCCATCCCGGGATGAGCTG
361 ----------+---------+---------+---------+---------+---------+ 420
    CGGTTTCCCGTCGGGGCTCTTGGTGTCCACATGTGGGACGGGGGTAGGGCCCTACTCGAC a       A  K  G  Q  P  R  E  P  Q  V  Y  T  L  P  P  S  R  D  E  L  -

ACCAAGAACCAGGTCAGCCTGACCTGCCTGGTCAAAGGCTTCTATCCCAGCGACATCGCC
421 ----------+---------+---------+---------+---------+---------+ 480
    TGGTTCTTGGTCCAGTCGGACTGGACGGACCAGTTTCCGAAGATAGGGTCGCTGTAGCGG a       T  K  N  Q  V  S  L  T  C  L  V  K  G  F  Y  P  S  D  I  A  -

GTGGAGTGGGAGAGCAATGGGCAGCCGGAGAACAACTACAAGACCACGCCTCCCGTGCTG
481 ----------+---------+---------+---------+---------+---------+ 540
    CACCTCACCCTCTCGTTACCCGTCGGCCTCTTGTTGATGTTCTGGTGCGGAGGGCACGAC a       V  E  W  E  S  N  G  Q  P  E  N  N  Y  K  T  T  P  P  V  L  -

GACTCCGACGGCTCCTTCTTCCTCTACAGCAAGCTCACCGTGGACAAGAGCAGGTGGCAG
541 ----------+---------+---------+---------+---------+---------+ 600
    CTGAGGCTGCCGAGGAAGAAGGAGATGTCGTTCGAGTGGCACCTGTTCTCGTCCACCGTC a       D  S  D  G  S  F  F  L  Y  S  K  L  T  V  D  K  S  R  W  Q  -
```

FIG. 21B

```
        CAGGGGAACGTCTTCTCATGCTCCGTGATGCATGAGGCTCTGCACAACCACTACACGCAG
    601 ---------+---------+---------+---------+---------+---------+ 660
        GTCCCCTTGCAGAAGAGTACGAGGCACTACGTACTCCGAGACGTGTTGGTGATGTGCGTC a          Q  G  N  V  F  S  C  S  V  M  H  E  A  L  H  N  H  Y  T  Q   -

AAGAGCCTCTCCCTGTCTCCGGGTAAAGGTGGAGGTGGTGGTTTCGAATGGACCCCGGGT
    661 ---------+---------+---------+---------+---------+---------+ 720
        TTCTCGGAGAGGGACAGAGGCCCATTTCCACCTCCACCACCAAAGCTTACCTGGGGCCCA a          K  S  L  S  L  S  P  G  K  G  G  G  G  F  E  W  T  P  G   -

BamHI
                                              |
        TACTGGCAGCCGTACGCTCTGCCGCTGTAATGGATCCCTCGAG
    721 ---------+---------+---------+---------+--- 763
        ATGACCGTCGGCATGCGAGACGGCGACATTACCTAGGGAGCTC a          Y  W  Q  P  Y  A  L  P  L  *
```

FIG. 22A

```
     NdeI
     |
     CATATGTTCGAATGGACCCCGGGTTACTGGCAGCCGTACGCTCTGCCGCTGGGTGGAGGC
  1  ---------+---------+---------+---------+---------+---------+  60
     GTATACAAGCTTACCTGGGGCCCAATGACCGTCGGCATGCGAGACGGCGACCCACCTCCG a        M  F  E  W  T  P  G  Y  W  Q  P  Y  A  L  P  L  G  G  G   -

GGTGGGGACAAAACTCACACATGTCCACCTTGCCCAGCACCTGAACTCCTGGGGGGACCG
 61  ---------+---------+---------+---------+---------+---------+ 120
     CCACCCCTGTTTTGAGTGTGTACAGGTGGAACGGGTCGTGGACTTGAGGACCCCCCTGGC a        G  G  D  K  T  H  T  C  P  P  C  P  A  P  E  L  L  G  G  P   -

TCAGTTTTCCTCTTCCCCCCAAAACCCAAGGACACCCTCATGATCTCCCGGACCCCTGAG
121  ---------+---------+---------+---------+---------+---------+ 180
     AGTCAAAAGGAGAAGGGGGGTTTTGGGTTCCTGTGGGAGTACTAGAGGGCCTGGGGACTC a        S  V  F  L  F  P  P  K  P  K  D  T  L  M  I  S  R  T  P  E   -

GTCACATGCGTGGTGGTGGACGTGAGCCACGAAGACCCTGAGGTCAAGTTCAACTGGTAC
181  ---------+---------+---------+---------+---------+---------+ 240
     CAGTGTACGCACCACCACCTGCACTCGGTGCTTCTGGGACTCCAGTTCAAGTTGACCATG a        V  T  C  V  V  V  D  V  S  H  E  D  P  E  V  K  F  N  W  Y   -

GTGGACGGCGTGGAGGTGCATAATGCCAAGACAAAGCCGCGGGAGGAGCAGTACAACAGC
241  ---------+---------+---------+---------+---------+---------+ 300
     CACCTGCCGCACCTCCACGTATTACGGTTCTGTTTCGGCGCCCTCCTCGTCATGTTGTCG a        V  D  G  V  E  V  H  N  A  K  T  K  P  R  E  E  Q  Y  N  S   -

ACGTACCGTGTGGTCAGCGTCCTCACCGTCCTGCACCAGGACTGGCTGAATGGCAAGGAG
301  ---------+---------+---------+---------+---------+---------+ 360
     TGCATGGCACACCAGTCGCAGGAGTGGCAGGACGTGGTCCTGACCGACTTACCGTTCCTC a        T  Y  R  V  V  S  V  L  T  V  L  H  Q  D  W  L  N  G  K  E   -

TACAAGTGCAAGGTCTCCAACAAAGCCCTCCCAGCCCCCATCGAGAAAACCATCTCCAAA
361  ---------+---------+---------+---------+---------+---------+ 420
     ATGTTCACGTTCCAGAGGTTGTTTCGGGAGGGTCGGGGGTAGCTCTTTTGGTAGAGGTTT a        Y  K  C  K  V  S  N  K  A  L  P  A  P  I  E  K  T  I  S  K   -

GCCAAAGGGCAGCCCCGAGAACCACAGGTGTACACCCTGCCCCCATCCCGGGATGAGCTG
421  ---------+---------+---------+---------+---------+---------+ 480
     CGGTTTCCCGTCGGGGCTCTTGGTGTCCACATGTGGGACGGGGGTAGGGCCCTACTCGAC a        A  K  G  Q  P  R  E  P  Q  V  Y  T  L  P  P  S  R  D  E  L   -

ACCAAGAACCAGGTCAGCCTGACCTGCCTGGTCAAAGGCTTCTATCCCAGCGACATCGCC
481  ---------+---------+---------+---------+---------+---------+ 540
     TGGTTCTTGGTCCAGTCGGACTGGACGGACCAGTTTCCGAAGATAGGGTCGCTGTAGCGG a        T  K  N  Q  V  S  L  T  C  L  V  K  G  F  Y  P  S  D  I  A   -

GTGGAGTGGGAGAGCAATGGGCAGCCGGAGAACAACTACAAGACCACGCCTCCCGTGCTG
541  ---------+---------+---------+---------+---------+---------+ 600
     CACCTCACCCTCTCGTTACCCGTCGGCCTCTTGTTGATGTTCTGGTGCGGAGGGCACGAC a        V  E  W  E  S  N  G  Q  P  E  N  N  Y  K  T  T  P  P  V  L   -
```

FIG. 22B

```
        GACTCCGACGGCTCCTTCTTCCTCTACAGCAAGCTCACCGTGGACAAGAGCAGGTGGCAG
    601 --------+---------+---------+---------+---------+---------+ 660
        CTGAGGCTGCCGAGGAAGAAGGAGATGTCGTTCGAGTGGCACCTGTTCTCGTCCACCGTC a        D  S  D  G  S  F  F  L  Y  S  K  L  T  V  D  K  S  R  W  Q  -

CAGGGGAACGTCTTCTCATGCTCCGTGATGCATGAGGCTCTGCACAACCACTACACGCAG
    661 --------+---------+---------+---------+---------+---------+ 720
        GTCCCCTTGCAGAAGAGTACGAGGCACTACGTACTCCGAGACGTGTTGGTGATGTGCGTC a        Q  G  N  V  F  S  C  S  V  M  H  E  A  L  H  N  H  Y  T  Q  -

BamHI
                                         |
        AAGAGCCTCTCCCTGTCTCCGGGTAAATAATGGATCC
    721 --------+---------+---------+------- 757
        TTCTCGGAGAGGGACAGAGGCCCATTTATTACCTAGG a        K  S  L  S  L  S  P  G  K  *
```

FIG. 23A

```
      NdeI
       |
       CATATGGACAAAACTCACACATGTCCACCGTGCCCAGCACCTGAACTCCTGGGGGACCG
    1  ------------+------------+------------+------------+------------+  60
       GTATACCTGTTTTGAGTGTGTACAGGTGGCACGGGTCGTGGACTTGAGGACCCCCCTGGC a            M  D  K  T  H  T  C  P  P  C  P  A  P  E  L  L  G  G  P  -

TCAGTTTTCCTCTTCCCCCCAAAACCCAAGGACACCCTCATGATCTCCCGGACCCCTGAG
   61  ------------+------------+------------+------------+------------+  120
       AGTCAAAAGGAGAAGGGGGGTTTTGGGTTCCTGTGGGAGTACTAGAGGGCCTGGGGACTC a         S  V  F  L  F  P  P  K  P  K  D  T  L  M  I  S  R  T  P  E. -

GTCACATGCGTGGTGGTGGACGTGAGCCACGAAGACCCTGAGGTCAAGTTCAACTGGTAC
  121  ------------+------------+------------+------------+------------+  180
       CAGTGTACGCACCACCACCTGCACTCGGTGCTTCTGGGACTCCAGTTCAAGTTGACCATG a         V  T  C  V  V  V  D  V  S  H  E  D  P  E  V  K  F  N  W  Y  -

GTGGACGGCGTGGAGGTGCATAATGCCAAGACAAAGCCGCGGGAGGAGCAGTACAACAGC
  181  ------------+------------+------------+------------+------------+  240
       CACCTGCCGCACCTCCACGTATTACGGTTCTGTTTCGGCGCCCTCCTCGTCATGTTGTCG a         V  D  G  V  E  V  H  N  A  K  T  K  P  R  E  E  Q  Y  N  S  -

ACGTACCGTGTGGTCAGCGTCCTCACCGTCCTGCACCAGGACTGGCTGAATGGCAAGGAG
  241  ------------+------------+------------+------------+------------+  300
       TGCATGGCACACCAGTCGCAGGAGTGGCAGGACGTGGTCCTGACCGACTTACCGTTCCTC a         T  Y  R  V  V  S  V  L  T  V  L  H  Q  D  W  L  N  G  K  E  -

TACAAGTGCAAGGTCTCCAACAAAGCCCTCCCAGCCCCCATCGAGAAAACCATCTCCAAA
  301  ------------+------------+------------+------------+------------+  360
       ATGTTCACGTTCCAGAGGTTGTTTCGGGAGGGTCGGGGGTAGCTCTTTTGGTAGAGGTTT a         Y  K  C  K  V  S  N  K  A  L  P  A  P  I  E  K  T  I  S  K  -

GCCAAAGGGCAGCCCCGAGAACCACAGGTGTACACCCTGCCCCCATCCCGGGATGAGCTG
  361  ------------+------------+------------+------------+------------+  420
       CGGTTTCCCGTCGGGGCTCTTGGTGTCCACATGTGGGACGGGGGTAGGGCCCTACTCGAC a         A  K  G  Q  P  R  E  P  Q  V  Y  T  L  P  P  S  R  D  E  L  -

ACCAAGAACCAGGTCAGCCTGACCTGCCTGGTCAAAGGCTTCTATCCCAGCGACATCGCC
  421  ------------+------------+------------+------------+------------+  480
       TGGTTCTTGGTCCAGTCGGACTGGACGGACCAGTTTCCGAAGATAGGGTCGCTGTAGCGG a         T  K  N  Q  V  S  L  T  C  L  V  K  G  F  Y  P  S  D  I  A  -

GTGGAGTGGGAGAGCAATGGGCAGCCGGAGAACAACTACAAGACCACGCCTCCCGTGCTG
  481  ------------+------------+------------+------------+------------+  540
       CACCTCACCCTCTCGTTACCCGTCGGCCTCTTGTTGATGTTCTGGTGCGGAGGGCACGAC a         V  E  W  E  S  N  G  Q  P  E  N  N  Y  K  T  T  P  P  V  L  -

GACTCCGACGGCTCCTTCTTCCTCTACAGCAAGCTCACCGTGGACAAGAGCAGGTGGCAG
  541  ------------+------------+------------+------------+------------+  600
       CTGAGGCTGCCGAGGAAGAAGGAGATGTCGTTCGAGTGGCACCTGTTCTCGTCCACCGTC a         D  S  D  G  S  F  F  L  Y  S  K  L  T  V  D  K  S  R  W  Q  -
```

FIG. 23B

```
        CAGGGGAACGTCTTCTCATGCTCCGTGATGCATGAGGCTCTGCACAACCACTACACGCAG
   601  ------+---------+---------+---------+---------+---------+ 660
        GTCCCCTTGCAGAAGAGTACGAGGCACTACGTACTCCGAGACGTGTTGGTGATGTGCGTC a        Q  G  N  V  F  S  C  S  V  M  H  E  A  L  H  N  H  Y  T  Q

AAGAGCCTCTCCCTGTCTCCGGGTAAAGGTGGTGGTGGTGGTGTTGAACCGAACTGTGAC
   661  ------+---------+---------+---------+---------+---------+ 720
        TTCTCGGAGAGGGACAGAGGCCCATTTCCACCACCACCACCACAACTTGGCTTGACACTG a        K  S  L  S  L  S  P  G  K  G  G  G  G  V  E  P  N  C  D

BamHI
                                                          |
        ATCCATGTTATGTGGGAATGGGAATGTTTTGAACGTCTGTAACTCGAGGATCC
   721  ------+---------+---------+---------+---------+---    773
        TAGGTACAATACACCCTTACCCTTACAAAACTTGCAGACATTGAGCTCCTAGG a        I  H  V  M  W  E  W  E  C  F  E  R  L  *
```

FIG. 24A

```
     NdeI
      |
     CATATGGTTGAACCGAACTGTGACATCCATGTTATGTGGGAATGGGAATGTTTTGAACGT
  1  ---------+---------+---------+---------+---------+---------+  60
     GTATACCAACTTGGCTTGACACTGTAGGTACAATACACCCTTACCCTTACAAAACTTGCA a       M  V  E  P  N  C  D  I  H  V  M  W  E  W  E  C  F  E  R   -

CTGGGTGGTGGTGGTGGTGACAAAACTCACACATGTCCACCGTGCCCAGCACCTGAACTC
 61  ---------+---------+---------+---------+---------+---------+ 120
     GACCCACCACCACCACCACTGTTTTGAGTGTGTACAGGTGGCACGGGTCGTGGACTTGAG a       L  G  G  G  G  D  K  T  H  T  C  P  P  C  P  A  P  E  L   -

CTGGGGGGACCGTCAGTTTTCCTCTTCCCCCCAAAACCCAAGGACACCCTCATGATCTCC
121  ---------+---------+---------+---------+---------+---------+ 180
     GACCCCCCTGGCAGTCAAAAGGAGAAGGGGGGTTTTGGGTTCCTGTGGGAGTACTAGAGG a       L  G  G  P  S  V  F  L  F  P  P  K  P  K  D  T  L  M  I  S  -

CGGACCCCTGAGGTCACATGCGTGGTGGTGGACGTGAGCCACGAAGACCCTGAGGTCAAG
181  ---------+---------+---------+---------+---------+---------+ 240
     GCCTGGGGACTCCAGTGTACGCACCACCACCTGCACTCGGTGCTTCTGGGACTCCAGTTC a       R  T  P  E  V  T  C  V  V  V  D  V  S  H  E  D  P  E  V  K  -

TTCAACTGGTACGTGGACGGCGTGGAGGTGCATAATGCCAAGACAAAGCCGCGGGAGGAG
241  ---------+---------+---------+---------+---------+---------+ 300
     AAGTTGACCATGCACCTGCCGCACCTCCACGTATTACGGTTCTGTTTCGGCGCCCTCCTC a       F  N  W  Y  V  D  G  V  E  V  H  N  A  K  T  K  P  R  E  E  -

CAGTACAACAGCACGTACCGTGTGGTCAGCGTCCTCACCGTCCTGCACCAGGACTGGCTG
301  ---------+---------+---------+---------+---------+---------+ 360
     GTCATGTTGTCGTGCATGGCACACCAGTCGCAGGAGTGGCAGGACGTGGTCCTGACCGAC a       Q  Y  N  S  T  Y  R  V  V  S  V  L  T  V  L  H  Q  D  W  L  -

AATGGCAAGGAGTACAAGTGCAAGGTCTCCAACAAAGCCCTCCCAGCCCCCATCGAGAAA
361  ---------+---------+---------+---------+---------+---------+ 420
     TTACCGTTCCTCATGTTCACGTTCCAGAGGTTGTTTCGGGAGGGTCGGGGGTAGCTCTTT a       N  G  K  E  Y  K  C  K  V  S  N  K  A  L  P  A  P  I  E  K  -

ACCATCTCCAAAGCCAAAGGGCAGCCCCGAGAACCACAGGTGTACACCCTGCCCCCATCC
421  ---------+---------+---------+---------+---------+---------+ 480
     TGGTAGAGGTTTCGGTTTCCCGTCGGGGCTCTTGGTGTCCACATGTGGGACGGGGGTAGG a       T  I  S  K  A  K  G  Q  P  R  E  P  Q  V  Y  T  L  P  P  S  -

CGGGATGAGCTGACCAAGAACCAGGTCAGCCTGACCTGCCTGGTCAAAGGCTTCTATCCC
481  ---------+---------+---------+---------+---------+---------+ 540
     GCCCTACTCGACTGGTTCTTGGTCCAGTCGGACTGGACGGACCAGTTTCCGAAGATAGGG a       R  D  E  L  T  K  N  Q  V  S  L  T  C  L  V  K  G  F  Y  P  -

AGCGACATCGCCGTGGAGTGGGAGAGCAATGGGCAGCCGGAGAACAACTACAAGACCACG
541  ---------+---------+---------+---------+---------+---------+ 600
     TCGCTGTAGCGGCACCTCACCCTCTCGTTACCCGTCGGCCTCTTGTTGATGTTCTGGTGC a       S  D  I  A  V  E  W  E  S  N  G  Q  P  E  N  N  Y  K  T  T  -
```

FIG. 24B

```
        CCTCCCGTGCTGGACTCCGACGGCTCCTTCTTCCTCTACAGCAAGCTCACCGTGGACAAG
    601 ---------+---------+---------+---------+---------+---------+ 660
        GGAGGGCACGACCTGAGGCTGCCGAGGAAGAAGGAGATGTCGTTCGAGTGGCACCTGTTC a        P   P   V   L   D   S   D   G   S   F   F   L   Y   S   K   L   T   V   D   K   -

AGCAGGTGGCAGCAGGGGAACGTCTTCTCATGCTCCGTGATGCATGAGGCTCTGCACAAC
    661 ---------+---------+---------+---------+---------+---------+ 720
        TCGTCCACCGTCGTCCCCTTGCAGAAGAGTACGAGGCACTACGTACTCCGAGACGTGTTG a        S   R   W   Q   Q   G   N   V   F   S   C   S   V   M   H   E   A   L   H   N   -

BamHI
                                                                |
        CACTACACGCAGAAGAGCCTCTCCCTGTCTCCGGGTAAATAACTCGAGGATCC
    721 ---------+---------+---------+---------+---------+--- 773
        GTGATGTGCGTCTTCTCGGAGAGGGACAGAGGCCCATTTATTGAGCTCCTAGG a        H   Y   T   Q   K   S   L   S   L   S   P   G   K   *
```

FIG. 25A

```
    NdeI
     |
    CATATGGACAAAACTCACACATGTCCACCTTGTCCAGCTCCGGAACTCCTGGGGGGACCG
  1 ---------+---------+---------+---------+---------+---------+  60
    GTATACCTGTTTTGAGTGTGTACAGGTGGAACAGGTCGAGGCCTTGAGGACCCCCCTGGC a       M  D  K  T  H  T  C  P  P  C  P  A  P  E  L  L  G  G  P   -

TCAGTCTTCCTCTTCCCCCCAAAACCCAAGGACACCCTCATGATCTCCCGGACCCCTGAG
 61 ---------+---------+---------+---------+---------+---------+ 120
    AGTCAGAAGGAGAAGGGGGGTTTTGGGTTCCTGTGGGAGTACTAGAGGGCCTGGGGACTC a       S  V  F  L  F  P  P  K  P  K  D  T  L  M  I  S  R  T  P  E   -

GTCACATGCGTGGTGGTGGACGTGAGCCACGAAGACCCTGAGGTCAAGTTCAACTGGTAC
121 ---------+---------+---------+---------+---------+---------+ 180
    CAGTGTACGCACCACCACCTGCACTCGGTGCTTCTGGGACTCCAGTTCAAGTTGACCATG a       V  T  C  V  V  V  D  V  S  H  E  D  P  E  V  K  F  N  W  Y   -

GTGGACGGCGTGGAGGTGCATAATGCCAAGACAAAGCCGCGGGAGGAGCAGTACAACAGC
181 ---------+---------+---------+---------+---------+---------+ 240
    CACCTGCCGCACCTCCACGTATTACGGTTCTGTTTCGGCGCCCTCCTCGTCATGTTGTCG a       V  D  G  V  E  V  H  N  A  K  T  K  P  R  E  E  Q  Y  N  S   -

ACGTACCGTGTGGTCAGCGTCCTCACCGTCCTGCACCAGGACTGGCTGAATGGCAAGGAG
241 ---------+---------+---------+---------+---------+---------+ 300
    TGCATGGCACACCAGTCGCAGGAGTGGCAGGACGTGGTCCTGACCGACTTACCGTTCCTC a       T  Y  R  V  V  S  V  L  T  V  L  H  Q  D  W  L  N  G  K  E   -

TACAAGTGCAAGGTCTCCAACAAAGCCCTCCCAGCCCCCATCGAGAAAACCATCTCCAAA
301 ---------+---------+---------+---------+---------+---------+ 360
    ATGTTCACGTTCCAGAGGTTGTTTCGGGAGGGTCGGGGGTAGCTCTTTTGGTAGAGGTTT a       Y  K  C  K  V  S  N  K  A  L  P  A  P  I  E  K  T  I  S  K   -

GCCAAAGGGCAGCCCCGAGAACCACAGGTGTACACCCTGCCCCCATCCCGGGATGAGCTG
361 ---------+---------+---------+---------+---------+---------+ 420
    CGGTTTCCCGTCGGGGCTCTTGGTGTCCACATGTGGGACGGGGGTAGGGCCCTACTCGAC a       A  K  G  Q  P  R  E  P  Q  V  Y  T  L  P  P  S  R  D  E  L   -

ACCAAGAACCAGGTCAGCCTGACCTGCCTGGTCAAAGGCTTCTATCCCAGCGACATCGCC
421 ---------+---------+---------+---------+---------+---------+ 480
    TGGTTCTTGGTCCAGTCGGACTGGACGGACCAGTTTCCGAAGATAGGGTCGCTGTAGCGG a       T  K  N  Q  V  S  L  T  C  L  V  K  G  F  Y  P  S  D  I  A   -

GTGGAGTGGGAGAGCAATGGGCAGCCGGAGAACAACTACAAGACCACGCCTCCCGTGCTG
481 ---------+---------+---------+---------+---------+---------+ 540
    CACCTCACCCTCTCGTTACCCGTCGGCCTCTTGTTGATGTTCTGGTGCGGAGGGCACGAC a       V  E  W  E  S  N  G  Q  P  E  N  N  Y  K  T  T  P  P  V  L   -

GACTCCGACGGCTCCTTCTTCCTCTACAGCAAGCTCACCGTGGACAAGAGCAGGTGGCAG
541 ---------+---------+---------+---------+---------+---------+ 600
    CTGAGGCTGCCGAGGAAGAAGGAGATGTCGTTCGAGTGGCACCTGTTCTCGTCCACCGTC a       D  S  D  G  S  F  F  L  Y  S  K  L  T  V  D  K  S  R  W  Q   -
```

FIG. 25B

```
        CAGGGGAACGTCTTCTCATGCTCCGTGATGCATGAGGCTCTGCACAACCACTACACGCAG
    601 ---------+---------+---------+---------+---------+---------+ 660
        GTCCCCTTGCAGAAGAGTACGAGGCACTACGTACTCCGAGACGTGTTGGTGATGTGCGTC a         Q  G  N  V  F  S  C  S  V  M  H  E  A  L  H  N  H  Y  T  Q   -

AAGAGCCTCTCCCTGTCTCCGGGTAAAGGTGGAGGTGGTGGTTGCACCACCCACTGGGGT
    661 ---------+---------+---------+---------+---------+---------+ 720
        TTCTCGGAGAGGGACAGAGGCCCATTTCCACCTCCACCACCAACGTGGTGGGTGACCCCA

A         K  S  L  S  L  S  P  G  K  G  G  G  G  C  T  T  H  W  G   -

BamHI
                          |
        TTCACCCTGTGCTAATGGATCCCTCGAG
    721 ---------+---------+-------- 748
        AAGTGGGACACGATTACCTAGGGAGCTC a         F  T  L  C  *
```

FIG. 26A

```
     NdeI
      |
     CATATGTGCACCACCCACTGGGGTTTCACCCTGTGCGGTGGAGGCGGTGGGGACAAAGGT
   1 ---------+---------+---------+---------+---------+---------+ 60
     GTATACACGTGGTGGGTGACCCCAAAGTGGGACACGCCACCTCCGCCACCCCTGTTTCCA a         M  C  T  T  H  W  G  F  T  L  C  G  G  G  G  D  K  G    -

GGAGGCGGTGGGGACAAAACTCACACATGTCCACCTTGCCCAGCACCTGAACTCCTGGGG
  61 ---------+---------+---------+---------+---------+---------+ 120
     CCTCCGCCACCCCTGTTTTGAGTGTGTACAGGTGGAACGGGTCGTGGACTTGAGGACCCC a         G  G  G  D  K  T  H  T  C  P  P  C  P  A  P  E  L  L  G  -

GGACCGTCAGTTTTCCTCTTCCCCCCAAAACCCAAGGACACCCTCATGATCTCCCGGACC
 121 ---------+---------+---------+---------+---------+---------+ 180
     CCTGGCAGTCAAAAGGAGAAGGGGGGTTTTGGGTTCCTGTGGGAGTACTAGAGGGCCTGG a         G  P  S  V  F  L  F  P  P  K  P  K  D  T  L  M  I  S  R  T  -

CCTGAGGTCACATGCGTGGTGGTGGACGTGAGCCACGAAGACCCTGAGGTCAAGTTCAAC
 181 ---------+---------+---------+---------+---------+---------+ 240
     GGACTCCAGTGTACGCACCACCACCTGCACTCGGTGCTTCTGGGACTCCAGTTCAAGTTG a         P  E  V  T  C  V  V  V  D  V  S  H  E  D  P  E  V  K  F  N  -

TGGTACGTGGACGGCGTGGAGGTGCATAATGCCAAGACAAAGCCGCGGGAGGAGCAGTAC
 241 ---------+---------+---------+---------+---------+---------+ 300
     ACCATGCACCTGCCGCACCTCCACGTATTACGGTTCTGTTTCGGCGCCCTCCTCGTCATG a         W  Y  V  D  G  V  E  V  H  N  A  K  T  K  P  R  E  E  Q  Y  -

AACAGCACGTACCGTGTGGTCAGCGTCCTCACCGTCCTGCACCAGGACTGGCTGAATGGC
 301 ---------+---------+---------+---------+---------+---------+ 360
     TTGTCGTGCATGGCACACCAGTCGCAGGAGTGGCAGGACGTGGTCCTGACCGACTTACCG a         N  S  T  Y  R  V  V  S  V  L  T  V  L  H  Q  D  W  L  N  G  -

AAGGAGTACAAGTGCAAGGTCTCCAACAAAGCCCTCCCAGCCCCCATCGAGAAAACCATC
 361 ---------+---------+---------+---------+---------+---------+ 420
     TTCCTCATGTTCACGTTCCAGAGGTTGTTTCGGGAGGGTCGGGGGTAGCTCTTTTGGTAG a         K  E  Y  K  C  K  V  S  N  K  A  L  P  A  P  I  E  K  T  I  -

TCCAAAGCCAAAGGGCAGCCCCGAGAACCACAGGTGTACACCCTGCCCCCATCCCGGGAT
 421 ---------+---------+---------+---------+---------+---------+ 480
     AGGTTTCGGTTTCCCGTCGGGGCTCTTGGTGTCCACATGTGGGACGGGGGTAGGGCCCTA a         S  K  A  K  G  Q  P  R  E  P  Q  V  Y  T  L  P  P  S  R  D  -

GAGCTGACCAAGAACCAGGTCAGCCTGACCTGCCTGGTCAAAGGCTTCTATCCCAGCGAC
 481 ---------+---------+---------+---------+---------+---------+ 540
     CTCGACTGGTTCTTGGTCCAGTCGGACTGGACGGACCAGTTTCCGAAGATAGGGTCGCTG a         E  L  T  K  N  Q  V  S  L  T  C  L  V  K  G  F  Y  P  S  D  -

ATCGCCGTGGAGTGGGAGAGCAATGGGCAGCCGGAGAACAACTACAAGACCACGCCTCCC
 541 ---------+---------+---------+---------+---------+---------+ 600
     TAGCGGCACCTCACCCTCTCGTTACCCGTCGGCCTCTTGTTGATGTTCTGGTGCGGAGGG a         I  A  V  E  W  E  S  N  G  Q  P  E  N  N  Y  K  T  T  P  P  -
```

FIG. 26B

```
     GTGCTGGACTCCGACGGCTCCTTCTTCCTCTACAGCAAGCTCACCGTGGACAAGAGCAGG
601  ---------+---------+---------+---------+---------+---------+ 660
     CACGACCTGAGGCTGCCGAGGAAGAAGGAGATGTCGTTCGAGTGGCACCTGTTCTCGTCC a      V  L  D  S  D  G  S  F  F  L  Y  S  K  L  T  V  D  K  S  R   -

TGGCAGCAGGGGAACGTCTTCTCATGCTCCGTGATGCATGAGGCTCTGCACAACCACTAC
661  ---------+---------+---------+---------+---------+---------+ 72
     ACCGTCGTCCCCTTGCAGAAGAGTACGAGGCACTACGTACTCCGAGACGTGTTGGTGATG a      W  Q  Q  G  N  V  F  S  C  S  V  M  H  E  A  L  H  N  H  Y   -

BamHI
                                                     |
     ACGCAGAAGAGCCTCTCCCTGTCTCCGGGTAAATAATGGATCC
721  ---------+---------+---------+---------+--- 763
     TGCGTCTTCTCGGAGAGGGACAGAGGCCCATTTATTACCTAGG a      T  Q  K  S  L  S  L  S  P  G  K  *
```

MODIFIED PEPTIDES AS THERAPEUTIC AGENTS

CROSS-REFERENCE TO RELATED APPLICATIONS

This applications is a divisional of application Ser. No. 09/428,082, filed Oct. 22, 1999, now U.S. Pat. No. 6,660,843 which claims the benefit of U.S. Provisional application 60/105,371, filed Oct. 23, 1998, which are incorporated by reference herein.

BACKGROUND OF THE INVENTION

Recombinant proteins are an emerging class of therapeutic agents. Such recombinant therapeutics have engendered advances in protein formulation and chemical modification. Such modifications can protect therapeutic proteins, primarily by blocking their exposure to proteolytic enzymes. Protein modifications may also increase the therapeutic protein's stability, circulation time, and biological activity. A review article describing protein modification and fusion proteins is Francis (1992), *Focus on Growth Factors* 3:4–10 (Mediscript, London), which is hereby incorporated by reference.

One useful modification is combination with the "Fc" domain of an antibody. Antibodies comprise two functionally independent parts, a variable domain known as "Fab", which binds antigen, and a constant domain known as "Fc", which links to such effector functions as complement activation and attack by phagocytic cells. An Fc has a long serum half-life, whereas an Fab is short-lived. Capon et al. (1989), *Nature* 337: 525–31. When constructed together with a therapeutic protein, an Fc domain can provide longer half-life or incorporate such functions as Fc receptor binding, protein A binding, complement fixation and perhaps even placental transfer. Id. Table 1 summarizes use of Fc fusions known in the art.

A much different approach to development of therapeutic agents is peptide library screening. The interaction of a protein ligand with its receptor often takes place at a relatively large interface. However, as demonstrated for human growth hormone and its receptor, only a few key residues at the interface contribute to most of the binding energy. Clackson et al. (1995), *Science* 267: 383–6. The bulk of the protein ligand merely displays the binding epitopes in the right topology or serves functions unrelated to binding. Thus, molecules of only "peptide" length (2 to 40 amino acids) can bind to the receptor protein of a given large protein ligand. Such peptides may mimic the bioactivity of the large protein ligand ("peptide agonists") or, through competitive binding, inhibit the bioactivity of the large protein ligand ("peptide antagonists").

Phage display peptide libraries have emerged as a powerful method in identifying such peptide agonists and antagonists. See, for example, Scott et al. (1990), *Science* 249: 386; Devlin et al. (1990), *Science* 249: 404; U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference). In such libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides may be sequenced to identify key residues within one or more structurally related families of peptides. See, e.g., Cwirla et al. (1997), *Science* 276: 1696–9, in which two distinct families were identified. The peptide sequences may also suggest which residues may be safely replaced by alanine scanning or by

TABLE 1

Fc fusion with therapeutic proteins

| Form of Fc | Fusion partner | Therapeutic implications | Reference |
| --- | --- | --- | --- |
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al. (1995), J. Immunol. 154: 5590–600 |
| IgG1 | TNF receptor | septic shock | Fisher et al. (1996), N. Engl. J. Med. 334: 1697–1702; Van Zee, K. et al. (1996), J. Immunol. 156: 2221–30 |
| IgG, IgA, IgM, or IgE (excluding the first domain) | TNF receptor | inflammation, autoimmune disorders | U.S. Pat. No. 5,808,029, issued Sep. 15, 1998 |
| IgG1 | CD4 receptor | AIDS | Capon et al. (1989), Nature 337: 525–31 |
| IgG1, IgG3 | N-terminus of IL-2 | anti-cancer, antiviral | Harvill et al. (1995), Immunotech. 1: 95–105 |
| IgG1 | C-terminus of OPG | osteoarthritis; bone density | WO 97/23614, published Jul. 3, 1997 |
| IgG1 | N-terminus of leptin | anti-obesity | PCT/US 97/23183, filed Dec. 11, 1997 |
| Human Ig Cγ1 | CTLA-4 | autoimmune disorders | Linsley (1991), J. Exp. Med. 174: 561–9 | mutagenesis at the DNA level. Mutagenesis libraries may be created and screened to further optimize the sequence of the best binders. Lowman (1997), *Ann. Rev. Biophys. Biomol. Struct.* 26:401–24.

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed. See, e.g., Takasaki et al. (1997), *Nature Biotech.* 15: 1266–70. These analytical methods may also be used to investigate the interaction between a receptor protein and peptides selected by phage display, which may suggest further modification of the peptides to increase binding affinity.

Other methods compete with phage display in peptide research. A peptide library can be fused to the carboxyl terminus of the lac repressor and expressed in *E. coli*. Another *E. coli*-based method allows display on the cell's outer membrane by fusion with a peptidoglycan-associated lipoprotein (PAL). Hereinafter, these and related methods are collectively referred to as "*E. coli* display." In another method, translation of random RNA is halted prior to ribosome release, resulting in a library of polypeptides with their associated RNA still attached. Hereinafter, this and related methods are collectively referred to as "ribosome display." Other methods employ chemical linkage of peptides to RNA; see, for example, Roberts & Szostak (1997), *Proc. Natl. Acad. Sci. USA*, 94: 12297–303. Hereinafter, this and related methods are collectively referred to as "RNA-peptide screening." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells & Lowman (1992), *Curr. Opin. Biotechnol.* 3: 355–62.

Conceptually, one may discover peptide mimetics of any protein using phage display and the other methods mentioned above. These methods have been used for epitope mapping, for identification of critical amino acids in protein-protein interactions, and as leads for the discovery of new therapeutic agents. E.g., Cortese et al. (1996), *Curr. Opin. Biotech.* 7: 616–21. Peptide libraries are now being used most often in immunological studies, such as epitope mapping. Kreeger (1996), *The Scientist* 10(13): 19–20.

Of particular interest here is use of peptide libraries and other techniques in the discovery of pharmacologically active peptides. A number of such peptides identified in the art are summarized in Table 2. The peptides are described in the listed publications, each of which is hereby incorporated by reference. The pharmacologic activity of the peptides is described, and in many instances is followed by a shorthand term therefor in parentheses. Some of these peptides have been modified (e.g., to form C-terminally cross-linked dimers). Typically, peptide libraries were screened for binding to a receptor for a pharmacologically active protein (e.g., EPO receptor). In at least one instance (CTLA4), the peptide library was screened for binding to a monclonal antibody.

TABLE 2

Pharmacologically active peptides

| Form of peptide | Binding partner/ protein of interest[a] | Pharmacologic activity | Reference |
| --- | --- | --- | --- |
| intrapeptide disulfide-bonded | EPO receptor | EPO-mimetic | Wrighton et al. (1996), Science 273: 458–63; U.S. Pat. No. 5,773,569, issued Jun. 30, 1998 to Wrighton et al. |
| C-terminally cross-linked dimer | EPO receptor | EPO-mimetic | Livnah et al. (1996), Science 273: 464–71; Wrighton et al. (1997), Nature Biotechnology 15: 1261–5; International patent application WO 96/40772, published Dec. 19, 1996 |
| linear | EPO receptor | EPO-mimetic | Naranda et al. (1999), Proc. Natl. Acad. Sci. USA, 96: 7569–74 |
| linear | c-Mpl | TPO-mimetic | Cwirla et al. (1997) Science 276: 1696–9; U.S. Pat. No. 5,869,451, issued Feb. 9, 1999; U.S. Pat. No. 5,932,946, issued Aug. 3, 1999 |
| C-terminally cross-linked dimer | c-Mpl | TPO-mimetic | Cwirla et al. (1997), Science 276: 1696–9 |
| disulfide-linked dimer | | stimulation of hematopoiesis ("G-CSF-mimetic") | Paukovits et al. (1984), Hoppe-Seylers Z. Physiol. Chem. 365: 303–11; Laerum et al. (1988), Exp. Hemat. 16: 274–80 |

TABLE 2-continued

Pharmacologically active peptides

| Form of peptide | Binding partner/ protein of interest[a] | Pharmacologic activity | Reference |
|---|---|---|---|
| alkylene-linked dimer | | G-CSF-mimetic | Bhatnagar et al. (1996), J. Med. Chem. 39: 3814–9; Cuthbertson et al. (1997), J. Med. Chem. 40: 2876–82; King et al. (1991), Exp. Hematol. 19: 481; King et al. (1995), Blood 86 (Suppl. 1): 309a |
| linear | IL-1 receptor | inflammatory and autoimmune diseases ("IL-1 antagonist" or "IL-1ra-mimetic") | U.S. Pat. No. 5,608,035; U.S. Pat. No. 5,786,331; U.S. Pat. No. 5,880,096; Yanofsky et al. (1996), Proc. Natl. Acad. Sci. 93: 7381–6; Akeson et al. (1996), J. Biol. Chem. 271: 30517–23; Wiekzorek et al. (1997), Pol. J. Pharmacol. 49: 107–17; Yanofsky (1996), PNAs, 93: 7381–7386. |
| linear | Facteur thymique serique (FTS) | stimulation of lymphocytes ("FTS-mimetic") | Inagaki-Ohara et al. (1996), Cellular Immunol. 171: 30–40; Yoshida (1984), Int. J. Immunopharmacol, 6: 141–6. |
| intrapeptide disulfide bonded | CTLA4 MAb | CTLA4-mimetic | Fukumoto et al. (1998), Nature Biotech. 16: 267–70 |
| exocyclic | TNF-α receptor | TNF-α antagonist | Takasaki et al. (1997), Nature Biotech. 15: 1266–70; WO 98/53842, published Dec. 3, 1998 |
| linear | TNF-α receptor | TNF-α antagonist | Chirinos-Rojas ( ), J. Imm., 5621–5626. |
| intrapeptide disulfide bonded | C3b | inhibition of complement activation; autoimmune diseases ("C3b-antagonist") | Sahu et al. (1996), J. Immunol. 157: 884–91; Morikis et al. (1998), Protein Sci. 7: 619–27 |
| linear | vinculin | cell adhesion processes- cell growth, differentiation, wound healing, tumor metastasis ("vinculin binding") | Adey et al. (1997), Biochem. J. 324: 523–8 |
| linear | C4 binding protein (C4BP) | anti-thrombotic | Linse et al. (1997), J. Biol. Chem. 272: 14658–65 |
| linear | urokinase receptor | processes associated with urokinase interaction with its receptor (e.g., angiogenesis, tumor cell invasion and metastasis); ("UKR antagonist") | Goodson et al. (1994), Proc. Natl. Acad. Sci. 91: 7129–33; International application WO 97/35969, published Oct. 2, 1997 |
| linear | Mdm2, Hdm2 | Inhibition of inactivation of p53 mediated by Mdm2 or hdm2; anti-tumor ("Mdm/hdm antagonist") | Picksley et al. (1994), Oncogene 9: 2523–9; Bottger et al. (1997) J. Mol. Biol. 269: 744–56; Bottger et al. (1996), Oncogene 13: 2141–7 |
| linear | $p21^{WAF1}$ | anti-tumor by mimicking the activity of $p21^{WAF1}$ | Ball et al. (1997), Curr. Biol. 7: 71–80 |
| linear | farnesyl transferase | anti-cancer by preventing activation of ras oncogene | Gibbs et al. (1994), Cell 77: 175–178 |
| linear | Ras effector domain | anti-cancer by inhibiting biological function of the ras oncogene | Moodie et al. (1994), Trends Genet 10: 44–48 Rodriguez et al. (1994), Nature 370: 527–532 |
| linear | SH2/SH3 domains | anti-cancer by inhibiting tumor growth with activated tyrosine kinases | Pawson et al (1993), Curr. Biol. 3: 434–432 Yu et al. (1994), Cell 76: 933–945 |
| linear | $p16^{INK4}$ | anti-cancer by mimicking activity of p16; e.g., | Fåhraeus et al. (1996), Curr. Biol. 6: 84–91 |

TABLE 2-continued

Pharmacologically active peptides

| Form of peptide | Binding partner/ protein of interest[a] | Pharmacologic activity | Reference |
|---|---|---|---|
| linear | Src, Lyn | inhibiting cyclin D-Cdk complex ("p16-mimetic") inhibition of Mast cell activation, IgE-related conditions, type I hypersensitivity ("Mast cell antagonist") | Stauffer et al. (1997), Biochem. 36: 9388–94 |
| linear | Mast cell protease | treatment of inflammatory disorders mediated by release of tryptase-6 ("Mast cell protease inhibitors") | International application WO 98/33812, published Aug. 6, 1998 |
| linear | SH3 domains | treatment of SH3-mediated disease states ("SH3 antagonist") | Rickles et al. (1994), EMBO J. 13: 5598–5604; Sparks et al. (1994), J. Biol. Chem. 269: 23853–6; Sparks et al. (1996), Proc. Natl. Acad. Sci. 93: 1540–4 |
| linear | HBV core antigen (HBcAg) | treatment of HBV viral infections ("anti-HBV") | Dyson & Muray (1995), Proc. Natl. Acad. Sci. 92: 2194–8 |
| linear | selectins | neutrophil adhesion; inflammatory diseases ("selectin antagonist") | Martens et al. (1995), J. Biol. Chem. 270: 21129–36; European patent application EP 0 714 912, published Jun. 5, 1996 |
| linear, cyclized | calmodulin | calmodulin antagonist | Pierce et al. (1995), Molec. Diversity 1: 259–65; Dedman et al. (1993), J. Biol. Chem. 268: 23025–30; Adey & Kay (1996), Gene 169: 133–4 |
| linear, cyclized- | integrins | tumor-homing; treatment for conditions related to integrin-mediated cellular events, including platelet aggregation, thrombosis, wound healing, osteoporosis, tissue repair, angiogenesis (e.g., for treatment of cancer), and tumor invasion ("integrin-binding") | International applications WO 95/14714, published Jun. 1, 1995; WO 97/08203, published Mar. 6, 1997; WO 98/10795, published Mar. 19, 1998; WO 99/24462, published May 20, 1999; Kraft et al. (1999), J. Biol. Chem. 274: 1979–1985 |
| cyclic, linear | fibronectin and extracellular matrix components of T cells and macrophages | treatment of inflammatory and autoimmune conditions | WO 98/09985, published Mar. 12, 1998 |
| linear | somatostatin and cortistatin | treatment or prevention of hormone-producing tumors, acromegaly, giantism, dementia, gastric ulcer, tumor growth, inhibition of hormone secretion, modulation of sleep or neural activity | European patent application 0 911 393, published Apr. 28, 1999 |
| linear | bacterial lipopolysaccharide | antibiotic; septic shock; disorders modulatable by CAP37 | U.S. Pat. No. 5,877,151, issued Mar. 2, 1999 |
| linear or cyclic, including D-amino acids | pardaxin, mellitin | antipathogenic | WO 97/31019, published Aug. 28, 1997 |
| linear, cyclic | VIP | impotence, neurodegenerative disorders | WO 97/40070, published Oct. 30, 1997 |
| linear | CTLs | cancer | EP 0 770 624, published May 2, 1997 |

TABLE 2-continued

Pharmacologically active peptides

| Form of peptide | Binding partner/ protein of interest[a] | Pharmacologic activity | Reference |
|---|---|---|---|
| linear | THF-gamma2 | | Burnstein (1988), Biochem., 27: 4066–71. |
| linear | Amylin | | Cooper (1987), Proc. Natl. Acad. Sci., 84: 8628–32. |
| linear | Adrenomedullin | | Kitamura (1993), BBRC, 192: 553–60. |
| cyclic, linear | VEGF | anti-angiogenic; cancer, rheumatoid arthritis, diabetic retinopathy, psoriasis ("VEGF antagonist") | Fairbrother (1998), Biochem., 37: 17754–17764. |
| cyclic | MMP | inflammation and autoimmune disorders; tumor growth ("MMP inhibitor") | Koivunen (1999), Nature Biotech., 17: 768–774. |
| | HGH fragment | | U.S. Pat. No. 5,869,452 |
| | Echistatin | inhibition of platelet aggregation | Gan (1988), J. Biol. Chem., 263: 19827–32. |
| linear | SLE autoantibody | SLE | WO 96/30057, published Oct. 3, 1996 |
| | GD1alpha | suppression of tumor metastasis | Ishikawa et al. (1998), FEBS Lett. 441 (1): 20–4 |
| | antiphospholipid beta-2-glycoprotein-I (β2GPI) antibodies | endothelial cell activation, antiphospholipid syndrome (APS), thromboembolic phenomena, thrombocytopenia, and recurrent fetal loss | Blank et al. (1999), Proc. Natl. Acad. Sci. USA 96: 5164–8 |
| linear | T Cell Receptor beta chain | diabetes | WO 96/11214, published Apr. 18, 1996 |

[a]The protein listed in this column may be bound by the associated peptide (e.g., EPO receptor, IL-1 receptor) or mimicked by the associated peptide. The references listed for each clarify whether the molecule is bound by or mimicked by the peptides.
[b]FTS is a thymic hormone mimicked by the molecule of this invention rather than a receptor bound by the molecule of this invention.

Peptides identified by peptide library screening have been regarded as "leads" in development of therapeutic agents rather than as therapeutic agents themselves. Like other proteins and peptides, they would be rapidly removed in vivo either by renal filtration, cellular clearance mechanisms in the reticuloendothelial system, or proteolytic degradation. Francis (1992), *Focus on Growth Factors* 3: 4–11. As a result, the art presently uses the identified peptides to validate drug targets or as scaffolds for design of organic compounds that might not have been as easily or as quickly identified through chemical library screening. Lowman (1997), *Ann. Rev. Biophys. Biomol. Struct.* 26: 401–24; Kay et al. (1998), *Drug Disc. Today* 3: 370–8. The art would benefit from a process by which such peptides could more readily yield therapeutic agents.

SUMMARY OF THE INVENTION

The present invention concerns a process by which the in vivo half-life of one or more biologically active peptides is increased by fusion with a vehicle. In this invention, pharmacologically active compounds are prepared by a process comprising:

a) selecting at least one peptide that modulates the activity of a protein of interest; and b) preparing a pharmacologic agent comprising at least one vehicle covalently linked to at least one amino acid sequence of the selected peptide.

The preferred vehicle is an Fc domain. The peptides screened in step (a) are preferably expressed in a phage display library. The vehicle and the peptide may be linked through the N- or C-terminus of the peptide or the vehicle, as described further below. Derivatives of the above compounds (described below) are also encompassed by this invention.

The compounds of this invention may be prepared by standard synthetic methods, recombinant DNA techniques, or any other methods of preparing peptides and fusion proteins. Compounds of this invention that encompass non-peptide portions may be synthesized by standard organic chemistry reactions, in addition to standard peptide chemistry reactions when applicable.

The primary use contemplated is as therapeutic or prophylactic agents. The vehicle-linked peptide may have activity comparable to—or even greater than—the natural ligand mimicked by the peptide. In addition, certain natural ligand-based therapeutic agents might induce antibodies against the patient's own endogenous ligand; the vehicle-linked peptide avoids this pitfall by having little or typically no sequence identity with the natural ligand.

Although mostly contemplated as therapeutic agents, compounds of this invention may also be useful in screening for such agents. For example, one could use an Fc-peptide (e.g., Fc-SH2 domain peptide) in an assay employing anti-Fc coated plates. The vehicle, especially Fc, may make insoluble peptides soluble and thus useful in a number of assays.

The compounds of this invention may be used for therapeutic or prophylactic purposes by formulating them with appropriate pharmaceutical carrier materials and administering an effective amount to a patient, such as a human (or other mammal) in need thereof. Other related aspects are also included in the instant invention.

Numerous additional aspects and advantages of the present invention will become apparent upon consideration of the figures and detailed description of the invention.

BRIEF DESCRIPTION OF THE FIGURES

A, D: Single disulfide-bonded dimers. IgG1 antibodies typically have two disulfide bonds at the hinge region between the constant and variable domains. The Fc domain in FIGS. 2A and 2D may be formed by truncation between the two disulfide bond sites or by substitution of a cysteinyl residue with an unreactive residue (e.g., alanyl). In FIG. 2A, the Fc domain is linked at the amino terminus of the peptides; in 2D, at the carboxyl terminus.

B, E: Doubly disulfide-bonded dimers. This Fc domain may be formed by truncation of the parent antibody to retain both cysteinyl residues in the Fc domain chains or by expression from a construct including a sequence encoding such an Fc domain. In FIG. 2B, the Fc domain is linked at the amino terminus of the peptides; in 2E, at the carboxyl terminus.

C, F: Noncovalent dimers. This Fc domain may be formed by elimination of the cysteinyl residues by either truncation or substitution. One may desire to eliminate the cysteinyl residues to avoid impurities formed by reaction of the cysteinyl residue with cysteinyl residues of other proteins present in the host cell. The noncovalent bonding of the Fc domains is sufficient to hold together the dimer. Other dimers may be formed by using Fc domains derived from different types of antibodies (e.g., IgG2, IgM).

Figure 3A:
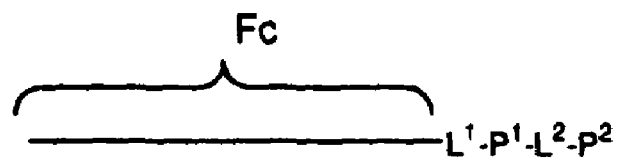
Figure 3B:
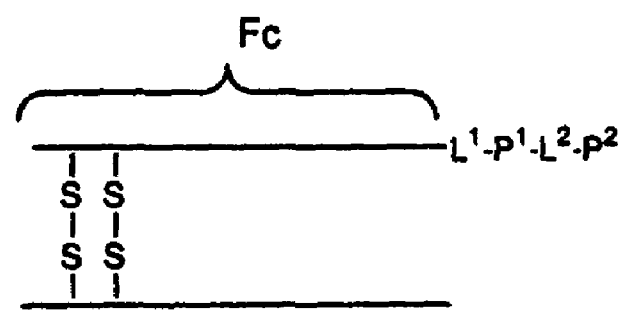
Figure 3C:
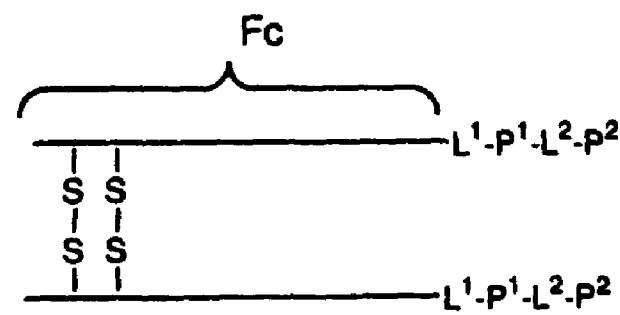
Figures 1, 18A:
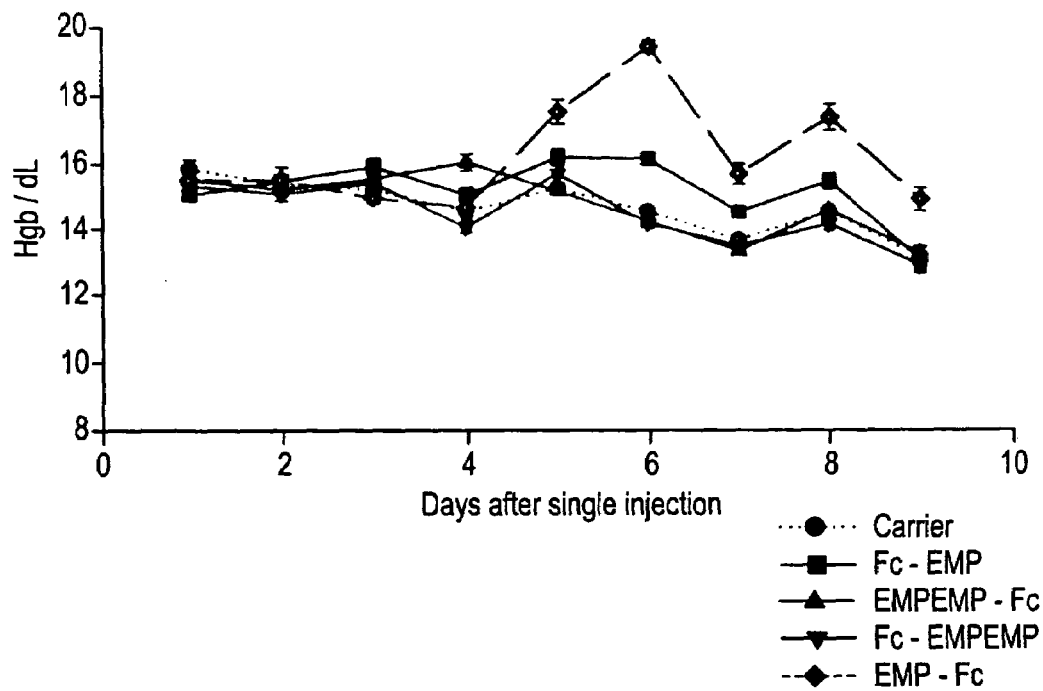
FIG. 1 shows a schematic representation of an exemplary process of the invention. In this preferred process, the vehicle is an Fc domain, which is linked to the peptide covalently by expression from a DNA construct encoding both the Fc domain and the peptide. As noted in FIG. 1, the Fc domains spontaneously form a dimer in this process.
Figures 2, 18A:
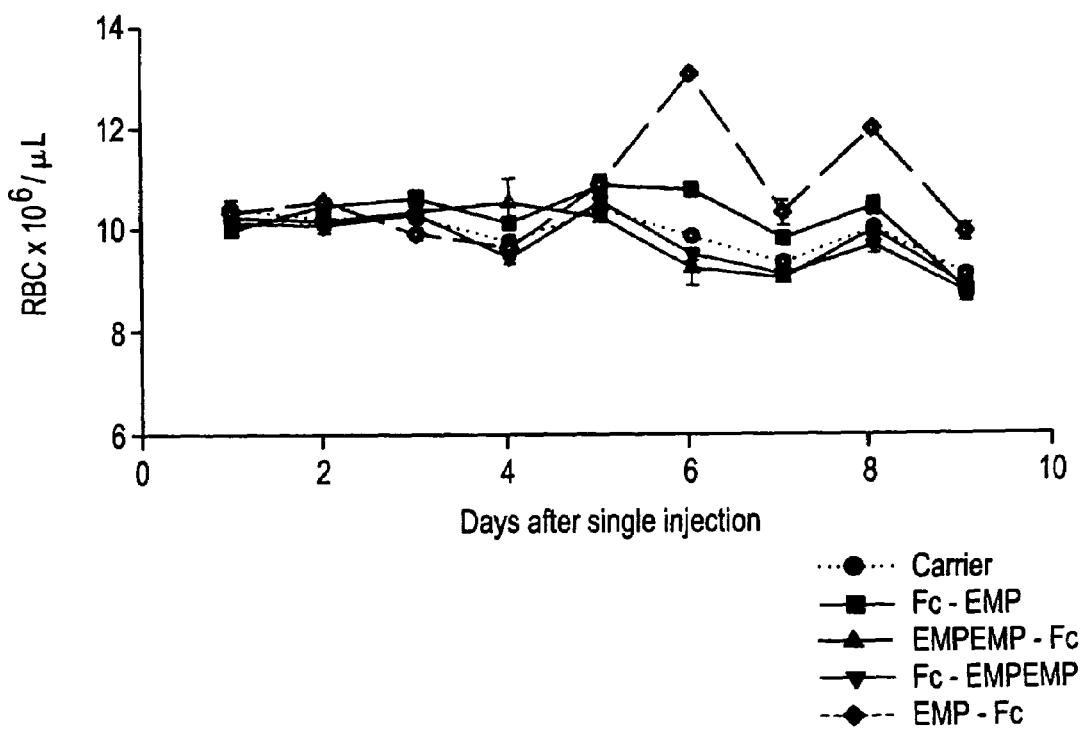
FIG. 2 shows exemplary Fc dimers that may be derived from an IgG1 antibody. "Fc" in the figure represents any of the Fc variants within the meaning of "Fc domain" herein. "X¹" and "X²" represent peptides or linker-peptide combinations as defined hereinafter. The specific dimers are as follows.
Figures 3, 18A:
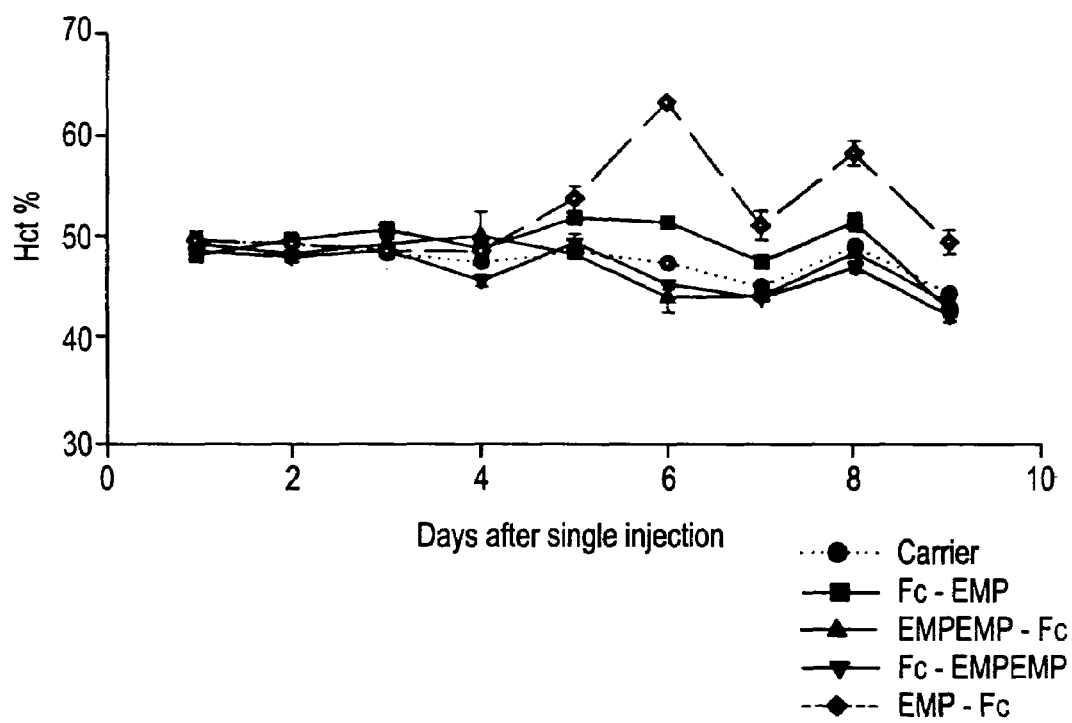

FIG. 3 shows the structure of preferred compounds of the invention that feature tandem repeats of the pharmacologically active peptide. FIG. 3A shows a single chain molecule and may also represent the DNA construct for the molecule. FIG. 3B shows a dimer in which the linker-peptide portion is present on only one chain of the dimer. FIG. 3C shows a dimer having the peptide portion on both chains. The dimer of FIG. 3C will form spontaneously in certain host cells upon expression of a DNA construct encoding the single chain shown in FIG. 3A. In other host cells, the cells could be placed in conditions favoring formation of dimers or the dimers can be formed in vitro.

FIG. 4 shows exemplary nucleic acid and amino acid sequences (SEQ ID NOS: 1 and 2, respectively) of human IgG1 Fc that may be used in this invention.

Figure 5:
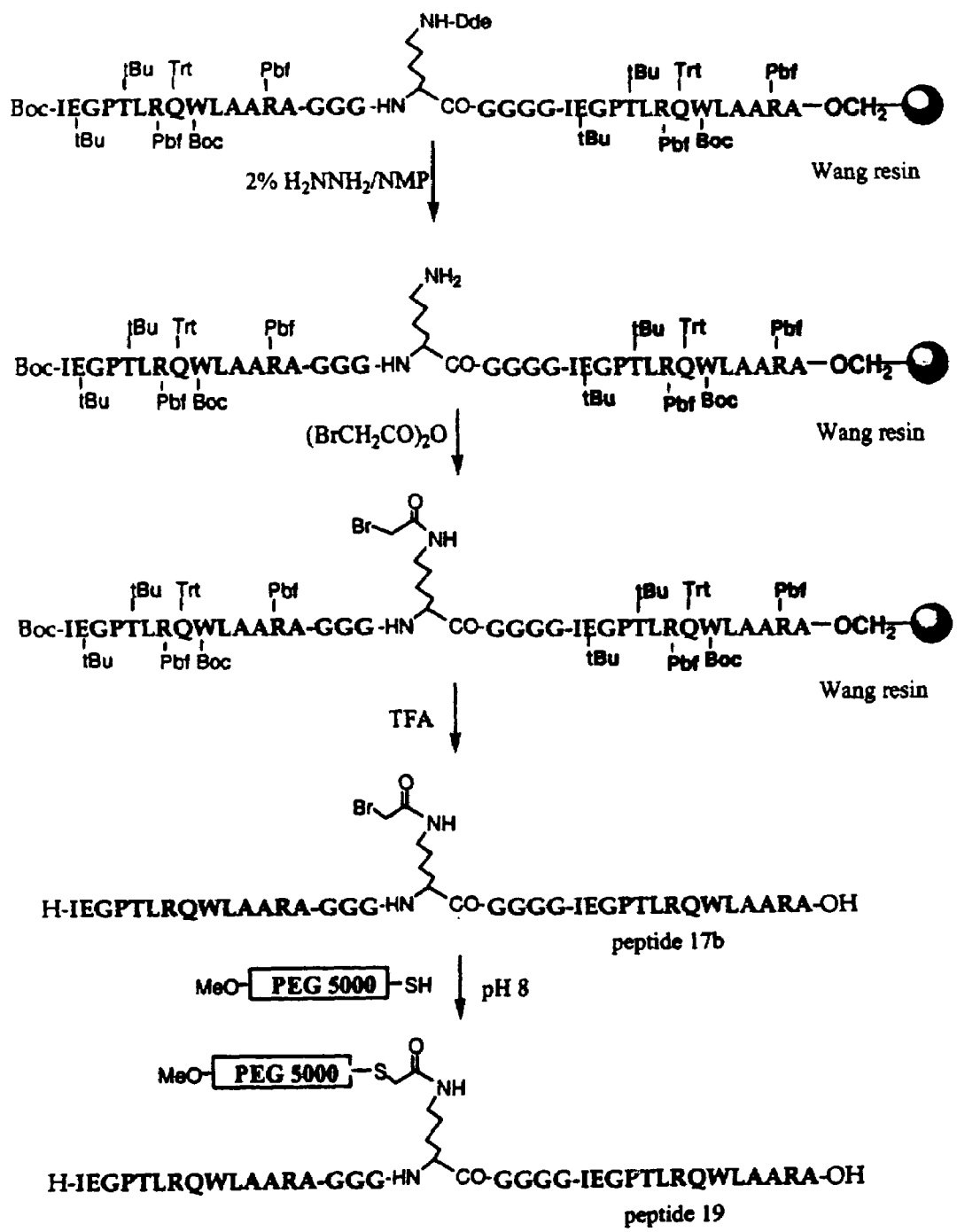

FIG. 5 shows a synthetic scheme for the preparation of PEGylated peptide 19 (SEQ ID NO: 3) as prepared through intermediates having SEQ ID NOS: 1128 through 1131, respectively.

Figure 6:
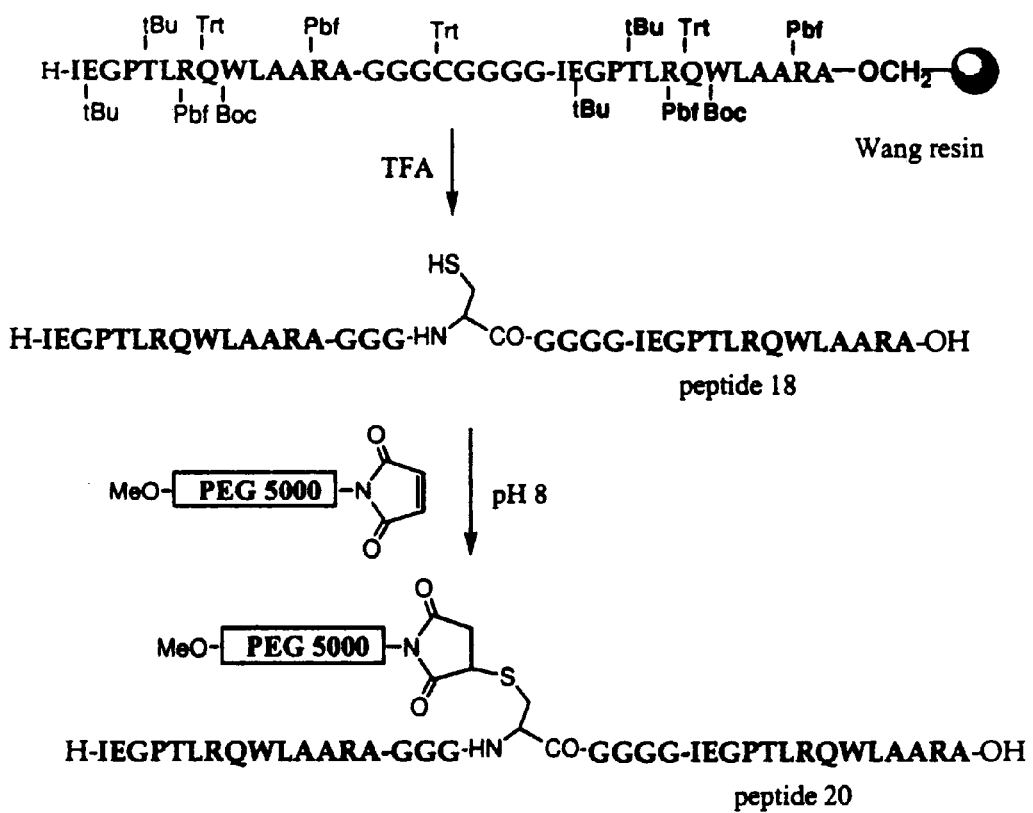

FIG. 6 shows a synthetic scheme for the preparation of PEGylated peptide 20 (SEQ ID NO: 4) as prepared through intermediates having SEQ ID NOS: 1132 and 1133, respectively.

FIG. 7 shows the nucleotide and amino acid sequences (SEQ ID NOS: 5 and 6, respectively) of the molecule identified as "Fc-TMP" in Example 2 hereinafter.

FIG. 8 shows the nucleotide and amino acid sequences (SEQ. ID. NOS: 7 and 8, respectively) of the molecule identified as "Fc-TMP-TMP" in Example 2 hereinafter.

FIG. 9 shows the nucleotide and amino acid sequences (SEQ. ID. NOS: 9 and 10, respectively) of the molecule identified as "TMP-TMP-Fc" in Example 2 hereinafter.

FIG. 10 shows the nucleotide and amino acid sequences (SEQ. ID. NOS: 11 and 12, respectively) of the molecule identified as "TMP-Fc" in Example 2 hereinafter.

FIG. 11 shows the number of platelets generated in vivo in normal female BDF1 mice treated with one 100 μg/kg bolus injection of various compounds, with the terms defined as follows.

PEG-MGDF: 20 kD average molecular weight PEG attached by reductive amination to the N-terminal amino group of amino acids 1–163 of native human TPO, which is expressed in $E.$ $coli$ (so that it is not glycosylated);

TMP: the TPO-mimetic peptide having the amino acid sequence IEGPTLRQWLAARA (SEQ ID NO: 13);

TMP-TMP: the TPO-mimetic peptide having the amino acid sequence IEGPTLRQWLAARA-GGGGGGGG-IEGPTLRQWLAARA (SEQ ID NO: 14);

PEG-TMP-TMP: the peptide of SEQ ID NO: 14, wherein the PEG group is a 5 kD average molecular weight PEG attached as shown in FIG. 6;

Fc-TMP-TMP: the compound of SEQ ID NO: 8 (FIG. 8) dimerized with an identical second monomer (i.e., Cys residues 7 and 10 are bound to the corresponding Cys residues in the second monomer to form a dimer, as shown in FIG. 2); and TMP-TMP-Fc is the compound of SEQ ID NO: 10 (FIG. 9) dimerized in the same way as TMP-TMP-Fc except that the Fc domain is attached at the C-terminal end rather than the N-terminal end of the TMP-TMP peptide.

Figure 12:
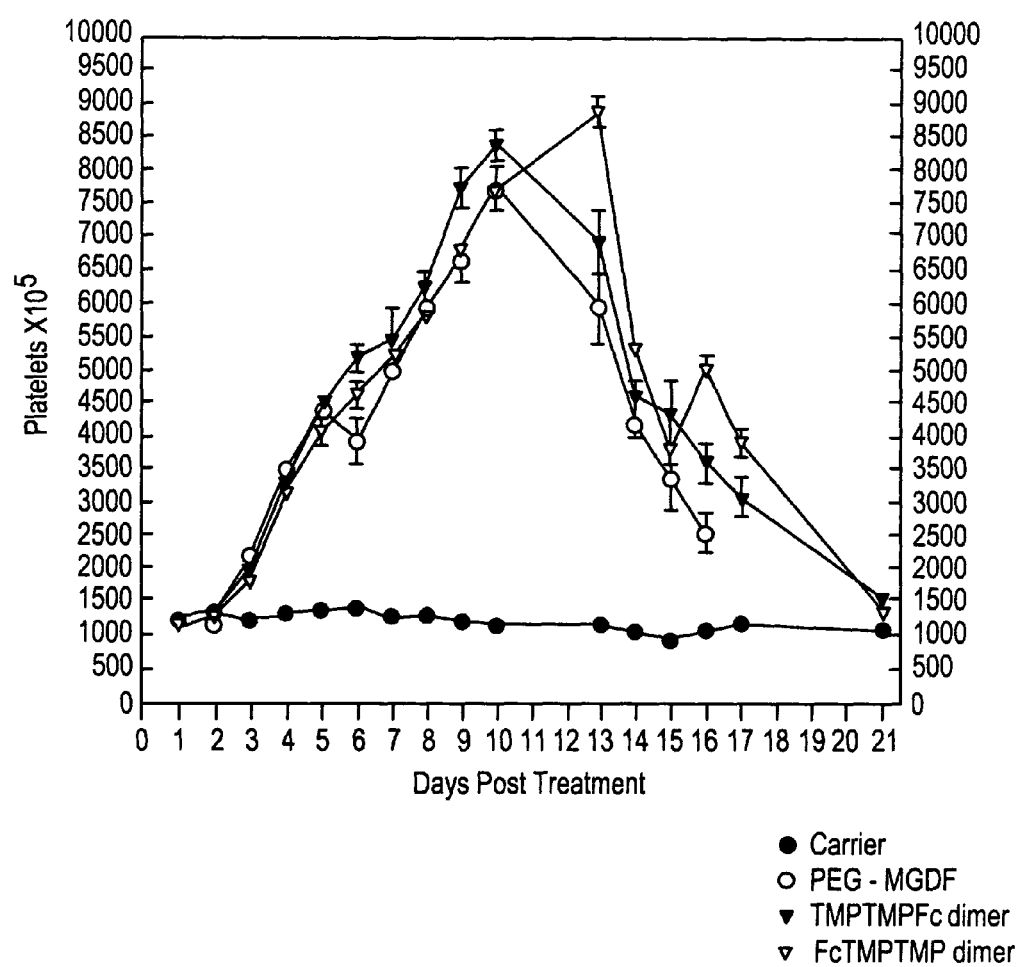

FIG. 12 shows the number of platelets generated in vivo in normal BDF1 mice treated with various compounds delivered via implanted osmotic pumps over a 7-day period. The compounds are as defined for FIG. 7.

FIG. 13 shows the nucleotide and amino acid sequences (SEQ. ID. NOS: 15 and 16, respectively) of the molecule identified as "Fc-EMP" in Example 3 hereinafter.

FIG. 14 shows the nucleotide and amino acid sequences (SEQ ID NOS: 17 and 18, respectively) of the molecule identified as "EMP-Fc" in Example 3 hereinafter.

FIG. 15 shows the nucleotide and amino acid sequences (SEQ ID NOS:19 and 20, respectively) of the molecule identified as "EMP-EMP-Fc" in Example 3 hereinafter.

FIG. 16 shows the nucleotide and amino acid sequences (SEQ ID NOS: 21 and 22, respectively) of the molecule identified as "Fc-EMP-EMP" in Example 3 hereinafter.

FIGS. 17A and 17B show the DNA sequence (SEQ ID NO: 23) inserted into pCFM1656 between the unique AatII (position #4364 in pCFM1656) and SacII (position #4585 in pCFM1656) restriction sites to form expression plasmid pAMG21 (ATCC accession no. 98113).

Figures 1, 18B:
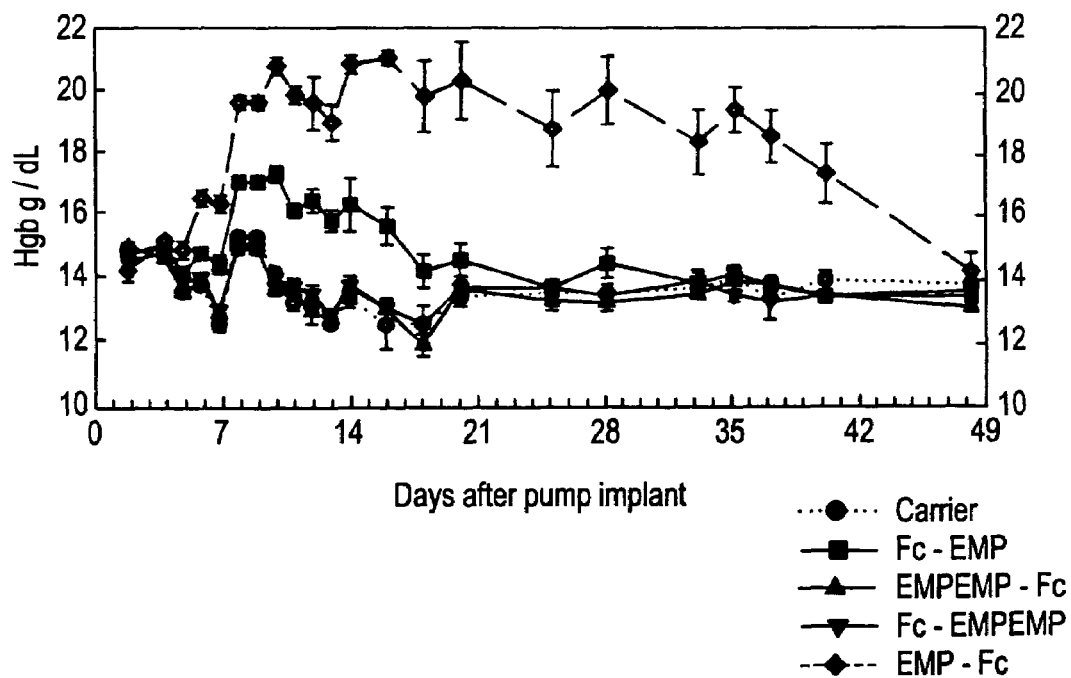
Figures 2, 18B:
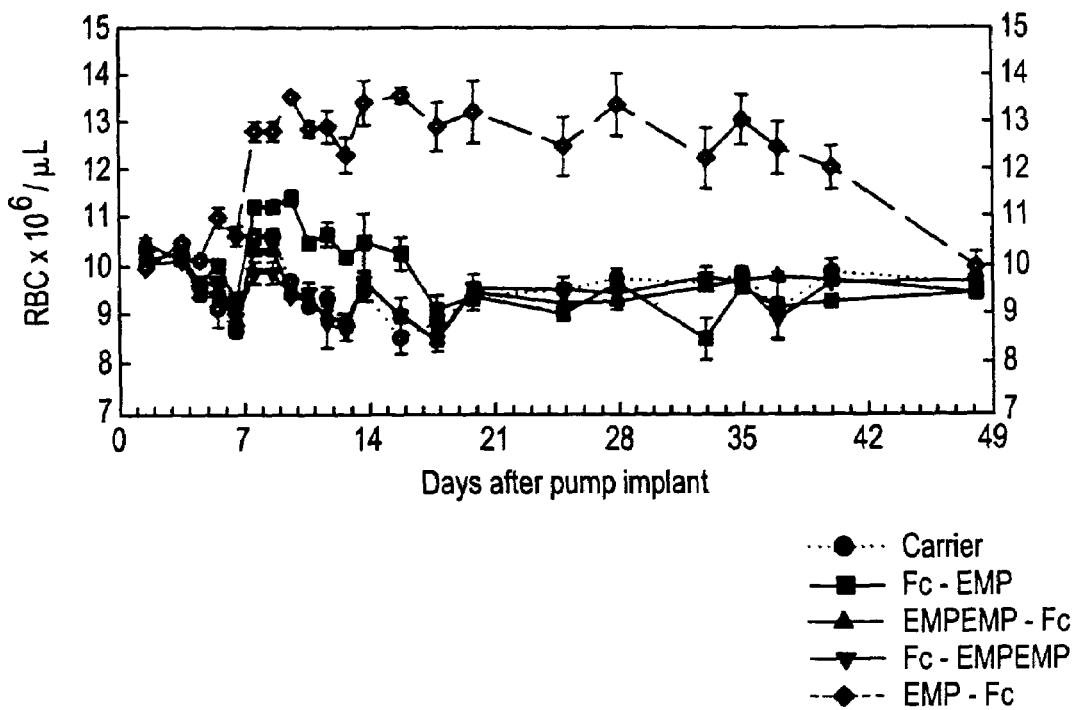
Figures 3, 18B:
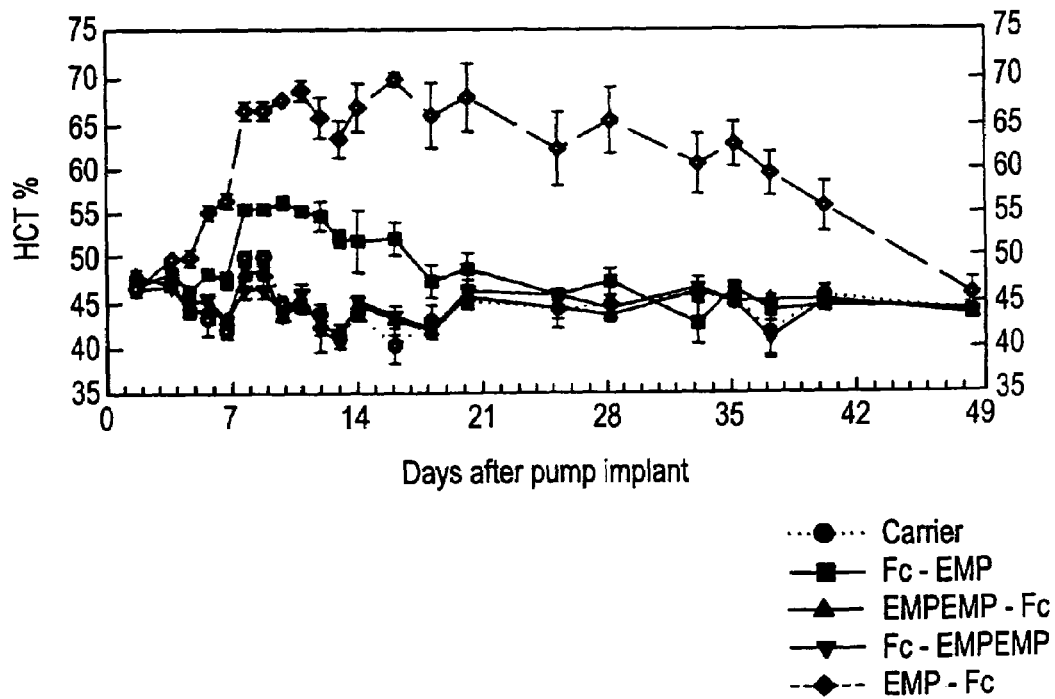

FIG. 18A shows the hemoglobin, red blood cells, and hematocrit generated in vivo in normal female BDF1 mice treated with one 100 μg/kg bolus injection of various compounds. FIG. 18B shows the same results with mice treated with 100 μg/kg per day delivered the same dose by 7-day micro-osmotic pump with the EMPs delivered at 100 μg/kg, rhEPO at 30U/mouse. (In both experiments, neutrophils, lymphocytes, and platelets were unaffected.) In these figures, the terms are defined as follows.

- Fc-EMP: the compound of SEQ ID NO: 16 (FIG. 13) dimerized with an identical second monomer (i.e., Cys residues 7 and 10 are bound to the corresponding Cys residues in the second monomer to form a dimer, as shown in FIG. 2);
- EMP-Fc: the compound of SEQ ID NO: 18 (FIG. 14) dimerized in the same way as Fc-EMP except that the Fc domain is attached at the C-terminal end rather than the N-terminal end of the EMP peptide.
- "EMP-EMP-Fc" refers to a tandem repeat of the same peptide (SEQ ID NO: 20) attached to the same Fc domain by the carboxyl terminus of the peptides. "Fc-EMP-EMP" refers to the same tandem repeat of the peptide but with the same Fc domain attached at the amino terminus of the tandem repeat. All molecules are expressed in *E. coli* and so are not glycosylated.

FIGS. 19A and 19B show the nucleotide and amino acid sequences (SEQ ID NOS: 1055 and 1056) of the Fc-TNF-α inhibitor fusion molecule described in Example 4 hereinafter.

FIGS. 20A and 20B show the nucleotide and amino acid sequences (SEQ ID NOS: 1057 and 1058) of the TNF-α inhibitor-Fc fusion molecule described in Example 4 hereinafter.

FIGS. 21A and 21B show the nucleotide and amino acid sequences (SEQ ID NOS: 1059 and 1060) of the Fc-IL-1 antagonist fusion molecule described in Example 5 hereinafter.

FIGS. 22A and 22B show the nucleotide and amino acid sequences (SEQ ID NOS: 1061 and 1062) of the IL-1 antagonist-Fc fusion molecule described in Example 5 hereinafter.

FIGS. 23A and 23B show the nucleotide and amino acid sequences (SEQ ID NOS: 1063 and 1064) of the Fc-VEGF antagonist fusion molecule described in Example 6 hereinafter.

FIGS. 24A and 24B show the nucleotide and amino acid sequences (SEQ ID NOS: 1065 and 1066) of the VEGF antagonist-Fc fusion molecule described in Example 6 hereinafter.

FIGS. 25A and 25B show the nucleotide and amino acid sequences (SEQ ID NOS: 1067 and 1068) of the Fc-MMP inhibitor fusion molecule described in Example 7 hereinafter.

FIGS. 26A and 26B show the nucleotide and amino acid sequences (SEQ ID NOS: 1069 and 1070) of the MMP inhibitor-Fc fusion molecule described in Example 7 hereinafter.

DETAILED DESCRIPTION OF THE INVENTION

Definition of Terms

The terms used throughout this specification are defined as follows, unless otherwise limited in specific instances.

The term "comprising" means that a compound may include additional amino acids on either or both of the N- or C-termini of the given sequence. Of course, these additional amino acids should not significantly interfere with the activity of the compound.

The term "vehicle" refers to a molecule that prevents degradation and/or increases half-life, reduces toxicity, reduces immunogenicity, or increases biological activity of a therapeutic protein. Exemplary vehicles include an Fc domain (which is preferred) as well as a linear polymer (e.g., polyethylene glycol (PEG), polylysine, dextran, etc.); a branched-chain polymer (see, for example, U.S. Pat. No. 4,289,872 to Denkenwalter et al., issued Sep. 15, 1981; 5,229,490 to Tam, issued Jul. 20, 1993; WO 93/21259 by Frechet et al., published 28 Oct. 1993); a lipid; a cholesterol group (such as a steroid); a carbohydrate or oligosaccharide; or any natural or synthetic protein, polypeptide or peptide that binds to a salvage receptor. Vehicles are further described hereinafter.

The term "native Fc" refers to molecule or sequence comprising the sequence of a non-antigen-binding fragment resulting from digestion of whole antibody, whether in monomeric or multimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgA2). One example of a native Fc is a disulfide-bonded dimer resulting from papain digestion of an IgG (see Ellison et al. (1982), *Nucleic Acids Res.* 10: 4071–9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published 25 September 1997) and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by other means.

The term "multimer" as applied to Fc domains or molecules comprising Fc domains refers to molecules having two or more polypeptide chains associated covalently, non-covalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The term "dimer" as applied to Fc domains or molecules comprising Fc domains refers to molecules having two polypeptide chains associated covalently or non-covalently. Thus, exemplary dimers within the scope of this invention are as shown in FIG. 2.

The terms "derivatizing" and "derivative" or "derivatized" comprise processes and resulting compounds respectively in which (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by —NRR$^1$, NRC(O)R$^1$, —NRC(O)OR$^1$, —NRS(O)$_2$R$^1$, —NHC(O)NHR, a succinimide group, or substituted or unsubstituted benzyloxycarbonyl-NH—, wherein R and R$^1$ and the ring substituents are as defined hereinafter; (5) the C-terminus is replaced by —C(O)R$^2$ or —NR$^3$R$^4$ wherein R$^2$, R$^3$ and R$^4$ are as defined hereinafter; and (6) compounds in which individual amino acid moieties are modified through treatment with agents capable of reacting with selected side chains or terminal residues. Derivatives are further described hereinafter.

The term "peptide" refers to molecules of 2 to 40 amino acids, with molecules of 3 to 20 amino acids preferred and those of 6 to 15 amino acids most preferred. Exemplary peptides may be randomly generated by any of the methods cited above, carried in a peptide library (e.g., a phage display library), or derived by digestion of proteins.

The term "randomized" as used to refer to peptide sequences refers to fully random sequences (e.g., selected by phage display methods) and sequences in which one or more residues of a naturally occurring molecule is replaced by an amino acid residue not appearing in that position in the naturally occurring molecule. Exemplary methods for identifying peptide sequences include phage display, E. coli display, ribosome display, RNA-peptide screening, chemical screening, and the like.

The term "pharmacologically active" means that a substance so described is determined to have activity that affects a medical parameter (e.g., blood pressure, blood cell count, cholesterol level) or disease state (e.g., cancer, autoimmune disorders). Thus, pharmacologically active peptides comprise agonistic or mimetic and antagonistic peptides as defined below.

The terms "-mimetic peptide" and "-agonist peptide" refer to a peptide having biological activity comparable to a protein (e.g., EPO, TPO, G-CSF) that interacts with a protein of interest. These terms further include peptides that indirectly mimic the activity of a protein of interest, such as by potentiating the effects of the natural ligand of the protein of interest; see, for example, the G-CSF-mimetic peptides listed in Tables 2 and 7. Thus, the term "EPO-mimetic peptide" comprises any peptides that can be identified or derived as described in Wrighton et al. (1996), Science 273: 458–63, Naranda et al. (1999), Proc. Natl. Acad. Sci. USA 96: 7569–74, or any other reference in Table 2 identified as having EPO-mimetic subject matter. Those of ordinary skill in the art appreciate that each of these references enables one to select different peptides than actually disclosed therein by following the disclosed procedures with different peptide libraries.

The term "TPO-mimetic peptide" comprises peptides that can be identified or derived as described in Cwirla et al. (1997), Science 276: 1696–9, U.S. Pat. Nos. 5,869,451 and 5,932,946 and any other reference in Table 2 identified as having TPO-mimetic subject matter, as well as the U.S. patent application, "Thrombopoietic Compounds," filed on even date herewith and hereby incorporated by reference. Those of ordinary skill in the art appreciate that each of these references enables one to select different peptides than actually disclosed therein by following the disclosed procedures with different peptide libraries.

The term "G-CSF-mimetic peptide" comprises any peptides that can be identified or described in Paukovits et al. (1984), Hoppe-Seylers Z. Physiol. Chem. 365: 303–11 or any of the references in Table 2 identified as having G-CSF-mimetic subject matter. Those of ordinary skill in the art appreciate that each of these references enables one to select different peptides than actually disclosed therein by following the disclosed procedures with different peptide libraries.

The term "CTLA4-mimetic peptide" comprises any peptides that can be identified or derived as described in Fukumoto et al. (1998), Nature Biotech. 16: 267–70. Those of ordinary skill in the art appreciate that each of these references enables one to select different peptides than actually disclosed therein by following the disclosed procedures with different peptide libraries.

The term "-antagonist peptide" or "inhibitor peptide" refers to a peptide that blocks or in some way interferes with the biological activity of the associated protein of interest, or has biological activity comparable to a known antagonist or inhibitor of the associated protein of interest. Thus, the term "TNF-antagonist peptide" comprises peptides that can be identified or derived as described in Takasaki et al. (1997), Nature Biotech. 15: 1266–70 or any of the references in Table 2 identified as having TNF-antagonistic subject matter. Those of ordinary skill in the art appreciate that each of these references enables one to select different peptides than actually disclosed therein by following the disclosed procedures with different peptide libraries.

The terms "IL-1 antagonist" and "IL-1ra-mimetic peptide" comprises peptides that inhibit or down-regulate activation of the IL-1 receptor by IL-1. IL-1 receptor activation results from formation of a complex among IL-1, IL-1 receptor, and IL-1 receptor accessory protein. IL-1 antagonist or IL-1ra-mimetic peptides bind to IL-1, IL-1 receptor, or IL-1 receptor accessory protein and obstruct complex formation among any two or three components of the complex. Exemplary IL-1 antagonist or IL-1ra-mimetic peptides can be identified or derived as described in U.S. Pat. Nos. 5,608,035, 5,786,331, 5,880,096, or any of the references in Table 2 identified as having IL-1ra-mimetic or IL-1 antagonistic subject matter. Those of ordinary skill in the art appreciate that each of these references enables one to select different peptides than actually disclosed therein by following the disclosed procedures with different peptide libraries.

The term "VEGF-antagonist peptide" comprises peptides that can be identified or derived as described in Fairbrother (1998), Biochem. 37: 17754–64, and in any of the references in Table 2 identified as having VEGF-antagonistic subject matter. Those of ordinary skill in the art appreciate that each of these references enables one to select different peptides than actually disclosed therein by following the disclosed procedures with different peptide libraries.

The term "MMP inhibitor peptide" comprises peptides that can be identified or derived as described in Koivunen (1999), *Nature Biotech.* 17: 768–74 and in any of the references in Table 2 identified as having MMP inhibitory subject matter. Those of ordinary skill in the art appreciate that each of these references enables one to select different peptides than actually disclosed therein by following the disclosed procedures with different peptide libraries.

Additionally, physiologically acceptable salts of the compounds of this invention are also encompassed herein. By "physiologically acceptable salts" is meant any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate.

Structure of Compounds

In General. In the compositions of matter prepared in accordance with this invention, the peptide may be attached to the vehicle through the peptide's N-terminus or C-terminus. Thus, the vehicle-peptide molecules of this invention may be described by the following formula I:

$$(X^1)_a\text{-}F^1\text{-}(X^2)_b \qquad \text{I}$$

wherein:

$F^1$ is a vehicle (preferably an Fc domain);

$X^1$ and $X^2$ are each independently selected from $\text{-}(L^1)_c\text{-}P^1$, $\text{-}(L^1)_c\text{-}P^1\text{-}(L^2)_d\text{-}P^2$, $\text{-}(L^1)_c\text{-}P^1\text{-}(L^2)_d\text{-}P^2\text{-}(L^3)_e\text{-}P^3$, and $\text{-}(L^1)_c\text{-}P^1\text{-}(L^2)_d\text{-}P^2\text{-}(L^3)_e\text{-}P^3\text{-}(L^4)_f\text{-}P^4$ $P^1$, $P^2$, $P^3$, and $P^4$ are each independently sequences of pharmacologically active peptides;

$L^1$, $L^2$, $L^3$, and $L^4$ are each independently linkers; and a, b, c, d, e, and f are each independently 0 or 1, provided that at least one of a and b is 1.

Thus, compound I comprises preferred compounds of the formulae $$X^1\text{-}F^1 \qquad \text{II}$$

and multimers thereof wherein $F^1$ is an Fc domain and is attached at the C-terminus of $X^1$;

$$F^1\text{-}X^2 \qquad \text{III}$$

and multimers thereof wherein $F^1$ is an Fc domain and is attached at the N-terminus of $X^2$;

$$F^1\text{-}(L^1)_c\text{-}P^1 \qquad \text{IV}$$

and multimers thereof wherein $F^1$ is an Fc domain and is attached at the N-terminus of $\text{-}(L^1)_c\text{-}P^1$; and $$F^1\text{-}(L^1)_c\text{-}P^1\text{-}(L^2)_d\text{-}P^2 \qquad \text{V}$$

and multimers thereof wherein $F^1$ is an Fc domain and is attached at the N-terminus of $\text{-}L^1\text{-}P^1\text{-}L^2\text{-}P^2$.

Peptides. Any number of peptides may be used in conjunction with the present invention. Of particular interest are peptides that mimic the activity of EPO, TPO, growth hormone, G-CSF, GM-CSF, IL-1ra, leptin, CTLA4, TRAIL, TGF-α, and TGF-β. Peptide antagonists are also of interest, particularly those antagonistic to the activity of TNF, leptin, any of the interleukins (IL-1, 2, 3, . . . ), and proteins involved in complement activation (e.g., C3b). Targeting peptides are also of interest, including tumor-homing peptides, membrane-transporting peptides, and the like. All of these classes of peptides may be discovered by methods described in the references cited in this specification and other references.

Phage display, in particular, is useful in generating peptides for use in the present invention. It has been stated that affinity selection from libraries of random peptides can be used to identify peptide ligands for any site of any gene product. Dedman et al. (1993), *J. Biol. Chem.* 268: 23025–30. Phage display is particularly well suited for identifying peptides that bind to such proteins of interest as cell surface receptors or any proteins having linear epitopes. Wilson et al. (1998), *Can. J. Microbiol.* 44: 313–29; Kay et al. (1998), *Drug Disc. Today* 3: 370–8. Such proteins are extensively reviewed in Herz et al. (1997), *J. Receptor & Signal Transduction Res.* 17(5): 671–776, which is hereby incorporated by reference. Such proteins of interest are preferred for use in this invention.

A particularly preferred group of peptides are those that bind to cytokine receptors. Cytokines have recently been classified according to their receptor code. See Inglot (1997), *Archivum Immunologiae et Therapiae Experimentalis* 45: 353–7, which is hereby incorporated by reference. Among these receptors, most preferred are the CKRs (family I in Table 3). The receptor classification appears in Table 3.

TABLE 3

Cytokine Receptors Classified by Receptor Code

| Cytokines (ligands) | | Receptor Type | |
|---|---|---|---|
| family | subfamily | family | subfamily |
| I. Hematopoietic cytokines | 1. IL-2, IL-4, IL-7, IL-9, IL-13, IL-15 | I. Cytokine R (CKR) | 1. shared γCr |
| | 2. IL-3, IL-5, GM-CSF | | 2. shared GP 140 βR |
| | 3. IL-6, IL-11, IL-12, LIF, OSM, CNTF, leptin (OB) | | 3. 3.shared RP 130 |
| | 4. G-CSF, EPO, TPO, PRL, GH | | 4. "single chain" R |
| | 5. IL-17, HVS-IL-17 | | 5. other $R^c$ |

TABLE 3-continued

Cytokine Receptors Classified by Receptor Code

| Cytokines (ligands) | | Receptor Type | |
|---|---|---|---|
| family | subfamily | family | subfamily |
| II. IL-10 ligands | IL-10, BCRF-1, HSV-IL-10 | II. IL-10 R | |
| III. Interferons | 1. IFN-α1, α2, α4, m, t, IFN-β[d] | III. Interferon R | 1. IFNAR |
| | 2. IFN-γ | | 2. IFNGR |
| IV. IL-1 ligands | 1. IL-1α, IL-1β, IL-1Ra | IV. IL-1R | |
| V. TNF ligands | 1. TNF-α, TNF-β (LT), FAS1, CD40 L, CD30L, CD27 L | V. NGF/TNF R[e] | |
| VI. Chemokines | 1. α chemokines: IL-8, GRO α, β, γ, IF-10, PF-4, SDF-1 | VI. Chemokine R | 1. CXCR |
| | 2. β chemokines: MIP1α, MIP1β, MCP-1, 2, 3, 4, RANTES, eotaxin | | 2. CCR |
| | 3. γ chemokines: lymphotactin | | 3. CR |
| | | | 4. DARC[f] |
| VII. Growth factors | 1.1 SCF, M-CSF, PDGF-AA, AB, BB, FLT-3L, VEGF, SSV-PDGF | VII. RKF | 1. TK sub-family 1.1 IgTK III R |
| | 1.2 FGFα, FGFβ | | 1.2 IgTK IV R |
| | 1.3 EGF, TGF-α, VV-F19 (EGF-like) | | 1.3 Cysteine-rich TK-I |
| | 1.4 IGF-I, IGF-II, Insulin | | 1.4 Cysteine rich TK-II |
| | 1.5 NGF, BDNF, NT-3, NT-4[g] | | 1.5 Cysteine knot TK V |
| | 2. TGF-β1, β2, β3 | | 2. STK subfamily[h] |

[c]IL-17R belongs to the CKR family but is not assigned to any of the 4 indicated subjamilies.
[d]Other IFN type I subtypes remain unassigned. Hematopoietic cytokines, IL-10 ligands and interferons do not possess functional intrinsic protein kinases. The signaling molecules for the cytokines are JAK's, STATs and related non-receptor molecules. IL-14, IL-16 and IL-18 have been cloned but according to the receptor code they remain unassigned.
[e]TNF receptors use multiple, distinct intracellular molecules for signal transduction including "death domain" of FAS R and 55 kDa TNF-αR that participates in their cytotoxic effects. NGF/TNF R can bind both NGF and related factors as well as TNF ligands. Chemokine receptors are G protein-coupled, seven transmembrane (7TM, serpentine) domain receptors.
[f]The Duffy blood group antigen (DARC) is an erythrocyte receptor that can bind several different chemokines. It belongs to the immunoglobulin superfamily but characteristics of its signal transduction events remain unclear.
[g]The neurotrophic cytokines can associate with NGF/TNF receptors also
[h]STKS may encompass many other TGF-β-related factors that remain unassigned. The protein kinases are intrinsic part of the intracellular domain of receptor kinase family (RKF). The enzymes participate in the signals transmission via the receptors.

Exemplary peptides for this invention appear in Tables 4 through 20 below. These peptides may be prepared by methods disclosed in the art. Single letter amino acid abbreviations are used. The X in these sequences (and throughout this specification, unless specified otherwise in a particular instance) means that any of the 20 naturally occurring amino acid residues may be present. Any of these peptides may be linked in tandem (i.e., sequentially), with or without linkers, and a few tandem-linked examples are provided in the table. Linkers are listed as "Λ" and may be any of the linkers described herein. Tandem repeats and linkers are shown separated by dashes for clarity. Any peptide containing a cysteinyl residue may be cross-linked with another Cys-containing peptide, either or both of which may be linked to a vehicle. A few cross-linked examples are provided in the table. Any peptide having more than one Cys residue may form an intrapeptide disulfide bond, as well; see, for example, EPO-mimetic peptides in Table 5. A few examples of intrapeptide disulfide-bonded peptides are specified in the table. Any of these peptides may be derivatized as described herein, and a few derivatized examples are provided in the table. Derivatized peptides in the tables are exemplary rather than limiting, as the associated underivatized peptides may be employed in this invention, as well. For derivatives in which the carboxyl terminus may be capped with an amino group, the capping amino group is shown as —$NH_2$. For derivatives in which amino acid residues are substituted by moieties other than amino acid residues, the substitutions are denoted by σ, which signifies any of the moieties described in Bhatnagar et al. (1996), *J. Med. Chem.* 39: 3814–9 and Cuthbertson et al. (1997), *J. Med. Chem.* 40: 2876–82, which are incorporated by reference. The J substituent and the Z substituents ($Z_5$, $Z_6$, ... $Z_{40}$) are as defined in U.S. Pat. Nos. 5,608,035, 5,786,331, and 5,880,096, which are incorporated by reference. For the EPO-mimetic sequences (Table 5), the substituents $X_2$ through $X_{11}$ and the integer "n" are as defined in WO 96/40772, which is incorporated by reference. The substituents "Ψ," "Θ," and "+" are as defined in Sparks et al. (1996), *Proc. Natl. Acad. Sci.* 93: 1540–4, which is hereby incorporated by reference. $X_4$, $X_5$, $X_6$, and $X_7$ are as defined in U.S. Pat. No. 5,773,569, which is hereby incorporated by reference, except that: for integrin-binding peptides, $X_1$, $X_2$, $X_3$, $X_4$, $X_5$, $X_6$, $X_7$, and $X_8$ are as defined in International applications WO 95/14714, published Jun. 1, 1995 and WO 97/08203, published Mar. 6, 1997, which are also incorporated by reference; and for VIP-mimetic peptides, $X_1$, $X_1'$, $X_1''$, $X_2$, $X_3$, $X_4$, $X_5$, $X_6$ and Z and the integers m and n are as defined in WO 97/40070, published Oct. 30, 1997, which is also incorporated by reference. Xaa and Yaa below are as defined in WO 98/09985, published Mar. 12, 1998, which is incorporated by reference. $AA_1$, $AA_2$, $AB_1$, $AB_2$, and AC are as defined in International application WO 98/53842, published Dec. 3, 1998, which is incorporated by reference. $X^1$, $X^2$, $X^3$, and $X^4$ in Table 17 only are as defined in European application EP 0 911 393, published Apr. 28, 1999. Residues appearing in boldface are D-amino acids. All peptides are linked through peptide bonds unless otherwise noted. Abbreviations are listed at the end of this specification. In the "SEQ ID NO." column, "NR" means that no sequence listing is required for the given sequence.

TABLE 4

IL-1 antagonist peptide sequences

| Sequence/structure | SEQ ID NO: |
|---|---|
| $Z_{11}Z_7Z_8QZ_5YZ_6Z_9Z_{10}$ | 212 |
| XXQZ$_5$YZ$_6$XX | 907 |
| Z$_7$XQZ$_5$YZ$_6$XX | 908 |
| Z$_7$Z$_8$QZ$_5$YZ$_6$Z$_9$Z$_{10}$ | 909 |
| Z$_{11}$Z$_7$Z$_8$QZ$_5$YZ$_6$Z$_9$Z$_{10}$ | 910 |
| Z$_{12}$Z$_{13}$Z$_{14}$Z$_{15}$Z$_{16}$Z$_{17}$Z$_{18}$Z$_{19}$Z$_{20}$Z$_{21}$Z$_{22}$Z$_{11}$Z$_7$Z$_8$QZ$_5$YZ$_6$Z$_9$Z$_{10}$L | 917 |
| Z$_{23}$NZ$_{24}$Z$_{39}$Z$_{25}$Z$_{26}$Z$_{27}$Z$_{28}$Z$_{29}$Z$_{30}$Z$_{40}$ | 979 |
| TANVSSFEWTPYYWQPYALPL | 213 |
| SWTDYGYWQPYALPISGL | 214 |
| ETPFTWEESNAYYWQPYALPL | 215 |
| ENTYSPNWADSMYWQPYALPL | 216 |
| SVGEDHNFWTSEYWQPYALPL | 217 |
| DGYDRWRQSGERYWQPYALPL | 218 |
| FEWTPGYWQPY | 219 |
| FEWTPGYWQHY | 220 |
| FEWTPGWYQJY | 221 |
| AcFEWTPGWYQJY | 222 |

TABLE 4-continued

IL-1 antagonist peptide sequences

| Sequence/structure | SEQ ID NO: |
|---|---|
| FEWTPGWpYQJY | 223 |
| FAWTPGYWQJY | 224 |
| FEWAPGYWQJY | 225 |
| FEWVPGYWQJY | 226 |
| FEWTPGYWQJY | 227 |
| AcFEWTPGYWQJY | 228 |
| FEWTPaWYQJY | 229 |
| FEWTPSarWYQJY | 230 |
| FEWTPGYYQPY | 231 |
| FEWTPGWWQPY | 232 |
| FEWTPNYWQPY | 233 |
| FEWTPvYWQJY | 234 |
| FEWTPecGYWQJY | 235 |
| FEWTPAibYWQJY | 236 |
| FEWTSarGYWQJY | 237 |
| FEWTPGYWQPY | 238 |
| FEWTPGYWQHY | 239 |
| FEWTPGYWQJY | 240 |
| AcFEWTPGYWQJY | 241 |
| FEWTPGW-pY-QJY | 242 |
| FAWTPGYWQJY | 243 |
| FEWAPGYWQJY | 244 |
| FEWVPGYWQJY | 245 |
| FEWTPGYWQJY | 246 |
| AcFEWTPGYWQJY | 247 |
| FEWTPAWYQJY | 248 |
| FEWTPSarWYQJY | 249 |
| FEWTPGYYQPY | 250 |
| FEWTPGWWQPY | 251 |
| FEWTPNYWQPY | 252 |
| FEWTPVYWQJY | 253 |
| FEWTPecGYWQJY | 254 |
| FEWTPAibYWQJY | 255 |
| FEWTSarGYWQJY | 256 |
| FEWTPGYWQPYALPL | 257 |
| 1NapEWTPGYYQJY | 258 |
| YEWTPGYYQJY | 259 |

TABLE 4-continued

IL-1 antagonist peptide sequences

| Sequence/structure | SEQ ID NO: |
|---|---|
| FEWVPGYYQJY | 260 |
| FEWTPSYYQJY | 261 |
| FEWTPNYYQJY | 262 |
| TKPR | 263 |
| RKSSK | 264 |
| RKQDK | 265 |
| NRKQDK | 266 |
| RKQDKR | 267 |
| ENRKQDKRF | 268 |
| VTKFYF | 269 |
| VTKFY | 270 |
| VTDFY | 271 |
| SHLYWQPYSVQ | 671 |
| TLVYWQPYSLQT | 672 |
| RGDYWQPYSVQS | 673 |
| VHVYWQPYSVQT | 674 |
| RLVYWQPYSVQT | 675 |
| SRVWFQPYSLQS | 676 |
| NMVYWQPYSIQT | 677 |
| SVVFWQPYSVQT | 678 |
| TFVYWQPYALPL | 679 |
| TLVYWQPYSIQR | 680 |
| RLVYWQPYSVQR | 681 |
| SPVFWQPYSIQI | 682 |
| WIEWWQPYSVQS | 683 |
| SLIYWQPYSLQM | 684 |
| TRLYWQPYSVQR | 685 |
| RCDYWQPYSVQT | 686 |
| MRVFWQPYSVQN | 687 |
| KIVYWQPYSVQT | 688 |
| RHLYWQPYSVQR | 689 |
| ALVWWQPYSEQI | 690 |
| SRVWFQPYSLQS | 691 |
| WEQPYALPLE | 692 |
| QLVWWQPYSVQR | 693 |
| DLRYWQPYSVQV | 694 |
| ELVWWQPYSLQL | 695 |
| DLVWWQPYSVQW | 696 |
| NGNYWQPYSFQV | 697 |
| ELVYWQPYSIQR | 698 |
| ELMYWQPYSVQE | 699 |
| NLLYWQPYSMQD | 700 |
| GYEWYQPYSVQR | 701 |
| SRVWYQPYSVQR | 702 |
| LSEQYQPYSVQR | 703 |
| GGGWWQPYSVQR | 704 |
| VGRWYQPYSVQR | 705 |
| VHVYWQPYSVQR | 706 |
| QARWYQPYSVQR | 707 |
| VHVYWQPYSVQT | 708 |
| RSVYWQPYSVQR | 709 |
| TRVWFQPYSVQR | 710 |
| GRIWFQPYSVQR | 711 |
| GRVWFQPYSVQR | 712 |
| ARTWYQPYSVQR | 713 |
| ARVWWQPYSVQM | 714 |
| RLMFYQPYSVQR | 715 |
| ESMWYQPYSVQR | 716 |
| HFGWWQPYSVHM | 717 |
| ARFWWQPYSVQR | 718 |
| RLVYWQ PYAPIY | 719 |
| RLVYWQ PYSYQT | 720 |
| RLVYWQ PYSLPI | 721 |
| RLVYWQ PYSVQA | 722 |
| SRVWYQ PYAKGL | 723 |
| SRVWYQ PYAQGL | 724 |
| SRVWYQ PYAMPL | 725 |
| SRVWYQ PYSVQA | 726 |
| SRVWYQ PYSLGL | 727 |
| SRVWYQ PYAREL | 728 |
| SRVWYQ PYSRQP | 729 |
| SRVWYQ PYFVQP | 730 |
| EYEWYQ PYALPL | 731 |
| IPEYWO PYALPL | 732 |

TABLE 4-continued

IL-1 antagonist peptide sequences

| Sequence/structure | SEQ ID NO: |
|---|---|
| SRIWWQ PYALPL | 733 |
| DPLFWQ PYALPL | 734 |
| SRQWVQ PYALPL | 735 |
| IRSWWQ PYALPL | 736 |
| RGYWQ PYALPL | 737 |
| RLLWVQ PYALPL | 738 |
| EYRWFQ PYALPL | 739 |
| DAYWVQ PYALPL | 740 |
| WSGYFQ PYALPL | 741 |
| NIEFWQ PYALPL | 742 |
| TRDWVQ PYALPL | 743 |
| DSSWYQ PYALPL | 744 |
| IGNWYQ PYALPL | 745 |
| NLRWDQ PYALPL | 746 |
| LPEFWQ PYALPL | 747 |
| DSYWQ PYALPL | 748 |
| RSQYYQ PYALPL | 749 |
| ARFWLQ PYALPL | 750 |
| NSYFWQ PYALPL | 751 |
| RFMYWQPYSVQR | 752 |
| AHLFWQPYSVQR | 753 |
| WWQPYALPL | 754 |
| YYQPYALPL | 755 |
| YFQPYALGL | 756 |
| YWYQPYALPL | 757 |
| RWWQPYATPL | 758 |
| GWYQPYALGF | 759 |
| YWYQPYALGL | 760 |
| IWYQPYAMPL | 761 |
| SNMQPYQRLS | 762 |
| TFVYWQPY AVGLPAAETACN | 763 |
| TFVYWQPY SVQMTITGKVTM | 764 |
| TFVYWQPY SSHXXVPXGFPL | 765 |
| TFVYWQPY YGNPQWAIHVRH | 766 |
| TFVYWQPY VLLELPEGAVRA | 767 |
| TFVYWQPY VDYVWPIPIAQV | 768 |
| GWYQPYVDGWR | 769 |

TABLE 4-continued

IL-1 antagonist peptide sequences

| Sequence/structure | SEQ ID NO: |
|---|---|
| RWEQPYVKDGWS | 770 |
| EWYQPYALGWAR | 771 |
| GWWQPYARGL | 772 |
| LFEQPYAKALGL | 773 |
| GWEQPYARGLAG | 774 |
| AWVQPYATPLDE | 775 |
| MWYQPYSSQPAE | 776 |
| GWTQPYSQQGEV | 777 |
| DWFQPYSIQSDE | 778 |
| PWIQPYARGFG | 779 |
| RPLYWQPYSVQV | 780 |
| TLIYWQPYSVQI | 781 |
| RFDYWQPYSDQT | 782 |
| WHQFVQPYALPL | 783 |
| EWDS VYWQPYSVQ TLLR | 784 |
| WEQN VYWQPYSVQ SFAD | 785 |
| SDV VYWQPYSVQ SLEM | 786 |
| YYDG VYWQPYSVQ VMPA | 787 |
| SDIWYQ PYALPL | 788 |
| QRIWWQ PYALPL | 789 |
| SRIWWQ PYALPL | 790 |
| RSLYWQ PYALPL | 791 |
| TIIWEQ PYALPL | 792 |
| WETWYQ PYALPL | 793 |
| SYDWEQ PYALPL | 794 |
| SRIWCQ PYALPL | 795 |
| EIMFWQ PYALPL | 796 |
| DYVWQQ PYALPL | 797 |
| MDLLVQ WYQPYALPL | 798 |
| GSKVIL WYQPYALPL | 799 |
| RQGANI WYQPYALPL | 800 |
| GGGDEP WYQPYALPL | 801 |
| SQLERT WYQPYALPL | 802 |
| ETWVRE WYQPYALPL | 803 |
| KKGSTQ WYQPYALPL | 804 |
| LQARMN WYQPYALPL | 805 |
| EPRSQK WYQPYALPL | 806 |

TABLE 4-continued

IL-1 antagonist peptide sequences

| Sequence/structure | SEQ ID NO: |
|---|---|
| VKQKWR WYQPYALPL | 807 |
| LRRHDV WYQPYALPL | 808 |
| RSTASI WYQPYALPL | 809 |
| ESKEDQ WYQPYALPL | 810 |
| EGLTMK WYQPYALPL | 811 |
| EGSREG WYQPYALPL | 812 |
| VIEWWQ PYALPL | 813 |
| VWYWEQ PYALPL | 814 |
| ASEWWQ PYALPL | 815 |
| FYEWWQ PYALPL | 816 |
| EGWWVQ PYALPL | 817 |
| WGEWLQ PYALPL | 818 |
| DYVWEQ PYALPL | 819 |
| AHTWWQ PYALPL | 820 |
| FIEWFQ PYALPL | 821 |
| WLAWEQ PYALPL | 822 |
| VMEWWQ PYALPL | 823 |
| ERMWQ PYALPL | 824 |
| NXXWXX PYALPL | 825 |
| WGNWYQ PYALPL | 826 |
| TLYWEQ PYALPL | 827 |
| VWRWEQ PYALPL | 828 |
| LLWTQ PYALPL | 829 |
| SRIWXX PYALPL | 830 |
| SDIWYQ PYALPL | 831 |
| WGYYXX PYALPL | 832 |
| TSGWYQ PYALPL | 833 |
| VHPYXX PYALPL | 834 |
| EHSYFQ PYALPL | 835 |
| XXIWYQ PYALPL | 836 |
| AQLHSQ PYALPL | 837 |
| WANWFQ PYALPL | 838 |
| SRLYSQ PYALPL | 839 |
| GVTFSQ PYALPL | 840 |
| SIVWSQ PYALPL | 841 |
| SRDLVQ PYALPL | 842 |
| HWGH VYWQPYSVQ DDLG | 843 |

TABLE 4-continued

IL-1 antagonist peptide sequences

| Sequence/structure | SEQ ID NO: |
|---|---|
| SWHS VYWQPYSVQ SVPE | 844 |
| WRDS VYWQPYSVQ PESA | 845 |
| TWDA VYWQPYSVQ KWLD | 846 |
| TPPW VYWQPYSVQ SLDP | 847 |
| YWSS VYWQPYSVQ SVHS | 848 |
| YWY QPY ALGL | 849 |
| YWY QPY ALPL | 850 |
| EWI QPY ATGL | 851 |
| NWE QPY AKPL | 852 |
| AFY QPY ALPL | 853 |
| FLY QPY ALPL | 854 |
| VCK QPY LEWC | 855 |
| ETPFTWEESNAYYWQPYALPL | 856 |
| QGWLTWQDSVDMYWQPYALPL | 857 |
| FSEAGYTWPENTYWQPYALPL | 858 |
| TESPGGLDWAKIYWQPYALPL | 859 |
| DGYDRWRQSGERYWQPYALPL | 860 |
| TANVSSFEWTPGYWQPYALPL | 861 |
| SVGEDHNFWTSE YWQPYALPL | 862 |
| MNDQTSEVSTFP YWQPYALPL | 863 |
| SWSEAFEQPRNL YWQPYALPL | 864 |
| QYAEPSALNDWG YWQPYALPL | 865 |
| NGDWATADWSNY YWQPYALPL | 866 |
| THDEHI YWQPYALPL | 867 |
| MLEKTYTTWTPG YWQPYALPL | 868 |
| WSDPLTRDADL YWQPYALPL | 869 |
| SDAFTTQDSQAM YWQPYALPL | 870 |
| GDDAAWRTDSLT YWQPYALPL | 871 |
| AIIRQLYRWSEM YWQPYALPL | 872 |
| ENTYSPNWADSM YWQPYALPL | 873 |
| MNDQTSEVSTFP YWQPYALPL | 874 |
| SVGEDHNFWTSE YWQPYALPL | 875 |
| QTPFTWEESNAY YWQPYALPL | 876 |
| ENPFTWQESNAY YWQPYALPL | 877 |
| VTPFTWEDSNVF YWQPYALPL | 878 |
| QIPFTWEQSNAY YWQPYALPL | 879 |
| QAPLTWQESAAY YWQPYALPL | 880 |

TABLE 4-continued
IL-1 antagonist peptide sequences

| Sequence/structure | SEQ ID NO: |
|---|---|
| EPTFTWEESKAT YWQPYALPL | 881 |
| TTTLTWEESNAY YWQPYALPL | 882 |
| ESPLTWEESSAL YWQPYALPL | 883 |
| ETPLTWEESNAY YWQPYALPL | 884 |
| EATFTWAESNAY YWQPYALPL | 885 |
| EALFTWKESTAY YWQPYALPL | 886 |
| STP-TWEESNAY YWQPYALPL | 887 |
| ETPFTWEESNAY YWQPYALPL | 888 |
| KAPFTWEESQAY YWQPYALPL | 889 |
| STSFTWEESNAY YWQPYALPL | 890 |
| DSTFTWEESNAY YWQPYALPL | 891 |
| YIPFTWEESNAY YWQPYALPL | 892 |
| QTAFTWEESNAY YWQPYALPL | 893 |
| ETLFTWEESNAT YWQPYALPL | 894 |
| VSSFTWEESNAY YWQPYALPL | 895 |
| QPYALPL | 896 |
| Py-1-NapPYQJYALPL | 897 |
| TANVSSFEWTPG YWQPYALPL | 898 |
| FEWTPGYWQPYALPL | 899 |
| FEWTPGYWQJYALPL | 900 |
| FEWTPGYYQJYALPL | 901 |
| ETPFTWEESNAYYWQPYALPL | 902 |
| FTWEESNAYYWQJYALPL | 903 |
| ADVL YWQPYA PVTLWV | 904 |
| GDVAE YWQPYA LPLTSL | 905 |
| SWTDYG YWQPYA LPISGL | 906 |
| FEWTPGYWQPYALPL | 911 |
| FEWTPGYWQJYALPL | 912 |
| FEWTPGWYQPYALPL | 913 |
| FEWTPGWYQJYALPL | 914 |
| FEWTPGYYQPYALPL | 915 |
| FEWTPGYYQJYALPL | 916 |
| TANVSSFEWTPGYWQPYALPL | 918 |
| SWTDYGYWQPYALPISGL | 919 |
| ETPFTWEESNAYYWQPYALPL | 920 |
| ENTYSPNWADSMYWQPYALPL | 921 |
| SVGEDHNFWTSEYWQPYALPL | 922 |
| DGYDRWRQSGERYWQPYALPL | 923 |
| FEWTPGYWQPYALPL | 924 |
| FEWTPGYWQPY | 925 |
| FEWTPGYWQJY | 926 |
| EWTPGYWQPY | 927 |
| FEWTPGWYQJY | 928 |
| AEWTPGYWQJY | 929 |
| FAWTPGYWQJY | 930 |
| FEATPGYWQJY | 931 |
| FEWAPGYWQJY | 932 |
| FEWTAGYWQJY | 933 |
| FEWTPAYWQJY | 934 |
| FEWTPGAWQJY | 935 |
| FEWTPGYAQJY | 936 |
| FEWTPGYWQJA | 937 |
| FEWTGGYWQJY | 938 |
| FEWTPGYWQJY | 939 |
| FEWTJGYWQJY | 940 |
| FEWTPecGYWQJY | 941 |
| FEWTPAibYWQJY | 942 |
| FEWTPSarWYQJY | 943 |
| FEWTSarGYWQJY | 944 |
| FEWTPNYWQJY | 945 |
| FEWTPVYWQJY | 946 |
| FEWTVPYWQJY | 947 |
| AcFEWTPGWYQJY | 948 |
| AcFEWTPGYWQJY | 949 |
| lNap-EWTPGYYQJY | 950 |
| YEWTPGYYQJY | 951 |
| FEWVPGYYQJY | 952 |
| FEWTPGYYQJY | 953 |
| FEWTPsYYQJY | 954 |
| FEWTPnYYQJY | 955 |
| SHLY-Nap-QPYSVQM | 956 |
| TLVY-Nap-QPYSLQT | 957 |
| RGDY-Nap-QPYSVQS | 958 |
| NMVY-Nap-QPYSIQT | 959 |

TABLE 4-continued

IL-1 antagonist peptide sequences

| Sequence/structure | SEQ ID NO: |
|---|---|
| VYWQPYSVQ | 960 |
| VY-Nap-QPYSVQ | 961 |
| TFVYWQJYALPL | 962 |
| FEWTPGYYQJ-Bpa | 963 |
| XaaFEWTPGYYQJ-Bpa | 964 |
| FEWTPGY-Bpa-QJY | 965 |
| AcFEWTPGY-Bpa-QJY | 966 |
| FEWTPG-Bpa-YQJY | 967 |
| AcFEWTPG-Bpa-YQJY | 968 |
| AcFE-Bpa-TPGYYQJY | 969 |
| AcFE-Bpa-TPGYYQJY | 970 |
| Bpa-EWTPGYYQJY | 971 |
| AcBpa-EWTPGYYQJY | 972 |
| VYWQPYSVQ | 973 |
| RLVYWQPYSVQR | 974 |
| RLVY-Nap-QPYSVQR | 975 |
| RLDYWQPYSVQR | 976 |
| RLVWFQPYSVQR | 977 |
| RLVYWQPYSIQR | 978 |
| DNSSWYDSFLL | 980 |
| DNTAWYESFLA | 981 |
| DNTAWYENFLL | 982 |
| PARE DNTAWYDSFLI WC | 983 |
| TSEY DNTTWYEKFLA SQ | 984 |
| SQIP DNTAWYQSFLL HG | 985 |
| SPFI DNTAWYENFLL TY | 986 |
| EQIY DNTAWYDHFLL SY | 987 |
| TPFI DNTAWYENFLL TY | 988 |
| TYTY DNTAWYERFLM SY | 989 |
| TMTQ DNTAWYENFLL SY | 990 |
| TI DNTAWYANLVQ TYPQ | 991 |
| TI DNTAWYERFLA QYPO | 992 |
| HI DNTAWYENFLL TYTP | 993 |
| SQ DNTAWYENFLL SYKA | 994 |
| QI DNTAWYERFLL QYNA | 995 |
| NQ DNTAWYESFLL QYNT | 996 |
| TI DNTAWYENFLL NHNL | 997 |
| HY DNTAWYERFLQ QGWH | 998 |
| ETPFTWEESNAYYWQPYALPL | 999 |
| YIPFTWEESNAYYWQPYALPL | 1000 |
| DGYDRWRQSGERYWQPYALPL | 1001 |
| pY-lNap-pY-QJYALPL | 1002 |
| TANVSSFEWTPGYWQPYALPL | 1003 |
| FEWTPGYWQJYALPL | 1004 |
| FEWTPGYWQPYALPLSD | 1005 |
| FEWTPGYYQJYALPL | 1006 |
| FEWTPGYWQJY | 1007 |
| AcFEWTPGYWQJY | 1008 |
| AcFEWTPGWYQJY | 1009 |
| AcFEWTPGYYQJY | 1010 |
| AcFEWTPaYWQJY | 1011 |
| AcFEWTPaWYQJY | 1012 |
| AcFEWTPaYYQJY | 1013 |
| FEWTPGYYQJYALPL | 1014 |
| FEWTPGYWQJYALPL | 1015 |
| FEWTPGWYQJYALPL | 1016 |
| TANVSSFEWTPGYWQPYALPL | 1017 |
| AcFEWTPGYWQJY | 1018 |
| AcFEWTPGWYQJY | 1019 |
| AcFEWTPGYYQJY | 1020 |
| AcFEWTPAYWQJY | 1021 |
| AcFEWTPAWYQJY | 1022 |
| AcFEWTPAYYQJY | 1023 |

TABLE 5

EPO-mimetic peptide sequences

| Sequence/structure | SEQ ID NO: |
|---|---|
| YXCXXG PXTWXCXP | 83 |
| YXCXXGPXTWXCXP-YXCXXGPXTWXCXP | 84 |
| YXCXXG PXTWXCXP-Λ-YXCXXG PXTWXCXP | 85 |
| YXCXXGPXTWXCXP-Λ-\(ε-amine)<br>\\<br>\\<br>K<br>/ | 86 |

TABLE 5-continued

EPO-mimetic peptide sequences

| Sequence/structure | SEQ ID NO: |
|---|---|
| YXCXXGPXTWXCXP-Λ-<br>  / (α-amine)<br> βA<br>GGTYSCHFGPLTWVCKPQG | 86 |
| GGTYSCHFGPLTWVCKPQGG | 87 |
| GGDYHCRMGPLTWVCKPLGG | 88 |
| GGVYACRMGPITWVCSPLGG | 89 |
| YGNYMCHFGPITWVCRPGGG | 90 |
| GGLYLCRFGPVTWDCGYKGG | 91 |
| GGTYSCHFGPLTWVCKPQGG- | 92 |
| GGTYSCHFGPLTWVCKPQGG | |
| GGTYSCHFGPLTWVCKPQGG-Λ-<br>GGTYSCHFGPLTWVCKPQGG | 93 |
| GGTYSCHFGPLTWVCKPQGGSSK | 94 |
| GGTYSCHFGPLTWVCKPQGGSSK-<br>GGTYSCHFGPLTWVCKPQGGSSK | 95 |
| GGTYSCHFGPLTWVCKPQGGSSK-Λ-<br>GGTYSCHFGPLTWVCKPQGGSSK | 96 |
| GGTYSCHFGPLTWVCKPQGGSS<br>  \ (ε-amine)<br>   \<br>    \<br>     K<br>    /<br>   βA<br>  / (α-amine)<br>GGTYSCHFGPLTWVCKPQGGSS | 97<br><br><br><br><br><br>97 |
| GGTYSCHFGPLTWVCKPQGGSSK(-Λ-biotin) | 98 |
| $CX_4X_5GPX_6TWX_7C$ | 421 |
| GGTYSCHGPLTWVCKPQGG | 422 |
| VGNYMAHMGPITWVCRPGG | 423 |
| GGPHHVYACRMGPLTWIC | 424 |
| GGTYSCHFGPLTWVCKPQ | 425 |
| GGLYACHMGPMTWVCQPLRG | 426 |
| TIAQYICYMGPETWECRPSPKA | 427 |
| YSCHFGPLTWVCK | 428 |
| YCHFGPLTWVC | 429 |
| $X_3X_4X_5GPX_6TWX_7X_8$ | 124 |
| $YX_2X_3X_4X_5GPX_6TWX_7X_8$ | 461 |
| $X_1YX_2X_3X_4X_5GPX_6TWX_7X_8X_9X_{10}X_{11}$ | 419 |
| $X_1YX_2CX_4X_5GPX_6TWX_7CX_9X_{10}X_1$ | 420 |
| GGLYLCRFGPVTWDCGYKGG | 1024 |
| GGTYSCHFGPLTWVCKPQGG | 1025 |
| GGDYHCRMGPLTWVCKPLGG | 1026 |
| VGNYMCHFGPITWVCRPGGG | 1029 |
| GGVYACRMGPITWVCSPLGG | 1030 |
| VGNYMAHMGPITWVCRPGG | 1035 |
| GGTYSCHFGPLTWVCKPQ | 1036 |
| GGLYACHMGPMTWVCQPLRG | 1037 |
| TIAQYICYMGPETWECRPSPKA | 1038 |
| YSCHFGPLTWVCK | 1039 |
| YCHFGPLTWVC | 1040 |
| SCHFGPLTWVCK | 1041 |
| $(AX_2)_nX_3X_4X_5GPX_6TWX_7X_8$ | 1042 |

TABLE 6

TPO-mimetic peptide sequences

| Sequence/structure | SEQ ID NO: |
|---|---|
| IEGPTLRQWLAARA | 13 |
| IEGPTLRQWLAAKA | 24 |
| IEGPTLREWLAARA | 25 |
| IEGPTLRQWLAARA-Λ-IEGPTLRQWLAARA | 26 |
| IEGPTLRQWLAAKA-Λ-IEGPTLRQWLAAKA | 27 |
| IEGPTLRQCLAARA-Λ-IEGPTLRQCLAARA | 28 |
| IEGPTLRQWLAARA-Λ-K(BrAc)-Λ-IEGPTLRQWLAARA | 29 |
| IEGPTLRQWLAARA-Λ-K(PEG)-Λ-IEGPTLRQWLAARA | 30 |
| IEGPTLRQCLAARA-Λ-IEGPTLRQWLAARA | 31 |
| IEGPTLRQCLAARA-Λ-IEGPTLRQWLAARA | 31 |
| IEGPTLRQWLAARA-Λ-IEGPTLRQCLAARA | 32 |
| IEGPTLRQWLAARA-Λ-IEGPTLRQCLAARA | 32 |
| VRDQIXXXL | 33 |
| TLREWL | 34 |
| GRVRDQVAGW | 35 |
| GRVKDQIAQL | 36 |
| GVRDQVSWAL | 37 |
| ESVREQVMKY | 38 |
| SVRSQISASL | 39 |
| GVRETVYRHM | 40 |
| GVREVIVMHML | 41 |

TABLE 6-continued

TPO-mimetic peptide sequences

| Sequence/structure | SEQ ID NO: |
|---|---|
| GRVRDQIWAAL | 42 |
| AGVRDQILIWL | 43 |
| GRVRDQIMLSL | 44 |
| GRVRDQI(X)$_5$L | 45 |
| CTLRQWLQGC | 46 |
| CTLQEFLEGC | 47 |
| CTRTEWLHGC | 48 |
| CTLREWLHGGFC | 49 |
| CTLREWVFAGLC | 50 |
| CTLRQWLILLGMC | 51 |
| CTLAEFLASGVEQC | 52 |
| CSLQEFLSHGGYVC | 53 |
| CTLREFLDPTTAVC | 54 |
| CTLKEWLVSHEVWC | 55 |
| CTLREWL(X)$_{2-6}$C | 56–60 |
| REGPTLRQWM | 61 |
| EGPTLRQWLA | 62 |
| ERGPFWAKAC | 63 |
| REGPRCVMWM | 64 |
| CGTEGPTLSTWLDC | 65 |
| CEQDGPTLLEWLKC | 66 |
| CELVGPSLMSWLTC | 67 |
| CLTGPFVTQWLYEC | 68 |
| CRAGPTLLEWLTLC | 69 |
| CADGPTLREWISFC | 70 |
| C(X)$_{1-2}$EGPTLREWL(X)$_{1-2}$C | 71–74 |
| GGCTLREWLHGGFCGG | 75 |
| GGCADGPTLREWISFCGG | 76 |
| GNADGPTLRQWLEGRRPKN | 77 |
| LAIEGPTLRQWLHGNGRDT | 78 |
| HGRVGPTLREWKTQVATKK | 79 |
| TIKGPTLRQWLKSREHTS | 80 |
| ISDGPTLKEWLSVTRGAS | 81 |
| SIEGPTLREWLTSRTPHS | 82 |

TABLE 7

G-CSF-mimetic peptide sequences

| Sequence/structure | SEQ ID NO: |
|---|---|
| EEDCK | 99 |
| EEDCK\|EEDCK | 99 |
| EEDσK | 100 |
| EEDσK\|EEDσJK | 100 |
| pGluEDσK | 101 |
| pGluEDσK\|pGluEDσK | 101 |
| PicSDσK | 102 |
| PicSDσK\|PicSDσK | 102 |
| EEDCK-Λ-EEDCK | 103 |
| EEDXK-Λ-EEDXK | 104 |

TABLE 8

TNF-antagonist peptide sequences

| Sequence/structure | SEQ ID NO: |
|---|---|
| YCFTASENHCY | 106 |
| YCFTNSENHCY | 107 |
| YCFTRSENHCY | 108 |
| FCASENHCY | 109 |
| YCASENHCY | 110 |
| FCNSENHCY | 111 |
| FCNSENRCY | 112 |
| FCNSVENRCY | 113 |
| YCSQSVSNDCF | 114 |
| FCVSNDRCY | 115 |
| YCRKELGQVCY | 116 |
| YCKEPGQCY | 117 |
| YCRKEMGCY | 118 |
| FCRKEMGCY | 119 |
| YCWSQNLCY | 120 |
| YCELSQYLCY | 121 |
| YCWSQNYCY | 122 |
| YCWSQYLCY | 123 |

TABLE 8-continued

TNF-antagonist peptide sequences

| Sequence/structure | SEQ ID NO: |
|---|---|
| DFLPHYKNTSLGHRP | 1085 |
| $AA_1$-$AB_1$<br>\\<br>AC<br>/<br>$AA_2$-$AB_2$ | NR |

TABLE 9

Integrin-binding peptide sequences

| Sequence/structure | SEQ ID NO: |
|---|---|
| $RX_1ETX_2WX_3$ | 441 |
| $RX_1ETX_2WX_3$ | 442 |
| RGDGX | 443 |
| CRGDGXC | 444 |
| $CX_1X_2RLDX_3X_4C$ | 445 |
| CARRLDAPC | 446 |
| CPSRLDSPC | 447 |
| $X_1X_2X_3RGDX_4X_5X_6$ | 448 |
| $CX_2CRGDCX_5C$ | 449 |
| CDCRGDCFC | 450 |
| CDCRGDCLC | 451 |
| CLCRGDCIC | 452 |
| $X_1X_2DDX_4X_5X_7X_8$ | 453 |
| $X_1X_2X_3DDX_4X_5X_6X_7X_8$ | 454 |
| CWDDGWLC | 455 |
| CWDDLWWLC | 456 |
| CWDDGLMC | 457 |
| CWDDGWMC | 458 |
| CSWDDGWLC | 459 |
| CPDDLWWLC | 460 |
| NGR | NR |
| GSL | NR |
| RGD | NR |
| CGRECPRLCQSSC | 1071 |
| CNGRCVSGCAGRC | 1072 |
| CLSGSLSC | 1073 |
| RGD | NR |
| NGR | NR |

TABLE 9-continued

Integrin-binding peptide sequences

| Sequence/structure | SEQ ID NO: |
|---|---|
| GSL | NR |
| NGRAHA | 1074 |
| CNGRC | 1075 |
| CDCRGDCFC | 1076 |
| CGSLVRC | 1077 |
| DLXXL | 1043 |
| RTDLDSLRTYTL | 1044 |
| RTDLDSLRTY | 1053 |
| RTDLDSLRT | 1054 |
| RTDLDSLR | 1078 |
| GDLDLLKLRLTL | 1079 |
| GDLHSLRQLLSR | 1080 |
| RDDLHMLRLQLW | 1081 |
| SSDLHALKKRYG | 1082 |
| RGDLKQLSELTW | 1083 |
| RGDLAALSAPPV | 1084 |

TABLE 10

Selectin antagonist peptide sequences

| Sequence/structure | SEQ ID NO: |
|---|---|
| DITWDQLWDLMK | 147 |
| DITWDELWKIMN | 148 |
| DYTWFELWDMMQ | 149 |
| QITWAQLWNMMK | 150 |
| DMTWHDLWTLMS | 151 |
| DYSWHDLWEMMS | 152 |
| EITWDQLWEVMN | 153 |
| HVSWEQLWDIMN | 154 |
| HITWDQLWRIMT | 155 |
| RNMSWLELWEHMK | 156 |
| AEWTWDQLWHVMNPAESQ | 157 |
| HRAEWLALWEQMSP | 158 |
| KKEDWLALWRIMSV | 159 |
| ITWDQLWDLMK | 160 |
| DITWDQLWDLMK | 161 |
| DITWDQLWDLMK | 162 |

TABLE 10-continued
Selectin antagonist peptide sequences

| Sequence/structure | SEQ ID NO: |
| --- | --- |
| DITWDQLWDLMK | 163 |
| CQNRYTDLVAIQNKNE | 462 |
| AENWADNEPNNKRNNED | 463 |
| RKNNKTWTWVGTKKALTNE | 464 |
| KKALTNEAENWAD | 465 |
| CQXRYTDLVAIQNKXE | 466 |
| RKXNXXWTWVGTXKXLTEE | 467 |
| AENWADGEPNNKXNXED | 468 |
| CXXXYTXLVAIQNKXE | 469 |
| RKXXXXWXWVGTXKXLTXE | 470 |
| AXNWXXXEPNNXXXED | 471 |
| XKXKTXEAXNWXX | 472 |

TABLE 11
Antipathogenic peptide sequences

| Sequence/structure | SEQ ID NO: |
| --- | --- |
| GFFALIPKIISSPLFKTLLSAVGSALSSSGGQQ | 503 |
| GFFALIPKIISSPLFKTLLSAVGSALSSSGGQE | 504 |
| GFFALIPKIISSPLFKTLLSAV | 505 |
| GFFALIPKIISSPLFKTLLSAV | 506 |
| KGFFALIPKIISSPLFKTLLSAV | 507 |
| KKGFFALIPKIISSPLFKTLLSAV | 508 |
| KKGFFALIPKIISSPLFKTLLSAV | 509 |
| GFFALIPKIIS | 510 |
| GIGAVLKVLTTGLPALISWIKRKRQQ | 511 |
| GIGAVLKVLTTGLPALISWIKRKRQQ | 512 |
| GIGAVLKVLTTGLPALISWIKRKRQQ | 513 |
| GIGAVLKVLTTGLPALISWIKR | 514 |
| AVLKVLTTGLPALISWIKR | 515 |
| KLLLLLKLLLLK | 516 |
| KLLLKLLLKLLK | 517 |
| KLLLKLKLKLLK | 518 |
| KKLLKLKLKLKK | 519 |
| KLLLKLLLKLLK | 520 |
| KLLLKLKLKLLK | 521 |
| KLLLLK | 522 |

TABLE 11-continued
Antipathogenic peptide sequences

| Sequence/structure | SEQ ID NO: |
| --- | --- |
| KLLLKLLK | 523 |
| KLLLKLKLKLLK | 524 |
| KLLLKLKLKLLK | 525 |
| KLLLKLKLKLLK | 526 |
| KAAAKAAAKAAK | 527 |
| KVVKVVVKVVK | 528 |
| KVVKVKVKVK | 529 |
| KVVKVKVKVK | 530 |
| KVVKVKVKVVK | 531 |
| KLILKL | 532 |
| KVLHLL | 533 |
| LKLRLL | 534 |
| KPLHLL | 535 |
| KLILKLVR | 536 |
| KVFHLLHL | 537 |
| HKFRILKL | 538 |
| KPFHILHL | 539 |
| KIIIKIKIKIIK | 540 |
| KIIIKIKIKIIK | 541 |
| KIIIKIKIKIIK | 542 |
| KIPIKIKIKIPK | 543 |
| KIPIKIKIKIVK | 544 |
| RIIIRIRIRIIR | 545 |
| RIIIRIRIRIIR | 546 |
| RIIIRIRIRIIR | 547 |
| RIVIRIRIRLIR | 548 |
| RIIVRIRLRIIR | 549 |
| RIGIRLRVRIIR | 550 |
| KIVIRIRIRLIR | 551 |
| RIAVKWRLRFIK | 552 |
| KIGWKLRVRIIR | 553 |
| KKIGWLIIRVRR | 554 |
| RIVIRIRIRLIRIR | 555 |
| RIIVRIRLRIIRVR | 556 |
| RIGIRLRVRIIRRV | 557 |
| KIVIRIRARLIRIRIR | 558 |
| RIIVKIRLRIIKKIRL | 559 |

TABLE 11-continued

Antipathogenic peptide sequences

| Sequence/structure | SEQ ID NO: |
|---|---|
| KIGIKARVRIIRVKII | 560 |
| RIIVHIRLRIIHHIRL | 561 |
| HIGIKAHVRIIRVHII | 562 |
| RIYVKIHLRYIKKIRL | 563 |
| KIGHKARVHIIRYKII | 564 |
| RIYVKPHPRYIKKIRL | 565 |
| KPGHKARPHIIRYKII | 566 |
| KIVIRIRIRLIRIRIRKIV | 567 |
| RIIVKIRLRIIKKIRLIKK | 568 |
| KIGWKLRVRIIRVKIGRLR | 569 |
| KIVIRIRIRLIRIRIRKIVKVKRIR | 570 |
| RFAVKIRLRIIKKIRLIKKIRKRVIK | 571 |
| KAGWKLRVRIIRVKIGRLRKIGWKKRVRIK | 572 |
| RIYVKPHPRYIKKIRL | 573 |
| KPGHKARPHIIRYKII | 574 |
| KIVIRIRIRLIRIRIRKIV | 575 |
| RIIVKIRLRIIKKIRLIKK | 576 |
| RIYVSKISIYIKKIRL | 577 |
| KIVIFTRIRLTSIRIRSIV | 578 |
| KPIHKARPTIIRYKMI | 579 |
| cyclicCKGFFALIPKIISSPLFKTLLSAVC | 580 |
| CKKGFFALIPKIISSPLFKTLLSAVC | 581 |
| CKKKGFFALIPKIISSPLFKTLLSAVC | 582 |
| CyclicCAIVIRIRIRLIRIRC | 583 |
| CyclicCKPGHKARPHIIRYKIIC | 584 |
| CyclicCRFAVKIRLRIIKKIRLIKKIRKRVIKC | 585 |
| KLLLKLLLKLLKC | 586 |
| KLLLKLLLKLLK | 587 |
| KLLLKLKLKLLKC | 588 |
| KLLLKLLLKLLK | 589 |

TABLE 12

VIP-mimetic peptide sequences

| Sequence/structure | SEQ ID NO: |
|---|---|
| HSDAVFYDNYTR LRKQMAVKKYLN SILN | 590 |
| Nle HSDAVFYDNYTR LRKQMAVKKYLN SILN | 591 |
| $X_1X_1'X_1''X_2$ | 592 |
| $X_3SX_4LN$ | 593 |
| NH CH CO KKYX5 NH CH CO X6<br>       |                 |<br>  (CH2)m____Z____(CH2)n | 594 |
| KKYL | 595 |
| NSILN | 596 |
| KKYL | 597 |
| KKYA | 598 |
| AVKKYL | 599 |
| NSILN | 600 |
| KKYV | 601 |
| SILauN | 602 |
| KKYLNIe | 603 |
| NSYLN | 604 |
| NSIYN | 605 |
| KKYLPPNSILN | 606 |
| LauKKYL | 607 |
| CapKKYL | 608 |
| KYL | NR |
| KKYNIe | 609 |
| VKKYL | 610 |
| LNSILN | 611 |
| YLNSILN | 612 |
| KKYLN | 613 |
| KKYLNS | 614 |
| KKYLNSI | 615 |
| KKYLNSIL | 616 |
| KKYL | 617 |
| KKYDA | 618 |
| AVKKYL | 619 |
| NSILN | 620 |
| KKYV | 621 |
| SILauN | 622 |
| NSYLN | 623 |
| NSIYN | 624 |
| KKYLNIe | 625 |
| KKYLPPNSILN | 626 |

TABLE 12-continued

VIP-mimetic peptide sequences

| Sequence/structure | SEQ ID NO: |
|---|---|
| KKYL | 627 |
| KKYDA | 628 |
| AVKKYL | 629 |
| NSILN | 630 |
| KKYV | 631 |
| SILauN | 632 |
| LauKKYL | 633 |
| CapKKYL | 634 |
| KYL | NR |
| KYL | NR |
| KKYNle | 635 |
| VKKYL | 636 |
| LNSILN | 637 |
| YLNSILN | 638 |
| KKYLNle | 639 |
| KKYLN | 640 |
| KKYLNS | 641 |
| KKYLNSI | 642 |
| KKYLNSIL | 643 |
| KKKYLD | 644 |
| cyclicCKKYLC | 645 |
| CKKYLK<br>\|    \\<br>S-CH$_2$-CO | 646 |
| KKYA | 647 |
| WWTDTGLW | 648 |
| WWTDDGLW | 649 |
| WWDTRGLWVWTI | 650 |
| FWGNDGLWLESG | 651 |
| DWDQFGLWRGAA | 652 |
| RWDDNGLWVWL | 653 |
| SGMWSHYGIWMG | 654 |
| GGRWDQAGLWVA | 655 |
| KLWSEQGIWMGE | 656 |
| CWSMHGLWLC | 657 |
| GCWDNTGIWVPC | 658 |
| DWDTRGLWVY | 659 |
| SLWDENGAWI | 660 |

TABLE 12-continued

VIP-mimetic peptide sequences

| Sequence/structure | SEQ ID NO: |
|---|---|
| KWDDRGLWMH | 661 |
| QAWNERGLWT | 662 |
| QWDTRGLWVA | 663 |
| WNVHGIWQE | 664 |
| SWDTRGLWVE | 665 |
| DWDTRGLWVA | 666 |
| SWGRDGLWIE | 667 |
| EWTDNGLWAL | 668 |
| SWDEKGLWSA | 669 |
| SWDSSGLWMD | 670 |

TABLE 13

Mdm/hdm antagonist peptide sequences

| Sequence/structure | SEQ ID NO: |
|---|---|
| TFSDLW | 130 |
| QETFSDLWKLLP | 131 |
| QPTFSDLWKLLP | 132 |
| QETFSDYWKLLP | 133 |
| QPTFSDYWKLLP | 134 |
| MPRFMDYWEGLN | 135 |
| VQNFIDYWTQQF | 136 |
| TGPAFTHYWATF | 137 |
| IDRAPTFRDHW-FALV | 138 |
| PRPALVFADY-WETLY | 139 |
| PAFSRFWSDLSA-GAH | 140 |
| PAFSRFWSKLSA-GAH | 141 |
| PXFXDYWXXL | 142 |
| QETFSDLWKLLP | 143 |
| QPTFSDLWKLLP | 144 |
| QETFSDYWKLLP | 145 |
| QPTFSDYWKLLP | 146 |

TABLE 14

Calmodulin antagonist peptide sequences

| Sequence/structure | SEQ ID NO: |
|---|---|
| SCVKWGKKEFCGS | 164 |
| SCWKYWGKECGS | 165 |
| SCYEWGKLRWCGS | 166 |
| SCLRWGKWSNCGS | 167 |
| SCWRWGKYQICGS | 168 |
| SCVSWGALKLCGS | 169 |
| SCIRWGQNTFCGS | 170 |
| SCWQWGNLKICGS | 171 |
| SCVRWGQLSICGS | 172 |
| LKKFNARRKLKGAILTTMLAK | 173 |
| RRWKKNFIAVSAANRFKK | 174 |
| RKWQKTGHAVRAIGRLSS | 175 |
| INLKALAALAKKIL | 176 |
| KIWSILAPLGTTLVKLVA | 177 |
| LKKLLKLLKKLLKL | 178 |
| LKWKKLLKLLKKLLKKLL | 179 |
| AEWPSLTEIKTLSHFSV | 180 |
| AEWPSPTRVISTTYFGS | 181 |
| AELAHWPPVKTVLRSFT | 182 |
| AEGSWLQLLNLMKQMNN | 183 |
| AEWPSLTEIK | 184 |

TABLE 15

Mast cell antagonists/Mast cell protease inhibitor peptide sequences

| Sequence/structure | SEQ ID NO: |
|---|---|
| SGSGVLKRPLPILPVTR | 272 |
| RWLSSRPLPPLPLPPRT | 273 |
| GSGSYDTLALPSLPLHPMSS | 274 |
| GSGSYDTRALPSLPLHPMSS | 275 |
| GSGSSGVTMYPKLPPHWSMA | 276 |
| GSGSSGVRMYPKLPPHWSMA | 277 |
| GSGSSSMRMVPTIPGSAKHG | 278 |
| RNR | NR |
| QT | NR |
| RQK | NR |
| NRQ | NR |

TABLE 15-continued

Mast cell antagonists/Mast cell protease inhibitor peptide sequences

| Sequence/structure | SEQ ID NO: |
|---|---|
| RQK | NR |
| RNRQKT | 436 |
| RNRQ | 437 |
| RNRQK | 438 |
| NRQKT | 439 |
| RQKT | 440 |

TABLE 16

SH3 antagonist peptide sequences

| Sequence/structure | SEQ ID NO: |
|---|---|
| RPLPPLP | 282 |
| RELPPLP | 283 |
| SPLPPLP | 284 |
| GPLPPLP | 285 |
| RPLPIPP | 286 |
| RPLPIPP | 287 |
| RRLPPTP | 288 |
| RQLPPTP | 289 |
| RPLPSRP | 290 |
| RPLPTRP | 291 |
| SRLPPLP | 292 |
| RALPSPP | 293 |
| RRLPRTP | 294 |
| RPVPPIT | 295 |
| ILAPPVP | 296 |
| RPLPMLP | 297 |
| RPLPILP | 298 |
| RPLPSLP | 299 |
| RPLPSLP | 300 |
| RPLPMIP | 301 |
| RPLPLIP | 302 |
| RPLPPTP | 303 |

TABLE 16-continued

SH3 antagonist peptide sequences

| Sequence/structure | SEQ ID NO: |
|---|---|
| RSLPPLP | 304 |
| RPQPPPP | 305 |
| RQLPIPP | 306 |
| XXXRPLPPLPXP | 307 |
| XXXRPLPPIPXX | 308 |
| XXXRPLPPLPXX | 309 |
| RXXRPLPPLPXP | 310 |
| RXXRPLPPLPPP | 311 |
| PPPYPPPPIPXX | 312 |
| PPPYPPPPVPXX | 313 |
| LXXRPLPXΨPP | 314 |
| ΨXXRPLPXLP | 315 |
| PPXΘXPPPΨP | 316 |
| +PPΨPXKPXWL | 317 |
| RPXΨPΨR+SXP | 318 |
| PPVPPRPXXTL | 319 |
| ΨPΨLPΨK | 320 |
| +ΘDXPLPXLP | 321 |

TABLE 17

Somatostatin or cortistatin mimetic peptide sequences

| Sequence/structure | SEQ ID NO: |
|---|---|
| $X^1$-$X^2$-Asn-Phe-Phe-Trp-Lys-Thr-Phe-$X^3$-Ser-$X^4$ | 473 |
| Asp Arg Met Pro Cys Arg Asn Phe Phe Trp Lys Thr Phe Ser Ser Cys Lys | 474 |
| Met Pro Cys Arg Asn Phe Phe Trp Lys Thr Phe Ser Ser Cys Lys | 475 |
| Cys Arg Asn Phe Phe Trp Lys Thr Phe Ser Ser Cys Lys | 476 |
| Asp Arg Met Pro Cys Arg Asn Phe Phe Trp Lys Thr Phe Ser Ser Cys | 477 |
| Met Pro Cys Arg Asn Phe Phe Trp Lys Thr Phe Ser Ser Cys | 478 |
| Cys Arg Asn Phe Phe Trp Lys Thr Phe Ser Ser Cys | 479 |
| Asp Arg Met Pro Cys Lys Asn Phe Phe Trp Lys Thr Phe Ser Ser Cys | 480 |
| Met Pro Cys Lys Asn Phe Phe Trp Lys Thr Phe Ser Ser Cys Lys | 481 |
| Cys Lys Asn Phe Phe Trp Lys Thr Phe Ser Ser Cys Lys | 482 |
| Asp Arg Met Pro Cys Lys Asn Phe Phe Trp Lys Thr Phe Ser Ser Cys | 483 |
| Met Pro Cys Lys Asn Phe Phe Trp Lys Thr Phe Ser Ser Cys | 484 |
| Cys Lys Asn Phe Phe Trp Lys Thr Phe Ser Ser Cys | 485 |
| Asp Arg Met Pro Cys Arg Asn Phe Phe Trp Lys Thr Phe Thr Ser Cys Lys | 486 |
| Met Pro Cys Arg Asn Phe Phe Trp Lys Thr Phe Thr Ser Cys Lys | 487 |
| Cys Arg Asn Phe Phe Trp Lys Thr Phe Thr Ser Cys Lys | 488 |

TABLE 17-continued

Somatostatin or cortistatin mimetic peptide sequences

| Sequence/structure | SEQ ID NO: |
|---|---|
| Asp Arg Met Pro Cys Arg Asn Phe Phe Trp Lys Thr Phe Thr Ser Cys | 489 |
| Met Pro Cys Arg Asn Phe Phe Trp Lys Thr Phe Thr Ser Cys | 490 |
| Cys Arg Asn Phe Phe Trp Lys Thr Phe Thr Ser Cys | 491 |
| Asp Arg Met Pro Cys Lys Asn Phe Phe Trp Lys Thr Phe Thr Ser Cys Lys | 492 |
| Met Pro Cys Lys Asn Phe Phe Trp Lys Thr Phe Thr Ser Cys Lys | 493 |
| Cys Lys Asn Phe Phe Trp Lys Thr Phe Thr Ser Cys Lys | 494 |
| Asp Arg Met Pro Cys Lys Asn Phe Phe Trp Lys Thr Phe Thr Ser Cys | 495 |
| Met Pro Cys Lys Asn Phe Phe Trp Lys Thr Phe Thr Ser Cys | 496 |
| Cys Lys Asn Phe Phe Trp Lys Thr Phe Thr Ser Cys | 497 |

TABLE 18

UKR antagonist peptide sequences

| Sequence/structure | SEQ ID NO: |
|---|---|
| AEPMPHSLNFSQYLWYT | 196 |
| AEHTYSSLWDTYSPLAF | 197 |
| AELDLWMRHYPLSFSNR | 198 |
| AESSLWTRYAWPSMPSY | 199 |
| AEWHPGLSFGSYLWSKT | 200 |
| AEPALLNWSFFFNPGLH | 201 |
| AEWSFYNLHLPEPQTIF | 202 |
| AEPLDLWSLYSLPPLAM | 203 |
| AEPTLWQLYOFPLRLSG | 204 |
| AEISFSELMWLRSTPAF | 205 |
| AELSEADLWTTWFGMGS | 206 |
| AESSLWRIFSPSALMMS | 207 |
| AESLPTLTSILWGKESV | 208 |
| AETLFMDLWHDKHILLT | 209 |
| AEILNFPLWHEPLWSTE | 210 |
| AESQTGTLNTLFWNTLR | 211 |
| AEPVYQYELDSYLRSYY | 430 |
| AELDLSTFYDIQYLLRT | 431 |
| AEFFKLGPNGYVYLHSA | 432 |
| FKLXXXGYVYL | 433 |
| AESTYHHLSLGYMYTLN | 434 |
| YHXLXXGYMYT | 435 |

TABLE 19

Macrophage and/or T-cell inhibiting peptide sequences

| Sequence/structure | SEQ ID NO: |
|---|---|
| Xaa-Yaa-Arg | NR |
| Arg-Yaa-Xaa | NR |
| Xaa-Arg-Yaa | NR |
| Yaa-Arg-Xaa | NR |
| Ala-Arg | NR |
| Arg-Arg | NR |
| Asn-Arg | NR |
| Asp-Arg | NR |
| Cys-Arg | NR |
| Gln-Arg | NR |
| Glu-Arg | NR |
| Gly-Arg | NR |
| His-arg | NR |
| Ile-Arg | NR |
| Leu-Arg | NR |
| Lys-Arg | NR |
| Met-Arg | NR |
| Phe-Arg | NR |
| Ser-Arg | NR |
| Thr-Arg | NR |
| Trp-Arg | NR |
| Tyr-Arg | NR |

TABLE 19-continued

Macrophage and/or T-cell inhibiting peptide sequences

| Sequence/structure | SEQ ID NO: |
|---|---|
| Val-Arg | NR |
| Ala-Glu-Arg | NR |
| Arg-Glu-Arg | NR |
| Asn-Glu-Arg | NR |
| Asp-Glu-Arg | NR |
| Cys-Glu-Arg | NR |
| Gln-Glu-Arg | NR |
| Glu-Glu-Arg | NR |
| Gly-Glu-Arg | NR |
| His-Glu-Arg | NR |
| Ile-Glu-Arg | NR |
| Leu-Glu-Arg | NR |
| Lys-Glu-Arg | NR |
| Met-Glu-Arg | NR |
| Phe-Glu-Arg | NR |
| Pro-Glu-Arg | NR |
| Ser-Glu-Arg | NR |
| Thr-Glu-Arg | NR |
| Trp-Glu-Arg | NR |
| Tyr-Glu-Arg | NR |
| Val-Glu-Arg | NR |
| Arg-Ala | NR |
| Arg-Asp | NR |
| Arg-Cys | NR |
| Arg-Gln | NR |
| Arg-Glu | NR |
| Arg-Gly | NR |
| Arg-His | NR |
| Arg-Ile | NR |
| Arg-Leu | NR |
| Arg-Lys | NR |
| Arg-Met | NR |
| Arg-Phe | NR |
| Arg-Pro | NR |
| Arg-Ser | NR |
| Arg-Thr | NR |
| Arg-Trp | NR |

TABLE 19-continued

Macrophage and/or T-cell inhibiting peptide sequences

| Sequence/structure | SEQ ID NO: |
|---|---|
| Arg-Tyr | NR |
| Arg-Val | NR |
| Arg-Glu-Ala | NR |
| Arg-Glu-Asn | NR |
| Arg-Glu-Asp | NR |
| Arg-Glu-Cys | NR |
| Arg-Glu-Gln | NR |
| Arg-Glu-Glu | NR |
| Arg-Glu-Gly | NR |
| Arg-Glu-His | NR |
| Arg-Glu-Ile | NR |
| Arg-Glu-Leu | NR |
| Arg-Glu-Lys | NR |
| Arg-Glu-Met | NR |
| Arg-Glu-Phe | NR |
| Arg-Glu-Pro | NR |
| Arg-Glu-Ser | NR |
| Arg-Glu-Thr | NR |
| Arg-Glu-Trp | NR |
| Arg-Glu-Tyr | NR |
| Arg-Glu-Val | NR |
| Ala-Arg-Glu | NR |
| Arg-Arg-Glu | NR |
| Asn-Arg-Glu | NR |
| Asp-Arg-Glu | NR |
| Cys-Arg-Glu | NR |
| Gln-Arg-Glu | NR |
| Glu-Arg-Glu | NR |
| Gly-Arg-Glu | NR |
| His-Arg-Glu | NR |
| Ile-Arg-Glu | NR |
| Leu-Arg-Glu | NR |
| Lys-Arg-Glu | NR |
| Met-Arg-Glu | NR |
| Phe-Arg-Glu | NR |
| Pro-Arg-Glu | NR |

TABLE 19-continued

Macrophage and/or T-cell inhibiting peptide sequences

| Sequence/structure | SEQ ID NO: |
|---|---|
| Ser-Arg-Glu | NR |
| Thr-Arg-Glu | NR |
| Trp-Arg-Glu | NR |
| Tyr-Arg-Glu | NR |
| Val-Arg-Glu | NR |
| Glu-Arg-Ala, | NR |
| Glu-Arg-Arg | NR |
| Glu-Arg-Asn | NR |
| Glu-Arg-Asp | NR |
| Glu-Arg-Cys | NR |
| Glu-Arg-Gln | NR |
| Glu-Arg-Gly | NR |
| Glu-Arg-His | NR |
| Glu-Arg-Ile | NR |
| Glu-Arg-Leu | NR |
| Glu-Arg-Lys | NR |
| Glu-Arg-Met | NR |
| Glu-Arg-Phe | NR |
| Glu-Arg-Pro | NR |
| Glu-Arg-Ser | NR |
| Glu-Arg-Thr | NR |
| Glu-Arg-Trp | NR |
| Glu-Arg-Tyr | NR |
| Glu-Arg-Val | NR |

TABLE 20

Additional Exemplary Pharmacologically Active Peptides

| Sequence/structure | SEQ ID NO: | Activity |
|---|---|---|
| VEPNCDIHVMWEWECFERL | 1027 | VEGF-antagonist |
| GERWCFDGPLTWVCGEES | 1084 | VEGF-antagonist |
| RGWVEICVADDNGMCVTEAQ | 398 | VEGE-antagonist |
| GWDECDVARMWEWECFAGV | 1086 | VEGF-antagonist |
| GERWCFDGPRAWVCGWEI | 501 | VEGE-antagonist |
| EELWCFDGPRAWVCGYVK | 502 | VEGF-antagonist |
| RGWVEICAADDYGRCLTEAQ | 1031 | VEGF-antagonist |
| RGWVEICESDVWGRCL | 1087 | VEGF-antagonist |
| RGWVEICESDVWGRCL | 1088 | VEGF-antagonist |
| GGNECDIARMWEWECFERL | 1089 | VEGF-antagonist |
| RGWVEICMDDYGRCL | 1090 | VEGE-antagonist |
| CTTHWGFTLC | 1028 | MMP inhibitor |

TABLE 20-continued

Additional Exemplary Pharmacologically Active Peptides

| Sequence/structure | SEQ ID NO: | Activity |
|---|---|---|
| CLRSGXGC | 1091 | MMP inhibitor |
| CXXHWGFXXC | 1092 | MMP inhibitor |
| CXPXC | 1093 | MMP inhibitor |
| CRRHWGFEFC | 1094 | MMP inhibitor |
| STTHWGFTLS | 1095 | MMP inhibitor |
| CSLHWGFWWC | 1096 | CTLA4-mimetic |
| GFVCSGIFAVGVGRC | 125 | CTLA4-mimetic |
| APGVRLGCAVLGRYC | 126 | CTLA4-mimetic |
| LLGRMK | 105 | Antiviral (HBV) |
| ICVVQDWGHHRCTAGHMANLTSHASAI | 127 | C3b antagonist |
| ICVVQDWGHHRCT | 128 | C3b antagonist |
| CVVQDWGHHAC | 129 | C3b antagonist |
| STGGFDDVYDWARGVSSALTTTLVATR | 185 | Vinculin-binding |
| STGGFDDVYDWARRVSSALTTTLVATR | 186 | Vinculin-binding |
| SRGVNFSEWLYDMSAAMKEASNVFPSRRSR | 187 | Vinculin-binding |
| SSQNWDMEAGVEDLTAAMLGLLSTIHSSSR | 188 | Vinculin-binding |
| SSPSLYTQFLVNYESAATRIQDLLIASRPSR | 189 | Vinculin-binding |
| SSTGWVDLLGALQRAADATRTSIPPSLQNSR | 190 | Vinculin-binding |
| DVYTKKELIECARRVSEK | 191 | Vinculin-binding |
| EKGSYYPGSGIAQFHIDYNNVS | 192 | C4BP-binding |
| SGIAQFHIDYNNVSSAEGWHVN | 193 | C4BP-binding |
| LVTVEKGSYYPGSGIAQFHIDYNNVSSAEGWHVN | 194 | C4BP-binding |
| SGIAQFHIDYNNVS | 195 | C4BP-binding |
| LLGRMK | 279 | anti-HBV |
| ALLGRMKG | 280 | anti-HBV |
| LDPAFR | 281 | anti-HBV |
| CXXRGDC | 322 | Inhibition of platelet aggregation |
| RPLPPLP | 323 | Src antagonist |
| PPVPPR | 324 | Src antagonist |
| XFXDXWXXLXX | 325 | Anti-cancer (particularly for sarcomas |
| KACRRLFGPVDSEQLSRDCD | 326 | p16-mimetic |
| RERWNFDFVTETPLEGDFAW | 327 | p16-mimetic |
| KRRQTSMTDFYHSKRRLIFS | 328 | p16-mimetic |
| TSMTDFYHSKRRLIFSKRKP | 329 | p16-mimetic |
| RRLIF | 330 | p16-mimetic |

TABLE 20-continued

Additional Exemplary Pharmacologically Active Peptides

| Sequence/structure | SEQ ID NO: | Activity |
|---|---|---|
| KRRQTSATDFYHSKRRLIFSRQIKIWFQNRRMKWKK | 331 | p16-mimetic |
| KRRLIFSKRQIKIWFQNRRMKWKK | 332 | p16-mimetic |
| Asn Gln Gly Arg His Phe Cys Gly Gly Ala Leu Ile His Ala Arg Phe Val Met Thr Ala Ala Ser Cys Phe Gln | 498 | CAP37 mimetic/LPS binding |
| Arg His Phe Cys Gly Gly Ala Leu Ile His Ala Arg Phe Val Met Thr Ala Ala Ser Cys | 499 | CAP37 mimetic/LPS binding |
| Gly Thr Arg Cys Gln Val Ala Gly Trp Gly Ser Gln Arg Ser Gly Gly Arg Leu Ser Arg Phe Pro Arg Phe Val Asn Val | 500 | CAP37 mimetic/LPS binding |
| WHWRHRIPLQLAAGR | 1097 | carbohydrate (GD1 alpha) mimetic |
| LKTPRV | 1098 | β2GPI Ab binding |
| NTLKTPRV | 1099 | β2GPI Ab binding |
| NTLKTPRVGGC | 1100 | β2GPI Ab binding |
| KDKATF | 1101 | β2GPI Ab binding |
| KDKATFGCHD | 1102 | β2GPI Ab binding |
| KDKATFGCHDGC | 1103 | β2GPI Ab binding |
| TLRVYK | 1104 | β2GPI Ab binding |
| ATLRVYKGG | 1105 | β2GPI Ab binding |
| CATLRVYKGG | 1106 | β2GPI Ab binding |
| INLKALAALAKKIL | 1107 | Membrane-transporting |
| GWT | NR | Membrane-transporting |
| GWTLNSAGYLLG | 1108 | Membrane-transporting |
| GWTLNSAGYLLGKINLKALAALAKKIL | 1109 | Membrane-transporting |

The present invention is also particularly useful with peptides having activity in treatment of:
cancer, wherein the peptide is a VEGF-mimetic or a VEGF receptor antagonist, a HER2 agonist or antagonist, a CD20 antagonist and the like;
asthma, wherein the protein of interest is a CKR3 antagonist, an IL-5 receptor antagonist, and the like;
thrombosis, wherein the protein of interest is a GPIIb antagonist, a GPIIIa antagonist, and the like;
autoimmune diseases and other conditions involving immune modulation, wherein the protein of interest is an IL-2 receptor antagonist, a CD40 agonist or antagonist, a CD40L agonist or antagonist, a thymopoietin mimetic and the like.

Vehicles. This invention requires the presence of at least one vehicle ($F^1$, $F^2$) attached to a peptide through the N-terminus, C-terminus or a sidechain of one of the amino acid residues. Multiple vehicles may also be used; e.g., Fc's at each terminus or an Fc at a terminus and a PEG group at the other terminus or a sidechain.

An Fc domain is the preferred vehicle. The Fc domain may be fused to the N or C termini of the peptides or at both the N and C termini. For the TPO-mimetic peptides, molecules having the Fc domain fused to the N terminus of the peptide portion of the molecule are more bioactive than other such fusions, so fusion to the N terminus is preferred.

As noted above, Fc variants are suitable vehicles within the scope of this invention. A native Fc may be extensively modified to form an Fc variant in accordance with this invention, provided binding to the salvage receptor is maintained; see, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). In particular, one may truncate the N-terminal 20-amino acid segment of SEQ ID NO: 2 or delete or substitute the cysteine residues at positions 7 and 10 of SEQ ID NO: 2. Even when cysteine residues are removed, the single chain Fc domains can still form a dimeric Fc domain that is held together non-covalently.
2. A native Fc is modified to make it more compatible with a selected host cell. For example, one may remove the PA sequence near the N-terminus of a typical native Fc, which may be recognized by a digestive enzyme in E. coli such as proline iminopeptidase. One may also add an N-terminal methionine residue, especially when the molecule is expressed recombinantly in a bacterial cell such as E. coli. The Fc domain of SEQ ID NO: 2 (FIG. 4) is one such Fc variant.
3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.
4. One or more glycosylation sites are removed. Residues that are typically glycosylated (e.g., asparagine) may confer cytolytic response. Such residues may be deleted or substituted with unglycosylated residues (e.g., alanine).
5. Sites involved in interaction with complement, such as the C1q binding site, are removed. For example, one may delete or substitute the EKK sequence of human IgG1. Complement recruitment may not be advantageous for the molecules of this invention and so may be avoided with such an Fc variant.
6. Sites are removed that affect binding to Fc receptors other than a salvage receptor. A native Fc may have sites for interaction with certain white blood cells that are not required for the fusion molecules of the present invention and so may be removed.
7. The ADCC site is removed. ADCC sites are known in the art; see, for example, *Molec. Immunol.* 29 (5): 633–9 (1992) with regard to ADCC sites in IgG1. These sites, as well, are not required for the fusion molecules of the present invention and so may be removed.
8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

Preferred Fc variants include the following. In SEQ ID NO: 2 (FIG. 4) the leucine at position 15 may be substituted with glutamate; the glutamate at position 99, with alanine; and the lysines at positions 101 and 103, with alanines. In addition, one or more tyrosine residues can be replaced by phenylanaline residues.

An alternative vehicle would be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display for binding to the FcRn salvage receptor. Such salvage receptor-binding compounds are also included within the meaning of "vehicle" and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

As noted above, polymer vehicles may also be used for $F^1$ and $F^2$. Various means for attaching chemical moieties useful as vehicles are currently available, see e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

A preferred polymer vehicle is polyethylene glycol (PEG). The PEG group may be of any convenient molecular weight and may be linear or branched. The average molecular weight of the PEG will preferably range from about 2 kiloDalton ("kD") to about 100 kDa, more preferably from about 5 kDa to about 50 kDa, most preferably from about 5 kDa to about 10 kDa. The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group).

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis (see, for example, FIGS. 5 and 6 and the accompanying text herein). The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which may be used for protein modification. Dextrans are polysaccharide polymers comprised of individual subunits of glucose predominantly linked by α1-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kD to about 20 kD is preferred when dextran is used as a vehicle in accordance with the present invention.

Linkers. Any "linker" group is optional. When present, its chemical structure is not critical, since it serves primarily as a spacer. The linker is preferably made up of amino acids linked together by peptide bonds. Thus, in preferred embodiments, the linker is made up of from 1 to 20 amino acids linked by peptide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly $(Gly)_4$, $(Gly)_5$), poly(Gly-Ala), and polyalanines. Other specific examples of linkers are:

```
(Gly)₃Lys(Gly)₄;            (SEQ ID NO:333)

(Gly)₃AsnGlySer(Gly)₂;      (SEQ ID NO:334)

(Gly)₃Cys(Gly)₄;            (SEQ ID NO:335)
and

GlyProAsnGlyGly.            (SEQ ID
                             NO:336)
```

To explain the above nomenclature, for example, $(Gly)_3Lys(Gly)_4$ means Gly-Gly-Gly-Lys-Gly-Gly-Gly-Gly. Combinations of Gly and Ala are also preferred. The linkers shown here are exemplary; linkers within the scope of this invention may be much longer and may include other residues.

Non-peptide linkers are also possible. For example, alkyl linkers such as $-NH-(CH_2)_s-C(O)-$, wherein s=2–20 could be used. These alkyl linkers may further be substituted by any non-sterically hindering group such as lower alkyl (e.g., $C_1-C_6$) lower acyl, halogen (e.g., Cl, Br), CN, $NH_2$, phenyl, etc. An exemplary non-peptide linker is a PEG linker,

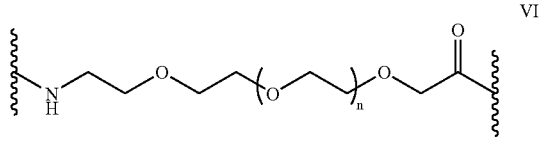

VI wherein n is such that the linker has a molecular weight of 100 to 5000 kD, preferably 100 to 500 kD. The peptide linkers may be altered to form derivatives in the same manner as described above.

Derivatives. The inventors also contemplate derivatizing the peptide and/or vehicle portion of the compounds. Such derivatives may improve the solubility, absorption, biological half life, and the like of the compounds. The moieties may alternatively eliminate or attenuate any undesirable side-effect of the compounds and the like. Exemplary derivatives include compounds in which:

1. The compound or some portion thereof is cyclic. For example, the peptide portion may be modified to contain two or more Cys residues (e.g., in the linker), which could cyclize by disulfide bond formation. For citations to references on preparation of cyclized derivatives, see Table 2.

2. The compound is cross-linked or is rendered capable of cross-linking between molecules. For example, the peptide portion may be modified to contain one Cys residue and thereby be able to form an intermolecular disulfide bond with a like molecule. The compound may also be cross-linked through its C-terminus, as in the molecule shown below.

3.

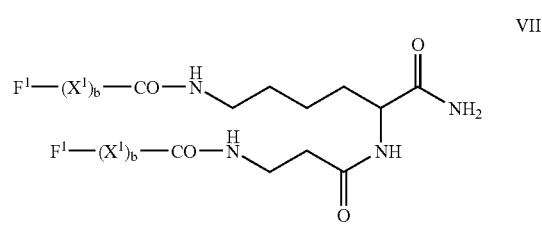

VII

4. One or more peptidyl [—C(O)NR—] linkages (bonds) is replaced by a non-peptidyl linkage. Exemplary non-peptidyl linkages are —$CH_2$-carbamate [—$CH_2$—OC(O) NR—], phosphonate, —$CH_2$-sulfonamide [—$CH_2$—S(O)$_2$NR—], urea [—NHC(O)NH—], —$CH_2$-secondary amine, and alkylated peptide [—C(O)NR$^6$— wherein R$^6$ is lower alkyl].

5. The N-terminus is derivatized. Typically, the N-terminus may be acylated or modified to a substituted amine. Exemplary N-terminal derivative groups include —NRR$^1$ (other than —$NH_2$), —NRC(O)R$^1$, —NRC(O)OR$^1$, —NRS(O)$_2$R$^1$, —NHC(O)NHR$^1$, succinimide, or benzyloxycarbonyl-NH—(CBZ—NH—), wherein R and R$^1$ are each independently hydrogen or lower alkyl and wherein the phenyl ring may be substituted with 1 to 3 substituents selected from the group consisting of $C_1$–$C_4$ alkyl, $C_1$–$C_4$ alkoxy, chloro, and bromo.

6. The free C-terminus is derivatized. Typically, the C-terminus is esterified or amidated. For example, one may use methods described in the art to add (NH—$CH_2$—$CH_2$—$NH_2$)$_2$ to compounds of this invention having any of SEQ ID NOS: 504 to 508 at the C-terminus. Likewise, one may use methods described in the art to add —$NH_2$ to compounds of this invention having any of SEQ ID NOS: 924 to 955,963 to 972, 1005 to 1013, or 1018 to 1023 at the C-terminus. Exemplary C-terminal derivative groups include, for example, —C(O)R$^2$ wherein R$^2$ is lower alkoxy or —NR$^3$R$^4$ wherein R$^3$ and R$^4$ are independently hydrogen or $C_1$–$C_8$ alkyl (preferably $C_1$–$C_4$ alkyl).

7. A disulfide bond is replaced with another, preferably more stable, cross-linking moiety (e.g., an alkylene). See, e.g., Bhatnagar et al. (1996), *J. Med. Chem.* 39: 3814–9; Alberts et al. (1993) *Thirteenth Am. Pep. Symp.,* 357–9.

8. One or more individual amino acid residues is modified. Various derivatizing agents are known to react specifically with selected sidechains or terminal residues, as described in detail below.

Lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been studied extensively, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl sidechain groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Cysteinyl residues can be replaced by amino acid residues or other moieties either to eliminate disulfide bonding or, conversely, to stabilize cross-linking. See, e.g., Bhatnagar et al. (1996), *J. Med. Chem.* 39: 3814–9.

Derivatization with bifunctional agents is useful for cross-linking the peptides or their functional derivatives to a water-insoluble support matrix or to other macromolecular vehicles. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains. Creighton, *Proteins: Structure and Molecule Properties* (W. H. Freeman & Co., San Francisco), pp. 79–86 (1983).

Compounds of the present invention may be changed at the DNA level, as well. The DNA sequence of any portion of the compound may be changed to codons more compatible with the chosen host cell. For *E. coli*, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Methods of Making

The compounds of this invention largely may be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the peptides in an appropriate host. The vector comprises the DNA molecule that codes for the peptides operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), *Chem. Polypeptides,*

*pp.* 335–61 (Katsoyannis and Panayotis eds.); Merrifield (1963), *J. Am. Chem. Soc.* 85: 2149; Davis et al. (1985), *Biochem. Intl.* 10: 394–414; Stewart and Young (1969), *Solid Phase Peptide Synthesis*; U.S. Pat. No. 3,941,763; Finn et al. (1976), *The Proteins* (3rd ed.) 2: 105–253; and Erickson et al. (1976), *The Proteins* (3rd ed.) 2: 257–527. Solid phase synthesis is the preferred technique of making individual peptides since it is the most cost-effective method of making small peptides.

Compounds that contain derivatized peptides or which contain non-peptide groups may be synthesized by well-known organic chemistry techniques.

Uses of the Compounds

In general. The compounds of this invention have pharmacologic activity resulting from their ability to bind to proteins of interest as agonists, mimetics or antagonists of the native ligands of such proteins of interest. The utility of specific compounds is shown in Table 2. The activity of these compounds can be measured by assays known in the art. For the TPO-mimetic and EPO-mimetic compounds, in vivo assays are further described in the Examples section herein.

In addition to therapeutic uses, the compounds of the present invention are useful in diagnosing diseases characterized by dysfunction of their associated protein of interest. In one embodiment, a method of detecting in a biological sample a protein of interest (e.g., a receptor) that is capable of being activated comprising the steps of: (a) contacting the sample with a compound of this invention; and (b) detecting activation of the protein of interest by the compound. The biological samples include tissue specimens, intact cells, or extracts thereof. The compounds of this invention may be used as part of a diagnostic kit to detect the presence of their associated proteins of interest in a biological sample. Such kits employ the compounds of the invention having an attached label to allow for detection. The compounds are useful for identifying normal or abnormal proteins of interest. For the EPO-mimetic compounds, for example, presence of abnormal protein of interest in a biological sample may be indicative of such disorders as Diamond Blackfan anemia, where it is believed that the EPO receptor is dysfunctional.

Therapeutic uses of EPO-mimetic compounds. The EPO-mimetic compounds of the invention are useful for treating disorders characterized by low red blood cell levels. Included in the invention are methods of modulating the endogenous activity of an EPO receptor in a mammal, preferably methods of increasing the activity of an EPO receptor. In general, any condition treatable by erythropoietin, such as anemia, may also be treated by the EPO-mimetic compounds of the invention. These compounds are administered by an amount and route of delivery that is appropriate for the nature and severity of the condition being treated and may be ascertained by one skilled in the art. Preferably, administration is by injection, either subcutaneous, intramuscular, or intravenous.

Therapeutic uses of TPO-mimetic compounds. For the TPO-mimetic compounds, one can utilize such standard assays as those described in WO95/26746 entitled "Compositions and Methods for Stimulating Megakaryocyte Growth and Differentiation". In vivo assays also appear in the Examples hereinafter.

The conditions to be treated are generally those that involve an existing megakaryocyte/platelet deficiency or an expected megakaryocyte/platelet deficiency (e.g., because of planned surgery or platelet donation). Such conditions will usually be the result of a deficiency (temporary or permanent) of active Mpl ligand in vivo. The generic term for platelet deficiency is thrombocytopenia, and hence the methods and compositions of the present invention are generally available for treating thrombocytopenia in patients in need thereof.

Thrombocytopenia (platelet deficiencies) may be present for various reasons, including chemotherapy and other therapy with a variety of drugs, radiation therapy, surgery, accidental blood loss, and other specific disease conditions. Exemplary specific disease conditions that involve thrombocytopenia and may be treated in accordance with this invention are: a plastic anemia, idiopathic thrombocytopenia, metastatic tumors which result in thrombocytopenia, systemic lupus erythematosus, splenomegaly, Fanconi's syndrome, vitamin B12 deficiency, folic acid deficiency, May-Hegglin anomaly, Wiskott-Aldrich syndrome, and paroxysmal nocturnal hemoglobinuria. Also, certain treatments for AIDS result in thrombocytopenia (e.g., AZT). Certain wound healing disorders might also benefit from an increase in platelet numbers.

With regard to anticipated platelet deficiencies, e.g., due to future surgery, a compound of the present invention could be administered several days to several hours prior to the need for platelets. With regard to acute situations, e.g., accidental and massive blood loss, a compound of this invention could be administered along with blood or purified platelets.

The TPO-mimetic compounds of this invention may also be useful in stimulating certain cell types other than megakaryocytes if such cells are found to express Mpl receptor. Conditions associated with such cells that express the Mpl receptor, which are responsive to stimulation by the Mpl ligand, are also within the scope of this invention.

The TPO-mimetic compounds of this invention may be used in any situation in which production of platelets or platelet precursor cells is desired, or in which stimulation of the c-Mpl receptor is desired. Thus, for example, the compounds of this invention may be used to treat any condition in a mammal wherein there is a need of platelets, megakaryocytes, and the like. Such conditions are described in detail in the following exemplary sources: WO95/26746; WO95/21919; WO95/18858; WO95/21920 and are incorporated herein.

The TPO-mimetic compounds of this invention may also be useful in maintaining the viability or storage life of platelets and/or megakaryocytes and related cells. Accordingly, it could be useful to include an effective amount of one or more such compounds in a composition containing such cells.

The therapeutic methods, compositions and compounds of the present invention may also be employed, alone or in combination with other cytokines, soluble Mpl receptor, hematopoietic factors, interleukins, growth factors or antibodies in the treatment of disease states characterized by other symptoms as well as platelet deficiencies. It is anticipated that the inventive compound will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with Mpl ligand. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), SCF, GM-CSF, granulocyte colony stimulating factor (G-CSF), EPO, interferon-alpha (IFN-alpha), consensus interferon, IFN-beta, or IFN-gamma. It may further be useful to administer, either simultaneously or sequentially, an effective amount of a soluble mammalian Mpl receptor, which appears to have an effect of causing megakaryocytes to fragment into platelets once the megakaryocytes have reached mature form. Thus, administration of an inventive compound (to enhance the number of mature megakaryocytes) followed by administration of the soluble Mpl receptor (to inactivate the ligand and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

In cases where the inventive compounds are added to compositions of platelets and/or megakaryocytes and related cells, the amount to be included will generally be ascertained experimentally by techniques and assays known in the art. An exemplary range of amounts is 0.1 µg–1 mg inventive compound per $10^6$ cells.

PHARMACEUTICAL COMPOSITIONS

In General. The present invention also provides methods of using pharmaceutical compositions of the inventive compounds. Such pharmaceutical compositions may be for administration for injection, or for oral, pulmonary, nasal, transdermal or other forms of administration. In general, the invention encompasses pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435–1712 which are herein incorporated by reference. The compositions may be prepared in liquid form, or may be in dried powder, such as lyophilized form. Implantable sustained release formulations are also contemplated, as are transdermal formulations.

Oral dosage forms. Contemplated for use herein are oral solid dosage forms, which are described generally in Chapter 89 of *Remington's Pharmaceutical Sciences* (1990), 18th Ed., Mack Publishing Co. Easton Pa. 18042, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given in Chapter 10 of Marshall, K., *Modern Pharmaceutics* (1979), edited by G. S. Banker and C. T. Rhodes, herein incorporated by reference. In general, the formulation will include the inventive compound, and inert ingredients which allow for protection against the stomach environment, and release of the biologically active material in the intestine.

Also specifically contemplated are oral dosage forms of the above inventive compounds. If necessary, the compounds may be chemically modified so that oral delivery is efficacious. Generally, the chemical modification contemplated is the attachment of at least one moiety to the compound molecule itself, where said moiety permits (a) inhibition of proteolysis; and (b) uptake into the blood stream from the stomach or intestine. Also desired is the increase in overall stability of the compound and increase in circulation time in the body. Moieties useful as covalently attached vehicles in this invention may also be used for this purpose. Examples of such moieties include: PEG, copolymers of ethylene glycol and propylene glycol, carboxymethyl cellulose, dextran, polyvinyl alcohol, polyvinyl pyrrolidone and polyproline. See, for example, Abuchowski and Davis, *Soluble Polymer-Enzyme Adducts, Enzymes as Drugs* (1981), Hocenberg and Roberts, eds., Wiley-Interscience, New York, N.Y., pp 367–83; Newmark, et al. (1982), *J. Appl. Biochem.* 4:185–9. Other polymers that could be used are poly-1,3-dioxolane and poly-1,3,6-tioxocane. Preferred for pharmaceutical usage, as indicated above, are PEG moieties.

For oral delivery dosage forms, it is also possible to use a salt of a modified aliphatic amino acid, such as sodium N-(8-[2-hydroxybenzoyl] amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The compounds of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the compound of the invention with an inert material. These diluents could include carbohydrates, especially mannitol, α-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the compound of this invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives may also be included in the formulation to enhance uptake of the compound. Additives potentially having this property are for instance the fatty acids oleic acid, linoleic acid and linolenic acid.

Controlled release formulation may be desirable. The compound of this invention could be incorporated into an inert matrix which permits release by either diffusion or leaching mechanisms e.g., gums. Slowly degenerating matrices may also be incorporated into the formulation, e.g., alginates, polysaccharides. Another form of a controlled release of the compounds of this invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Pulmonary delivery forms. Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., *Pharma. Res.* (1990) 7: 565–9; Adjei et al. (1990), *Internatl. J. Pharmaceutics* 63: 135–44 (leuprolide acetate); Braquet et al. (1989), *J. Cardiovasc. Pharmacol.* 13 (suppl.5): s.143–146 (endothelin-1); Hubbard et al. (1989), *Annals Int. Med.* 3: 206–12 ($\alpha$1-antitrypsin); Smith et al. (1989), *J. Clin. Invest.* 84: 1145–6 ($\alpha$1-proteinase); Oswein et al. (March 1990), "Aerosolization of Proteins", *Proc. Symp. Resp. Drug Delivery II, Keystone, Colorado (recombinant human growth hormone); Debs et al. (1988), J. Immunol.* 140: 3482–8 (interferon-$\gamma$ and tumor necrosis factor $\alpha$) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 $\mu$m (or microns), most preferably 0.5 to 5 $\mu$m, for most effective delivery to the distal lung.

Pharmaceutically acceptable carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery forms. Nasal delivery of the inventive compound is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes is also contemplated.

Dosages. The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the daily regimen should be in the range of 0.1–1000 micrograms of the inventive compound per kilogram of body weight, preferably 0.1–150 micrograms per kilogram.

SPECIFIC PREFERRED EMBODIMENTS

The inventors have determined preferred peptide sequences for molecules having many different kinds of activity. The inventors have further determined preferred structures of these preferred peptides combined with preferred linkers and vehicles. Preferred structures for these preferred peptides listed in Table 21 below.

TABLE 21

Preferred embodiments

| Sequence/structure | SEQ ID NO: | Activity |
|---|---|---|
| $F^1$-(G)$_5$-IEGPTLRQWLAARA-(G)$_8$-IEGPTLRQWLAARA | 337 | TPO-mimetic |
| IEGPTLRQWLAARA-(G)$_8$-IEGPTLRQWLAARA-(G)$_5$-$F^1$ | 338 | TPO-mimetic |
| $F^1$-(G)$_5$-IEGPTLRQWLAARA | 1032 | TPO-mimetic |
| IEGPTLRQWLAARA-(G)$_5$-$F^1$ | 1033 | TPO-mimetic |
| $F^1$-(G)$_5$-GGTYSCHFGPLTWVCKPQGG-(G)$_4$-GGTYSCHFGPLTWVCKPQGG | 339 | EPO-mimetic |
| GGTYSCHFGPLTWVCKPQGG-(G)$_4$-GGTYSCHFGPLTWVCKPQGG-(G)$_5$-$F^1$ | 340 | EPO-mimetic |
| GGTYSCHFGPLTWVCKPQGG-(G)$_5$-$F^1$ | 1034 | EPO-mimetic |
| $F^1$-(G)$_5$-DFLPHYKNTSLGHRP | 1045 | TNF-α inhibitor |
| DFLPHYKNTSLGHRP-(G)$_5$-$F^1$ | 1046 | TNF-α inhibitor |
| $F^1$-(G)$_5$-FEWTPGYWQPYALPL | 1047 | IL-1 R antagonist |
| FEWTPGYWQPYALPL-(G)$_5$-$F^1$ | 1048 | IL-1 R antagonist |
| $F^1$-(G)$_5$-VEPNCDIHVMWEWECFERL | 1049 | VEGF-antagonist |
| VEPNCDIHVMWEWECFERL-(G)$_5$-$F^1$ | 1050 | VEGF-antagonist |
| $F^1$-(G)$_5$-CTTHWGFTLC | 1051 | MMP inhibitor |
| CTTHWGFTLC-(G)$_5$-$F^1$ | 1052 | MMP inhibitor |

"$F^1$" is an Fc domain as defined previously herein.

WORKING EXAMPLES

The compounds described above may be prepared as described below. These examples comprise preferred embodiments of the invention and are illustrative rather than limiting.

Example 1

TPO-Mimetics

The following example uses peptides identified by the numbers appearing in Table A hereinafter.

Preparation of peptide 19. Peptide 17b (12 mg) and MeO-PEG-SH 5000 (30 mg, 2 equiv.) were dissolved in 1 ml aqueous buffer (pH 8). The mixture was incubated at RT for about 30 minutes and the reaction was checked by analytical HPLC, which showed a >80% completion of the reaction. The pegylated material was isolated by preparative HPLC.

Preparation of peptide 20. Peptide 18 (14 mg) and MeO-PEG-maleimide (25 mg) were dissolved in about 1.5 ml aqueous buffer (pH 8). The mixture was incubated at RT for about 30 minutes, at which time about 70% transformation was complete as monitored with analytical HPLC by applying an aliquot of sample to the HPLC column. The pegylated material was purified by preparative HPLC.

Bioactivity assay. The TPO in vitro bioassay is a mitogenic assay utilizing an IL-3 dependent clone of murine 32D cells that have been transfected with human mpl receptor. This assay is described in greater detail in WO 95/26746. Cells are maintained in MEM medium containing 10% Fetal Clone II and 1 ng/ml mIL-3. Prior to sample addition, cells are prepared by rinsing twice with growth medium lacking mIL-3. An extended twelve point TPO standard curve is prepared, ranging from 33 to 39 pg/ml. Four dilutions, estimated to fall within the linear portion of the standard curve, (100 to 125 pg/ml), are prepared for each sample and run in triplicate. A volume of 100 µl of each dilution of sample or standard is added to appropriate wells of a 96 well microtiter plate containing 10,000 cells/well. After forty-four hours at 37° C. and 10% $CO_2$, MTS (a tetrazolium compound which is bioreduced by cells to a formazan) is added to each well. Approximately six hours later, the optical density is read on a plate reader at 490 nm. A dose response curve (log TPO concentration vs. O.D.- Background) is generated and linear regression analysis of points which fall in the linear portion of the standard curve is performed. Concentrations of unknown test samples are determined using the resulting linear equation and a correction for the dilution factor.

TMP tandem repeats with polyglycine linkers. Our design of sequentially linked TMP repeats was based on the assumption that a dimeric form of TMP was required for its effective interaction with c-Mpl (the TPO receptor) and that depending on how they were wound up against each other in the receptor context, the two TMP molecules could be tethered together in the C- to N-terminus configuration in a way that would not perturb the global dimeric conformation. Clearly, the success of the design of tandem linked repeats depends on proper selection of the length and composition of the linker that joins the C- and N-termini of the two sequentially aligned TMP monomers. Since no structural information of the TMP bound to c-Mpl was available, a series of repeated peptides with linkers composed of 0 to 10 and 14 glycine residues (Table A) were synthesized. Glycine was chosen because of its simplicity and flexibility, based on the rationale that a flexible polyglycine peptide chain might allow for the free folding of the two tethered TMP repeats into the required conformation, while other amino acid sequences may adopt undesired secondary structures whose rigidity might disrupt the correct packing of the repeated peptide in the receptor context.

The resulting peptides are readily accessible by conventional solid phase peptide synthesis methods (Merrifield (1963), *J. Amer. Chem. Soc.* 85: 2149) with either Fmoc or t-Boc chemistry. Unlike the synthesis of the C-terminally linked parallel dimer which required the use of an orthogonally protected lysine residue as the initial branch point to build the two peptide chains in a pseudosymmetrical way (Cwirla et al. (1997), *Science* 276: 1696–9), the synthesis of these tandem repeats was a straightforward, stepwise assembly of the continuous peptide chains from the C- to N-terminus. Since dimerization of TMP had a more dramatic effect on the proliferative activity than binding affinity as shown for the C-terminal dimer (Cwirla et al. (1997)), the synthetic peptides were tested directly for biological activity in a TPO-dependent cell-proliferation assay using an IL-3 dependent clone of murine 32D cells transfected with the full-length c-Mpl (Palacios et al., Cell 41:727 (1985)). As the test results showed, all the polyglycine linked tandem repeats demonstrated >1000 fold increases in potency as compared to the monomer, and were even more potent than the C-terminal dimer in this cell proliferation assay. The absolute activity of the C-terminal dimer in our assay was lower than that of the native TPO protein, which is different from the previously reported findings in which the C-terminal dimer was found to be as active as the natural ligand (Cwirla et al. (1997)). This might be due to differences in the conditions used in the two assays. Nevertheless, the difference in activity between tandem (C terminal of first monomer linked to N terminal of second monomer) and C-terminal (C terminal of first monomer linked to C terminal of second monomer; also referred to as parallel) dimers in the same assay clearly demonstrated the superiority of tandem repeat strategy over parallel peptide dimerization. It is interesting to note that a wide range of length is tolerated by the linker. The optimal linker between tandem peptides with the selected TMP monomers apparently is composed of 8 glycines.

Other tandem repeats. Subsequent to this first series of TMP tandem repeats, several other molecules were designed either with different linkers or containing modifications within the monomer itself. The first of these molecules, peptide 13, has a linker composed of GPNG, a sequence known to have a high propensity to form a β-turn-type secondary structure. Although still about 100-fold more potent than the monomer, this peptide was found to be >10-fold less active than the equivalent GGGG-linked analog. Thus, introduction of a relatively rigid β-turn at the linker region seemed to have caused a slight distortion of the optimal agonist conformation in this short linker form.

The Trp9 in the TMP sequence is a highly conserved residue among the active peptides isolated from random peptide libraries. There is also a highly conserved Trp in the consensus sequences of EPO mimetic peptides and this Trp residue was found to be involved in the formation of a hydrophobic core between the two EMPs and contributed to hydrophobic interactions with the EPO receptor. Livnah et al. (1996), *Science* 273: 464–71). By analogy, the Trp9 residue in TMP might have a similar function in dimerization of the peptide ligand, and as an attempt to modulate and estimate the effects of noncovalent hydrophobic forces exerted by the two indole rings, several analogs were made resulting from mutations at the Trp. So in peptide 14, the Trp residue was replaced in each of the two TMP monomers with a Cys, and an intramolecular disulfide bond was formed between the two cysteines by oxidation which was envisioned to mimic the hydrophobic interactions between the two Trp residues in peptide dimerization. Peptide 15 is the reduced form of peptide 14. In peptide 16, the two Trp residues were replaced by Ala. As the assay data show, all three analogs were inactive. These data further demonstrated that Trp is critical for the activity of the TPO mimetic peptide, not just for dimer formation.

The next two peptides (peptide 17a, and 18) each contain in their 8-amino acid linker a Lys or Cys residue. These two compounds are precursors to the two PEGylated peptides (peptide 19 and 20) in which the side chain of the Lys or Cys is modified by a PEG moiety. A PEG moiety was introduced at the middle of a relatively long linker, so that the large PEG component (5 kDa) is far enough away from the critical binding sites in the peptide molecule. PEG is a known biocompatible polymer which is increasingly used as a covalent modifier to improve the pharmacokinetic profiles of peptide- and protein-based therapeutics.

A modular, solution-based method was devised for convenient PEGylation of synthetic or recombinant peptides. The method is based on the now well established chemoselective ligation strategy which utilizes the specific reaction between a pair of mutually reactive functionalities. So, for pegylated peptide 19, the lysine side chain was preactivated with a bromoacetyl group to give peptide 17b to accommodate reaction with a thiol-derivatized PEG. To do that, an orthogonal protecting group, Dde, was employed for the protection of the lysine ε-amine. Once the whole peptide chain was assembled, the N-terminal amine was reprotected with t-Boc. Dde was then removed to allow for the bromoacetylation. This strategy gave a high quality crude peptide which was easily purified using conventional reverse phase HPLC. Ligation of the peptide with the thiol-modified PEG took place in aqueous buffer at pH 8 and the reaction completed within 30 minutes. MALDI-MS analysis of the purified, pegylated material revealed a characteristic, bell-shaped spectrum with an increment of 44 Da between the adjacent peaks. For PEG-peptide 20, a cysteine residue was placed in the linker region and its side chain thiol group would serve as an attachment site for a maleimide-containing PEG. Similar conditions were used for the pegylation of this peptide. As the assay data revealed, these two pegylated peptides had even higher in vitro bioactivity as compared to their unpegylated counterparts.

Peptide 21 has in its 8-amino acid linker a potential glycosylation motif, NGS. Since our exemplary tandem repeats are made up of natural amino acids linked by peptide bonds, expression of such a molecule in an appropriate eukaryotic cell system should produce a glycopeptide with the carbohydrate moiety added on the side chain carboxyamide of Asn. Glycosylation is a common post-translational modification process which can have many positive impacts on the biological activity of a given protein by increasing its aqueous solubility and in vivo stability. As the assay data show, incorporation of this glycosylation motif into the linker maintained high bioactivity. The synthetic precursor of the potential glycopeptide had in effect an activity comparable to that of the $-(G)_8$-linked analog. Once glycosylated, this peptide is expected to have the same order of activity as the pegylated peptides, because of the similar chemophysical properties exhibited by a PEG and a carbohydrate moiety.

The last peptide is a dimer of a tandem repeat. It was prepared by oxidizing peptide 18, which formed an intermolecular disulfide bond between the two cysteine residues located at the linker. This peptide was designed to address the possibility that TMP was active as a tetramer. The assay data showed that this peptide was not more active than an average tandem repeat on an adjusted molar basis, which indirectly supports the idea that the active form of TMP is indeed a dimer, otherwise dimerization of a tandem repeat would have a further impact on the bioactivity.

In order to confirm the in vitro data in animals, one pegylated TMP tandem repeat (compound 20 in Table A) was delivered subcutaneously to normal mice via osmotic pumps. Time and dose-dependent increases were seen in platelet numbers for the duration of treatment. Peak platelet levels over 4-fold baseline were seen on day 8. A dose of 10 μg/kg/day of the pegylated TMP repeat produced a similar response to rHuMGDF (non-pegylated) at 100 μg/kg/day delivered by the same route.

TABLE A

TPO-mimetic Peptides

| Peptide No. | Compound | SEQ ID NO: | Relative Potency |
|---|---|---|---|
| | TPO | | ++++ |
| | TMP monomer | 13 | + |
| | TMP C-C dimer | | +++- |
| | TMP-(G)$_N$-TMP: | | |
| 1 | n = 0 | 341 | ++++- |
| 2 | n = 1 | 342 | ++++ |
| 3 | n = 2 | 343 | ++++ |
| 4 | n = 3 | 344 | ++++ |
| 5 | n = 4 | 345 | ++++ |
| 6 | n = 5 | 346 | ++++ |
| 7 | n = 6 | 347 | ++++ |
| 8 | n = 7 | 348 | ++++ |
| 9 | n = 8 | 349 | ++++- |
| 10 | n = 9 | 350 | ++++ |
| 11 | n = 10 | 351 | ++++ |
| 12 | n = 14 | 352 | ++++ |
| 13 | TMP-GPNG-TMP | 353 | +++ |

TABLE A-continued

TPO-mimetic Peptides

| Peptide No. | Compound | SEQ ID NO: | Relative Potency |
|---|---|---|---|
| 14 | IEGPTLRQCLAARA-GGGGGGGG-IEGPTLRQCLAARA (cyclic) | 354 | – |
| 15 | IEGPTLRQCLAARA-GGGGGGGG-IEGPTLRQCLAARA (linear) | 355 | – |
| 16 | IEGPTLRQALAARA-GGGGGGGG-IEGPTLRQALAARA | 356 | – |
| 17a | TMP-GGGKGGGG-TMP | 357 | ++++ |
| 17b | TMP-GGGK(BrAc)GGGG-TMP | 358 | ND |
| 18 | TMP-GGGCGGGG-TMP | 359 | ++++ |
| 19 | TMP-GGGK(PEG)GGGG-TMP | 360 | +++++ |
| 20 | TMP-GGGC(PEG)GGGG-TMP | 361 | +++++ |
| 21 | TMP-GGGN*GSGG-TMP | 362 | ++++ |
| 22 | TMP-GGGCGGGG-TMP<br>TMP-GGGCGGGG-TMP | 363<br>363 | ++++ |

Discussion. It is well accepted that MGDF acts in a way similar to hGH, i.e., one molecule of the protein ligand binds two molecules of the receptor for its activation. Wells et al.(1996), *Ann. Rev. Biochem.* 65: 609–34. Now, this interaction is mimicked by the action of a much smaller peptide, TMP. However, the present studies suggest that this mimicry requires the concerted action of two TMP molecules, as covalent dimerization of TMP in either a C-C parallel or C-N sequential fashion increased the in vitro biological potency of the original monomer by a factor of greater than $10^3$. The relatively low biopotency of the monomer is probably due to inefficient formation of the noncovalent dimer. A preformed covalent repeat has the ability to eliminate the entropy barrier for the formation of a noncovalent dimer which is exclusively driven by weak, noncovalent interactions between two molecules of the small, 14-residue peptide.

It is intriguing that this tandem repeat approach had a similar effect on enhancing bioactivity as the reported C-C dimerization is intriguing. These two strategies brought about two very different molecular configurations. The C-C dimer is a quasi-symmetrical molecule, while the tandem repeats have no such symmetry in their linear structures. Despite this difference in their primary structures, these two types of molecules appeared able to fold effectively into a similar biologically active conformation and cause the dimerization and activation of c-Mpl. These experimental observations provide a number of insights into how the two TMP molecules may interact with one another in binding to c-Mpl. First, the two C-termini of the two bound TMP molecules must be in relatively close proximity with each other, as suggested by data on the C-terminal dimer. Second, the respective N- and C-termini of the two TMP molecules in the receptor complex must also be very closely aligned with each other, such that they can be directly tethered together with a single peptide bond to realize the near maximum activity-enhancing effect brought about by the tandem repeat strategy. Insertion of one or more (up to 14) glycine residues at the junction did not increase (or decrease) significantly the activity any further. This may be due to the fact that a flexible polyglycine peptide chain is able to loop out easily from the junction without causing any significant changes in the overall conformation. This flexibility seems to provide the freedom of orientation for the TMP peptide chains to fold into the required conformation in interacting with the receptor and validate it as a site of modification. Indirect evidence supporting this came from the study on peptide 13, in which a much more rigid b-turn-forming sequence as the linker apparently forced a deviation of the backbone alignment around the linker which might have resulted in a slight distortion of the optimal conformation, thus resulting in a moderate (10-fold) decrease in activity as compared with the analogous compound with a 4-Gly linker. Third, Trp9 in TMP plays a similar role as Trp13 in EMP, which is involved not only in peptide:peptide interaction for the formation of dimers but also is important for contributing hydrophobic forces in peptide:receptor interaction. Results obtained with the W to C mutant analog, peptide 14, suggest that a covalent disulfide linkage is not sufficient to approximate the hydrophobic interactions provided by the Trp pair and that, being a short linkage, it might bring the two TMP monomers too close, therefore perturbing the overall conformation of the optimal dimeric structure.

An analysis of the possible secondary structure of the TMP peptide can provide further understanding on the interaction between TMP and c-Mpl. This can be facilitated by making reference to the reported structure of the EPO mimetic peptide. Livnah et al. (1996), *Science* 273:464–75 The receptor-bound EMP has a b-hairpin structure with a b-turn formed by the highly consensus Gly-Pro-Leu-Thr at the center of its sequence. Instead of GPLT, TMP has a highly selected GPTL sequence which is likely to form a similar turn. However, this turn-like motif is located near the N-terminal part in TMP. Secondary structure prediction using Chau-Fasman method suggests that the C-terminal half of the peptide has a tendency to adopt a helical conformation. Together with the highly conserved Trp at position 9, this C-terminal helix may contribute to the stabilization of the dimeric structure. It is interesting to note that most of our tandem repeats are more potent than the C-terminal parallel dimer. Tandem repeats seem to give the molecule a better fit conformation than does the C-C parallel dimerization. The seemingly asymmetric feature of a tandem repeat might have brought it closer to the natural ligand which, as an asymmetric molecule, uses two different sites to bind two identical receptor molecules.

Introduction of a PEG moiety was envisaged to enhance the in vivo activity of the modified peptide by providing it a protection against proteolytic degradation and by slowing down its clearance through renal filtration. It was unexpected that pegylation could further increase the in vitro bioactivity of a tandem repeated TMP peptide in the cell-based proliferation assay.

Example 2

Fc-TMP Fusions

TMPs (and EMPs as described in Example 3) were expressed in either monomeric or dimeric form as either N-terminal or C-terminal fusions to the Fc region of human IgG1. In all cases, the expression construct utilized the luxPR promoter promoter in the plasmid expression vector pAMG21.

Fc-TMP. A DNA sequence coding for the Fc region of human IgG1 fused in-frame to a monomer of the TPO-mimetic peptide was constructed using standard PCR technology. Templates for PCR reactions were the pFc-A3 vector and a synthetic TMP gene. The synthetic gene was constructed from the 3 overlapping oligonucleotides (SEQ ID NOS: 364, 365, and 366, respectively) shown below:

```
1842-97   AAA AAA GGA TCC TCG AGA TTA AGC ACG AGC
          AGC CAG CCA CTG ACG CAG AGT CGG ACC 1842-98   AAA GGT GGA GGT GGT GGT ATC GAA GGT CCG
          ACT CTG CGT 1842-99   CAG TGG CTG GCT GCT CGT GCT TAA TCT CGA
          GGA TCC TTT TTT
```

These oligonucleotides were annealed to form the duplex encoding an amino acid sequence (SEQ ID NOS: 367 and 368, respectively) shown below:

The oligonucleotides 1830-51 and 1842-98 contain an overlap of 24 nucleotides, allowing the two genes to be fused together in the correct reading frame by combining the above PCR products in a third reaction using the outside primers, 1216-52 and 1842-97.

The final PCR gene product (the full length fusion gene) was digested with restriction endonucleases XbaI and BamHI, and then ligated into the vector pAMG21 and transformed into competent E. coli strain 2596 cells as described for EMP-Fc herein. Clones were screened for the ability to produce the recombinant protein product and to possess the gene fusion having the correct nucleotide sequence. A single such clone was selected and designated Amgen strain #3728.

The nucleotide and amino acid sequences (SEQ ID NOS: 5 and 6) of the fusion protein are shown in FIG. 7.

Fc-TMP-TMP. A DNA sequence coding for the Fc region of human IgG1 fused in-frame to a dimer of the TPO-mimetic peptide was constructed using standard PCR technology. Templates for PCR reactions were the pFc-A3 vector and a synthetic TMP-TMP gene. The synthetic gene was constructed from the 4 overlapping oligonucleotides (SEQ ID NOS: 371 to 374, respectively) shown below:

```
1830-52   AAA GGT GGA GGT GGT GGT ATC GAA GGT CCG
          ACT CTG CGT CAG TGG CTG GCT GCT CGT GCT 1830-53   ACC TCC ACC ACC AGC ACG AGC AGC CAG
          CCA CTG ACG CAG AGT CGG ACC 1830-54   GGT GGT GGA GGT GGC GGC GGA GGT ATT GAG
          GGC CCA ACC CTT CGC CAA TGG CTT GCA GCA
          CGC GCA 1830-55   AAA AAA AGG ATC CTC GAG ATT ATG CGC GTG
          CTG CAA GCC ATT GGC GAA GGG TTG GGC CCT
          CAA TAC CTC CGC CGC C
```

The 4 oligonucleotides were annealed to form the duplex encoding an amino acid sequence (SEQ ID NOS: 375 and 376, respectively) shown below:

```
    AAAGGTGGAGGTGGTGGTATCGAAGGTCCGACTCTGCGTCAGTGGCTGGCTGCTCGTGCT
 1  ---------+---------+---------+---------+---------+---------+  60
    CCAGGCTGAGACGCAGTCACCGACCGACGAGCACGA
a   K  G  G  G  G  I  E  G  P  T  L  R  Q  W  L  A  A  R  A    -

TAATCTCGAGGATCCTTTTTT
61  ---------+---------+- 81
    ATTAGAGCTCCTAGGAAAAAA
a    *
```

This duplex was amplified in a PCR reaction using 1842-98 and 1842-97 as the sense and antisense primers.

The Fc portion of the molecule was generated in a PCR reaction with pFc-A3 using the primers shown below (SEQ ID NOS: 369 and 370):

```
1216-52   AAC ATA AGT ACC TGT AGG ATC G 1830-51   TTCGATACCA CCACCTCCAC CTTTACCCGG AGACAGGGAG AGGCTCTTCTGC
```

```
        AAAGGTGGAGGTGGTGGTATCGAAGGTCCGACTCTGCGTCAGTGGCTGGCTGCTCGTGCT
     1  ---------+---------+---------+---------+---------+---------+  60
                                      CCAGGCTGAGACGCAGTCACCGACCGACGAGCACGA
     a    K  G  G  G  G  G  I  E  G  P  T  L  R  Q  W  L  A  A  R  A   -

GGTGGTGGAGGTGGCGGCGGAGGTATTGAGGGCCCAACCCTTCGCCAATGGCTTGCAGCA
    61  ---------+---------+---------+---------+---------+---------+  120
        CCACCACCTCCACCGCCGCCTCCATAACTCCCGGGTTGGGAAGCGGTTACCGAACGTCGT
     a    G  G  G  G  G  G  G  I  E  G  P  T  K  R  Q  W  L  A  A     -

CGCGCA
   121  --------------------------148
        GCGCGTATTAGAGCTCCTAGGAAAAAAA
     a    R  A  *-
```

This duplex was amplified in a PCR reaction using 1830-52 and 1830-55 as the sense and antisense primers.

The Fc portion of the molecule was generated in a PCR reaction with pFc-A3 using the primers 1216-52 and 1830-51 as described above for Fc-TMP. The full length fusion gene was obtained from a third PCR reaction using the outside primers 1216-52 and 1830-55.

The final PCR gene product (the full length fusion gene) was digested with restriction endonucleases XbaI and BamHI, and then ligated into the vector pAMG21 and transformed into competent E. coli strain 2596 cells as described in example 1. Clones were screened for the ability to produce the recombinant protein product and to possess the gene fusion having the correct nucleotide sequence. A single such clone was selected and designated Amgen strain #3727.

The nucleotide and amino acid sequences (SEQ ID NOS: 7 and 8) of the fusion protein are shown in FIG. 8.

TMP-TMP-Fc. A DNA sequence coding for a tandem repeat of the TPO-mimetic peptide fused in-frame to the Fc region of human IgG1 was constructed using standard PCR technology. Templates for PCR reactions were the EMP-Fc plasmid from strain #3688 (see Example 3) and a synthetic gene encoding the TMP dimer. The synthetic gene for the tandem repeat was constructed from the 7 overlapping oligonucleotides shown below (SEQ ID NOS: 377 to 383, respectively):

```
1885-52    TTT TTT CAT ATG ATC GAA GGT CCG ACT CTG
           CGT CAG TGG 1885-53    AGC ACG AGC AGC CAG CCA CTG ACG CAG AGT
           CGG ACC TTC GAT CAT ATG
```

-continued
```
1885-54    CTG GCT GCT CGT GCT GGT GGA GGC GGT GGG
           GAC AAA ACT CAC ACA 1885-55    CTG GCT GCT CGT GCT GGC GGT GGT GGC GGA
           GGG GGT GGC ATT GAG GGC CCA 1885-56    AAG CCA TTG GCG AAG GGT TGG GCC CTC AAT
           GCC ACC CCC TCC GCC ACC ACC GCC 1885-57    ACC CTT CGC CAA TGG CTT GCA GCA CGC GCA
           GGG GGA GGC GGT GGG GAC AAA ACT 1885-58    CCC ACC GCC TCC CCC TGC GCG TGC TGC
```

These oligonucleotides were annealed to form the duplex shown encoding an amino acid sequence shown below (SEQ ID NOS 384 and 385):

```
        TTTTTTCATATGATCGAAGGTCCGACTCTGCGTCAGTGGCTGGCTGCTCGTGCTGGCGGT
     1  ---------+---------+---------+---------+---------+---------+  60
                 GTATACTAGCTTCCAGGCTGAGACGCAGTCACCGACCGACGAGCACGACCGCCA
     a       M  I  E  G  P  T  L  R  Q  W  L  A  A  R  A  G  G     -

GGTGGCGGAGGGGGTGGCATTGAGGGCCCAACCCTTCGCCAATGGCTGGCTGCTCGTGCT
    61  ---------+---------+---------+---------+---------+---------+  120
     a  CCACCGCCTCCCCCACCGTAACTCCCGGGTTGGGAAGCGGTTACCGAACGTCGTGCGCGT
         G  G  G  G  G  G  I  E  G  P  T  L  R  Q  W  L  A  A  R  A   -

GGTGGAGGCGGTGGGGACAAAACTCTGGCTGCTCGTGCTGGTGGAGGCGGTGGGGACAAA
   121  ---------+---------+---------+---------+---------+---------+  180
        CCCCCTCCGCCACCC
     a   G  G  G  G  G  D  K  T  L  A  A  R  A  G  G  G  G  G  D  K   -

ACTCACACA
   181  --------- 189
     a    T  H  T -
```

This duplex was amplified in a PCR reaction using 1885-52 and 1885-58 as the sense and antisense primers.

The Fc portion of the molecule was generated in a PCR reaction with DNA from the EMP-Fc fusion strain #3688 (see Example 3) using the primers 1885-54 and 1200-54. The full length fusion gene was obtained from a third PCR reaction using the outside primers 1885-52 and 1200-54.

The final PCR gene product (the full length fusion gene) was digested with restriction endonucleases XbaI and BamHI, and then ligated into the vector pAMG21 and transformed into competent E. coli strain 2596 cells as described for Fc-EMP herein. Clones were screened for the ability to produce the recombinant protein product and to possess the gene fusion having the correct nucleotide sequence. A single such clone was selected and designated Amgen strain #3798.

The nucleotide and amino acid sequences (SEQ ID NOS: 9 and 10) of the fusion protein are shown in FIG. 9.

TMP-Fc. A DNA sequence coding for a monomer of the TPO-mimetic peptide fused in-frame to the Fc region of human IgG1 was obtained fortuitously in the ligation in TMP-TMP-Fc, presumably due to the ability of primer 1885-54 to anneal to 1885-53 as well as to 1885–58. A single clone having the correct nucleotide sequence for the TMP-Fc construct was selected and designated Amgen strain #3788.

The nucleotide and amino acid sequences (SEQ ID NOS: 11 and 12) of the fusion protein are shown in FIG. 10.

Expression in *E. coli*. Cultures of each of the pAMG21-Fc-fusion constructs in *E. coli* GM221 were grown at 37° C. in Luria Broth medium containing 50 mg/ml kanamycin. Induction of gene product expression from the luxPR promoter was achieved following the addition of the synthetic autoinducer N-(3-oxohexanoyl)-DL-homoserine lactone to the culture media to a final concentration of 20 ng/ml. Cultures were incubated at 37° C. for a further 3 hours. After 3 hours, the bacterial cultures were examined by microscopy for the presence of inclusion bodies and were then collected by centrifugation. Refractile inclusion bodies were observed in induced cultures indicating that the Fc-fusions were most likely produced in the insoluble fraction in *E. coli*. Cell pellets were lysed directly by resuspension in Laemmli sample buffer containing 10% b-mercaptoethanol and were analyzed by SDS-PAGE. In each case, an intense coomassie-stained band of the appropriate molecular weight was observed on an SDS-PAGE gel.

pAMG21. The expression plasmid pAMG21 can be derived from the Amgen expression vector pCFM1656 (ATCC #69576) which in turn be derived from the Amgen expression vector system described in U.S. Pat. No. 4,710,473. The pCFM1656 plasmid can be derived from the described pCFM836 plasmid (U.S. Pat. No. 4,710,473) by:
(a) destroying the two endogenous NdeI restriction sites by end filling with T4 polymerase enzyme followed by blunt end ligation;
(b) replacing the DNA sequence between the unique AatII and ClaI restriction sites containing the synthetic $P_L$ promoter with a similar fragment obtained from pCFM636 (U.S. Pat. No. 4,710,473) containing the PL promoter (see SEQ ID NO: 386 below); and
(c) substituting the small DNA sequence between the unique ClaI and KpnI restriction sites with the oligonucleotide having the sequence of SEQ ID NO: 388.

The expression plasmid pAMG21 can then be derived from pCFM1656 by making a series of site-directed base changes by PCR overlapping oligo mutagenesis and DNA sequence substitutions. Starting with the BglII site (plasmid bp # 180) immediately 5' to the plasmid replication promoter $P_{copB}$ and proceeding toward the plasmid replication genes, the base pair changes are as shown in Table B below.

TABLE B

Base pair changes resulting in pAMG21

| pAMG21 bp # | bp in pCFM1656 | bp changed to in pAMG21 |
|---|---|---|
| # 204 | T/A | C/G |
| # 428 | A/T | G/C |
| # 509 | G/C | A/T |
| # 617 | – | insert two G/C bp |
| # 679 | G/C | T/A |
| # 980 | T/A | C/G |
| # 994 | G/C | A/T |
| # 1004 | A/T | C/G |
| # 1007 | C/G | T/A |
| # 1028 | A/T | T/A |
| # 1047 | C/G | T/A |
| # 1178 | G/C | T/A |
| # 1466 | G/C | T/A |
| # 2028 | G/C | bp deletion |
| # 2187 | C/G | T/A |
| # 2480 | A/T | T/A |
| # 2499–2502 | AGTG<br>TCAC | GTCA<br>CAGT |
| # 2642 | TCCGAGC<br>AGGCTCG | 7 bp deletion |
| # 3435 | G/C | A/T |
| # 3446 | G/C | A/T |
| # 3643 | A/T | T/A |

SEQ ID NO: 386:
<u>AatII</u>
5' CTAATTCCGCTCTCACCTACCAAACAATGCCCCCCTGCAAAAAATAAATTCATAT-
3' TGCAGATTAAGGCGAGAGTGGATGGTTTGTTACGGGGGGACGTTTTTTATTTAAGTATA-

-AAAAAACATACAGATAACCATCTGCGGTGATAAATTATCTCTGGCGGTGTTGACATAAA-
-TTTTTTGTATGTCTATTGGTAGACGCCACTATTTAATAGAGACCGCCACAACTGTATTT-

-TACCACTGGCGGTGATACTGAGCACAT      3'
-ATGGTGACCGCCACTATGACTCGTGTAGC   5'
                            <u>ClaI</u>

SEQ ID NO: 387:
5' CGATTTGATTCTAGAAGGAGGAATAACATATGGTTAACGCGTTGGAATTCGGTAC 3'
3'    TAAACTAAGATCTTCCTCCTTATTGTATACCAATTGCGCAACCTTAAGC       5'
   <u>ClaI</u>                                                  <u>KpnI</u>

The DNA sequence between the unique AatII (position #4364 in pCFM1656) and SacII (position #4585 in pCFM1656) restriction sites is substituted with the DNA sequence (SEQ ID NO: 23) shown in FIGS. 17A and 17B. During the ligation of the sticky ends of this substitution DNA sequence, the outside AatII and SacII sites are destroyed. There are unique AatII and SacII sites in the substituted DNA.

GM221 (Amgen #2596). The Amgen host strain #2596 is an *E. coli* K-12 strain derived from Amgen strain #393. It has been modified to contain both the temperature sensitive lambda repressor cI857s7 in the early ebg region and the lacI$^Q$ repressor in the late ebg region (68 minutes). The presence of these two repressor genes allows the use of this host with a variety of expression systems, however both of these repressors are irrelevant to the expression from luXP$_R$. The untransformed host has no antibiotic resistances.

The ribosome binding site of the cI857s7 gene has been modified to include an enhanced RBS. It has been inserted into the ebg operon between nucleotide position 1170 and 1411 as numbered in Genbank accession number M64441Gb_Ba with deletion of the intervening ebg sequence. The sequence of the insert is shown below with lower case letters representing the ebg sequences flanking the insert shown below (SEQ ID NO: 388):

```
ttattttcgtGCGGCCGCACCATTATCACCGCCAGAGGTAAACTAGTCAACACGCACGGTGTTAGATATTTAT

CCCTTGCGGTGATAGATTGAGCACATCGATTTGATTCTAGAAGGAGGGATAATATATGAGCACAAAAAAGAAA

CCATTAACACAAGAGCAGCTTGAGGACGCACGTCGCCTTAAAGCAATTTATGAAAAAAAGAAAAATGAACTTG

GCTTATCCCAGGAATCTGTCGCAGACAAGATGGGGATGGGGCAGTCAGGCGTTGGTGCTTTATTTAATGGCAT

CAATGCATTAAATGCTTATAACGCCGCATTGCTTACAAAAATTCTCAAAGTTAGCGTTGAAGAATTTAGCCCT

TCAATCGCCAGAGAATCTACGAGATGTATGAAGCGGTTAGTATGCAGCCGTCACTTAGAAGTGAGTATGAGTA

CCCTGTTTTTTCTCATGTTCAGGCAGGGATGTTCTCACCTAAGCTTAGAACCTTTACCAAAGGTGATGCGGAG

AGATGGGTAAGCACAACCAAAAAAGCCAGTGATTCTGCATTCTGGCTTGAGGTTGAAGGTAATTCCATGACCG

CACCAACAGGCTCCAAGCCAAGCTTTCCTGACGGAATGTTAATTCTCGTTGACCCTGAGCAGGCTGTTGAGCC

AGGTGATTTCTGCATAGCCAGACTTGGGGGTGATGAGTTTACCTTCAAGAAACTGATCAGGGATAGCGGTCAG

GTGTTTTTACAACCACTAAACCCACAGTACCCAATGATCCCATGCAATGAGAGTTGTTCCGTTGTGGGGAAAG

TTATCGCTAGTCAGTGGCCTGAAGAGACGTTTGGCTGATAGACTAGTGGATCCACTAGTgtttctgccc
```

The construct was delivered to the chromosome using a recombinant phage called MMebg-cI857s7enhanced RBS #4 into F'tet/393. After recombination and resolution only the chromosomal insert described above remains in the cell. It was renamed F'tet/GM101. F'tet/GM101 was then modified by the delivery of a lacI$^Q$ construct into the ebg operon between nucleotide position 2493 and 2937 as numbered in the Genbank accession number M64441Gb_Ba with the deletion of the intervening ebg sequence. The sequence of the insert is shown below with the lower case letters representing the ebg sequences flanking the insert (SEQ ID NO: 389) shown below:

```
ggcggaaaccGACGTCCATCGAATGGTGCAAAACCTTTCGCGGTATGGCATGATAGCGCCCGGAAGAGAGTCA

ATTCAGGGTGGTGAATGTGAAACCAGTAACGTTATACGATGTCGCAGAGTATGCCGGTGTCTCTTATCAGACC

GTTTCCCGCGTGGTGAACCAGGCCAGCCACGTTTCTGCGAAAACGCGGGAAAAAGTCGAAGCGGCGATGGCGG

AGCTGAATTACATTCCCAACCGCGTGGCACAACAACTGGCGGGCAAACAGTCGCTCCTGATTGGCGTTGCCAC

CTCCAGTCTGGCCCTGCACGCGCCGTCGCAAATTGTCGCGGCGATTAAATCTCGCGCCGATCAACTGGGTGCC

AGCGTGGTGGTGTCGATGGTAGAACGAAGCGGCGTCGAAGCCTGTAAAGCGGCGGTGCACAATCTTCTCGCGC

AACGCGTCAGTGGGCTGATCATTAACTATCCGCTGGATGACCAGGATGCCATTGCTGTGGAAGCTGCCTGCAC

TAATGTTCCGGCGTTATTTCTTGATGTCTCTGACCAGACACCCATCAACAGTATTATTTTCTCCCATGAAGAC

GGTACGCGACTGGGCGTGGAGCATCTGGTCGCATTGGGTCACCAGCAAATCGCGCTGTTAGCGGGCCCATTAA

GGAACGGGAAGGCGACTGGAGTGCCATGTCCGGTTTTCAACAAACCATGCAAATGCTGAATGAGGGCATCGTT

CCCACTGCGATGCTGGTTGCCAACGATCAGATGGCGCTGGGCGCAATGCGCGCCATTACCGAGTCCGGCTGC

GCGTTGGTGCGGATATCTCGGTAGTGGGATACGACGATACCGAAGACAGCTCATGTTATATCCCGCCGTTAAC

CACCATCAAACAGGATTTTCGCCTGCTGGGGCAAACCAGCGTGGACCGCTTGCTGCAACTCTCTCAGGGCCAG

GCGGTGAAGGGCAATCAGCTGTTGCCCGTCTCACTGGTGAAAAGAAAAACCACCCTGGCGCCCAATACGCAAA

CCGCCTCTCCCCGCGCGTTGGCCGATTCATTAATGCAGCTGGCACGACAGGTTTCCCGACTGGAAAGCGGACA

GTAAGGTACCATAGGATCCaggcacagga
```

The construct was delivered to the chromosome using a recombinant phage called AGebg-LacIQ#5 into F'tet/GM101. After recombination and resolution only the chromosomal insert described above remains in the cell. It was renamed F'tet/GM221. The F'tet episome was cured from the strain using acridine orange at a concentration of 25 μg/ml in LB. The cured strain was identified as tetracyline sensitive and was stored as GM221.

Expression. Cultures of pAMG21-Fc-TMP-TMP in *E. coli* GM221 in Luria Broth medium containing 50 μg/ml kanamycin were incubated at 37° C. prior to induction. Induction of Fc-TMP-TMP gene product expression from the luxPR promoter was achieved following the addition of the synthetic autoinducer N-(3-oxohexanoyl)-DL-homoserine lactone to the culture media to a final concentration of 20 ng/ml and cultures were incubated at 37° C. for a further 3 hours. After 3 hours, the bacterial cultures were examined by microscopy for the presence of inclusion bodies and were then collected by centrifugation. Refractile inclusion bodies were observed in induced cultures indicating that the Fc-TMP-TMP was most likely produced in the insoluble fraction in *E. coli*. Cell pellets were lysed directly by resuspension in Laemmli sample buffer containing 10% •-mercaptoethanol and were analyzed by SDS-PAGE. An intense Coomassie stained band of approximately 30 kDa was observed on an SDS-PAGE gel. The expected gene product would be 269 amino acids in length and have an expected molecular weight of about 29.5 kDa. Fermentation was also carried out under standard batch conditions at the 10 L scale, resulting in similar expression levels of the Fc-TMP-TMP to those obtained at bench scale.

Purification of Fc-TMP-TMP. Cells are broken in water (1/10) by high pressure homogenization (2 passes at 14,000 PSI) and inclusion bodies are harvested by centrifugation (4200 RPM in J-6B for 1 hour). Inclusion bodies are solubilized in 6M guanidine, 50 mM Tris, 8 mM DTT, pH 8.7 for 1 hour at a 1/10 ratio. The solubilized mixture is diluted 20 times into 2M urea, 50 mM tris, 160 mM arginine, 3 mM cysteine, pH 8.5. The mixture is stirred overnight in the cold and then concentrated about 10 fold by ultafiltration. It is then diluted 3 fold with 10 mM Tris, 1.5M urea, pH 9. The pH of this mixture is then adjusted to pH 5 with acetic acid. The precipitate is removed by centrifugation and the supernatant is loaded onto a SP-Sepharose Fast Flow column equilibrated in 20 mM NaAc, 100 mM NaCl, pH 5(10 mg/ml protein load, room temperature). The protein is eluted off using a 20 column volume gradient in the same buffer ranging from 100 mM NaCl to 500 mM NaCl. The pool from the column is diluted 3 fold and loaded onto a SP-Sepharose HP column in 20 mM NaAc, 150 mM NaCl, pH 5(10 mg/ml protein load, room temperature). The protein is eluted off using a 20 column volume gradient in the same buffer ranging from 150 mM NaCl to 400 mM NaCl. The peak is pooled and filtered.

Characterization of Fc-TMP activity. The following is a summary of in vivo data in mice with various compounds of this invention.

Mice: Normal female BDF1 approximately 10–12 weeks of age.

Bleed schedule: Ten mice per group treated on day 0, two groups started 4 days apart for a total of 20 mice per group. Five mice bled at each time point, mice were bled a minimum of three times a week. Mice were anesthetized with isoflurane and a total volume of 140–160 μl of blood was obtained by puncture of the orbital sinus. Blood was counted on a Technicon H1E blood analyzer running software for murine blood. Parameters measured were white blood cells, red blood cells, hematocrit, hemoglobin, platelets, neutrophils.

Treatments: Mice were either injected subcutaneously for a bolus treatment or implanted with 7-day micro-osmotic pumps for continuous delivery. Subcutaneous injections were delivered in a volume of 0.2 ml. Osmotic pumps were inserted into a subcutaneous incision made in the skin between the scapulae of anesthetized mice. Compounds were diluted in PBS with 0.1% BSA. All experiments included one control group, labeled "carrier" that were treated with this diluent only. The concentration of the test articles in the pumps was adjusted so that the calibrated flow rate from the pumps gave the treatment levels indicated in the graphs.

Compounds: A dose titration of the compound was delivered to mice in 7 day micro-osmotic pumps. Mice were treated with various compounds at a single dose of 100 µg/kg in 7 day osmotic pumps. Some of the same compounds were then given to mice as a single bolus injection.

Activity test results: The results of the activity experiments are shown in FIGS. 11 and 12. In dose response assays using 7-day micro-osmotic pumps, the maximum effect was seen with the compound of SEQ ID NO: 18 was at 100 µg/kg/day; the 10 µg/kg/day dose was about 50% maximally active and 1 µg/kg/day was the lowest dose at which activity could be seen in this assay system. The compound at 10 µg/kg/day dose was about equally active as 100 µg/kg/day unpegylated rHu-MGDF in the same experiment.

Example 3

Fc-EMP Fusions

Fc-EMP. A DNA sequence coding for the Fc region of human IgG1 fused in-frame to a monomer of the EPO-mimetic peptide was constructed using standard PCR technology. Templates for PCR reactions were a vector containing the Fc sequence (pFc-A3, described in International application WO 97/23614, published Jul. 3, 1997) and a synthetic gene encoding EPO monomer. The synthetic gene for the monomer was constructed from the 4 overlapping oligonucleotides (SEQ ID NOS: 390 to 393, respectively) shown below:

```
1782-3 TAT GAA AGG TGG AGG TGG TGG TGG AGG TAC TTA
       CTC TTG CCA CTT CGG CCC GCT GAC TTG G 1798-3 CGG TTT GCA AAC CCA AGT CAG CGG GCC GAA GTG
       GCA AGA GTA AGT ACC TCC ACC ACC TCC ACC TTT
       CAT 1798-4 GTT TGC AAA CCG CAG GGT GGC GGC GGC GGC GGC
       GGT GGT ACC TAT TCC TGT CAT TTT 1798-5 CCA GGT CAG CGG GCC AAA ATG ACA GGA ATA GGT
       ACC ACC GCC GCC GCC GCC GCC ACC CTG
```

The 4 oligonucleotides were annealed to form the duplex encoding an amino acid sequence (SEQ ID NOS: 394 and 395, respectively) shown below:

```
         CTC T
and
1798-19  CTA ATT GGA TCC ACG AGA TTA ACC ACC
         CTG CGG TTT GCA A
``` as the sense and antisense primers (SEQ ID NOS: 396 and 397, respectively).

The Fc portion of the molecule was generated in a PCR reaction with pFc-A3 using the primers

```
1216-52  AAC ATA AGT ACC TGT AGG ATC G 1798-17  AGA GTA AGT ACC TCC ACC ACC TCC ACC
         TTT ACC CGG AGA CAG GGA GAG GCT CTT CTG
         C
``` which are SEQ ID NOS: 369 and 399, respectively. The oligonucleotides 1798-17 and 1798-18 contain an overlap of 61 nucleotides, allowing the two genes to be fused together in the correct reading frame by combining the above PCR products in a third reaction using the outside primers, 1216-52 and 1798-19.

The final PCR gene product (the full length fusion gene) was digested with restriction endonucleases XbaI and BamHI, and then ligated into the vector pAMG21 (described below), also digested with XbaI and BamHI. Ligated DNA was transformed into competent host cells of E. coli strain 2596 (GM221, described herein). Clones were screened for the ability to produce the recombinant protein product and to possess the gene fusion having the correct nucleotide sequence. A single such clone was selected and designated Amgen strain #3718.

The nucleotide and amino acid sequence of the resulting fusion protein (SEQ ID NOS: 15 and 16) are shown in FIG. 13.

EMP-Fc. A DNA sequence coding for a monomer of the EPO-mimetic peptide fused in-frame to the Fc region of human IgG1 was constructed using standard PCR technology. Templates for PCR reactions were the pFC-A3a vector and a synthetic gene encoding EPO monomer. The synthetic gene for the monomer was constructed from the 4 overlapping oligonucleotides 1798-4 and 1798-5 (above) and 1798-6 and 1798-7 (SEQ ID NOS: 400 and 401, respectively) shown below:

```
      TATGAAAGGTGGAGGTGGTGGTGGAGGTACTTACTCTTGCCACTTCGGCCCGCTGACTTG
1     ---------+---------+---------+---------+---------+---------+ 60
      TACTTTCCACCTCCACCACCACCTCCATGAATGAGAACGGTGAAGCCGGGCGACTGAAC
b      M   K   G   G   G   G   G   G   T   Y   S   C   H   F   G   P   L   T   W   -

GGTTTGCAAACCGCAGGGTGGCGGCGGCGGCGGCGGTGGTACCTATTCCTGTCATTTT
61    ---------+---------+---------+---------+---------+--- 133
      CCAAACGTTTGGCGTCCCACCGCCGCCGCCGCCGCCACCATGGATAAGGACAGTAAAACCGGGCGACTGGACC
b      V   C   K   P   Q   G   G   G   G   G   G   T   Y   S   C   H   F  +31
```

This duplex was amplified in a PCR reaction using

```
1798-18  GCA GAA GAG CCT CTC CCT GTC TCC GGG TAA
         AGG TGG AGG TGG TGG TGG AGG TAC TTA 1798-6 GGC CCG CTG ACC TGG GTA TGT AAG CCA CAA GGG
       GGT GGG GGA GGC GGG GGG TAA TCT CGA G 1798-7 GAT CCT CGA GAT TAC CCC CCG CCT CCC CCA CCC
```

```
        CCT TGT GGC TTA CAT AC
```

The 4 oligonucleotides were annealed to form the duplex encoding an amino acid sequence (SEQ ID NOS: 402 and 403, respectively) shown below:

```
    GTTTGCAAACCGCAGGGTGGCGGCGGCGCGGCGGTGGTACCTATTCCTGTCATTTTGGC
  1 ---------+---------+---------+---------+---------+---------+  60
    GTCCCACCGCCGCCGCCGCCGCCACCATGGATAAGGACAGTAAAACCG
  A  V  C  K  P  Q  G  G  G  G  G  G  G  T  Y  S  C  H  F  G  -

CCGCTGACCTGGGTATGTAAGCCACAAGGGGTGGGGGAGGCGGGGGGTAATCTCGAG
 61 ---------+---------+---------+---------+---------+---------+- 122
    GGCGACTGGACCCATACATTCGGTGTTCCCCCACCCCCTCCGCCCCCATTAGAGCTCCTAG
  A  P  L  T  W  V  C  K  P  Q  G  G  G  G  G  G  *
```

This duplex was amplified in a PCR reaction using

```
1798-21   TTA TTT CAT ATG AAA GGT GGT AAC TAT TCC
          TGT CAT TTT
and
1798-22   TGG ACA TGT GTG AGT TTT GTC CCC CCC GCC
          TCC CCC ACC CCC T
``` as the sense and antisense primers (SEQ ID NOS: 404 and 405, respectively).

The Fc portion of the molecule was generated in a PCR reaction with pFc-A3 using the primers

```
1798-23   AGG GGG TGG GGG AGG CGG GGG GGA CAA AAC
          TCA CAC ATG TCC A
and
1200-54   GTT ATT GCT CAG CGG TGG CA
``` which are SEQ ID NOS: 406 and 407, respectively. The oligonucleotides 1798-22 and 1798-23 contain an overlap of 43 nucleotides, allowing the two genes to be fused together in the correct reading frame by combining the above PCR products in a third reaction using the outside primers, 1787-21 and 1200-54.

The final PCR gene product (the full length fusion gene) was digested with restriction endonucleases XbaI and BamHI, and then ligated into the vector pAMG21 and transformed into competent *E. coli* strain 2596 cells as described above. Clones were screened for the ability to produce the recombinant protein product and to possess the gene fusion having the correct nucleotide sequence. A single such clone was selected and designated Amgen strain #3688.

The nucleotide and amino acid sequences (SEQ ID NOS: 17 and 18) of the resulting fusion protein are shown in FIG. 14.

EMP-EMP-Fc. A DNA sequence coding for a dimer of the EPO-mimetic peptide fused in-frame to the Fc region of human IgG1 was constructed using standard PCR technology. Templates for PCR reactions were the EMP-Fc plasmid from strain #3688 above and a synthetic gene encoding the EPO dimer. The synthetic gene for the dimer was constructed from the 8 overlapping oligonucleotides (SEQ ID NOS:408 to 415, respectively) shown below:

```
1869-23   TTT TTT ATC GAT TTG ATT CTA GAT TTG AGT
          TTT AAC TTT TAG AAG GAG GAA TAA AAT ATG 1869-48   TAA AAG TTA AAA CTC AAA TCT AGA ATC AAA
          TCG ATA AAA AA 1871-72   GGA GGT ACT TAC TCT TGC CAC TTC GGC CCG
          CTG ACT TGG GTT TGC AAA CCG 1871-73   AGT CAG CGG GCC GAA GTG GCA AGA GTA AGT
          ACC TCC CAT ATT TTA TTC CTC CTT C 1871-74   CAG GGT GGC GGC GGC GGC GGC GGT GGT ACC
          TAT TCC TGT CAT TTT GGC CCG CTG ACC TGG 1871-75   AAA ATG ACA GGA ATA GGT ACC ACC GCC GCC
          GCC GCC GCC ACC CTG CGG TTT GCA AAC CCA 1871-78   GTA TGT AAG CCA CAA GGG GGT GGG GGA GGC
          GGG GGG GAC AAA ACT CAC ACA TGT CCA 1871-79   AGT TTT GTC CCC CCC GCC TCC CCC ACC CCC
          TTG TGG CTT ACA TAC CCA GGT CAG CGG GCC
```

The 8 oligonucleotides were annealed to form the duplex encoding an amino acid sequence (SEQ ID NOS: 416 and 417, respectively) shown below:

```
      TTTTTTATCGATTTGATTCTAGATTTGAGTTTTAACTTTTAGAAGGAGGAATAAAATATG
   1  ---------+---------+---------+---------+---------+---------+ 60
      AAAAAATAGCTAAACTAAGATCTAAACTCAAAATTGAAATCTTCCTCCTTATTTTATAC
   a                                                              M  -

GGAGGTACTTACTCTTGCCACTTCGGCCCGCTGACTTGGGTTTGCAAACCGCAGGGTGGC
  61  ---------+---------+---------+---------+---------+---------+120
      CCTCCATGAATGAGAACGGTGAAGCCGGGCGACTGAACCCAAACGTTTGGCGTCCCACCG
   a   G  G  T  Y  S  C  H  F  G  P  L  T  W  V  C  K  P  Q  G  G  -

GGCGGCGGCGGCGGTGGTACCTATTCCTGTCATTTTGGCCCGCTGACCTGGGTATGTAAG
 121  ---------+---------+---------+---------+---------+---------+180
      CCGCCGCCGCCGCCACCATGGATAAGGACAGTAAAACCGGGCGACTGGACCCATACATTC
```

```
                 -continued
      CCTCCATGAATGAGAACGGTGAAGCCGGGCGACTGAACCCAAACGTTTGGCGTCCCACCG
a       G   G   G   G   G   T   Y   S   C   H   F   G   P   L   T   W   V   C   K    -

CCACAAGGGGTGGGGGAGGCGGGGGGGACAAAACTCACACATGTCCA
   181 ---------+---------+---------+---------+--------- 228
      GGTGTTCCCCCACCCCCTCCGCCCCCCCTGTTTTGA
a       P   Q   G   G   G   G   G   G   D   K   T   H   T   C   P    -
```

This duplex was amplified in a PCR reaction using 1869-23 and 1871-79 (shown above) as the sense and antisense primers.

The Fc portion of the molecule was generated in a PCR reaction with strain 3688 DNA using the primers 1798-23 and 1200-54 (shown above).

The oligonucleotides 1871-79 and 1798-23 contain an overlap of 31 nucleotides, allowing the two genes to be fused together in the correct reading frame by combining the above PCR products in a third reaction using the outside primers, 1869-23 and 1200-54.

The final PCR gene product (the full length fusion gene) was digested with restriction endonucleases XbaI and BamHI, and then ligated into the vector pAMG21 and transformed into competent *E. coli* strain 2596 cells as described for Fc-EMP. Clones were screened for ability to produce the recombinant protein product and possession of the gene fusion having the correct nucleotide sequence. A single such clone was selected and designated Amgen strain #3813.

The nucleotide and amino acid sequences (SEQ ID NOS: 19 and 20, respectively) of the resulting fusion protein are shown in FIG. 15. There is a silent mutation at position 145 (A to G, shown in boldface) such that the final construct has a different nucleotide sequence than the oligonucleotide 1871-72 from which it was derived.

Fc-EMP-EMP. A DNA sequence coding for the Fc region of human IgG1 fused in-frame to a dimer of the EPO-mimetic peptide was constructed using standard PCR technology. Templates for PCR reactions were the plasmids from strains 3688 and 3813 above.

The Fc portion of the molecule was generated in a PCR reaction with strain 3688 DNA using the primers 1216-52 and 1798-17 (shown above). The EMP dimer portion of the molecule was the product of a second PCR reaction with strain 3813 DNA using the primers 1798-18 (also shown above) and SEQ ID NO: 418, shown below:

```
1798-20 CTA ATT GGA TCC TCG AGA TTA ACC CCC TTG TGG CTT ACAT
```

The oligonucleotides 1798-17 and 1798-18 contain an overlap of 61 nucleotides, allowing the two genes to be fused together in the correct reading frame by combining the above PCR products in a third reaction using the outside primers, 1216-52 and 1798-20.

The final PCR gene product (the full length fusion gene) was digested with restriction endonucleases XbaI and BamHI, and then ligated into the vector pAMG21 and transformed into competent *E. coli* strain 2596 cells as described for Fc-EMP. Clones were screened for the ability to produce the recombinant protein product and to possess the gene fusion having the correct nucleotide sequence. A single such clone was selected and designated Amgen strain #3822.

The nucleotide and amino acid sequences (SEQ ID NOS: 20 and 22, respectively) of the fusion protein are shown in FIG. 16.

Characterization of Fc-EMP activity. Characterization was carried out in vivo as follows.

Mice: Normal female BDF1 approximately 10–12 weeks of age.

Bleed schedule: Ten mice per group treated on day 0, two groups started 4 days apart for a total of 20 mice per group. Five mice bled at each time point, mice were bled a maximum of three times a week. Mice were anesthetized with isoflurane and a total volume of 140–160 ml of blood was obtained by puncture of the orbital sinus. Blood was counted on a Technicon H1E blood analyzer running software for murine blood. Parameters measured were WBC, RBC, HCT, HGB, PLT, NEUT, LYMPH.

Treatments: Mice were either injected subcutaneously for a bolus treatment or implanted with 7 day micro-osmotic pumps for continuous delivery. Subcutaneous injections were delivered in a volume of 0.2 ml. Osmotic pumps were inserted into a subcutaneous incision made in the skin between the scapulae of anesthetized mice. Compounds were diluted in PBS with 0.1% BSA. All experiments included one control group, labeled "carrier" that were treated with this diluent only. The concentration of the test articles in the pumps was adjusted so that the calibrated flow rate from the pumps gave the treatment levels indicated in the graphs.

Experiments: Various Fc-conjugated EPO mimetic peptides (EMPs) were delivered to mice as a single bolus injection at a dose of 100 μg/kg. Fc-EMPs were delivered to mice in 7-day micro-osmotic pumps. The pumps were not replaced at the end of 7 days. Mice were bled until day 51 when HGB and HCT returned to baseline levels.

Example 4

TNF-α Inhibitors

Fc-TNF-α inhibitors. A DNA sequence coding for the Fc region of human IgG1 fused in-frame to a monomer of the TNF-α inhibitory peptide was constructed using standard PCR technology. The Fc and 5 glycine linker portion of the molecule was generated in a PCR reaction with DNA from the Fc-EMP fusion strain #3718 (see Example 3) using the sense primer 1216-52 and the antisense primer 2295-89 (SEQ ID NOS: 369 and 1112, respectively). The nucleotides encoding the TNF-α inhibitory peptide were provided by the PCR primer 2295-89 shown below:

```
1216-52  AAC ATA AGT ACC TGT AGG ATC G 2295-89  CCG CGG ATC CAT TAC GGA CGG TGA CCC AGA
         GAG GTG TTT TTG TAG TGC GGC AGG AAG TCA
         CCA CCA CCT CCA CCT TTA CCC
```

The oligonucleotide 2295-89 overlaps the glycine linker and Fc portion of the template by 22 nucleotides, with the PCR resulting in the two genes being fused together in the correct reading frame.

The PCR gene product (the full length fusion gene) was digested with restriction endonucleases NdeI and BamHI, and then ligated into the vector pAMG21 and transformed into competent *E. coli* strain 2596 cells as described for EMP-Fc herein. Clones were screened for the ability to produce the recombinant protein product and to possess the gene fusion having the correct nucleotide sequence. A single such clone was selected and designated Amgen strain #4544.

The nucleotide and amino acid sequences (SEQ ID NOS: 1055 and 1056) of the fusion protein are shown in FIGS. 19A and 19B.

TNF-α inhibitor-Fc. A DNA sequence coding for a TNF-α inhibitory peptide fused in-frame to the Fc region of human IgG1 was constructed using standard PCR technology. The template for the PCR reaction was a plasmid containing an unrelated peptide fused via a five glycine linker to Fc. The nucleotides encoding the TNF-α inhibitory peptide were provided by the sense PCR primer 2295-88, with primer 1200-54 serving as the antisense primer (SEQ ID NOS: 1117 and 407, respectively). The primer sequences are shown below:

```
2295-88  GAA TAA CAT ATG GAC TTC CTG CCG CAC TAC
         AAA AAC ACC TCT CTG GGT CAC CGT CCG GGT
         GGA GGC GGT GGG GAC AAA ACT 1200-54  GTT ATT GCT CAG CGG TGG CA
```

The oligonucleotide 2295-88 overlaps the glycine linker and Fc portion of the template by 24 nucleotides, with the PCR resulting in the two genes being fused together in the correct reading frame.

The PCR gene product (the full length fusion gene) was digested with restriction endonucleases NdeI and BamHI, and then ligated into the vector pAMG21 and transformed into competent *E. coli* strain 2596 cells as described for EMP-Fc herein. Clones were screened for the ability to produce the recombinant protein product and to possess the gene fusion having the correct nucleotide sequence. A single such clone was selected and designated Amgen strain #4543.

The nucleotide and amino acid sequences (SEQ ID NOS: 1057 and 1058) of the fusion protein are shown in FIGS. 20A and 20B.

Expression in *E. coli*. Cultures of each of the pAMG21-Fc-fusion constructs in *E. coli* GM221 were grown at 37° C. in Luria Broth medium containing 50 mg/ml kanamycin. Induction of gene product expression from the luxPR promoter was achieved following the addition of the synthetic autoinducer N-(3-oxohexanoyl)-DL-homoserine lactone to the culture media to a final concentration of 20 ng/ml. Cultures were incubated at 37° C. for a further 3 hours. After 3 hours, the bacterial cultures were examined by microscopy for the presence of inclusion bodies and were then collected by centrifugation. Refractile inclusion bodies were observed in induced cultures indicating that the Fc-fusions were most likely produced in the insoluble fraction in *E. coli*. Cell pellets were lysed directly by resuspension in Laemmli sample buffer containing 10% β-mercaptoethanol and were analyzed by SDS-PAGE. In each case, an intense coomassie-stained band of the appropriate molecular weight was observed on an SDS-PAGE gel.

Purification of Fc-peptide fusion proteins. Cells are broken in water (1/10) by high pressure homogenization (2 passes at 14,000 PSI) and inclusion bodies are harvested by centrifugation (4200 RPM in J-6B for 1 hour). Inclusion bodies are solubilized in 6M guanidine, 50 mM Tris, 8 mM DTT, pH 8.7 for 1 hour at a 1/10 ratio. The solubilized mixture is diluted 20 times into 2M urea, 50 mM tris, 160 mM arginine, 3 mM cysteine, pH 8.5. The mixture is stirred overnight in the cold and then concentrated about 10 fold by ultafiltration. It is then diluted 3 fold with 10 mM Tris, 1.5M urea, pH 9. The pH of this mixture is then adjusted to pH 5 with acetic acid. The precipitate is removed by centrifugation and the supernatant is loaded onto a SP-Sepharose Fast Flow column equilibrated in 20 mM NaAc, 100 mM NaCl, pH 5 (10 mg/ml protein load, room temperature). The protein is eluted from the column using a 20 column volume gradient in the same buffer ranging from 100 mM NaCl to 500 mM NaCl. The pool from the column is diluted 3 fold and loaded onto a SP-Sepharose HP column in 20 mM NaAc, 150 mM NaCl, pH 5(10 mg/ml protein load, room temperature). The protein is eluted using a 20 column volume gradient in the same buffer ranging from 150 mM NaCl to 400 mM NaCl. The peak is pooled and filtered.

Characterization of activity of Fc-TNF-α inhibitor and TNF-α inhibitor-Fc. Binding of these peptide fusion proteins to TNF-α can be characterized by BIAcore by methods available to one of ordinary skill in the art who is armed with the teachings of the present specification.

Example 5

IL-1 Antagonists

Fc-IL-1 antagonist. A DNA sequence coding for the Fc region of human IgG1 fused in-frame to a monomer of an IL-1 antagonist peptide was constructed using standard PCR technology. The Fc and 5 glycine linker portion of the molecule was generated in a PCR reaction with DNA from the Fc-EMP fusion strain #3718 (see Example 3) using the sense primer 1216-52 and the antisense primer 2269-70 (SEQ ID NOS: 369 and 1118, respectively). The nucleotides encoding the IL-1 antagonist peptide were provided by the PCR primer 2269-70 shown below:

```
1216-52  AAC ATA AGT ACC TGT AGG ATC G 2269-70  CCG CGG ATC CAT TAC AGC GGC AGA GCG TAC
         GGC TGC AGT AA CCC GGG GTC CAT TCG AAA
         CCA CCA CCT CCA CCT TTA CCC
```

The oligonucleotide 2269-70 overlaps the glycine linker and Fc portion of the template by 22 nucleotides, with the PCR resulting in the two genes being fused together in the correct reading frame.

The PCR gene product (the full length fusion gene) was digested with restriction endonucleases NdeI and BamHI, and then ligated into the vector pAMG21 and transformed into competent *E. coli* strain 2596 cells as described for EMP-Fc herein. Clones were screened for the ability to produce the recombinant protein product and to possess the gene fusion having the correct nucleotide sequence. A single such clone was selected and designated Amgen strain #4506.

The nucleotide and amino acid sequences (SEQ ID NOS: 1059 and 1060) of the fusion protein are shown in FIGS. 21A and 21B.

IL-1 antagonist-Fc. A DNA sequence coding for an IL-1 antagonist peptide fused in-frame to the Fc region of human IgG1 was constructed using standard PCR technology. The template for the PCR reaction was a plasmid containing an unrelated peptide fused via a five glycine linker to Fc. The nucleotides encoding the IL-1 antagonist peptide were provided by the sense PCR primer 2269-69, with primer 1200-54 serving as the antisense primer (SEQ ID NOS: 1119 and 407, respectively). The primer sequences are shown below:

```
2269-69 GAA TAA CAT ATG TTC GAA TGG ACC CCG GGT
        TAC TGG CAG CCG TAC GCT CTG CCG CTG GGT
        GGA GGC GGT GGG GAC AAA ACT 1200-54 GTT ATT GCT CAG CGG TGG CA
```

The oligonucleotide 2269-69 overlaps the glycine linker and Fc portion of the template by 24 nucleotides, with the PCR resulting in the two genes being fused together in the correct reading frame.

The PCR gene product (the full length fusion gene) was digested with restriction endonucleases NdeI and BamHI, and then ligated into the vector pAMG21 and transformed into competent *E. coli* strain 2596 cells as described for EMP-Fc herein. Clones were screened for the ability to produce the recombinant protein product and to possess the gene fusion having the correct nucleotide sequence. A single such clone was selected and designated Amgen strain #4505.

The nucleotide and amino acid sequences (SEQ ID NOS: 1061 and 1062) of the fusion protein are shown in FIGS. 22A and 22B. Expression and purification were carried out as in previous examples.

Characterization of Fc-IL-1 antagonist peptide and IL-1 antagonist peptide-Fc activity. IL-1 Receptor Binding competition between IL-1β, IL-1RA and Fc-conjugated IL-1 peptide sequences was carried out using the IGEN system. Reactions contained 0.4 nM biotin-IL-1R+15 nM IL-1-TAG+3 uM competitor+20 ug/ml streptavidin-conjugate beads, where competitors were IL-1RA, Fc-IL-1 antagonist, IL-1 antagonist-Fc). Competition was assayed over a range of competitor concentrations from 3 uM to 1.5 pM. The results are shown in Table C below:

TABLE C

Results from IL-1 Receptor Binding Competition Assay

|  | IL-1pep-Fc | Fc-IL-1pep | IL-1ra |
|---|---|---|---|
| KI | 281.5 | 59.58 | 1.405 |
| EC50 | 530.0 | 112.2 | 2.645 |
| 95% Confidence Intervals |  |  |  |
| EC50 | 280.2 to 1002 | 54.75 to 229.8 | 1.149 to 6.086 |
| KI | 148.9 to 532.5 | 29.08 to 122.1 | 0.6106 to 3.233 |
| Goodness of Fit |  |  |  |
| $R^2$ | 0.9790 | 0.9687 | 0.9602 |

Example 6

VEGF-Antagonists

Fc-VEGF Antagonist. A DNA sequence coding for the Fc region of human IgG1 fused in-frame to a monomer of the VEGF mimetic peptide was constructed using standard PCR technology. The templates for the PCR reaction were the pFc-A3 plasmid and a synthetic VEGF mimetic peptide gene. The synthetic gene was assembled by annealing the following two oligonucleotides primer (SEQ ID NOS: 1110 and 1111, respectively):

```
2293-11 GTT GAA CCG AAC TGT GAC ATC CAT GTT ATG
        TGG GAA TGG GAA TGT TTT GAA CGT CTG 2293-12 CAG ACG TTC AAA ACA TTC CCA TTC CCA TTC
        CCA CAT AAC ATG GAT GTC ACA GTT CGG TTC
        AAC
```

The two oligonucleotides anneal to form the following duplex encoding an amino acid sequence shown below (SEQ ID NOS: 1113 and 1114):

```
    GTTGAACCGAACTGTGACATCCATGTTATGTGGGAATGGGAATGTTTTGAACGTCTG
1 ---------+---------+---------+---------+---------+------- 57
    CAACTTGGCTTGACACTGTAGGTACAATACACCCTTACCCTTACAAAACTTGCAGAC a  V  E  P  N  C  D  I  H  V  M  W  E  W  E  C  F  E  R  L
```

This duplex was amplified in a PCR reaction using 2293-05 and 2293-06 as the sense and antisense primers (SEQ ID NOS: 1122 and 1123).

The Fc portion of the molecule was generated in a PCR reaction with the pFc-A3 plasmid using the primers 2293-03 and 2293-04 as the sense and antisense primers (SEQ ID NOS: 1120 and 1121, respectively). The full length fusion gene was obtained from a third PCR reaction using the outside primers 2293-03 and 2293-06. These primers are shown below:

```
2293-03 ATT TGA TTC TAG AAG GAG GAA TAA CAT ATG
        GAC AAA ACT CAC ACA TGT 2293-04 GTC ACA GTT CGG TTC AAC ACC ACC ACC ACC
        ACC TTT ACC CGG AGA CAG GGA 2293-05 TCC CTG TCT CCG GGT AAA GGT GGT GGT GGT
        GGT GTT GAA CCG AAC TGT GAC ATC 2293-06 CCG CGG ATC CTC GAG TTA CAG ACG TTC AAA
        ACA TTC CCA
```

The PCR gene product (the full length fusion gene) was digested with restriction endonucleases NdeI and BamHI, and then ligated into the vector pAMG21 and transformed into competent *E. coli* strain 2596 cells as described for EMP-Fc herein. Clones were screened for the ability to produce the recombinant protein product and to possess the gene fusion having the correct nucleotide sequence. A single such clone was selected and designated Amgen strain #4523.

The nucleotide and amino acid sequences (SEQ ID NOS: 1063 and 1064) of the fusion protein are shown in FIGS. 23A and 23B.

VEGF antagonist-Fc. A DNA sequence coding for a VEGF mimetic peptide fused in-frame to the Fc region of human IgG1 was constructed using standard PCR technology. The templates for the PCR reaction were the pFc-A3 plasmid and the synthetic VEGF mimetic peptide gene described above. The synthetic duplex was amplified in a PCR reaction using 2293-07 and 2293-08 as the sense and antisense primers (SEQ ID NOS: 1124 and 1125, respectively).

The Fc portion of the molecule was generated in a PCR reaction with the pFc-A3 plasmid using the primers 2293-09 and 2293-10 as the sense and antisense primers (SEQ ID NOS: 1126 and 1127, respectively).

The full length fusion gene was obtained from a third PCR reaction using the outside primers 2293-07 and 2293-10. These primers are shown below:

```
2293-07  ATT TGA TTC TAG AAG GAG GAA TAA CAT ATG
         GTT GAA CCG AAC TGT GAC 2293-08  ACA TGT GTG AGT TTT GTC ACC ACC ACC ACC
         ACC CAG ACG TTC AAA ACA TTC 2293-09  GAA TGT TTT GAA CGT CTG GGT GGT GGT GGT
         GGT GAC AAA ACT CAC ACA TGT 2293-10  CCG CGG ATC CTC GAG TTA TTT ACC CGG AGA
         CAG GGA GAG
```

The PCR gene product (the full length fusion gene) was digested with restriction endonucleases NdeI and BamHI, and then ligated into the vector pAMG21 and transformed into competent *E. coli* strain 2596 cells as described for EMP-Fc herein. Clones were screened for the ability to produce the recombinant protein product and to possess the gene fusion having the correct nucleotide sequence. A single such clone was selected and designated Amgen strain #4524.

The nucleotide and amino acid sequences (SEQ ID NOS: 1065 and 1066) of the fusion protein are shown in FIGS. 24A and 24B. Expression and purification were carried out as in previous examples.

Example 7

MMP Inhibitors

Fc-MMP inhibitor. A DNA sequence coding for the Fc region of human IgG1 fused in-frame to a monomer of an MMP inhibitory peptide was constructed using standard PCR technology. The Fc and 5 glycine linker portion of the molecule was generated in a PCR reaction with DNA from the Fc-TNF-α inhibitor fusion strain #4544 (see Example 4) using the sense primer 1216-52 and the antisense primer 2308-67 (SEQ ID NOS: 369 and 1115, respectively). The nucleotides encoding the MMP inhibitor peptide were provided by the PCR primer 2308-67 shown below:

```
1216-52  AAC ATA AGT ACC TGT AGG ATC G 2308-67  CCG CGG ATC CAT TAG CAC AGG GTG AAA CCC
         CAG TGG GTG GTG CAA CCA CCA CCT CCA CCT
         TTA CCC
```

The oligonucleotide 2308-67 overlaps the glycine linker and Fc portion of the template by 22 nucleotides, with the PCR resulting in the two genes being fused together in the correct reading frame.

The PCR gene product (the full length fusion gene) was digested with restriction endonucleases NdeI and BamHI, and then ligated into the vector pAMG21 and transformed into competent *E. coli* strain 2596 cells as described for EMP-Fc herein. Clones were screened for the ability to produce the recombinant protein product and to possess the gene fusion having the correct nucleotide sequence. A single such clone was selected and designated Amgen strain #4597.

The nucleotide and amino acid sequences (SEQ ID NOS: 1067 and 1068) of the fusion protein are shown in FIGS. 25A and 25B. Expression and purification were carried out as in previous examples.

MMP Inhibitor-Fc. A DNA sequence coding for an MMP inhibitory peptide fused in-frame to the Fc region of human IgG1 was constructed using standard PCR technology. The Fc and 5 glycine linker portion of the molecule was generated in a PCR reaction with DNA from the Fc-TNF-α inhibitor fusion strain #4543 (see Example 4). The nucleotides encoding the MMP inhibitory peptide were provided by the sense PCR primer 2308-66, with primer 1200-54 serving as the antisense primer (SEQ ID NOS: 1116 and 407, respectively). The primer sequences are shown below:

```
2308-66  GAA TAA CAT ATG TGC ACC ACC CAC TGG GGT
         TTC ACC CTG TGC GGT GGA GGC GGT GGG GAC
         AAA 1200-54  GTT ATT GCT CAG CGG TGG CA
```

The two oligonucleotides anneal to form the following duplex encoding an amino acid sequence shown below (SEQ ID NOS: 1113 and 1114):

The oligonucleotide 2269-69 overlaps the glycine linker and Fc portion of the template by 24 nucleotides, with the PCR resulting in the two genes being fused together in the correct reading frame.

The PCR gene product (the full length fusion gene) was digested with restriction endonucleases NdeI and BamHI, and then ligated into the vector pAMG21 and transformed into competent *E. coli* strain 2596 cells as described for EMP-Fc herein. Clones were screened for the ability to produce the recombinant protein product and to possess the gene fusion having the correct nucleotide sequence. A single such clone was selected and designated Amgen strain #4598.

The nucleotide and amino acid sequences (SEQ ID NOS: 1069 and 1070) of the fusion protein are shown in FIGS. 26A and 26B.

The invention now being fully described, it will be apparent to one of ordinary skill in the art that many changes and modifications can be made thereto, without departing from the spirit and scope of the invention as set forth herein.

ABBREVIATIONS

Abbreviations used throughout this specification are as defined below, unless otherwise defined in specific circumstances.

| | |
|---|---|
| Ac | acetyl (used to refer to acetylated residues) |
| AcBpa | acetylated p-benzoyl-L-phenylalanine |
| ADCC | antibody-dependent cellular cytotoxicity |
| Aib | aminoisobutyric acid |
| bA | beta-alanine |
| Bpa | p-benzoyl-L-phenylalanine |
| BrAc | bromoacetyl (BrCH$_2$C(O)) |
| BSA | Bovine serum albumin |
| Bzl | Benzyl |
| Cap | Caproic acid |

-continued

| | |
|---|---|
| CTL | Cytotoxic T lymphocytes |
| CTLA4 | Cytotoxic T lymphocyte antigen 4 |
| DARC | Duffy blood group antigen receptor |
| DCC | Dicylcohexylcarbodiimide |
| Dde | 1-(4,4-dimethyl-2,6-dioxo-cyclohexylidene)ethyl |
| EMP | Erythropoietin-mimetic peptide |
| ESI-MS | Electron spray ionization mass spectrometry |
| EPO | Erythropoietin |
| Fmoc | fluorenylmethoxycarbonyl |
| G-CSF | Granulocyte colony stimulating factor |
| GH | Growth hormone |
| HCT | hematocrit |
| HGB | hemoglobin |
| hGH | Human growth hormone |
| HOBt | 1-Hydroxybenzotriazole |
| HPLC | high performance liquid chromatography |
| IL | interleukin |
| IL-R | interleukin receptor |
| IL-1R | interleukin-1 receptor |
| IL-1ra | interleukin-1 receptor antagonist |
| Lau | Lauric acid |
| LPS | lipopolysaccharide |
| LYMPH | lymphocytes |
| MALDI-MS | Matrix-assisted laser desorption ionization mass spectrometry |
| Me | methyl |
| MeO | methoxy |
| MHC | major histocompatibility complex |
| MMP | matrix metalloproteinase |
| MMPI | matrix metalloproteinase inhibitor |
| 1-Nap | 1-napthylalanine |
| NEUT | neutrophils |
| NGF | nerve growth factor |
| Nle | norleucine |
| NMP | N-methyl-2-pyrrolidinone |
| PAGE | polyacrylamide gel electrophoresis |
| PBS | Phosphate-buffered saline |
| Pbf | 2,2,4,6,7-pendamethyldihydrobenzofuran-5-sulfonyl |
| PCR | polymerase chain reaction |
| Pec | pipecolic acid |

-continued

| | |
|---|---|
| PEG | Poly(ethylene glycol) |
| pGlu | pyroglutamic acid |
| Pic | picolinic acid |
| PLT | platelets |
| pY | phosphotyrosine |
| RBC | red blood cells |
| RBS | ribosome binding site |
| RT | room temperature (25° C.) |
| Sar | sarcosine |
| SDS | sodium dodecyl sulfate |
| STK | serine-threonine kinases |
| t-Boc | tert-Butoxycarbonyl |
| tBu | tert-Butyl |
| TGF | tissue growth factor |
| THF | thymic humoral factor |
| TK | tyrosine kinase |
| TMP | Thrombopoietin-mimetic peptide |
| TNF | Tissue necrosis factor |
| TPO | Thrombopoietin |
| TRAIL | TNF-related apoptosis-inducing ligand |
| Trt | trityl |
| UK | urokinase |
| UKR | urokinase receptor |
| VEGF | vascular endothelial cell growth factor |
| VIP | vasoactive intestinal peptide |
| WBC | white blood cells |

SEQUENCE LISTING

<160> NUMBER OF SEQ ID NOS: 1133

<210> SEQ ID NO 1
<211> LENGTH: 684
<212> TYPE: DNA
<213> ORGANISM: HUMAN
<220> FEATURE:
<221> NAME/KEY: CDS
<222> LOCATION: (1)..(684)
<223> OTHER INFORMATION:

<400> SEQUENCE: 1

```
atg gac aaa act cac aca tgt cca cct tgt cca gct ccg gaa ctc ctg      48
Met Asp Lys Thr His Thr Cys Pro Pro Cys Pro Ala Pro Glu Leu Leu
1               5                   10                  15 ggg gga ccg tca gtc ttc ctc ttc ccc cca aaa ccc aag gac acc ctc      96
Gly Gly Pro Ser Val Phe Leu Phe Pro Pro Lys Pro Lys Asp Thr Leu
            20                  25                  30 atg atc tcc cgg acc cct gag gtc aca tgc gtg gtg gtg gac gtg agc      144
Met Ile Ser Arg Thr Pro Glu Val Thr Cys Val Val Val Asp Val Ser
        35                  40                  45 cac gaa gac cct gag gtc aag ttc aac tgg tac gtg gac ggc gtg gag      192
His Glu Asp Pro Glu Val Lys Phe Asn Trp Tyr Val Asp Gly Val Glu
    50                  55                  60 gtg cat aat gcc aag aca aag ccg cgg gag gag cag tac aac agc acg      240
```

| | | | | | | | | | | | | |
|---|---|---|---|---|---|---|---|---|---|---|---|---|
| Val | His | Asn | Ala | Lys | Thr | Lys | Pro | Arg | Glu | Glu | Gln | Tyr | Asn | Ser | Thr |
| 65 | | | | 70 | | | | | 75 | | | | | | 80 |

```
tac cgt gtg gtc agc gtc ctc acc gtc ctg cac cag gac tgg ctg aat      288
Tyr Arg Val Val Ser Val Leu Thr Val Leu His Gln Asp Trp Leu Asn
                85                  90                  95 ggc aag gag tac aag tgc aag gtc tcc aac aaa gcc ctc cca gcc ccc      336
Gly Lys Glu Tyr Lys Cys Lys Val Ser Asn Lys Ala Leu Pro Ala Pro
            100                 105                 110 atc gag aaa acc atc tcc aaa gcc aaa ggg cag ccc cga gaa cca cag      384
Ile Glu Lys Thr Ile Ser Lys Ala Lys Gly Gln Pro Arg Glu Pro Gln
            115                 120                 125 gtg tac acc ctg ccc cca tcc cgg gat gag ctg acc aag aac cag gtc      432
Val Tyr Thr Leu Pro Pro Ser Arg Asp Glu Leu Thr Lys Asn Gln Val
    130                 135                 140 agc ctg acc tgc ctg gtc aaa ggc ttc tat ccc agc gac atc gcc gtg      480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct      528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc      576
Pro Val Leu Asp Ser Asp Gly Ser Phe Phe Leu Tyr Ser Lys Leu Thr
            180                 185                 190 gtg gac aag agc agg tgg cag cag ggg aac gtc ttc tca tgc tcc gtg      624
Val Asp Lys Ser Arg Trp Gln Gln Gly Asn Val Phe Ser Cys Ser Val
            195                 200                 205 atg cat gag gct ctg cac aac cac tac acg cag aag agc ctc tcc ctg      672
Met His Glu Ala Leu His Asn His Tyr Thr Gln Lys Ser Leu Ser Leu
210                 215                 220 tct ccg ggt aaa                                                      684
Ser Pro Gly Lys
225

<210> SEQ ID NO 2
<211> LENGTH: 228
<212> TYPE: PRT
<213> ORGANISM: HUMAN

<400> SEQUENCE: 2

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
```

-continued

```
               145                 150                 155                 160
Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 3
<211> LENGTH: 36
<212> TYPE: PRT
<213> ORGANISM: Artificial Sequence
<220> FEATURE:
<223> OTHER INFORMATION: SYNTHETIC SCHEME FOR PREPARATION OF PEGYLATED
      PEPTIDE
<220> FEATURE:
<221> NAME/KEY: misc_feature
<222> LOCATION: (18)..(18)
<223> OTHER INFORMATION: Methoxy-polyethylene glycol (5000 Dalton)-
      sulfoacetyl group attached to the sidechain.

<400> SEQUENCE: 3

Ile Glu Gly Pro Thr Leu Arg Gln Trp Leu Ala Ala Arg Ala Gly Gly
1               5                   10                  15

Gly Lys Gly Gly Gly Ile Glu Gly Pro Thr Leu Arg Gln Trp Leu
            20                  25                  30

Ala Ala Arg Ala
        35

<210> SEQ ID NO 4
<211> LENGTH: 36
<212> TYPE: PRT
<213> ORGANISM: Artificial Sequence
<220> FEATURE:
<223> OTHER INFORMATION: SYNTHETIC SCHEME FOR PREPARATION OF PEGYLATED
      PEPTIDE
<220> FEATURE:
<221> NAME/KEY: misc_feature
<222> LOCATION: (18)..(18)
<223> OTHER INFORMATION: Methoxy-polyethylene glycol (5000 Dalton)-
      succinimidyl group attached to the sidechain.

<400> SEQUENCE: 4

Ile Glu Gly Pro Thr Leu Arg Gln Trp Leu Ala Ala Arg Ala Gly Gly
1               5                   10                  15

Gly Cys Gly Gly Gly Ile Glu Gly Pro Thr Leu Arg Gln Trp Leu
            20                  25                  30

Ala Ala Arg Ala
        35

<210> SEQ ID NO 5
<211> LENGTH: 794
<212> TYPE: DNA
<213> ORGANISM: Artificial Sequence
<220> FEATURE:
<223> OTHER INFORMATION: Fc-TMP
<220> FEATURE:
<221> NAME/KEY: CDS
<222> LOCATION: (39)..(779)
<223> OTHER INFORMATION:
```

-continued

```
<400> SEQUENCE: 5
tctagatttg ttttaactaa ttaaaggagg aataacat atg gac aaa act cac aca      56
                                          Met Asp Lys Thr His Thr
                                          1               5 tgt cca cct tgt cca gct ccg gaa ctc ctg ggg gga ccg tca gtc ttc       104
Cys Pro Pro Cys Pro Ala Pro Glu Leu Leu Gly Gly Pro Ser Val Phe
            10                  15                  20 ctc ttc ccc cca aaa ccc aag gac acc ctc atg atc tcc cgg acc cct       152
Leu Phe Pro Pro Lys Pro Lys Asp Thr Leu Met Ile Ser Arg Thr Pro
        25                  30                  35 gag gtc aca tgc gtg gtg gtg gac gtg agc cac gaa gac cct gag gtc       200
Glu Val Thr Cys Val Val Val Asp Val Ser His Glu Asp Pro Glu Val
40                  45                  50 aag ttc aac tgg tac gtg gac ggc gtg gag gtg cat aat gcc aag aca       248
Lys Phe Asn Trp Tyr Val Asp Gly Val Glu Val His Asn Ala Lys Thr
55                  60                  65                  70 aag ccg cgg gag gag cag tac aac agc acg tac cgt gtg gtc agc gtc       296
Lys Pro Arg Glu Glu Gln Tyr Asn Ser Thr Tyr Arg Val Val Ser Val
                75                  80                  85 ctc acc gtc ctg cac cag gac tgg ctg aat ggc aag gag tac aag tgc       344
Leu Thr Val Leu His Gln Asp Trp Leu Asn Gly Lys Glu Tyr Lys Cys
            90                  95                 100 aag gtc tcc aac aaa gcc ctc cca gcc ccc atc gag aaa acc atc tcc       392
Lys Val Ser Asn Lys Ala Leu Pro Ala Pro Ile Glu Lys Thr Ile Ser
        105                 110                 115 aaa gcc aaa ggg cag ccc cga gaa cca cag gtg tac acc ctg ccc cca       440
Lys Ala Lys Gly Gln Pro Arg Glu Pro Gln Val Tyr Thr Leu Pro Pro
    120                 125                 130 tcc cgg gat gag ctg acc aag aac cag gtc agc ctg acc tgc ctg gtc       488
Ser Arg Asp Glu Leu Thr Lys Asn Gln Val Ser Leu Thr Cys Leu Val
135                 140                 145                 150 aaa ggc ttc tat ccc agc gac atc gcc gtg gag tgg gag agc aat ggg       536
Lys Gly Phe Tyr Pro Ser Asp Ile Ala Val Glu Trp Glu Ser Asn Gly
                155                 160                 165 cag ccg gag aac aac tac aag acc acg cct ccc gtg ctg gac tcc gac       584
Gln Pro Glu Asn Asn Tyr Lys Thr Thr Pro Pro Val Leu Asp Ser Asp
            170                 175                 180 ggc tcc ttc ttc ctc tac agc aag ctc acc gtg gac aag agc agg tgg       632
Gly Ser Phe Phe Leu Tyr Ser Lys Leu Thr Val Asp Lys Ser Arg Trp
        185                 190                 195 cag cag ggg aac gtc ttc tca tgc tcc gtg atg cat gag gct ctg cac       680
Gln Gln Gly Asn Val Phe Ser Cys Ser Val Met His Glu Ala Leu His
    200                 205                 210 aac cac tac acg cag aag agc ctc tcc ctg tct ccg ggt aaa ggt gga       728
Asn His Tyr Thr Gln Lys Ser Leu Ser Leu Ser Pro Gly Lys Gly Gly
215                 220                 225                 230 ggt ggt ggt atc gaa ggt ccg act ctg cgt cag tgg ctg gct gct cgt       776
Gly Gly Gly Ile Glu Gly Pro Thr Leu Arg Gln Trp Leu Ala Ala Arg
                235                 240                 245 gct taatctcgag gatcc                                                  794
Ala

<210> SEQ ID NO 6
<211> LENGTH: 247
<212> TYPE: PRT
<213> ORGANISM: Artificial Sequence
<220> FEATURE:
<223> OTHER INFORMATION: Fc-TMP

<400> SEQUENCE: 6
```

-continued

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Ile Glu Gly Pro Thr Leu Arg
225                 230                 235                 240

Gln Trp Leu Ala Ala Arg Ala
                245
```

<210> SEQ ID NO 7
<211> LENGTH: 861
<212> TYPE: DNA
<213> ORGANISM: Artificial Sequence
<220> FEATURE:
<223> OTHER INFORMATION: Fc-TMP-TMP
<220> FEATURE:
<221> NAME/KEY: CDS
<222> LOCATION: (39)..(842)
<223> OTHER INFORMATION:

<400> SEQUENCE: 7

```
tctagatttg ttttaactaa ttaaaggagg aataacat atg gac aaa act cac aca      56
                                        Met Asp Lys Thr His Thr
                                        1               5 tgt cca cct tgt cca gct ccg gaa ctc ctg ggg gga ccg tca gtc ttc       104
Cys Pro Pro Cys Pro Ala Pro Glu Leu Leu Gly Gly Pro Ser Val Phe
            10                  15                  20 ctc ttc ccc cca aaa ccc aag gac acc ctc atg atc tcc cgg acc cct      152
Leu Phe Pro Pro Lys Pro Lys Asp Thr Leu Met Ile Ser Arg Thr Pro
        25                  30                  35 gag gtc aca tgc gtg gtg gtg gac gtg agc cac gaa gac cct gag gtc      200
Glu Val Thr Cys Val Val Val Asp Val Ser His Glu Asp Pro Glu Val
    40                  45                  50 aag ttc aac tgg tac gtg gac ggc gtg gag gtg cat aat gcc aag aca      248
```

-continued

| | | |
|---|---|---|
| Lys Phe Asn Trp Tyr Val Asp Gly Val Glu Val His Asn Ala Lys Thr<br>55                        60                      65                            70 | |
| aag ccg cgg gag gag cag tac aac agc acg tac cgt gtg gtc agc gtc<br>Lys Pro Arg Glu Glu Gln Tyr Asn Ser Thr Tyr Arg Val Val Ser Val<br>                        75                      80                            85 | 296 |
| ctc acc gtc ctg cac cag gac tgg ctg aat ggc aag gag tac aag tgc<br>Leu Thr Val Leu His Gln Asp Trp Leu Asn Gly Lys Glu Tyr Lys Cys<br>                    90                      95                      100 | 344 |
| aag gtc tcc aac aaa gcc ctc cca gcc ccc atc gag aaa acc atc tcc<br>Lys Val Ser Asn Lys Ala Leu Pro Ala Pro Ile Glu Lys Thr Ile Ser<br>         105                    110                    115 | 392 |
| aaa gcc aaa ggg cag ccc cga gaa cca cag gtg tac acc ctg ccc cca<br>Lys Ala Lys Gly Gln Pro Arg Glu Pro Gln Val Tyr Thr Leu Pro Pro<br>120                        125                    130 | 440 |
| tcc cgg gat gag ctg acc aag aac cag gtc agc ctg acc tgc ctg gtc<br>Ser Arg Asp Glu Leu Thr Lys Asn Gln Val Ser Leu Thr Cys Leu Val<br>135                        140                    145                    150 | 488 |
| aaa ggc ttc tat ccc agc gac atc gcc gtg gag tgg gag agc aat ggg<br>Lys Gly Phe Tyr Pro Ser Asp Ile Ala Val Glu Trp Glu Ser Asn Gly<br>                        155                    160                    165 | 536 |
| cag ccg gag aac aac tac aag acc acg cct ccc gtg ctg gac tcc gac<br>Gln Pro Glu Asn Asn Tyr Lys Thr Thr Pro Pro Val Leu Asp Ser Asp<br>                170                    175                    180 | 584 |
| ggc tcc ttc ttc ctc tac agc aag ctc acc gtg gac aag agc agg tgg<br>Gly Ser Phe Phe Leu Tyr Ser Lys Leu Thr Val Asp Lys Ser Arg Trp<br>         185                    190                    195 | 632 |
| cag cag ggg aac gtc ttc tca tgc tcc gtg atg cat gag gct ctg cac<br>Gln Gln Gly Asn Val Phe Ser Cys Ser Val Met His Glu Ala Leu His<br>200                        205                    210 | 680 |
| aac cac tac acg cag aag agc ctc tcc ctg tct ccg ggt aaa ggt gga<br>Asn His Tyr Thr Gln Lys Ser Leu Ser Leu Ser Pro Gly Lys Gly Gly<br>215                        220                    225                    230 | 728 |
| ggt ggt ggt atc gaa ggt ccg act ctg cgt cag tgg ctg gct gct cgt<br>Gly Gly Gly Ile Glu Gly Pro Thr Leu Arg Gln Trp Leu Ala Ala Arg<br>                235                    240                    245 | 776 |
| gct ggt ggt gga ggt ggc ggc gga ggt att gag ggc cca acc ctt cgc<br>Ala Gly Gly Gly Gly Gly Gly Gly Ile Glu Gly Pro Thr Leu Arg<br>         250                    255                    260 | 824 |
| caa tgg ctt gca gca cgc gcataatctc gaggatccg<br>Gln Trp Leu Ala Ala Arg<br>         265 | 861 |

<210> SEQ ID NO 8
<211> LENGTH: 268
<212> TYPE: PRT
<213> ORGANISM: Artificial Sequence
<220> FEATURE:
<223> OTHER INFORMATION: Fc-TMP-TMP

<400> SEQUENCE: 8

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

```
Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Ile Glu Gly Pro Thr Leu Arg
225                 230                 235                 240

Gln Trp Leu Ala Ala Arg Ala Gly Gly Gly Gly Gly Gly Gly Ile
                245                 250                 255

Glu Gly Pro Thr Leu Arg Gln Trp Leu Ala Ala Arg
            260                 265
```

<210> SEQ ID NO 9
<211> LENGTH: 855
<212> TYPE: DNA
<213> ORGANISM: Artificial Sequence
<220> FEATURE:
<223> OTHER INFORMATION: TMP-TMP-Fc
<220> FEATURE:
<221> NAME/KEY: CDS
<222> LOCATION: (39)..(845)
<223> OTHER INFORMATION:

<400> SEQUENCE: 9

```
tctagatttg ttttaactaa ttaaaggagg aataacat atg atc gaa ggt ccg act        56
                                         Met Ile Glu Gly Pro Thr
                                          1               5 ctg cgt cag tgg ctg gct gct cgt gct ggc ggt ggt ggc gga ggg ggt        104
Leu Arg Gln Trp Leu Ala Ala Arg Ala Gly Gly Gly Gly Gly Gly
         10                  15                  20 ggc att gag ggc cca acc ctt cgc caa tgg ctt gca gca cgc gca ggg        152
Gly Ile Glu Gly Pro Thr Leu Arg Gln Trp Leu Ala Ala Arg Ala Gly
         25                  30                  35 gga ggt ggg gac aaa act cac aca tgt cca cct tgc cca gca cct            200
Gly Gly Gly Asp Lys Thr His Thr Cys Pro Pro Cys Pro Ala Pro
    40                  45                  50 gaa ctc ctg ggg gga ccg tca gtt ttc ctc ttc ccc cca aaa ccc aag        248
Glu Leu Leu Gly Gly Pro Ser Val Phe Leu Phe Pro Pro Lys Pro Lys
55                  60                  65                  70 gac acc ctc atg atc tcc cgg acc cct gag gtc aca tgc gtg gtg gtg        296
Asp Thr Leu Met Ile Ser Arg Thr Pro Glu Val Thr Cys Val Val Val
             75                  80                  85 gac gtg agc cac gaa gac cct gag gtc aag ttc aac tgg tac gtg gac        344
Asp Val Ser His Glu Asp Pro Glu Val Lys Phe Asn Trp Tyr Val Asp
         90                  95                 100
```

```
ggc gtg gag gtg cat aat gcc aag aca aag ccg cgg gag gag cag tac      392
Gly Val Glu Val His Asn Ala Lys Thr Lys Pro Arg Glu Glu Gln Tyr
            105                 110                 115 aac agc acg tac cgt gtg gtc agc gtc ctc acc gtc ctg cac cag gac      440
Asn Ser Thr Tyr Arg Val Val Ser Val Leu Thr Val Leu His Gln Asp
    120                 125                 130 tgg ctg aat ggc aag gag tac aag tgc aag gtc tcc aac aaa gcc ctc      488
Trp Leu Asn Gly Lys Glu Tyr Lys Cys Lys Val Ser Asn Lys Ala Leu
135                 140                 145                 150 cca gcc ccc atc gag aaa acc atc tcc aaa gcc aaa ggg cag ccc cga      536
Pro Ala Pro Ile Glu Lys Thr Ile Ser Lys Ala Lys Gly Gln Pro Arg
                155                 160                 165 gaa cca cag gtg tac acc ctg ccc cca tcc cgg gat gag ctg acc aag      584
Glu Pro Gln Val Tyr Thr Leu Pro Pro Ser Arg Asp Glu Leu Thr Lys
            170                 175                 180 aac cag gtc agc ctg acc tgc ctg gtc aaa ggc ttc tat ccc agc gac      632
Asn Gln Val Ser Leu Thr Cys Leu Val Lys Gly Phe Tyr Pro Ser Asp
    185                 190                 195 atc gcc gtg gag tgg gag agc aat ggg cag ccg gag aac aac tac aag      680
Ile Ala Val Glu Trp Glu Ser Asn Gly Gln Pro Glu Asn Asn Tyr Lys
200                 205                 210 acc acg cct ccc gtg ctg gac tcc gac ggc tcc ttc ttc ctc tac agc      728
Thr Thr Pro Pro Val Leu Asp Ser Asp Gly Ser Phe Phe Leu Tyr Ser
215                 220                 225                 230 aag ctc acc gtg gac aag agc agg tgg cag cag ggg aac gtc ttc tca      776
Lys Leu Thr Val Asp Lys Ser Arg Trp Gln Gln Gly Asn Val Phe Ser
                235                 240                 245 tgc tcc gtg atg cat gag gct ctg cac aac cac tac acg cag aag agc      824
Cys Ser Val Met His Glu Ala Leu His Asn His Tyr Thr Gln Lys Ser
            250                 255                 260 ctc tcc ctg tct ccg ggt aaa taatggatcc                                855
Leu Ser Leu Ser Pro Gly Lys
    265

<210> SEQ ID NO 10
<211> LENGTH: 269
<212> TYPE: PRT
<213> ORGANISM: Artificial Sequence
<220> FEATURE:
<223> OTHER INFORMATION: TMP-TMP-Fc

<400> SEQUENCE: 10

Met Ile Glu Gly Pro Thr Leu Arg Gln Trp Leu Ala Ala Arg Ala Gly
1               5                   10                  15

Gly Gly Gly Gly Gly Gly Ile Glu Gly Pro Thr Leu Arg Gln Trp
            20                  25                  30

Leu Ala Ala Arg Ala Gly Gly Gly Gly Asp Lys Thr His Thr Cys
        35                  40                  45

Pro Pro Cys Pro Ala Pro Glu Leu Leu Gly Gly Pro Ser Val Phe Leu
    50                  55                  60

Phe Pro Pro Lys Pro Lys Asp Thr Leu Met Ile Ser Arg Thr Pro Glu
65                  70                  75                  80

Val Thr Cys Val Val Val Asp Val Ser His Glu Asp Pro Glu Val Lys
                85                  90                  95

Phe Asn Trp Tyr Val Asp Gly Val Glu Val His Asn Ala Lys Thr Lys
            100                 105                 110

Pro Arg Glu Glu Gln Tyr Asn Ser Thr Tyr Arg Val Val Ser Val Leu
        115                 120                 125

Thr Val Leu His Gln Asp Trp Leu Asn Gly Lys Glu Tyr Lys Cys Lys
```

-continued

```
            130                 135                 140
Val Ser Asn Lys Ala Leu Pro Ala Pro Ile Glu Lys Thr Ile Ser Lys
145                 150                 155                 160

Ala Lys Gly Gln Pro Arg Glu Pro Gln Val Tyr Thr Leu Pro Pro Ser
                165                 170                 175

Arg Asp Glu Leu Thr Lys Asn Gln Val Ser Leu Thr Cys Leu Val Lys
                180                 185                 190

Gly Phe Tyr Pro Ser Asp Ile Ala Val Glu Trp Glu Ser Asn Gly Gln
                195                 200                 205

Pro Glu Asn Asn Tyr Lys Thr Thr Pro Pro Val Leu Asp Ser Asp Gly
            210                 215                 220

Ser Phe Phe Leu Tyr Ser Lys Leu Thr Val Asp Lys Ser Arg Trp Gln
225                 230                 235                 240

Gln Gly Asn Val Phe Ser Cys Ser Val Met His Glu Ala Leu His Asn
                245                 250                 255

His Tyr Thr Gln Lys Ser Leu Ser Leu Ser Pro Gly Lys
                260                 265
```

<210> SEQ ID NO 11
<211> LENGTH: 789
<212> TYPE: DNA
<213> ORGANISM: Artificial Sequence
<220> FEATURE:
<223> OTHER INFORMATION: TMP-Fc
<220> FEATURE:
<221> NAME/KEY: CDS
<222> LOCATION: (39)..(779)
<223> OTHER INFORMATION:

<400> SEQUENCE: 11

```
tctagatttg ttttaactaa ttaaaggagg aataacat atg atc gaa ggt ccg act     56
                                         Met Ile Glu Gly Pro Thr
                                           1               5 ctg cgt cag tgg ctg gct gct cgt gct ggt gga ggc ggt ggg gac aaa    104
Leu Arg Gln Trp Leu Ala Ala Arg Ala Gly Gly Gly Gly Gly Asp Lys
            10                  15                  20 act cac aca tgt cca cct tgc cca gca cct gaa ctc ctg ggg gga ccg    152
Thr His Thr Cys Pro Pro Cys Pro Ala Pro Glu Leu Leu Gly Gly Pro
        25                  30                  35 tca gtt ttc ctc ttc ccc cca aaa ccc aag gac acc ctc atg atc tcc    200
Ser Val Phe Leu Phe Pro Pro Lys Pro Lys Asp Thr Leu Met Ile Ser
    40                  45                  50 cgg acc cct gag gtc aca tgc gtg gtg gtg gac gtg agc cac gaa gac    248
Arg Thr Pro Glu Val Thr Cys Val Val Val Asp Val Ser His Glu Asp
55                  60                  65                  70 cct gag gtc aag ttc aac tgg tac gtg gac ggc gtg gag gtg cat aat    296
Pro Glu Val Lys Phe Asn Trp Tyr Val Asp Gly Val Glu Val His Asn
                75                  80                  85 gcc aag aca aag ccg cgg gag gag cag tac aac agc acg tac cgt gtg    344
Ala Lys Thr Lys Pro Arg Glu Glu Gln Tyr Asn Ser Thr Tyr Arg Val
            90                  95                 100 gtc agc gtc ctc acc gtc ctg cac cag gac tgg ctg aat ggc aag gag    392
Val Ser Val Leu Thr Val Leu His Gln Asp Trp Leu Asn Gly Lys Glu
        105                 110                 115 tac aag tgc aag gtc tcc aac aaa gcc ctc cca gcc ccc atc gag aaa    440
Tyr Lys Cys Lys Val Ser Asn Lys Ala Leu Pro Ala Pro Ile Glu Lys
    120                 125                 130 acc atc tcc aaa gcc aaa ggg cag ccc cga gaa cca cag gtg tac acc    488
Thr Ile Ser Lys Ala Lys Gly Gln Pro Arg Glu Pro Gln Val Tyr Thr
135                 140                 145                 150
```

```
ctg ccc cca tcc cgg gat gag ctg acc aag aac cag gtc agc ctg acc    536
Leu Pro Pro Ser Arg Asp Glu Leu Thr Lys Asn Gln Val Ser Leu Thr
            155                 160                 165 tgc ctg gtc aaa ggc ttc tat ccc agc gac atc gcc gtg gag tgg gag    584
Cys Leu Val Lys Gly Phe Tyr Pro Ser Asp Ile Ala Val Glu Trp Glu
        170                 175                 180 agc aat ggg cag ccg gag aac aac tac aag acc acg cct ccc gtg ctg    632
Ser Asn Gly Gln Pro Glu Asn Asn Tyr Lys Thr Thr Pro Pro Val Leu
185                 190                 195 gac tcc gac ggc tcc ttc ttc ctc tac agc aag ctc acc gtg gac aag    680
Asp Ser Asp Gly Ser Phe Phe Leu Tyr Ser Lys Leu Thr Val Asp Lys
    200                 205                 210 agc agg tgg cag cag ggg aac gtc ttc tca tgc tcc gtg atg cat gag    728
Ser Arg Trp Gln Gln Gly Asn Val Phe Ser Cys Ser Val Met His Glu
215                 220                 225                 230 gct ctg cac aac cac tac acg cag aag agc ctc tcc ctg tct ccg ggt    776
Ala Leu His Asn His Tyr Thr Gln Lys Ser Leu Ser Leu Ser Pro Gly
            235                 240                 245 aaa taatggatcc                                                     789
Lys

<210> SEQ ID NO 12
<211> LENGTH: 247
<212> TYPE: PRT
<213> ORGANISM: Artificial Sequence
<220> FEATURE:
<223> OTHER INFORMATION: TMP-Fc

<400> SEQUENCE: 12

Met Ile Glu Gly Pro Thr Leu Arg Gln Trp Leu Ala Ala Arg Ala Gly
1               5                   10                  15

Gly Gly Gly Gly Asp Lys Thr His Thr Cys Pro Pro Cys Pro Ala Pro
                20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
        50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220
```

-continued

```
Cys Ser Val Met His Glu Ala Leu His Asn His Tyr Thr Gln Lys Ser
225                 230                 235                 240

Leu Ser Leu Ser Pro Gly Lys
            245

<210> SEQ ID NO 13
<211> LENGTH: 14
<212> TYPE: PRT
<213> ORGANISM: Artificial Sequence
<220> FEATURE:
<223> OTHER INFORMATION: TMP

<400> SEQUENCE: 13

Ile Glu Gly Pro Thr Leu Arg Gln Trp Leu Ala Ala Arg Ala
1               5                   10

<210> SEQ ID NO 14
<211> LENGTH: 36
<212> TYPE: PRT
<213> ORGANISM: Artificial Sequence
<220> FEATURE:
<223> OTHER INFORMATION: TMP-TMP

<400> SEQUENCE: 14

Ile Glu Gly Pro Thr Leu Arg Gln Trp Leu Ala Ala Arg Ala Gly Gly
1               5                   10                  15

Gly Gly Gly Gly Gly Ile Glu Gly Pro Thr Leu Arg Gln Trp Leu
            20                  25                  30

Ala Ala Arg Ala
        35

<210> SEQ ID NO 15
<211> LENGTH: 812
<212> TYPE: DNA
<213> ORGANISM: Artificial Sequence
<220> FEATURE:
<223> OTHER INFORMATION: Fc-EMP
<220> FEATURE:
<221> NAME/KEY: CDS
<222> LOCATION: (39)..(797)
<223> OTHER INFORMATION:

<400> SEQUENCE: 15
```

| | |
|---|---:|
| tctagatttg ttttaactaa ttaaaggagg aataacat atg gac aaa act cac aca<br>                                                                 Met Asp Lys Thr His Thr<br>                                                                  1                 5 | 56 |
| tgt cca cct tgt cca gct ccg gaa ctc ctg ggg gga ccg tca gtc ttc<br>Cys Pro Pro Cys Pro Ala Pro Glu Leu Leu Gly Gly Pro Ser Val Phe<br>         10                      15                       20 | 104 |
| ctc ttc ccc cca aaa ccc aag gac acc ctc atg atc tcc cgg acc cct<br>Leu Phe Pro Pro Lys Pro Lys Asp Thr Leu Met Ile Ser Arg Thr Pro<br>        25                      30                       35 | 152 |
| gag gtc aca tgc gtg gtg gtg gac gtg agc cac gaa gac cct gag gtc<br>Glu Val Thr Cys Val Val Val Asp Val Ser His Glu Asp Pro Glu Val<br>      40                      45                      50 | 200 |
| aag ttc aac tgg tac gtg gac ggc gtg gag gtg cat aat gcc aag aca<br>Lys Phe Asn Trp Tyr Val Asp Gly Val Glu Val His Asn Ala Lys Thr<br>55                     60                      65                      70 | 248 |
| aag ccg cgg gag gag cag tac aac agc acg tac cgt gtg gtc agc gtc<br>Lys Pro Arg Glu Glu Gln Tyr Asn Ser Thr Tyr Arg Val Val Ser Val<br>                 75                      80                      85 | 296 |
| ctc acc gtc ctg cac cag gac tgg ctg aat ggc aag gag tac aag tgc<br>Leu Thr Val Leu His Gln Asp Trp Leu Asn Gly Lys Glu Tyr Lys Cys | 344 |

```
                90                      95                     100
aag gtc tcc aac aaa gcc ctc cca gcc ccc atc gag aaa acc atc tcc    392
Lys Val Ser Asn Lys Ala Leu Pro Ala Pro Ile Glu Lys Thr Ile Ser
            105                 110                 115 aaa gcc aaa ggg cag ccc cga gaa cca cag gtg tac acc ctg ccc cca    440
Lys Ala Lys Gly Gln Pro Arg Glu Pro Gln Val Tyr Thr Leu Pro Pro
    120                 125                 130 tcc cgg gat gag ctg acc aag aac cag gtc agc ctg acc tgc ctg gtc    488
Ser Arg Asp Glu Leu Thr Lys Asn Gln Val Ser Leu Thr Cys Leu Val
135                 140                 145                 150 aaa ggc ttc tat ccc agc gac atc gcc gtg gag tgg gag agc aat ggg    536
Lys Gly Phe Tyr Pro Ser Asp Ile Ala Val Glu Trp Glu Ser Asn Gly
                155                 160                 165 cag ccg gag aac aac tac aag acc acg cct ccc gtg ctg gac tcc gac    584
Gln Pro Glu Asn Asn Tyr Lys Thr Thr Pro Pro Val Leu Asp Ser Asp
            170                 175                 180 ggc tcc ttc ttc ctc tac agc aag ctc acc gtg gac aag agc agg tgg    632
Gly Ser Phe Phe Leu Tyr Ser Lys Leu Thr Val Asp Lys Ser Arg Trp
        185                 190                 195 cag cag ggg aac gtc ttc tca tgc tcc gtg atg cat gag gct ctg cac    680
Gln Gln Gly Asn Val Phe Ser Cys Ser Val Met His Glu Ala Leu His
    200                 205                 210 aac cac tac acg cag aag agc ctc tcc ctg tct ccg ggt aaa ggt gga    728
Asn His Tyr Thr Gln Lys Ser Leu Ser Leu Ser Pro Gly Lys Gly Gly
215                 220                 225                 230 ggt ggt ggt gga ggt act tac tct tgc cac ttc ggc ccg ctg act tgg    776
Gly Gly Gly Gly Gly Thr Tyr Ser Cys His Phe Gly Pro Leu Thr Trp
                235                 240                 245 gtt tgc aaa ccg cag ggt ggt taatctcgtg gatcc                       812
Val Cys Lys Pro Gln Gly Gly
            250
```

<210> SEQ ID NO 16
<211> LENGTH: 253
<212> TYPE: PRT
<213> ORGANISM: Artificial Sequence
<220> FEATURE:
<223> OTHER INFORMATION: Fc-EMP

<400> SEQUENCE: 16

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140
```

-continued

```
Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Gly Thr Tyr Ser Cys His
225                 230                 235                 240

Phe Gly Pro Leu Thr Trp Val Cys Lys Pro Gln Gly Gly
                245                 250
```

<210> SEQ ID NO 17
<211> LENGTH: 807
<212> TYPE: DNA
<213> ORGANISM: Artificial Sequence
<220> FEATURE:
<223> OTHER INFORMATION: EMP-Fc
<220> FEATURE:
<221> NAME/KEY: CDS
<222> LOCATION: (39)..(797)
<223> OTHER INFORMATION:

<400> SEQUENCE: 17

```
tctagatttg ttttaactaa ttaaaggagg aataacat atg gga ggt act tac tct      56
                                        Met Gly Gly Thr Tyr Ser
                                        1               5 tgc cac ttc ggc ccg ctg act tgg gta tgt aag cca caa ggg ggt ggg       104
Cys His Phe Gly Pro Leu Thr Trp Val Cys Lys Pro Gln Gly Gly Gly
            10                  15                  20 gga ggc ggg ggg gac aaa act cac aca tgt cca cct tgc cca gca cct       152
Gly Gly Gly Gly Asp Lys Thr His Thr Cys Pro Pro Cys Pro Ala Pro
        25                  30                  35 gaa ctc ctg ggg gga ccg tca gtt ttc ctc ttc ccc cca aaa ccc aag       200
Glu Leu Leu Gly Gly Pro Ser Val Phe Leu Phe Pro Pro Lys Pro Lys
    40                  45                  50 gac acc ctc atg atc tcc cgg acc cct gag gtc aca tgc gtg gtg gtg       248
Asp Thr Leu Met Ile Ser Arg Thr Pro Glu Val Thr Cys Val Val Val
55                  60                  65                  70 gac gtg agc cac gaa gac cct gag gtc aag ttc aac tgg tac gtg gac       296
Asp Val Ser His Glu Asp Pro Glu Val Lys Phe Asn Trp Tyr Val Asp
                75                  80                  85 ggc gtg gag gtg cat aat gcc aag aca aag ccg cgg gag gag cag tac       344
Gly Val Glu Val His Asn Ala Lys Thr Lys Pro Arg Glu Glu Gln Tyr
            90                  95                  100 aac agc acg tac cgt gtg gtc agc gtc ctc acc gtc ctg cac cag gac       392
Asn Ser Thr Tyr Arg Val Val Ser Val Leu Thr Val Leu His Gln Asp
        105                 110                 115 tgg ctg aat ggc aag gag tac aag tgc aag gtc tcc aac aaa gcc ctc       440
Trp Leu Asn Gly Lys Glu Tyr Lys Cys Lys Val Ser Asn Lys Ala Leu
    120                 125                 130 cca gcc ccc atc gag aaa acc atc tcc aaa gcc aaa ggg cag ccc cga       488
Pro Ala Pro Ile Glu Lys Thr Ile Ser Lys Ala Lys Gly Gln Pro Arg
135                 140                 145                 150 gaa cca cag gtg tac acc ctg ccc cca tcc cgg gat gag ctg acc aag       536
Glu Pro Gln Val Tyr Thr Leu Pro Pro Ser Arg Asp Glu Leu Thr Lys
                155                 160                 165
```

```
aac cag gtc agc ctg acc tgc ctg gtc aaa ggc ttc tat ccc agc gac        584
Asn Gln Val Ser Leu Thr Cys Leu Val Lys Gly Phe Tyr Pro Ser Asp
            170                 175                 180 atc gcc gtg gag tgg gag agc aat ggg cag ccg gag aac aac tac aag        632
Ile Ala Val Glu Trp Glu Ser Asn Gly Gln Pro Glu Asn Asn Tyr Lys
        185                 190                 195 acc acg cct ccc gtg ctg gac tcc gac ggc tcc ttc ttc ctc tac agc        680
Thr Thr Pro Pro Val Leu Asp Ser Asp Gly Ser Phe Phe Leu Tyr Ser
200                 205                 210 aag ctc acc gtg gac aag agc agg tgg cag cag ggg aac gtc ttc tca        728
Lys Leu Thr Val Asp Lys Ser Arg Trp Gln Gln Gly Asn Val Phe Ser
215                 220                 225                 230 tgc tcc gtg atg cat gag gct ctg cac aac cac tac acg cag aag agc        776
Cys Ser Val Met His Glu Ala Leu His Asn His Tyr Thr Gln Lys Ser
                235                 240                 245 ctc tcc ctg tct ccg ggt aaa taatggatcc                                 807
Leu Ser Leu Ser Pro Gly Lys
                250

<210> SEQ ID NO 18
<211> LENGTH: 253
<212> TYPE: PRT
<213> ORGANISM: Artificial Sequence
<220> FEATURE:
<223> OTHER INFORMATION: EMP-Fc

<400> SEQUENCE: 18

Met Gly Gly Thr Tyr Ser Cys His Phe Gly Pro Leu Thr Trp Val Cys
1               5                   10                  15

Lys Pro Gln Gly Gly Gly Gly Gly Asp Lys Thr His Thr Cys
            20                  25                  30

Pro Pro Cys Pro Ala Pro Glu Leu Leu Gly Gly Pro Ser Val Phe Leu
        35                  40                  45

Phe Pro Pro Lys Pro Lys Asp Thr Leu Met Ile Ser Arg Thr Pro Glu
    50                  55                  60

Val Thr Cys Val Val Val Asp Val Ser His Glu Asp Pro Glu Val Lys
65                  70                  75                  80

Phe Asn Trp Tyr Val Asp Gly Val Glu Val His Asn Ala Lys Thr Lys
                85                  90                  95

Pro Arg Glu Glu Gln Tyr Asn Ser Thr Tyr Arg Val Val Ser Val Leu
            100                 105                 110

Thr Val Leu His Gln Asp Trp Leu Asn Gly Lys Glu Tyr Lys Cys Lys
        115                 120                 125

Val Ser Asn Lys Ala Leu Pro Ala Pro Ile Glu Lys Thr Ile Ser Lys
    130                 135                 140

Ala Lys Gly Gln Pro Arg Glu Pro Gln Val Tyr Thr Leu Pro Pro Ser
145                 150                 155                 160

Arg Asp Glu Leu Thr Lys Asn Gln Val Ser Leu Thr Cys Leu Val Lys
                165                 170                 175

Gly Phe Tyr Pro Ser Asp Ile Ala Val Glu Trp Glu Ser Asn Gly Gln
            180                 185                 190

Pro Glu Asn Asn Tyr Lys Thr Thr Pro Pro Val Leu Asp Ser Asp Gly
        195                 200                 205

Ser Phe Phe Leu Tyr Ser Lys Leu Thr Val Asp Lys Ser Arg Trp Gln
    210                 215                 220

Gln Gly Asn Val Phe Ser Cys Ser Val Met His Glu Ala Leu His Asn
225                 230                 235                 240
```

His Tyr Thr Gln Lys Ser Leu Ser Leu Ser Pro Gly Lys
                245                 250

<210> SEQ ID NO 19
<211> LENGTH: 881
<212> TYPE: DNA
<213> ORGANISM: Artificial Sequence
<220> FEATURE:
<223> OTHER INFORMATION: EMP-EMP-Fc
<220> FEATURE:
<221> NAME/KEY: CDS
<222> LOCATION: (41)..(871)
<223> OTHER INFORMATION:

<400> SEQUENCE: 19

```
tctagatttg agtttaact tttagaagga ggaataaaat atg gga ggt act tac      55
                                             Met Gly Gly Thr Tyr
                                             1               5 tct tgc cac ttc ggc cca ctg act tgg gtt tgc aaa ccg cag ggt ggc    103
Ser Cys His Phe Gly Pro Leu Thr Trp Val Cys Lys Pro Gln Gly Gly
                10                  15                  20 ggc ggc ggc ggt ggt acc tat tcc tgt cat ttt ggc ccg ctg acc        151
Gly Gly Gly Gly Gly Gly Thr Tyr Ser Cys His Phe Gly Pro Leu Thr
            25                  30                  35 tgg gta tgt aag cca caa ggg ggt ggg gga ggc ggg ggg gac aaa act    199
Trp Val Cys Lys Pro Gln Gly Gly Gly Gly Gly Gly Asp Lys Thr
        40                  45                  50 cac aca tgt cca cct tgc cca gca cct gaa ctc ctg ggg gga ccg tca    247
His Thr Cys Pro Pro Cys Pro Ala Pro Glu Leu Leu Gly Gly Pro Ser
    55                  60                  65 gtt ttc ctc ttc ccc cca aaa ccc aag gac acc ctc atg atc tcc cgg    295
Val Phe Leu Phe Pro Pro Lys Pro Lys Asp Thr Leu Met Ile Ser Arg
70                  75                  80                  85 acc cct gag gtc aca tgc gtg gtg gtg gac gtg agc cac gaa gac cct    343
Thr Pro Glu Val Thr Cys Val Val Val Asp Val Ser His Glu Asp Pro
                90                  95                 100 gag gtc aag ttc aac tgg tac gtg gac ggc gtg gag gtg cat aat gcc    391
Glu Val Lys Phe Asn Trp Tyr Val Asp Gly Val Glu Val His Asn Ala
            105                 110                 115 aag aca aag ccg cgg gag gag cag tac aac agc acg tac cgt gtg gtc    439
Lys Thr Lys Pro Arg Glu Glu Gln Tyr Asn Ser Thr Tyr Arg Val Val
        120                 125                 130 agc gtc ctc acc gtc ctg cac cag gac tgg ctg aat ggc aag gag tac    487
Ser Val Leu Thr Val Leu His Gln Asp Trp Leu Asn Gly Lys Glu Tyr
    135                 140                 145 aag tgc aag gtc tcc aac aaa gcc ctc cca gcc ccc atc gag aaa acc    535
Lys Cys Lys Val Ser Asn Lys Ala Leu Pro Ala Pro Ile Glu Lys Thr
150                 155                 160                 165 atc tcc aaa gcc aaa ggg cag ccc cga gaa cca cag gtg tac acc ctg    583
Ile Ser Lys Ala Lys Gly Gln Pro Arg Glu Pro Gln Val Tyr Thr Leu
                170                 175                 180 ccc cca tcc cgg gat gag ctg acc aag aac cag gtc agc ctg acc tgc    631
Pro Pro Ser Arg Asp Glu Leu Thr Lys Asn Gln Val Ser Leu Thr Cys
            185                 190                 195 ctg gtc aaa ggc ttc tat ccc agc gac atc gcc gtg gag tgg gag agc    679
Leu Val Lys Gly Phe Tyr Pro Ser Asp Ile Ala Val Glu Trp Glu Ser
        200                 205                 210 aat ggg cag ccg gag aac aac tac aag acc acg cct ccc gtg ctg gac    727
Asn Gly Gln Pro Glu Asn Asn Tyr Lys Thr Thr Pro Pro Val Leu Asp
    215                 220                 225 tcc gac ggc tcc ttc ttc ctc tac agc aag ctc acc gtg gac aag agc    775
Ser Asp Gly Ser Phe Phe Leu Tyr Ser Lys Leu Thr Val Asp Lys Ser
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| agg | tgg | cag | cag | ggg | aac | gtc | ttc | tca | tgc | tcc | gtg | atg | cat | gag | gct | 823 |
| Arg | Trp | Gln | Gln | Gly | Asn | Val | Phe | Ser | Cys | Ser | Val | Met | His | Glu | Ala | |
| | | | | 250 | | | | | 255 | | | | | 260 | | |
| ctg | cac | aac | cac | tac | acg | cag | aag | agc | ctc | tcc | ctg | tct | ccg | ggt | aaa | 871 |
| Leu | His | Asn | His | Tyr | Thr | Gln | Lys | Ser | Leu | Ser | Leu | Ser | Pro | Gly | Lys | |
| | | | | 265 | | | | | 270 | | | | | 275 | | |
| taatggatcc | | | | | | | | | | | | | | | | 881 |

<210> SEQ ID NO 20
<211> LENGTH: 277
<212> TYPE: PRT
<213> ORGANISM: Artificial Sequence
<220> FEATURE:
<223> OTHER INFORMATION: EMP-EMP-Fc

<400> SEQUENCE: 20

Met Gly Gly Thr Tyr Ser Cys His Phe Gly Pro Leu Thr Trp Val Cys
1               5                   10                  15

Lys Pro Gln Gly Gly Gly Gly Gly Gly Thr Tyr Ser Cys His
            20                  25                  30

Phe Gly Pro Leu Thr Trp Val Cys Lys Pro Gln Gly Gly Gly Gly
        35                  40                  45

Gly Gly Asp Lys Thr His Thr Cys Pro Pro Cys Pro Ala Pro Glu Leu
50                  55                  60

Leu Gly Gly Pro Ser Val Phe Leu Phe Pro Pro Lys Pro Lys Asp Thr
65                  70                  75                  80

Leu Met Ile Ser Arg Thr Pro Glu Val Thr Cys Val Val Val Asp Val
                85                  90                  95

Ser His Glu Asp Pro Glu Val Lys Phe Asn Trp Tyr Val Asp Gly Val
            100                 105                 110

Glu Val His Asn Ala Lys Thr Lys Pro Arg Glu Glu Gln Tyr Asn Ser
        115                 120                 125

Thr Tyr Arg Val Val Ser Val Leu Thr Val Leu His Gln Asp Trp Leu
    130                 135                 140

Asn Gly Lys Glu Tyr Lys Cys Lys Val Ser Asn Lys Ala Leu Pro Ala
145                 150                 155                 160

Pro Ile Glu Lys Thr Ile Ser Lys Ala Lys Gly Gln Pro Arg Glu Pro
                165                 170                 175

Gln Val Tyr Thr Leu Pro Pro Ser Arg Asp Glu Leu Thr Lys Asn Gln
            180                 185                 190

Val Ser Leu Thr Cys Leu Val Lys Gly Phe Tyr Pro Ser Asp Ile Ala
        195                 200                 205

Val Glu Trp Glu Ser Asn Gly Gln Pro Glu Asn Asn Tyr Lys Thr Thr
    210                 215                 220

Pro Pro Val Leu Asp Ser Asp Gly Ser Phe Phe Leu Tyr Ser Lys Leu
225                 230                 235                 240

Thr Val Asp Lys Ser Arg Trp Gln Gln Gly Asn Val Phe Ser Cys Ser
                245                 250                 255

Val Met His Glu Ala Leu His Asn His Tyr Thr Gln Lys Ser Leu Ser
            260                 265                 270

Leu Ser Pro Gly Lys
        275

<210> SEQ ID NO 21
<211> LENGTH: 885

```
<212> TYPE: DNA
<213> ORGANISM: Artificial Sequence
<220> FEATURE:
<223> OTHER INFORMATION: Fc-EMP-EMP
<220> FEATURE:
<221> NAME/KEY: CDS
<222> LOCATION: (39)..(869)
<223> OTHER INFORMATION:

<400> SEQUENCE: 21
```

| | | | | | | | | | | | | | | | | |
|---|---|---|---|---|---|---|---|---|---|---|---|---|---|---|---|---|
| tctagatttg ttttaactaa ttaaaggagg aataacat | atg | gac | aaa | act | cac | aca | | | | | | | | | | 56 |
| | Met | Asp | Lys | Thr | His | Thr | | | | | | | | | | |
| | 1 | | | | 5 | | | | | | | | | | | |
| tgt | cca | cct | tgc | cca | gca | cct | gaa | ctc | ctg | ggg | gga | ccg | tca | gtt | ttc | 104 |
| Cys | Pro | Pro | Cys | Pro | Ala | Pro | Glu | Leu | Leu | Gly | Gly | Pro | Ser | Val | Phe | |
| | | 10 | | | | | 15 | | | | | 20 | | | | |
| ctc | ttc | ccc | cca | aaa | ccc | aag | gac | acc | ctc | atg | atc | tcc | cgg | acc | cct | 152 |
| Leu | Phe | Pro | Pro | Lys | Pro | Lys | Asp | Thr | Leu | Met | Ile | Ser | Arg | Thr | Pro | |
| | | 25 | | | | | 30 | | | | | 35 | | | | |
| gag | gtc | aca | tgc | gtg | gtg | gtg | gac | gtg | agc | cac | gaa | gac | cct | gag | gtc | 200 |
| Glu | Val | Thr | Cys | Val | Val | Val | Asp | Val | Ser | His | Glu | Asp | Pro | Glu | Val | |
| | 40 | | | | | 45 | | | | | 50 | | | | | |
| aag | ttc | aac | tgg | tac | gtg | gac | ggc | gtg | gag | gtg | cat | aat | gcc | aag | aca | 248 |
| Lys | Phe | Asn | Trp | Tyr | Val | Asp | Gly | Val | Glu | Val | His | Asn | Ala | Lys | Thr | |
| 55 | | | | | 60 | | | | | 65 | | | | | 70 | |
| aag | ccg | cgg | gag | gag | cag | tac | aac | agc | acg | tac | cgt | gtg | gtc | agc | gtc | 296 |
| Lys | Pro | Arg | Glu | Glu | Gln | Tyr | Asn | Ser | Thr | Tyr | Arg | Val | Val | Ser | Val | |
| | | | 75 | | | | | 80 | | | | | 85 | | | |
| ctc | acc | gtc | ctg | cac | cag | gac | tgg | ctg | aat | ggc | aag | gag | tac | aag | tgc | 344 |
| Leu | Thr | Val | Leu | His | Gln | Asp | Trp | Leu | Asn | Gly | Lys | Glu | Tyr | Lys | Cys | |
| | | | 90 | | | | | 95 | | | | | 100 | | | |
| aag | gtc | tcc | aac | aaa | gcc | ctc | cca | gcc | ccc | atc | gag | aaa | acc | atc | tcc | 392 |
| Lys | Val | Ser | Asn | Lys | Ala | Leu | Pro | Ala | Pro | Ile | Glu | Lys | Thr | Ile | Ser | |
| | | 105 | | | | | 110 | | | | | 115 | | | | |
| aaa | gcc | aaa | ggg | cag | ccc | cga | gaa | cca | cag | gtg | tac | acc | ctg | cct | cca | 440 |
| Lys | Ala | Lys | Gly | Gln | Pro | Arg | Glu | Pro | Gln | Val | Tyr | Thr | Leu | Pro | Pro | |
| 120 | | | | | 125 | | | | | 130 | | | | | | |
| tcc | cgg | gat | gag | ctg | acc | aag | aac | cag | gtc | agc | ctg | acc | tgc | ctg | gtc | 488 |
| Ser | Arg | Asp | Glu | Leu | Thr | Lys | Asn | Gln | Val | Ser | Leu | Thr | Cys | Leu | Val | |
| 135 | | | | | 140 | | | | | 145 | | | | | 150 | |
| aaa | ggc | ttc | tat | ccc | agc | gac | atc | gcc | gtg | gag | tgg | gag | agc | aat | ggg | 536 |
| Lys | Gly | Phe | Tyr | Pro | Ser | Asp | Ile | Ala | Val | Glu | Trp | Glu | Ser | Asn | Gly | |
| | | | 155 | | | | | 160 | | | | | 165 | | | |
| cag | ccg | gag | aac | aac | tac | aag | acc | acg | cct | ccc | gtg | ctg | gac | tcc | gac | 584 |
| Gln | Pro | Glu | Asn | Asn | Tyr | Lys | Thr | Thr | Pro | Pro | Val | Leu | Asp | Ser | Asp | |
| | | 170 | | | | | 175 | | | | | 180 | | | | |
| ggc | tcc | ttc | ttc | ctc | tac | agc | aag | ctc | acc | gtg | gac | aag | agc | agg | tgg | 632 |
| Gly | Ser | Phe | Phe | Leu | Tyr | Ser | Lys | Leu | Thr | Val | Asp | Lys | Ser | Arg | Trp | |
| | 185 | | | | | 190 | | | | | 195 | | | | | |
| cag | cag | ggg | aac | gtc | ttc | tca | tgc | tcc | gtg | atg | cat | gag | gct | ctg | cac | 680 |
| Gln | Gln | Gly | Asn | Val | Phe | Ser | Cys | Ser | Val | Met | His | Glu | Ala | Leu | His | |
| | 200 | | | | | 205 | | | | | 210 | | | | | |
| aac | cac | tac | acg | cag | aag | agc | ctc | tcc | ctg | tct | ccg | ggt | aaa | ggt | gga | 728 |
| Asn | His | Tyr | Thr | Gln | Lys | Ser | Leu | Ser | Leu | Ser | Pro | Gly | Lys | Gly | Gly | |
| 215 | | | | 220 | | | | | 225 | | | | | 230 | | |
| ggt | ggt | ggc | gga | ggt | act | tac | tct | tgc | cac | ttc | ggc | cca | ctg | act | tgg | 776 |
| Gly | Gly | Gly | Gly | Gly | Thr | Tyr | Ser | Cys | His | Phe | Gly | Pro | Leu | Thr | Trp | |
| | | | | 235 | | | | | 240 | | | | | 245 | | |
| gtt | tgc | aaa | ccg | cag | ggt | ggc | ggc | ggc | ggc | ggt | ggt | acc | tat | tcc | | 824 |
| Val | Cys | Lys | Pro | Gln | Gly | Gly | Gly | Gly | Gly | Gly | Gly | Thr | Tyr | Ser | | |
| | | 250 | | | | | 255 | | | | | 260 | | | | |

```
                    tgt cat ttt ggc ccg ctg acc tgg gta tgt aag cca caa ggg ggt        869
                    Cys His Phe Gly Pro Leu Thr Trp Val Cys Lys Pro Gln Gly Gly
                        265                 270                 275 taatctcgag gatcca                                                  885
```

<210> SEQ ID NO 22
<211> LENGTH: 277
<212> TYPE: PRT
<213> ORGANISM: Artificial Sequence
<220> FEATURE:
<223> OTHER INFORMATION: Fc-EMP-EMP

<400> SEQUENCE: 22

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Gly Thr Tyr Ser Cys His
225                 230                 235                 240

Phe Gly Pro Leu Thr Trp Val Cys Lys Pro Gln Gly Gly Gly Gly
                245                 250                 255

Gly Gly Gly Thr Tyr Ser Cys His Phe Gly Pro Leu Thr Trp Val Cys
            260                 265                 270

Lys Pro Gln Gly Gly
        275
```

<210> SEQ ID NO 23
<211> LENGTH: 1546
<212> TYPE: DNA
<213> ORGANISM: Artificial Sequence
<220> FEATURE:
<223> OTHER INFORMATION: pAMG21

<400> SEQUENCE: 23

-continued

```
gcgtaacgta tgcatggtct ccccatgcga gagtagggaa ctgccaggca tcaaataaaa      60
cgaaaggctc agtcgaaaga ctgggccttt cgttttatct gttgtttgtc ggtgaacgct     120
ctcctgagta ggacaaatcc gccgggagcg gatttgaacg ttgcgaagca acggcccgga     180
gggtggcggg caggacgccc gccataaact gccaggcatc aaattaagca gaaggccatc     240
ctgacggatg gcctttttgc gtttctacaa actcttttgt ttattttcct aaatacattc     300
aaatatggac gtcgtactta acttttaaag tatgggcaat caattgctcc tgttaaaatt     360
gctttagaaa tactttggca gcggtttgtt gtattgagtt tcatttgcgc attggttaaa     420
tggaaagtga ccgtgcgctt actacagcct aatatttttg aaatatccca agagcttttt     480
ccttcgcatg cccacgctaa acattctttt tctcttttgg ttaaatcgtt gtttgattta     540
ttatttgcta tatttatttt tcgataatta tcaactagag aaggaacaat taatggtatg     600
ttcatacacg catgtaaaaa taactatct atatagttgt ctttctctga atgtgcaaaa      660
ctaagcattc cgaagccatt attagcagta tgaatagggga aactaaaccc agtgataaga     720
cctgatgatt tcgcttcttt aattacattt ggagattttt tatttacagc attgttttca     780
aatatattcc aattaatcgg tgaatgattg gagttagaat aatctactat aggatcatat     840
tttattaaat tagcgtcatc ataatattgc ctccattttt tagggtaatt atccagaatt     900
gaaatatcag atttaaccat agaatgagga taaatgatcg cgagtaaata atattcacaa     960
tgtaccattt tagtcatatc agataagcat tgattaatat cattattgct tctacaggct    1020
ttaattttat taattattct gtaagtgtcg tcggcattta tgtctttcat acccatctct    1080
ttatccttac ctattgtttg tcgcaagttt tgcgtgttat atatcattaa aacggtaata    1140
gattgacatt tgattctaat aaattggatt tttgtcacac tattatatcg cttgaaatac    1200
aattgtttaa cataagtacc tgtaggatcg tacaggttta cgcaagaaaa tggtttgtta    1260
tagtcgatta atcgatttga ttctagattt gttttaacta attaaaggag gaataacata    1320
tggttaacgc gttggaattc gagctcacta gtgtcgacct gcagggtacc atggaagctt    1380
actcgaggat ccgcggaaag aagaagaaga agaagaaagc ccgaaaggaa gctgagttgg    1440
ctgctgccac cgctgagcaa taactagcat aaccccttgg ggcctctaaa cgggtcttga    1500
gggttttttt gctgaaagga ggaaccgctc ttcacgctct tcacgc                   1546
```

<210> SEQ ID NO 24
<211> LENGTH: 14
<212> TYPE: PRT
<213> ORGANISM: Artificial Sequence
<220> FEATURE:
<223> OTHER INFORMATION: TPO-MIMETIC PEPTIDE

<400> SEQUENCE: 24

Ile Glu Gly Pro Thr Leu Arg Gln Trp Leu Ala Ala Lys Ala
1               5                   10

<210> SEQ ID NO 25
<211> LENGTH: 14
<212> TYPE: PRT
<213> ORGANISM: Artificial Sequence
<220> FEATURE:
<223> OTHER INFORMATION: TPO-MIMETIC PEPTIDE

<400> SEQUENCE: 25

Ile Glu Gly Pro Thr Leu Arg Glu Trp Leu Ala Ala Arg Ala
1               5                   10

```
<210> SEQ ID NO 26
<211> LENGTH: 14
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (14)..(14)
<223> OTHER INFORMATION: At position 14, amino acid linker to an
      identical sequence

<400> SEQUENCE: 26

Ile Glu Gly Pro Thr Leu Arg Gln Trp Leu Ala Ala Arg Ala
1               5                   10

<210> SEQ ID NO 27
<211> LENGTH: 14
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (14)..(14)
<223> OTHER INFORMATION: At position 14, amino acid linker to an
      identical sequence

<400> SEQUENCE: 27

Ile Glu Gly Pro Thr Leu Arg Gln Trp Leu Ala Ala Lys Ala
1               5                   10

<210> SEQ ID NO 28
<211> LENGTH: 14
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (9)..(9)
<223> OTHER INFORMATION: At position 9 disulfide linkage to position 9
      of an identical sequence
<220> FEATURE:
<221> NAME/KEY: misc_feature
<222> LOCATION: (14)..(14)
<223> OTHER INFORMATION: At position 14, amino acid linker to an
      identical sequence

<400> SEQUENCE: 28

Ile Glu Gly Pro Thr Leu Arg Gln Cys Leu Ala Ala Arg Ala
1               5                   10

<210> SEQ ID NO 29
<211> LENGTH: 14
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (16)..(16)
<223> OTHER INFORMATION: Position 16 bromoacetyl group linked to
      sidechain
<220> FEATURE:
<221> NAME/KEY: misc_feature
<222> LOCATION: (14)..(14)
<223> OTHER INFORMATION: At position 14, amino acid linker attached N-
      to-C to Lys and to another linker and an identical sequence

<400> SEQUENCE: 29
```

```
Ile Glu Gly Pro Thr Leu Arg Gln Trp Leu Ala Ala Arg Ala
1               5                   10
```

<210> SEQ ID NO 30
<211> LENGTH: 14
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (16)..(16)
<223> OTHER INFORMATION: Position 16 polyethylene glycol linked to
      sidechain
<220> FEATURE:
<221> NAME/KEY: misc_feature
<222> LOCATION: (14)..(14)
<223> OTHER INFORMATION: At position 14, amino acid linker attached N-
      to-C to Lys and to another linker and an identical sequence

<400> SEQUENCE: 30

```
Ile Glu Gly Pro Thr Leu Arg Gln Trp Leu Ala Ala Arg Ala
1               5                   10
```

<210> SEQ ID NO 31
<211> LENGTH: 14
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (9)..(9)
<223> OTHER INFORMATION: Position 9 disulfide bond to residue 9 of a
      separate identical sequence
<220> FEATURE:
<221> NAME/KEY: misc_feature
<222> LOCATION: (14)..(14)
<223> OTHER INFORMATION: At position 14, amino acid linker to an
      identical sequence

<400> SEQUENCE: 31

```
Ile Glu Gly Pro Thr Leu Arg Gln Cys Leu Ala Ala Arg Ala
1               5                   10
```

<210> SEQ ID NO 32
<211> LENGTH: 14
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (14)..(14)
<223> OTHER INFORMATION: At position 14, amino acid linker attachment
      site

<400> SEQUENCE: 32

```
Ile Glu Gly Pro Thr Leu Arg Gln Trp Leu Ala Ala Arg Ala
1               5                   10
```

<210> SEQ ID NO 33
<211> LENGTH: 9
<212> TYPE: PRT
<213> ORGANISM: Artificial Sequence
<220> FEATURE:
<223> OTHER INFORMATION: TPO MIMETIC PEPTIDE
<220> FEATURE:
<221> NAME/KEY: misc_feature
<222> LOCATION: (6, 7 and)..(8)
<223> OTHER INFORMATION: Xaa = any amino acid

```
<400> SEQUENCE: 33

Val Arg Asp Gln Ile Xaa Xaa Xaa Leu
1               5

<210> SEQ ID NO 34
<211> LENGTH: 6
<212> TYPE: PRT
<213> ORGANISM: Artificial Sequence
<220> FEATURE:
<223> OTHER INFORMATION: TPO-MIMETIC PEPTIDE

<400> SEQUENCE: 34

Thr Leu Arg Glu Trp Leu
1               5

<210> SEQ ID NO 35
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 35

Gly Arg Val Arg Asp Gln Val Ala Gly Trp
1               5                   10

<210> SEQ ID NO 36
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 36

Gly Arg Val Lys Asp Gln Ile Ala Gln Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 37

Gly Val Arg Asp Gln Val Ser Trp Ala Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 38

Glu Ser Val Arg Glu Gln Val Met Lys Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 39
```

```
Ser Val Arg Ser Gln Ile Ser Ala Ser Leu
1               5                   10

<210> SEQ ID NO 40
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 40

Gly Val Arg Glu Thr Val Tyr Arg His Met
1               5                   10

<210> SEQ ID NO 41
<211> LENGTH: 11
<212> TYPE: PRT
<213> ORGANISM: Artificial Sequence
<220> FEATURE:
<223> OTHER INFORMATION: TPO-MIMETIC PEPTIDE

<400> SEQUENCE: 41

Gly Val Arg Glu Val Ile Val Met His Met Leu
1               5                   10

<210> SEQ ID NO 42
<211> LENGTH: 11
<212> TYPE: PRT
<213> ORGANISM: Artificial Sequence
<220> FEATURE:
<223> OTHER INFORMATION: TPO-MIMETIC PEPTIDE

<400> SEQUENCE: 42

Gly Arg Val Arg Asp Gln Ile Trp Ala Ala Leu
1               5                   10

<210> SEQ ID NO 43
<211> LENGTH: 11
<212> TYPE: PRT
<213> ORGANISM: Artificial Sequence
<220> FEATURE:
<223> OTHER INFORMATION: TPO-MIMETIC PEPTIDE

<400> SEQUENCE: 43

Ala Gly Val Arg Asp Gln Ile Leu Ile Trp Leu
1               5                   10

<210> SEQ ID NO 44
<211> LENGTH: 11
<212> TYPE: PRT
<213> ORGANISM: Artificial Sequence
<220> FEATURE:
<223> OTHER INFORMATION: TPO-MIMETIC PEPTIDE

<400> SEQUENCE: 44

Gly Arg Val Arg Asp Gln Ile Met Leu Ser Leu
1               5                   10

<210> SEQ ID NO 45
<211> LENGTH: 11
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (8)..(10)
```

<223> OTHER INFORMATION: Xaa = any amino acid

<400> SEQUENCE: 45

Gly Arg Val Arg Asp Gln Ile Xaa Xaa Xaa Leu
1               5                   10

<210> SEQ ID NO 46
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 46

Cys Thr Leu Arg Gln Trp Leu Gln Gly Cys
1               5                   10

<210> SEQ ID NO 47
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 47

Cys Thr Leu Gln Glu Phe Leu Glu Gly Cys
1               5                   10

<210> SEQ ID NO 48
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 48

Cys Thr Arg Thr Glu Trp Leu His Gly Cys
1               5                   10

<210> SEQ ID NO 49
<211> LENGTH: 12
<212> TYPE: PRT
<213> ORGANISM: Artificial Sequence
<220> FEATURE:
<223> OTHER INFORMATION: TPO-MIMETIC PEPTIDE

<400> SEQUENCE: 49

Cys Thr Leu Arg Glu Trp Leu His Gly Gly Phe Cys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: TPO-MIMETIC PEPTIDE

<400> SEQUENCE: 50

Cys Thr Leu Arg Glu Trp Val Phe Ala Gly Leu Cys
1               5                   10

<210> SEQ ID NO 51
<211> LENGTH: 13
<212> TYPE: PRT
<213> ORGANISM: Artificial Sequence
<220> FEATURE:
<223> OTHER INFORMATION: TPO-MIMETIC PEPTIDE

```
<400> SEQUENCE: 51

Cys Thr Leu Arg Gln Trp Leu Ile Leu Leu Gly Met Cys
1               5                   10

<210> SEQ ID NO 52
<211> LENGTH: 14
<212> TYPE: PRT
<213> ORGANISM: Artificial Sequence
<220> FEATURE:
<223> OTHER INFORMATION: TPO-MIMETIC PEPTIDE

<400> SEQUENCE: 52

Cys Thr Leu Ala Glu Phe Leu Ala Ser Gly Val Glu Gln Cys
1               5                   10

<210> SEQ ID NO 53
<211> LENGTH: 14
<212> TYPE: PRT
<213> ORGANISM: Artificial Sequence
<220> FEATURE:
<223> OTHER INFORMATION: TPO-MIMETIC PEPTIDE

<400> SEQUENCE: 53

Cys Ser Leu Gln Glu Phe Leu Ser His Gly Gly Tyr Val Cys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: TPO-MIMETIC PEPTIDE

<400> SEQUENCE: 54

Cys Thr Leu Arg Glu Phe Leu Asp Pro Thr Thr Ala Val Cys
1               5                   10

<210> SEQ ID NO 55
<211> LENGTH: 14
<212> TYPE: PRT
<213> ORGANISM: Artificial Sequence
<220> FEATURE:
<223> OTHER INFORMATION: TPO-MIMETIC PEPTIDE

<400> SEQUENCE: 55

Cys Thr Leu Lys Glu Trp Leu Val Ser His Glu Val Trp Cys
1               5                   10

<210> SEQ ID NO 56
<211> LENGTH: 10
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (8)..(9)
<223> OTHER INFORMATION: Xaa = any amino acid

<400> SEQUENCE: 56

Cys Thr Leu Arg Glu Trp Leu Xaa Xaa Cys
1               5                   10

<210> SEQ ID NO 57
<211> LENGTH: 11
<212> TYPE: PRT
```

<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (8)..(10)
<223> OTHER INFORMATION: Xaa = any amino acid

<400> SEQUENCE: 57

Cys Thr Leu Arg Glu Trp Leu Xaa Xaa Xaa Cys
1               5                   10

<210> SEQ ID NO 58
<211> LENGTH: 12
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (8)..(11)
<223> OTHER INFORMATION: Xaa = any amino acid

<400> SEQUENCE: 58

Cys Thr Leu Arg Glu Trp Leu Xaa Xaa Xaa Xaa Cys
1               5                   10

<210> SEQ ID NO 59
<211> LENGTH: 13
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (8)..(12)
<223> OTHER INFORMATION: Xaa = any amino acid

<400> SEQUENCE: 59

Cys Thr Leu Arg Glu Trp Leu Xaa Xaa Xaa Xaa Xaa Cys
1               5                   10

<210> SEQ ID NO 60
<211> LENGTH: 14
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (8)..(13)
<223> OTHER INFORMATION: Xaa = any amino acid

<400> SEQUENCE: 60

Cys Thr Leu Arg Glu Trp Leu Xaa Xaa Xaa Xaa Xaa Xaa Cys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 61

Arg Glu Gly Pro Thr Leu Arg Gln Trp Met
1               5                   10

<210> SEQ ID NO 62

```
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 62

Glu Gly Pro Thr Leu Arg Gln Trp Leu Ala
1               5                   10

<210> SEQ ID NO 63
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 63

Glu Arg Gly Pro Phe Trp Ala Lys Ala Cys
1               5                   10

<210> SEQ ID NO 64
<211> LENGTH: 10
<212> TYPE: PRT
<213> ORGANISM: Artificial Sequence
<220> FEATURE:
<223> OTHER INFORMATION: TPO-MIMETIC PEPTIDE

<400> SEQUENCE: 64

Arg Glu Gly Pro Arg Cys Val Met Trp Met
1               5                   10

<210> SEQ ID NO 65
<211> LENGTH: 14
<212> TYPE: PRT
<213> ORGANISM: Artificial Sequence
<220> FEATURE:
<223> OTHER INFORMATION: TPO-MIMETIC PEPTIDE

<400> SEQUENCE: 65

Cys Gly Thr Glu Gly Pro Thr Leu Ser Thr Trp Leu Asp Cys
1               5                   10

<210> SEQ ID NO 66
<211> LENGTH: 14
<212> TYPE: PRT
<213> ORGANISM: Artificial Sequence
<220> FEATURE:
<223> OTHER INFORMATION: TPO-MIMETIC PEPTIDE

<400> SEQUENCE: 66

Cys Glu Gln Asp Gly Pro Thr Leu Leu Glu Trp Leu Lys Cys
1               5                   10

<210> SEQ ID NO 67
<211> LENGTH: 14
<212> TYPE: PRT
<213> ORGANISM: Artificial Sequence
<220> FEATURE:
<223> OTHER INFORMATION: TPO-MIMETIC PEPTIDE

<400> SEQUENCE: 67

Cys Glu Leu Val Gly Pro Ser Leu Met Ser Trp Leu Thr Cys
1               5                   10

<210> SEQ ID NO 68
<211> LENGTH: 14
```

```
<212> TYPE: PRT
<213> ORGANISM: Artificial Sequence
<220> FEATURE:
<223> OTHER INFORMATION: TPO-MIMETIC PEPTIDE

<400> SEQUENCE: 68

Cys Leu Thr Gly Pro Phe Val Thr Gln Trp Leu Tyr Glu Cys
1               5                   10

<210> SEQ ID NO 69
<211> LENGTH: 14
<212> TYPE: PRT
<213> ORGANISM: Artificial Sequence
<220> FEATURE:
<223> OTHER INFORMATION: TPO-MIMETIC PEPTIDE

<400> SEQUENCE: 69

Cys Arg Ala Gly Pro Thr Leu Leu Glu Trp Leu Thr Leu Cys
1               5                   10

<210> SEQ ID NO 70
<211> LENGTH: 14
<212> TYPE: PRT
<213> ORGANISM: Artificial Sequence
<220> FEATURE:
<223> OTHER INFORMATION: TPO-MIMETIC PEPTIDE

<400> SEQUENCE: 70

Cys Ala Asp Gly Pro Thr Leu Arg Glu Trp Ile Ser Phe Cys
1               5                   10

<210> SEQ ID NO 71
<211> LENGTH: 13
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (2 )..(12)
<223> OTHER INFORMATION: Xaa = any amino acid

<400> SEQUENCE: 71

Cys Xaa Glu Gly Pro Thr Leu Arg Glu Trp Leu Xaa Cys
1               5                   10

<210> SEQ ID NO 72
<211> LENGTH: 14
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (2, 3 )..(13)
<223> OTHER INFORMATION: Xaa = any amino acid

<400> SEQUENCE: 72

Cys Xaa Xaa Glu Gly Pro Thr Leu Arg Glu Trp Leu Xaa Cys
1               5                   10

<210> SEQ ID NO 73
<211> LENGTH: 14
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
```

```
<222> LOCATION: (2, 12 )..(13)
<223> OTHER INFORMATION: Xaa = any amino acid

<400> SEQUENCE: 73

Cys Xaa Glu Gly Pro Thr Leu Arg Glu Trp Leu Xaa Xaa Cys
1               5                   10

<210> SEQ ID NO 74
<211> LENGTH: 15
<212> TYPE: PRT
<213> ORGANISM: Artificial Sequence
<220> FEATURE:
<223> OTHER INFORMATION: TPO-MIMETIC PEPTIDE
<220> FEATURE:
<221> NAME/KEY: misc_feature
<222> LOCATION: (2, 3, 13 )..(14)
<223> OTHER INFORMATION: Xaa = any amino acid

<400> SEQUENCE: 74

Cys Xaa Xaa Glu Gly Pro Thr Leu Arg Glu Trp Leu Xaa Xaa Cys
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: TPO-MIMETIC PEPTIDE

<400> SEQUENCE: 75

Gly Gly Cys Thr Leu Arg Glu Trp Leu His Gly Gly Phe Cys Gly Gly
1               5                   10                  15

<210> SEQ ID NO 76
<211> LENGTH: 18
<212> TYPE: PRT
<213> ORGANISM: Artificial Sequence
<220> FEATURE:
<223> OTHER INFORMATION: TPO-MIMETIC PEPTIDE

<400> SEQUENCE: 76

Gly Gly Cys Ala Asp Gly Pro Thr Leu Arg Glu Trp Ile Ser Phe Cys
1               5                   10                  15

Gly Gly

<210> SEQ ID NO 77
<211> LENGTH: 19
<212> TYPE: PRT
<213> ORGANISM: Artificial Sequence
<220> FEATURE:
<223> OTHER INFORMATION: TPO-MIMETIC PEPTIDE

<400> SEQUENCE: 77

Gly Asn Ala Asp Gly Pro Thr Leu Arg Gln Trp Leu Glu Gly Arg Arg
1               5                   10                  15

Pro Lys Asn

<210> SEQ ID NO 78
<211> LENGTH: 19
<212> TYPE: PRT
<213> ORGANISM: Artificial Sequence
<220> FEATURE:
<223> OTHER INFORMATION: TPO-MIMETIC PEPTIDE

<400> SEQUENCE: 78

Leu Ala Ile Glu Gly Pro Thr Leu Arg Gln Trp Leu His Gly Asn Gly
```

```
1               5                  10                 15
Arg Asp Thr

<210> SEQ ID NO 79
<211> LENGTH: 19
<212> TYPE: PRT
<213> ORGANISM: Artificial Sequence
<220> FEATURE:
<223> OTHER INFORMATION: TPO-MIMETIC PEPTIDE

<400> SEQUENCE: 79

His Gly Arg Val Gly Pro Thr Leu Arg Glu Trp Lys Thr Gln Val Ala
1               5                  10                 15
Thr Lys Lys

<210> SEQ ID NO 80
<211> LENGTH: 18
<212> TYPE: PRT
<213> ORGANISM: Artificial Sequence
<220> FEATURE:
<223> OTHER INFORMATION: TPO-MIMETIC PEPTIDE

<400> SEQUENCE: 80

Thr Ile Lys Gly Pro Thr Leu Arg Gln Trp Leu Lys Ser Arg Glu His
1               5                  10                 15
Thr Ser

<210> SEQ ID NO 81
<211> LENGTH: 18
<212> TYPE: PRT
<213> ORGANISM: Artificial Sequence
<220> FEATURE:
<223> OTHER INFORMATION: TPO-MIMETIC PEPTIDE

<400> SEQUENCE: 81

Ile Ser Asp Gly Pro Thr Leu Lys Glu Trp Leu Ser Val Thr Arg Gly
1               5                  10                 15
Ala Ser

<210> SEQ ID NO 82
<211> LENGTH: 18
<212> TYPE: PRT
<213> ORGANISM: Artificial Sequence
<220> FEATURE:
<223> OTHER INFORMATION: TPO MIMETIC PEPTIDE

<400> SEQUENCE: 82

Ser Ile Glu Gly Pro Thr Leu Arg Glu Trp Leu Thr Ser Arg Thr Pro
1               5                  10                 15
His Ser

<210> SEQ ID NO 83
<211> LENGTH: 14
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (2, 4, 5, 8, 11 )..(13)
<223> OTHER INFORMATION: Xaa = any amino acid

<400> SEQUENCE: 83

Tyr Xaa Cys Xaa Xaa Gly Pro Xaa Thr Trp Xaa Cys Xaa Pro
```

```
                      1               5                    10
```

<210> SEQ ID NO 84
<211> LENGTH: 28
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (2, 4, 5, 8, 11, 13, 16, 18, 19, 22, 25 )..(27)
<223> OTHER INFORMATION: Xaa = any amino acid

<400> SEQUENCE: 84

```
Tyr Xaa Cys Xaa Xaa Gly Pro Xaa Thr Trp Xaa Cys Xaa Pro Tyr Xaa
1               5                   10                  15

Cys Xaa Xaa Gly Pro Xaa Thr Trp Xaa Cys Xaa Pro
            20                  25
```

<210> SEQ ID NO 85
<211> LENGTH: 14
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (14)..(14)
<223> OTHER INFORMATION: At position 14, amino acid linker to an
      identical sequence
<220> FEATURE:
<221> NAME/KEY: misc_feature
<222> LOCATION: (2, 4, 5, 8, 11)..(13)
<223> OTHER INFORMATION: Xaa = any amino acid

<400> SEQUENCE: 85

```
Tyr Xaa Cys Xaa Xaa Gly Pro Xaa Thr Trp Xaa Cys Xaa Pro
1               5                   10
```

<210> SEQ ID NO 86
<211> LENGTH: 14
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (2, 4, 5, 8, 11 )..(13)
<223> OTHER INFORMATION: Xaa = any amino acid

<400> SEQUENCE: 86

```
Tyr Xaa Cys Xaa Xaa Gly Pro Xaa Thr Trp Xaa Cys Xaa Pro
1               5                   10
```

<210> SEQ ID NO 87
<211> LENGTH: 20
<212> TYPE: PRT
<213> ORGANISM: Artificial Sequence
<220> FEATURE:
<223> OTHER INFORMATION: EPO-MIMETIC PEPTIDE

<400> SEQUENCE: 87

```
Gly Gly Thr Tyr Ser Cys His Phe Gly Pro Leu Thr Trp Val Cys Lys
1               5                   10                  15

Pro Gln Gly Gly
            20
```

<210> SEQ ID NO 88

```
<211> LENGTH: 20
<212> TYPE: PRT
<213> ORGANISM: Artificial Sequence
<220> FEATURE:
<223> OTHER INFORMATION: EPO-MIMETIC PEPTIDE

<400> SEQUENCE: 88

Gly Gly Asp Tyr His Cys Arg Met Gly Pro Leu Thr Trp Val Cys Lys
1               5                   10                  15

Pro Leu Gly Gly
            20

<210> SEQ ID NO 89
<211> LENGTH: 20
<212> TYPE: PRT
<213> ORGANISM: Artificial Sequence
<220> FEATURE:
<223> OTHER INFORMATION: EPO-MIMETIC PEPTIDE

<400> SEQUENCE: 89

Gly Gly Val Tyr Ala Cys Arg Met Gly Pro Ile Thr Trp Val Cys Ser
1               5                   10                  15

Pro Leu Gly Gly
            20

<210> SEQ ID NO 90
<211> LENGTH: 20
<212> TYPE: PRT
<213> ORGANISM: Artificial Sequence
<220> FEATURE:
<223> OTHER INFORMATION: EPO-MIMETIC PEPTIDE

<400> SEQUENCE: 90

Val Gly Asn Tyr Met Cys His Phe Gly Pro Ile Thr Trp Val Cys Arg
1               5                   10                  15

Pro Gly Gly Gly
            20

<210> SEQ ID NO 91
<211> LENGTH: 20
<212> TYPE: PRT
<213> ORGANISM: Artificial Sequence
<220> FEATURE:
<223> OTHER INFORMATION: EPO-MIMETIC PEPTIDE

<400> SEQUENCE: 91

Gly Gly Leu Tyr Leu Cys Arg Phe Gly Pro Val Thr Trp Asp Cys Gly
1               5                   10                  15

Tyr Lys Gly Gly
            20

<210> SEQ ID NO 92
<211> LENGTH: 40
<212> TYPE: PRT
<213> ORGANISM: Artificial Sequence
<220> FEATURE:
<223> OTHER INFORMATION: EPO-MIMETIC PEPTIDE

<400> SEQUENCE: 92

Gly Gly Thr Tyr Ser Cys His Phe Gly Pro Leu Thr Trp Val Cys Lys
1               5                   10                  15

Pro Gln Gly Gly Gly Gly Thr Tyr Ser Cys His Phe Gly Pro Leu Thr
            20                  25                  30

Trp Val Cys Lys Pro Gln Gly Gly
```

```
            35                  40

<210> SEQ ID NO 93
<211> LENGTH: 20
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (20)..(20)
<223> OTHER INFORMATION: Position 20, amino acid linker to an
      identical sequence

<400> SEQUENCE: 93

Gly Gly Thr Tyr Ser Cys His Phe Gly Pro Leu Thr Trp Val Cys Lys
1               5                   10                  15

Pro Gln Gly Gly
            20

<210> SEQ ID NO 94
<211> LENGTH: 23
<212> TYPE: PRT
<213> ORGANISM: Artificial Sequence
<220> FEATURE:
<223> OTHER INFORMATION: EPO-MIMETIC PEPTIDE

<400> SEQUENCE: 94

Gly Gly Thr Tyr Ser Cys His Phe Gly Pro Leu Thr Trp Val Cys Lys
1               5                   10                  15

Pro Gln Gly Gly Ser Ser Lys
            20

<210> SEQ ID NO 95
<211> LENGTH: 46
<212> TYPE: PRT
<213> ORGANISM: Artificial Sequence
<220> FEATURE:
<223> OTHER INFORMATION: EPO-MIMETIC PEPTIDE

<400> SEQUENCE: 95

Gly Gly Thr Tyr Ser Cys His Phe Gly Pro Leu Thr Trp Val Cys Lys
1               5                   10                  15

Pro Gln Gly Gly Ser Ser Lys Gly Gly Thr Tyr Ser Cys His Phe Gly
            20                  25                  30

Pro Leu Thr Trp Val Cys Lys Pro Gln Gly Gly Ser Ser Lys
        35                  40                  45

<210> SEQ ID NO 96
<211> LENGTH: 23
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (23)..(23)
<223> OTHER INFORMATION: Position 23, amino acid linker to an identical
      sequence

<400> SEQUENCE: 96

Gly Gly Thr Tyr Ser Cys His Phe Gly Pro Leu Thr Trp Val Cys Lys
1               5                   10                  15

Pro Gln Gly Gly Ser Ser Lys
            20
```

```
<210> SEQ ID NO 97
<211> LENGTH: 22
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (22)..(22)
<223> OTHER INFORMATION: Position 22 linked through epsilon amine to
      lysyl, which is linked to a separate identical sequence through
      that sequence's alpha amine

<400> SEQUENCE: 97

Gly Gly Thr Tyr Ser Cys His Phe Gly Pro Leu Thr Trp Val Cys Lys
 1               5                  10                  15

Pro Gln Gly Gly Ser Ser
            20

<210> SEQ ID NO 98
<211> LENGTH: 23
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (23)..(23)
<223> OTHER INFORMATION: At position 23 biotin linked to the sidechain
      through a linker

<400> SEQUENCE: 98

Gly Gly Thr Tyr Ser Cys His Phe Gly Pro Leu Thr Trp Val Cys Lys
 1               5                  10                  15

Pro Gln Gly Gly Ser Ser Lys
            20

<210> SEQ ID NO 99
<211> LENGTH: 5
<212> TYPE: PRT
<213> ORGANISM: Artificial Sequence
<220> FEATURE:
<223> OTHER INFORMATION: G-CSF-MIMETIC PEPTIDE
<220> FEATURE:
<221> NAME/KEY: misc_feature
<222> LOCATION: (4)..(4)
<223> OTHER INFORMATION: At position 4 disulfide bond to residue 4 of a
      separate identical sequence

<400> SEQUENCE: 99

Glu Glu Asp Cys Lys
 1               5

<210> SEQ ID NO 100
<211> LENGTH: 5
<212> TYPE: PRT
<213> ORGANISM: Artificial Sequence
<220> FEATURE:
<223> OTHER INFORMATION: G-CSF-MIMETIC PEPTIDE
<220> FEATURE:
<221> NAME/KEY: misc_feature
<222> LOCATION: (4)..(4)
<223> OTHER INFORMATION: At position 4, Xaa is an isoteric ethylene
      spacer linked to a separate identical sequence

<400> SEQUENCE: 100

Glu Glu Asp Xaa Lys
 1               5
```

```
<210> SEQ ID NO 101
<211> LENGTH: 6
<212> TYPE: PRT
<213> ORGANISM: Artificial Sequence
<220> FEATURE:
<223> OTHER INFORMATION: G-CSF-MIMETIC PEPTIDE
<220> FEATURE:
<221> NAME/KEY: misc_feature
<222> LOCATION: (1)..(1)
<223> OTHER INFORMATION: Position 1, Xaa is a pyroglutamic acid residue
<220> FEATURE:
<221> NAME/KEY: misc_feature
<222> LOCATION: (5)..(5)
<223> OTHER INFORMATION: Position 5, Xaa is an isoteric ethylene spacer
      linked to a separate identical sequence.

<400> SEQUENCE: 101

Xaa Gly Glu Asp Xaa Lys
1               5

<210> SEQ ID NO 102
<211> LENGTH: 5
<212> TYPE: PRT
<213> ORGANISM: Artificial Sequence
<220> FEATURE:
<223> OTHER INFORMATION: G-CSF-MIMETIC PEPTIDE
<220> FEATURE:
<221> NAME/KEY: misc_feature
<222> LOCATION: (1)..(1)
<223> OTHER INFORMATION: Position 1, Xaa is a picolinic acid residue
<220> FEATURE:
<221> NAME/KEY: misc_feature
<222> LOCATION: (4)..(4)
<223> OTHER INFORMATION: Position 4, Xaa is an isoteric ethylene spacer
      linked to a separate identical sequence.

<400> SEQUENCE: 102

Xaa Ser Asp Xaa Lys
1               5

<210> SEQ ID NO 103
<211> LENGTH: 5
<212> TYPE: PRT
<213> ORGANISM: Artificial Sequence
<220> FEATURE:
<223> OTHER INFORMATION: G-CSF-MIMETIC PEPTIDE
<220> FEATURE:
<221> NAME/KEY: misc_feature
<222> LOCATION: (5)..(5)
<223> OTHER INFORMATION: At position 5, amino acid linker to an
      identical sequence

<400> SEQUENCE: 103

Glu Glu Asp Cys Lys
1               5

<210> SEQ ID NO 104
<211> LENGTH: 5
<212> TYPE: PRT
<213> ORGANISM: Artificial Sequence
<220> FEATURE:
<223> OTHER INFORMATION: G-CSF-MIMETIC PEPTIDE
<220> FEATURE:
<221> NAME/KEY: misc_feature
<222> LOCATION: (5)..(5)
<223> OTHER INFORMATION: At position 5, amino acid linker to an
      identical sequence
<220> FEATURE:
<221> NAME/KEY: misc_feature
<222> LOCATION: (4)..(4)
<223> OTHER INFORMATION: Xaa = any amino acid
```

```
<400> SEQUENCE: 104

Glu Glu Asp Xaa Lys
1               5

<210> SEQ ID NO 105
<211> LENGTH: 6
<212> TYPE: PRT
<213> ORGANISM: Artificial Sequence
<220> FEATURE:
<223> OTHER INFORMATION: ANTIVIRAL (HBV)

<400> SEQUENCE: 105

Leu Leu Gly Arg Met Lys
1               5

<210> SEQ ID NO 106
<211> LENGTH: 11
<212> TYPE: PRT
<213> ORGANISM: Artificial Sequence
<220> FEATURE:
<223> OTHER INFORMATION: TNF ANTAGONIST PEPTIDE

<400> SEQUENCE: 106

Tyr Cys Phe Thr Ala Ser Glu Asn His Cys Tyr
1               5                   10

<210> SEQ ID NO 107
<211> LENGTH: 11
<212> TYPE: PRT
<213> ORGANISM: Artificial Sequence
<220> FEATURE:
<223> OTHER INFORMATION: TNF ANTAGONIST PEPTIDE

<400> SEQUENCE: 107

Tyr Cys Phe Thr Asn Ser Glu Asn His Cys Tyr
1               5                   10

<210> SEQ ID NO 108
<211> LENGTH: 11
<212> TYPE: PRT
<213> ORGANISM: Artificial Sequence
<220> FEATURE:
<223> OTHER INFORMATION: TNF ANTAGONIST PEPTIDE

<400> SEQUENCE: 108

Tyr Cys Phe Thr Arg Ser Glu Asn His Cys Tyr
1               5                   10

<210> SEQ ID NO 109
<211> LENGTH: 9
<212> TYPE: PRT
<213> ORGANISM: Artificial Sequence
<220> FEATURE:
<223> OTHER INFORMATION: TNF ANTAGONIST PEPTIDE

<400> SEQUENCE: 109

Phe Cys Ala Ser Glu Asn His Cys Tyr
1               5

<210> SEQ ID NO 110
<211> LENGTH: 9
<212> TYPE: PRT
<213> ORGANISM: Artificial Sequence
<220> FEATURE:
<223> OTHER INFORMATION: TNF ANTAGONIST PEPTIDE

<400> SEQUENCE: 110
```

```
Tyr Cys Ala Ser Glu Asn His Cys Tyr
1               5
```

<210> SEQ ID NO 111
<211> LENGTH: 9
<212> TYPE: PRT
<213> ORGANISM: Artificial Sequence
<220> FEATURE:
<223> OTHER INFORMATION: TNF ANTAGONIST PEPTIDE

<400> SEQUENCE: 111

```
Phe Cys Asn Ser Glu Asn His Cys Tyr
1               5
```

<210> SEQ ID NO 112
<211> LENGTH: 9
<212> TYPE: PRT
<213> ORGANISM: Artificial Sequence
<220> FEATURE:
<223> OTHER INFORMATION: TNF ANTAGONIST PEPTIDE

<400> SEQUENCE: 112

Phe Cys Asn Ser Glu Asn Arg Cys Tyr
1 5

<210> SEQ ID NO 113
<211> LENGTH: 10
<212> TYPE: PRT
<213> ORGANISM: Artificial Sequence
<220> FEATURE:
<223> OTHER INFORMATION: TNF ANTAGONIST PEPTIDE

<400> SEQUENCE: 113

Phe Cys Asn Ser Val Glu Asn Arg Cys Tyr
1 5 10

<210> SEQ ID NO 114
<211> LENGTH: 11
<212> TYPE: PRT
<213> ORGANISM: Artificial Sequence
<220> FEATURE:
<223> OTHER INFORMATION: TNF ANTAGONIST PEPTIDE

<400> SEQUENCE: 114

Tyr Cys Ser Gln Ser Val Ser Asn Asp Cys Phe
1 5 10

<210> SEQ ID NO 115
<211> LENGTH: 9
<212> TYPE: PRT
<213> ORGANISM: Artificial Sequence
<220> FEATURE:
<223> OTHER INFORMATION: TNF ANTAGONIST PEPTIDE

<400> SEQUENCE: 115

Phe Cys Val Ser Asn Asp Arg Cys Tyr
1 5

<210> SEQ ID NO 116
<211> LENGTH: 11
<212> TYPE: PRT
<213> ORGANISM: Artificial Sequence
<220> FEATURE:
<223> OTHER INFORMATION: TNF ANTAGONIST PEPTIDE

<400> SEQUENCE: 116

-continued

Tyr Cys Arg Lys Glu Leu Gly Gln Val Cys Tyr
1 5 10

<210> SEQ ID NO 117
<211> LENGTH: 9
<212> TYPE: PRT
<213> ORGANISM: Artificial Sequence
<220> FEATURE:
<223> OTHER INFORMATION: TNF ANTAGONIST PEPTIDE

<400> SEQUENCE: 117

Tyr Cys Lys Glu Pro Gly Gln Cys Tyr
1 5

<210> SEQ ID NO 118
<211> LENGTH: 9
<212> TYPE: PRT
<213> ORGANISM: Artificial Sequence
<220> FEATURE:
<223> OTHER INFORMATION: TNF ANTAGONIST PEPTIDE

<400> SEQUENCE: 118

Tyr Cys Arg Lys Glu Met Gly Cys Tyr
1 5

<210> SEQ ID NO 119
<211> LENGTH: 9
<212> TYPE: PRT
<213> ORGANISM: Artificial Sequence
<220> FEATURE:
<223> OTHER INFORMATION: TNF ANTAGONIST PEPTIDE

<400> SEQUENCE: 119

Phe Cys Arg Lys Glu Met Gly Cys Tyr
1 5

<210> SEQ ID NO 120
<211> LENGTH: 9
<212> TYPE: PRT
<213> ORGANISM: Artificial Sequence
<220> FEATURE:
<223> OTHER INFORMATION: TNF ANTAGONIST PEPTIDE

<400> SEQUENCE: 120

Tyr Cys Trp Ser Gln Asn Leu Cys Tyr
1 5

<210> SEQ ID NO 121
<211> LENGTH: 10
<212> TYPE: PRT
<213> ORGANISM: Artificial Sequence
<220> FEATURE:
<223> OTHER INFORMATION: TNF ANTAGONIST PEPTIDE

<400> SEQUENCE: 121

Tyr Cys Glu Leu Ser Gln Tyr Leu Cys Tyr
1 5 10

<210> SEQ ID NO 122
<211> LENGTH: 9
<212> TYPE: PRT
<213> ORGANISM: Artificial Sequence
<220> FEATURE:
<223> OTHER INFORMATION: TNF ANTAGONIST PEPTIDE

<400> SEQUENCE: 122

Tyr Cys Trp Ser Gln Asn Tyr Cys Tyr

```
1               5
```

<210> SEQ ID NO 123
<211> LENGTH: 9
<212> TYPE: PRT
<213> ORGANISM: Artificial Sequence
<220> FEATURE:
<223> OTHER INFORMATION: TNF ANTAGONIST PEPTIDE

<400> SEQUENCE: 123

```
Tyr Cys Trp Ser Gln Tyr Leu Cys Tyr
1               5
```

<210> SEQ ID NO 124
<211> LENGTH: 10
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (1)..(1)
<223> OTHER INFORMATION: Xaa (Pos1) can be C, A, a-amino-g-bromobutyric
    acid or Hoc.
<220> FEATURE:
<221> NAME/KEY: misc_feature
<222> LOCATION: (2)..(2)
<223> OTHER INFORMATION: Xaa can be R, H, L or W.
<220> FEATURE:
<221> NAME/KEY: misc_feature
<222> LOCATION: (3)..(3)
<223> OTHER INFORMATION: Xaa can be M, F or I.
<220> FEATURE:
<221> NAME/KEY: misc_feature
<222> LOCATION: (6)..(6)
<223> OTHER INFORMATION: Xaa can be any one of the 20 L-amino acids or
    the stereoisomeric D-amino acids.
<220> FEATURE:
<221> NAME/KEY: misc_feature
<222> LOCATION: (9)..(9)
<223> OTHER INFORMATION: Xaa can be D, E, I, L or V.
<220> FEATURE:
<221> NAME/KEY: misc_feature
<222> LOCATION: (10)..(10)
<223> OTHER INFORMATION: Xaa can be a-amino-g-bromobutyric acid or Hoc,
    provided that either Xaa (Pos1) or Xaa (Pos10) is C or Hoc.

<400> SEQUENCE: 124

```
Xaa Xaa Xaa Gly Pro Xaa Thr Trp Xaa Xaa
1               5                   10
```

<210> SEQ ID NO 125
<211> LENGTH: 15
<212> TYPE: PRT
<213> ORGANISM: Artificial Sequence
<220> FEATURE:
<223> OTHER INFORMATION: CTLA4-MIMETIC

<400> SEQUENCE: 125

```
Gly Phe Val Cys Ser Gly Ile Phe Ala Val Gly Val Gly Arg Cys
1               5                   10                  15
```

<210> SEQ ID NO 126
<211> LENGTH: 15
<212> TYPE: PRT
<213> ORGANISM: Artificial Sequence
<220> FEATURE:
<223> OTHER INFORMATION: CTLA4-MIMETIC

<400> SEQUENCE: 126

```
Ala Pro Gly Val Arg Leu Gly Cys Ala Val Leu Gly Arg Tyr Cys
```

-continued

```
1               5                  10                 15
```

<210> SEQ ID NO 127
<211> LENGTH: 27
<212> TYPE: PRT
<213> ORGANISM: Artificial Sequence
<220> FEATURE:
<223> OTHER INFORMATION: C3B ANTAGONIST

<400> SEQUENCE: 127

```
Ile Cys Val Val Gln Asp Trp Gly His His Arg Cys Thr Ala Gly His
1               5                  10                 15

Met Ala Asn Leu Thr Ser His Ala Ser Ala Ile
            20                  25
```

<210> SEQ ID NO 128
<211> LENGTH: 13
<212> TYPE: PRT
<213> ORGANISM: Artificial Sequence
<220> FEATURE:
<223> OTHER INFORMATION: C3B ANTAGONIST

<400> SEQUENCE: 128

```
Ile Cys Val Val Gln Asp Trp Gly His His Arg Cys Thr
1               5                  10
```

<210> SEQ ID NO 129
<211> LENGTH: 11
<212> TYPE: PRT
<213> ORGANISM: Artificial Sequence
<220> FEATURE:
<223> OTHER INFORMATION: C3B ANTAGONIST

<400> SEQUENCE: 129

```
Cys Val Val Gln Asp Trp Gly His His Ala Cys
1               5                  10
```

<210> SEQ ID NO 130
<211> LENGTH: 6
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 130

```
Thr Phe Ser Asp Leu Trp
1               5
```

<210> SEQ ID NO 131
<211> LENGTH: 12
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 131

```
Gln Glu Thr Phe Ser Asp Leu Trp Lys Leu Leu Pro
1               5                  10
```

<210> SEQ ID NO 132
<211> LENGTH: 12
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 132

```
Gln Pro Thr Phe Ser Asp Leu Trp Lys Leu Leu Pro
1               5                   10

<210> SEQ ID NO 133
<211> LENGTH: 12
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 133

Gln Glu Thr Phe Ser Asp Tyr Trp Lys Leu Leu Pro
1               5                   10

<210> SEQ ID NO 134
<211> LENGTH: 12
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 134

Gln Pro Thr Phe Ser Asp Tyr Trp Lys Leu Leu Pro
1               5                   10

<210> SEQ ID NO 135
<211> LENGTH: 12
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 135

Met Pro Arg Phe Met Asp Tyr Trp Glu Gly Leu Asn
1               5                   10

<210> SEQ ID NO 136
<211> LENGTH: 12
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 136

Val Gln Asn Phe Ile Asp Tyr Trp Thr Gln Gln Phe
1               5                   10

<210> SEQ ID NO 137
<211> LENGTH: 12
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 137

Thr Gly Pro Ala Phe Thr His Tyr Trp Ala Thr Phe
1               5                   10

<210> SEQ ID NO 138
<211> LENGTH: 15
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 138
```

```
Ile Asp Arg Ala Pro Thr Phe Arg Asp His Trp Phe Ala Leu Val
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 139

Pro Arg Pro Ala Leu Val Phe Ala Asp Tyr Trp Glu Thr Leu Tyr
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 140

Pro Ala Phe Ser Arg Phe Trp Ser Asp Leu Ser Ala Gly Ala His
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 141

Pro Ala Phe Ser Arg Phe Trp Ser Lys Leu Ser Ala Gly Ala His
1               5                   10                  15

<210> SEQ ID NO 142
<211> LENGTH: 10
<212> TYPE: PRT
<213> ORGANISM: Artificial Sequence
<220> FEATURE:
<223> OTHER INFORMATION: MDM/HDM ANTAGONIST PEPTIDE
<220> FEATURE:
<221> NAME/KEY: misc_feature
<222> LOCATION: (2, 4, 8 )..(9)
<223> OTHER INFORMATION: Xaa = any amino acid

<400> SEQUENCE: 142

Pro Xaa Phe Xaa Asp Tyr Trp Xaa Xaa Leu
1               5                   10

<210> SEQ ID NO 143
<211> LENGTH: 12
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 143

Gln Glu Thr Phe Ser Asp Leu Trp Lys Leu Leu Pro
1               5                   10

<210> SEQ ID NO 144
<211> LENGTH: 12
<212> TYPE: PRT
<213> ORGANISM: Artificial Sequence
<220> FEATURE:
<223> OTHER INFORMATION: MDM/HDM ANTAGONIST PEPTIDE
```

```
<400> SEQUENCE: 144

Gln Pro Thr Phe Ser Asp Leu Trp Lys Leu Leu Pro
1               5                   10

<210> SEQ ID NO 145
<211> LENGTH: 12
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 145

Gln Glu Thr Phe Ser Asp Tyr Trp Lys Leu Leu Pro
1               5                   10

<210> SEQ ID NO 146
<211> LENGTH: 12
<212> TYPE: PRT
<213> ORGANISM: Artificial Sequence
<220> FEATURE:
<223> OTHER INFORMATION: MDM/HDM ANTAGONIST PEPTIDE

<400> SEQUENCE: 146

Gln Pro Thr Phe Ser Asp Tyr Trp Lys Leu Leu Pro
1               5                   10

<210> SEQ ID NO 147
<211> LENGTH: 12
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 147

Asp Ile Thr Trp Asp Gln Leu Trp Asp Leu Met Lys
1               5                   10

<210> SEQ ID NO 148
<211> LENGTH: 12
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 148

Asp Ile Thr Trp Asp Glu Leu Trp Lys Ile Met Asn
1               5                   10

<210> SEQ ID NO 149
<211> LENGTH: 12
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 149

Asp Tyr Thr Trp Phe Glu Leu Trp Asp Met Met Gln
1               5                   10

<210> SEQ ID NO 150
<211> LENGTH: 12
<212> TYPE: PRT
<213> ORGANISM: Artificial Sequence
<220> FEATURE:
<223> OTHER INFORMATION: SELECTIN ANTAGONIST PEPTIDE
```

```
<400> SEQUENCE: 150

Gln Ile Thr Trp Ala Gln Leu Trp Asn Met Met Lys
1               5                   10

<210> SEQ ID NO 151
<211> LENGTH: 12
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 151

Asp Met Thr Trp His Asp Leu Trp Thr Leu Met Ser
1               5                   10

<210> SEQ ID NO 152
<211> LENGTH: 12
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 152

Asp Tyr Ser Trp His Asp Leu Trp Glu Met Met Ser
1               5                   10

<210> SEQ ID NO 153
<211> LENGTH: 12
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 153

Glu Ile Thr Trp Asp Gln Leu Trp Glu Val Met Asn
1               5                   10

<210> SEQ ID NO 154
<211> LENGTH: 12
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 154

His Val Ser Trp Glu Gln Leu Trp Asp Ile Met Asn
1               5                   10

<210> SEQ ID NO 155
<211> LENGTH: 12
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 155

His Ile Thr Trp Asp Gln Leu Trp Arg Ile Met Thr
1               5                   10

<210> SEQ ID NO 156
<211> LENGTH: 13
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 156
```

```
Arg Asn Met Ser Trp Leu Glu Leu Trp Glu His Met Lys
1               5                   10
```

<210> SEQ ID NO 157
<211> LENGTH: 18
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 157

```
Ala Glu Trp Thr Trp Asp Gln Leu Trp His Val Met Asn Pro Ala Glu
1               5                   10                  15

Ser Gln
```

<210> SEQ ID NO 158
<211> LENGTH: 14
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 158

```
His Arg Ala Glu Trp Leu Ala Leu Trp Glu Gln Met Ser Pro
1               5                   10
```

<210> SEQ ID NO 159
<211> LENGTH: 14
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 159

```
Lys Lys Glu Asp Trp Leu Ala Leu Trp Arg Ile Met Ser Val
1               5                   10
```

<210> SEQ ID NO 160
<211> LENGTH: 11
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 160

```
Ile Thr Trp Asp Gln Leu Trp Asp Leu Met Lys
1               5                   10
```

<210> SEQ ID NO 161
<211> LENGTH: 12
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 161

```
Asp Ile Thr Trp Asp Gln Leu Trp Asp Leu Met Lys
1               5                   10
```

<210> SEQ ID NO 162
<211> LENGTH: 12
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 162

Asp Ile Thr Trp Asp Gln Leu Trp Asp Leu Met Lys
1               5                   10

<210> SEQ ID NO 163
<211> LENGTH: 12
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 163

Asp Ile Thr Trp Asp Gln Leu Trp Asp Leu Met Lys
1               5                   10

<210> SEQ ID NO 164
<211> LENGTH: 13
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 164

Ser Cys Val Lys Trp Gly Lys Lys Glu Phe Cys Gly Ser
1               5                   10

<210> SEQ ID NO 165
<211> LENGTH: 12
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 165

Ser Cys Trp Lys Tyr Trp Gly Lys Glu Cys Gly Ser
1               5                   10

<210> SEQ ID NO 166
<211> LENGTH: 13
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 166

Ser Cys Tyr Glu Trp Gly Lys Leu Arg Trp Cys Gly Ser
1               5                   10

<210> SEQ ID NO 167
<211> LENGTH: 13
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 167

Ser Cys Leu Arg Trp Gly Lys Trp Ser Asn Cys Gly Ser
1               5                   10

<210> SEQ ID NO 168
<211> LENGTH: 13
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 168

```
Ser Cys Trp Arg Trp Gly Lys Tyr Gln Ile Cys Gly Ser
1               5                   10

<210> SEQ ID NO 169
<211> LENGTH: 13
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 169

Ser Cys Val Ser Trp Gly Ala Leu Lys Leu Cys Gly Ser
1               5                   10

<210> SEQ ID NO 170
<211> LENGTH: 13
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 170

Ser Cys Ile Arg Trp Gly Gln Asn Thr Phe Cys Gly Ser
1               5                   10

<210> SEQ ID NO 171
<211> LENGTH: 13
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 171

Ser Cys Trp Gln Trp Gly Asn Leu Lys Ile Cys Gly Ser
1               5                   10

<210> SEQ ID NO 172
<211> LENGTH: 13
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 172

Ser Cys Val Arg Trp Gly Gln Leu Ser Ile Cys Gly Ser
1               5                   10

<210> SEQ ID NO 173
<211> LENGTH: 21
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 173

Leu Lys Lys Phe Asn Ala Arg Arg Lys Leu Lys Gly Ala Ile Leu Thr
1               5                   10                  15

Thr Met Leu Ala Lys
            20

<210> SEQ ID NO 174
<211> LENGTH: 18
<212> TYPE: PRT
<213> ORGANISM: Artificial Sequence
<220> FEATURE:
<223> OTHER INFORMATION: CALMODULIN ANTAGONIST PEPTIDE
```

```
<400> SEQUENCE: 174

Arg Arg Trp Lys Lys Asn Phe Ile Ala Val Ser Ala Ala Asn Arg Phe
1               5                   10                  15

Lys Lys

<210> SEQ ID NO 175
<211> LENGTH: 18
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 175

Arg Lys Trp Gln Lys Thr Gly His Ala Val Arg Ala Ile Gly Arg Leu
1               5                   10                  15

Ser Ser

<210> SEQ ID NO 176
<211> LENGTH: 14
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 176

Ile Asn Leu Lys Ala Leu Ala Ala Leu Ala Lys Lys Ile Leu
1               5                   10

<210> SEQ ID NO 177
<211> LENGTH: 18
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 177

Lys Ile Trp Ser Ile Leu Ala Pro Leu Gly Thr Thr Leu Val Lys Leu
1               5                   10                  15

Val Ala

<210> SEQ ID NO 178
<211> LENGTH: 14
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 178

Leu Lys Lys Leu Leu Lys Leu Leu Lys Lys Leu Leu Lys Leu
1               5                   10

<210> SEQ ID NO 179
<211> LENGTH: 18
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 179

Leu Lys Trp Lys Lys Leu Leu Lys Leu Leu Lys Lys Leu Leu Lys Lys
1               5                   10                  15

Leu Leu
```

```
<210> SEQ ID NO 180
<211> LENGTH: 17
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 180

Ala Glu Trp Pro Ser Leu Thr Glu Ile Lys Thr Leu Ser His Phe Ser
1               5                   10                  15
Val

<210> SEQ ID NO 181
<211> LENGTH: 17
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 181

Ala Glu Trp Pro Ser Pro Thr Arg Val Ile Ser Thr Thr Tyr Phe Gly
1               5                   10                  15
Ser

<210> SEQ ID NO 182
<211> LENGTH: 17
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 182

Ala Glu Leu Ala His Trp Pro Pro Val Lys Thr Val Leu Arg Ser Phe
1               5                   10                  15
Thr

<210> SEQ ID NO 183
<211> LENGTH: 17
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 183

Ala Glu Gly Ser Trp Leu Gln Leu Leu Asn Leu Met Lys Gln Met Asn
1               5                   10                  15
Asn

<210> SEQ ID NO 184
<211> LENGTH: 10
<212> TYPE: PRT
<213> ORGANISM: Artificial Sequence
<220> FEATURE:
<223> OTHER INFORMATION: CALMODULIN ANTAGONIST PEPTIDE

<400> SEQUENCE: 184

Ala Glu Trp Pro Ser Leu Thr Glu Ile Lys
1               5                   10

<210> SEQ ID NO 185
<211> LENGTH: 27
<212> TYPE: PRT
<213> ORGANISM: Artificial Sequence
<220> FEATURE:
```

<223> OTHER INFORMATION: VINCULIN-BINDING

<400> SEQUENCE: 185

Ser Thr Gly Gly Phe Asp Asp Val Tyr Asp Trp Ala Arg Gly Val Ser
1               5                   10                  15

Ser Ala Leu Thr Thr Thr Leu Val Ala Thr Arg
            20                  25

<210> SEQ ID NO 186
<211> LENGTH: 27
<212> TYPE: PRT
<213> ORGANISM: Artificial Sequence
<220> FEATURE:
<223> OTHER INFORMATION: VINCULIN-BINDING

<400> SEQUENCE: 186

Ser Thr Gly Gly Phe Asp Asp Val Tyr Asp Trp Ala Arg Arg Val Ser
1               5                   10                  15

Ser Ala Leu Thr Thr Thr Leu Val Ala Thr Arg
            20                  25

<210> SEQ ID NO 187
<211> LENGTH: 30
<212> TYPE: PRT
<213> ORGANISM: Artificial Sequence
<220> FEATURE:
<223> OTHER INFORMATION: VINCULIN-BINDING

<400> SEQUENCE: 187

Ser Arg Gly Val Asn Phe Ser Glu Trp Leu Tyr Asp Met Ser Ala Ala
1               5                   10                  15

Met Lys Glu Ala Ser Asn Val Phe Pro Ser Arg Arg Ser Arg
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: VINCULIN-BINDING

<400> SEQUENCE: 188

Ser Ser Gln Asn Trp Asp Met Glu Ala Gly Val Glu Asp Leu Thr Ala
1               5                   10                  15

Ala Met Leu Gly Leu Leu Ser Thr Ile His Ser Ser Ser Arg
            20                  25                  30

<210> SEQ ID NO 189
<211> LENGTH: 31
<212> TYPE: PRT
<213> ORGANISM: Artificial Sequence
<220> FEATURE:
<223> OTHER INFORMATION: VINCULIN-BINDING

<400> SEQUENCE: 189

Ser Ser Pro Ser Leu Tyr Thr Gln Phe Leu Val Asn Tyr Glu Ser Ala
1               5                   10                  15

Ala Thr Arg Ile Gln Asp Leu Leu Ile Ala Ser Arg Pro Ser Arg
            20                  25                  30

<210> SEQ ID NO 190
<211> LENGTH: 31
<212> TYPE: PRT
<213> ORGANISM: Artificial Sequence

```
<220> FEATURE:
<223> OTHER INFORMATION: VINCULIN-BINDING

<400> SEQUENCE: 190

Ser Ser Thr Gly Trp Val Asp Leu Leu Gly Ala Leu Gln Arg Ala Ala
1               5                   10                  15

Asp Ala Thr Arg Thr Ser Ile Pro Pro Ser Leu Gln Asn Ser Arg
            20                  25                  30

<210> SEQ ID NO 191
<211> LENGTH: 18
<212> TYPE: PRT
<213> ORGANISM: Artificial Sequence
<220> FEATURE:
<223> OTHER INFORMATION: VINCULIN-BINDING

<400> SEQUENCE: 191

Asp Val Tyr Thr Lys Lys Glu Leu Ile Glu Cys Ala Arg Arg Val Ser
1               5                   10                  15

Glu Lys

<210> SEQ ID NO 192
<211> LENGTH: 22
<212> TYPE: PRT
<213> ORGANISM: Artificial Sequence
<220> FEATURE:
<223> OTHER INFORMATION: C4BP-BINDING

<400> SEQUENCE: 192

Glu Lys Gly Ser Tyr Tyr Pro Gly Ser Gly Ile Ala Gln Phe His Ile
1               5                   10                  15

Asp Tyr Asn Asn Val Ser
            20

<210> SEQ ID NO 193
<211> LENGTH: 22
<212> TYPE: PRT
<213> ORGANISM: Artificial Sequence
<220> FEATURE:
<223> OTHER INFORMATION: C4BP-BINDING

<400> SEQUENCE: 193

Ser Gly Ile Ala Gln Phe His Ile Asp Tyr Asn Asn Val Ser Ser Ala
1               5                   10                  15

Glu Gly Trp His Val Asn
            20

<210> SEQ ID NO 194
<211> LENGTH: 34
<212> TYPE: PRT
<213> ORGANISM: Artificial Sequence
<220> FEATURE:
<223> OTHER INFORMATION: C4BP-BINDING

<400> SEQUENCE: 194

Leu Val Thr Val Glu Lys Gly Ser Tyr Tyr Pro Gly Ser Gly Ile Ala
1               5                   10                  15

Gln Phe His Ile Asp Tyr Asn Asn Val Ser Ser Ala Glu Gly Trp His
            20                  25                  30

Val Asn

<210> SEQ ID NO 195
<211> LENGTH: 14
```

<212> TYPE: PRT
<213> ORGANISM: Artificial Sequence
<220> FEATURE:
<223> OTHER INFORMATION: C4BP-BINDING

<400> SEQUENCE: 195

Ser Gly Ile Ala Gln Phe His Ile Asp Tyr Asn Asn Val Ser
1               5                   10

<210> SEQ ID NO 196
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 196

Ala Glu Pro Met Pro His Ser Leu Asn Phe Ser Gln Tyr Leu Trp Tyr
1               5                   10                  15

Thr

<210> SEQ ID NO 197
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 197

Ala Glu His Thr Tyr Ser Ser Leu Trp Asp Thr Tyr Ser Pro Leu Ala
1               5                   10                  15

Phe

<210> SEQ ID NO 198
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 198

Ala Glu Leu Asp Leu Trp Met Arg His Tyr Pro Leu Ser Phe Ser Asn
1               5                   10                  15

Arg

<210> SEQ ID NO 199
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 199

Ala Glu Ser Ser Leu Trp Thr Arg Tyr Ala Trp Pro Ser Met Pro Ser
1               5                   10                  15

Tyr

<210> SEQ ID NO 200
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 200

```
Ala Glu Trp His Pro Gly Leu Ser Phe Gly Ser Tyr Leu Trp Ser Lys
1               5                   10                  15

Thr

<210> SEQ ID NO 201
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 201

Ala Glu Pro Ala Leu Leu Asn Trp Ser Phe Phe Asn Pro Gly Leu
1               5                   10                  15

His

<210> SEQ ID NO 202
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 202

Ala Glu Trp Ser Phe Tyr Asn Leu His Leu Pro Glu Pro Gln Thr Ile
1               5                   10                  15

Phe

<210> SEQ ID NO 203
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 203

Ala Glu Pro Leu Asp Leu Trp Ser Leu Tyr Ser Leu Pro Pro Leu Ala
1               5                   10                  15

Met

<210> SEQ ID NO 204
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 204

Ala Glu Pro Thr Leu Trp Gln Leu Tyr Gln Phe Pro Leu Arg Leu Ser
1               5                   10                  15

Gly

<210> SEQ ID NO 205
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 205

Ala Glu Ile Ser Phe Ser Glu Leu Met Trp Leu Arg Ser Thr Pro Ala
1               5                   10                  15
```

Phe

<210> SEQ ID NO 206
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 206

Ala Glu Leu Ser Glu Ala Asp Leu Trp Thr Thr Trp Phe Gly Met Gly
1               5                   10                  15

Ser

<210> SEQ ID NO 207
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 207

Ala Glu Ser Ser Leu Trp Arg Ile Phe Ser Pro Ser Ala Leu Met Met
1               5                   10                  15

Ser

<210> SEQ ID NO 208
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 208

Ala Glu Ser Leu Pro Thr Leu Thr Ser Ile Leu Trp Gly Lys Glu Ser
1               5                   10                  15

Val

<210> SEQ ID NO 209
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 209

Ala Glu Thr Leu Phe Met Asp Leu Trp His Asp Lys His Ile Leu Leu
1               5                   10                  15

Thr

<210> SEQ ID NO 210
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 210

Ala Glu Ile Leu Asn Phe Pro Leu Trp His Glu Pro Leu Trp Ser Thr
1               5                   10                  15

Glu

<210> SEQ ID NO 211

```
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 211

Ala Glu Ser Gln Thr Gly Thr Leu Asn Thr Leu Phe Trp Asn Thr Leu
1               5                   10                  15

Arg

<210> SEQ ID NO 212
<211> LENGTH: 9
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Xaa is V, L, I, E, P, G, Y, M, T or D.
<220> FEATURE:
<221> NAME/KEY: misc_feature
<222> LOCATION: (2)..(2)
<223> OTHER INFORMATION: Xaa is Y, W or F.
<220> FEATURE:
<221> NAME/KEY: misc_feature
<222> LOCATION: (3)..(3)
<223> OTHER INFORMATION: Xaa is F, W or Y.
<220> FEATURE:
<221> NAME/KEY: misc_feature
<222> LOCATION: (5)..(5)
<223> OTHER INFORMATION: Xaa is P or Azetidine.
<220> FEATURE:
<221> NAME/KEY: misc_feature
<222> LOCATION: (7)..(7)
<223> OTHER INFORMATION: Xaa is S, A, V or L.
<220> FEATURE:
<221> NAME/KEY: misc_feature
<222> LOCATION: (8)..(8)
<223> OTHER INFORMATION: Xaa is V, L, I or E.
<220> FEATURE:
<221> NAME/KEY: misc_feature
<222> LOCATION: (9)..(9)
<223> OTHER INFORMATION: Xaa is Q or P.

<400> SEQUENCE: 212

Xaa Xaa Xaa Gln Xaa Tyr Xaa Xaa Xaa
1               5

<210> SEQ ID NO 213
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 213

Thr Ala Asn Val Ser Ser Phe Glu Trp Thr Pro Tyr Tyr Trp Gln Pro
1               5                   10                  15

Tyr Ala Leu Pro Leu
            20

<210> SEQ ID NO 214
<211> LENGTH: 18
<212> TYPE: PRT
<213> ORGANISM: Artificial Sequence
<220> FEATURE:
<223> OTHER INFORMATION: IL-1 ANTAGONIST PEPTIDE

<400> SEQUENCE: 214
```

```
Ser Trp Thr Asp Tyr Gly Tyr Trp Gln Pro Tyr Ala Leu Pro Ile Ser
1               5                   10                  15

Gly Leu
```

<210> SEQ ID NO 215
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 215

```
Glu Thr Pro Phe Thr Trp Glu Glu Ser Asn Ala Tyr Tyr Trp Gln Pro
1               5                   10                  15

Tyr Ala Leu Pro Leu
            20
```

<210> SEQ ID NO 216
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 216

```
Glu Asn Thr Tyr Ser Pro Asn Trp Ala Asp Ser Met Tyr Trp Gln Pro
1               5                   10                  15

Tyr Ala Leu Pro Leu
            20
```

<210> SEQ ID NO 217
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 217

```
Ser Val Gly Glu Asp His Asn Phe Trp Thr Ser Glu Tyr Trp Gln Pro
1               5                   10                  15

Tyr Ala Leu Pro Leu
            20
```

<210> SEQ ID NO 218
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 218

```
Asp Gly Tyr Asp Arg Trp Arg Gln Ser Gly Glu Arg Tyr Trp Gln Pro
1               5                   10                  15

Tyr Ala Leu Pro Leu
            20
```

<210> SEQ ID NO 219
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 219

```
Phe Glu Trp Thr Pro Gly Tyr Trp Gln Pro Tyr
1               5                   10
```

<210> SEQ ID NO 220
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 220

```
Phe Glu Trp Thr Pro Gly Tyr Trp Gln His Tyr
1               5                   10
```

<210> SEQ ID NO 221
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa = azetidine

<400> SEQUENCE: 221

```
Phe Glu Trp Thr Pro Gly Trp Tyr Gln Xaa Tyr
1               5                   10
```

<210> SEQ ID NO 222
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, optionally acetlated at N terminus
<220> FEATURE:
<221> NAME/KEY: misc_feature
<222> LOCATION: (10)..(10)
<223> OTHER INFORMATION: Position 10, Xaa = azetidine

<400> SEQUENCE: 222

```
Phe Glu Trp Thr Pro Gly Trp Tyr Gln Xaa Tyr
1               5                   10
```

<210> SEQ ID NO 223
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (11)..(11)
<223> OTHER INFORMATION: Position 11, Xaa = azetidine

<400> SEQUENCE: 223

```
Phe Glu Trp Thr Pro Gly Trp Pro Tyr Gln Xaa Tyr
1               5                   10
```

<210> SEQ ID NO 224
<211> LENGTH: 11
<212> TYPE: PRT
<213> ORGANISM: Artificial Sequence
<220> FEATURE:
<223> OTHER INFORMATION: IL-1 ANTAGONIST PEPTIDE

```
<220> FEATURE:
<221> NAME/KEY: misc_feature
<222> LOCATION: (10)..(10)
<223> OTHER INFORMATION: Position 10, Xaa = azetidine

<400> SEQUENCE: 224

Phe Ala Trp Thr Pro Gly Tyr Trp Gln Xaa Tyr
1               5                   10

<210> SEQ ID NO 225
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa = azetidine

<400> SEQUENCE: 225

Phe Glu Trp Ala Pro Gly Tyr Trp Gln Xaa Tyr
1               5                   10

<210> SEQ ID NO 226
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa = azetidine

<400> SEQUENCE: 226

Phe Glu Trp Val Pro Gly Tyr Trp Gln Xaa Tyr
1               5                   10

<210> SEQ ID NO 227
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa = azetidine

<400> SEQUENCE: 227

Phe Glu Trp Thr Pro Gly Tyr Trp Gln Xaa Tyr
1               5                   10

<210> SEQ ID NO 228
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, optionally acetylated at N terminus
<220> FEATURE:
<221> NAME/KEY: misc_feature
<222> LOCATION: (10)..(10)
<223> OTHER INFORMATION: Position 10, Xaa = azetidine

<400> SEQUENCE: 228
```

Phe Glu Trp Thr Pro Gly Tyr Trp Gln Xaa Tyr
1               5                   10

<210> SEQ ID NO 229
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (6)..(6)
<223> OTHER INFORMATION: Position 6, Xaa products = "MeGly"
<220> FEATURE:
<221> NAME/KEY: misc_feature
<222> LOCATION: (10)..(10)
<223> OTHER INFORMATION: Position 10, Xaa = azetidine

<400> SEQUENCE: 229

Phe Glu Trp Thr Pro Xaa Trp Tyr Gln Xaa Tyr
1               5                   10

<210> SEQ ID NO 230
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (6)..(6)
<223> OTHER INFORMATION: Position 6, Xaa = MeGly
<220> FEATURE:
<221> NAME/KEY: misc_feature
<222> LOCATION: (10)..(10)
<223> OTHER INFORMATION: Position 10, Xaa = azetidine

<400> SEQUENCE: 230

Phe Glu Trp Thr Pro Xaa Trp Tyr Gln Xaa Tyr
1               5                   10

<210> SEQ ID NO 231
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 231

Phe Glu Trp Thr Pro Gly Tyr Tyr Gln Pro Tyr
1               5                   10

<210> SEQ ID NO 232
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 232

Phe Glu Trp Thr Pro Gly Trp Trp Gln Pro Tyr
1               5                   10

<210> SEQ ID NO 233
<211> LENGTH: 11
<212> TYPE: PRT
<213> ORGANISM: Artificial Sequence
<220> FEATURE:
<223> OTHER INFORMATION: IL-1 ANTAGONIST PEPTIDE

```
<400> SEQUENCE: 233

Phe Glu Trp Thr Pro Asn Tyr Trp Gln Pro Tyr
1               5                   10

<210> SEQ ID NO 234
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(5)
<223> OTHER INFORMATION: Position 5, Xaa = pipecolic acid
<220> FEATURE:
<221> NAME/KEY: misc_feature
<222> LOCATION: (10)..(10)
<223> OTHER INFORMATION: Position 10, Xaa = azetidine

<400> SEQUENCE: 234

Phe Glu Trp Thr Xaa Val Tyr Trp Gln Xaa Tyr
1               5                   10

<210> SEQ ID NO 235
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(5)
<223> OTHER INFORMATION: Position 5, Xaa = pipecolic acid
<220> FEATURE:
<221> NAME/KEY: misc_feature
<222> LOCATION: (10)..(10)
<223> OTHER INFORMATION: Position 10, Xaa = azetidine

<400> SEQUENCE: 235

Phe Glu Trp Thr Xaa Gly Tyr Trp Gln Xaa Tyr
1               5                   10

<210> SEQ ID NO 236
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (6 )..(6)
<223> OTHER INFORMATION: Position 6, Xaa = Aib
<220> FEATURE:
<221> NAME/KEY: misc_feature
<222> LOCATION: (10)..(10)
<223> OTHER INFORMATION: Position 10, Xaa = azetidine

<400> SEQUENCE: 236

Phe Glu Trp Thr Pro Xaa Tyr Trp Gln Xaa Tyr
1               5                   10

<210> SEQ ID NO 237
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5 )..(5)
<223> OTHER INFORMATION: Position 5, Xaa = MeGly
```

```
<220> FEATURE:
<221> NAME/KEY: misc_feature
<222> LOCATION: (10)..(10)
<223> OTHER INFORMATION: Position 10, Xaa = azetidine

<400> SEQUENCE: 237

Phe Glu Trp Thr Xaa Gly Tyr Trp Gln Xaa Tyr
1               5                   10

<210> SEQ ID NO 238
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (11)..(11)
<223> OTHER INFORMATION: Position 11, amino group added at C terminus

<400> SEQUENCE: 238

Phe Glu Trp Thr Pro Gly Tyr Trp Gln Pro Tyr
1               5                   10

<210> SEQ ID NO 239
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (11)..(11)
<223> OTHER INFORMATION: Position 11, amino group added at C-terminus

<400> SEQUENCE: 239

Phe Glu Trp Thr Pro Gly Tyr Trp Gln His Tyr
1               5                   10

<210> SEQ ID NO 240
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue
      Position 11 amino group added at C-terminus
<220> FEATURE:
<221> NAME/KEY: misc_feature
<222> LOCATION: (11)..(11)
<223> OTHER INFORMATION: Position 11 amino group added at C-terminus

<400> SEQUENCE: 240

Phe Glu Trp Thr Pro Gly Trp Tyr Gln Xaa Tyr
1               5                   10

<210> SEQ ID NO 241
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 optionally acetylated at N-terminus
<220> FEATURE:
<221> NAME/KEY: misc_feature
```

<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 241

Phe Glu Trp Thr Pro Gly Trp Tyr Gln Xaa Tyr
1               5                   10

<210> SEQ ID NO 242
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (8)..(8)
<223> OTHER INFORMATION: Position 8, Xaa is a phyosphotyrosyl residue
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 242

Phe Glu Trp Thr Pro Gly Trp Xaa Gln Xaa Tyr
1               5                   10

<210> SEQ ID NO 243
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 243

Phe Ala Trp Thr Pro Gly Tyr Trp Gln Xaa Tyr
1               5                   10

<210> SEQ ID NO 244
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 244

Phe Glu Trp Ala Pro Gly Tyr Trp Gln Xaa Tyr
1               5                   10

```
<210> SEQ ID NO 245
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 245

Phe Glu Trp Val Pro Gly Tyr Trp Gln Xaa Tyr
1               5                   10

<210> SEQ ID NO 246
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 246

Phe Glu Trp Thr Pro Gly Tyr Trp Gln Xaa Tyr
1               5                   10

<210> SEQ ID NO 247
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 acetylated at N-terminus
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 247

Phe Glu Trp Thr Pro Gly Tyr Trp Gln Xaa Tyr
1               5                   10

<210> SEQ ID NO 248
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (6)..(6)
<223> OTHER INFORMATION: Position 6, D amino acid residue
<220> FEATURE:
```

```
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 248

Phe Glu Trp Thr Pro Ala Trp Tyr Gln Xaa Tyr
1               5                   10

<210> SEQ ID NO 249
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (6)..(6)
<223> OTHER INFORMATION: Position 6, Xaa is a sarcosine residue
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 249

Phe Glu Trp Thr Pro Xaa Trp Tyr Gln Xaa Tyr
1               5                   10

<210> SEQ ID NO 250
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (11)..(11)
<223> OTHER INFORMATION: Position 11 amino group added at C-terminus

<400> SEQUENCE: 250

Phe Glu Trp Thr Pro Gly Tyr Tyr Gln Pro Tyr
1               5                   10

<210> SEQ ID NO 251
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (11)..(11)
<223> OTHER INFORMATION: Position 11 amino group added at C-terminus

<400> SEQUENCE: 251

Phe Glu Trp Thr Pro Gly Trp Trp Gln Pro Tyr
1               5                   10

<210> SEQ ID NO 252
<211> LENGTH: 11
<212> TYPE: PRT
<213> ORGANISM: Artificial Sequence
<220> FEATURE:
<223> OTHER INFORMATION: IL-1 ANTAGONIST PEPTIDE
```

```
<220> FEATURE:
<221> NAME/KEY: misc_feature
<222> LOCATION: (11)..(11)
<223> OTHER INFORMATION: Position 11 amino group added at C-terminus

<400> SEQUENCE: 252

Phe Glu Trp Thr Pro Asn Tyr Trp Gln Pro Tyr
1               5                   10

<210> SEQ ID NO 253
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (6)..(6)
<223> OTHER INFORMATION: Position 6, D amino acid residue
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 253

Phe Glu Trp Thr Pro Val Tyr Trp Gln Xaa Tyr
1               5                   10

<210> SEQ ID NO 254
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(5)
<223> OTHER INFORMATION: Position 5, Xaa is a pipecolic acid residue
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 254

Phe Glu Trp Thr Xaa Gly Tyr Trp Gln Xaa Tyr
1               5                   10

<210> SEQ ID NO 255
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (6)..(6)
<223> OTHER INFORMATION: Position 6, Xaa = pipecolic acid
<220> FEATURE:
<221> NAME/KEY: misc_feature
<222> LOCATION: (10)..(10)
<223> OTHER INFORMATION: Position 10, Xaa = azetidine

<400> SEQUENCE: 255

Phe Glu Trp Thr Pro Xaa Tyr Trp Gln Xaa Tyr
```

<210> SEQ ID NO 256
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(5)
<223> OTHER INFORMATION: Position 5, Xaa = MeGly
<220> FEATURE:
<221> NAME/KEY: misc_feature
<222> LOCATION: (10)..(10)
<223> OTHER INFORMATION: Position 10, Xaa = azetidine

<400> SEQUENCE: 256

Phe Glu Trp Thr Xaa Gly Tyr Trp Gln Xaa Tyr
1               5                   10

<210> SEQ ID NO 257
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 257

Phe Glu Trp Thr Pro Gly Tyr Trp Gln Pro Tyr Ala Leu Pro Leu
1               5                   10                  15

<210> SEQ ID NO 258
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa is a 1-naphthylalanine residue
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 258

Xaa Glu Trp Thr Pro Gly Tyr Tyr Gln Xaa Tyr
1               5                   10

<210> SEQ ID NO 259
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 259

```
Tyr Glu Trp Thr Pro Gly Tyr Tyr Gln Xaa Tyr
1               5                   10
```

<210> SEQ ID NO 260
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 260

```
Phe Glu Trp Val Pro Gly Tyr Tyr Gln Xaa Tyr
1               5                   10
```

<210> SEQ ID NO 261
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (6)..(6)
<223> OTHER INFORMATION: Position 6, D amino acid residue
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 261

```
Phe Glu Trp Thr Pro Ser Tyr Tyr Gln Xaa Tyr
1               5                   10
```

<210> SEQ ID NO 262
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (6)..(6)
<223> OTHER INFORMATION: Position 6, D amino acid residue
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11 amino group added at C-terminus

<400> SEQUENCE: 262

```
Phe Glu Trp Thr Pro Asn Tyr Tyr Gln Xaa Tyr
1               5                   10
```

<210> SEQ ID NO 263
<211> LENGTH: 4
<212> TYPE: PRT
<213> ORGANISM: Artificial Sequence

```
<220> FEATURE:
<223> OTHER INFORMATION: IL-1 ANTAGONIST PEPTIDE

<400> SEQUENCE: 263

Thr Lys Pro Arg
1

<210> SEQ ID NO 264
<211> LENGTH: 5
<212> TYPE: PRT
<213> ORGANISM: Artificial Sequence
<220> FEATURE:
<223> OTHER INFORMATION: IL-1 ANTAGONIST PEPTIDE

<400> SEQUENCE: 264

Arg Lys Ser Ser Lys
1               5

<210> SEQ ID NO 265
<211> LENGTH: 5
<212> TYPE: PRT
<213> ORGANISM: Artificial Sequence
<220> FEATURE:
<223> OTHER INFORMATION: IL-1 ANTAGONIST PEPTIDE

<400> SEQUENCE: 265

Arg Lys Gln Asp Lys
1               5

<210> SEQ ID NO 266
<211> LENGTH: 6
<212> TYPE: PRT
<213> ORGANISM: Artificial Sequence
<220> FEATURE:
<223> OTHER INFORMATION: IL-1 ANTAGONIST PEPTIDE

<400> SEQUENCE: 266

Asn Arg Lys Gln Asp Lys
1               5

<210> SEQ ID NO 267
<211> LENGTH: 6
<212> TYPE: PRT
<213> ORGANISM: Artificial Sequence
<220> FEATURE:
<223> OTHER INFORMATION: IL-1 ANTAGONIST PEPTIDE

<400> SEQUENCE: 267

Arg Lys Gln Asp Lys Arg
1               5

<210> SEQ ID NO 268
<211> LENGTH: 9
<212> TYPE: PRT
<213> ORGANISM: Artificial Sequence
<220> FEATURE:
<223> OTHER INFORMATION: IL-1 ANTAGONIST PEPTIDE

<400> SEQUENCE: 268

Glu Asn Arg Lys Gln Asp Lys Arg Phe
1               5

<210> SEQ ID NO 269
<211> LENGTH: 6
<212> TYPE: PRT
<213> ORGANISM: Artificial Sequence
<220> FEATURE:
```

<223> OTHER INFORMATION: IL-1 ANTAGONIST PEPTIDE

<400> SEQUENCE: 269

Val Thr Lys Phe Tyr Phe
1               5

<210> SEQ ID NO 270
<211> LENGTH: 5
<212> TYPE: PRT
<213> ORGANISM: Artificial Sequence
<220> FEATURE:
<223> OTHER INFORMATION: IL-1 ANTAGONIST PEPTIDE

<400> SEQUENCE: 270

Val Thr Lys Phe Tyr
1               5

<210> SEQ ID NO 271
<211> LENGTH: 5
<212> TYPE: PRT
<213> ORGANISM: Artificial Sequence
<220> FEATURE:
<223> OTHER INFORMATION: IL-1 ANTAGONIST PEPTIDE

<400> SEQUENCE: 271

Val Thr Asp Phe Tyr
1               5

<210> SEQ ID NO 272
<211> LENGTH: 17
<212> TYPE: PRT
<213> ORGANISM: Artificial Sequence
<220> FEATURE:
<223> OTHER INFORMATION: MAST CELL ANTAGONISTS/ PROTEASE INHIBITOR
      PEPTIDE

<400> SEQUENCE: 272

Ser Gly Ser Gly Val Leu Lys Arg Pro Leu Pro Ile Leu Pro Val Thr
1               5                   10                  15

Arg

<210> SEQ ID NO 273
<211> LENGTH: 17
<212> TYPE: PRT
<213> ORGANISM: Artificial SEquence
<220> FEATURE:
<223> OTHER INFORMATION: MAST CELL ANTAGONISTS/ PROTEASE INHIBITOR
      PEPTIDE

<400> SEQUENCE: 273

Arg Trp Leu Ser Ser Arg Pro Leu Pro Pro Leu Pro Leu Pro Pro Arg
1               5                   10                  15

Thr

<210> SEQ ID NO 274
<211> LENGTH: 20
<212> TYPE: PRT
<213> ORGANISM: Artificial Sequence
<220> FEATURE:
<223> OTHER INFORMATION: MAST CELL ANTAGONISTS/ PROTEASE INHIBITOR
      PEPTIDE

<400> SEQUENCE: 274

Gly Ser Gly Ser Tyr Asp Thr Leu Ala Leu Pro Ser Leu Pro Leu His
1               5                   10                  15

```
Pro Met Ser Ser
            20

<210> SEQ ID NO 275
<211> LENGTH: 20
<212> TYPE: PRT
<213> ORGANISM: Artificial Sequence
<220> FEATURE:
<223> OTHER INFORMATION: MAST CELL ANTAGONISTS/ PROTEASE INHIBITOR
      PEPTIDE

<400> SEQUENCE: 275

Gly Ser Gly Ser Tyr Asp Thr Arg Ala Leu Pro Ser Leu Pro Leu His
1               5                   10                  15

Pro Met Ser Ser
            20

<210> SEQ ID NO 276
<211> LENGTH: 20
<212> TYPE: PRT
<213> ORGANISM: Artificial Sequence
<220> FEATURE:
<223> OTHER INFORMATION: MAST CELL ANTAGONISTS/ PROTEASE INHIBITOR
      PEPTIDE

<400> SEQUENCE: 276

Gly Ser Gly Ser Ser Gly Val Thr Met Tyr Pro Lys Leu Pro Pro His
1               5                   10                  15

Trp Ser Met Ala
            20

<210> SEQ ID NO 277
<211> LENGTH: 20
<212> TYPE: PRT
<213> ORGANISM: Artificial Sequence
<220> FEATURE:
<223> OTHER INFORMATION: MAST CELL ANTAGONISTS/ PROTEASE INHIBITOR
      PEPTIDE

<400> SEQUENCE: 277

Gly Ser Gly Ser Ser Gly Val Arg Met Tyr Pro Lys Leu Pro Pro His
1               5                   10                  15

Trp Ser Met Ala
            20

<210> SEQ ID NO 278
<211> LENGTH: 20
<212> TYPE: PRT
<213> ORGANISM: Artificial Sequence
<220> FEATURE:
<223> OTHER INFORMATION: MAST CELL ANTAGONISTS/ PROTEASE INHIBITOR
      PEPTIDE

<400> SEQUENCE: 278

Gly Ser Gly Ser Ser Ser Met Arg Met Val Pro Thr Ile Pro Gly Ser
1               5                   10                  15

Ala Lys His Gly
            20

<210> SEQ ID NO 279
<211> LENGTH: 6
<212> TYPE: PRT
<213> ORGANISM: Artificial Sequence
<220> FEATURE:
<223> OTHER INFORMATION: ANTI-HBV
```

```
<400> SEQUENCE: 279

Leu Leu Gly Arg Met Lys
1               5

<210> SEQ ID NO 280
<211> LENGTH: 8
<212> TYPE: PRT
<213> ORGANISM: Artificial Sequence
<220> FEATURE:
<223> OTHER INFORMATION: ANTI-HBV

<400> SEQUENCE: 280

Ala Leu Leu Gly Arg Met Lys Gly
1               5

<210> SEQ ID NO 281
<211> LENGTH: 6
<212> TYPE: PRT
<213> ORGANISM: Artificial Sequence
<220> FEATURE:
<223> OTHER INFORMATION: ANTI-HBV

<400> SEQUENCE: 281

Leu Asp Pro Ala Phe Arg
1               5

<210> SEQ ID NO 282
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 282

Arg Pro Leu Pro Pro Leu Pro
1               5

<210> SEQ ID NO 283
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 283

Arg Glu Leu Pro Pro Leu Pro
1               5

<210> SEQ ID NO 284
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 284

Ser Pro Leu Pro Pro Leu Pro
1               5

<210> SEQ ID NO 285
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 285
```

```
Gly Pro Leu Pro Pro Leu Pro
1               5

<210> SEQ ID NO 286
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 286

Arg Pro Leu Pro Ile Pro Pro
1               5

<210> SEQ ID NO 287
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 287

Arg Pro Leu Pro Ile Pro Pro
1               5

<210> SEQ ID NO 288
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 288

Arg Arg Leu Pro Pro Thr Pro
1               5

<210> SEQ ID NO 289
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 289

Arg Gln Leu Pro Pro Thr Pro
1               5

<210> SEQ ID NO 290
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 290

Arg Pro Leu Pro Ser Arg Pro
1               5

<210> SEQ ID NO 291
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 291
```

Arg Pro Leu Pro Thr Arg Pro
1               5

<210> SEQ ID NO 292
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 292

Ser Arg Leu Pro Pro Leu Pro
1               5

<210> SEQ ID NO 293
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 293

Arg Ala Leu Pro Ser Pro Pro
1               5

<210> SEQ ID NO 294
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 294

Arg Arg Leu Pro Arg Thr Pro
1               5

<210> SEQ ID NO 295
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 295

Arg Pro Val Pro Pro Ile Thr
1               5

<210> SEQ ID NO 296
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 296

Ile Leu Ala Pro Pro Val Pro
1               5

<210> SEQ ID NO 297
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 297

Arg Pro Leu Pro Met Leu Pro

-continued

<210> SEQ ID NO 298
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 298

Arg Pro Leu Pro Ile Leu Pro
1               5

<210> SEQ ID NO 299
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 299

Arg Pro Leu Pro Ser Leu Pro
1               5

<210> SEQ ID NO 300
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 300

Arg Pro Leu Pro Ser Leu Pro
1               5

<210> SEQ ID NO 301
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 301

Arg Pro Leu Pro Met Ile Pro
1               5

<210> SEQ ID NO 302
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 302

Arg Pro Leu Pro Leu Ile Pro
1               5

<210> SEQ ID NO 303
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 303

Arg Pro Leu Pro Pro Thr Pro
1               5

```
<210> SEQ ID NO 304
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 304

Arg Ser Leu Pro Pro Leu Pro
1               5

<210> SEQ ID NO 305
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 305

Arg Pro Gln Pro Pro Pro Pro
1               5

<210> SEQ ID NO 306
<211> LENGTH: 7
<212> TYPE: PRT
<213> ORGANISM: Artificial Sequence
<220> FEATURE:
<223> OTHER INFORMATION: SH3 ANTAGONIST PEPTIDE

<400> SEQUENCE: 306

Arg Gln Leu Pro Ile Pro Pro
1               5

<210> SEQ ID NO 307
<211> LENGTH: 12
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (1, 2, 3)..(11)
<223> OTHER INFORMATION: Xaa = any amino acid

<400> SEQUENCE: 307

Xaa Xaa Xaa Arg Pro Leu Pro Pro Leu Pro Xaa Pro
1               5                   10

<210> SEQ ID NO 308
<211> LENGTH: 12
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (1, 2, 3, 11)..(12)
<223> OTHER INFORMATION: Xaa = any amino acid

<400> SEQUENCE: 308

Xaa Xaa Xaa Arg Pro Leu Pro Pro Ile Pro Xaa Xaa
1               5                   10

<210> SEQ ID NO 309
<211> LENGTH: 12
<212> TYPE: PRT
<213> ORGANISM: Artificial Sequence
```

```
<220> FEATURE:
<223> OTHER INFORMATION: SH3 ANTAGONIST PEPTIDE
<220> FEATURE:
<221> NAME/KEY: misc_feature
<222> LOCATION: (1, 2, 3, 11,)..(12)
<223> OTHER INFORMATION: Xaa = any amino acid

<400> SEQUENCE: 309

Xaa Xaa Xaa Arg Pro Leu Pro Pro Leu Pro Xaa Xaa
1               5                   10

<210> SEQ ID NO 310
<211> LENGTH: 12
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (2, 3, 10)..(11)
<223> OTHER INFORMATION: Xaa = any amino acid

<400> SEQUENCE: 310

Arg Xaa Xaa Arg Pro Leu Pro Pro Leu Pro Xaa Pro
1               5                   10

<210> SEQ ID NO 311
<211> LENGTH: 12
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (2)..(3)
<223> OTHER INFORMATION: Xaa = any amino acid

<400> SEQUENCE: 311

Arg Xaa Xaa Arg Pro Leu Pro Pro Leu Pro Pro Pro
1               5                   10

<210> SEQ ID NO 312
<211> LENGTH: 12
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (11)..(12)
<223> OTHER INFORMATION: Xaa = any amino acid

<400> SEQUENCE: 312

Pro Pro Pro Tyr Pro Pro Pro Pro Ile Pro Xaa Xaa
1               5                   10

<210> SEQ ID NO 313
<211> LENGTH: 12
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (11)..(12)
<223> OTHER INFORMATION: Xaa = any amino acid

<400> SEQUENCE: 313

Pro Pro Pro Tyr Pro Pro Pro Pro Val Pro Xaa Xaa
1               5                   10
```

```
<210> SEQ ID NO 314
<211> LENGTH: 10
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (2, 3)..(8)
<223> OTHER INFORMATION: Xaa (Pos2, 3, 8) is any amino acid
<220> FEATURE:
<221> NAME/KEY: misc_feature
<222> LOCATION: (9)..(9)
<223> OTHER INFORMATION: Xaa (Pos 9) represents an aliphatic amino acid
      residue

<400> SEQUENCE: 314

Leu Xaa Xaa Arg Pro Leu Pro Xaa Xaa Pro
1               5                   10

<210> SEQ ID NO 315
<211> LENGTH: 10
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (1)..(1)
<223> OTHER INFORMATION: Position 1, Xaa is an aliphatic amino acid
      residue
<220> FEATURE:
<221> NAME/KEY: misc_feature
<222> LOCATION: (2, 3)..(8)
<223> OTHER INFORMATION: Positions 2, 3 & 8, Xaa is any amino acid

<400> SEQUENCE: 315

Xaa Xaa Xaa Arg Pro Leu Pro Xaa Leu Pro
1               5                   10

<210> SEQ ID NO 316
<211> LENGTH: 10
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (3)..(3)
<223> OTHER INFORMATION: Position 3, Xaa is any amino acid residue
<220> FEATURE:
<221> NAME/KEY: misc_feature
<222> LOCATION: (4)..(4)
<223> OTHER INFORMATION: Position 4, Xaa is an aromatic amino acid
      residue
<220> FEATURE:
<221> NAME/KEY: misc_feature
<222> LOCATION: (9)..(9)
<223> OTHER INFORMATION: Position 9, Xaa is an aliphatic amino acid
      residue

<400> SEQUENCE: 316

Pro Pro Xaa Xaa Tyr Pro Pro Pro Xaa Pro
1               5                   10

<210> SEQ ID NO 317
<211> LENGTH: 11
<212> TYPE: PRT
<213> ORGANISM: Artificial Sequence
<220> FEATURE:
<223> OTHER INFORMATION: SH3 ANTAGONIST PEPTIDE
```

```
<220> FEATURE:
<221> NAME/KEY: misc_feature
<222> LOCATION: (1)..(1)
<223> OTHER INFORMATION: Position 1, Xaa is a basic amino acid residue
<220> FEATURE:
<221> NAME/KEY: misc_feature
<222> LOCATION: (4)..(4)
<223> OTHER INFORMATION: Position 4, Xaa is an aliphatic amino acid
      residue
<220> FEATURE:
<221> NAME/KEY: misc_feature
<222> LOCATION: (6)..(9)
<223> OTHER INFORMATION: Positions 6 & 9, Xaa is any amino acid
      residue

<400> SEQUENCE: 317

Xaa Pro Pro Xaa Pro Xaa Lys Pro Xaa Trp Leu
1               5                   10

<210> SEQ ID NO 318
<211> LENGTH: 11
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (3, 4)..(6)
<223> OTHER INFORMATION: Positions 3, 4 & 6, Xaa is an aliphatic amino
      acid
      residue
<220> FEATURE:
<221> NAME/KEY: misc_feature
<222> LOCATION: (8)..(8)
<223> OTHER INFORMATION: Position 8, Xaa is a basic amino acid
      residue
<220> FEATURE:
<221> NAME/KEY: misc_feature
<222> LOCATION: (10)..(10)
<223> OTHER INFORMATION: Position 10, Xaa is any amino acid
      residue

<400> SEQUENCE: 318

Arg Pro Xaa Xaa Pro Xaa Arg Xaa Ser Xaa Pro
1               5                   10

<210> SEQ ID NO 319
<211> LENGTH: 11
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (8)..(9)
<223> OTHER INFORMATION: Xaa = any amino acid

<400> SEQUENCE: 319

Pro Pro Val Pro Pro Arg Pro Xaa Xaa Thr Leu
1               5                   10

<210> SEQ ID NO 320
<211> LENGTH: 7
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (1, 3)..(6)
<223> OTHER INFORMATION: Positions 1, 3 and 6, Xaa is an aliphatic amino
      acid residue
```

```
<400> SEQUENCE: 320

Xaa Pro Xaa Leu Pro Xaa Lys
1               5

<210> SEQ ID NO 321
<211> LENGTH: 10
<212> TYPE: PRT
<213> ORGANISM: Artificial Sequence
<220> FEATURE:
<223> OTHER INFORMATION: SH3 ANTAGONIST PEPTIDE
<220> FEATURE:
<221> NAME/KEY: misc_feature
<222> LOCATION: (1)..(1)
<223> OTHER INFORMATION: Position 1, Xaa is a basic amino acid residue
<220> FEATURE:
<221> NAME/KEY: misc_feature
<222> LOCATION: (2)..(2)
<223> OTHER INFORMATION: Position 2, Xaa is an aromatic amino acid
      residue
<220> FEATURE:
<221> NAME/KEY: misc_feature
<222> LOCATION: (4)..(8)
<223> OTHER INFORMATION: Positions 4 & 8, Xaa is any amino acid residue

<400> SEQUENCE: 321

Xaa Xaa Asp Xaa Pro Leu Pro Xaa Leu Pro
1               5                   10

<210> SEQ ID NO 322
<211> LENGTH: 7
<212> TYPE: PRT
<213> ORGANISM: Artificial Sequence
<220> FEATURE:
<223> OTHER INFORMATION: INHIBITION OF PLATELET AGGREGATION
<220> FEATURE:
<221> NAME/KEY: misc_feature
<222> LOCATION: (2)..(3)
<223> OTHER INFORMATION: Xaa = any amino acid

<400> SEQUENCE: 322

Cys Xaa Xaa Arg Gly Asp Cys
1               5

<210> SEQ ID NO 323
<211> LENGTH: 7
<212> TYPE: PRT
<213> ORGANISM: Artificial Sequence
<220> FEATURE:
<223> OTHER INFORMATION: SRC ANTAGONIST

<400> SEQUENCE: 323

Arg Pro Leu Pro Pro Leu Pro
1               5

<210> SEQ ID NO 324
<211> LENGTH: 6
<212> TYPE: PRT
<213> ORGANISM: Artificial Sequence
<220> FEATURE:
<223> OTHER INFORMATION: SRC ANTAGONIST

<400> SEQUENCE: 324

Pro Pro Val Pro Pro Arg
1               5

<210> SEQ ID NO 325
<211> LENGTH: 11
<212> TYPE: PRT
<213> ORGANISM: Artificial Sequence
```

```
<220> FEATURE:
<223> OTHER INFORMATION: ANTI-CANCER (PARTICULARLY FOR SARCOMAS)
<220> FEATURE:
<221> NAME/KEY: misc_feature
<222> LOCATION: (1, 3, 5, 7, 8, 10)..(11)
<223> OTHER INFORMATION: Xaa = any amino acid

<400> SEQUENCE: 325

Xaa Phe Xaa Asp Xaa Trp Xaa Xaa Leu Xaa Xaa
1               5                   10

<210> SEQ ID NO 326
<211> LENGTH: 20
<212> TYPE: PRT
<213> ORGANISM: Artificial Sequence
<220> FEATURE:
<223> OTHER INFORMATION: P16-MIMETIC

<400> SEQUENCE: 326

Lys Ala Cys Arg Arg Leu Phe Gly Pro Val Asp Ser Glu Gln Leu Ser
1               5                   10                  15

Arg Asp Cys Asp
            20

<210> SEQ ID NO 327
<211> LENGTH: 20
<212> TYPE: PRT
<213> ORGANISM: Artificial Sequence
<220> FEATURE:
<223> OTHER INFORMATION: P16-MIMETIC

<400> SEQUENCE: 327

Arg Glu Arg Trp Asn Phe Asp Phe Val Thr Glu Thr Pro Leu Glu Gly
1               5                   10                  15

Asp Phe Ala Trp
            20

<210> SEQ ID NO 328
<211> LENGTH: 20
<212> TYPE: PRT
<213> ORGANISM: Artificial Sequence
<220> FEATURE:
<223> OTHER INFORMATION: P16-MIMETIC

<400> SEQUENCE: 328

Lys Arg Arg Gln Thr Ser Met Thr Asp Phe Tyr His Ser Lys Arg Arg
1               5                   10                  15

Leu Ile Phe Ser
            20

<210> SEQ ID NO 329
<211> LENGTH: 20
<212> TYPE: PRT
<213> ORGANISM: Artificial Sequence
<220> FEATURE:
<223> OTHER INFORMATION: P16-MIMETIC

<400> SEQUENCE: 329

Thr Ser Met Thr Asp Phe Tyr His Ser Lys Arg Arg Leu Ile Phe Ser
1               5                   10                  15

Lys Arg Lys Pro
            20

<210> SEQ ID NO 330
<211> LENGTH: 5
```

```
<212> TYPE: PRT
<213> ORGANISM: Artificial Sequence
<220> FEATURE:
<223> OTHER INFORMATION: P16-MIMETIC

<400> SEQUENCE: 330

Arg Arg Leu Ile Phe
1               5

<210> SEQ ID NO 331
<211> LENGTH: 36
<212> TYPE: PRT
<213> ORGANISM: Artificial Sequence
<220> FEATURE:
<223> OTHER INFORMATION: P16-MIMETIC

<400> SEQUENCE: 331

Lys Arg Arg Gln Thr Ser Ala Thr Asp Phe Tyr His Ser Lys Arg Arg
1               5                   10                  15

Leu Ile Phe Ser Arg Gln Ile Lys Ile Trp Phe Gln Asn Arg Arg Met
            20                  25                  30

Lys Trp Lys Lys
        35

<210> SEQ ID NO 332
<211> LENGTH: 24
<212> TYPE: PRT
<213> ORGANISM: Artificial Sequence
<220> FEATURE:
<223> OTHER INFORMATION: P16-MIMETIC

<400> SEQUENCE: 332

Lys Arg Arg Leu Ile Phe Ser Lys Arg Gln Ile Lys Ile Trp Phe Gln
1               5                   10                  15

Asn Arg Arg Met Lys Trp Lys Lys
            20

<210> SEQ ID NO 333
<211> LENGTH: 8
<212> TYPE: PRT
<213> ORGANISM: Artificial Sequence
<220> FEATURE:
<223> OTHER INFORMATION: PREFERRED LINKER

<400> SEQUENCE: 333

Gly Gly Gly Lys Gly Gly Gly Gly
1               5

<210> SEQ ID NO 334
<211> LENGTH: 8
<212> TYPE: PRT
<213> ORGANISM: Artificial Sequence
<220> FEATURE:
<223> OTHER INFORMATION: PREFERRED LINKER

<400> SEQUENCE: 334

Gly Gly Gly Asn Gly Ser Gly Gly
1               5

<210> SEQ ID NO 335
<211> LENGTH: 8
<212> TYPE: PRT
<213> ORGANISM: Artificial Sequence
<220> FEATURE:
<223> OTHER INFORMATION: PREFERRED LINKER
```

```
<400> SEQUENCE: 335

Gly Gly Gly Cys Gly Gly Gly Gly
1               5

<210> SEQ ID NO 336
<211> LENGTH: 5
<212> TYPE: PRT
<213> ORGANISM: Artificial Sequence
<220> FEATURE:
<223> OTHER INFORMATION: PREFERRED LINKER

<400> SEQUENCE: 336

Gly Pro Asn Gly Gly
1               5

<210> SEQ ID NO 337
<211> LENGTH: 41
<212> TYPE: PRT
<213> ORGANISM: Artificial Sequence
<220> FEATURE:
<223> OTHER INFORMATION: TPO-MIMETIC
<220> FEATURE:
<221> NAME/KEY: misc_feature
<222> LOCATION: (1)..(1)
<223> OTHER INFORMATION: Fc domain attached at Position 1 of the N-
      terminus

<400> SEQUENCE: 337

Gly Gly Gly Gly Gly Ile Glu Gly Pro Thr Leu Arg Gln Trp Leu Ala
1               5                   10                  15

Ala Arg Ala Gly Gly Gly Gly Gly Gly Gly Ile Glu Gly Pro Thr
            20                  25                  30

Leu Arg Gln Trp Leu Ala Ala Arg Ala
        35                  40

<210> SEQ ID NO 338
<211> LENGTH: 41
<212> TYPE: PRT
<213> ORGANISM: Artificial Sequence
<220> FEATURE:
<223> OTHER INFORMATION: TPO-MIMETIC
<220> FEATURE:
<221> NAME/KEY: misc_feature
<222> LOCATION: (41)..(41)
<223> OTHER INFORMATION: Fc domain attached at Position 41 of the C-
      terminus

<400> SEQUENCE: 338

Ile Glu Gly Pro Thr Leu Arg Gln Trp Leu Ala Ala Arg Ala Gly Gly
1               5                   10                  15

Gly Gly Gly Gly Gly Ile Glu Gly Pro Thr Leu Arg Gln Trp Leu
            20                  25                  30

Ala Ala Arg Ala Gly Gly Gly Gly Gly
        35                  40

<210> SEQ ID NO 339
<211> LENGTH: 49
<212> TYPE: PRT
<213> ORGANISM: Artificial Sequence
<220> FEATURE:
<223> OTHER INFORMATION: EPO-MIMETIC
<220> FEATURE:
<221> NAME/KEY: misc_feature
<222> LOCATION: (1)..(1)
<223> OTHER INFORMATION: Fc domain attached at Position 1 of the N-
      terminus
```

<400> SEQUENCE: 339

Gly Gly Gly Gly Gly Gly Gly Thr Tyr Ser Cys His Phe Gly Pro Leu
1               5                   10                  15

Thr Trp Val Cys Lys Pro Gln Gly Gly Gly Gly Gly Gly Gly Thr
            20                  25                  30

Tyr Ser Cys His Phe Gly Pro Leu Thr Trp Val Cys Lys Pro Gln Gly
        35                  40                  45

Gly

<210> SEQ ID NO 340
<211> LENGTH: 49
<212> TYPE: PRT
<213> ORGANISM: Artificial Sequence
<220> FEATURE:
<223> OTHER INFORMATION: EPO-MIMETIC
<220> FEATURE:
<221> NAME/KEY: misc_feature
<222> LOCATION: (49)..(49)
<223> OTHER INFORMATION: Fc domain attached at Position 49 of the C-
      terminus

<400> SEQUENCE: 340

Gly Gly Thr Tyr Ser Cys His Phe Gly Pro Leu Thr Trp Val Cys Lys
1               5                   10                  15

Pro Gln Gly Gly Gly Gly Gly Gly Gly Thr Tyr Ser Cys His Phe
            20                  25                  30

Gly Pro Leu Thr Trp Val Cys Lys Pro Gln Gly Gly Gly Gly Gly
        35                  40                  45

Gly

<210> SEQ ID NO 341
<211> LENGTH: 28
<212> TYPE: PRT
<213> ORGANISM: Artificial Sequence
<220> FEATURE:
<223> OTHER INFORMATION: TPO-MIMETIC PEPTIDES

<400> SEQUENCE: 341

Ile Glu Gly Pro Thr Leu Arg Gln Trp Leu Ala Ala Arg Ala Ile Glu
1               5                   10                  15

Gly Pro Thr Leu Arg Gln Trp Leu Ala Ala Arg Ala
            20                  25

<210> SEQ ID NO 342
<211> LENGTH: 29
<212> TYPE: PRT
<213> ORGANISM: Artificial Sequence
<220> FEATURE:
<223> OTHER INFORMATION: TPO-MIMETIC PEPTIDES

<400> SEQUENCE: 342

Ile Glu Gly Pro Thr Leu Arg Gln Trp Leu Ala Ala Arg Ala Gly Ile
1               5                   10                  15

Glu Gly Pro Thr Leu Arg Gln Trp Leu Ala Ala Arg Ala
            20                  25

<210> SEQ ID NO 343
<211> LENGTH: 30
<212> TYPE: PRT
<213> ORGANISM: Artificial Sequence
<220> FEATURE:
<223> OTHER INFORMATION: TPO-MIMETIC PEPTIDES -continued

```
<400> SEQUENCE: 343

Ile Glu Gly Pro Thr Leu Arg Gln Trp Leu Ala Ala Arg Ala Gly Gly
1               5                   10                  15

Ile Glu Gly Pro Thr Leu Arg Gln Trp Leu Ala Ala Arg Ala
            20                  25                  30

<210> SEQ ID NO 344
<211> LENGTH: 31
<212> TYPE: PRT
<213> ORGANISM: Artificial Sequence
<220> FEATURE:
<223> OTHER INFORMATION: TPO-MIMETIC PEPTIDES

<400> SEQUENCE: 344

Ile Glu Gly Pro Thr Leu Arg Gln Trp Leu Ala Ala Arg Ala Gly Gly
1               5                   10                  15

Gly Ile Glu Gly Pro Thr Leu Arg Gln Trp Leu Ala Ala Arg Ala
            20                  25                  30

<210> SEQ ID NO 345
<211> LENGTH: 32
<212> TYPE: PRT
<213> ORGANISM: Artificial Sequence
<220> FEATURE:
<223> OTHER INFORMATION: TPO-MIMETIC PEPTIDES

<400> SEQUENCE: 345

Ile Glu Gly Pro Thr Leu Arg Gln Trp Leu Ala Ala Arg Ala Gly Gly
1               5                   10                  15

Gly Gly Ile Glu Gly Pro Thr Leu Arg Gln Trp Leu Ala Ala Arg Ala
            20                  25                  30

<210> SEQ ID NO 346
<211> LENGTH: 33
<212> TYPE: PRT
<213> ORGANISM: Artificial Sequence
<220> FEATURE:
<223> OTHER INFORMATION: TPO-MIMETIC PEPTIDES

<400> SEQUENCE: 346

Ile Glu Gly Pro Thr Leu Arg Gln Trp Leu Ala Ala Arg Ala Gly Gly
1               5                   10                  15

Gly Gly Gly Ile Glu Gly Pro Thr Leu Arg Gln Trp Leu Ala Ala Arg
            20                  25                  30

Ala

<210> SEQ ID NO 347
<211> LENGTH: 34
<212> TYPE: PRT
<213> ORGANISM: Artificial Sequence
<220> FEATURE:
<223> OTHER INFORMATION: TPO-MIMETIC PEPTIDES

<400> SEQUENCE: 347

Ile Glu Gly Pro Thr Leu Arg Gln Trp Leu Ala Ala Arg Ala Gly Gly
1               5                   10                  15

Gly Gly Gly Gly Ile Glu Gly Pro Thr Leu Arg Gln Trp Leu Ala Ala
            20                  25                  30

Arg Ala

<210> SEQ ID NO 348
<211> LENGTH: 35
```

<212> TYPE: PRT
<213> ORGANISM: Artificial Sequence
<220> FEATURE:
<223> OTHER INFORMATION: TPO-MIMETIC PEPTIDES

<400> SEQUENCE: 348

Ile Glu Gly Pro Thr Leu Arg Gln Trp Leu Ala Ala Arg Ala Gly Gly
1               5                   10                  15

Gly Gly Gly Gly Gly Ile Glu Gly Pro Thr Leu Arg Gln Trp Leu Ala
            20                  25                  30

Ala Arg Ala
        35

<210> SEQ ID NO 349
<211> LENGTH: 36
<212> TYPE: PRT
<213> ORGANISM: Artificial Sequence
<220> FEATURE:
<223> OTHER INFORMATION: TPO-MIMETIC PEPTIDES

<400> SEQUENCE: 349

Ile Glu Gly Pro Thr Leu Arg Gln Trp Leu Ala Ala Arg Ala Gly Gly
1               5                   10                  15

Gly Gly Gly Gly Gly Gly Ile Glu Gly Pro Thr Leu Arg Gln Trp Leu
            20                  25                  30

Ala Ala Arg Ala
        35

<210> SEQ ID NO 350
<211> LENGTH: 37
<212> TYPE: PRT
<213> ORGANISM: Artificial Sequence
<220> FEATURE:
<223> OTHER INFORMATION: TPO-MIMETIC PEPTIDES

<400> SEQUENCE: 350

Ile Glu Gly Pro Thr Leu Arg Gln Trp Leu Ala Ala Arg Ala Gly Gly
1               5                   10                  15

Gly Gly Gly Gly Gly Gly Gly Ile Glu Gly Pro Thr Leu Arg Gln Trp
            20                  25                  30

Leu Ala Ala Arg Ala
        35

<210> SEQ ID NO 351
<211> LENGTH: 38
<212> TYPE: PRT
<213> ORGANISM: Artificial Sequence
<220> FEATURE:
<223> OTHER INFORMATION: TPO-MIMETIC PEPTIDES

<400> SEQUENCE: 351

Ile Glu Gly Pro Thr Leu Arg Gln Trp Leu Ala Ala Arg Ala Gly Gly
1               5                   10                  15

Gly Gly Gly Gly Gly Gly Gly Gly Ile Glu Gly Pro Thr Leu Arg Gln
            20                  25                  30

Trp Leu Ala Ala Arg Ala
        35

<210> SEQ ID NO 352
<211> LENGTH: 42
<212> TYPE: PRT
<213> ORGANISM: Artificial Sequence
<220> FEATURE:

```
<223> OTHER INFORMATION: TPO-MIMETIC PEPTIDES

<400> SEQUENCE: 352

Ile Glu Gly Pro Thr Leu Arg Gln Trp Leu Ala Ala Arg Ala Gly Gly
1               5                   10                  15

Gly Gly Gly Gly Gly Gly Gly Gly Gly Gly Ile Glu Gly Pro
            20                  25                  30

Thr Leu Arg Gln Trp Leu Ala Ala Arg Ala
        35                  40

<210> SEQ ID NO 353
<211> LENGTH: 32
<212> TYPE: PRT
<213> ORGANISM: Artificial Sequence
<220> FEATURE:
<223> OTHER INFORMATION: TPO-MIMETIC PEPTIDES

<400> SEQUENCE: 353

Ile Glu Gly Pro Thr Leu Arg Gln Trp Leu Ala Ala Arg Ala Gly Pro
1               5                   10                  15

Asn Gly Ile Glu Gly Pro Thr Leu Arg Gln Trp Leu Ala Ala Arg Ala
            20                  25                  30

<210> SEQ ID NO 354
<211> LENGTH: 36
<212> TYPE: PRT
<213> ORGANISM: Artificial Sequence
<220> FEATURE:
<223> OTHER INFORMATION: TPO-MIMETIC PEPTIDES

<400> SEQUENCE: 354

Ile Glu Gly Pro Thr Leu Arg Gln Trp Leu Ala Ala Arg Ala Gly Gly
1               5                   10                  15

Gly Gly Gly Gly Gly Gly Ile Glu Gly Pro Thr Leu Arg Gln Trp Leu
            20                  25                  30

Ala Ala Arg Ala
        35

<210> SEQ ID NO 355
<211> LENGTH: 36
<212> TYPE: PRT
<213> ORGANISM: Artificial Sequence
<220> FEATURE:
<223> OTHER INFORMATION: TPO-MIMETIC PEPTIDES

<400> SEQUENCE: 355

Ile Glu Gly Pro Thr Leu Arg Gln Trp Leu Ala Ala Arg Ala Gly Gly
1               5                   10                  15

Gly Gly Gly Gly Gly Gly Ile Glu Gly Pro Thr Leu Arg Gln Trp Leu
            20                  25                  30

Ala Ala Arg Ala
        35

<210> SEQ ID NO 356
<211> LENGTH: 36
<212> TYPE: PRT
<213> ORGANISM: Artificial Sequence
<220> FEATURE:
<223> OTHER INFORMATION: TPO-MIMETIC PEPTIDES

<400> SEQUENCE: 356

Ile Glu Gly Pro Thr Leu Arg Gln Trp Leu Ala Ala Arg Ala Gly Gly
1               5                   10                  15
```

-continued

```
Gly Gly Gly Gly Gly Ile Glu Gly Pro Thr Leu Arg Gln Trp Leu
            20                  25                  30

Ala Ala Arg Ala
        35

<210> SEQ ID NO 357
<211> LENGTH: 36
<212> TYPE: PRT
<213> ORGANISM: Artificial Sequence
<220> FEATURE:
<223> OTHER INFORMATION: TPO-MIMETIC PEPTIDES

<400> SEQUENCE: 357

Ile Glu Gly Pro Thr Leu Arg Gln Trp Leu Ala Ala Arg Ala Gly Gly
1               5                   10                  15

Gly Lys Gly Gly Gly Gly Ile Glu Gly Pro Thr Leu Arg Gln Trp Leu
            20                  25                  30

Ala Ala Arg Ala
        35

<210> SEQ ID NO 358
<211> LENGTH: 37
<212> TYPE: PRT
<213> ORGANISM: Artificial Sequence
<220> FEATURE:
<223> OTHER INFORMATION: TPO-MIMETIC PEPTIDES
<220> FEATURE:
<221> NAME/KEY: misc_feature
<222> LOCATION: (19)..(19)
<223> OTHER INFORMATION: Position 19, Xaa = bromoacetyl

<400> SEQUENCE: 358

Ile Glu Gly Pro Thr Leu Arg Gln Trp Leu Ala Ala Arg Ala Gly Gly
1               5                   10                  15

Gly Lys Xaa Gly Gly Gly Gly Ile Glu Gly Pro Thr Leu Arg Gln Trp
            20                  25                  30

Leu Ala Ala Arg Ala
        35

<210> SEQ ID NO 359
<211> LENGTH: 36
<212> TYPE: PRT
<213> ORGANISM: Artificial Sequence
<220> FEATURE:
<223> OTHER INFORMATION: TPO-MIMETIC PEPTIDES

<400> SEQUENCE: 359

Ile Glu Gly Pro Thr Leu Arg Gln Trp Leu Ala Ala Arg Ala Gly Gly
1               5                   10                  15

Gly Cys Gly Gly Gly Gly Ile Glu Gly Pro Thr Leu Arg Gln Trp Leu
            20                  25                  30

Ala Ala Arg Ala
        35

<210> SEQ ID NO 360
<211> LENGTH: 37
<212> TYPE: PRT
<213> ORGANISM: Artificial Sequence
<220> FEATURE:
<223> OTHER INFORMATION: TPO-MIMETIC PEPTIDES
<220> FEATURE:
<221> NAME/KEY: misc_feature
<222> LOCATION: (19)..(19)
<223> OTHER INFORMATION: Position 19, Xaa = Poly(ethylene glycol)
```

```
<400> SEQUENCE: 360

Ile Glu Gly Pro Thr Leu Arg Gln Trp Leu Ala Ala Arg Ala Gly Gly
1               5                  10                  15

Gly Lys Xaa Gly Gly Gly Gly Ile Glu Gly Pro Thr Leu Arg Gln Trp
            20                  25                  30

Leu Ala Ala Arg Ala
        35

<210> SEQ ID NO 361
<211> LENGTH: 37
<212> TYPE: PRT
<213> ORGANISM: Artificial Sequence
<220> FEATURE:
<223> OTHER INFORMATION: TPO-MIMETIC PEPTIDES
<220> FEATURE:
<221> NAME/KEY: misc_feature
<222> LOCATION: (19)..(19)
<223> OTHER INFORMATION: Position 19, Xaa = Poly(ethylene glycol)

<400> SEQUENCE: 361

Ile Glu Gly Pro Thr Leu Arg Gln Trp Leu Ala Ala Arg Ala Gly Gly
1               5                  10                  15

Gly Cys Xaa Gly Gly Gly Gly Ile Glu Gly Pro Thr Leu Arg Gln Trp
            20                  25                  30

Leu Ala Ala Arg Ala
        35

<210> SEQ ID NO 362
<211> LENGTH: 36
<212> TYPE: PRT
<213> ORGANISM: Artificial Sequence
<220> FEATURE:
<223> OTHER INFORMATION: TPO-MIMETIC PEPTIDES

<400> SEQUENCE: 362

Ile Glu Gly Pro Thr Leu Arg Gln Trp Leu Ala Ala Arg Ala Gly Gly
1               5                  10                  15

Gly Asn Gly Ser Gly Gly Ile Glu Gly Pro Thr Leu Arg Gln Trp Leu
            20                  25                  30

Ala Ala Arg Ala
        35

<210> SEQ ID NO 363
<211> LENGTH: 36
<212> TYPE: PRT
<213> ORGANISM: Artificial Sequence
<220> FEATURE:
<223> OTHER INFORMATION: TPO-MIMETIC PEPTIDES

<400> SEQUENCE: 363

Ile Glu Gly Pro Thr Leu Arg Gln Trp Leu Ala Ala Arg Ala Gly Gly
1               5                  10                  15

Gly Cys Gly Gly Gly Gly Ile Glu Gly Pro Thr Leu Arg Gln Trp Leu
            20                  25                  30

Ala Ala Arg Ala
        35

<210> SEQ ID NO 364
<211> LENGTH: 57
<212> TYPE: DNA
<213> ORGANISM: Artificial Sequence
<220> FEATURE:
```

-continued

<223> OTHER INFORMATION: Fc-TMP

<400> SEQUENCE: 364
aaaaaaggat cctcgagatt aagcacgagc agccagccac tgacgcagag tcggacc       57

<210> SEQ ID NO 365
<211> LENGTH: 39
<212> TYPE: DNA
<213> ORGANISM: Artificial Sequence
<220> FEATURE:
<223> OTHER INFORMATION: Fc-TMP

<400> SEQUENCE: 365
aaaggtggag gtggtggtat cgaaggtccg actctgcgt                           39

<210> SEQ ID NO 366
<211> LENGTH: 42
<212> TYPE: DNA
<213> ORGANISM: Artificial Sequence
<220> FEATURE:
<223> OTHER INFORMATION: Fc-TMP

<400> SEQUENCE: 366
cagtggctgg ctgctcgtgc ttaatctcga ggatcctttt tt                       42

<210> SEQ ID NO 367
<211> LENGTH: 81
<212> TYPE: DNA
<213> ORGANISM: Artificial Sequence
<220> FEATURE:
<223> OTHER INFORMATION: Fc-TMP
<220> FEATURE:
<221> NAME/KEY: CDS
<222> LOCATION: (1)..(60)
<223> OTHER INFORMATION:

<400> SEQUENCE: 367 aaa ggt gga ggt ggt ggt atc gaa ggt ccg act ctg cgt cag tgg ctg      48
Lys Gly Gly Gly Gly Gly Ile Glu Gly Pro Thr Leu Arg Gln Trp Leu
1               5                   10                  15 gct gct cgt gct taatctcgag gatccttttt t                              81
Ala Ala Arg Ala
            20

<210> SEQ ID NO 368
<211> LENGTH: 20
<212> TYPE: PRT
<213> ORGANISM: Artificial Sequence
<220> FEATURE:
<223> OTHER INFORMATION: Fc-TMP

<400> SEQUENCE: 368

Lys Gly Gly Gly Gly Gly Ile Glu Gly Pro Thr Leu Arg Gln Trp Leu
1               5                   10                  15

Ala Ala Arg Ala
            20

<210> SEQ ID NO 369
<211> LENGTH: 22
<212> TYPE: DNA
<213> ORGANISM: Artificial Sequence
<220> FEATURE:
<223> OTHER INFORMATION: Fc-TMP

<400> SEQUENCE: 369
aacataagta cctgtaggat cg                                             22

<210> SEQ ID NO 370
<211> LENGTH: 52
<212> TYPE: DNA
<213> ORGANISM: Artificial Sequence
<220> FEATURE:
<223> OTHER INFORMATION: Fc-TMP

<400> SEQUENCE: 370

```
ttcgatacca ccacctccac ctttacccgg agacagggag aggctcttct gc          52
```

<210> SEQ ID NO 371
<211> LENGTH: 60
<212> TYPE: DNA
<213> ORGANISM: Artificial Sequence
<220> FEATURE:
<223> OTHER INFORMATION: Fc-TMP-TMP

<400> SEQUENCE: 371

```
aaaggtggag gtggtggtat cgaaggtccg actctgcgtc agtggctggc tgctcgtgct   60
```

<210> SEQ ID NO 372
<211> LENGTH: 48
<212> TYPE: DNA
<213> ORGANISM: Artificial Sequence
<220> FEATURE:
<223> OTHER INFORMATION: Fc-TMP-TMP

<400> SEQUENCE: 372

```
acctccacca ccagcacgag cagccagcca ctgacgcaga gtcggacc                48
```

<210> SEQ ID NO 373
<211> LENGTH: 66
<212> TYPE: DNA
<213> ORGANISM: Artificial Sequence
<220> FEATURE:
<223> OTHER INFORMATION: Fc-TMP-TMP

<400> SEQUENCE: 373

```
ggtggtggag gtggcggcgg aggtattgag ggcccaaccc ttcgccaatg gcttgcagca   60
cgcgca                                                              66
```

<210> SEQ ID NO 374
<211> LENGTH: 76
<212> TYPE: PRT
<213> ORGANISM: Artificial Sequence
<220> FEATURE:
<223> OTHER INFORMATION: Fc-TMP-TMP

<400> SEQUENCE: 374

```
Ala Ala Ala Ala Ala Ala Gly Gly Ala Thr Cys Cys Thr Cys Gly
1               5                   10                  15
Ala Gly Ala Thr Thr Ala Thr Gly Cys Gly Cys Gly Thr Gly Cys Thr
                20                  25                  30
Gly Cys Ala Ala Gly Cys Cys Ala Thr Thr Gly Gly Cys Gly Ala Ala
            35                  40                  45
Gly Gly Gly Thr Thr Gly Gly Gly Cys Cys Cys Thr Cys Ala Ala Thr
        50                  55                  60
Ala Cys Cys Thr Cys Cys Gly Cys Cys Gly Cys Cys
65                  70                  75
```

<210> SEQ ID NO 375
<211> LENGTH: 126

```
<212> TYPE: DNA
<213> ORGANISM: Artificial Sequence
<220> FEATURE:
<223> OTHER INFORMATION: Fc-TMP-TMP
<220> FEATURE:
<221> NAME/KEY: CDS
<222> LOCATION: (1)..(126)
<223> OTHER INFORMATION:

<400> SEQUENCE: 375 aaa ggt gga ggt ggt ggt atc gaa ggt ccg act ctg cgt cag tgg ctg     48
Lys Gly Gly Gly Gly Gly Ile Glu Gly Pro Thr Leu Arg Gln Trp Leu
1               5                   10                  15 gct gct cgt gct ggt ggt gga ggt ggc ggc gga ggt att gag ggc cca     96
Ala Ala Arg Ala Gly Gly Gly Gly Gly Gly Gly Ile Glu Gly Pro
            20                  25                  30 acc ctt cgc caa tgg ctt gca gca cgc gca                            126
Thr Leu Arg Gln Trp Leu Ala Ala Arg Ala
        35                  40

<210> SEQ ID NO 376
<211> LENGTH: 42
<212> TYPE: PRT
<213> ORGANISM: Artificial Sequence
<220> FEATURE:
<223> OTHER INFORMATION: Fc-TMP-TMP

<400> SEQUENCE: 376

Lys Gly Gly Gly Gly Gly Ile Glu Gly Pro Thr Leu Arg Gln Trp Leu
1               5                   10                  15

Ala Ala Arg Ala Gly Gly Gly Gly Gly Gly Gly Ile Glu Gly Pro
            20                  25                  30

Thr Leu Arg Gln Trp Leu Ala Ala Arg Ala
        35                  40

<210> SEQ ID NO 377
<211> LENGTH: 39
<212> TYPE: PRT
<213> ORGANISM: Artificial Sequence
<220> FEATURE:
<223> OTHER INFORMATION: TMP-TMP-Fc

<400> SEQUENCE: 377

Thr Thr Thr Thr Thr Thr Cys Ala Thr Ala Thr Gly Ala Thr Cys Gly
1               5                   10                  15

Ala Ala Gly Gly Thr Cys Cys Gly Ala Cys Thr Cys Thr Gly Cys Gly
            20                  25                  30

Thr Cys Ala Gly Thr Gly Gly
        35

<210> SEQ ID NO 378
<211> LENGTH: 48
<212> TYPE: PRT
<213> ORGANISM: Artificial Sequence
<220> FEATURE:
<223> OTHER INFORMATION: TMP-TMP-Fc

<400> SEQUENCE: 378

Ala Gly Cys Ala Cys Gly Ala Gly Cys Ala Gly Cys Ala Gly Cys
1               5                   10                  15

Cys Ala Cys Thr Gly Ala Cys Gly Cys Ala Gly Ala Gly Thr Cys Gly
            20                  25                  30

Gly Ala Cys Cys Thr Thr Cys Gly Ala Thr Cys Ala Thr Ala Thr Gly
        35              40                  45
```

<210> SEQ ID NO 379
<211> LENGTH: 45
<212> TYPE: DNA
<213> ORGANISM: Artificial Sequence
<220> FEATURE:
<223> OTHER INFORMATION: TMP-TMP-Fc

<400> SEQUENCE: 379
ctggctgctc gtgctggtgg aggcggtggg gacaaaactc acaca       45

<210> SEQ ID NO 380
<211> LENGTH: 51
<212> TYPE: DNA
<213> ORGANISM: Artificial Sequence
<220> FEATURE:
<223> OTHER INFORMATION: TMP-TMP-Fc

<400> SEQUENCE: 380
ctggctgctc gtgctggcgg tggtggcgga gggggtggca ttgagggccc a       51

<210> SEQ ID NO 381
<211> LENGTH: 54
<212> TYPE: DNA
<213> ORGANISM: Artificial Sequence
<220> FEATURE:
<223> OTHER INFORMATION: TMP-TMP-Fc

<400> SEQUENCE: 381
aagccattgg cgaagggttg ggccctcaat gccaccccct ccgccaccac cgcc       54

<210> SEQ ID NO 382
<211> LENGTH: 54
<212> TYPE: DNA
<213> ORGANISM: Artificial Sequence
<220> FEATURE:
<223> OTHER INFORMATION: TMP-TMP-Fc

<400> SEQUENCE: 382
acccttcgcc aatggcttgc agcacgcgca gggggaggcg gtggggacaa aact       54

<210> SEQ ID NO 383
<211> LENGTH: 27
<212> TYPE: DNA
<213> ORGANISM: Artificial Sequence
<220> FEATURE:
<223> OTHER INFORMATION: TMP-TMP-Fc

<400> SEQUENCE: 383
cccaccgcct ccccctgcgc gtgctgc       27

<210> SEQ ID NO 384
<211> LENGTH: 189
<212> TYPE: DNA
<213> ORGANISM: Artificial Sequence
<220> FEATURE:
<223> OTHER INFORMATION: TMP-TMP-Fc
<220> FEATURE:
<221> NAME/KEY: CDS
<222> LOCATION: (10)..(180)
<223> OTHER INFORMATION:

<400> SEQUENCE: 384
tttttttcat atg atc gaa ggt ccg act ctg cgt cag tgg ctg gct gct cgt       51
          Met Ile Glu Gly Pro Thr Leu Arg Gln Trp Leu Ala Ala Arg
          1               5                   10

```
gct ggc ggt ggt ggc gga ggg ggt ggc att gag ggc cca acc ctt cgc      99
Ala Gly Gly Gly Gly Gly Gly Gly Gly Ile Glu Gly Pro Thr Leu Arg
 15              20                  25                  30 caa tgg ctg gct gct cgt gct ggt gga ggc ggt ggg gac aaa act ctg     147
Gln Trp Leu Ala Ala Arg Ala Gly Gly Gly Gly Gly Asp Lys Thr Leu
                 35                  40                  45 gct gct cgt gct ggt gga ggc ggt ggg gac aaa actcacaca              189
Ala Ala Arg Ala Gly Gly Gly Gly Gly Asp Lys
         50                  55
```

<210> SEQ ID NO 385
<211> LENGTH: 57
<212> TYPE: PRT
<213> ORGANISM: Artificial Sequence
<220> FEATURE:
<223> OTHER INFORMATION: TMP-TMP-Fc

<400> SEQUENCE: 385

```
Met Ile Glu Gly Pro Thr Leu Arg Gln Trp Leu Ala Ala Arg Ala Gly
 1               5                  10                  15

Gly Gly Gly Gly Gly Gly Ile Glu Gly Pro Thr Leu Arg Gln Trp
             20                  25                  30

Leu Ala Ala Arg Ala Gly Gly Gly Gly Gly Asp Lys Thr Leu Ala Ala
         35                  40                  45

Arg Ala Gly Gly Gly Gly Gly Asp Lys
         50                  55
```

<210> SEQ ID NO 386
<211> LENGTH: 141
<212> TYPE: DNA
<213> ORGANISM: Artificial Sequence
<220> FEATURE:
<223> OTHER INFORMATION: pAMG21

<400> SEQUENCE: 386

```
ctaattccgc tctcacctac caaacaatgc cccctgcaa aaataaatt catataaaaa      60 acatacagat aaccatctgc ggtgataaat tatctctggc ggtgttgaca taaataccac    120
tggcggtgat actgagcaca t                                             141
```

<210> SEQ ID NO 387
<211> LENGTH: 55
<212> TYPE: DNA
<213> ORGANISM: Artificial Sequence
<220> FEATURE:
<223> OTHER INFORMATION: pAMG21

<400> SEQUENCE: 387

```
cgatttgatt ctagaaggag gaataacata tggttaacgc gttggaattc ggtac         55
```

<210> SEQ ID NO 388
<211> LENGTH: 872
<212> TYPE: DNA
<213> ORGANISM: Artificial Sequence
<220> FEATURE:
<223> OTHER INFORMATION: GM221

<400> SEQUENCE: 388

```
ttattttcgt gcggccgcac cattatcacc gccagaggta aactagtcaa cacgcacggt     60
gttagatatt tatcccttgc ggtgatagat tgagcacatc gatttgattc tagaaggagg   120
gataatatat gagcacaaaa aagaaaccat taacacaaga gcagcttgag gacgcacgtc   180
gccttaaagc aatttatgaa aaaaagaaaa atgaacttgg cttatcccag gaatctgtcg   240
```

-continued

```
cagacaagat ggggatgggg cagtcaggcg ttggtgcttt atttaatggc atcaatgcat      300
taaatgctta taacgccgca ttgcttacaa aaattctcaa agttagcgtt gaagaattta      360
gcccttcaat cgccagagaa tctacgagat gtatgaagcg gttagtatgc agccgtcact      420
tagaagtgag tatgagtacc ctgttttttc tcatgttcag gcagggatgt tctcacctaa      480
gcttagaacc tttaccaaag gtgatgcgga gagatgggta agcacaacca aaaaagccag      540
tgattctgca ttctggcttg aggttgaagg taattccatg accgcaccaa caggctccaa      600
gccaagcttt cctgacggaa tgttaattct cgttgaccct gagcaggctg ttgagccagg      660
tgatttctgc atagccagac ttgggggtga tgagtttacc ttcaagaaac tgatcaggga      720
tagcggtcag gtgtttttac aaccactaaa cccacagtac ccaatgatcc catgcaatga      780
gagttgttcc gttgtgggga aagttatcgc tagtcagtgg cctgaagaga cgtttggctg      840
atagactagt ggatccacta gtgtttctgc cc                                    872
```

<210> SEQ ID NO 389
<211> LENGTH: 1197
<212> TYPE: DNA
<213> ORGANISM: Artificial Sequence
<220> FEATURE:
<223> OTHER INFORMATION: GM221

<400> SEQUENCE: 389

```
ggcggaaacc gacgtccatc gaatggtgca aaacctttcg cggtatggca tgatagcgcc      60
cggaagagag tcaattcagg gtggtgaatg tgaaaccagt aacgttatac gatgtcgcag     120
agtatgccgg tgtctcttat cagaccgttt cccgcgtggt gaaccaggcc agccacgttt     180
ctgcgaaaac gcgggaaaaa gtcgaagcgg cgatggcgga gctgaattac attcccaacc     240
gcgtggcaca acaactggcg ggcaaacagt cgctcctgat tggcgttgcc acctccagtc     300
tggccctgca cgcgccgtcg caaattgtcg cggcgattaa atctcgcgcc gatcaactgg     360
gtgccagcgt ggtggtgtcg atggtagaac gaagcggcgt cgaagcctgt aaagcggcgg     420
tgcacaatct tctcgcgcaa cgcgtcagtg gctgatcat taactatccg ctggatgacc     480
aggatgccat tgctgtggaa gctgcctgca ctaatgttcc ggcgttattt cttgatgtct     540
ctgaccagac acccatcaac agtattattt tctcccatga agacggtacg cgactgggcg     600
tggagcatct ggtcgcattg ggtcaccagc aaatcgcgct gttagcgggc ccattaagtt     660
ctgtctcggc gcgtctgcgt ctggctggct ggcataaata tctcactcgc aatcaaattc     720
agccgatagc ggaacgggaa ggcgactgga gtgccatgtc cggttttcaa caaaccatgc     780
aaatgctgaa tgagggcatc gttcccactg cgatgctggt tgccaacgat cagatggcgc     840
tgggcgcaat gcgcgccatt accgagtccg ggctgcgcgt tggtgcggat atctcggtag     900
tgggatacga cgataccgaa gacagctcat gttatatccc gccgttaacc accatcaaac     960
aggattttcg cctgctgggg caaaccagcg tggaccgctt gctgcaactc tctcagggcc    1020
aggcggtgaa gggcaatcag ctgttgcccg tctcactggt gaaagaaaaa accaccctgg    1080
cgcccaatac gcaaaccgcc tctccccgcg cgttggccga ttcattaatg cagctggcac    1140
gacaggtttc ccgactggaa agcggacagt aagtaccat aggatccagg cacagga         1197
```

<210> SEQ ID NO 390
<211> LENGTH: 61
<212> TYPE: DNA
<213> ORGANISM: Artificial Sequence
<220> FEATURE:

<223> OTHER INFORMATION: Fc-EMP

<400> SEQUENCE: 390
tatgaaaggt ggaggtggtg gtggaggtac ttactcttgc cacttcggcc cgctgacttg    60
g                                                                   61

<210> SEQ ID NO 391
<211> LENGTH: 72
<212> TYPE: DNA
<213> ORGANISM: Artificial Sequence
<220> FEATURE:
<223> OTHER INFORMATION: Fc-EMP

<400> SEQUENCE: 391
cggtttgcaa acccaagtca gcgggccgaa gtggcaagag taagtacctc caccaccacc    60
tccacctttc at                                                       72

<210> SEQ ID NO 392
<211> LENGTH: 57
<212> TYPE: DNA
<213> ORGANISM: Artificial Sequence
<220> FEATURE:
<223> OTHER INFORMATION: Fc-EMP

<400> SEQUENCE: 392
gtttgcaaac cgcagggtgg cggcggcggc ggcggtggta cctattcctg tcatttt      57

<210> SEQ ID NO 393
<211> LENGTH: 60
<212> TYPE: DNA
<213> ORGANISM: Artificial Sequence
<220> FEATURE:
<223> OTHER INFORMATION: Fc-EMP

<400> SEQUENCE: 393
ccaggtcagc gggccaaaat gacaggaata ggtaccaccg ccgccgccgc cgccaccctg    60

<210> SEQ ID NO 394
<211> LENGTH: 118
<212> TYPE: DNA
<213> ORGANISM: Artificial Sequence
<220> FEATURE:
<223> OTHER INFORMATION: Fc-EMP
<220> FEATURE:
<221> NAME/KEY: CDS
<222> LOCATION: (2)..(118)
<223> OTHER INFORMATION:

<400> SEQUENCE: 394 t atg aaa ggt gga ggt ggt ggt gga ggt act tac tct tgc cac ttc ggc    49
  Met Lys Gly Gly Gly Gly Gly Gly Gly Thr Tyr Ser Cys His Phe Gly
  1               5                   10                  15 ccg ctg act tgg gtt tgc aaa ccg cag ggt ggc ggc ggc ggc ggc ggt      97
Pro Leu Thr Trp Val Cys Lys Pro Gln Gly Gly Gly Gly Gly Gly Gly
            20                  25                  30 ggt acc tat tcc tgt cat ttt                                         118
Gly Thr Tyr Ser Cys His Phe
        35

<210> SEQ ID NO 395
<211> LENGTH: 39
<212> TYPE: PRT
<213> ORGANISM: Artificial Sequence
<220> FEATURE:
<223> OTHER INFORMATION: Fc-EMP

<400> SEQUENCE: 395

Met Lys Gly Gly Gly Gly Gly Gly Thr Tyr Ser Cys His Phe Gly
1               5                   10                  15

Pro Leu Thr Trp Val Cys Lys Pro Gln Gly Gly Gly Gly Gly
            20                  25                  30

Gly Thr Tyr Ser Cys His Phe
        35

<210> SEQ ID NO 396
<211> LENGTH: 61
<212> TYPE: DNA
<213> ORGANISM: Artificial Sequence
<220> FEATURE:
<223> OTHER INFORMATION: Fc-EMP

<400> SEQUENCE: 396
gcagaagagc ctctccctgt ctccgggtaa aggtggaggt ggtggtggag gtacttactc     60
t                                                                     61

<210> SEQ ID NO 397
<211> LENGTH: 40
<212> TYPE: DNA
<213> ORGANISM: Artificial Sequence
<220> FEATURE:
<223> OTHER INFORMATION: Fc-EMP

<400> SEQUENCE: 397
ctaattggat ccacgagatt aaccaccctg cggtttgcaa                            40

<210> SEQ ID NO 398
<211> LENGTH: 18
<212> TYPE: PRT
<213> ORGANISM: Artificial Sequence
<220> FEATURE:
<223> OTHER INFORMATION: Fc-EMP

<400> SEQUENCE: 398

Gly Glu Arg Trp Cys Phe Asp Gly Pro Leu Thr Trp Val Cys Gly Glu
1               5                   10                  15

Glu Ser

<210> SEQ ID NO 399
<211> LENGTH: 61
<212> TYPE: DNA
<213> ORGANISM: Artificial Sequence
<220> FEATURE:
<223> OTHER INFORMATION: Fc-EMP

<400> SEQUENCE: 399
agagtaagta cctccaccac cacctccacc tttacccgga gacaggagag gctcttctg       60
c                                                                     61

<210> SEQ ID NO 400
<211> LENGTH: 61
<212> TYPE: DNA
<213> ORGANISM: Artificial Sequence
<220> FEATURE:
<223> OTHER INFORMATION: EMP-Fc

<400> SEQUENCE: 400
ggcccgctga cctgggtatg taagccacaa gggggtgggg gaggcggggg gtaatctcga     60 g								61

<210> SEQ ID NO 401
<211> LENGTH: 50
<212> TYPE: DNA
<213> ORGANISM: Artificial Sequence
<220> FEATURE:
<223> OTHER INFORMATION: EMP-Fc

<400> SEQUENCE: 401
gatcctcgag attaccccccc gcctccccca ccccttgtg gcttacatac						50

<210> SEQ ID NO 402
<211> LENGTH: 118
<212> TYPE: DNA
<213> ORGANISM: Artificial Sequence
<220> FEATURE:
<223> OTHER INFORMATION: EMP-Fc
<220> FEATURE:
<221> NAME/KEY: CDS
<222> LOCATION: (1)..(108)
<223> OTHER INFORMATION:

<400> SEQUENCE: 402

```
gtt tgc aaa ccg cag ggt ggc ggc ggc ggc ggt ggt acc tat tcc      48
Val Cys Lys Pro Gln Gly Gly Gly Gly Gly Gly Gly Thr Tyr Ser
1               5                   10                  15 tgt cat ttt ggc ccg ctg acc tgg gta tgt aag cca caa ggg ggt ggg  96
Cys His Phe Gly Pro Leu Thr Trp Val Cys Lys Pro Gln Gly Gly Gly
                20                  25                  30 gga ggc ggg ggg taatctcgag                                       118
Gly Gly Gly Gly
        35
```

<210> SEQ ID NO 403
<211> LENGTH: 36
<212> TYPE: PRT
<213> ORGANISM: Artificial Sequence
<220> FEATURE:
<223> OTHER INFORMATION: EMP-Fc

<400> SEQUENCE: 403

```
Val Cys Lys Pro Gln Gly Gly Gly Gly Gly Gly Gly Thr Tyr Ser
1               5                   10                  15

Cys His Phe Gly Pro Leu Thr Trp Val Cys Lys Pro Gln Gly Gly Gly
                20                  25                  30

Gly Gly Gly Gly
        35
```

<210> SEQ ID NO 404
<211> LENGTH: 39
<212> TYPE: DNA
<213> ORGANISM: Artificial Sequence
<220> FEATURE:
<223> OTHER INFORMATION: EMP-Fc

<400> SEQUENCE: 404
ttatttcata tgaaaggtgg taactattcc tgtcatttt						39

<210> SEQ ID NO 405
<211> LENGTH: 43
<212> TYPE: DNA
<213> ORGANISM: Artificial Sequence
<220> FEATURE:
<223> OTHER INFORMATION: EMP-Fc

```
<400> SEQUENCE: 405
tggacatgtg tgagttttgt ccccccccgcc tcccccaccc cct        43

<210> SEQ ID NO 406
<211> LENGTH: 43
<212> TYPE: DNA
<213> ORGANISM: Artificial Sequence
<220> FEATURE:
<223> OTHER INFORMATION: EMP-Fc

<400> SEQUENCE: 406 aggggtggg ggaggcgggg gggacaaaac tcacacatgt cca         43

<210> SEQ ID NO 407
<211> LENGTH: 20
<212> TYPE: DNA
<213> ORGANISM: Artificial Sequence
<220> FEATURE:
<223> OTHER INFORMATION: EMP-Fc

<400> SEQUENCE: 407
gttattgctc agcggtggca                                   20

<210> SEQ ID NO 408
<211> LENGTH: 60
<212> TYPE: DNA
<213> ORGANISM: Artificial Sequence
<220> FEATURE:
<223> OTHER INFORMATION: EMP-EMP-Fc

<400> SEQUENCE: 408 tttttatcg atttgattct agatttgagt tttaactttt agaaggagga ataaaatatg    60

<210> SEQ ID NO 409
<211> LENGTH: 41
<212> TYPE: DNA
<213> ORGANISM: Artificial Sequence
<220> FEATURE:
<223> OTHER INFORMATION: EMP-EMP-Fc

<400> SEQUENCE: 409
taaaagttaa aactcaaatc tagaatcaaa tcgataaaaa a           41

<210> SEQ ID NO 410
<211> LENGTH: 51
<212> TYPE: DNA
<213> ORGANISM: Artificial Sequence
<220> FEATURE:
<223> OTHER INFORMATION: EMP-EMP-Fc

<400> SEQUENCE: 410
ggaggtactt actcttgcca cttcggcccg ctgacttggg tttgcaaacc g   51

<210> SEQ ID NO 411
<211> LENGTH: 55
<212> TYPE: DNA
<213> ORGANISM: Artificial Sequence
<220> FEATURE:
<223> OTHER INFORMATION: EMP-EMP-Fc

<400> SEQUENCE: 411
agtcagcggg ccgaagtggc aagagtaagt acctcccata ttttattcct ccttc   55

<210> SEQ ID NO 412
<211> LENGTH: 60
```

<212> TYPE: DNA
<213> ORGANISM: Artificial Sequence
<220> FEATURE:
<223> OTHER INFORMATION: EMP-EMP-Fc

<400> SEQUENCE: 412
cagggtggcg gcggcggcgg cggtggtacc tattcctgtc attttggccc gctgacctgg    60

<210> SEQ ID NO 413
<211> LENGTH: 60
<212> TYPE: DNA
<213> ORGANISM: Artificial Sequence
<220> FEATURE:
<223> OTHER INFORMATION: EMP-EMP-Fc

<400> SEQUENCE: 413
aaaatgacag gaataggtac caccgccgcc gccgccgcca ccctgcggtt tgcaaaccca    60

<210> SEQ ID NO 414
<211> LENGTH: 57
<212> TYPE: DNA
<213> ORGANISM: Artificial Sequence
<220> FEATURE:
<223> OTHER INFORMATION: EMP-EMP-Fc

<400> SEQUENCE: 414
gtatgtaagc cacaaggggg tgggggaggc gggggggaca aaactcacac atgtcca    57

<210> SEQ ID NO 415
<211> LENGTH: 60
<212> TYPE: DNA
<213> ORGANISM: Artificial Sequence
<220> FEATURE:
<223> OTHER INFORMATION: EMP-EMP-Fc

<400> SEQUENCE: 415
agttttgtcc ccccgcctc ccccaccccc ttgtggctta catacccagg tcagcgggcc    60

<210> SEQ ID NO 416
<211> LENGTH: 228
<212> TYPE: DNA
<213> ORGANISM: Artificial Sequence
<220> FEATURE:
<223> OTHER INFORMATION: EMP-EMP-Fc
<220> FEATURE:
<221> NAME/KEY: CDS
<222> LOCATION: (58)..(228)
<223> OTHER INFORMATION:

<400> SEQUENCE: 416 tttttatcg atttgattct agatttgagt tttaactttt agaaggagga ataaaat    57 atg gga ggt act tac tct tgc cac ttc ggc ccg ctg act tgg gtt tgc    105
Met Gly Gly Thr Tyr Ser Cys His Phe Gly Pro Leu Thr Trp Val Cys
1               5                   10                  15 aaa ccg cag ggt ggc ggc ggc ggc ggt ggt acc tat tcc tgt cat    153
Lys Pro Gln Gly Gly Gly Gly Gly Gly Gly Thr Tyr Ser Cys His
            20                  25                  30 ttt ggc ccg ctg acc tgg gta tgt aag cca caa ggg ggt ggg gga ggc    201
Phe Gly Pro Leu Thr Trp Val Cys Lys Pro Gln Gly Gly Gly Gly
        35                  40                  45 ggg ggg gac aaa act cac aca tgt cca    228
Gly Gly Asp Lys Thr His Thr Cys Pro
    50                  55

<210> SEQ ID NO 417

```
<211> LENGTH: 57
<212> TYPE: PRT
<213> ORGANISM: Artificial Sequence
<220> FEATURE:
<223> OTHER INFORMATION: EMP-EMP-Fc

<400> SEQUENCE: 417

Met Gly Gly Thr Tyr Ser Cys His Phe Gly Pro Leu Thr Trp Val Cys
1               5                   10                  15

Lys Pro Gln Gly Gly Gly Gly Gly Gly Thr Tyr Ser Cys His
            20                  25                  30

Phe Gly Pro Leu Thr Trp Val Cys Lys Pro Gln Gly Gly Gly Gly
        35                  40                  45

Gly Gly Asp Lys Thr His Thr Cys Pro
    50                  55

<210> SEQ ID NO 418
<211> LENGTH: 40
<212> TYPE: DNA
<213> ORGANISM: Artificial Sequence
<220> FEATURE:
<223> OTHER INFORMATION: Fc-EMP-EMP

<400> SEQUENCE: 418
ctaattggat cctcgagatt aaccccttg tggcttacat                                40

<210> SEQ ID NO 419
<211> LENGTH: 16
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (1, 3, 9, 14, 15)..(16)
<223> OTHER INFORMATION: Xaa (Positions 1, 3, 9, 14, 15 & 16) can be
      any one of the 20 L-amino acids
<220> FEATURE:
<221> NAME/KEY: misc_feature
<222> LOCATION: (5)..(5)
<223> OTHER INFORMATION: Xaa can be R, H, L or W
<220> FEATURE:
<221> NAME/KEY: misc_feature
<222> LOCATION: (6)..(6)
<223> OTHER INFORMATION: Xaa can be M, F or I
<220> FEATURE:
<221> NAME/KEY: misc_feature
<222> LOCATION: (12)..(12)
<223> OTHER INFORMATION: Xaa can be D, E, I, L or V
<220> FEATURE:
<221> NAME/KEY: misc_feature
<222> LOCATION: (13)..(13)
<223> OTHER INFORMATION: Xaa can be C, A, a-amino-y-bromobutyric acid or
      Hoc

<400> SEQUENCE: 419

Xaa Tyr Xaa Xaa Xaa Xaa Gly Pro Xaa Thr Trp Xaa Xaa Xaa Xaa Xaa
1               5                   10                  15

<210> SEQ ID NO 420
<211> LENGTH: 16
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (1, 3, 5, 6, 9, 12, 14, 15)..(16)
<223> OTHER INFORMATION: Xaa = any amino acid residue
```

```
<400> SEQUENCE: 420

Xaa Tyr Xaa Cys Xaa Xaa Gly Pro Xaa Thr Trp Xaa Cys Xaa Xaa Xaa
1               5                   10                  15

<210> SEQ ID NO 421
<211> LENGTH: 10
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (2)..(2)
<223> OTHER INFORMATION: Xaa can be R, H, L, or W
<220> FEATURE:
<221> NAME/KEY: misc_feature
<222> LOCATION: (3)..(3)
<223> OTHER INFORMATION: Xaa can be M, F, or I
<220> FEATURE:
<221> NAME/KEY: misc_feature
<222> LOCATION: (6)..(6)
<223> OTHER INFORMATION: Xaa is independently selected from any one of
      the 20 genetically coded L-amino acids or the steroisomeric D-
      amino acids
<220> FEATURE:
<221> NAME/KEY: misc_feature
<222> LOCATION: (9)..(9)
<223> OTHER INFORMATION: Xaa can be D, E, I, L, or V.

<400> SEQUENCE: 421

Cys Xaa Xaa Gly Pro Xaa Thr Trp Xaa Cys
1               5                   10

<210> SEQ ID NO 422
<211> LENGTH: 19
<212> TYPE: PRT
<213> ORGANISM: Artificial Sequence
<220> FEATURE:
<223> OTHER INFORMATION: EPO-MIMETIC PEPTIDE

<400> SEQUENCE: 422

Gly Gly Thr Tyr Ser Cys His Gly Pro Leu Thr Trp Val Cys Lys Pro
1               5                   10                  15

Gln Gly Gly

<210> SEQ ID NO 423
<211> LENGTH: 19
<212> TYPE: PRT
<213> ORGANISM: Artificial Sequence
<220> FEATURE:
<223> OTHER INFORMATION: EPO-MIMETIC PEPTIDE

<400> SEQUENCE: 423

Val Gly Asn Tyr Met Ala His Met Gly Pro Ile Thr Trp Val Cys Arg
1               5                   10                  15

Pro Gly Gly

<210> SEQ ID NO 424
<211> LENGTH: 18
<212> TYPE: PRT
<213> ORGANISM: Artificial Sequence
<220> FEATURE:
<223> OTHER INFORMATION: EPO-MIMETIC PEPTIDE

<400> SEQUENCE: 424

Gly Gly Pro His His Val Tyr Ala Cys Arg Met Gly Pro Leu Thr Trp
1               5                   10                  15
```

Ile Cys

<210> SEQ ID NO 425
<211> LENGTH: 18
<212> TYPE: PRT
<213> ORGANISM: Artificial Sequence
<220> FEATURE:
<223> OTHER INFORMATION: EPO-MIMETIC PEPTIDE

<400> SEQUENCE: 425

Gly Gly Thr Tyr Ser Cys His Phe Gly Pro Leu Thr Trp Val Cys Lys
1               5                   10                  15

Pro Gln

<210> SEQ ID NO 426
<211> LENGTH: 20
<212> TYPE: PRT
<213> ORGANISM: Artificial Sequence
<220> FEATURE:
<223> OTHER INFORMATION: EPO-MIMETIC PEPTIDE

<400> SEQUENCE: 426

Gly Gly Leu Tyr Ala Cys His Met Gly Pro Met Thr Trp Val Cys Gln
1               5                   10                  15

Pro Leu Arg Gly
            20

<210> SEQ ID NO 427
<211> LENGTH: 22
<212> TYPE: PRT
<213> ORGANISM: Artificial Sequence
<220> FEATURE:
<223> OTHER INFORMATION: EPO-MIMETIC PEPTIDE

<400> SEQUENCE: 427

Thr Ile Ala Gln Tyr Ile Cys Tyr Met Gly Pro Glu Thr Trp Glu Cys
1               5                   10                  15

Arg Pro Ser Pro Lys Ala
            20

<210> SEQ ID NO 428
<211> LENGTH: 13
<212> TYPE: PRT
<213> ORGANISM: Artificial Sequence
<220> FEATURE:
<223> OTHER INFORMATION: EPO-MIMETIC PEPTIDE

<400> SEQUENCE: 428

Tyr Ser Cys His Phe Gly Pro Leu Thr Trp Val Cys Lys
1               5                   10

<210> SEQ ID NO 429
<211> LENGTH: 11
<212> TYPE: PRT
<213> ORGANISM: Artificial Sequence
<220> FEATURE:
<223> OTHER INFORMATION: EPO-MIMETIC PEPTIDE

<400> SEQUENCE: 429

Tyr Cys His Phe Gly Pro Leu Thr Trp Val Cys
1               5                   10

<210> SEQ ID NO 430
<211> LENGTH: 17
<212> TYPE: PRT

```
<213> ORGANISM: Artificial Sequence
<220> FEATURE:
<223> OTHER INFORMATION: UKR ANTAGONIST PEPTIDE

<400> SEQUENCE: 430

Ala Glu Pro Val Tyr Gln Tyr Glu Leu Asp Ser Tyr Leu Arg Ser Tyr
1               5                   10                  15
Tyr

<210> SEQ ID NO 431
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 431

Ala Glu Leu Asp Leu Ser Thr Phe Tyr Asp Ile Gln Tyr Leu Leu Arg
1               5                   10                  15
Thr

<210> SEQ ID NO 432
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 432

Ala Glu Phe Phe Lys Leu Gly Pro Asn Gly Tyr Val Tyr Leu His Ser
1               5                   10                  15
Ala

<210> SEQ ID NO 433
<211> LENGTH: 11
<212> TYPE: PRT
<213> ORGANISM: Artificial Sequence
<220> FEATURE:
<223> OTHER INFORMATION: UKR ANTAGONIST PEPTIDE
<220> FEATURE:
<221> NAME/KEY: misc_feature
<222> LOCATION: (4, 5)..(6)
<223> OTHER INFORMATION: Xaa = any amino acid

<400> SEQUENCE: 433

Phe Lys Leu Xaa Xaa Xaa Gly Tyr Val Tyr Leu
1               5                   10

<210> SEQ ID NO 434
<211> LENGTH: 17
<212> TYPE: PRT
<213> ORGANISM: Artificial Sequence
<220> FEATURE:
<223> OTHER INFORMATION: UKR ANTAGONIST PEPTIDE

<400> SEQUENCE: 434

Ala Glu Ser Thr Tyr His His Leu Ser Leu Gly Tyr Met Tyr Thr Leu
1               5                   10                  15
Asn

<210> SEQ ID NO 435
<211> LENGTH: 11
<212> TYPE: PRT
<213> ORGANISM: Artificial Sequence
<220> FEATURE:
```

```
<223> OTHER INFORMATION: UKR ANTAGONIST PEPTIDE
<220> FEATURE:
<221> NAME/KEY: misc_feature
<222> LOCATION: (3, 5)..(6)
<223> OTHER INFORMATION: Xaa = any amino acid

<400> SEQUENCE: 435

Tyr His Xaa Leu Xaa Xaa Gly Tyr Met Tyr Thr
1               5                   10

<210> SEQ ID NO 436
<211> LENGTH: 6
<212> TYPE: PRT
<213> ORGANISM: Artificial Sequence
<220> FEATURE:
<223> OTHER INFORMATION: MAST CELL ANTAGONISTS/PROTEASE INHIBITOR
      PEPTIDE

<400> SEQUENCE: 436

Arg Asn Arg Gln Lys Thr
1               5

<210> SEQ ID NO 437
<211> LENGTH: 4
<212> TYPE: PRT
<213> ORGANISM: Artificial Sequence
<220> FEATURE:
<223> OTHER INFORMATION: MAST CELL ANTAGONISTS/PROTEASE INHIBITOR
      PEPTIDE

<400> SEQUENCE: 437

Arg Asn Arg Gln
1

<210> SEQ ID NO 438
<211> LENGTH: 5
<212> TYPE: PRT
<213> ORGANISM: Artificial Sequence
<220> FEATURE:
<223> OTHER INFORMATION: MAST CELL ANTAGONISTS/PROTEASE INHIBITOR
      PEPTIDE

<400> SEQUENCE: 438

Arg Asn Arg Gln Lys
1               5

<210> SEQ ID NO 439
<211> LENGTH: 5
<212> TYPE: PRT
<213> ORGANISM: Artificial Sequence
<220> FEATURE:
<223> OTHER INFORMATION: MAST CELL ANTAGONISTS/PROTEASE INHIBITOR
      PEPTIDE

<400> SEQUENCE: 439

Asn Arg Gln Lys Thr
1               5

<210> SEQ ID NO 440
<211> LENGTH: 4
<212> TYPE: PRT
<213> ORGANISM: Artificial Sequence
<220> FEATURE:
<223> OTHER INFORMATION: MAST CELL ANTAGONISTS/PROTEASE INHIBITOR
      PEPTIDE

<400> SEQUENCE: 440

Arg Gln Lys Thr
```

```
<210> SEQ ID NO 441
<211> LENGTH: 7
<212> TYPE: PRT
<213> ORGANISM: Artificial Sequence
<220> FEATURE:
<223> OTHER INFORMATION: INTEGRIN-BINDING PEPTIDE
<220> FEATURE:
<221> NAME/KEY: misc_feature
<222> LOCATION: (2, 5)..(7)
<223> OTHER INFORMATION: Xaa = any amino acid

<400> SEQUENCE: 441

Arg Xaa Glu Thr Xaa Trp Xaa
1               5

<210> SEQ ID NO 442
<211> LENGTH: 7
<212> TYPE: PRT
<213> ORGANISM: Artificial Sequence
<220> FEATURE:
<223> OTHER INFORMATION: INTEGRIN-BINDING PEPTIDE
<220> FEATURE:
<221> NAME/KEY: misc_feature
<222> LOCATION: (2, 5)..(7)
<223> OTHER INFORMATION: Xaa = any amino acid

<400> SEQUENCE: 442

Arg Xaa Glu Thr Xaa Trp Xaa
1               5

<210> SEQ ID NO 443
<211> LENGTH: 5
<212> TYPE: PRT
<213> ORGANISM: Artificial Sequence
<220> FEATURE:
<223> OTHER INFORMATION: INTEGRIN-BINDING PEPTIDE
<220> FEATURE:
<221> NAME/KEY: misc_feature
<222> LOCATION: (5)..(6)
<223> OTHER INFORMATION: Xaa = any amino acid

<400> SEQUENCE: 443

Arg Gly Asp Gly Xaa
1               5

<210> SEQ ID NO 444
<211> LENGTH: 7
<212> TYPE: PRT
<213> ORGANISM: Artificial Sequence
<220> FEATURE:
<223> OTHER INFORMATION: INTEGRIN-BINDING PEPTIDE
<220> FEATURE:
<221> NAME/KEY: misc_feature
<222> LOCATION: (6)..(6)
<223> OTHER INFORMATION: Xaa = any amino acid

<400> SEQUENCE: 444

Cys Arg Gly Asp Gly Xaa Cys
1               5

<210> SEQ ID NO 445
<211> LENGTH: 15
<212> TYPE: PRT
<213> ORGANISM: Artificial Sequence
<220> FEATURE:
<223> OTHER INFORMATION: INTEGRIN-BINDING PEPTIDE
<220> FEATURE:
<221> NAME/KEY: misc_feature
```

```
<222> LOCATION: (2, 3, 4, 8, 9, 10, 11, 12, 13)..(14)
<223> OTHER INFORMATION: Xaa = any amino acid

<400> SEQUENCE: 445

Cys Xaa Xaa Xaa Arg Leu Asp Xaa Xaa Xaa Xaa Xaa Xaa Xaa Cys
1               5                   10                  15

<210> SEQ ID NO 446
<211> LENGTH: 9
<212> TYPE: PRT
<213> ORGANISM: Artificial Sequence
<220> FEATURE:
<223> OTHER INFORMATION: INTEGRIN-BINDING PEPTIDE

<400> SEQUENCE: 446

Cys Ala Arg Arg Leu Asp Ala Pro Cys
1               5

<210> SEQ ID NO 447
<211> LENGTH: 9
<212> TYPE: PRT
<213> ORGANISM: Artificial Sequence
<220> FEATURE:
<223> OTHER INFORMATION: INTEGRIN-BINDING PEPTIDE

<400> SEQUENCE: 447

Cys Pro Ser Arg Leu Asp Ser Pro Cys
1               5

<210> SEQ ID NO 448
<211> LENGTH: 9
<212> TYPE: PRT
<213> ORGANISM: Artificial Sequence
<220> FEATURE:
<223> OTHER INFORMATION: INTEGRIN-BINDING PEPTIDE
<220> FEATURE:
<221> NAME/KEY: misc_feature
<222> LOCATION: (1, 2, 3, 7, 8)..(9)
<223> OTHER INFORMATION: Xaa are capable of forming a cyclizing bond
<220> FEATURE:
<221> NAME/KEY: misc_feature
<222> LOCATION: (2)..(5)
<223> OTHER INFORMATION: Feature at 1, 5 is an amino acid capable of
      forming a cyclying bond and attached to 1-5 amino acid linker

<400> SEQUENCE: 448

Xaa Xaa Xaa Arg Gly Asp Xaa Xaa Xaa
1               5

<210> SEQ ID NO 449
<211> LENGTH: 9
<212> TYPE: PRT
<213> ORGANISM: Artificial Sequence
<220> FEATURE:
<223> OTHER INFORMATION: INTEGRIN-BINDING PEPTIDE
<220> FEATURE:
<221> NAME/KEY: misc_feature
<222> LOCATION: (2)..(8)
<223> OTHER INFORMATION: Xaa = any amino acid

<400> SEQUENCE: 449

Cys Xaa Cys Arg Gly Asp Cys Xaa Cys
1               5

<210> SEQ ID NO 450
<211> LENGTH: 9
<212> TYPE: PRT
<213> ORGANISM: Artificial Sequence
<220> FEATURE:
```

```
<223> OTHER INFORMATION: INTEGRIN-BINDING PEPTIDE

<400> SEQUENCE: 450

Cys Asp Cys Arg Gly Asp Cys Phe Cys
1               5

<210> SEQ ID NO 451
<211> LENGTH: 9
<212> TYPE: PRT
<213> ORGANISM: Artificial Sequence
<220> FEATURE:
<223> OTHER INFORMATION: INTEGRIN-BINDING PEPTIDE

<400> SEQUENCE: 451

Cys Asp Cys Arg Gly Asp Cys Leu Cys
1               5

<210> SEQ ID NO 452
<211> LENGTH: 9
<212> TYPE: PRT
<213> ORGANISM: Artificial Sequence
<220> FEATURE:
<223> OTHER INFORMATION: INTEGRIN-BINDING PEPTIDE

<400> SEQUENCE: 452

Cys Leu Cys Arg Gly Asp Cys Ile Cys
1               5

<210> SEQ ID NO 453
<211> LENGTH: 8
<212> TYPE: PRT
<213> ORGANISM: Artificial Sequence
<220> FEATURE:
<223> OTHER INFORMATION: INTEGRIN-BINDING PEPTIDE
<220> FEATURE:
<221> NAME/KEY: misc_feature
<222> LOCATION: (1, 2, 5, 6, 7)..(8)
<223> OTHER INFORMATION: Xaa = any amino acid

<400> SEQUENCE: 453

Xaa Xaa Asp Asp Xaa Xaa Xaa Xaa
1               5

<210> SEQ ID NO 454
<211> LENGTH: 10
<212> TYPE: PRT
<213> ORGANISM: Artificial Sequence
<220> FEATURE:
<223> OTHER INFORMATION: INTEGRIN-BINDING PEPTIDE
<220> FEATURE:
<221> NAME/KEY: misc_feature
<222> LOCATION: (1, 2, 3, 6, 7, 8, 9)..(10)
<223> OTHER INFORMATION: Xaa = any amino acid

<400> SEQUENCE: 454

Xaa Xaa Xaa Asp Asp Xaa Xaa Xaa Xaa Xaa
1               5                   10

<210> SEQ ID NO 455
<211> LENGTH: 8
<212> TYPE: PRT
<213> ORGANISM: Artificial Sequence
<220> FEATURE:
<223> OTHER INFORMATION: INTEGRIN-BINDING PEPTIDE

<400> SEQUENCE: 455

Cys Trp Asp Asp Gly Trp Leu Cys
1               5
```

```
<210> SEQ ID NO 456
<211> LENGTH: 9
<212> TYPE: PRT
<213> ORGANISM: Artificial Sequence
<220> FEATURE:
<223> OTHER INFORMATION: INTEGRIN-BINDING PEPTIDE

<400> SEQUENCE: 456

Cys Trp Asp Asp Leu Trp Trp Leu Cys
1               5

<210> SEQ ID NO 457
<211> LENGTH: 8
<212> TYPE: PRT
<213> ORGANISM: Artificial Sequence
<220> FEATURE:
<223> OTHER INFORMATION: INTEGRIN-BINDING PEPTIDE

<400> SEQUENCE: 457

Cys Trp Asp Asp Gly Leu Met Cys
1               5

<210> SEQ ID NO 458
<211> LENGTH: 8
<212> TYPE: PRT
<213> ORGANISM: Artificial Sequence
<220> FEATURE:
<223> OTHER INFORMATION: INTEGRIN-BINDING PEPTIDE

<400> SEQUENCE: 458

Cys Trp Asp Asp Gly Trp Met Cys
1               5

<210> SEQ ID NO 459
<211> LENGTH: 9
<212> TYPE: PRT
<213> ORGANISM: Artificial Sequence
<220> FEATURE:
<223> OTHER INFORMATION: INTEGRIN-BINDING PEPTIDE

<400> SEQUENCE: 459

Cys Ser Trp Asp Asp Gly Trp Leu Cys
1               5

<210> SEQ ID NO 460
<211> LENGTH: 9
<212> TYPE: PRT
<213> ORGANISM: Artificial Sequence
<220> FEATURE:
<223> OTHER INFORMATION: INTEGRIN-BINDING PEPTIDE

<400> SEQUENCE: 460

Cys Pro Asp Asp Leu Trp Trp Leu Cys
1               5

<210> SEQ ID NO 461
<211> LENGTH: 12
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (2)..(8)
<223> OTHER INFORMATION: Xaa can be any of the 20 L-amino acids
<220> FEATURE:
<221> NAME/KEY: misc_feature
```

```
<222> LOCATION: (3)..(3)
<223> OTHER INFORMATION: Xaa can be C, A, a-amino-y-bromobutyric acid
      or Hoc
<220> FEATURE:
<221> NAME/KEY: misc_feature
<222> LOCATION: (4)..(4)
<223> OTHER INFORMATION: Xaa can be R, H, L or W
<220> FEATURE:
<221> NAME/KEY: misc_feature
<222> LOCATION: (5)..(5)
<223> OTHER INFORMATION: Xaa can be M, F or I; Xaa
<220> FEATURE:
<221> NAME/KEY: misc_feature
<222> LOCATION: (11)..(11)
<223> OTHER INFORMATION: Xaa can be D, E, I, L or V
<220> FEATURE:
<221> NAME/KEY: misc_feature
<222> LOCATION: (12)..(12)
<223> OTHER INFORMATION: Xaa can be C, A, a-amino-y-bromobutyric acid or
      Hoc; provided that Xaa (Pos3 or 12) is C or Hoc.

<400> SEQUENCE: 461

Tyr Xaa Xaa Xaa Xaa Gly Pro Xaa Thr Trp Xaa Xaa
1               5                   10

<210> SEQ ID NO 462
<211> LENGTH: 16
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 462

Cys Gln Asn Arg Tyr Thr Asp Leu Val Ala Ile Gln Asn Lys Asn Glu
1               5                   10                  15

<210> SEQ ID NO 463
<211> LENGTH: 17
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 463

Ala Glu Asn Trp Ala Asp Asn Glu Pro Asn Asn Lys Arg Asn Asn Glu
1               5                   10                  15

Asp

<210> SEQ ID NO 464
<211> LENGTH: 19
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 464

Arg Lys Asn Asn Lys Thr Trp Thr Trp Val Gly Thr Lys Lys Ala Leu
1               5                   10                  15

Thr Asn Glu

<210> SEQ ID NO 465
<211> LENGTH: 13
<212> TYPE: PRT
<213> ORGANISM: Artificial Sequence
<220> FEATURE:
<223> OTHER INFORMATION: SELECTIN ANTAGONIST PEPTIDE

<400> SEQUENCE: 465
```

```
Lys Lys Ala Leu Thr Asn Glu Ala Glu Asn Trp Ala Asp
1               5                  10

<210> SEQ ID NO 466
<211> LENGTH: 16
<212> TYPE: PRT
<213> ORGANISM: Artificial Sequence
<220> FEATURE:
<223> OTHER INFORMATION: SELECTIN ANTAGONIST PEPTIDE
<220> FEATURE:
<221> NAME/KEY: misc_feature
<222> LOCATION: (3)..(15)
<223> OTHER INFORMATION: Xaa = any amino acid

<400> SEQUENCE: 466

Cys Gln Xaa Arg Tyr Thr Asp Leu Val Ala Ile Gln Asn Lys Xaa Glu
1               5                  10                  15

<210> SEQ ID NO 467
<211> LENGTH: 19
<212> TYPE: PRT
<213> ORGANISM: Artificial Sequence
<220> FEATURE:
<223> OTHER INFORMATION: SELECTIN ANTAGONIST PEPTIDE
<220> FEATURE:
<221> NAME/KEY: misc_feature
<222> LOCATION: (3, 5, 6, 13)..(15)
<223> OTHER INFORMATION: Xaa = any amino acid

<400> SEQUENCE: 467

Arg Lys Xaa Asn Xaa Xaa Trp Thr Trp Val Gly Thr Xaa Lys Xaa Leu
1               5                  10                  15

Thr Glu Glu

<210> SEQ ID NO 468
<211> LENGTH: 17
<212> TYPE: PRT
<213> ORGANISM: Artificial Sequence
<220> FEATURE:
<223> OTHER INFORMATION: SELECTIN ANTAGONIST PEPTIDE
<220> FEATURE:
<221> NAME/KEY: misc_feature
<222> LOCATION: (13)..(15)
<223> OTHER INFORMATION: Xaa = any amino acid

<400> SEQUENCE: 468

Ala Glu Asn Trp Ala Asp Gly Glu Pro Asn Asn Lys Xaa Asn Xaa Glu
1               5                  10                  15

Asp

<210> SEQ ID NO 469
<211> LENGTH: 16
<212> TYPE: PRT
<213> ORGANISM: Artificial Sequence
<220> FEATURE:
<223> OTHER INFORMATION: SELECTIN ANTAGONIST PEPTIDE
<220> FEATURE:
<221> NAME/KEY: misc_feature
<222> LOCATION: (2, 3, 4, 7)..(15)
<223> OTHER INFORMATION: Xaa = any amino acid

<400> SEQUENCE: 469

Cys Xaa Xaa Xaa Tyr Thr Xaa Leu Val Ala Ile Gln Asn Lys Xaa Glu
1               5                  10                  15

<210> SEQ ID NO 470
<211> LENGTH: 19
<212> TYPE: PRT
```

```
<213> ORGANISM: Artificial Sequence
<220> FEATURE:
<223> OTHER INFORMATION: SELECTIN ANTAGONIST PEPTIDE
<220> FEATURE:
<221> NAME/KEY: misc_feature
<222> LOCATION: (3, 4, 5, 6, 8, 13, 15)..(18)
<223> OTHER INFORMATION: Xaa = any amino acid

<400> SEQUENCE: 470

Arg Lys Xaa Xaa Xaa Xaa Trp Xaa Trp Val Gly Thr Xaa Lys Xaa Leu
1               5                   10                  15

Thr Xaa Glu

<210> SEQ ID NO 471
<211> LENGTH: 16
<212> TYPE: PRT
<213> ORGANISM: Artificial Sequence
<220> FEATURE:
<223> OTHER INFORMATION: SELECTIN ANTAGONIST PEPTIDE
<220> FEATURE:
<221> NAME/KEY: misc_feature
<222> LOCATION: (2, 5, 6, 7, 12, 13)..(14)
<223> OTHER INFORMATION: Xaa = any amino acid

<400> SEQUENCE: 471

Ala Xaa Asn Trp Xaa Xaa Xaa Glu Pro Asn Asn Xaa Xaa Xaa Glu Asp
1               5                   10                  15

<210> SEQ ID NO 472
<211> LENGTH: 13
<212> TYPE: PRT
<213> ORGANISM: Artificial Sequence
<220> FEATURE:
<223> OTHER INFORMATION: SELECTIN ANTAGONIST PEPTIDE
<220> FEATURE:
<221> NAME/KEY: misc_feature
<222> LOCATION: (1, 3, 6, 9, 12)..(13)
<223> OTHER INFORMATION: Xaa = any amino acid

<400> SEQUENCE: 472

Xaa Lys Xaa Lys Thr Xaa Glu Ala Xaa Asn Trp Xaa Xaa
1               5                   10

<210> SEQ ID NO 473
<211> LENGTH: 12
<212> TYPE: PRT
<213> ORGANISM: Artificial Sequence
<220> FEATURE:
<223> OTHER INFORMATION: SOMATOSTATIN OR CORTISTATIN MIMETIC PEPTIDE
<220> FEATURE:
<221> NAME/KEY: misc_feature
<222> LOCATION: (1)..(1)
<223> OTHER INFORMATION: Xaa is Asp-Arg-Met-Pro-Cys, Arg-Met-Pro-Cys,
      Met-Pro-Cys, Pro-Cys or Cys
<220> FEATURE:
<221> NAME/KEY: misc_feature
<222> LOCATION: (2)..(2)
<223> OTHER INFORMATION: Xaa is Arg or Lys
<220> FEATURE:
<221> NAME/KEY: misc_feature
<222> LOCATION: (10)..(10)
<223> OTHER INFORMATION: Xaa is Ser or Thr
<220> FEATURE:
<221> NAME/KEY: misc_feature
<222> LOCATION: (12)..(12)
<223> OTHER INFORMATION: Xaa is Cys-Lys or Cys

<400> SEQUENCE: 473

Xaa Xaa Asn Phe Phe Trp Lys Thr Phe Xaa Ser Xaa
1               5                   10
```

```
<210> SEQ ID NO 474
<211> LENGTH: 17
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 474

Asp Arg Met Pro Cys Arg Asn Phe Phe Trp Lys Thr Phe Ser Ser Cys
1               5                   10                  15

Lys

<210> SEQ ID NO 475
<211> LENGTH: 15
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 475

Met Pro Cys Arg Asn Phe Phe Trp Lys Thr Phe Ser Ser Cys Lys
1               5                   10                  15

<210> SEQ ID NO 476
<211> LENGTH: 13
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 476

Cys Arg Asn Phe Phe Trp Lys Thr Phe Ser Ser Cys Lys
1               5                   10

<210> SEQ ID NO 477
<211> LENGTH: 16
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 477

Asp Arg Met Pro Cys Arg Asn Phe Phe Trp Lys Thr Phe Ser Ser Cys
1               5                   10                  15

<210> SEQ ID NO 478
<211> LENGTH: 14
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 478

Met Pro Cys Arg Asn Phe Phe Trp Lys Thr Phe Ser Ser Cys
1               5                   10

<210> SEQ ID NO 479
<211> LENGTH: 12
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 479

Cys Arg Asn Phe Phe Trp Lys Thr Phe Ser Ser Cys
1               5                   10
```

<210> SEQ ID NO 480
<211> LENGTH: 16
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 480

Asp Arg Met Pro Cys Lys Asn Phe Phe Trp Lys Thr Phe Ser Ser Cys
1               5                   10                  15

<210> SEQ ID NO 481
<211> LENGTH: 15
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 481

Met Pro Cys Lys Asn Phe Phe Trp Lys Thr Phe Ser Ser Cys Lys
1               5                   10                  15

<210> SEQ ID NO 482
<211> LENGTH: 13
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 482

Cys Lys Asn Phe Phe Trp Lys Thr Phe Ser Ser Cys Lys
1               5                   10

<210> SEQ ID NO 483
<211> LENGTH: 16
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 483

Asp Arg Met Pro Cys Lys Asn Phe Phe Trp Lys Thr Phe Ser Ser Cys
1               5                   10                  15

<210> SEQ ID NO 484
<211> LENGTH: 14
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 484

Met Pro Cys Lys Asn Phe Phe Trp Lys Thr Phe Ser Ser Cys
1               5                   10

<210> SEQ ID NO 485
<211> LENGTH: 12
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 485

Cys Lys Asn Phe Phe Trp Lys Thr Phe Ser Ser Cys
1               5                   10

```
<210> SEQ ID NO 486
<211> LENGTH: 17
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 486

Asp Arg Met Pro Cys Arg Asn Phe Phe Trp Lys Thr Phe Thr Ser Cys
1               5                   10                  15
Lys

<210> SEQ ID NO 487
<211> LENGTH: 15
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 487

Met Pro Cys Arg Asn Phe Phe Trp Lys Thr Phe Thr Ser Cys Lys
1               5                   10                  15

<210> SEQ ID NO 488
<211> LENGTH: 13
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 488

Cys Arg Asn Phe Phe Trp Lys Thr Phe Thr Ser Cys Lys
1               5                   10

<210> SEQ ID NO 489
<211> LENGTH: 16
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 489

Asp Arg Met Pro Cys Arg Asn Phe Phe Trp Lys Thr Phe Thr Ser Cys
1               5                   10                  15

<210> SEQ ID NO 490
<211> LENGTH: 14
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 490

Met Pro Cys Arg Asn Phe Phe Trp Lys Thr Phe Thr Ser Cys
1               5                   10

<210> SEQ ID NO 491
<211> LENGTH: 12
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 491

Cys Arg Asn Phe Phe Trp Lys Thr Phe Thr Ser Cys
1               5                   10
```

<210> SEQ ID NO 492
<211> LENGTH: 17
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 492

Asp Arg Met Pro Cys Lys Asn Phe Phe Trp Lys Thr Phe Thr Ser Cys
1               5                   10                  15
Lys

<210> SEQ ID NO 493
<211> LENGTH: 15
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 493

Met Pro Cys Lys Asn Phe Phe Trp Lys Thr Phe Thr Ser Cys Lys
1               5                   10                  15

<210> SEQ ID NO 494
<211> LENGTH: 13
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 494

Cys Lys Asn Phe Phe Trp Lys Thr Phe Thr Ser Cys Lys
1               5                   10

<210> SEQ ID NO 495
<211> LENGTH: 16
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 495

Asp Arg Met Pro Cys Lys Asn Phe Phe Trp Lys Thr Phe Thr Ser Cys
1               5                   10                  15

<210> SEQ ID NO 496
<211> LENGTH: 14
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 496

Met Pro Cys Lys Asn Phe Phe Trp Lys Thr Phe Thr Ser Cys
1               5                   10

<210> SEQ ID NO 497
<211> LENGTH: 12
<212> TYPE: PRT
<213> ORGANISM: Artificial Sequence
<220> FEATURE:
<223> OTHER INFORMATION: SOMATOSTATIN OR CORTISTATIN MIMETIC PEPTIDE

<400> SEQUENCE: 497

Cys Lys Asn Phe Phe Trp Lys Thr Phe Thr Ser Cys

-continued

```
<210> SEQ ID NO 498
<211> LENGTH: 25
<212> TYPE: PRT
<213> ORGANISM: Artificial Sequence
<220> FEATURE:
<223> OTHER INFORMATION: CAP37 MIMETIC/LPS BINDING

<400> SEQUENCE: 498

Asn Gln Gly Arg His Phe Cys Gly Gly Ala Leu Ile His Ala Arg Phe
1               5                   10                  15

Val Met Thr Ala Ala Ser Cys Phe Gln
            20                  25

<210> SEQ ID NO 499
<211> LENGTH: 20
<212> TYPE: PRT
<213> ORGANISM: Artificial Sequence
<220> FEATURE:
<223> OTHER INFORMATION: CAP37 MIMETIC/LPS BINDING

<400> SEQUENCE: 499

Arg His Phe Cys Gly Gly Ala Leu Ile His Ala Arg Phe Val Met Thr
1               5                   10                  15

Ala Ala Ser Cys
            20

<210> SEQ ID NO 500
<211> LENGTH: 27
<212> TYPE: PRT
<213> ORGANISM: Artificial Sequence
<220> FEATURE:
<223> OTHER INFORMATION: CAP37 MIMETIC/LPS BINDING

<400> SEQUENCE: 500

Gly Thr Arg Cys Gln Val Ala Gly Trp Gly Ser Gln Arg Ser Gly Gly
1               5                   10                  15

Arg Leu Ser Arg Phe Pro Arg Phe Val Asn Val
            20                  25

<210> SEQ ID NO 501
<211> LENGTH: 18
<212> TYPE: PRT
<213> ORGANISM: Artificial Sequence
<220> FEATURE:
<223> OTHER INFORMATION: VEGF- ANTAGONIST

<400> SEQUENCE: 501

Gly Glu Arg Trp Cys Phe Asp Gly Pro Arg Ala Trp Val Cys Gly Trp
1               5                   10                  15

Glu Ile

<210> SEQ ID NO 502
<211> LENGTH: 18
<212> TYPE: PRT
<213> ORGANISM: Artificial Sequence
<220> FEATURE:
<223> OTHER INFORMATION: VEGF- ANTAGONIST

<400> SEQUENCE: 502

Glu Glu Leu Trp Cys Phe Asp Gly Pro Arg Ala Trp Val Cys Gly Tyr
1               5                   10                  15

Val Lys
```

```
<210> SEQ ID NO 503
<211> LENGTH: 33
<212> TYPE: PRT
<213> ORGANISM: Artificial Sequence
<220> FEATURE:
<223> OTHER INFORMATION: ANTIPATHOGENIC PEPTIDE

<400> SEQUENCE: 503

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Gln

<210> SEQ ID NO 504
<211> LENGTH: 33
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (7, 18,)..(19)
<223> OTHER INFORMATION: Positions 7, 18, and 19, D amino acid residue

<400> SEQUENCE: 504

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu

<210> SEQ ID NO 505
<211> LENGTH: 22
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (18)..(19)
<223> OTHER INFORMATION: Positions 18 and 19, D amino acid residues

<400> SEQUENCE: 505

Gly Phe Phe Ala Leu Ile Pro Lys Ile Ile Ser Ser Pro Leu Phe Lys
1               5                   10                  15

Thr Leu Leu Ser Ala Val
            20

<210> SEQ ID NO 506
<211> LENGTH: 22
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (7, 18)..(19)
<223> OTHER INFORMATION: Positions 7, 18 and 19, D amino acid residues

<400> SEQUENCE: 506

Gly Phe Phe Ala Leu Ile Pro Lys Ile Ile Ser Ser Pro Leu Phe Lys
1               5                   10                  15

Thr Leu Leu Ser Ala Val
```

```
<210> SEQ ID NO 507
<211> LENGTH: 23
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (8, 19)..(20)
<223> OTHER INFORMATION: Positions 8, 19 and 20, D amino acid residues

<400> SEQUENCE: 507

Lys Gly Phe Phe Ala Leu Ile Pro Lys Ile Ile Ser Ser Pro Leu Phe
1               5                   10                  15

Lys Thr Leu Leu Ser Ala Val
            20

<210> SEQ ID NO 508
<211> LENGTH: 24
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (9, 20)..(21)
<223> OTHER INFORMATION: Positions 9, 20 and 21, D amino acid residues

<400> SEQUENCE: 508

Lys Lys Gly Phe Phe Ala Leu Ile Pro Lys Ile Ile Ser Ser Pro Leu
1               5                   10                  15

Phe Lys Thr Leu Leu Ser Ala Val
            20

<210> SEQ ID NO 509
<211> LENGTH: 24
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (9, 20)..(21)
<223> OTHER INFORMATION: Positions 9, 20 and 21, D amino acid residues

<400> SEQUENCE: 509

Lys Lys Gly Phe Phe Ala Leu Ile Pro Lys Ile Ile Ser Ser Pro Leu
1               5                   10                  15

Phe Lys Thr Leu Leu Ser Ala Val
            20

<210> SEQ ID NO 510
<211> LENGTH: 11
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (7)..(7)
<223> OTHER INFORMATION: Position 7, D amino acid residue

<400> SEQUENCE: 510

Gly Phe Phe Ala Leu Ile Pro Lys Ile Ile Ser
1               5                   10
```

<210> SEQ ID NO 511
<211> LENGTH: 26
<212> TYPE: PRT
<213> ORGANISM: Artificial Sequence
<220> FEATURE:
<223> OTHER INFORMATION: ANTIPATHOGENIC PEPTIDE

<400> SEQUENCE: 511

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 512
<211> LENGTH: 26
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (5, 8, 17)..(23)
<223> OTHER INFORMATION: Positions 5, 8, 17 and 23, D amino acid
      residues

<400> SEQUENCE: 512

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 513
<211> LENGTH: 26
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (5, 18, 17)..(23)
<223> OTHER INFORMATION: Positions 5, 18, 17 and 23, D amino acid
      residues

<400> SEQUENCE: 513

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 514
<211> LENGTH: 22
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (5, 8, 17)..(21)
<223> OTHER INFORMATION: Positions 5, 8, 17 and 21, D amino acid
      residues

<400> SEQUENCE: 514

Gly Ile Gly Ala Val Leu Lys Val Leu Thr Thr Gly Leu Pro Ala Leu
1               5                   10                  15

Ile Ser Trp Ile Lys Arg
            20

```
<210> SEQ ID NO 515
<211> LENGTH: 19
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (2, 5, 14)..(18)
<223> OTHER INFORMATION: Positions 2, 5, 14 and 18, D amino acid
      residues

<400> SEQUENCE: 515

Ala Val Leu Lys Val Leu Thr Thr Gly Leu Pro Ala Leu Ile Ser Trp
1               5                   10                  15

Ile Lys Arg

<210> SEQ ID NO 516
<211> LENGTH: 12
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (3, 4, 8)..(10)
<223> OTHER INFORMATION: Positions 3, 4, 8 and 10, D amino acid residues

<400> SEQUENCE: 516

Lys Leu Leu Leu Leu Leu Lys Leu Leu Leu Leu Lys
1               5                   10

<210> SEQ ID NO 517
<211> LENGTH: 12
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (3, 4, 8)..(10)
<223> OTHER INFORMATION: Positions 3, 4, 8 and 10, D amino acid residues

<400> SEQUENCE: 517

Lys Leu Leu Leu Lys Leu Leu Leu Lys Leu Leu Lys
1               5                   10

<210> SEQ ID NO 518
<211> LENGTH: 12
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (3, 4, 8)..(10)
<223> OTHER INFORMATION: Positions 3, 4, 8 and 10, D amino acid residues

<400> SEQUENCE: 518

Lys Leu Leu Leu Lys Leu Lys Leu Lys Leu Leu Lys
1               5                   10

<210> SEQ ID NO 519
<211> LENGTH: 12
<212> TYPE: PRT
<213> ORGANISM: Artificial Sequence
<220> FEATURE:
<223> OTHER INFORMATION: ANTIPATHOGENIC PEPTIDE
```

```
<400> SEQUENCE: 519

Lys Lys Leu Leu Lys Leu Lys Leu Lys Leu Lys Lys
 1               5                  10

<210> SEQ ID NO 520
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 520

Lys Leu Leu Leu Lys Leu Leu Leu Lys Leu Leu Lys
 1               5                  10

<210> SEQ ID NO 521
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 521

Lys Leu Leu Leu Lys Leu Lys Leu Lys Leu Leu Lys
 1               5                  10

<210> SEQ ID NO 522
<211> LENGTH: 6
<212> TYPE: PRT
<213> ORGANISM: Artificial Sequence
<220> FEATURE:
<223> OTHER INFORMATION: ANTIPATHOGENIC PEPTIDE

<400> SEQUENCE: 522

Lys Leu Leu Leu Leu Lys
 1               5

<210> SEQ ID NO 523
<211> LENGTH: 8
<212> TYPE: PRT
<213> ORGANISM: Artificial Sequence
<220> FEATURE:
<223> OTHER INFORMATION: ANTIPATHOGENIC PEPTIDE

<400> SEQUENCE: 523

Lys Leu Leu Leu Lys Leu Leu Lys
 1               5

<210> SEQ ID NO 524
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 524

Lys Leu Leu Leu Lys Leu Lys Leu Lys Leu Leu Lys
 1               5                  10

<210> SEQ ID NO 525
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 525
```

```
Lys Leu Leu Leu Lys Leu Lys Leu Lys Leu Leu Lys
1               5                   10
```

<210> SEQ ID NO 526
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 526

```
Lys Leu Leu Leu Lys Leu Lys Leu Lys Leu Leu Lys
1               5                   10
```

<210> SEQ ID NO 527
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 527

```
Lys Ala Ala Ala Lys Ala Ala Ala Lys Ala Ala Lys
1               5                   10
```

<210> SEQ ID NO 528
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 528

```
Lys Val Val Val Lys Val Val Lys Val Val Lys
1               5                   10
```

<210> SEQ ID NO 529
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 529

```
Lys Val Val Val Lys Val Lys Val Lys Val Val Lys
1               5                   10
```

<210> SEQ ID NO 530
<211> LENGTH: 11
<212> TYPE: PRT
<213> ORGANISM: Artificial Sequence
<220> FEATURE:
<223> OTHER INFORMATION: ANTIPATHOGENIC PEPTIDE

<400> SEQUENCE: 530

```
Lys Val Val Val Lys Val Lys Val Lys Val Lys
1               5                   10
```

<210> SEQ ID NO 531
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 531

```
Lys Val Val Lys Val Lys Val Val Lys
1               5                   10
```

<210> SEQ ID NO 532
<211> LENGTH: 6
<212> TYPE: PRT
<213> ORGANISM: Artificial Sequence
<220> FEATURE:
<223> OTHER INFORMATION: ANTIPATHOGENIC PEPTIDE

<400> SEQUENCE: 532

```
Lys Leu Ile Leu Lys Leu
1               5
```

<210> SEQ ID NO 533
<211> LENGTH: 6
<212> TYPE: PRT
<213> ORGANISM: Artificial Sequence
<220> FEATURE:
<223> OTHER INFORMATION: ANTIPATHOGENIC PEPTIDE

<400> SEQUENCE: 533

```
Lys Val Leu His Leu Leu
1               5
```

<210> SEQ ID NO 534
<211> LENGTH: 6
<212> TYPE: PRT
<213> ORGANISM: Artificial Sequence
<220> FEATURE:
<223> OTHER INFORMATION: ANTIPATHOGENIC PEPTIDE

<400> SEQUENCE: 534

```
Leu Lys Leu Arg Leu Leu
1               5
```

<210> SEQ ID NO 535
<211> LENGTH: 6
<212> TYPE: PRT
<213> ORGANISM: Artificial Sequence
<220> FEATURE:
<223> OTHER INFORMATION: ANTIPATHOGENIC PEPTIDE

<400> SEQUENCE: 535

```
Lys Pro Leu His Leu Leu
1               5
```

<210> SEQ ID NO 536
<211> LENGTH: 8
<212> TYPE: PRT
<213> ORGANISM: Artificial Sequence
<220> FEATURE:
<223> OTHER INFORMATION: ANTIPATHOGENIC PEPTIDE

<400> SEQUENCE: 536

```
Lys Leu Ile Leu Lys Leu Val Arg
1               5
```

<210> SEQ ID NO 537
<211> LENGTH: 8
<212> TYPE: PRT
<213> ORGANISM: Artificial Sequence
<220> FEATURE:
<223> OTHER INFORMATION: ANTIPATHOGENIC PEPTIDE

<400> SEQUENCE: 537

```
Lys Val Phe His Leu Leu His Leu
```

-continued

```
<210> SEQ ID NO 538
<211> LENGTH: 8
<212> TYPE: PRT
<213> ORGANISM: Artificial Sequence
<220> FEATURE:
<223> OTHER INFORMATION: ANTIPATHOGENIC PEPTIDE

<400> SEQUENCE: 538

His Lys Phe Arg Ile Leu Lys Leu
1               5

<210> SEQ ID NO 539
<211> LENGTH: 8
<212> TYPE: PRT
<213> ORGANISM: Artificial Sequence
<220> FEATURE:
<223> OTHER INFORMATION: ANTIPATHOGENIC PEPTIDE

<400> SEQUENCE: 539

Lys Pro Phe His Ile Leu His Leu
1               5

<210> SEQ ID NO 540
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 540

Lys Ile Ile Ile Lys Ile Lys Ile Lys Ile Ile Lys
1               5                   10

<210> SEQ ID NO 541
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 541

Lys Ile Ile Ile Lys Ile Lys Ile Lys Ile Ile Lys
1               5                   10

<210> SEQ ID NO 542
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 542

Lys Ile Ile Ile Lys Ile Lys Ile Lys Ile Ile Lys
1               5                   10

<210> SEQ ID NO 543
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 543

Lys Ile Pro Ile Lys Ile Lys Ile Lys Ile Pro Lys
1               5                   10
```

<210> SEQ ID NO 544
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 544

Lys Ile Pro Ile Lys Ile Lys Ile Lys Ile Val Lys
1               5                   10

<210> SEQ ID NO 545
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 545

Arg Ile Ile Ile Arg Ile Arg Ile Arg Ile Ile Arg
1               5                   10

<210> SEQ ID NO 546
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 546

Arg Ile Ile Ile Arg Ile Arg Ile Arg Ile Ile Arg
1               5                   10

<210> SEQ ID NO 547
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 547

Arg Ile Ile Ile Arg Ile Arg Ile Arg Ile Ile Arg
1               5                   10

<210> SEQ ID NO 548
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 548

Arg Ile Val Ile Arg Ile Arg Ile Arg Leu Ile Arg
1               5                   10

<210> SEQ ID NO 549
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 549

Arg Ile Ile Val Arg Ile Arg Leu Arg Ile Ile Arg
1               5                   10

-continued

<210> SEQ ID NO 550
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 550

Arg Ile Gly Ile Arg Leu Arg Val Arg Ile Ile Arg
1               5                   10

<210> SEQ ID NO 551
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 551

Lys Ile Val Ile Arg Ile Arg Ile Arg Leu Ile Arg
1               5                   10

<210> SEQ ID NO 552
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 552

Arg Ile Ala Val Lys Trp Arg Leu Arg Phe Ile Lys
1               5                   10

<210> SEQ ID NO 553
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 553

Lys Ile Gly Trp Lys Leu Arg Val Arg Ile Ile Arg
1               5                   10

<210> SEQ ID NO 554
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 554

Lys Lys Ile Gly Trp Leu Ile Ile Arg Val Arg Arg
1               5                   10

<210> SEQ ID NO 555
<211> LENGTH: 14
<212> TYPE: PRT
<213> ORGANISM: Artificial Sequence
<220> FEATURE:
<223> OTHER INFORMATION: ANTIPATHOGENIC PEPTIDE

<400> SEQUENCE: 555

Arg Ile Val Ile Arg Ile Arg Ile Arg Leu Ile Arg Ile Arg
1               5                   10

```
<210> SEQ ID NO 556
<211> LENGTH: 14
<212> TYPE: PRT
<213> ORGANISM: Artificial Sequence
<220> FEATURE:
<223> OTHER INFORMATION: ANTIPATHOGENIC PEPTIDE

<400> SEQUENCE: 556

Arg Ile Ile Val Arg Ile Arg Leu Arg Ile Ile Arg Val Arg
1               5                   10

<210> SEQ ID NO 557
<211> LENGTH: 14
<212> TYPE: PRT
<213> ORGANISM: Artificial Sequence
<220> FEATURE:
<223> OTHER INFORMATION: ANTIPATHOGENIC PEPTIDE

<400> SEQUENCE: 557

Arg Ile Gly Ile Arg Leu Arg Val Arg Ile Ile Arg Arg Val
1               5                   10

<210> SEQ ID NO 558
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 558

Lys Ile Val Ile Arg Ile Arg Ala Arg Leu Ile Arg Ile Arg Ile Arg
1               5                   10                  15

<210> SEQ ID NO 559
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 559

Arg Ile Ile Val Lys Ile Arg Leu Arg Ile Ile Lys Lys Ile Arg Leu
1               5                   10                  15

<210> SEQ ID NO 560
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 560

Lys Ile Gly Ile Lys Ala Arg Val Arg Ile Ile Arg Val Lys Ile Ile
1               5                   10                  15

<210> SEQ ID NO 561
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 561

Arg Ile Ile Val His Ile Arg Leu Arg Ile Ile His His Ile Arg Leu
1               5                   10                  15

<210> SEQ ID NO 562
```

```
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 562

His Ile Gly Ile Lys Ala His Val Arg Ile Ile Arg Val His Ile Ile
1               5                   10                  15

<210> SEQ ID NO 563
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 563

Arg Ile Tyr Val Lys Ile His Leu Arg Tyr Ile Lys Lys Ile Arg Leu
1               5                   10                  15

<210> SEQ ID NO 564
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 564

Lys Ile Gly His Lys Ala Arg Val His Ile Ile Arg Tyr Lys Ile Ile
1               5                   10                  15

<210> SEQ ID NO 565
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 565

Arg Ile Tyr Val Lys Pro His Pro Arg Tyr Ile Lys Lys Ile Arg Leu
1               5                   10                  15

<210> SEQ ID NO 566
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 566

Lys Pro Gly His Lys Ala Arg Pro His Ile Ile Arg Tyr Lys Ile Ile
1               5                   10                  15

<210> SEQ ID NO 567
<211> LENGTH: 19
<212> TYPE: PRT
<213> ORGANISM: Artificial Sequence
<220> FEATURE:
<223> OTHER INFORMATION: ANTIPATHOGENIC PEPTIDE

<400> SEQUENCE: 567

Lys Ile Val Ile Arg Ile Arg Ile Arg Leu Ile Arg Ile Arg Ile Arg
1               5                   10                  15

Lys Ile Val
```

<210> SEQ ID NO 568
<211> LENGTH: 19
<212> TYPE: PRT
<213> ORGANISM: Artificial Sequence
<220> FEATURE:
<223> OTHER INFORMATION: ANTIPATHOGENIC PEPTIDE

<400> SEQUENCE: 568

Arg Ile Ile Val Lys Ile Arg Leu Arg Ile Ile Lys Lys Ile Arg Leu
1               5                   10                  15

Ile Lys Lys

<210> SEQ ID NO 569
<211> LENGTH: 19
<212> TYPE: PRT
<213> ORGANISM: Artificial Sequence
<220> FEATURE:
<223> OTHER INFORMATION: ANTIPATHOGENIC PEPTIDE

<400> SEQUENCE: 569

Lys Ile Gly Trp Lys Leu Arg Val Arg Ile Ile Arg Val Lys Ile Gly
1               5                   10                  15

Arg Leu Arg

<210> SEQ ID NO 570
<211> LENGTH: 25
<212> TYPE: PRT
<213> ORGANISM: Artificial Sequence
<220> FEATURE:
<223> OTHER INFORMATION: ANTIPATHOGENIC PEPTIDE

<400> SEQUENCE: 570

Lys Ile Val Ile Arg Ile Arg Ile Arg Leu Ile Arg Ile Arg Ile Arg
1               5                   10                  15

Lys Ile Val Lys Val Lys Arg Ile Arg
            20                  25

<210> SEQ ID NO 571
<211> LENGTH: 26
<212> TYPE: PRT
<213> ORGANISM: Artificial Sequence
<220> FEATURE:
<223> OTHER INFORMATION: ANTIPATHOGENIC PEPTIDE

<400> SEQUENCE: 571

Arg Phe Ala Val Lys Ile Arg Leu Arg Ile Ile Lys Lys Ile Arg Leu
1               5                   10                  15

Ile Lys Lys Ile Arg Lys Arg Val Ile Lys
            20                  25

<210> SEQ ID NO 572
<211> LENGTH: 30
<212> TYPE: PRT
<213> ORGANISM: Artificial Sequence
<220> FEATURE:
<223> OTHER INFORMATION: ANTIPATHOGENIC PEPTIDE

<400> SEQUENCE: 572

Lys Ala Gly Trp Lys Leu Arg Val Arg Ile Ile Arg Val Lys Ile Gly
1               5                   10                  15

Arg Leu Arg Lys Ile Gly Trp Lys Lys Arg Val Arg Ile Lys
            20                  25                  30

<210> SEQ ID NO 573

```
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 573

Arg Ile Tyr Val Lys Pro His Pro Arg Tyr Ile Lys Lys Ile Arg Leu
1               5                   10                  15

<210> SEQ ID NO 574
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 574

Lys Pro Gly His Lys Ala Arg Pro His Ile Ile Arg Tyr Lys Ile Ile
1               5                   10                  15

<210> SEQ ID NO 575
<211> LENGTH: 19
<212> TYPE: PRT
<213> ORGANISM: Artificial Sequence
<220> FEATURE:
<223> OTHER INFORMATION: ANTIPATHOGENIC PEPTIDE

<400> SEQUENCE: 575

Lys Ile Val Ile Arg Ile Arg Ile Arg Leu Ile Arg Ile Arg Ile Arg
1               5                   10                  15

Lys Ile Val

<210> SEQ ID NO 576
<211> LENGTH: 19
<212> TYPE: PRT
<213> ORGANISM: Artificial Sequence
<220> FEATURE:
<223> OTHER INFORMATION: ANTIPATHOGENIC PEPTIDE

<400> SEQUENCE: 576

Arg Ile Ile Val Lys Ile Arg Leu Arg Ile Ile Lys Lys Ile Arg Leu
1               5                   10                  15

Ile Lys Lys

<210> SEQ ID NO 577
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 577

Arg Ile Tyr Val Ser Lys Ile Ser Ile Tyr Lys Lys Ile Arg Leu
1               5                   10                  15

<210> SEQ ID NO 578
<211> LENGTH: 19
<212> TYPE: PRT
<213> ORGANISM: Artificial Sequence
<220> FEATURE:
<223> OTHER INFORMATION: ANTIPATHOGENIC PEPTIDE

<400> SEQUENCE: 578

Lys Ile Val Ile Phe Thr Arg Ile Arg Leu Thr Ser Ile Arg Ile Arg
1               5                   10                  15
```

```
<210> SEQ ID NO 579
<211> LENGTH: 16
<212> TYPE: PRT
<213> ORGANISM: Artificial Sequence
<220> FEATURE:
<223> OTHER INFORMATION: ANTIPATHOGENIC PEPTIDE

<400> SEQUENCE: 579

Lys Pro Ile His Lys Ala Arg Pro Thr Ile Ile Arg Tyr Lys Met Ile
1               5                   10                  15

<210> SEQ ID NO 580
<211> LENGTH: 26
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (1)..(1)
<223> OTHER INFORMATION: Position 1, disulfide bond to position 26
<220> FEATURE:
<221> NAME/KEY: misc_feature
<222> LOCATION: (26)..(26)
<223> OTHER INFORMATION: Position 26, disulfide bond to position 1

<400> SEQUENCE: 580

Xaa Cys Lys Gly Phe Phe Ala Leu Ile Pro Lys Ile Ile Ser Ser Pro
1               5                   10                  15

Leu Phe Lys Thr Leu Leu Ser Ala Val Cys
            20                  25

<210> SEQ ID NO 581
<211> LENGTH: 26
<212> TYPE: PRT
<213> ORGANISM: Artificial Sequence
<220> FEATURE:
<223> OTHER INFORMATION: ANTIPATHOGENIC PEPTIDE

<400> SEQUENCE: 581

Cys Lys Lys Gly Phe Phe Ala Leu Ile Pro Lys Ile Ile Ser Ser Pro
1               5                   10                  15

Leu Phe Lys Thr Leu Leu Ser Ala Val Cys
            20                  25

<210> SEQ ID NO 582
<211> LENGTH: 27
<212> TYPE: PRT
<213> ORGANISM: Artificial Sequence
<220> FEATURE:
<223> OTHER INFORMATION: ANTIPATHOGENIC PEPTIDE

<400> SEQUENCE: 582

Cys Lys Lys Lys Gly Phe Phe Ala Leu Ile Pro Lys Ile Ile Ser Ser
1               5                   10                  15

Pro Leu Phe Lys Thr Leu Leu Ser Ala Val Cys
            20                  25

<210> SEQ ID NO 583
<211> LENGTH: 17
<212> TYPE: PRT
<213> ORGANISM: Artificial Sequence
<220> FEATURE:
<223> OTHER INFORMATION: ANTIPATHOGENIC PEPTIDE
```

```
<220> FEATURE:
<221> NAME/KEY: misc_feature
<222> LOCATION: (1)..(1)
<223> OTHER INFORMATION: Position 1, disulfide bond to position 17
<220> FEATURE:
<221> NAME/KEY: misc_feature
<222> LOCATION: (17)..(17)
<223> OTHER INFORMATION: Position 17, disulfide bond to position 1

<400> SEQUENCE: 583

Xaa Cys Arg Ile Val Ile Arg Ile Arg Ile Arg Leu Ile Arg Ile Arg
1               5                   10                  15

Cys

<210> SEQ ID NO 584
<211> LENGTH: 19
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (1)..(1)
<223> OTHER INFORMATION: Position 1, disulfide bond to position 19
<220> FEATURE:
<221> NAME/KEY: misc_feature
<222> LOCATION: (19)..(19)
<223> OTHER INFORMATION: Position 19, disulfide bond to position 1

<400> SEQUENCE: 584

Xaa Cys Lys Pro Gly His Lys Ala Arg Pro His Ile Ile Arg Tyr Lys
1               5                   10                  15

Ile Ile Cys

<210> SEQ ID NO 585
<211> LENGTH: 29
<212> TYPE: PRT
<213> ORGANISM: Artificial Sequence
<220> FEATURE:
<223> OTHER INFORMATION: ANTIPATHOGENIC PEPTIDE
<220> FEATURE:
<221> NAME/KEY: misc_feature
<222> LOCATION: (1)..(1)
<223> OTHER INFORMATION: Position 1, disulfide bond to position 29
<220> FEATURE:
<221> NAME/KEY: misc_feature
<222> LOCATION: (29)..(29)
<223> OTHER INFORMATION: Position 29, disulfide bond to position 1

<400> SEQUENCE: 585

Xaa Cys Arg Phe Ala Val Lys Ile Arg Leu Arg Ile Ile Lys Lys Ile
1               5                   10                  15

Arg Leu Ile Lys Lys Ile Arg Lys Arg Val Ile Lys Cys
            20                  25

<210> SEQ ID NO 586
<211> LENGTH: 13
<212> TYPE: PRT
<213> ORGANISM: Artificial Sequence
<220> FEATURE:
<223> OTHER INFORMATION: ANTIPATHOGENIC PEPTIDE

<400> SEQUENCE: 586

Lys Leu Leu Leu Lys Leu Leu Leu Lys Leu Leu Lys Cys
1               5                   10

<210> SEQ ID NO 587
<211> LENGTH: 12
```

-continued

<212> TYPE: PRT
<213> ORGANISM: Artificial Sequence
<220> FEATURE:
<223> OTHER INFORMATION: ANTIPATHOGENIC PEPTIDE

<400> SEQUENCE: 587

Lys Leu Leu Leu Lys Leu Leu Leu Lys Leu Leu Lys
1               5                   10

<210> SEQ ID NO 588
<211> LENGTH: 13
<212> TYPE: PRT
<213> ORGANISM: Artificial Sequence
<220> FEATURE:
<223> OTHER INFORMATION: ANTIPATHOGENIC PEPTIDE

<400> SEQUENCE: 588

Lys Leu Leu Leu Lys Leu Lys Leu Lys Leu Leu Lys Cys
1               5                   10

<210> SEQ ID NO 589
<211> LENGTH: 12
<212> TYPE: PRT
<213> ORGANISM: Artificial Sequence
<220> FEATURE:
<223> OTHER INFORMATION: ANTIPATHOGENIC PEPTIDE

<400> SEQUENCE: 589

Lys Leu Leu Leu Lys Leu Leu Leu Lys Leu Leu Lys
1               5                   10

<210> SEQ ID NO 590
<211> LENGTH: 28
<212> TYPE: PRT
<213> ORGANISM: Artificial Sequence
<220> FEATURE:
<223> OTHER INFORMATION: VIP-MIMETIC PEPTIDE

<400> SEQUENCE: 590

His Ser Asp Ala Val Phe Tyr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 591
<211> LENGTH: 28
<212> TYPE: PRT
<213> ORGANISM: Artificial Sequence
<220> FEATURE:
<223> OTHER INFORMATION: VIP-MIMETIC PEPTIDE

<400> SEQUENCE: 591

His Ser Asp Ala Val Phe Tyr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 592
<211> LENGTH: 3
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (1)..(1)
<223> OTHER INFORMATION: Position 1, Xaa is L-Lys, D-Lys or an

```
                  ornithinyl residue
<220> FEATURE:
<221> NAME/KEY: misc_feature
<222> LOCATION: (2)..(2)
<223> OTHER INFORMATION: Position 2, Xaa is L-Tyr, D-Tyr, Phe, Trp or a
      p-aminophenylalanyl residue
<220> FEATURE:
<221> NAME/KEY: misc_feature
<222> LOCATION: (3)..(3)
<223> OTHER INFORMATION: Position 3 is a hydrophobic aliphatic amino
      acid residue, Position 3, optional attachment to Leu, norleucyl,
      D-Ala, Asn-Ser, Asn-Ser-Ile-, Asn-Ser-Tyr, Ser-Ile-Leu, Asn-Ser-
      Tyr-Leu or Asn-Ser-Tyr-Leu-Asn

<400> SEQUENCE: 592

Xaa Xaa Xaa
1

<210> SEQ ID NO 593
<211> LENGTH: 5
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (1)..(3)
<223> OTHER INFORMATION: Position 1, Xaa is either absent, a hydrophobic
      aliphatic residue (X5), X5-Asn, Tyr-X5, Lys-X5, Lys-X5-Asn, Lys-
      Tyr-X5, Lys-Tyr-X5-Asn, Lys-Lys-Tyr-X5, Lys-Lys-Tyr-X5-Asn, Val-
      Lys-Lys-Tyr-X5, Val-Ala-Lys-Lys-Tyr-X5-Asn, or Ala-Val-Lys-Lys-
      Tyr-X5-Asn

<400> SEQUENCE: 593

Xaa Ser Xaa Leu Asn
1               5

<210> SEQ ID NO 594
<211> LENGTH: 7
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (1, 5, 6)..(7)
<223> OTHER INFORMATION: Positions 1 and 6, Xaa are cross-linked amino
      acid residues as defined in WO97/40070
<220> FEATURE:
<221> NAME/KEY: misc_feature
<222> LOCATION: (5)..(5)
<223> OTHER INFORMATION: Position 5, Xaa is a hydrophobic aliphatic
      aminod acid residue
<220> FEATURE:
<221> NAME/KEY: misc_feature
<222> LOCATION: (7)..(7)
<223> OTHER INFORMATION: Position 7, is a covalent bond or Asn, Ser,
      Ile, Tyr, Leu, Asn-Ser, Asn-Ser-Ile, Asn-Ser-Tyr, Asn-Ser-Ile-Leu,
      Asn-Ser-Tyr-Leu, Asn-Ser-Ile-Leu-Asn or Asn-Ser-Tyr-Leu-Asn.

<400> SEQUENCE: 594

Xaa Lys Lys Tyr Xaa Xaa Xaa
1               5

<210> SEQ ID NO 595
<211> LENGTH: 4
<212> TYPE: PRT
<213> ORGANISM: Artificial Sequence
<220> FEATURE:
<223> OTHER INFORMATION: VIP-MIMETIC PEPTIDE

<400> SEQUENCE: 595
```

```
Lys Lys Tyr Leu
1

<210> SEQ ID NO 596
<211> LENGTH: 5
<212> TYPE: PRT
<213> ORGANISM: Artificial Sequence
<220> FEATURE:
<223> OTHER INFORMATION: VIP-MIMETIC PEPTIDE

<400> SEQUENCE: 596

Asn Ser Ile Leu Asn
1               5

<210> SEQ ID NO 597
<211> LENGTH: 4
<212> TYPE: PRT
<213> ORGANISM: Artificial Sequence
<220> FEATURE:
<223> OTHER INFORMATION: VIP-MIMETIC PEPTIDE

<400> SEQUENCE: 597

Lys Lys Tyr Leu
1

<210> SEQ ID NO 598
<211> LENGTH: 4
<212> TYPE: PRT
<213> ORGANISM: Artificial Sequence
<220> FEATURE:
<223> OTHER INFORMATION: VIP-MIMETIC PEPTIDE

<400> SEQUENCE: 598

Lys Lys Tyr Ala
1

<210> SEQ ID NO 599
<211> LENGTH: 6
<212> TYPE: PRT
<213> ORGANISM: Artificial Sequence
<220> FEATURE:
<223> OTHER INFORMATION: VIP-MIMETIC PEPTIDE

<400> SEQUENCE: 599

Ala Val Lys Lys Tyr Leu
1               5

<210> SEQ ID NO 600
<211> LENGTH: 4
<212> TYPE: PRT
<213> ORGANISM: Artificial Sequence
<220> FEATURE:
<223> OTHER INFORMATION: VIP-MIMETIC PEPTIDE

<400> SEQUENCE: 600

Ser Ile Leu Asn
1

<210> SEQ ID NO 601
<211> LENGTH: 4
<212> TYPE: PRT
<213> ORGANISM: Artificial Sequence
<220> FEATURE:
<223> OTHER INFORMATION: VIP-MIMETIC PEPTIDE

<400> SEQUENCE: 601

Lys Lys Tyr Val
```

```
<210> SEQ ID NO 602
<211> LENGTH: 4
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (3)..(3)
<223> OTHER INFORMATION: Position 3, Xaa is a lauric acid residue

<400> SEQUENCE: 602

Ser Ile Xaa Asn
1

<210> SEQ ID NO 603
<211> LENGTH: 5
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (5)..(5)
<223> OTHER INFORMATION: Position 5, Xaa is a norleucyl residue

<400> SEQUENCE: 603

Lys Lys Tyr Leu Xaa
1               5

<210> SEQ ID NO 604
<211> LENGTH: 5
<212> TYPE: PRT
<213> ORGANISM: Artificial Sequence
<220> FEATURE:
<223> OTHER INFORMATION: VIP-MIMETIC PEPTIDE

<400> SEQUENCE: 604

Asn Ser Tyr Leu Asn
1               5

<210> SEQ ID NO 605
<211> LENGTH: 5
<212> TYPE: PRT
<213> ORGANISM: Artificial Sequence
<220> FEATURE:
<223> OTHER INFORMATION: VIP-MIMETIC PEPTIDE

<400> SEQUENCE: 605

Asn Ser Ile Tyr Asn
1               5

<210> SEQ ID NO 606
<211> LENGTH: 11
<212> TYPE: PRT
<213> ORGANISM: Artificial Sequence
<220> FEATURE:
<223> OTHER INFORMATION: VIP-MIMETIC PEPTIDE

<400> SEQUENCE: 606

Lys Lys Tyr Leu Pro Pro Asn Ser Ile Leu Asn
1               5                   10

<210> SEQ ID NO 607
<211> LENGTH: 5
<212> TYPE: PRT
```

<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (1)..(1)
<223> OTHER INFORMATION: Position 1, Xaa is a lauric acid residue

<400> SEQUENCE: 607

Xaa Lys Lys Tyr Leu
1               5

<210> SEQ ID NO 608
<211> LENGTH: 5
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (1)..(1)
<223> OTHER INFORMATION: Position 1, Xaa is a caproic acid residue

<400> SEQUENCE: 608

Xaa Lys Lys Tyr Leu
1               5

<210> SEQ ID NO 609
<211> LENGTH: 4
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (4)..(4)
<223> OTHER INFORMATION: Position 4, Xaa is a norleucyl residue

<400> SEQUENCE: 609

Lys Lys Tyr Xaa
1

<210> SEQ ID NO 610
<211> LENGTH: 5
<212> TYPE: PRT
<213> ORGANISM: Artificial Sequence
<220> FEATURE:
<223> OTHER INFORMATION: VIP-MIMETIC PEPTIDE

<400> SEQUENCE: 610

Val Lys Lys Tyr Leu
1               5

<210> SEQ ID NO 611
<211> LENGTH: 6
<212> TYPE: PRT
<213> ORGANISM: Artificial Sequence
<220> FEATURE:
<223> OTHER INFORMATION: VIP-MIMETIC PEPTIDE

<400> SEQUENCE: 611

Leu Asn Ser Ile Leu Asn
1               5

<210> SEQ ID NO 612
<211> LENGTH: 7
<212> TYPE: PRT
<213> ORGANISM: Artificial Sequence
<220> FEATURE:

<223> OTHER INFORMATION: VIP-MIMETIC PEPTIDE

<400> SEQUENCE: 612

Tyr Leu Asn Ser Ile Leu Asn
1               5

<210> SEQ ID NO 613
<211> LENGTH: 5
<212> TYPE: PRT
<213> ORGANISM: Artificial Sequence
<220> FEATURE:
<223> OTHER INFORMATION: VIP-MIMETIC PEPTIDE

<400> SEQUENCE: 613

Lys Lys Tyr Leu Asn
1               5

<210> SEQ ID NO 614
<211> LENGTH: 6
<212> TYPE: PRT
<213> ORGANISM: Artificial Sequence
<220> FEATURE:
<223> OTHER INFORMATION: VIP-MIMETIC PEPTIDE

<400> SEQUENCE: 614

Lys Lys Tyr Leu Asn Ser
1               5

<210> SEQ ID NO 615
<211> LENGTH: 7
<212> TYPE: PRT
<213> ORGANISM: Artificial Sequence
<220> FEATURE:
<223> OTHER INFORMATION: VIP-MIMETIC PEPTIDE

<400> SEQUENCE: 615

Lys Lys Tyr Leu Asn Ser Ile
1               5

<210> SEQ ID NO 616
<211> LENGTH: 8
<212> TYPE: PRT
<213> ORGANISM: Artificial Sequence
<220> FEATURE:
<223> OTHER INFORMATION: VIP-MIMETIC PEPTIDE

<400> SEQUENCE: 616

Lys Lys Tyr Leu Asn Ser Ile Leu
1               5

<210> SEQ ID NO 617
<211> LENGTH: 4
<212> TYPE: PRT
<213> ORGANISM: Artificial Sequence
<220> FEATURE:
<223> OTHER INFORMATION: VIP-MIMETIC PEPTIDE

<400> SEQUENCE: 617

Lys Lys Tyr Leu
1

<210> SEQ ID NO 618
<211> LENGTH: 5
<212> TYPE: PRT
<213> ORGANISM: Artificial Sequence
<220> FEATURE:
<223> OTHER INFORMATION: VIP-MIMETIC PEPTIDE

```
<400> SEQUENCE: 618

Lys Lys Tyr Asp Ala
1               5

<210> SEQ ID NO 619
<211> LENGTH: 6
<212> TYPE: PRT
<213> ORGANISM: Artificial Sequence
<220> FEATURE:
<223> OTHER INFORMATION: VIP-MIMETIC PEPTIDE

<400> SEQUENCE: 619

Ala Val Lys Lys Tyr Leu
1               5

<210> SEQ ID NO 620
<211> LENGTH: 5
<212> TYPE: PRT
<213> ORGANISM: Artificial Sequence
<220> FEATURE:
<223> OTHER INFORMATION: VIP-MIMETIC PEPTIDE

<400> SEQUENCE: 620

Asn Ser Ile Leu Asn
1               5

<210> SEQ ID NO 621
<211> LENGTH: 4
<212> TYPE: PRT
<213> ORGANISM: Artificial Sequence
<220> FEATURE:
<223> OTHER INFORMATION: VIP-MIMETIC PEPTIDE

<400> SEQUENCE: 621

Lys Lys Tyr Val
1

<210> SEQ ID NO 622
<211> LENGTH: 4
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (1)..(3)
<223> OTHER INFORMATION: Position 3, Xaa is a lauric acid residue

<400> SEQUENCE: 622

Xaa Ile Xaa Asn
1

<210> SEQ ID NO 623
<211> LENGTH: 5
<212> TYPE: PRT
<213> ORGANISM: Artificial Sequence
<220> FEATURE:
<223> OTHER INFORMATION: VIP-MIMETIC PEPTIDE

<400> SEQUENCE: 623

Asn Ser Tyr Leu Asn
1               5

<210> SEQ ID NO 624
<211> LENGTH: 5
<212> TYPE: PRT
```

```
<213> ORGANISM: Artificial Sequence
<220> FEATURE:
<223> OTHER INFORMATION: VIP-MIMETIC PEPTIDE

<400> SEQUENCE: 624

Asn Ser Ile Tyr Asn
1               5

<210> SEQ ID NO 625
<211> LENGTH: 5
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (5)..(5)
<223> OTHER INFORMATION: Position 5, Xaa is a norleucyl residue

<400> SEQUENCE: 625

Lys Lys Tyr Leu Xaa
1               5

<210> SEQ ID NO 626
<211> LENGTH: 11
<212> TYPE: PRT
<213> ORGANISM: Artificial Sequence
<220> FEATURE:
<223> OTHER INFORMATION: VIP-MIMETIC PEPTIDE

<400> SEQUENCE: 626

Lys Lys Tyr Leu Pro Pro Asn Ser Ile Leu Asn
1               5                   10

<210> SEQ ID NO 627
<211> LENGTH: 4
<212> TYPE: PRT
<213> ORGANISM: Artificial Sequence
<220> FEATURE:
<223> OTHER INFORMATION: VIP-MIMETIC PEPTIDE

<400> SEQUENCE: 627

Lys Lys Tyr Leu
1

<210> SEQ ID NO 628
<211> LENGTH: 5
<212> TYPE: PRT
<213> ORGANISM: Artificial Sequence
<220> FEATURE:
<223> OTHER INFORMATION: VIP-MIMETIC PEPTIDE

<400> SEQUENCE: 628

Lys Lys Tyr Asp Ala
1               5

<210> SEQ ID NO 629
<211> LENGTH: 6
<212> TYPE: PRT
<213> ORGANISM: Artificial Sequence
<220> FEATURE:
<223> OTHER INFORMATION: VIP-MIMETIC PEPTIDE

<400> SEQUENCE: 629

Ala Val Lys Lys Tyr Leu
1               5
```

```
<210> SEQ ID NO 630
<211> LENGTH: 5
<212> TYPE: PRT
<213> ORGANISM: Artificial Sequence
<220> FEATURE:
<223> OTHER INFORMATION: VIP-MIMETIC PEPTIDE

<400> SEQUENCE: 630

Asn Ser Ile Leu Asn
1               5

<210> SEQ ID NO 631
<211> LENGTH: 4
<212> TYPE: PRT
<213> ORGANISM: Artificial Sequence
<220> FEATURE:
<223> OTHER INFORMATION: VIP-MIMETIC PEPTIDE

<400> SEQUENCE: 631

Lys Lys Tyr Val
1

<210> SEQ ID NO 632
<211> LENGTH: 4
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (1)..(3)
<223> OTHER INFORMATION: Position 3, Xaa is a lauric acid residue

<400> SEQUENCE: 632

Xaa Ile Xaa Asn
1

<210> SEQ ID NO 633
<211> LENGTH: 5
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (1)..(1)
<223> OTHER INFORMATION: Position 1, Xaa is a lauric acid residue

<400> SEQUENCE: 633

Xaa Lys Lys Tyr Leu
1               5

<210> SEQ ID NO 634
<211> LENGTH: 5
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (1)..(1)
<223> OTHER INFORMATION: Position 1, Xaa is a caproic acid residue

<400> SEQUENCE: 634

Xaa Lys Lys Tyr Leu
1               5

<210> SEQ ID NO 635
<211> LENGTH: 4
```

```
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (4)..(4)
<223> OTHER INFORMATION: Position 4, Xaa is a norleucyl residue

<400> SEQUENCE: 635

Lys Lys Tyr Xaa
1

<210> SEQ ID NO 636
<211> LENGTH: 5
<212> TYPE: PRT
<213> ORGANISM: Artificial Sequence
<220> FEATURE:
<223> OTHER INFORMATION: VIP-MIMETIC PEPTIDE

<400> SEQUENCE: 636

Val Lys Lys Tyr Leu
1               5

<210> SEQ ID NO 637
<211> LENGTH: 6
<212> TYPE: PRT
<213> ORGANISM: Artificial Sequence
<220> FEATURE:
<223> OTHER INFORMATION: VIP-MIMETIC PEPTIDE

<400> SEQUENCE: 637

Leu Asn Ser Ile Leu Asn
1               5

<210> SEQ ID NO 638
<211> LENGTH: 7
<212> TYPE: PRT
<213> ORGANISM: Artificial Sequence
<220> FEATURE:
<223> OTHER INFORMATION: VIP-MIMETIC PEPTIDE

<400> SEQUENCE: 638

Tyr Leu Asn Ser Ile Leu Asn
1               5

<210> SEQ ID NO 639
<211> LENGTH: 5
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (5)..(5)
<223> OTHER INFORMATION: Position 5, Xaa is a norleucyl residue

<400> SEQUENCE: 639

Lys Lys Tyr Leu Xaa
1               5

<210> SEQ ID NO 640
<211> LENGTH: 5
<212> TYPE: PRT
<213> ORGANISM: Artificial Sequence
<220> FEATURE:
<223> OTHER INFORMATION: VIP-MIMETIC PEPTIDE

<400> SEQUENCE: 640
```

```
Lys Lys Tyr Leu Asn
1               5

<210> SEQ ID NO 641
<211> LENGTH: 6
<212> TYPE: PRT
<213> ORGANISM: Artificial Sequence
<220> FEATURE:
<223> OTHER INFORMATION: VIP-MIMETIC PEPTIDE

<400> SEQUENCE: 641

Lys Lys Tyr Leu Asn Ser
1               5

<210> SEQ ID NO 642
<211> LENGTH: 7
<212> TYPE: PRT
<213> ORGANISM: Artificial Sequence
<220> FEATURE:
<223> OTHER INFORMATION: VIP-MIMETIC PEPTIDE

<400> SEQUENCE: 642

Lys Lys Tyr Leu Asn Ser Ile
1               5

<210> SEQ ID NO 643
<211> LENGTH: 8
<212> TYPE: PRT
<213> ORGANISM: Artificial Sequence
<220> FEATURE:
<223> OTHER INFORMATION: VIP-MIMETIC PEPTIDE

<400> SEQUENCE: 643

Lys Lys Tyr Leu Asn Ser Ile Leu
1               5

<210> SEQ ID NO 644
<211> LENGTH: 6
<212> TYPE: PRT
<213> ORGANISM: Artificial Sequence
<220> FEATURE:
<223> OTHER INFORMATION: VIP-MIMETIC PEPTIDE

<400> SEQUENCE: 644

Lys Lys Lys Tyr Leu Asp
1               5

<210> SEQ ID NO 645
<211> LENGTH: 7
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<222> LOCATION: (1)..(1)
<223> OTHER INFORMATION: Positions 1 and 6 disulfide cross-linked

<400> SEQUENCE: 645

Xaa Cys Lys Lys Tyr Leu Cys
1               5

<210> SEQ ID NO 646
<211> LENGTH: 6
<212> TYPE: PRT
<213> ORGANISM: Artificial Sequence
<220> FEATURE:
```

```
<223> OTHER INFORMATION: VIP-MIMETIC PEPTIDE
<220> FEATURE:
<221> NAME/KEY: misc_feature
<223> OTHER INFORMATION: Positions 1 and 6 cross-linked by S-CH2-CO

<400> SEQUENCE: 646

Cys Lys Lys Tyr Leu Lys
1               5

<210> SEQ ID NO 647
<211> LENGTH: 4
<212> TYPE: PRT
<213> ORGANISM: Artificial Sequence
<220> FEATURE:
<223> OTHER INFORMATION: VIP-MIMETIC PEPTIDE
<220> FEATURE:
<221> NAME/KEY: misc_feature
<223> OTHER INFORMATION: Position 4, D amino acid residue

<400> SEQUENCE: 647

Lys Lys Tyr Ala
1

<210> SEQ ID NO 648
<211> LENGTH: 8
<212> TYPE: PRT
<213> ORGANISM: Artificial Sequence
<220> FEATURE:
<223> OTHER INFORMATION: VIP-MIMETIC PEPTIDE

<400> SEQUENCE: 648

Trp Trp Thr Asp Thr Gly Leu Trp
1               5

<210> SEQ ID NO 649
<211> LENGTH: 8
<212> TYPE: PRT
<213> ORGANISM: Artificial Sequence
<220> FEATURE:
<223> OTHER INFORMATION: VIP-MIMETIC PEPTIDE

<400> SEQUENCE: 649

Trp Trp Thr Asp Asp Gly Leu Trp
1               5

<210> SEQ ID NO 650
<211> LENGTH: 12
<212> TYPE: PRT
<213> ORGANISM: Artificial Sequence
<220> FEATURE:
<223> OTHER INFORMATION: VIP-MIMETIC PEPTIDE

<400> SEQUENCE: 650

Trp Trp Asp Thr Arg Gly Leu Trp Val Trp Thr Ile
1               5                   10

<210> SEQ ID NO 651
<211> LENGTH: 12
<212> TYPE: PRT
<213> ORGANISM: Artificial Sequence
<220> FEATURE:
<223> OTHER INFORMATION: VIP-MIMETIC PEPTIDE

<400> SEQUENCE: 651

Phe Trp Gly Asn Asp Gly Ile Trp Leu Glu Ser Gly
1               5                   10
```

<210> SEQ ID NO 652
<211> LENGTH: 12
<212> TYPE: PRT
<213> ORGANISM: Artificial Sequence
<220> FEATURE:
<223> OTHER INFORMATION: VIP-MIMETIC PEPTIDE

<400> SEQUENCE: 652

Asp Trp Asp Gln Phe Gly Leu Trp Arg Gly Ala Ala
1               5                   10

<210> SEQ ID NO 653
<211> LENGTH: 12
<212> TYPE: PRT
<213> ORGANISM: Artificial Sequence
<220> FEATURE:
<223> OTHER INFORMATION: VIP-MIMETIC PEPTIDE

<400> SEQUENCE: 653

Arg Trp Asp Asp Asn Gly Leu Trp Val Val Val Leu
1               5                   10

<210> SEQ ID NO 654
<211> LENGTH: 12
<212> TYPE: PRT
<213> ORGANISM: Artificial Sequence
<220> FEATURE:
<223> OTHER INFORMATION: VIP-MIMETIC PEPTIDE

<400> SEQUENCE: 654

Ser Gly Met Trp Ser His Tyr Gly Ile Trp Met Gly
1               5                   10

<210> SEQ ID NO 655
<211> LENGTH: 12
<212> TYPE: PRT
<213> ORGANISM: Artificial Sequence
<220> FEATURE:
<223> OTHER INFORMATION: VIP-MIMETIC PEPTIDE

<400> SEQUENCE: 655

Gly Gly Arg Trp Asp Gln Ala Gly Leu Trp Val Ala
1               5                   10

<210> SEQ ID NO 656
<211> LENGTH: 12
<212> TYPE: PRT
<213> ORGANISM: Artificial Sequence
<220> FEATURE:
<223> OTHER INFORMATION: VIP-MIMETIC PEPTIDE

<400> SEQUENCE: 656

Lys Leu Trp Ser Glu Gln Gly Ile Trp Met Gly Glu
1               5                   10

<210> SEQ ID NO 657
<211> LENGTH: 10
<212> TYPE: PRT
<213> ORGANISM: Artificial Sequence
<220> FEATURE:
<223> OTHER INFORMATION: VIP-MIMETIC PEPTIDE

<400> SEQUENCE: 657

Cys Trp Ser Met His Gly Leu Trp Leu Cys
1               5                   10

<210> SEQ ID NO 658

```
<211> LENGTH: 12
<212> TYPE: PRT
<213> ORGANISM: Artificial Sequence
<220> FEATURE:
<223> OTHER INFORMATION: VIP-MIMETIC PEPTIDE

<400> SEQUENCE: 658

Gly Cys Trp Asp Asn Thr Gly Ile Trp Val Pro Cys
1               5                   10

<210> SEQ ID NO 659
<211> LENGTH: 10
<212> TYPE: PRT
<213> ORGANISM: Artificial Sequence
<220> FEATURE:
<223> OTHER INFORMATION: VIP-MIMETIC PEPTIDE

<400> SEQUENCE: 659

Asp Trp Asp Thr Arg Gly Leu Trp Val Tyr
1               5                   10

<210> SEQ ID NO 660
<211> LENGTH: 10
<212> TYPE: PRT
<213> ORGANISM: Artificial Sequence
<220> FEATURE:
<223> OTHER INFORMATION: VIP-MIMETIC PEPTIDE

<400> SEQUENCE: 660

Ser Leu Trp Asp Glu Asn Gly Ala Trp Ile
1               5                   10

<210> SEQ ID NO 661
<211> LENGTH: 10
<212> TYPE: PRT
<213> ORGANISM: Artificial Sequence
<220> FEATURE:
<223> OTHER INFORMATION: VIP-MIMETIC PEPTIDE

<400> SEQUENCE: 661

Lys Trp Asp Asp Arg Gly Leu Trp Met His
1               5                   10

<210> SEQ ID NO 662
<211> LENGTH: 10
<212> TYPE: PRT
<213> ORGANISM: Artificial Sequence
<220> FEATURE:
<223> OTHER INFORMATION: VIP-MIMETIC PEPTIDE

<400> SEQUENCE: 662

Gln Ala Trp Asn Glu Arg Gly Leu Trp Thr
1               5                   10

<210> SEQ ID NO 663
<211> LENGTH: 10
<212> TYPE: PRT
<213> ORGANISM: Artificial Sequence
<220> FEATURE:
<223> OTHER INFORMATION: VIP-MIMETIC PEPTIDE

<400> SEQUENCE: 663

Gln Trp Asp Thr Arg Gly Leu Trp Val Ala
1               5                   10

<210> SEQ ID NO 664
<211> LENGTH: 9
```

<212> TYPE: PRT
<213> ORGANISM: Artificial Sequence
<220> FEATURE:
<223> OTHER INFORMATION: VIP-MIMETIC PEPTIDE

<400> SEQUENCE: 664

Trp Asn Val His Gly Ile Trp Gln Glu
1               5

<210> SEQ ID NO 665
<211> LENGTH: 10
<212> TYPE: PRT
<213> ORGANISM: Artificial Sequence
<220> FEATURE:
<223> OTHER INFORMATION: VIP-MIMETIC PEPTIDE

<400> SEQUENCE: 665

Ser Trp Asp Thr Arg Gly Leu Trp Val Glu
1               5                   10

<210> SEQ ID NO 666
<211> LENGTH: 10
<212> TYPE: PRT
<213> ORGANISM: Artificial Sequence
<220> FEATURE:
<223> OTHER INFORMATION: VIP-MIMETIC PEPTIDE

<400> SEQUENCE: 666

Asp Trp Asp Thr Arg Gly Leu Trp Val Ala
1               5                   10

<210> SEQ ID NO 667
<211> LENGTH: 10
<212> TYPE: PRT
<213> ORGANISM: Artificial Sequence
<220> FEATURE:
<223> OTHER INFORMATION: VIP-MIMETIC PEPTIDE

<400> SEQUENCE: 667

Ser Trp Gly Arg Asp Gly Leu Trp Ile Glu
1               5                   10

<210> SEQ ID NO 668
<211> LENGTH: 10
<212> TYPE: PRT
<213> ORGANISM: Artificial Sequence
<220> FEATURE:
<223> OTHER INFORMATION: VIP-MIMETIC PEPTIDE

<400> SEQUENCE: 668

Glu Trp Thr Asp Asn Gly Leu Trp Ala Leu
1               5                   10

<210> SEQ ID NO 669
<211> LENGTH: 10
<212> TYPE: PRT
<213> ORGANISM: Artificial Sequence
<220> FEATURE:
<223> OTHER INFORMATION: VIP-MIMETIC PEPTIDE

<400> SEQUENCE: 669

Ser Trp Asp Glu Lys Gly Leu Trp Ser Ala
1               5                   10

<210> SEQ ID NO 670
<211> LENGTH: 10
<212> TYPE: PRT

```
<213> ORGANISM: Artificial Sequence
<220> FEATURE:
<223> OTHER INFORMATION: VIP-MIMETIC PEPTIDE

<400> SEQUENCE: 670

Ser Trp Asp Ser Ser Gly Leu Trp Met Asp
1               5                   10

<210> SEQ ID NO 671
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 671

Ser His Leu Tyr Trp Gln Pro Tyr Ser Val Gln
1               5                   10

<210> SEQ ID NO 672
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 672

Thr Leu Val Tyr Trp Gln Pro Tyr Ser Leu Gln Thr
1               5                   10

<210> SEQ ID NO 673
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 673

Arg Gly Asp Tyr Trp Gln Pro Tyr Ser Val Gln Ser
1               5                   10

<210> SEQ ID NO 674
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 674

Val His Val Tyr Trp Gln Pro Tyr Ser Val Gln Thr
1               5                   10

<210> SEQ ID NO 675
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 675

Arg Leu Val Tyr Trp Gln Pro Tyr Ser Val Gln Thr
1               5                   10

<210> SEQ ID NO 676
<211> LENGTH: 12
<212> TYPE: PRT
<213> ORGANISM: Artificial Sequence
```

```
<220> FEATURE:
<223> OTHER INFORMATION: IL-1 ANTAGONIST PEPTIDE

<400> SEQUENCE: 676

Ser Arg Val Trp Phe Gln Pro Tyr Ser Leu Gln Ser
1               5                   10

<210> SEQ ID NO 677
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 677

Asn Met Val Tyr Trp Gln Pro Tyr Ser Ile Gln Thr
1               5                   10

<210> SEQ ID NO 678
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 678

Ser Val Val Phe Trp Gln Pro Tyr Ser Val Gln Thr
1               5                   10

<210> SEQ ID NO 679
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 679

Thr Phe Val Tyr Trp Gln Pro Tyr Ala Leu Pro Leu
1               5                   10

<210> SEQ ID NO 680
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 680

Thr Leu Val Tyr Trp Gln Pro Tyr Ser Ile Gln Arg
1               5                   10

<210> SEQ ID NO 681
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 681

Arg Leu Val Tyr Trp Gln Pro Tyr Ser Val Gln Arg
1               5                   10

<210> SEQ ID NO 682
<211> LENGTH: 12
<212> TYPE: PRT
<213> ORGANISM: Artificial Sequence
<220> FEATURE:
```

<223> OTHER INFORMATION: IL-1 ANTAGONIST PEPTIDE

<400> SEQUENCE: 682

Ser Pro Val Phe Trp Gln Pro Tyr Ser Ile Gln Ile
1               5                   10

<210> SEQ ID NO 683
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 683

Trp Ile Glu Trp Trp Gln Pro Tyr Ser Val Gln Ser
1               5                   10

<210> SEQ ID NO 684
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 684

Ser Leu Ile Tyr Trp Gln Pro Tyr Ser Leu Gln Met
1               5                   10

<210> SEQ ID NO 685
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 685

Thr Arg Leu Tyr Trp Gln Pro Tyr Ser Val Gln Arg
1               5                   10

<210> SEQ ID NO 686
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 686

Arg Cys Asp Tyr Trp Gln Pro Tyr Ser Val Gln Thr
1               5                   10

<210> SEQ ID NO 687
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 687

Met Arg Val Phe Trp Gln Pro Tyr Ser Val Gln Asn
1               5                   10

<210> SEQ ID NO 688
<211> LENGTH: 12
<212> TYPE: PRT
<213> ORGANISM: Artificial Sequence
<220> FEATURE:
<223> OTHER INFORMATION: IL-1 ANTAGONIST PEPTIDE -continued

<400> SEQUENCE: 688

Lys Ile Val Tyr Trp Gln Pro Tyr Ser Val Gln Thr
1               5                   10

<210> SEQ ID NO 689
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 689

Arg His Leu Tyr Trp Gln Pro Tyr Ser Val Gln Arg
1               5                   10

<210> SEQ ID NO 690
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 690

Ala Leu Val Trp Trp Gln Pro Tyr Ser Glu Gln Ile
1               5                   10

<210> SEQ ID NO 691
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 691

Ser Arg Val Trp Phe Gln Pro Tyr Ser Leu Gln Ser
1               5                   10

<210> SEQ ID NO 692
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 692

Trp Glu Gln Pro Tyr Ala Leu Pro Leu Glu
1               5                   10

<210> SEQ ID NO 693
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 693

Gln Leu Val Trp Trp Gln Pro Tyr Ser Val Gln Arg
1               5                   10

<210> SEQ ID NO 694
<211> LENGTH: 12
<212> TYPE: PRT
<213> ORGANISM: Artificial Sequence
<220> FEATURE:
<223> OTHER INFORMATION: IL-1 ANTAGONIST PEPTIDE

```
<400> SEQUENCE: 694

Asp Leu Arg Tyr Trp Gln Pro Tyr Ser Val Gln Val
1               5                   10

<210> SEQ ID NO 695
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 695

Glu Leu Val Trp Trp Gln Pro Tyr Ser Leu Gln Leu
1               5                   10

<210> SEQ ID NO 696
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 696

Asp Leu Val Trp Trp Gln Pro Tyr Ser Val Gln Trp
1               5                   10

<210> SEQ ID NO 697
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 697

Asn Gly Asn Tyr Trp Gln Pro Tyr Ser Phe Gln Val
1               5                   10

<210> SEQ ID NO 698
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 698

Glu Leu Val Tyr Trp Gln Pro Tyr Ser Ile Gln Arg
1               5                   10

<210> SEQ ID NO 699
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 699

Glu Leu Met Tyr Trp Gln Pro Tyr Ser Val Gln Glu
1               5                   10

<210> SEQ ID NO 700
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 700
```

Asn Leu Leu Tyr Trp Gln Pro Tyr Ser Met Gln Asp
1               5                   10

<210> SEQ ID NO 701
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 701

Gly Tyr Glu Trp Tyr Gln Pro Tyr Ser Val Gln Arg
1               5                   10

<210> SEQ ID NO 702
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 702

Ser Arg Val Trp Tyr Gln Pro Tyr Ser Val Gln Arg
1               5                   10

<210> SEQ ID NO 703
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 703

Leu Ser Glu Gln Tyr Gln Pro Tyr Ser Val Gln Arg
1               5                   10

<210> SEQ ID NO 704
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 704

Gly Gly Gly Trp Trp Gln Pro Tyr Ser Val Gln Arg
1               5                   10

<210> SEQ ID NO 705
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 705

Val Gly Arg Trp Tyr Gln Pro Tyr Ser Val Gln Arg
1               5                   10

<210> SEQ ID NO 706
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 706

```
Val His Val Tyr Trp Gln Pro Tyr Ser Val Gln Arg
1               5                   10
```

<210> SEQ ID NO 707
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 707

```
Gln Ala Arg Trp Tyr Gln Pro Tyr Ser Val Gln Arg
1               5                   10
```

<210> SEQ ID NO 708
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 708

```
Val His Val Tyr Trp Gln Pro Tyr Ser Val Gln Thr
1               5                   10
```

<210> SEQ ID NO 709
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 709

```
Arg Ser Val Tyr Trp Gln Pro Tyr Ser Val Gln Arg
1               5                   10
```

<210> SEQ ID NO 710
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 710

```
Thr Arg Val Trp Phe Gln Pro Tyr Ser Val Gln Arg
1               5                   10
```

<210> SEQ ID NO 711
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 711

```
Gly Arg Ile Trp Phe Gln Pro Tyr Ser Val Gln Arg
1               5                   10
```

<210> SEQ ID NO 712
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 712

```
Gly Arg Val Trp Phe Gln Pro Tyr Ser Val Gln Arg
```

-continued

```
1               5                   10

<210> SEQ ID NO 713
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 713

Ala Arg Thr Trp Tyr Gln Pro Tyr Ser Val Gln Arg
1               5                   10

<210> SEQ ID NO 714
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 714

Ala Arg Val Trp Trp Gln Pro Tyr Ser Val Gln Met
1               5                   10

<210> SEQ ID NO 715
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 715

Arg Leu Met Phe Tyr Gln Pro Tyr Ser Val Gln Arg
1               5                   10

<210> SEQ ID NO 716
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 716

Glu Ser Met Trp Tyr Gln Pro Tyr Ser Val Gln Arg
1               5                   10

<210> SEQ ID NO 717
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 717

His Phe Gly Trp Trp Gln Pro Tyr Ser Val His Met
1               5                   10

<210> SEQ ID NO 718
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 718

Ala Arg Phe Trp Trp Gln Pro Tyr Ser Val Gln Arg
1               5                   10
```

<210> SEQ ID NO 719
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 719

Arg Leu Val Tyr Trp Gln Pro Tyr Ala Pro Ile Tyr
1               5                   10

<210> SEQ ID NO 720
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 720

Arg Leu Val Tyr Trp Gln Pro Tyr Ser Tyr Gln Thr
1               5                   10

<210> SEQ ID NO 721
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 721

Arg Leu Val Tyr Trp Gln Pro Tyr Ser Leu Pro Ile
1               5                   10

<210> SEQ ID NO 722
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 722

Arg Leu Val Tyr Trp Gln Pro Tyr Ser Val Gln Ala
1               5                   10

<210> SEQ ID NO 723
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 723

Ser Arg Val Trp Tyr Gln Pro Tyr Ala Lys Gly Leu
1               5                   10

<210> SEQ ID NO 724
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 724

Ser Arg Val Trp Tyr Gln Pro Tyr Ala Gln Gly Leu
1               5                   10

```
<210> SEQ ID NO 725
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 725

Ser Arg Val Trp Tyr Gln Pro Tyr Ala Met Pro Leu
1               5                   10

<210> SEQ ID NO 726
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 726

Ser Arg Val Trp Tyr Gln Pro Tyr Ser Val Gln Ala
1               5                   10

<210> SEQ ID NO 727
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 727

Ser Arg Val Trp Tyr Gln Pro Tyr Ser Leu Gly Leu
1               5                   10

<210> SEQ ID NO 728
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 728

Ser Arg Val Trp Tyr Gln Pro Tyr Ala Arg Glu Leu
1               5                   10

<210> SEQ ID NO 729
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 729

Ser Arg Val Trp Tyr Gln Pro Tyr Ser Arg Gln Pro
1               5                   10

<210> SEQ ID NO 730
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 730

Ser Arg Val Trp Tyr Gln Pro Tyr Phe Val Gln Pro
1               5                   10
```

<210> SEQ ID NO 731
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 731

Glu Tyr Glu Trp Tyr Gln Pro Tyr Ala Leu Pro Leu
1               5                   10

<210> SEQ ID NO 732
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 732

Ile Pro Glu Tyr Trp Gln Pro Tyr Ala Leu Pro Leu
1               5                   10

<210> SEQ ID NO 733
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 733

Ser Arg Ile Trp Trp Gln Pro Tyr Ala Leu Pro Leu
1               5                   10

<210> SEQ ID NO 734
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 734

Asp Pro Leu Phe Trp Gln Pro Tyr Ala Leu Pro Leu
1               5                   10

<210> SEQ ID NO 735
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 735

Ser Arg Gln Trp Val Gln Pro Tyr Ala Leu Pro Leu
1               5                   10

<210> SEQ ID NO 736
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 736

Ile Arg Ser Trp Trp Gln Pro Tyr Ala Leu Pro Leu
1               5                   10

<210> SEQ ID NO 737

-continued

```
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 737

Arg Gly Tyr Trp Gln Pro Tyr Ala Leu Pro Leu
1               5                   10

<210> SEQ ID NO 738
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 738

Arg Leu Leu Trp Val Gln Pro Tyr Ala Leu Pro Leu
1               5                   10

<210> SEQ ID NO 739
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 739

Glu Tyr Arg Trp Phe Gln Pro Tyr Ala Leu Pro Leu
1               5                   10

<210> SEQ ID NO 740
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 740

Asp Ala Tyr Trp Val Gln Pro Tyr Ala Leu Pro Leu
1               5                   10

<210> SEQ ID NO 741
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 741

Trp Ser Gly Tyr Phe Gln Pro Tyr Ala Leu Pro Leu
1               5                   10

<210> SEQ ID NO 742
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 742

Asn Ile Glu Phe Trp Gln Pro Tyr Ala Leu Pro Leu
1               5                   10

<210> SEQ ID NO 743
<211> LENGTH: 12
```

```
<212> TYPE: PRT
<213> ORGANISM: Artificial Sequence
<220> FEATURE:
<223> OTHER INFORMATION: IL-1 ANTAGONIST PEPTIDE

<400> SEQUENCE: 743

Thr Arg Asp Trp Val Gln Pro Tyr Ala Leu Pro Leu
1               5                   10

<210> SEQ ID NO 744
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 744

Asp Ser Ser Trp Tyr Gln Pro Tyr Ala Leu Pro Leu
1               5                   10

<210> SEQ ID NO 745
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 745

Ile Gly Asn Trp Tyr Gln Pro Tyr Ala Leu Pro Leu
1               5                   10

<210> SEQ ID NO 746
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 746

Asn Leu Arg Trp Asp Gln Pro Tyr Ala Leu Pro Leu
1               5                   10

<210> SEQ ID NO 747
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 747

Leu Pro Glu Phe Trp Gln Pro Tyr Ala Leu Pro Leu
1               5                   10

<210> SEQ ID NO 748
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 748

Asp Ser Tyr Trp Trp Gln Pro Tyr Ala Leu Pro Leu
1               5                   10

<210> SEQ ID NO 749
<211> LENGTH: 12
<212> TYPE: PRT
```

```
<213> ORGANISM: Artificial Sequence
<220> FEATURE:
<223> OTHER INFORMATION: IL-1 ANTAGONIST PEPTIDE

<400> SEQUENCE: 749

Arg Ser Gln Tyr Tyr Gln Pro Tyr Ala Leu Pro Leu
1               5                   10

<210> SEQ ID NO 750
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 750

Ala Arg Phe Trp Leu Gln Pro Tyr Ala Leu Pro Leu
1               5                   10

<210> SEQ ID NO 751
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 751

Asn Ser Tyr Phe Trp Gln Pro Tyr Ala Leu Pro Leu
1               5                   10

<210> SEQ ID NO 752
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 752

Arg Phe Met Tyr Trp Gln Pro Tyr Ser Val Gln Arg
1               5                   10

<210> SEQ ID NO 753
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 753

Ala His Leu Phe Trp Gln Pro Tyr Ser Val Gln Arg
1               5                   10

<210> SEQ ID NO 754
<211> LENGTH: 9
<212> TYPE: PRT
<213> ORGANISM: Artificial Sequence
<220> FEATURE:
<223> OTHER INFORMATION: IL-1 ANTAGONIST PEPTIDE

<400> SEQUENCE: 754

Trp Trp Gln Pro Tyr Ala Leu Pro Leu
1               5

<210> SEQ ID NO 755
<211> LENGTH: 9
<212> TYPE: PRT
<213> ORGANISM: Artificial Sequence
```

```
<220> FEATURE:
<223> OTHER INFORMATION: IL-1 ANTAGONIST PEPTIDE

<400> SEQUENCE: 755

Tyr Tyr Gln Pro Tyr Ala Leu Pro Leu
1               5

<210> SEQ ID NO 756
<211> LENGTH: 9
<212> TYPE: PRT
<213> ORGANISM: Artificial Sequence
<220> FEATURE:
<223> OTHER INFORMATION: IL-1 ANTAGONIST PEPTIDE

<400> SEQUENCE: 756

Tyr Phe Gln Pro Tyr Ala Leu Gly Leu
1               5

<210> SEQ ID NO 757
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 757

Tyr Trp Tyr Gln Pro Tyr Ala Leu Pro Leu
1               5                   10

<210> SEQ ID NO 758
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 758

Arg Trp Trp Gln Pro Tyr Ala Thr Pro Leu
1               5                   10

<210> SEQ ID NO 759
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 759

Gly Trp Tyr Gln Pro Tyr Ala Leu Gly Phe
1               5                   10

<210> SEQ ID NO 760
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 760

Tyr Trp Tyr Gln Pro Tyr Ala Leu Gly Leu
1               5                   10

<210> SEQ ID NO 761
<211> LENGTH: 10
<212> TYPE: PRT
<213> ORGANISM: Artificial Sequence
<220> FEATURE:
```

<223> OTHER INFORMATION: IL-1 ANTAGONIST PEPTIDE

<400> SEQUENCE: 761

Ile Trp Tyr Gln Pro Tyr Ala Met Pro Leu
1               5                   10

<210> SEQ ID NO 762
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 762

Ser Asn Met Gln Pro Tyr Gln Arg Leu Ser
1               5                   10

<210> SEQ ID NO 763
<211> LENGTH: 20
<212> TYPE: PRT
<213> ORGANISM: Artificial Sequence
<220> FEATURE:
<223> OTHER INFORMATION: IL-1 ANTAGONIST PEPTIDE

<400> SEQUENCE: 763

Thr Phe Val Tyr Trp Gln Pro Tyr Ala Val Gly Leu Pro Ala Ala Glu
1               5                   10                  15

Thr Ala Cys Asn
            20

<210> SEQ ID NO 764
<211> LENGTH: 20
<212> TYPE: PRT
<213> ORGANISM: Artificial Sequence
<220> FEATURE:
<223> OTHER INFORMATION: IL-1 ANTAGONIST PEPTIDE

<400> SEQUENCE: 764

Thr Phe Val Tyr Trp Gln Pro Tyr Ser Val Gln Met Thr Ile Thr Gly
1               5                   10                  15

Lys Val Thr Met
            20

<210> SEQ ID NO 765
<211> LENGTH: 20
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (12, 13)..(16)
<223> OTHER INFORMATION: Xaa = any amino acid

<400> SEQUENCE: 765

Thr Phe Val Tyr Trp Gln Pro Tyr Ser Ser His Xaa Xaa Val Pro Xaa
1               5                   10                  15

Gly Phe Pro Leu
            20

<210> SEQ ID NO 766
<211> LENGTH: 20
<212> TYPE: PRT
<213> ORGANISM: Artificial Sequence
<220> FEATURE:
<223> OTHER INFORMATION: IL-1 ANTAGONIST PEPTIDE -continued

```
<400> SEQUENCE: 766

Thr Phe Val Tyr Trp Gln Pro Tyr Tyr Gly Asn Pro Gln Trp Ala Ile
1               5                   10                  15

His Val Arg His
            20

<210> SEQ ID NO 767
<211> LENGTH: 20
<212> TYPE: PRT
<213> ORGANISM: Artificial Sequence
<220> FEATURE:
<223> OTHER INFORMATION: IL-1 ANTAGONIST PEPTIDE

<400> SEQUENCE: 767

Thr Phe Val Tyr Trp Gln Pro Tyr Val Leu Leu Glu Leu Pro Glu Gly
1               5                   10                  15

Ala Val Arg Ala
            20

<210> SEQ ID NO 768
<211> LENGTH: 20
<212> TYPE: PRT
<213> ORGANISM: Artificial Sequence
<220> FEATURE:
<223> OTHER INFORMATION: IL-1 ANTAGONIST PEPTIDE

<400> SEQUENCE: 768

Thr Phe Val Tyr Trp Gln Pro Tyr Val Asp Tyr Val Trp Pro Ile Pro
1               5                   10                  15

Ile Ala Gln Val
            20

<210> SEQ ID NO 769
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 769

Gly Trp Tyr Gln Pro Tyr Val Asp Gly Trp Arg
1               5                   10

<210> SEQ ID NO 770
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 770

Arg Trp Glu Gln Pro Tyr Val Lys Asp Gly Trp Ser
1               5                   10

<210> SEQ ID NO 771
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 771

Glu Trp Tyr Gln Pro Tyr Ala Leu Gly Trp Ala Arg
1               5                   10
```

```
<210> SEQ ID NO 772
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 772

Gly Trp Trp Gln Pro Tyr Ala Arg Gly Leu
1               5                   10

<210> SEQ ID NO 773
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 773

Leu Phe Glu Gln Pro Tyr Ala Lys Ala Leu Gly Leu
1               5                   10

<210> SEQ ID NO 774
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 774

Gly Trp Glu Gln Pro Tyr Ala Arg Gly Leu Ala Gly
1               5                   10

<210> SEQ ID NO 775
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 775

Ala Trp Val Gln Pro Tyr Ala Thr Pro Leu Asp Glu
1               5                   10

<210> SEQ ID NO 776
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 776

Met Trp Tyr Gln Pro Tyr Ser Ser Gln Pro Ala Glu
1               5                   10

<210> SEQ ID NO 777
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 777

Gly Trp Thr Gln Pro Tyr Ser Gln Gln Gly Glu Val
1               5                   10
```

```
<210> SEQ ID NO 778
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 778

Asp Trp Phe Gln Pro Tyr Ser Ile Gln Ser Asp Glu
1               5                   10

<210> SEQ ID NO 779
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 779

Pro Trp Ile Gln Pro Tyr Ala Arg Gly Phe Gly
1               5                   10

<210> SEQ ID NO 780
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 780

Arg Pro Leu Tyr Trp Gln Pro Tyr Ser Val Gln Val
1               5                   10

<210> SEQ ID NO 781
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 781

Thr Leu Ile Tyr Trp Gln Pro Tyr Ser Val Gln Ile
1               5                   10

<210> SEQ ID NO 782
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 782

Arg Phe Asp Tyr Trp Gln Pro Tyr Ser Asp Gln Thr
1               5                   10

<210> SEQ ID NO 783
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 783

Trp His Gln Phe Val Gln Pro Tyr Ala Leu Pro Leu
1               5                   10
```

<210> SEQ ID NO 784
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 784

Glu Trp Asp Ser Val Tyr Trp Gln Pro Tyr Ser Val Gln Thr Leu Leu
1               5                   10                  15

Arg

<210> SEQ ID NO 785
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 785

Trp Glu Gln Asn Val Tyr Trp Gln Pro Tyr Ser Val Gln Ser Phe Ala
1               5                   10                  15

Asp

<210> SEQ ID NO 786
<211> LENGTH: 16
<212> TYPE: PRT
<213> ORGANISM: Artificial Sequence
<220> FEATURE:
<223> OTHER INFORMATION: IL-1 ANTAGONIST PEPTIDE

<400> SEQUENCE: 786

Ser Asp Val Val Tyr Trp Gln Pro Tyr Ser Val Gln Ser Leu Glu Met
1               5                   10                  15

<210> SEQ ID NO 787
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 787

Tyr Tyr Asp Gly Val Tyr Trp Gln Pro Tyr Ser Val Gln Val Met Pro
1               5                   10                  15

Ala

<210> SEQ ID NO 788
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 788

Ser Asp Ile Trp Tyr Gln Pro Tyr Ala Leu Pro Leu
1               5                   10

<210> SEQ ID NO 789
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 789

```
Gln Arg Ile Trp Trp Gln Pro Tyr Ala Leu Pro Leu
1               5                   10
```

<210> SEQ ID NO 790
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 790

```
Ser Arg Ile Trp Trp Gln Pro Tyr Ala Leu Pro Leu
1               5                   10
```

<210> SEQ ID NO 791
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 791

```
Arg Ser Leu Tyr Trp Gln Pro Tyr Ala Leu Pro Leu
1               5                   10
```

<210> SEQ ID NO 792
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 792

```
Thr Ile Ile Trp Glu Gln Pro Tyr Ala Leu Pro Leu
1               5                   10
```

<210> SEQ ID NO 793
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 793

```
Trp Glu Thr Trp Tyr Gln Pro Tyr Ala Leu Pro Leu
1               5                   10
```

<210> SEQ ID NO 794
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 794

```
Ser Tyr Asp Trp Glu Gln Pro Tyr Ala Leu Pro Leu
1               5                   10
```

<210> SEQ ID NO 795
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 795

Ser Arg Ile Trp Cys Gln Pro Tyr Ala Leu Pro Leu
1               5                   10

<210> SEQ ID NO 796
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 796

Glu Ile Met Phe Trp Gln Pro Tyr Ala Leu Pro Leu
1               5                   10

<210> SEQ ID NO 797
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 797

Asp Tyr Val Trp Gln Gln Pro Tyr Ala Leu Pro Leu
1               5                   10

<210> SEQ ID NO 798
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 798

Met Asp Leu Leu Val Gln Trp Tyr Gln Pro Tyr Ala Leu Pro Leu
1               5                   10                  15

<210> SEQ ID NO 799
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 799

Gly Ser Lys Val Ile Leu Trp Tyr Gln Pro Tyr Ala Leu Pro Leu
1               5                   10                  15

<210> SEQ ID NO 800
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 800

Arg Gln Gly Ala Asn Ile Trp Tyr Gln Pro Tyr Ala Leu Pro Leu
1               5                   10                  15

<210> SEQ ID NO 801
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 801

Gly Gly Gly Asp Glu Pro Trp Tyr Gln Pro Tyr Ala Leu Pro Leu

```
                    1               5              10              15

<210> SEQ ID NO 802
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 802

Ser Gln Leu Glu Arg Thr Trp Tyr Gln Pro Tyr Ala Leu Pro Leu
1               5                  10                  15

<210> SEQ ID NO 803
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 803

Glu Thr Trp Val Arg Glu Trp Tyr Gln Pro Tyr Ala Leu Pro Leu
1               5                  10                  15

<210> SEQ ID NO 804
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 804

Lys Lys Gly Ser Thr Gln Trp Tyr Gln Pro Tyr Ala Leu Pro Leu
1               5                  10                  15

<210> SEQ ID NO 805
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 805

Leu Gln Ala Arg Met Asn Trp Tyr Gln Pro Tyr Ala Leu Pro Leu
1               5                  10                  15

<210> SEQ ID NO 806
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 806

Glu Pro Arg Ser Gln Lys Trp Tyr Gln Pro Tyr Ala Leu Pro Leu
1               5                  10                  15

<210> SEQ ID NO 807
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 807

Val Lys Gln Lys Trp Arg Trp Tyr Gln Pro Tyr Ala Leu Pro Leu
1               5                  10                  15
```

```
<210> SEQ ID NO 808
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 808

Leu Arg Arg His Asp Val Trp Tyr Gln Pro Tyr Ala Leu Pro Leu
1               5                   10                  15

<210> SEQ ID NO 809
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 809

Arg Ser Thr Ala Ser Ile Trp Tyr Gln Pro Tyr Ala Leu Pro Leu
1               5                   10                  15

<210> SEQ ID NO 810
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 810

Glu Ser Lys Glu Asp Gln Trp Tyr Gln Pro Tyr Ala Leu Pro Leu
1               5                   10                  15

<210> SEQ ID NO 811
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 811

Glu Gly Leu Thr Met Lys Trp Tyr Gln Pro Tyr Ala Leu Pro Leu
1               5                   10                  15

<210> SEQ ID NO 812
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 812

Glu Gly Ser Arg Glu Gly Trp Tyr Gln Pro Tyr Ala Leu Pro Leu
1               5                   10                  15

<210> SEQ ID NO 813
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 813

Val Ile Glu Trp Trp Gln Pro Tyr Ala Leu Pro Leu
1               5                   10
```

```
<210> SEQ ID NO 814
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 814

Val Trp Tyr Trp Glu Gln Pro Tyr Ala Leu Pro Leu
1               5                   10

<210> SEQ ID NO 815
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 815

Ala Ser Glu Trp Trp Gln Pro Tyr Ala Leu Pro Leu
1               5                   10

<210> SEQ ID NO 816
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 816

Phe Tyr Glu Trp Trp Gln Pro Tyr Ala Leu Pro Leu
1               5                   10

<210> SEQ ID NO 817
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 817

Glu Gly Trp Trp Val Gln Pro Tyr Ala Leu Pro Leu
1               5                   10

<210> SEQ ID NO 818
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 818

Trp Gly Glu Trp Leu Gln Pro Tyr Ala Leu Pro Leu
1               5                   10

<210> SEQ ID NO 819
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 819

Asp Tyr Val Trp Glu Gln Pro Tyr Ala Leu Pro Leu
1               5                   10
```

```
<210> SEQ ID NO 820
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 820

Ala His Thr Trp Trp Gln Pro Tyr Ala Leu Pro Leu
1               5                   10

<210> SEQ ID NO 821
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 821

Phe Ile Glu Trp Phe Gln Pro Tyr Ala Leu Pro Leu
1               5                   10

<210> SEQ ID NO 822
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 822

Trp Leu Ala Trp Glu Gln Pro Tyr Ala Leu Pro Leu
1               5                   10

<210> SEQ ID NO 823
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 823

Val Met Glu Trp Trp Gln Pro Tyr Ala Leu Pro Leu
1               5                   10

<210> SEQ ID NO 824
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 824

Glu Arg Met Trp Gln Pro Tyr Ala Leu Pro Leu
1               5                   10

<210> SEQ ID NO 825
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (2, 3, 5)..(6)
<223> OTHER INFORMATION: Xaa = any amino acid

<400> SEQUENCE: 825

Asn Xaa Xaa Trp Xaa Xaa Pro Tyr Ala Leu Pro Leu
```

-continued

```
                1               5                  10
```

<210> SEQ ID NO 826
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 826

```
Trp Gly Asn Trp Tyr Gln Pro Tyr Ala Leu Pro Leu
1               5                  10
```

<210> SEQ ID NO 827
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 827

```
Thr Leu Tyr Trp Glu Gln Pro Tyr Ala Leu Pro Leu
1               5                  10
```

<210> SEQ ID NO 828
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 828

```
Val Trp Arg Trp Glu Gln Pro Tyr Ala Leu Pro Leu
1               5                  10
```

<210> SEQ ID NO 829
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 829

```
Leu Leu Trp Thr Gln Pro Tyr Ala Leu Pro Leu
1               5                  10
```

<210> SEQ ID NO 830
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(6)
<223> OTHER INFORMATION: Xaa = any amino acid

<400> SEQUENCE: 830

```
Ser Arg Ile Trp Xaa Xaa Pro Tyr Ala Leu Pro Leu
1               5                  10
```

<210> SEQ ID NO 831
<211> LENGTH: 12
<212> TYPE: PRT
<213> ORGANISM: Artificial Sequence
<220> FEATURE:
<223> OTHER INFORMATION: IL-1 ANTAGONIST PEPTIDE

```
<400> SEQUENCE: 831

Ser Asp Ile Trp Tyr Gln Pro Tyr Ala Leu Pro Leu
1               5                   10

<210> SEQ ID NO 832
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(6)
<223> OTHER INFORMATION: Xaa = any amino acid

<400> SEQUENCE: 832

Trp Gly Tyr Tyr Xaa Xaa Pro Tyr Ala Leu Pro Leu
1               5                   10

<210> SEQ ID NO 833
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 833

Thr Ser Gly Trp Tyr Gln Pro Tyr Ala Leu Pro Leu
1               5                   10

<210> SEQ ID NO 834
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(6)
<223> OTHER INFORMATION: Xaa = any amino acid

<400> SEQUENCE: 834

Val His Pro Tyr Xaa Xaa Pro Tyr Ala Leu Pro Leu
1               5                   10

<210> SEQ ID NO 835
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 835

Glu His Ser Tyr Phe Gln Pro Tyr Ala Leu Pro Leu
1               5                   10

<210> SEQ ID NO 836
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(2)
<223> OTHER INFORMATION: Xaa = any amino acid

<400> SEQUENCE: 836
```

-continued

```
Xaa Xaa Ile Trp Tyr Gln Pro Tyr Ala Leu Pro Leu
1               5                   10

<210> SEQ ID NO 837
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 837

Ala Gln Leu His Ser Gln Pro Tyr Ala Leu Pro Leu
1               5                   10

<210> SEQ ID NO 838
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 838

Trp Ala Asn Trp Phe Gln Pro Tyr Ala Leu Pro Leu
1               5                   10

<210> SEQ ID NO 839
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 839

Ser Arg Leu Tyr Ser Gln Pro Tyr Ala Leu Pro Leu
1               5                   10

<210> SEQ ID NO 840
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 840

Gly Val Thr Phe Ser Gln Pro Tyr Ala Leu Pro Leu
1               5                   10

<210> SEQ ID NO 841
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 841

Ser Ile Val Trp Ser Gln Pro Tyr Ala Leu Pro Leu
1               5                   10

<210> SEQ ID NO 842
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 842

Ser Arg Asp Leu Val Gln Pro Tyr Ala Leu Pro Leu
```

-continued

<210> SEQ ID NO 843
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 843

His Trp Gly His Val Tyr Trp Gln Pro Tyr Ser Val Gln Asp Asp Leu
1               5                   10                  15
Gly

<210> SEQ ID NO 844
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 844

Ser Trp His Ser Val Tyr Trp Gln Pro Tyr Ser Val Gln Ser Val Pro
1               5                   10                  15
Glu

<210> SEQ ID NO 845
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 845

Trp Arg Asp Ser Val Tyr Trp Gln Pro Tyr Ser Val Gln Pro Glu Ser
1               5                   10                  15
Ala

<210> SEQ ID NO 846
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 846

Thr Trp Asp Ala Val Tyr Trp Gln Pro Tyr Ser Val Gln Lys Trp Leu
1               5                   10                  15
Asp

<210> SEQ ID NO 847
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 847

Thr Pro Pro Trp Val Tyr Trp Gln Pro Tyr Ser Val Gln Ser Leu Asp
1               5                   10                  15
Pro

<210> SEQ ID NO 848

```
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 848

Tyr Trp Ser Ser Val Tyr Trp Gln Pro Tyr Ser Val Gln Ser Val His
1               5                   10                  15
Ser

<210> SEQ ID NO 849
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 849

Tyr Trp Tyr Gln Pro Tyr Ala Leu Gly Leu
1               5                   10

<210> SEQ ID NO 850
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 850

Tyr Trp Tyr Gln Pro Tyr Ala Leu Pro Leu
1               5                   10

<210> SEQ ID NO 851
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 851

Glu Trp Ile Gln Pro Tyr Ala Thr Gly Leu
1               5                   10

<210> SEQ ID NO 852
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 852

Asn Trp Glu Gln Pro Tyr Ala Lys Pro Leu
1               5                   10

<210> SEQ ID NO 853
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 853

Ala Phe Tyr Gln Pro Tyr Ala Leu Pro Leu
1               5                   10
```

-continued

```
<210> SEQ ID NO 854
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 854

Phe Leu Tyr Gln Pro Tyr Ala Leu Pro Leu
1               5                   10

<210> SEQ ID NO 855
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 855

Val Cys Lys Gln Pro Tyr Leu Glu Trp Cys
1               5                   10

<210> SEQ ID NO 856
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 856

Glu Thr Pro Phe Thr Trp Glu Glu Ser Asn Ala Tyr Tyr Trp Gln Pro
1               5                   10                  15

Tyr Ala Leu Pro Leu
            20

<210> SEQ ID NO 857
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 857

Gln Gly Trp Leu Thr Trp Gln Asp Ser Val Asp Met Tyr Trp Gln Pro
1               5                   10                  15

Tyr Ala Leu Pro Leu
            20

<210> SEQ ID NO 858
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 858

Phe Ser Glu Ala Gly Tyr Thr Trp Pro Glu Asn Thr Tyr Trp Gln Pro
1               5                   10                  15

Tyr Ala Leu Pro Leu
            20

<210> SEQ ID NO 859
<211> LENGTH: 21
<212> TYPE: PRT
<213> ORGANISM: Artificial Sequence
<220> FEATURE:
```

<223> OTHER INFORMATION: IL-1 ANTAGONIST PEPTIDE

<400> SEQUENCE: 859

Thr Glu Ser Pro Gly Gly Leu Asp Trp Ala Lys Ile Tyr Trp Gln Pro
1               5                   10                  15

Tyr Ala Leu Pro Leu
            20

<210> SEQ ID NO 860
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 860

Asp Gly Tyr Asp Arg Trp Arg Gln Ser Gly Glu Arg Tyr Trp Gln Pro
1               5                   10                  15

Tyr Ala Leu Pro Leu
            20

<210> SEQ ID NO 861
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 861

Thr Ala Asn Val Ser Ser Phe Glu Trp Thr Pro Gly Tyr Trp Gln Pro
1               5                   10                  15

Tyr Ala Leu Pro Leu
            20

<210> SEQ ID NO 862
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 862

Ser Val Gly Glu Asp His Asn Phe Trp Thr Ser Glu Tyr Trp Gln Pro
1               5                   10                  15

Tyr Ala Leu Pro Leu
            20

<210> SEQ ID NO 863
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 863

Met Asn Asp Gln Thr Ser Glu Val Ser Thr Phe Pro Tyr Trp Gln Pro
1               5                   10                  15

Tyr Ala Leu Pro Leu
            20

<210> SEQ ID NO 864
<211> LENGTH: 21
<212> TYPE: PRT
<213> ORGANISM: Artificial Sequence

```
<220> FEATURE:
<223> OTHER INFORMATION: IL-1 ANTAGONIST PEPTIDE

<400> SEQUENCE: 864

Ser Trp Ser Glu Ala Phe Glu Gln Pro Arg Asn Leu Tyr Trp Gln Pro
1               5                   10                  15

Tyr Ala Leu Pro Leu
            20

<210> SEQ ID NO 865
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 865

Gln Tyr Ala Glu Pro Ser Ala Leu Asn Asp Trp Gly Tyr Trp Gln Pro
1               5                   10                  15

Tyr Ala Leu Pro Leu
            20

<210> SEQ ID NO 866
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 866

Asn Gly Asp Trp Ala Thr Ala Asp Trp Ser Asn Tyr Tyr Trp Gln Pro
1               5                   10                  15

Tyr Ala Leu Pro Leu
            20

<210> SEQ ID NO 867
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 867

Thr His Asp Glu His Ile Tyr Trp Gln Pro Tyr Ala Leu Pro Leu
1               5                   10                  15

<210> SEQ ID NO 868
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 868

Met Leu Glu Lys Thr Tyr Thr Thr Trp Thr Pro Gly Tyr Trp Gln Pro
1               5                   10                  15

Tyr Ala Leu Pro Leu
            20

<210> SEQ ID NO 869
<211> LENGTH: 20
<212> TYPE: PRT
<213> ORGANISM: Artificial Sequence
<220> FEATURE:
<223> OTHER INFORMATION: IL-1 ANTAGONIST PEPTIDE
```

-continued

```
<400> SEQUENCE: 869

Trp Ser Asp Pro Leu Thr Arg Asp Ala Asp Leu Tyr Trp Gln Pro Tyr
1               5                   10                  15

Ala Leu Pro Leu
            20

<210> SEQ ID NO 870
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 870

Ser Asp Ala Phe Thr Thr Gln Asp Ser Gln Ala Met Tyr Trp Gln Pro
1               5                   10                  15

Tyr Ala Leu Pro Leu
            20

<210> SEQ ID NO 871
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 871

Gly Asp Asp Ala Ala Trp Arg Thr Asp Ser Leu Thr Tyr Trp Gln Pro
1               5                   10                  15

Tyr Ala Leu Pro Leu
            20

<210> SEQ ID NO 872
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 872

Ala Ile Ile Arg Gln Leu Tyr Arg Trp Ser Glu Met Tyr Trp Gln Pro
1               5                   10                  15

Tyr Ala Leu Pro Leu
            20

<210> SEQ ID NO 873
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 873

Glu Asn Thr Tyr Ser Pro Asn Trp Ala Asp Ser Met Tyr Trp Gln Pro
1               5                   10                  15

Tyr Ala Leu Pro Leu
            20

<210> SEQ ID NO 874
<211> LENGTH: 21
<212> TYPE: PRT
<213> ORGANISM: Artificial Sequence
<220> FEATURE:
```

<223> OTHER INFORMATION: IL-1 ANTAGONIST PEPTIDE

<400> SEQUENCE: 874

Met Asn Asp Gln Thr Ser Glu Val Ser Thr Phe Pro Tyr Trp Gln Pro
1               5                   10                  15

Tyr Ala Leu Pro Leu
            20

<210> SEQ ID NO 875
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 875

Ser Val Gly Glu Asp His Asn Phe Trp Thr Ser Glu Tyr Trp Gln Pro
1               5                   10                  15

Tyr Ala Leu Pro Leu
            20

<210> SEQ ID NO 876
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 876

Gln Thr Pro Phe Thr Trp Glu Glu Ser Asn Ala Tyr Tyr Trp Gln Pro
1               5                   10                  15

Tyr Ala Leu Pro Leu
            20

<210> SEQ ID NO 877
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 877

Glu Asn Pro Phe Thr Trp Gln Glu Ser Asn Ala Tyr Tyr Trp Gln Pro
1               5                   10                  15

Tyr Ala Leu Pro Leu
            20

<210> SEQ ID NO 878
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 878

Val Thr Pro Phe Thr Trp Glu Asp Ser Asn Val Phe Tyr Trp Gln Pro
1               5                   10                  15

Tyr Ala Leu Pro Leu
            20

<210> SEQ ID NO 879
<211> LENGTH: 21
<212> TYPE: PRT
<213> ORGANISM: Artificial Sequence

```
<220> FEATURE:
<223> OTHER INFORMATION: IL-1 ANTAGONIST PEPTIDE

<400> SEQUENCE: 879

Gln Ile Pro Phe Thr Trp Glu Gln Ser Asn Ala Tyr Tyr Trp Gln Pro
1               5                   10                  15

Tyr Ala Leu Pro Leu
            20

<210> SEQ ID NO 880
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 880

Gln Ala Pro Leu Thr Trp Gln Glu Ser Ala Ala Tyr Tyr Trp Gln Pro
1               5                   10                  15

Tyr Ala Leu Pro Leu
            20

<210> SEQ ID NO 881
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 881

Glu Pro Thr Phe Thr Trp Glu Glu Ser Lys Ala Thr Tyr Trp Gln Pro
1               5                   10                  15

Tyr Ala Leu Pro Leu
            20

<210> SEQ ID NO 882
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 882

Thr Thr Thr Leu Thr Trp Glu Glu Ser Asn Ala Tyr Tyr Trp Gln Pro
1               5                   10                  15

Tyr Ala Leu Pro Leu
            20

<210> SEQ ID NO 883
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 883

Glu Ser Pro Leu Thr Trp Glu Glu Ser Ser Ala Leu Tyr Trp Gln Pro
1               5                   10                  15

Tyr Ala Leu Pro Leu
            20

<210> SEQ ID NO 884
<211> LENGTH: 21
<212> TYPE: PRT
```

```
<213> ORGANISM: Artificial Sequence
<220> FEATURE:
<223> OTHER INFORMATION: IL-1 ANTAGONIST PEPTIDE

<400> SEQUENCE: 884

Glu Thr Pro Leu Thr Trp Glu Glu Ser Asn Ala Tyr Tyr Trp Gln Pro
1               5                   10                  15

Tyr Ala Leu Pro Leu
            20

<210> SEQ ID NO 885
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 885

Glu Ala Thr Phe Thr Trp Ala Glu Ser Asn Ala Tyr Tyr Trp Gln Pro
1               5                   10                  15

Tyr Ala Leu Pro Leu
            20

<210> SEQ ID NO 886
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 886

Glu Ala Leu Phe Thr Trp Lys Glu Ser Thr Ala Tyr Tyr Trp Gln Pro
1               5                   10                  15

Tyr Ala Leu Pro Leu
            20

<210> SEQ ID NO 887
<211> LENGTH: 20
<212> TYPE: PRT
<213> ORGANISM: Artificial Sequence
<220> FEATURE:
<223> OTHER INFORMATION: IL-1 ANTAGONIST PEPTIDE

<400> SEQUENCE: 887

Ser Thr Pro Thr Trp Glu Glu Ser Asn Ala Tyr Tyr Trp Gln Pro Tyr
1               5                   10                  15

Ala Leu Pro Leu
        20

<210> SEQ ID NO 888
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 888

Glu Thr Pro Phe Thr Trp Glu Glu Ser Asn Ala Tyr Tyr Trp Gln Pro
1               5                   10                  15

Tyr Ala Leu Pro Leu
            20

<210> SEQ ID NO 889
<211> LENGTH: 21
```

```
<212> TYPE: PRT
<213> ORGANISM: Artificial Sequence
<220> FEATURE:
<223> OTHER INFORMATION: IL-1 ANTAGONIST PEPTIDE

<400> SEQUENCE: 889

Lys Ala Pro Phe Thr Trp Glu Glu Ser Gln Ala Tyr Tyr Trp Gln Pro
1               5                   10                  15

Tyr Ala Leu Pro Leu
            20

<210> SEQ ID NO 890
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 890

Ser Thr Ser Phe Thr Trp Glu Glu Ser Asn Ala Tyr Tyr Trp Gln Pro
1               5                   10                  15

Tyr Ala Leu Pro Leu
            20

<210> SEQ ID NO 891
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 891

Asp Ser Thr Phe Thr Trp Glu Glu Ser Asn Ala Tyr Tyr Trp Gln Pro
1               5                   10                  15

Tyr Ala Leu Pro Leu
            20

<210> SEQ ID NO 892
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 892

Tyr Ile Pro Phe Thr Trp Glu Glu Ser Asn Ala Tyr Tyr Trp Gln Pro
1               5                   10                  15

Tyr Ala Leu Pro Leu
            20

<210> SEQ ID NO 893
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 893

Gln Thr Ala Phe Thr Trp Glu Glu Ser Asn Ala Tyr Tyr Trp Gln Pro
1               5                   10                  15

Tyr Ala Leu Pro Leu
            20

<210> SEQ ID NO 894
```

-continued

```
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 894

Glu Thr Leu Phe Thr Trp Glu Glu Ser Asn Ala Thr Tyr Trp Gln Pro
1               5                   10                  15

Tyr Ala Leu Pro Leu
            20

<210> SEQ ID NO 895
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 895

Val Ser Ser Phe Thr Trp Glu Glu Ser Asn Ala Tyr Tyr Trp Gln Pro
1               5                   10                  15

Tyr Ala Leu Pro Leu
            20

<210> SEQ ID NO 896
<211> LENGTH: 7
<212> TYPE: PRT
<213> ORGANISM: Artificial Sequence
<220> FEATURE:
<223> OTHER INFORMATION: IL-1 ANTAGONIST PEPTIDE

<400> SEQUENCE: 896

Gln Pro Tyr Ala Leu Pro Leu
1               5

<210> SEQ ID NO 897
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa is a phosphotyrosyl residue
<220> FEATURE:
<221> NAME/KEY: misc_feature
<222> LOCATION: (2)..(2)
<223> OTHER INFORMATION: Position 2, Xaa is a 1-napthylalanyl residue
<220> FEATURE:
<221> NAME/KEY: misc_feature
<222> LOCATION: (6)..(6)
<223> OTHER INFORMATION: Position 6, Xaa is an azetidine residue

<400> SEQUENCE: 897

Xaa Xaa Pro Tyr Gln Xaa Tyr Ala Leu Pro Leu
1               5                   10

<210> SEQ ID NO 898
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 898

Thr Ala Asn Val Ser Ser Phe Glu Trp Thr Pro Gly Tyr Trp Gln Pro
```

```
                1               5                  10                 15
Tyr Ala Leu Pro Leu
            20

<210> SEQ ID NO 899
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 899

Phe Glu Trp Thr Pro Gly Tyr Trp Gln Pro Tyr Ala Leu Pro Leu
1               5                  10                 15

<210> SEQ ID NO 900
<211> LENGTH: 15
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 900

Phe Glu Trp Thr Pro Gly Tyr Trp Gln Xaa Tyr Ala Leu Pro Leu
1               5                  10                 15

<210> SEQ ID NO 901
<211> LENGTH: 15
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 901

Phe Glu Trp Thr Pro Gly Tyr Tyr Gln Xaa Tyr Ala Leu Pro Leu
1               5                  10                 15

<210> SEQ ID NO 902
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 902

Glu Thr Pro Phe Thr Trp Glu Glu Ser Asn Ala Tyr Tyr Trp Gln Pro
1               5                  10                 15

Tyr Ala Leu Pro Leu
            20

<210> SEQ ID NO 903
<211> LENGTH: 18
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (13)..(13)
<223> OTHER INFORMATION: Position 13, Xaa is an azetidine residue
```

-continued

```
<400> SEQUENCE: 903

Phe Thr Trp Glu Glu Ser Asn Ala Tyr Tyr Trp Gln Xaa Tyr Ala Leu
1               5                   10                  15
Pro Leu

<210> SEQ ID NO 904
<211> LENGTH: 16
<212> TYPE: PRT
<213> ORGANISM: Artificial Sequence
<220> FEATURE:
<223> OTHER INFORMATION: IL-1 ANTAGONIST PEPTIDE

<400> SEQUENCE: 904

Ala Asp Val Leu Tyr Trp Gln Pro Tyr Ala Pro Val Thr Leu Trp Val
1               5                   10                  15

<210> SEQ ID NO 905
<211> LENGTH: 17
<212> TYPE: PRT
<213> ORGANISM: Artificial Sequence
<220> FEATURE:
<223> OTHER INFORMATION: IL-1 ANTAGONIST

<400> SEQUENCE: 905

Gly Asp Val Ala Glu Tyr Trp Gln Pro Tyr Ala Leu Pro Leu Thr Ser
1               5                   10                  15
Leu

<210> SEQ ID NO 906
<211> LENGTH: 18
<212> TYPE: PRT
<213> ORGANISM: Artificial Sequence
<220> FEATURE:
<223> OTHER INFORMATION: IL-1 ANTAGONIST PEPTIDE

<400> SEQUENCE: 906

Ser Trp Thr Asp Tyr Gly Tyr Trp Gln Pro Tyr Ala Leu Pro Ile Ser
1               5                   10                  15
Gly Leu

<210> SEQ ID NO 907
<211> LENGTH: 8
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1, 2, 7)..(8)
<223> OTHER INFORMATION: Xaa is any amino acid
<220> FEATURE:
<221> NAME/KEY: misc_feature
<222> LOCATION: (4)..(4)
<223> OTHER INFORMATION: Position 4, Xaa is prolyl or an azetidine
      residue
<220> FEATURE:
<221> NAME/KEY: misc_feature
<222> LOCATION: (6)..(6)
<223> OTHER INFORMATION: Position 6, Xaa is S, A, V or L

<400> SEQUENCE: 907

Xaa Xaa Gln Xaa Tyr Xaa Xaa Xaa
1               5

<210> SEQ ID NO 908
```

```
<211> LENGTH: 8
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa is Y, W or F
<220> FEATURE:
<221> NAME/KEY: misc_feature
<222> LOCATION: (2, 7)..(8)
<223> OTHER INFORMATION: Xaa is any amino acid
<220> FEATURE:
<221> NAME/KEY: misc_feature
<222> LOCATION: (4)..(4)
<223> OTHER INFORMATION: Position 4, Xaa is prolyl or an azetidine
      residue
<220> FEATURE:
<221> NAME/KEY: misc_feature
<222> LOCATION: (6)..(6)
<223> OTHER INFORMATION: Position 6, Xaa is S, A, V or L

<400> SEQUENCE: 908

Xaa Xaa Gln Xaa Tyr Xaa Xaa Xaa
1               5

<210> SEQ ID NO 909
<211> LENGTH: 8
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa is Y, W or F
<220> FEATURE:
<221> NAME/KEY: misc_feature
<222> LOCATION: (2)..(2)
<223> OTHER INFORMATION: Position 2, Xaa is E, F, V, W or Y
<220> FEATURE:
<221> NAME/KEY: misc_feature
<222> LOCATION: (4)..(4)
<223> OTHER INFORMATION: Position 4, Xaa is prolyl or an azetidine
      residue
<220> FEATURE:
<221> NAME/KEY: misc_feature
<222> LOCATION: (6)..(6)
<223> OTHER INFORMATION: Position 6, Xaa is S, A, V or L
<220> FEATURE:
<221> NAME/KEY: misc_feature
<222> LOCATION: (7)..(7)
<223> OTHER INFORMATION: Position 7, Xaa is M, F, V, R, Q, K, T, S, D,
      L, I or E
<220> FEATURE:
<221> NAME/KEY: misc_feature
<222> LOCATION: (8)..(8)
<223> OTHER INFORMATION: Position 8, Xaa is E, L, W, V, H, I, G, A, D,
      L, Y, N, Q or P

<400> SEQUENCE: 909

Xaa Xaa Gly Xaa Tyr Xaa Xaa Xaa
1               5

<210> SEQ ID NO 910
<211> LENGTH: 9
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa is V, L, I, E, P, G, Y, M, T
```

```
           or D
<220> FEATURE:
<221> NAME/KEY: misc_feature
<222> LOCATION: (2)..(2)
<223> OTHER INFORMATION: Position 2, Xaa is Y, W or F
<220> FEATURE:
<221> NAME/KEY: misc_feature
<222> LOCATION: (3)..(3)
<223> OTHER INFORMATION: Position 3, Xaa is E, F, V, W or Y
<220> FEATURE:
<221> NAME/KEY: misc_feature
<222> LOCATION: (5)..(5)
<223> OTHER INFORMATION: Position 5, Xaa is prolyl or an azetidine
      residue;
<220> FEATURE:
<221> NAME/KEY: misc_feature
<222> LOCATION: (7)..(7)
<223> OTHER INFORMATION: Position 7, Xaa is S, A, V or L
<220> FEATURE:
<221> NAME/KEY: misc_feature
<222> LOCATION: (8)..(8)
<223> OTHER INFORMATION: Position 8, Xaa is M, F, V, R, Q, K, T, S, D,
      L, I or E;
<220> FEATURE:
<221> NAME/KEY: misc_feature
<222> LOCATION: (9)..(9)
<223> OTHER INFORMATION: Position 9, Xaa is E, L, W, V, H, I, G, A, D,
      L, Y, N, Q or P

<400> SEQUENCE: 910

Xaa Xaa Xaa Gln Xaa Tyr Xaa Xaa Xaa
1               5

<210> SEQ ID NO 911
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 911

Phe Glu Trp Thr Pro Gly Tyr Trp Gln Pro Tyr Ala Leu Pro Leu
1               5                   10                  15

<210> SEQ ID NO 912
<211> LENGTH: 15
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Xaa = any amino acid

<400> SEQUENCE: 912

Phe Glu Trp Thr Pro Gly Tyr Trp Gln Xaa Tyr Ala Leu Pro Leu
1               5                   10                  15

<210> SEQ ID NO 913
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 913

Phe Glu Trp Thr Pro Gly Trp Tyr Gln Pro Tyr Ala Leu Pro Leu
1               5                   10                  15

<210> SEQ ID NO 914
```

```
<211> LENGTH: 15
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 914

Phe Glu Trp Thr Pro Gly Trp Tyr Gln Xaa Tyr Ala Leu Pro Leu
1               5                   10                  15

<210> SEQ ID NO 915
<211> LENGTH: 15
<212> TYPE: PRT
<213> ORGANISM: Artificial Sequence
<220> FEATURE:
<223> OTHER INFORMATION: IL-1 ANTAGONIST PEPTIDE

<400> SEQUENCE: 915

Phe Glu Trp Thr Pro Gly Tyr Tyr Gln Pro Tyr Ala Leu Pro Leu
1               5                   10                  15

<210> SEQ ID NO 916
<211> LENGTH: 15
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 916

Phe Glu Trp Thr Pro Gly Tyr Tyr Gln Xaa Tyr Ala Leu Pro Leu
1               5                   10                  15

<210> SEQ ID NO 917
<211> LENGTH: 21
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa is A, D, E, F, G, K, Q, S, T,
      V or Y
<220> FEATURE:
<221> NAME/KEY: misc_feature
<222> LOCATION: (2)..(2)
<223> OTHER INFORMATION: Position 2, Xaa is A, D, G, I, N, P, S, T,
      V or W
<220> FEATURE:
<221> NAME/KEY: misc_feature
<222> LOCATION: (3)..(3)
<223> OTHER INFORMATION: Position 3, Xaa is A, D, G, L, N, P, S, T,
      W or Y
<220> FEATURE:
<221> NAME/KEY: misc_feature
<222> LOCATION: (4)..(4)
<223> OTHER INFORMATION: Position 4, Xaa is A, D, E, F, L, N, R, V or Y
<220> FEATURE:
<221> NAME/KEY: misc_feature
<222> LOCATION: (5)..(5)
<223> OTHER INFORMATION: Position 5, Xaa is A, D, E, Q, R, S or T
<220> FEATURE:
<221> NAME/KEY: misc_feature
<222> LOCATION: (6)..(6)
<223> OTHER INFORMATION: Position 6, Xaa is H, I, L, P, S, T or W
```

```
<220> FEATURE:
<221> NAME/KEY: misc_feature
<222> LOCATION: (7)..(7)
<223> OTHER INFORMATION: Position 7, Xaa is A, E, F, K, N, Q, R, S or Y;
<220> FEATURE:
<221> NAME/KEY: misc_feature
<222> LOCATION: (8)..(8)
<223> OTHER INFORMATION: Position 8, Xaa is D, E, F, Q, R, T or W
<220> FEATURE:
<221> NAME/KEY: misc_feature
<222> LOCATION: (9)..(9)
<223> OTHER INFORMATION: Position 9, Xaa is A, D, P, S, T or W
<220> FEATURE:
<221> NAME/KEY: misc_feature
<222> LOCATION: (10)..(10)
<223> OTHER INFORMATION: Position 10, Xaa is A, D, G, K, N, Q, S or T
<220> FEATURE:
<221> NAME/KEY: misc_feature
<222> LOCATION: (11)..(11)
<223> OTHER INFORMATION: Position 11, Xaa is A, E, L, P, S, T, V or Y
<220> FEATURE:
<221> NAME/KEY: misc_feature
<222> LOCATION: (12)..(12)
<223> OTHER INFORMATION: Position 12, Xaa is V, L, I, E, P, G, Y, M, T
      or D
<220> FEATURE:
<221> NAME/KEY: misc_feature
<222> LOCATION: (13)..(13)
<223> OTHER INFORMATION: Position 13, Xaa is Y, W or F
<220> FEATURE:
<221> NAME/KEY: misc_feature
<222> LOCATION: (14)..(14)
<223> OTHER INFORMATION: Position 14, Xaa is E, F, V, W or Y
<220> FEATURE:
<221> NAME/KEY: misc_feature
<222> LOCATION: (16)..(16)
<223> OTHER INFORMATION: Position 16, Xaa is P or an azetidine residue;
<220> FEATURE:
<221> NAME/KEY: misc_feature
<222> LOCATION: (18)..(18)
<223> OTHER INFORMATION: Position 18, Xaa is S, A, V or L
<220> FEATURE:
<221> NAME/KEY: misc_feature
<222> LOCATION: (19)..(19)
<223> OTHER INFORMATION: Position 19, Xaa is M, F, V, R, Q, K, T, S, D,
      L, I or E
<220> FEATURE:
<221> NAME/KEY: misc_feature
<222> LOCATION: (20)..(20)
<223> OTHER INFORMATION: Position 20, Xaa is Q or P.

<400> SEQUENCE: 917

Xaa Xaa Xaa Xaa Xaa Xaa Xaa Xaa Xaa Xaa Xaa Xaa Xaa Xaa Gln Xaa
1               5                   10                  15

Tyr Xaa Xaa Xaa Leu
            20

<210> SEQ ID NO 918
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 918

Thr Ala Asn Val Ser Ser Phe Glu Trp Thr Pro Gly Tyr Trp Gln Pro
1               5                   10                  15

Tyr Ala Leu Pro Leu
            20

<210> SEQ ID NO 919
<211> LENGTH: 18
<212> TYPE: PRT
```

-continued

```
<213> ORGANISM: Artificial Sequence
<220> FEATURE:
<223> OTHER INFORMATION: IL-1 ANTAGONIST PEPTIDE

<400> SEQUENCE: 919

Ser Trp Thr Asp Tyr Gly Tyr Trp Gln Pro Tyr Ala Leu Pro Ile Ser
1               5                   10                  15

Gly Leu

<210> SEQ ID NO 920
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 920

Glu Thr Pro Phe Thr Trp Glu Glu Ser Asn Ala Tyr Tyr Trp Gln Pro
1               5                   10                  15

Tyr Ala Leu Pro Leu
            20

<210> SEQ ID NO 921
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 921

Glu Asn Thr Tyr Ser Pro Asn Trp Ala Asp Ser Met Tyr Trp Gln Pro
1               5                   10                  15

Tyr Ala Leu Pro Leu
            20

<210> SEQ ID NO 922
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 922

Ser Val Gly Glu Asp His Asn Phe Trp Thr Ser Glu Tyr Trp Gln Pro
1               5                   10                  15

Tyr Ala Leu Pro Leu
            20

<210> SEQ ID NO 923
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 923

Asp Gly Tyr Asp Arg Trp Arg Gln Ser Gly Glu Arg Tyr Trp Gln Pro
1               5                   10                  15

Tyr Ala Leu Pro Leu
            20

<210> SEQ ID NO 924
<211> LENGTH: 15
<212> TYPE: PRT
```

```
<213> ORGANISM: Artificial Sequence
<220> FEATURE:
<223> OTHER INFORMATION: IL-1 ANTAGONIST PEPTIDE

<400> SEQUENCE: 924

Phe Glu Trp Thr Pro Gly Tyr Trp Gln Pro Tyr Ala Leu Pro Leu
1               5                   10                  15

<210> SEQ ID NO 925
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 925

Phe Glu Trp Thr Pro Gly Tyr Trp Gln Pro Tyr
1               5                   10

<210> SEQ ID NO 926
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 926

Phe Glu Trp Thr Pro Gly Tyr Trp Gln Xaa Tyr
1               5                   10

<210> SEQ ID NO 927
<211> LENGTH: 10
<212> TYPE: PRT
<213> ORGANISM: Artificial Sequence
<220> FEATURE:
<223> OTHER INFORMATION: IL-1 ANTAGONIST PEPTIDE

<400> SEQUENCE: 927

Glu Trp Thr Pro Gly Tyr Trp Gln Pro Tyr
1               5                   10

<210> SEQ ID NO 928
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 928

Phe Glu Trp Thr Pro Gly Trp Tyr Gln Xaa Tyr
1               5                   10

<210> SEQ ID NO 929
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
```

<223> OTHER INFORMATION: Position 10, Xaa is an azetidine residue

<400> SEQUENCE: 929

Ala Glu Trp Thr Pro Gly Tyr Trp Gln Xaa Tyr
1               5                   10

<210> SEQ ID NO 930
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 930

Phe Ala Trp Thr Pro Gly Tyr Trp Gln Xaa Tyr
1               5                   10

<210> SEQ ID NO 931
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 931

Phe Glu Ala Thr Pro Gly Tyr Trp Gln Xaa Tyr
1               5                   10

<210> SEQ ID NO 932
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 932

Phe Glu Trp Ala Pro Gly Tyr Trp Gln Xaa Tyr
1               5                   10

<210> SEQ ID NO 933
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 933

Phe Glu Trp Thr Ala Gly Tyr Trp Gln Xaa Tyr
1               5                   10

<210> SEQ ID NO 934
<211> LENGTH: 11
<212> TYPE: PRT

```
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 934

Phe Glu Trp Thr Pro Ala Tyr Trp Gln Xaa Tyr
1               5                   10

<210> SEQ ID NO 935
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 935

Phe Glu Trp Thr Pro Gly Ala Trp Gln Xaa Tyr
1               5                   10

<210> SEQ ID NO 936
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 936

Phe Glu Trp Thr Pro Gly Tyr Ala Gln Xaa Tyr
1               5                   10

<210> SEQ ID NO 937
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 937

Phe Glu Trp Thr Pro Gly Tyr Trp Gln Xaa Ala
1               5                   10

<210> SEQ ID NO 938
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 938

Phe Glu Trp Thr Gly Gly Tyr Trp Gln Xaa Tyr
```

<210> SEQ ID NO 939
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 5, D amino acid residue
      Position 10, Xaa is an azetidine residue

<400> SEQUENCE: 939

Phe Glu Trp Thr Pro Gly Tyr Trp Gln Xaa Tyr
1               5                   10

<210> SEQ ID NO 940
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(10)
<223> OTHER INFORMATION: Position 10, Xaa is an azetidine residue

<400> SEQUENCE: 940

Phe Glu Trp Thr Xaa Gly Tyr Trp Gln Xaa Tyr
1               5                   10

<210> SEQ ID NO 941
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(5)
<223> OTHER INFORMATION: Position 5, Xaa is a pipecolic acid residue
<220> FEATURE:
<221> NAME/KEY: misc_feature
<222> LOCATION: (10)..(10)
<223> OTHER INFORMATION: Position 10, Xaa is an azetidine residue

<400> SEQUENCE: 941

Phe Glu Trp Thr Xaa Gly Tyr Trp Gln Xaa Tyr
1               5                   10

<210> SEQ ID NO 942
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (6)..(6)
<223> OTHER INFORMATION: Position 6, Xaa is an aminoisobutyric acid
      residue
<220> FEATURE:
<221> NAME/KEY: misc_feature
<222> LOCATION: (10)..(10)
<223> OTHER INFORMATION: Position 10, Xaa is an azetidine residue

<400> SEQUENCE: 942

Phe Glu Trp Thr Pro Xaa Tyr Trp Gln Xaa Tyr
1               5                   10

<210> SEQ ID NO 943
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (6)..(6)
<223> OTHER INFORMATION: Position 6, Xaa is a sarcosine residue
<220> FEATURE:
<221> NAME/KEY: misc_feature
<222> LOCATION: (10)..(10)
<223> OTHER INFORMATION: Position 10, Xaa is an azetidine residue

<400> SEQUENCE: 943

Phe Glu Trp Thr Pro Xaa Trp Tyr Gln Xaa Tyr
 1               5                  10

<210> SEQ ID NO 944
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(5)
<223> OTHER INFORMATION: Position 5, Xaa is a sarcosine residue
<220> FEATURE:
<221> NAME/KEY: misc_feature
<222> LOCATION: (10)..(10)
<223> OTHER INFORMATION: Position 10, Xaa is an azetidine residue

<400> SEQUENCE: 944

Phe Glu Trp Thr Xaa Gly Tyr Trp Gln Xaa Tyr
 1               5                  10

<210> SEQ ID NO 945
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 945

Phe Glu Trp Thr Pro Asn Tyr Trp Gln Xaa Tyr
 1               5                  10

<210> SEQ ID NO 946
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (5)..(5)
<223> OTHER INFORMATION: Position 5, D amino acid residue

<400> SEQUENCE: 946

Phe Glu Trp Thr Pro Val Tyr Trp Gln Xaa Tyr

```
                1               5                       10
```

<210> SEQ ID NO 947
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 947

```
Phe Glu Trp Thr Val Pro Tyr Trp Gln Xaa Tyr
1               5                   10
```

<210> SEQ ID NO 948
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, acetylated Phe
<220> FEATURE:
<221> NAME/KEY: misc_feature
<222> LOCATION: (10)..(10)
<223> OTHER INFORMATION: Position 10, Xaa is an azetidine residue

<400> SEQUENCE: 948

```
Phe Glu Trp Thr Pro Gly Trp Tyr Gln Xaa Tyr
1               5                   10
```

<210> SEQ ID NO 949
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, acetylated Phe
<220> FEATURE:
<221> NAME/KEY: misc_feature
<222> LOCATION: (10)..(10)
<223> OTHER INFORMATION: Position 10, Xaa is an azetidine residue

<400> SEQUENCE: 949

```
Phe Glu Trp Thr Pro Gly Tyr Trp Gln Xaa Tyr
1               5                   10
```

<210> SEQ ID NO 950
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa = 1-naphthylalanine
<220> FEATURE:
<221> NAME/KEY: misc_feature
<222> LOCATION: (10)..(10)
<223> OTHER INFORMATION: Position 10, Xaa is an azetidine residue

<400> SEQUENCE: 950

```
Xaa Glu Trp Thr Pro Gly Tyr Tyr Gln Xaa Tyr
 1               5                  10
```

<210> SEQ ID NO 951
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, xaa is an azetidine residue

<400> SEQUENCE: 951

```
Tyr Glu Trp Thr Pro Gly Tyr Tyr Gln Xaa Tyr
 1               5                  10
```

<210> SEQ ID NO 952
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 952

```
Phe Glu Trp Val Pro Gly Tyr Tyr Gln Xaa Tyr
 1               5                  10
```

<210> SEQ ID NO 953
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 953

```
Phe Glu Trp Thr Pro Gly Tyr Tyr Gln Xaa Tyr
 1               5                  10
```

<210> SEQ ID NO 954
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue

<400> SEQUENCE: 954

```
Phe Glu Trp Thr Pro Ser Tyr Tyr Gln Xaa Tyr
 1               5                  10
```

<210> SEQ ID NO 955
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:

<221> NAME/KEY: misc_feature
<222> LOCATION: (10)..(10)
<223> OTHER INFORMATION: Position 10, Xaa is an azetidine residue

<400> SEQUENCE: 955

Phe Glu Trp Thr Pro Asn Tyr Tyr Gln Xaa Tyr
1               5                   10

<210> SEQ ID NO 956
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(5)
<223> OTHER INFORMATION: Position 5, Xaa = naphthylalanine

<400> SEQUENCE: 956

Ser His Leu Tyr Xaa Gln Pro Tyr Ser Val Gln Met
1               5                   10

<210> SEQ ID NO 957
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(5)
<223> OTHER INFORMATION: Position 5, Xaa = naphthylalanine

<400> SEQUENCE: 957

Thr Leu Val Tyr Xaa Gln Pro Tyr Ser Leu Gln Thr
1               5                   10

<210> SEQ ID NO 958
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(5)
<223> OTHER INFORMATION: Position 5, Xaa = naphthylalanine

<400> SEQUENCE: 958

Arg Gly Asp Tyr Xaa Gln Pro Tyr Ser Val Gln Ser
1               5                   10

<210> SEQ ID NO 959
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(5)
<223> OTHER INFORMATION: Position 5, Xaa = naphthylalanine

<400> SEQUENCE: 959

Asn Met Val Tyr Xaa Gln Pro Tyr Ser Ile Gln Thr
1               5                   10

<210> SEQ ID NO 960

```
<211> LENGTH: 9
<212> TYPE: PRT
<213> ORGANISM: Artificial Sequence
<220> FEATURE:
<223> OTHER INFORMATION: IL-1 ANTAGONIST PEPTIDE

<400> SEQUENCE: 960

Val Tyr Trp Gln Pro Tyr Ser Val Gln
1               5

<210> SEQ ID NO 961
<211> LENGTH: 9
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (3)..(3)
<223> OTHER INFORMATION: Position 3, Xaa = naphthylalanine

<400> SEQUENCE: 961

Val Tyr Xaa Gln Pro Tyr Ser Val Gln
1               5

<210> SEQ ID NO 962
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (7)..(7)
<223> OTHER INFORMATION: Position 7, Xaa is an azetidine residue

<400> SEQUENCE: 962

Thr Phe Val Tyr Trp Gln Xaa Tyr Ala Leu Pro Leu
1               5                   10

<210> SEQ ID NO 963
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11, Xaa = p-benzoyl-L-phenylalanine

<400> SEQUENCE: 963

Phe Glu Trp Thr Pro Gly Tyr Tyr Gln Xaa Xaa
1               5                   10

<210> SEQ ID NO 964
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa = acetylated Phe
<220> FEATURE:
<221> NAME/KEY: misc_feature
```

<222> LOCATION: (10)..(10)
<223> OTHER INFORMATION: Position 10, Xaa is an azetidine residue
<220> FEATURE:
<221> NAME/KEY: misc_feature
<222> LOCATION: (11)..(11)
<223> OTHER INFORMATION: Position 11, Xaa = p-benzoyl-L-phenylalanine.

<400> SEQUENCE: 964

Xaa Glu Trp Thr Pro Gly Tyr Tyr Gln Xaa Xaa
1               5                   10

<210> SEQ ID NO 965
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (8)..(10)
<223> OTHER INFORMATION: Position 8, Xaa = p-benzoyl-L-phenylalanine
      Position 10, Xaa is an azetidine residue
<220> FEATURE:
<221> NAME/KEY: misc_feature
<222> LOCATION: (10)..(10)
<223> OTHER INFORMATION: Position 10, Xaa is an azetidine residue

<400> SEQUENCE: 965

Phe Glu Trp Thr Pro Gly Tyr Xaa Gln Xaa Tyr
1               5                   10

<210> SEQ ID NO 966
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa = acetylated Phe
<220> FEATURE:
<221> NAME/KEY: misc_feature
<222> LOCATION: (8)..(8)
<223> OTHER INFORMATION: Position 8, Xaa = p-benzoyl-L-phenylalanine
<220> FEATURE:
<221> NAME/KEY: misc_feature
<222> LOCATION: (10)..(10)
<223> OTHER INFORMATION: Position 10, Xaa is an azetidine residue.

<400> SEQUENCE: 966

Phe Glu Trp Thr Pro Gly Tyr Xaa Gln Xaa Tyr
1               5                   10

<210> SEQ ID NO 967
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (7)..(7)
<223> OTHER INFORMATION: Position 7, Xaa = p-benzoyl-L-phenylalanine
<220> FEATURE:
<221> NAME/KEY: misc_feature
<222> LOCATION: (10)..(10)
<223> OTHER INFORMATION: Position 10, Xaa is an azetidine residue.

<400> SEQUENCE: 967

Phe Glu Trp Thr Pro Gly Xaa Tyr Gln Xaa Tyr
1               5                   10

<210> SEQ ID NO 968
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa = acetylated Phe
<220> FEATURE:
<221> NAME/KEY: misc_feature
<222> LOCATION: (7)..(7)
<223> OTHER INFORMATION: Position 7, Xaa = p-benzoyl-L-phenylalanine
<220> FEATURE:
<221> NAME/KEY: misc_feature
<222> LOCATION: (10)..(10)
<223> OTHER INFORMATION: Position 10, Xaa is an azetidine residue.

<400> SEQUENCE: 968

Phe Glu Trp Thr Pro Gly Xaa Tyr Gln Xaa Tyr
1               5                   10

<210> SEQ ID NO 969
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa = acetylated Phe
<220> FEATURE:
<221> NAME/KEY: misc_feature
<222> LOCATION: (3)..(3)
<223> OTHER INFORMATION: Position 3, Xaa = p-benzoyl-L-phenylalanine
<220> FEATURE:
<221> NAME/KEY: misc_feature
<222> LOCATION: (10)..(10)
<223> OTHER INFORMATION: Position 10, Xaa is an azetidine residue.

<400> SEQUENCE: 969

Phe Glu Xaa Thr Pro Gly Tyr Tyr Gln Xaa Tyr
1               5                   10

<210> SEQ ID NO 970
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa = acetylated Phe
<220> FEATURE:
<221> NAME/KEY: misc_feature
<222> LOCATION: (3)..(3)
<223> OTHER INFORMATION: Position 3, Xaa = p-benzoyl-L-phenylalanine
<220> FEATURE:
<221> NAME/KEY: misc_feature
<222> LOCATION: (10)..(10)
<223> OTHER INFORMATION: Position 10, Xaa is an azetidine residue.

<400> SEQUENCE: 970

Phe Glu Xaa Thr Pro Gly Tyr Tyr Gln Xaa Tyr
1               5                   10

<210> SEQ ID NO 971
<211> LENGTH: 11

```
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa = p-benzoyl-L-phenylalanine
<220> FEATURE:
<221> NAME/KEY: misc_feature
<222> LOCATION: (10)..(10)
<223> OTHER INFORMATION: Position 10, Xaa is an azetidine residue.

<400> SEQUENCE: 971

Xaa Glu Trp Thr Pro Gly Tyr Tyr Gln Xaa Tyr
1               5                   10

<210> SEQ ID NO 972
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa = acetylated p-benzoyl-L-
      phenylalanine
<220> FEATURE:
<221> NAME/KEY: misc_feature
<222> LOCATION: (10)..(10)
<223> OTHER INFORMATION: Position 10, Xaa is an azetidine residue.

<400> SEQUENCE: 972

Xaa Glu Trp Thr Pro Gly Tyr Tyr Gln Xaa Tyr
1               5                   10

<210> SEQ ID NO 973
<211> LENGTH: 9
<212> TYPE: PRT
<213> ORGANISM: Artificial Sequence
<220> FEATURE:
<223> OTHER INFORMATION: IL-1 ANTAGONIST PEPTIDE

<400> SEQUENCE: 973

Val Tyr Trp Gln Pro Tyr Ser Val Gln
1               5

<210> SEQ ID NO 974
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 974

Arg Leu Val Tyr Trp Gln Pro Tyr Ser Val Gln Arg
1               5                   10

<210> SEQ ID NO 975
<211> LENGTH: 12
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (5)..(5)
<223> OTHER INFORMATION: Position 5, Xaa = naphthylalanine

<400> SEQUENCE: 975
```

```
Arg Leu Val Tyr Xaa Gln Pro Tyr Ser Val Gln Arg
1               5                   10

<210> SEQ ID NO 976
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 976

Arg Leu Asp Tyr Trp Gln Pro Tyr Ser Val Gln Arg
1               5                   10

<210> SEQ ID NO 977
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 977

Arg Leu Val Trp Phe Gln Pro Tyr Ser Val Gln Arg
1               5                   10

<210> SEQ ID NO 978
<211> LENGTH: 12
<212> TYPE: PRT
<213> ORGANISM: Artificial Sequence
<220> FEATURE:
<223> OTHER INFORMATION: IL-1 ANTAGONIST PEPTIDE

<400> SEQUENCE: 978

Arg Leu Val Tyr Trp Gln Pro Tyr Ser Ile Gln Arg
1               5                   10

<210> SEQ ID NO 979
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa = D or Y
<220> FEATURE:
<221> NAME/KEY: misc_feature
<222> LOCATION: (3)..(3)
<223> OTHER INFORMATION: Position 3, Xaa = D or S
<220> FEATURE:
<221> NAME/KEY: misc_feature
<222> LOCATION: (4)..(4)
<223> OTHER INFORMATION: Position 4, Xaa = S, T or A
<220> FEATURE:
<221> NAME/KEY: misc_feature
<222> LOCATION: (5)..(5)
<223> OTHER INFORMATION: Position 5, Xaa = S or W
<220> FEATURE:
<221> NAME/KEY: misc_feature
<222> LOCATION: (6)..(6)
<223> OTHER INFORMATION: Position 6, Xaa = S or Y
<220> FEATURE:
<221> NAME/KEY: misc_feature
<222> LOCATION: (7)..(7)
<223> OTHER INFORMATION: Xaa is any amino acid
<220> FEATURE:
<221> NAME/KEY: misc_feature
<222> LOCATION: (8)..(8)
<223> OTHER INFORMATION: Position 8, Xaa = N, S, K, H or W
<220> FEATURE:
```

```
<221> NAME/KEY: misc_feature
<222> LOCATION: (9)..(9)
<223> OTHER INFORMATION: Position 9, Xaa = F or L
<220> FEATURE:
<221> NAME/KEY: misc_feature
<222> LOCATION: (10)..(10)
<223> OTHER INFORMATION: Position 10, Xaa = D, N, S or L
<220> FEATURE:
<221> NAME/KEY: misc_feature
<222> LOCATION: (11)..(11)
<223> OTHER INFORMATION: Position 11, Xaa = L, I, Q, M or A.

<400> SEQUENCE: 979

Xaa Asn Xaa Xaa Xaa Xaa Xaa Xaa Xaa Xaa Xaa
1               5                   10

<210> SEQ ID NO 980
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 980

Asp Asn Ser Ser Trp Tyr Asp Ser Phe Leu Leu
1               5                   10

<210> SEQ ID NO 981
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 981

Asp Asn Thr Ala Trp Tyr Glu Ser Phe Leu Ala
1               5                   10

<210> SEQ ID NO 982
<211> LENGTH: 11
<212> TYPE: PRT
<213> ORGANISM: Artificial Sequence
<220> FEATURE:
<223> OTHER INFORMATION: IL-1 ANTAGONIST PEPTIDE

<400> SEQUENCE: 982

Asp Asn Thr Ala Trp Tyr Glu Asn Phe Leu Leu
1               5                   10

<210> SEQ ID NO 983
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 983

Pro Ala Arg Glu Asp Asn Thr Ala Trp Tyr Asp Ser Phe Leu Ile Trp
1               5                   10                  15

Cys

<210> SEQ ID NO 984
<211> LENGTH: 17
<212> TYPE: PRT
<213> ORGANISM: Artificial Sequence
<220> FEATURE:
<223> OTHER INFORMATION: IL-1 ANTAGONIST PEPTIDE
```

-continued

```
<400> SEQUENCE: 984

Thr Ser Glu Tyr Asp Asn Thr Thr Trp Tyr Glu Lys Phe Leu Ala Ser
1               5                   10                  15
Gln

<210> SEQ ID NO 985
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 985

Ser Gln Ile Pro Asp Asn Thr Ala Trp Tyr Gln Ser Phe Leu Leu His
1               5                   10                  15
Gly

<210> SEQ ID NO 986
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 986

Ser Pro Phe Ile Asp Asn Thr Ala Trp Tyr Glu Asn Phe Leu Leu Thr
1               5                   10                  15
Tyr

<210> SEQ ID NO 987
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 987

Glu Gln Ile Tyr Asp Asn Thr Ala Trp Tyr Asp His Phe Leu Leu Ser
1               5                   10                  15
Tyr

<210> SEQ ID NO 988
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 988

Thr Pro Phe Ile Asp Asn Thr Ala Trp Tyr Glu Asn Phe Leu Leu Thr
1               5                   10                  15
Tyr

<210> SEQ ID NO 989
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 989

Thr Tyr Thr Tyr Asp Asn Thr Ala Trp Tyr Glu Arg Phe Leu Met Ser
1               5                   10                  15
```

Tyr

<210> SEQ ID NO 990
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 990

Thr Met Thr Gln Asp Asn Thr Ala Trp Tyr Glu Asn Phe Leu Leu Ser
1               5                   10                  15

Tyr

<210> SEQ ID NO 991
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 991

Thr Ile Asp Asn Thr Ala Trp Tyr Ala Asn Leu Val Gln Thr Tyr Pro
1               5                   10                  15

Gln

<210> SEQ ID NO 992
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 992

Thr Ile Asp Asn Thr Ala Trp Tyr Glu Arg Phe Leu Ala Gln Tyr Pro
1               5                   10                  15

Asp

<210> SEQ ID NO 993
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 993

His Ile Asp Asn Thr Ala Trp Tyr Glu Asn Phe Leu Leu Thr Tyr Thr
1               5                   10                  15

Pro

<210> SEQ ID NO 994
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 994

Ser Gln Asp Asn Thr Ala Trp Tyr Glu Asn Phe Leu Leu Ser Tyr Lys
1               5                   10                  15

Ala

```
<210> SEQ ID NO 995
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 995

Gln Ile Asp Asn Thr Ala Trp Tyr Glu Arg Phe Leu Leu Gln Tyr Asn
1               5                   10                  15

Ala

<210> SEQ ID NO 996
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 996

Asn Gln Asp Asn Thr Ala Trp Tyr Glu Ser Phe Leu Leu Gln Tyr Asn
1               5                   10                  15

Thr

<210> SEQ ID NO 997
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 997

Thr Ile Asp Asn Thr Ala Trp Tyr Glu Asn Phe Leu Leu Asn His Asn
1               5                   10                  15

Leu

<210> SEQ ID NO 998
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 998

His Tyr Asp Asn Thr Ala Trp Tyr Glu Arg Phe Leu Gln Gln Gly Trp
1               5                   10                  15

His

<210> SEQ ID NO 999
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 999

Glu Thr Pro Phe Thr Trp Glu Glu Ser Asn Ala Tyr Tyr Trp Gln Pro
1               5                   10                  15

Tyr Ala Leu Pro Leu
            20

<210> SEQ ID NO 1000
<211> LENGTH: 21
<212> TYPE: PRT
```

```
<213> ORGANISM: Artificial Sequence
<220> FEATURE:
<223> OTHER INFORMATION: IL-1 ANTAGONIST PEPTIDE

<400> SEQUENCE: 1000

Tyr Ile Pro Phe Thr Trp Glu Glu Ser Asn Ala Tyr Tyr Trp Gln Pro
1               5                   10                  15

Tyr Ala Leu Pro Leu
            20

<210> SEQ ID NO 1001
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 1001

Asp Gly Tyr Asp Arg Trp Arg Gln Ser Gly Glu Arg Tyr Trp Gln Pro
1               5                   10                  15

Tyr Ala Leu Pro Leu
            20

<210> SEQ ID NO 1002
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1, Xaa = phosphotyrosine
<220> FEATURE:
<221> NAME/KEY: misc_feature
<222> LOCATION: (2)..(2)
<223> OTHER INFORMATION: Position 2, Xaa = naphthylalanine
<220> FEATURE:
<221> NAME/KEY: misc_feature
<222> LOCATION: (3)..(3)
<223> OTHER INFORMATION: Position 3, Xaa = phosphotyrosine
<220> FEATURE:
<221> NAME/KEY: misc_feature
<222> LOCATION: (6)..(6)
<223> OTHER INFORMATION: Position 6, Xaa is an azetidine residue.

<400> SEQUENCE: 1002

Xaa Xaa Xaa Gln Gln Xaa Tyr Ala Leu Pro Leu
1               5                   10

<210> SEQ ID NO 1003
<211> LENGTH: 21
<212> TYPE: PRT
<213> ORGANISM: Artificial Sequence
<220> FEATURE:
<223> OTHER INFORMATION: IL-1 ANTAGONIST PEPTIDE

<400> SEQUENCE: 1003

Thr Ala Asn Val Ser Ser Phe Glu Trp Thr Pro Gly Tyr Trp Gln Pro
1               5                   10                  15

Tyr Ala Leu Pro Leu
            20

<210> SEQ ID NO 1004
<211> LENGTH: 15
<212> TYPE: PRT
<213> ORGANISM: Artificial Sequence
<220> FEATURE:
```

```
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa = azetidine

<400> SEQUENCE: 1004

Phe Glu Trp Thr Pro Gly Tyr Trp Gln Xaa Tyr Ala Leu Pro Leu
1               5                   10                  15

<210> SEQ ID NO 1005
<211> LENGTH: 17
<212> TYPE: PRT
<213> ORGANISM: Artificial Sequence
<220> FEATURE:
<223> OTHER INFORMATION: IL-1 ANTAGONIST PEPTIDE

<400> SEQUENCE: 1005

Phe Glu Trp Thr Pro Gly Tyr Trp Gln Pro Tyr Ala Leu Pro Leu Ser
1               5                   10                  15

Asp

<210> SEQ ID NO 1006
<211> LENGTH: 15
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa = azetidine

<400> SEQUENCE: 1006

Phe Glu Trp Thr Pro Gly Tyr Tyr Gln Xaa Tyr Ala Leu Pro Leu
1               5                   10                  15

<210> SEQ ID NO 1007
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa = azetidine

<400> SEQUENCE: 1007

Phe Glu Trp Thr Pro Gly Tyr Trp Gln Xaa Tyr
1               5                   10

<210> SEQ ID NO 1008
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 is acetylated Phe
<220> FEATURE:
<221> NAME/KEY: misc_feature
<222> LOCATION: (10)..(10)
<223> OTHER INFORMATION: Position 10, Xaa = azetidine

<400> SEQUENCE: 1008

Phe Glu Trp Thr Pro Gly Tyr Trp Gln Xaa Tyr
```

```
1               5                  10

<210> SEQ ID NO 1009
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 1 is acetylated Phe
      Position 10, Xaa = azetidine

<400> SEQUENCE: 1009

Phe Glu Trp Thr Pro Gly Trp Tyr Gln Xaa Tyr
1               5                  10

<210> SEQ ID NO 1010
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 is acetylated Phe
<220> FEATURE:
<221> NAME/KEY: misc_feature
<222> LOCATION: (10)..(10)
<223> OTHER INFORMATION: Position 10, Xaa = azetidine

<400> SEQUENCE: 1010

Phe Glu Trp Thr Pro Gly Tyr Tyr Gln Xaa Tyr
1               5                  10

<210> SEQ ID NO 1011
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 is acetylated Phe
<220> FEATURE:
<221> NAME/KEY: misc_feature
<222> LOCATION: (10)..(10)
<223> OTHER INFORMATION: Position 10, Xaa = azetidine

<400> SEQUENCE: 1011

Phe Glu Trp Thr Pro Ala Tyr Trp Gln Xaa Tyr
1               5                  10

<210> SEQ ID NO 1012
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 is acetylated Phe
<220> FEATURE:
<221> NAME/KEY: misc_feature
<222> LOCATION: (10)..(10)
<223> OTHER INFORMATION: Position 10, Xaa = azetidine

<400> SEQUENCE: 1012
```

```
Phe Glu Trp Thr Pro Ala Trp Tyr Gln Xaa Tyr
1               5                   10
```

<210> SEQ ID NO 1013
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 is acetylated Phe
<220> FEATURE:
<221> NAME/KEY: misc_feature
<222> LOCATION: (10)..(10)
<223> OTHER INFORMATION: Position 10, Xaa = azetidine

<400> SEQUENCE: 1013

```
Phe Glu Trp Thr Pro Ala Tyr Tyr Gln Xaa Tyr
1               5                   10
```

<210> SEQ ID NO 1014
<211> LENGTH: 15
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa = azetidine

<400> SEQUENCE: 1014

```
Phe Glu Trp Thr Pro Gly Tyr Tyr Gln Xaa Tyr Ala Leu Pro Leu
1               5                   10                  15
```

<210> SEQ ID NO 1015
<211> LENGTH: 15
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa = azetidine

<400> SEQUENCE: 1015

```
Phe Glu Trp Thr Pro Gly Tyr Trp Gln Xaa Tyr Ala Leu Pro Leu
1               5                   10                  15
```

<210> SEQ ID NO 1016
<211> LENGTH: 15
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa = azetidine

<400> SEQUENCE: 1016

```
Phe Glu Trp Thr Pro Gly Trp Tyr Gln Xaa Tyr Ala Leu Pro Leu
1               5                   10                  15
```

<210> SEQ ID NO 1017
<211> LENGTH: 21

```
<212> TYPE: PRT
<213> ORGANISM: Artificial Sequence
<220> FEATURE:
<223> OTHER INFORMATION: IL-1 ANTAGONIST PEPTIDE

<400> SEQUENCE: 1017

Thr Ala Asn Val Ser Ser Phe Glu Trp Thr Pro Gly Tyr Trp Gln Pro
1               5                   10                  15

Tyr Ala Leu Pro Leu
            20

<210> SEQ ID NO 1018
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (10)..(10)
<223> OTHER INFORMATION: Position 10, Xaa = azetidine
<220> FEATURE:
<221> NAME/KEY: misc_feature
<222> LOCATION: (1)..(1)
<223> OTHER INFORMATION: Position 1 is acetylated Phe

<400> SEQUENCE: 1018

Phe Glu Trp Thr Pro Gly Tyr Trp Gln Xaa Tyr
1               5                   10

<210> SEQ ID NO 1019
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 is acetylated Phe
<220> FEATURE:
<221> NAME/KEY: misc_feature
<222> LOCATION: (10)..(10)
<223> OTHER INFORMATION: Position 10, Xaa = azetidine

<400> SEQUENCE: 1019

Phe Glu Trp Thr Pro Gly Trp Tyr Gln Xaa Tyr
1               5                   10

<210> SEQ ID NO 1020
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 is acetylated Phe
<220> FEATURE:
<221> NAME/KEY: misc_feature
<222> LOCATION: (10)..(10)
<223> OTHER INFORMATION: Position 10, Xaa = azetidine

<400> SEQUENCE: 1020

Phe Glu Trp Thr Pro Gly Tyr Tyr Gln Xaa Tyr
1               5                   10

<210> SEQ ID NO 1021
<211> LENGTH: 11
```

```
<212> TYPE: PRT
<213> ORGANIS: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 is acetylated Phe
<220> FEATURE:
<221> NAME/KEY: misc_feature
<222> LOCATION: (6)..(6)
<223> OTHER INFORMATION: Position 6, D amino acid residue
<220> FEATURE:
<221> NAME/KEY: misc_feature
<222> LOCATION: (10)..(10)
<223> OTHER INFORMATION: Position 10, Xaa = azetidine.

<400> SEQUENCE: 1021

Phe Glu Trp Thr Pro Ala Tyr Trp Gln Xaa Tyr
1               5                   10

<210> SEQ ID NO 1022
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 is acetylated Phe
<220> FEATURE:
<221> NAME/KEY: misc_feature
<222> LOCATION: (6)..(6)
<223> OTHER INFORMATION: Position 6, D amino acid residue
<220> FEATURE:
<221> NAME/KEY: misc_feature
<222> LOCATION: (10)..(10)
<223> OTHER INFORMATION: Position 10, Xaa = azetidine.

<400> SEQUENCE: 1022

Phe Glu Trp Thr Pro Ala Trp Tyr Gln Xaa Tyr
1               5                   10

<210> SEQ ID NO 1023
<211> LENGTH: 11
<212> TYPE: PRT
<213> ORGANISM: Artificial Sequence
<220> FEATURE:
<223> OTHER INFORMATION: IL-1 ANTAGONIST PEPTIDE
<220> FEATURE:
<221> NAME/KEY: misc_feature
<222> LOCATION: (1)..(1)
<223> OTHER INFORMATION: Position 1 is acetylated Phe
<220> FEATURE:
<221> NAME/KEY: misc_feature
<222> LOCATION: (6)..(6)
<223> OTHER INFORMATION: Position 6, D amino acid residue
<220> FEATURE:
<221> NAME/KEY: misc_feature
<222> LOCATION: (10)..(10)
<223> OTHER INFORMATION: Position 10, Xaa = azetidine.

<400> SEQUENCE: 1023

Phe Glu Trp Thr Pro Ala Tyr Tyr Gln Xaa Tyr
1               5                   10

<210> SEQ ID NO 1024
<211> LENGTH: 20
<212> TYPE: PRT
<213> ORGANISM: Artificial Sequence
<220> FEATURE:
<223> OTHER INFORMATION: EPO-MIMETIC PEPTIDE
```

-continued

```
<400> SEQUENCE: 1024

Gly Gly Leu Tyr Leu Cys Arg Phe Gly Pro Val Thr Trp Asp Cys Gly
1               5                   10                  15

Tyr Lys Gly Gly
            20

<210> SEQ ID NO 1025
<211> LENGTH: 20
<212> TYPE: PRT
<213> ORGANISM: Artificial Sequence
<220> FEATURE:
<223> OTHER INFORMATION: EPO-MIMETIC PEPTIDE

<400> SEQUENCE: 1025

Gly Gly Thr Tyr Ser Cys His Phe Gly Pro Leu Thr Trp Val Cys Lys
1               5                   10                  15

Pro Gln Gly Gly
            20

<210> SEQ ID NO 1026
<211> LENGTH: 20
<212> TYPE: PRT
<213> ORGANISM: Artificial Sequence
<220> FEATURE:
<223> OTHER INFORMATION: EPO-MIMETIC PEPTIDE

<400> SEQUENCE: 1026

Gly Gly Asp Tyr His Cys Arg Met Gly Pro Leu Thr Trp Val Cys Lys
1               5                   10                  15

Pro Leu Gly Gly
            20

<210> SEQ ID NO 1027
<211> LENGTH: 19
<212> TYPE: PRT
<213> ORGANISM: Artificial Sequence
<220> FEATURE:
<223> OTHER INFORMATION: VEGF-ANTAGONIST

<400> SEQUENCE: 1027

Val Glu Pro Asn Cys Asp Ile His Val Met Trp Glu Trp Glu Cys Phe
1               5                   10                  15

Glu Arg Leu

<210> SEQ ID NO 1028
<211> LENGTH: 10
<212> TYPE: PRT
<213> ORGANISM: Artificial Sequence
<220> FEATURE:
<223> OTHER INFORMATION: MMP INHIBITOR

<400> SEQUENCE: 1028

Cys Thr Thr His Trp Gly Phe Thr Leu Cys
1               5                   10

<210> SEQ ID NO 1029
<211> LENGTH: 20
<212> TYPE: PRT
<213> ORGANISM: Artificial Sequence
<220> FEATURE:
<223> OTHER INFORMATION: EPO-MIMETIC PEPTIDE

<400> SEQUENCE: 1029
```

-continued

```
Val Gly Asn Tyr Met Cys His Phe Gly Pro Ile Thr Trp Val Cys Arg
1               5                   10                  15

Pro Gly Gly Gly
            20

<210> SEQ ID NO 1030
<211> LENGTH: 20
<212> TYPE: PRT
<213> ORGANISM: Artificial Sequence
<220> FEATURE:
<223> OTHER INFORMATION: EPO-MIMETIC PEPTIDE

<400> SEQUENCE: 1030

Gly Gly Val Tyr Ala Cys Arg Met Gly Pro Ile Thr Trp Val Cys Ser
1               5                   10                  15

Pro Leu Gly Gly
            20

<210> SEQ ID NO 1031
<211> LENGTH: 20
<212> TYPE: PRT
<213> ORGANISM: Artificial Sequence
<220> FEATURE:
<223> OTHER INFORMATION: VEGF- ANTAGONIST

<400> SEQUENCE: 1031

Arg Gly Trp Val Glu Ile Cys Ala Ala Asp Asp Tyr Gly Arg Cys Leu
1               5                   10                  15

Thr Glu Ala Gln
            20

<210> SEQ ID NO 1032
<211> LENGTH: 19
<212> TYPE: PRT
<213> ORGANISM: Artificial Sequence
<220> FEATURE:
<223> OTHER INFORMATION: TPO-MIMETIC
<220> FEATURE:
<221> NAME/KEY: misc_feature
<222> LOCATION: (1)..(1)
<223> OTHER INFORMATION: Fc domain attached at Position 1 of the N-
      terminus

<400> SEQUENCE: 1032

Gly Gly Gly Gly Gly Ile Glu Gly Pro Thr Leu Arg Gln Trp Leu Ala
1               5                   10                  15

Ala Arg Ala

<210> SEQ ID NO 1033
<211> LENGTH: 19
<212> TYPE: PRT
<213> ORGANISM: Artificial Sequence
<220> FEATURE:
<223> OTHER INFORMATION: TPO-MIMETIC
<220> FEATURE:
<221> NAME/KEY: misc_feature
<222> LOCATION: (19)..(19)
<223> OTHER INFORMATION: Fc domain attached at Position 19 of the C-
      terminus

<400> SEQUENCE: 1033

Ile Glu Gly Pro Thr Leu Arg Gln Trp Leu Ala Ala Arg Ala Gly Gly
1               5                   10                  15

Gly Gly Gly
```

-continued

```
<210> SEQ ID NO 1034
<211> LENGTH: 25
<212> TYPE: PRT
<213> ORGANISM: Artificial Sequence
<220> FEATURE:
<223> OTHER INFORMATION: EPO-MIMETIC
<220> FEATURE:
<221> NAME/KEY: misc_feature
<222> LOCATION: (25)..(25)
<223> OTHER INFORMATION: Fc domain attached at Position 25 of the C-
      terminus

<400> SEQUENCE: 1034

Gly Gly Thr Tyr Ser Cys His Phe Gly Pro Leu Thr Trp Val Cys Lys
1               5                   10                  15

Pro Gln Gly Gly Gly Gly Gly Gly Gly
            20                  25

<210> SEQ ID NO 1035
<211> LENGTH: 19
<212> TYPE: PRT
<213> ORGANISM: Artificial Sequence
<220> FEATURE:
<223> OTHER INFORMATION: EPO-MIMETIC PEPTIDE

<400> SEQUENCE: 1035

Val Gly Asn Tyr Met Ala His Met Gly Pro Ile Thr Trp Val Cys Arg
1               5                   10                  15

Pro Gly Gly

<210> SEQ ID NO 1036
<211> LENGTH: 18
<212> TYPE: PRT
<213> ORGANISM: Artificial Sequence
<220> FEATURE:
<223> OTHER INFORMATION: EPO-MIMETIC PEPTIDE

<400> SEQUENCE: 1036

Gly Gly Thr Tyr Ser Cys His Phe Gly Pro Leu Thr Trp Val Cys Lys
1               5                   10                  15

Pro Gln

<210> SEQ ID NO 1037
<211> LENGTH: 20
<212> TYPE: PRT
<213> ORGANISM: Artificial Sequence
<220> FEATURE:
<223> OTHER INFORMATION: EPO-MIMETIC PEPTIDE

<400> SEQUENCE: 1037

Gly Gly Leu Tyr Ala Cys His Met Gly Pro Met Thr Trp Val Cys Gln
1               5                   10                  15

Pro Leu Arg Gly
            20

<210> SEQ ID NO 1038
<211> LENGTH: 22
<212> TYPE: PRT
<213> ORGANISM: Artificial Sequence
<220> FEATURE:
<223> OTHER INFORMATION: EPO-MIMETIC PEPTIDE

<400> SEQUENCE: 1038

Thr Ile Ala Gln Tyr Ile Cys Tyr Met Gly Pro Glu Thr Trp Glu Cys
1               5                   10                  15
```

Arg Pro Ser Pro Lys Ala
            20

<210> SEQ ID NO 1039
<211> LENGTH: 13
<212> TYPE: PRT
<213> ORGANISM: Artificial Sequence
<220> FEATURE:
<223> OTHER INFORMATION: EPO-MIMETIC PEPTIDE

<400> SEQUENCE: 1039

Tyr Ser Cys His Phe Gly Pro Leu Thr Trp Val Cys Lys
1               5                   10

<210> SEQ ID NO 1040
<211> LENGTH: 11
<212> TYPE: PRT
<213> ORGANISM: Artificial Sequence
<220> FEATURE:
<223> OTHER INFORMATION: EPO-MIMETIC PEPTIDE

<400> SEQUENCE: 1040

Tyr Cys His Phe Gly Pro Leu Thr Trp Val Cys
1               5                   10

<210> SEQ ID NO 1041
<211> LENGTH: 12
<212> TYPE: PRT
<213> ORGANISM: Artificial Sequence
<220> FEATURE:
<223> OTHER INFORMATION: EPO-MIMETIC PEPTIDE

<400> SEQUENCE: 1041

Ser Cys His Phe Gly Pro Leu Thr Trp Val Cys Lys
1               5                   10

<210> SEQ ID NO 1042
<211> LENGTH: 11
<212> TYPE: PRT
<213> ORGANISM: Artificial Sequence
<220> FEATURE:
<223> OTHER INFORMATION: EPO-MIMETIC PEPTIDE
<220> FEATURE:
<221> NAME/KEY: misc_feature
<222> LOCATION: (1)..(1)
<223> OTHER INFORMATION: Xaa (Pos1) can be any one of the 20 L-amino
      acids; except Xaa (Pos1) may/may not be Y and Xaa (Pos1) may be
      any non-naturally occurring aromatic acid analog when Xaa (Pos1)
      is Y.
<220> FEATURE:
<221> NAME/KEY: misc_feature
<222> LOCATION: (2)..(8)
<223> OTHER INFORMATION: Xaa (Pos2, 8) can be any one of the 20 L-amino
      acids
<220> FEATURE:
<221> NAME/KEY: misc_feature
<222> LOCATION: (3)..(3)
<223> OTHER INFORMATION: Xaa (Pos3) can be C, A, a-amino-y-bromobutyric
      acid or Hoc;
<220> FEATURE:
<221> NAME/KEY: misc_feature
<222> LOCATION: (4)..(4)
<223> OTHER INFORMATION: Xaa (Pos4) can be R, H, L or W
<220> FEATURE:
<221> NAME/KEY: misc_feature
<222> LOCATION: (5)..(5)
<223> OTHER INFORMATION: Xaa (Pos5) can be M, F or I
<220> FEATURE:
<221> NAME/KEY: misc_feature
<222> LOCATION: (10)..(10)
<223> OTHER INFORMATION: Xaa is any amino acid
<220> FEATURE:

```
<221> NAME/KEY: misc_feature
<222> LOCATION: (11)..(11)
<223> OTHER INFORMATION: Xaa (Pos11) can be D, E, I, L or V
<220> FEATURE:
<221> NAME/KEY: misc_feature
<222> LOCATION: (12)..(12)
<223> OTHER INFORMATION: Xaa (Pos12) can be C, A, a-amino-y-bromobutyric
      acid or Hoc provided that either Xaa (Pos3, 12) is C or Hoc.

<400> SEQUENCE: 1042

Xaa Xaa Xaa Xaa Gly Pro Xaa Thr Trp Xaa Xaa
1               5                   10

<210> SEQ ID NO 1043
<211> LENGTH: 5
<212> TYPE: PRT
<213> ORGANISM: Artificial Sequence
<220> FEATURE:
<223> OTHER INFORMATION: INTEGRIN-BINDING PEPTIDE
<220> FEATURE:
<221> NAME/KEY: misc_feature
<222> LOCATION: (3)..(4)
<223> OTHER INFORMATION: Xaa = any amino acid

<400> SEQUENCE: 1043

Asp Leu Xaa Xaa Leu
1               5

<210> SEQ ID NO 1044
<211> LENGTH: 12
<212> TYPE: PRT
<213> ORGANISM: Artificial Sequence
<220> FEATURE:
<223> OTHER INFORMATION: INTEGRIN-BINDING PEPTIDE

<400> SEQUENCE: 1044

Arg Thr Asp Leu Asp Ser Leu Arg Thr Tyr Thr Leu
1               5                   10

<210> SEQ ID NO 1045
<211> LENGTH: 20
<212> TYPE: PRT
<213> ORGANISM: Artificial Sequence
<220> FEATURE:
<223> OTHER INFORMATION: TNF-ALPHA INHIBITOR
<220> FEATURE:
<221> NAME/KEY: misc_feature
<222> LOCATION: (1)..(1)
<223> OTHER INFORMATION: Fc domain attached at Position 1 of the N-
      terminus

<400> SEQUENCE: 1045

Gly Gly Gly Gly Gly Asp Phe Leu Pro His Tyr Lys Asn Thr Ser Leu
1               5                   10                  15

Gly His Arg Pro
            20

<210> SEQ ID NO 1046
<211> LENGTH: 20
<212> TYPE: PRT
<213> ORGANISM: Artificial Sequence
<220> FEATURE:
<223> OTHER INFORMATION: TNF-ALPHA INHIBITOR
<220> FEATURE:
<221> NAME/KEY: misc_feature
<222> LOCATION: (20)..(20)
<223> OTHER INFORMATION: Fc domain attached at Position 20 of the C-
      terminus

<400> SEQUENCE: 1046
```

Asp Phe Leu Pro His Tyr Lys Asn Thr Ser Leu Gly His Arg Pro Gly
1               5                   10                  15

Gly Gly Gly Gly
            20

<210> SEQ ID NO 1047
<211> LENGTH: 20
<212> TYPE: PRT
<213> ORGANISM: Artificial Sequence
<220> FEATURE:
<223> OTHER INFORMATION: IL-1 ANTAGONIST
<220> FEATURE:
<221> NAME/KEY: misc_feature
<222> LOCATION: (1)..(1)
<223> OTHER INFORMATION: Fc domain attached at Position 1 of the N-
      terminus

<400> SEQUENCE: 1047

Gly Gly Gly Gly Gly Phe Glu Trp Thr Pro Gly Tyr Trp Gln Pro Tyr
1               5                   10                  15

Ala Leu Pro Leu
            20

<210> SEQ ID NO 1048
<211> LENGTH: 20
<212> TYPE: PRT
<213> ORGANISM: Artificial Sequence
<220> FEATURE:
<223> OTHER INFORMATION: IL-1 ANTAGONIST
<220> FEATURE:
<221> NAME/KEY: misc_feature
<222> LOCATION: (20)..(20)
<223> OTHER INFORMATION: Fc domain attached at Position 20 of the C-
      terminus

<400> SEQUENCE: 1048

Phe Glu Trp Thr Pro Gly Tyr Trp Gln Pro Tyr Ala Leu Pro Leu Gly
1               5                   10                  15

Gly Gly Gly Gly
            20

<210> SEQ ID NO 1049
<211> LENGTH: 24
<212> TYPE: PRT
<213> ORGANISM: Artificial Sequence
<220> FEATURE:
<223> OTHER INFORMATION: VEGF-ANTAGONIST
<220> FEATURE:
<221> NAME/KEY: misc_feature
<222> LOCATION: (1)..(1)
<223> OTHER INFORMATION: Fc domain attached at Position 1 of the N-
      terminus

<400> SEQUENCE: 1049

Gly Gly Gly Gly Gly Val Glu Pro Asn Cys Asp Ile His Val Met Trp
1               5                   10                  15

Glu Trp Glu Cys Phe Glu Arg Leu
            20

<210> SEQ ID NO 1050
<211> LENGTH: 24
<212> TYPE: PRT
<213> ORGANISM: Artificial Sequence
<220> FEATURE:
<223> OTHER INFORMATION: VEGF-ANTAGONIST
<220> FEATURE:
<221> NAME/KEY: misc_feature

```
<222> LOCATION: (24)..(24)
<223> OTHER INFORMATION: Fc domain attached at Position 24 of the C-
      terminus

<400> SEQUENCE: 1050

Val Glu Pro Asn Cys Asp Ile His Val Met Trp Glu Trp Glu Cys Phe
1               5                   10                  15

Glu Arg Leu Gly Gly Gly Gly Gly
            20

<210> SEQ ID NO 1051
<211> LENGTH: 15
<212> TYPE: PRT
<213> ORGANISM: Artificial Sequence
<220> FEATURE:
<223> OTHER INFORMATION: MMP INHIBITOR
<220> FEATURE:
<221> NAME/KEY: misc_feature
<222> LOCATION: (1)..(1)
<223> OTHER INFORMATION: Fc domain attached at Position 1 of the N-
      terminus

<400> SEQUENCE: 1051

Gly Gly Gly Gly Gly Cys Thr Thr His Trp Gly Phe Thr Leu Cys
1               5                   10                  15

<210> SEQ ID NO 1052
<211> LENGTH: 15
<212> TYPE: PRT
<213> ORGANISM: Artificial Sequence
<220> FEATURE:
<223> OTHER INFORMATION: MMP INHIBITOR
<220> FEATURE:
<221> NAME/KEY: misc_feature
<222> LOCATION: (15)..(15)
<223> OTHER INFORMATION: Fc domain attached at Position 15 of the C-
      terminus

<400> SEQUENCE: 1052

Cys Thr Thr His Trp Gly Phe Thr Leu Cys Gly Gly Gly Gly Gly
1               5                   10                  15

<210> SEQ ID NO 1053
<211> LENGTH: 10
<212> TYPE: PRT
<213> ORGANISM: Artificial Sequence
<220> FEATURE:
<223> OTHER INFORMATION: INTEGRIN-BINDING PEPTIDE

<400> SEQUENCE: 1053

Arg Thr Asp Leu Asp Ser Leu Arg Thr Tyr
1               5                   10

<210> SEQ ID NO 1054
<211> LENGTH: 9
<212> TYPE: PRT
<213> ORGANISM: Artificial Sequence
<220> FEATURE:
<223> OTHER INFORMATION: INTEGRIN-BINDING PEPTIDE

<400> SEQUENCE: 1054

Arg Thr Asp Leu Asp Ser Leu Arg Thr
1               5

<210> SEQ ID NO 1055
<211> LENGTH: 757
<212> TYPE: DNA
<213> ORGANISM: Artificial Sequence
```

-continued

```
<220> FEATURE:
<223> OTHER INFORMATION: FC-TNF-ALPA INHIBITORS
<220> FEATURE:
<221> NAME/KEY: CDS
<222> LOCATION: (4)..(747)
<223> OTHER INFORMATION:

<400> SEQUENCE: 1055
```

| | | | | | | | | | | | | | | | | |
|---|---|---|---|---|---|---|---|---|---|---|---|---|---|---|---|---|
| cat | atg | gac | aaa | act | cac | aca | tgt | cca | cct | tgt | cca | gct | ccg | gaa | ctc | 48 |
| | Met | Asp | Lys | Thr | His | Thr | Cys | Pro | Pro | Cys | Pro | Ala | Pro | Glu | Leu | |
| | 1 | | | | 5 | | | | | 10 | | | | | 15 | |
| ctg | ggg | gga | ccg | tca | gtc | ttc | ctc | ttc | ccc | cca | aaa | ccc | aag | gac | acc | 96 |
| Leu | Gly | Gly | Pro | Ser | Val | Phe | Leu | Phe | Pro | Pro | Lys | Pro | Lys | Asp | Thr | |
| | | | | 20 | | | | | 25 | | | | | 30 | | |
| ctc | atg | atc | tcc | cgg | acc | cct | gag | gtc | aca | tgc | gtg | gtg | gtg | gac | gtg | 144 |
| Leu | Met | Ile | Ser | Arg | Thr | Pro | Glu | Val | Thr | Cys | Val | Val | Val | Asp | Val | |
| | | | 35 | | | | | 40 | | | | | 45 | | | |
| agc | cac | gaa | gac | cct | gag | gtc | aag | ttc | aac | tgg | tac | gtg | gac | ggc | gtg | 192 |
| Ser | His | Glu | Asp | Pro | Glu | Val | Lys | Phe | Asn | Trp | Tyr | Val | Asp | Gly | Val | |
| | | 50 | | | | | 55 | | | | | 60 | | | | |
| gag | gtg | cat | aat | gcc | aag | aca | aag | ccg | cgg | gag | gag | cag | tac | aac | agc | 240 |
| Glu | Val | His | Asn | Ala | Lys | Thr | Lys | Pro | Arg | Glu | Glu | Gln | Tyr | Asn | Ser | |
| | 65 | | | | 70 | | | | | 75 | | | | | | |
| acg | tac | cgt | gtg | gtc | agc | gtc | ctc | acc | gtc | ctg | cac | cag | gac | tgg | ctg | 288 |
| Thr | Tyr | Arg | Val | Val | Ser | Val | Leu | Thr | Val | Leu | His | Gln | Asp | Trp | Leu | |
| 80 | | | | | 85 | | | | | 90 | | | | | 95 | |
| aat | ggc | aag | gag | tac | aag | tgc | aag | gtc | tcc | aac | aaa | gcc | ctc | cca | gcc | 336 |
| Asn | Gly | Lys | Glu | Tyr | Lys | Cys | Lys | Val | Ser | Asn | Lys | Ala | Leu | Pro | Ala | |
| | | | | 100 | | | | | 105 | | | | | 110 | | |
| ccc | atc | gag | aaa | acc | atc | tcc | aaa | gcc | aaa | ggg | cag | ccc | cga | gaa | cca | 384 |
| Pro | Ile | Glu | Lys | Thr | Ile | Ser | Lys | Ala | Lys | Gly | Gln | Pro | Arg | Glu | Pro | |
| | | | 115 | | | | | 120 | | | | | 125 | | | |
| cag | gtg | tac | acc | ctg | ccc | cca | tcc | cgg | gat | gag | ctg | acc | aag | aac | cag | 432 |
| Gln | Val | Tyr | Thr | Leu | Pro | Pro | Ser | Arg | Asp | Glu | Leu | Thr | Lys | Asn | Gln | |
| | | 130 | | | | | 135 | | | | | 140 | | | | |
| gtc | agc | ctg | acc | tgc | ctg | gtc | aaa | ggc | ttc | tat | ccc | agc | gac | atc | gcc | 480 |
| Val | Ser | Leu | Thr | Cys | Leu | Val | Lys | Gly | Phe | Tyr | Pro | Ser | Asp | Ile | Ala | |
| | 145 | | | | | 150 | | | | | 155 | | | | | |
| gtg | gag | tgg | gag | agc | aat | ggg | cag | ccg | gag | aac | aac | tac | aag | acc | acg | 528 |
| Val | Glu | Trp | Glu | Ser | Asn | Gly | Gln | Pro | Glu | Asn | Asn | Tyr | Lys | Thr | Thr | |
| 160 | | | | | 165 | | | | | 170 | | | | | 175 | |
| cct | ccc | gtg | ctg | gac | tcc | gac | ggc | tcc | ttc | ttc | ctc | tac | agc | aag | ctc | 576 |
| Pro | Pro | Val | Leu | Asp | Ser | Asp | Gly | Ser | Phe | Phe | Leu | Tyr | Ser | Lys | Leu | |
| | | | | 180 | | | | | 185 | | | | | 190 | | |
| acc | gtg | gac | aag | agc | agg | tgg | cag | cag | ggg | aac | gtc | ttc | tca | tgc | tcc | 624 |
| Thr | Val | Asp | Lys | Ser | Arg | Trp | Gln | Gln | Gly | Asn | Val | Phe | Ser | Cys | Ser | |
| | | | 195 | | | | | 200 | | | | | 205 | | | |
| gtg | atg | cat | gag | gct | ctg | cac | aac | cac | tac | acg | cag | aag | agc | ctc | tcc | 672 |
| Val | Met | His | Glu | Ala | Leu | His | Asn | His | Tyr | Thr | Gln | Lys | Ser | Leu | Ser | |
| | | 210 | | | | | 215 | | | | | 220 | | | | |
| ctg | tct | ccg | ggt | aaa | ggt | gga | ggt | ggt | ggt | gac | ttc | ctg | ccg | cac | tac | 720 |
| Leu | Ser | Pro | Gly | Lys | Gly | Gly | Gly | Gly | Gly | Asp | Phe | Leu | Pro | His | Tyr | |
| | 225 | | | | | 230 | | | | | 235 | | | | | |
| aaa | aac | acc | tct | ctg | ggt | cac | cgt | ccg | taatggatcc | | | | | | | 757 |
| Lys | Asn | Thr | Ser | Leu | Gly | His | Arg | Pro | | | | | | | | |
| 240 | | | | | 245 | | | | | | | | | | | |

```
<210> SEQ ID NO 1056
<211> LENGTH: 248
<212> TYPE: PRT
<213> ORGANISM: Artificial Sequence
<220> FEATURE:
```

-continued

<223> OTHER INFORMATION: FC-TNF-ALPA INHIBITORS

<400> SEQUENCE: 1056

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Asp Phe Leu Pro His Tyr Lys
225                 230                 235                 240

Asn Thr Ser Leu Gly His Arg Pro
                245
```

<210> SEQ ID NO 1057
<211> LENGTH: 761
<212> TYPE: DNA
<213> ORGANISM: Artificial Sequence
<220> FEATURE:
<223> OTHER INFORMATION: TNF-ALPHA INHIBITOR-Fc
<220> FEATURE:
<221> NAME/KEY: CDS
<222> LOCATION: (4)..(747)
<223> OTHER INFORMATION:

<400> SEQUENCE: 1057

```
cat atg gac ttc ctg ccg cac tac aaa aac acc tct ctg ggt cac cgt      48
    Met Asp Phe Leu Pro His Tyr Lys Asn Thr Ser Leu Gly His Arg
    1               5                   10                  15 ccg ggt gga ggc ggt ggg gac aaa act cac aca tgt cca cct tgc cca      96
Pro Gly Gly Gly Gly Gly Asp Lys Thr His Thr Cys Pro Pro Cys Pro
            20                  25                  30 gca cct gaa ctc ctg ggg gga ccg tca gtt ttc ctc ttc ccc cca aaa     144
Ala Pro Glu Leu Leu Gly Gly Pro Ser Val Phe Leu Phe Pro Pro Lys
        35                  40                  45 ccc aag gac acc ctc atg atc tcc cgg acc cct gag gtc aca tgc gtg     192
```

```
Pro Lys Asp Thr Leu Met Ile Ser Arg Thr Pro Glu Val Thr Cys Val
        50                  55                  60 gtg gtg gac gtg agc cac gaa gac cct gag gtc aag ttc aac tgg tac       240
Val Val Asp Val Ser His Glu Asp Pro Glu Val Lys Phe Asn Trp Tyr
 65                  70                  75 gtg gac ggc gtg gag gtg cat aat gcc aag aca aag ccg cgg gag gag       288
Val Asp Gly Val Glu Val His Asn Ala Lys Thr Lys Pro Arg Glu Glu
 80                  85                  90                  95 cag tac aac agc acg tac cgt gtg gtc agc gtc ctc acc gtc ctg cac       336
Gln Tyr Asn Ser Thr Tyr Arg Val Val Ser Val Leu Thr Val Leu His
                100                 105                 110 cag gac tgg ctg aat ggc aag gag tac aag tgc aag gtc tcc aac aaa       384
Gln Asp Trp Leu Asn Gly Lys Glu Tyr Lys Cys Lys Val Ser Asn Lys
        115                 120                 125 gcc ctc cca gcc ccc atc gag aaa acc atc tcc aaa gcc aaa ggg cag       432
Ala Leu Pro Ala Pro Ile Glu Lys Thr Ile Ser Lys Ala Lys Gly Gln
        130                 135                 140 ccc cga gaa cca cag gtg tac acc ctg ccc cca tcc cgg gat gag ctg       480
Pro Arg Glu Pro Gln Val Tyr Thr Leu Pro Pro Ser Arg Asp Glu Leu
145                 150                 155 acc aag aac cag gtc agc ctg acc tgc ctg gtc aaa ggc ttc tat ccc       528
Thr Lys Asn Gln Val Ser Leu Thr Cys Leu Val Lys Gly Phe Tyr Pro
160                 165                 170                 175 agc gac atc gcc gtg gag tgg gag agc aat ggg cag ccg gag aac aac       576
Ser Asp Ile Ala Val Glu Trp Glu Ser Asn Gly Gln Pro Glu Asn Asn
                180                 185                 190 tac aag acc acg cct ccc gtg ctg gac tcc gac ggc tcc ttc ttc ctc       624
Tyr Lys Thr Thr Pro Pro Val Leu Asp Ser Asp Gly Ser Phe Phe Leu
        195                 200                 205 tac agc aag ctc acc gtg gac aag agc agg tgg cag cag ggg aac gtc       672
Tyr Ser Lys Leu Thr Val Asp Lys Ser Arg Trp Gln Gln Gly Asn Val
        210                 215                 220 ttc tca tgc tcc gtg atg cat gag gct ctg cac aac cac tac acg cag       720
Phe Ser Cys Ser Val Met His Glu Ala Leu His Asn His Tyr Thr Gln
225                 230                 235 aag agc ctc tcc ctg tct ccg ggt aaa taatggatcc gcgg                   761
Lys Ser Leu Ser Leu Ser Pro Gly Lys
240                 245
```

<210> SEQ ID NO 1058
<211> LENGTH: 248
<212> TYPE: PRT
<213> ORGANISM: Artificial Sequence
<220> FEATURE:
<223> OTHER INFORMATION: TNF-ALPHA INHIBITOR-Fc

<400> SEQUENCE: 1058

```
Met Asp Phe Leu Pro His Tyr Lys Asn Thr Ser Leu Gly His Arg Pro
 1               5                  10                  15

Gly Gly Gly Gly Gly Asp Lys Thr His Thr Cys Pro Pro Cys Pro Ala
                20                  25                  30
Pro Glu Leu Leu Gly Gly Pro Ser Val Phe Leu Phe Pro Pro Lys Pro
        35                  40                  45

Lys Asp Thr Leu Met Ile Ser Arg Thr Pro Glu Val Thr Cys Val Val
    50                  55                  60

Val Asp Val Ser His Glu Asp Pro Glu Val Lys Phe Asn Trp Tyr Val
 65                  70                  75                  80
Asp Gly Val Glu Val His Asn Ala Lys Thr Lys Pro Arg Glu Glu Gln
                85                  90                  95

Tyr Asn Ser Thr Tyr Arg Val Val Ser Val Leu Thr Val Leu His Gln
                100                 105                 110
```

```
Asp Trp Leu Asn Gly Lys Glu Tyr Lys Cys Lys Val Ser Asn Lys Ala
        115                 120                 125
Leu Pro Ala Pro Ile Glu Lys Thr Ile Ser Lys Ala Lys Gly Gln Pro
    130                 135                 140
Arg Glu Pro Gln Val Tyr Thr Leu Pro Pro Ser Arg Asp Glu Leu Thr
145                 150                 155                 160
Lys Asn Gln Val Ser Leu Thr Cys Leu Val Lys Gly Phe Tyr Pro Ser
                165                 170                 175
Asp Ile Ala Val Glu Trp Glu Ser Asn Gly Gln Pro Glu Asn Asn Tyr
            180                 185                 190
Lys Thr Thr Pro Pro Val Leu Asp Ser Asp Gly Ser Phe Phe Leu Tyr
        195                 200                 205
Ser Lys Leu Thr Val Asp Lys Ser Arg Trp Gln Gln Gly Asn Val Phe
    210                 215                 220
Ser Cys Ser Val Met His Glu Ala Leu His Asn His Tyr Thr Gln Lys
225                 230                 235                 240
Ser Leu Ser Leu Ser Pro Gly Lys
                245

<210> SEQ ID NO 1059
<211> LENGTH: 763
<212> TYPE: DNA
<213> ORGANISM: Artificial Sequence
<220> FEATURE:
<223> OTHER INFORMATION: FC-IL-1 ANTAGONIST
<220> FEATURE:
<221> NAME/KEY: CDS
<222> LOCATION: (4)..(747)
<223> OTHER INFORMATION:

<400> SEQUENCE: 1059 cat atg gac aaa act cac aca tgt cca cct tgt cca gct ccg gaa ctc        48
    Met Asp Lys Thr His Thr Cys Pro Pro Cys Pro Ala Pro Glu Leu
    1               5                   10                  15 ctg ggg gga ccg tca gtc ttc ctc ttc ccc cca aaa ccc aag gac acc        96
Leu Gly Gly Pro Ser Val Phe Leu Phe Pro Pro Lys Pro Lys Asp Thr
            20                  25                  30 ctc atg atc tcc cgg acc cct gag gtc aca tgc gtg gtg gtg gac gtg       144
Leu Met Ile Ser Arg Thr Pro Glu Val Thr Cys Val Val Val Asp Val
        35                  40                  45 agc cac gaa gac cct gag gtc aag ttc aac tgg tac gtg gac ggc gtg       192
Ser His Glu Asp Pro Glu Val Lys Phe Asn Trp Tyr Val Asp Gly Val
    50                  55                  60 gag gtg cat aat gcc aag aca aag ccg cgg gag gag cag tac aac agc       240
Glu Val His Asn Ala Lys Thr Lys Pro Arg Glu Glu Gln Tyr Asn Ser
65                  70                  75 acg tac cgt gtg gtc agc gtc ctc acc gtc ctg cac cag gac tgg ctg       288
Thr Tyr Arg Val Val Ser Val Leu Thr Val Leu His Gln Asp Trp Leu
80                  85                  90                  95 aat ggc aag gag tac aag tgc aag gtc tcc aac aaa gcc ctc cca gcc       336
Asn Gly Lys Glu Tyr Lys Cys Lys Val Ser Asn Lys Ala Leu Pro Ala
                100                 105                 110 ccc atc gag aaa acc atc tcc aaa gcc aaa ggg cag ccc cga gaa cca       384
Pro Ile Glu Lys Thr Ile Ser Lys Ala Lys Gly Gln Pro Arg Glu Pro
            115                 120                 125 cag gtg tac acc ctg ccc cca tcc cgg gat gag ctg acc aag aac cag       432
Gln Val Tyr Thr Leu Pro Pro Ser Arg Asp Glu Leu Thr Lys Asn Gln
        130                 135                 140 gtc agc ctg acc tgc ctg gtc aaa ggc ttc tat ccc agc gac atc gcc       480
Val Ser Leu Thr Cys Leu Val Lys Gly Phe Tyr Pro Ser Asp Ile Ala
145                 150                 155
```

```
gtg gag tgg gag agc aat ggg cag ccg gag aac aac tac aag acc acg    528
Val Glu Trp Glu Ser Asn Gly Gln Pro Glu Asn Asn Tyr Lys Thr Thr
160             165                 170                 175 cct ccc gtg ctg gac tcc gac ggc tcc ttc ttc ctc tac agc aag ctc    576
Pro Pro Val Leu Asp Ser Asp Gly Ser Phe Phe Leu Tyr Ser Lys Leu
            180                 185                 190 acc gtg gac aag agc agg tgg cag cag ggg aac gtc ttc tca tgc tcc    624
Thr Val Asp Lys Ser Arg Trp Gln Gln Gly Asn Val Phe Ser Cys Ser
            195                 200                 205 gtg atg cat gag gct ctg cac aac cac tac acg cag aag agc ctc tcc    672
Val Met His Glu Ala Leu His Asn His Tyr Thr Gln Lys Ser Leu Ser
            210                 215                 220 ctg tct ccg ggt aaa ggt gga ggt ggt ggt ttc gaa tgg acc ccg ggt    720
Leu Ser Pro Gly Lys Gly Gly Gly Gly Gly Phe Glu Trp Thr Pro Gly
225                 230                 235 tac tgg cag ccg tac gct ctg ccg ctg taatggatcc ctcgag              763
Tyr Trp Gln Pro Tyr Ala Leu Pro Leu
240                 245
```

<210> SEQ ID NO 1060
<211> LENGTH: 248
<212> TYPE: PRT
<213> ORGANISM: Artificial Sequence
<220> FEATURE:
<223> OTHER INFORMATION: FC-IL-1 ANTAGONIST

<400> SEQUENCE: 1060

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Gly Phe Glu Trp Thr Pro Gly Tyr
225                 230                 235                 240
```

Trp Gln Pro Tyr Ala Leu Pro Leu
                245

<210> SEQ ID NO 1061
<211> LENGTH: 757
<212> TYPE: DNA
<213> ORGANISM: Artificial Sequence
<220> FEATURE:
<223> OTHER INFORMATION: IL-1 ANTAGONIST-FC
<220> FEATURE:
<221> NAME/KEY: CDS
<222> LOCATION: (4)..(747)
<223> OTHER INFORMATION:

<400> SEQUENCE: 1061

| | | |
|---|---|---|
| cat atg ttc gaa tgg acc ccg ggt tac tgg cag ccg tac gct ctg ccg<br>    Met Phe Glu Trp Thr Pro Gly Tyr Trp Gln Pro Tyr Ala Leu Pro<br>    1                      5                            10                          15 | | 48 |
| ctg ggt gga ggc ggt ggg gac aaa act cac aca tgt cca cct tgc cca<br>Leu Gly Gly Gly Gly Gly Asp Lys Thr His Thr Cys Pro Pro Cys Pro<br>                      20                            25                            30 | | 96 |
| gca cct gaa ctc ctg ggg gga ccg tca gtt ttc ctc ttc ccc cca aaa<br>Ala Pro Glu Leu Leu Gly Gly Pro Ser Val Phe Leu Phe Pro Pro Lys<br>            35                          40                              45 | | 144 |
| ccc aag gac acc ctc atg atc tcc cgg acc cct gag gtc aca tgc gtg<br>Pro Lys Asp Thr Leu Met Ile Ser Arg Thr Pro Glu Val Thr Cys Val<br>     50                           55                            60 | | 192 |
| gtg gtg gac gtg agc cac gaa gac cct gag gtc aag ttc aac tgg tac<br>Val Val Asp Val Ser His Glu Asp Pro Glu Val Lys Phe Asn Trp Tyr<br>    65                            70                          75 | | 240 |
| gtg gac ggc gtg gag gtg cat aat gcc aag aca aag ccg cgg gag gag<br>Val Asp Gly Val Glu Val His Asn Ala Lys Thr Lys Pro Arg Glu Glu<br>80                            85                            90                        95 | | 288 |
| cag tac aac agc acg tac cgt gtg gtc agc gtc ctc acc gtc ctg cac<br>Gln Tyr Asn Ser Thr Tyr Arg Val Val Ser Val Leu Thr Val Leu His<br>                    100                          105                      110 | | 336 |
| cag gac tgg ctg aat ggc aag gag tac aag tgc aag gtc tcc aac aaa<br>Gln Asp Trp Leu Asn Gly Lys Glu Tyr Lys Cys Lys Val Ser Asn Lys<br>              115                        120                          125 | | 384 |
| gcc ctc cca gcc ccc atc gag aaa acc atc tcc aaa gcc aaa ggg cag<br>Ala Leu Pro Ala Pro Ile Glu Lys Thr Ile Ser Lys Ala Lys Gly Gln<br>        130                          135                          140 | | 432 |
| ccc cga gaa cca cag gtg tac acc ctg ccc cca tcc cgg gat gag ctg<br>Pro Arg Glu Pro Gln Val Tyr Thr Leu Pro Pro Ser Arg Asp Glu Leu<br>    145                            150                            155 | | 480 |
| acc aag aac cag gtc agc ctg acc tgc ctg gtc aaa ggc ttc tat ccc<br>Thr Lys Asn Gln Val Ser Leu Thr Cys Leu Val Lys Gly Phe Tyr Pro<br>160                            165                            170                        175 | | 528 |
| agc gac atc gcc gtg gag tgg gag agc aat ggg cag ccg gag aac aac<br>Ser Asp Ile Ala Val Glu Trp Glu Ser Asn Gly Gln Pro Glu Asn Asn<br>                    180                          185                      190 | | 576 |
| tac aag acc acg cct ccc gtg ctg gac tcc gac ggc tcc ttc ttc ctc<br>Tyr Lys Thr Thr Pro Pro Val Leu Asp Ser Asp Gly Ser Phe Phe Leu<br>              195                        200                          205 | | 624 |
| tac agc aag ctc acc gtg gac aag agc agg tgg cag cag ggg aac gtc<br>Tyr Ser Lys Leu Thr Val Asp Lys Ser Arg Trp Gln Gln Gly Asn Val<br>        210                          215                          220 | | 672 |
| ttc tca tgc tcc gtg atg cat gag gct ctg cac aac cac tac acg cag<br>Phe Ser Cys Ser Val Met His Glu Ala Leu His Asn His Tyr Thr Gln<br>    225                            230                          235 | | 720 |
| aag agc ctc tcc ctg tct ccg ggt aaa taatggatcc<br>Lys Ser Leu Ser Leu Ser Pro Gly Lys | | 757 |

```
                        240                 245

<210> SEQ ID NO 1062
<211> LENGTH: 248
<212> TYPE: PRT
<213> ORGANISM: Artificial Sequence
<220> FEATURE:
<223> OTHER INFORMATION: IL-1 ANTAGONIST-FC

<400> SEQUENCE: 1062

Met Phe Glu Trp Thr Pro Gly Tyr Trp Gln Pro Tyr Ala Leu Pro Leu
1               5                   10                  15

Gly Gly Gly Gly Gly Asp Lys Thr His Thr Cys Pro Pro Cys Pro Ala
            20                  25                  30

Pro Glu Leu Leu Gly Gly Pro Ser Val Phe Leu Phe Pro Pro Lys Pro
        35                  40                  45

Lys Asp Thr Leu Met Ile Ser Arg Thr Pro Glu Val Thr Cys Val Val
    50                  55                  60

Val Asp Val Ser His Glu Asp Pro Glu Val Lys Phe Asn Trp Tyr Val
65                  70                  75                  80

Asp Gly Val Glu Val His Asn Ala Lys Thr Lys Pro Arg Glu Glu Gln
                85                  90                  95

Tyr Asn Ser Thr Tyr Arg Val Val Ser Val Leu Thr Val Leu His Gln
            100                 105                 110

Asp Trp Leu Asn Gly Lys Glu Tyr Lys Cys Lys Val Ser Asn Lys Ala
        115                 120                 125

Leu Pro Ala Pro Ile Glu Lys Thr Ile Ser Lys Ala Lys Gly Gln Pro
    130                 135                 140

Arg Glu Pro Gln Val Tyr Thr Leu Pro Pro Ser Arg Asp Glu Leu Thr
145                 150                 155                 160

Lys Asn Gln Val Ser Leu Thr Cys Leu Val Lys Gly Phe Tyr Pro Ser
                165                 170                 175

Asp Ile Ala Val Glu Trp Glu Ser Asn Gly Gln Pro Glu Asn Asn Tyr
            180                 185                 190

Lys Thr Thr Pro Pro Val Leu Asp Ser Asp Gly Ser Phe Phe Leu Tyr
        195                 200                 205

Ser Lys Leu Thr Val Asp Lys Ser Arg Trp Gln Gln Gly Asn Val Phe
    210                 215                 220

Ser Cys Ser Val Met His Glu Ala Leu His Asn His Tyr Thr Gln Lys
225                 230                 235                 240

Ser Leu Ser Leu Ser Pro Gly Lys
                245

<210> SEQ ID NO 1063
<211> LENGTH: 773
<212> TYPE: DNA
<213> ORGANISM: Artificial Sequence
<220> FEATURE:
<223> OTHER INFORMATION: Fc-VEGF ANTAGONIST
<220> FEATURE:
<221> NAME/KEY: CDS
<222> LOCATION: (4)..(759)
<223> OTHER INFORMATION:

<400> SEQUENCE: 1063 cat atg gac aaa act cac aca tgt cca ccg tgc cca gca cct gaa ctc        48
    Met Asp Lys Thr His Thr Cys Pro Pro Cys Pro Ala Pro Glu Leu
    1               5                   10                  15 ctg ggg gga ccg tca gtt ttc ctc ttc ccc cca aaa ccc aag gac acc        96
```

-continued

| | | |
|---|---|---|
| ctc atg atc tcc cgg acc cct gag gtc aca tgc gtg gtg gtg gac gtg<br>Leu Met Ile Ser Arg Thr Pro Glu Val Thr Cys Val Val Val Asp Val<br>35 40 45 | | 144 |
| agc cac gaa gac cct gag gtc aag ttc aac tgg tac gtg gac ggc gtg<br>Ser His Glu Asp Pro Glu Val Lys Phe Asn Trp Tyr Val Asp Gly Val<br>50 55 60 | | 192 |
| gag gtg cat aat gcc aag aca aag ccg cgg gag gag cag tac aac agc<br>Glu Val His Asn Ala Lys Thr Lys Pro Arg Glu Glu Gln Tyr Asn Ser<br>65 70 75 | | 240 |
| acg tac cgt gtg gtc agc gtc ctc acc gtc ctg cac cag gac tgg ctg<br>Thr Tyr Arg Val Val Ser Val Leu Thr Val Leu His Gln Asp Trp Leu<br>80 85 90 95 | | 288 |
| aat ggc aag gag tac aag tgc aag gtc tcc aac aaa gcc ctc cca gcc<br>Asn Gly Lys Glu Tyr Lys Cys Lys Val Ser Asn Lys Ala Leu Pro Ala<br>100 105 110 | | 336 |
| ccc atc gag aaa acc atc tcc aaa gcc aaa ggg cag ccc cga gaa cca<br>Pro Ile Glu Lys Thr Ile Ser Lys Ala Lys Gly Gln Pro Arg Glu Pro<br>115 120 125 | | 384 |
| cag gtg tac acc ctg ccc cca tcc cgg gat gag ctg acc aag aac cag<br>Gln Val Tyr Thr Leu Pro Pro Ser Arg Asp Glu Leu Thr Lys Asn Gln<br>130 135 140 | | 432 |
| gtc agc ctg acc tgc ctg gtc aaa ggc ttc tat ccc agc gac atc gcc<br>Val Ser Leu Thr Cys Leu Val Lys Gly Phe Tyr Pro Ser Asp Ile Ala<br>145 150 155 | | 480 |
| gtg gag tgg gag agc aat ggg cag ccg gag aac aac tac aag acc acg<br>Val Glu Trp Glu Ser Asn Gly Gln Pro Glu Asn Asn Tyr Lys Thr Thr<br>160 165 170 175 | | 528 |
| cct ccc gtg ctg gac tcc gac ggc tcc ttc ttc ctc tac agc aag ctc<br>Pro Pro Val Leu Asp Ser Asp Gly Ser Phe Phe Leu Tyr Ser Lys Leu<br>180 185 190 | | 576 |
| acc gtg gac aag agc agg tgg cag cag ggg aac gtc ttc tca tgc tcc<br>Thr Val Asp Lys Ser Arg Trp Gln Gln Gly Asn Val Phe Ser Cys Ser<br>195 200 205 | | 624 |
| gtg atg cat gag gct ctg cac aac cac tac acg cag aag agc ctc tcc<br>Val Met His Glu Ala Leu His Asn His Tyr Thr Gln Lys Ser Leu Ser<br>210 215 220 | | 672 |
| ctg tct ccg ggt aaa ggt ggt ggt ggt ggt gtt gaa ccg aac tgt gac<br>Leu Ser Pro Gly Lys Gly Gly Gly Gly Gly Val Glu Pro Asn Cys Asp<br>225 230 235 | | 720 |
| atc cat gtt atg tgg gaa tgg gaa tgt ttt gaa cgt ctg taactcgagg<br>Ile His Val Met Trp Glu Trp Glu Cys Phe Glu Arg Leu<br>240 245 250 | | 769 |
| atcc | | 773 |

<210> SEQ ID NO 1064
<211> LENGTH: 252
<212> TYPE: PRT
<213> ORGANISM: Artificial Sequence
<220> FEATURE:
<223> OTHER INFORMATION: Fc-VEGF ANTAGONIST

<400> SEQUENCE: 1064

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

```
His Glu Asp Pro Glu Val Lys Phe Asn Trp Tyr Val Asp Gly Val Glu
     50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Val Glu Pro Asn Cys Asp Ile
225                 230                 235                 240

His Val Met Trp Glu Trp Glu Cys Phe Glu Arg Leu
                245                 250

<210> SEQ ID NO 1065
<211> LENGTH: 773
<212> TYPE: DNA
<213> ORGANISM: Artificial Sequence
<220> FEATURE:
<223> OTHER INFORMATION: VEGF ANTAGONIST-Fc
<220> FEATURE:
<221> NAME/KEY: CDS
<222> LOCATION: (4)..(759)
<223> OTHER INFORMATION:

<400> SEQUENCE: 1065 cat atg gtt gaa ccg aac tgt gac atc cat gtt atg tgg gaa tgg gaa       48
    Met Val Glu Pro Asn Cys Asp Ile His Val Met Trp Glu Trp Glu
    1               5                   10                  15 tgt ttt gaa cgt ctg ggt ggt ggt ggt ggt gac aaa act cac aca tgt       96
Cys Phe Glu Arg Leu Gly Gly Gly Gly Gly Asp Lys Thr His Thr Cys
                 20                  25                  30 cca ccg tgc cca gca cct gaa ctc ctg ggg gga ccg tca gtt ttc ctc      144
Pro Pro Cys Pro Ala Pro Glu Leu Leu Gly Gly Pro Ser Val Phe Leu
             35                  40                  45 ttc ccc cca aaa ccc aag gac acc ctc atg atc tcc cgg acc cct gag      192
Phe Pro Pro Lys Pro Lys Asp Thr Leu Met Ile Ser Arg Thr Pro Glu
         50                  55                  60 gtc aca tgc gtg gtg gtg gac gtg agc cac gaa gac cct gag gtc aag      240
Val Thr Cys Val Val Val Asp Val Ser His Glu Asp Pro Glu Val Lys
65                  70                  75 ttc aac tgg tac gtg gac ggc gtg gag gtg cat aat gcc aag aca aag      288
Phe Asn Trp Tyr Val Asp Gly Val Glu Val His Asn Ala Lys Thr Lys
80                  85                  90                  95 ccg cgg gag gag cag tac aac agc acg tac cgt gtg gtc agc gtc ctc      336
```

-continued

|  |  |  |  |  |  |  |  |  |  |  |  |  |  |
|--|--|--|--|--|--|--|--|--|--|--|--|--|--|
| Pro | Arg | Glu | Glu | Gln | Tyr | Asn | Ser | Thr | Tyr | Arg | Val | Val | Ser | Val | Leu |
|  |  |  |  | 100 |  |  |  | 105 |  |  |  | 110 |  |

```
acc gtc ctg cac cag gac tgg ctg aat ggc aag gag tac aag tgc aag    384
Thr Val Leu His Gln Asp Trp Leu Asn Gly Lys Glu Tyr Lys Cys Lys
            115                 120                 125 gtc tcc aac aaa gcc ctc cca gcc ccc atc gag aaa acc atc tcc aaa    432
Val Ser Asn Lys Ala Leu Pro Ala Pro Ile Glu Lys Thr Ile Ser Lys
        130                 135                 140 gcc aaa ggg cag ccc cga gaa cca cag gtg tac acc ctg ccc cca tcc    480
Ala Lys Gly Gln Pro Arg Glu Pro Gln Val Tyr Thr Leu Pro Pro Ser
    145                 150                 155 cgg gat gag ctg acc aag aac cag gtc agc ctg acc tgc ctg gtc aaa    528
Arg Asp Glu Leu Thr Lys Asn Gln Val Ser Leu Thr Cys Leu Val Lys
160                 165                 170                 175 ggc ttc tat ccc agc gac atc gcc gtg gag tgg gag agc aat ggg cag    576
Gly Phe Tyr Pro Ser Asp Ile Ala Val Glu Trp Glu Ser Asn Gly Gln
                180                 185                 190 ccg gag aac aac tac aag acc acg cct ccc gtg ctg gac tcc gac ggc    624
Pro Glu Asn Asn Tyr Lys Thr Thr Pro Pro Val Leu Asp Ser Asp Gly
            195                 200                 205 tcc ttc ttc ctc tac agc aag ctc acc gtg gac aag agc agg tgg cag    672
Ser Phe Phe Leu Tyr Ser Lys Leu Thr Val Asp Lys Ser Arg Trp Gln
        210                 215                 220 cag ggg aac gtc ttc tca tgc tcc gtg atg cat gag gct ctg cac aac    720
Gln Gly Asn Val Phe Ser Cys Ser Val Met His Glu Ala Leu His Asn
    225                 230                 235 cac tac acg cag aag agc ctc tcc ctg tct ccg ggt aaa taactcgagg    769
His Tyr Thr Gln Lys Ser Leu Ser Leu Ser Pro Gly Lys
240                 245                 250 atcc                                                                773
```

<210> SEQ ID NO 1066
<211> LENGTH: 252
<212> TYPE: PRT
<213> ORGANISM: Artificial Sequence
<220> FEATURE:
<223> OTHER INFORMATION: VEGF ANTAGONIST-Fc

<400> SEQUENCE: 1066

```
Met Val Glu Pro Asn Cys Asp Ile His Val Met Trp Glu Trp Glu Cys
1               5                   10                  15

Phe Glu Arg Leu Gly Gly Gly Gly Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
```

-continued

```
                    145                 150                 155                 160
Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 1067
<211> LENGTH: 748
<212> TYPE: DNA
<213> ORGANISM: Artificial Sequence
<220> FEATURE:
<223> OTHER INFORMATION: Fc MMP INHIBITOR
<220> FEATURE:
<221> NAME/KEY: CDS
<222> LOCATION: (4)..(732)
<223> OTHER INFORMATION:

<400> SEQUENCE: 1067 cat atg gac aaa act cac aca tgt cca cct tgt cca gct ccg gaa ctc      48
    Met Asp Lys Thr His Thr Cys Pro Pro Cys Pro Ala Pro Glu Leu
    1               5                   10                  15 ctg ggg gga ccg tca gtc ttc ctc ttc ccc cca aaa ccc aag gac acc      96
Leu Gly Gly Pro Ser Val Phe Leu Phe Pro Pro Lys Pro Lys Asp Thr
                20                  25                  30 ctc atg atc tcc cgg acc cct gag gtc aca tgc gtg gtg gtg gac gtg    144
Leu Met Ile Ser Arg Thr Pro Glu Val Thr Cys Val Val Val Asp Val
            35                  40                  45 agc cac gaa gac cct gag gtc aag ttc aac tgg tac gtg gac ggc gtg    192
Ser His Glu Asp Pro Glu Val Lys Phe Asn Trp Tyr Val Asp Gly Val
        50                  55                  60 gag gtg cat aat gcc aag aca aag ccg cgg gag gag cag tac aac agc    240
Glu Val His Asn Ala Lys Thr Lys Pro Arg Glu Glu Gln Tyr Asn Ser
65                  70                  75 acg tac cgt gtg gtc agc gtc ctc acc gtc ctg cac cag gac tgg ctg    288
Thr Tyr Arg Val Val Ser Val Leu Thr Val Leu His Gln Asp Trp Leu
80                  85                  90                  95 aat ggc aag gag tac aag tgc aag gtc tcc aac aaa gcc ctc cca gcc    336
Asn Gly Lys Glu Tyr Lys Cys Lys Val Ser Asn Lys Ala Leu Pro Ala
                100                 105                 110 ccc atc gag aaa acc atc tcc aaa gcc aaa ggg cag ccc cga gaa cca    384
Pro Ile Glu Lys Thr Ile Ser Lys Ala Lys Gly Gln Pro Arg Glu Pro
            115                 120                 125 cag gtg tac acc ctg ccc cca tcc cgg gat gag ctg acc aag aac cag    432
Gln Val Tyr Thr Leu Pro Pro Ser Arg Asp Glu Leu Thr Lys Asn Gln
        130                 135                 140 gtc agc ctg acc tgc ctg gtc aaa ggc ttc tat ccc agc gac atc gcc    480
Val Ser Leu Thr Cys Leu Val Lys Gly Phe Tyr Pro Ser Asp Ile Ala
    145                 150                 155 gtg gag tgg gag agc aat ggg cag ccg gag aac aac tac aag acc acg    528
Val Glu Trp Glu Ser Asn Gly Gln Pro Glu Asn Asn Tyr Lys Thr Thr
160                 165                 170                 175 cct ccc gtg ctg gac tcc gac ggc tcc ttc ttc ctc tac agc aag ctc    576
```

-continued

```
                Pro Pro Val Leu Asp Ser Asp Gly Ser Phe Phe Leu Tyr Ser Lys Leu
                                180                 185                 190 acc gtg gac aag agc agg tgg cag cag ggg aac gtc ttc tca tgc tcc         624
Thr Val Asp Lys Ser Arg Trp Gln Gln Gly Asn Val Phe Ser Cys Ser
            195                 200                 205 gtg atg cat gag gct ctg cac aac cac tac acg cag aag agc ctc tcc         672
Val Met His Glu Ala Leu His Asn His Tyr Thr Gln Lys Ser Leu Ser
        210                 215                 220 ctg tct ccg ggt aaa ggt gga ggt ggt ggt tgc acc acc cac tgg ggt         720
Leu Ser Pro Gly Lys Gly Gly Gly Gly Gly Cys Thr Thr His Trp Gly
    225                 230                 235 ttc acc ctg tgc taatggatcc ctcgag                                       748
Phe Thr Leu Cys
240

<210> SEQ ID NO 1068
<211> LENGTH: 243
<212> TYPE: PRT
<213> ORGANISM: Artificial Sequence
<220> FEATURE:
<223> OTHER INFORMATION: Fc MMP INHIBITOR

<400> SEQUENCE: 1068

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Gly Cys Thr Thr His Trp Gly Phe
225                 230                 235                 240

Thr Leu Cys

<210> SEQ ID NO 1069
<211> LENGTH: 763
```

-continued

```
<212> TYPE: DNA
<213> ORGANISM: Artificial Sequence
<220> FEATURE:
<223> OTHER INFORMATION: MMP INHIBITOR-Fc
<220> FEATURE:
<221> NAME/KEY: CDS
<222> LOCATION: (4)..(753)
<223> OTHER INFORMATION:

<400> SEQUENCE: 1069 cat atg tgc acc acc cac tgg ggt ttc acc ctg tgc ggt gga ggc ggt      48
    Met Cys Thr Thr His Trp Gly Phe Thr Leu Cys Gly Gly Gly Gly
    1               5                   10                  15 ggg gac aaa ggt gga ggc ggt ggg gac aaa act cac aca tgt cca cct      96
Gly Asp Lys Gly Gly Gly Gly Gly Asp Lys Thr His Thr Cys Pro Pro
                20                  25                  30 tgc cca gca cct gaa ctc ctg ggg gga ccg tca gtt ttc ctc ttc ccc     144
Cys Pro Ala Pro Glu Leu Leu Gly Gly Pro Ser Val Phe Leu Phe Pro
            35                  40                  45 cca aaa ccc aag gac acc ctc atg atc tcc cgg acc cct gag gtc aca     192
Pro Lys Pro Lys Asp Thr Leu Met Ile Ser Arg Thr Pro Glu Val Thr
        50                  55                  60 tgc gtg gtg gtg gac gtg agc cac gaa gac cct gag gtc aag ttc aac     240
Cys Val Val Val Asp Val Ser His Glu Asp Pro Glu Val Lys Phe Asn
65                  70                  75 tgg tac gtg gac ggc gtg gag gtg cat aat gcc aag aca aag ccg cgg     288
Trp Tyr Val Asp Gly Val Glu Val His Asn Ala Lys Thr Lys Pro Arg
80                  85                  90                  95 gag gag cag tac aac agc acg tac cgt gtg gtc agc gtc ctc acc gtc     336
Glu Glu Gln Tyr Asn Ser Thr Tyr Arg Val Val Ser Val Leu Thr Val
                100                 105                 110 ctg cac cag gac tgg ctg aat ggc aag gag tac aag tgc aag gtc tcc     384
Leu His Gln Asp Trp Leu Asn Gly Lys Glu Tyr Lys Cys Lys Val Ser
            115                 120                 125 aac aaa gcc ctc cca gcc ccc atc gag aaa acc atc tcc aaa gcc aaa     432
Asn Lys Ala Leu Pro Ala Pro Ile Glu Lys Thr Ile Ser Lys Ala Lys
        130                 135                 140 ggg cag ccc cga gaa cca cag gtg tac acc ctg ccc cca tcc cgg gat     480
Gly Gln Pro Arg Glu Pro Gln Val Tyr Thr Leu Pro Pro Ser Arg Asp
145                 150                 155 gag ctg acc aag aac cag gtc agc ctg acc tgc ctg gtc aaa ggc ttc     528
Glu Leu Thr Lys Asn Gln Val Ser Leu Thr Cys Leu Val Lys Gly Phe
160                 165                 170                 175 tat ccc agc gac atc gcc gtg gag tgg gag agc aat ggg cag ccg gag     576
Tyr Pro Ser Asp Ile Ala Val Glu Trp Glu Ser Asn Gly Gln Pro Glu
                180                 185                 190 aac aac tac aag acc acg cct ccc gtg ctg gac tcc gac ggc tcc ttc     624
Asn Asn Tyr Lys Thr Thr Pro Pro Val Leu Asp Ser Asp Gly Ser Phe
            195                 200                 205 ttc ctc tac agc aag ctc acc gtg gac aag agc agg tgg cag cag ggg     672
Phe Leu Tyr Ser Lys Leu Thr Val Asp Lys Ser Arg Trp Gln Gln Gly
        210                 215                 220 aac gtc ttc tca tgc tcc gtg atg cat gag gct ctg cac aac cac tac     720
Asn Val Phe Ser Cys Ser Val Met His Glu Ala Leu His Asn His Tyr
225                 230                 235 acg cag aag agc ctc tcc ctg tct ccg ggt aaa taatggatcc              763
Thr Gln Lys Ser Leu Ser Leu Ser Pro Gly Lys
240                 245                 250

<210> SEQ ID NO 1070
<211> LENGTH: 250
<212> TYPE: PRT
```

```
<213> ORGANISM: Artificial Sequence
<220> FEATURE:
<223> OTHER INFORMATION: MMP INHIBITOR-Fc

<400> SEQUENCE: 1070

Met Cys Thr Thr His Trp Gly Phe Thr Leu Cys Gly Gly Gly Gly
1               5                   10                  15

Asp Lys Gly Gly Gly Gly Asp Lys Thr His Thr Cys Pro Pro Cys
            20                  25                  30

Pro Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
    50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 1071
<211> LENGTH: 13
<212> TYPE: PRT
<213> ORGANISM: Artificial Sequence
<220> FEATURE:
<223> OTHER INFORMATION: INTEGRIN-BINDING PEPTIDE

<400> SEQUENCE: 1071

Cys Gly Arg Glu Cys Pro Arg Leu Cys Gln Ser Ser Cys
1               5                   10

<210> SEQ ID NO 1072
<211> LENGTH: 13
<212> TYPE: PRT
<213> ORGANISM: Artificial Sequence
<220> FEATURE:
<223> OTHER INFORMATION: INTEGRIN-BINDING PEPTIDE

<400> SEQUENCE: 1072

Cys Asn Gly Arg Cys Val Ser Gly Cys Ala Gly Arg Cys
1               5                   10
```

```
<210> SEQ ID NO 1073
<211> LENGTH: 8
<212> TYPE: PRT
<213> ORGANISM: Artificial Sequence
<220> FEATURE:
<223> OTHER INFORMATION: INTEGRIN-BINDING PEPTIDE

<400> SEQUENCE: 1073

Cys Leu Ser Gly Ser Leu Ser Cys
1               5

<210> SEQ ID NO 1074
<211> LENGTH: 6
<212> TYPE: PRT
<213> ORGANISM: Artificial Sequence
<220> FEATURE:
<223> OTHER INFORMATION: INTEGRIN-BINDING PEPTIDE

<400> SEQUENCE: 1074

Asn Gly Arg Ala His Ala
1               5

<210> SEQ ID NO 1075
<211> LENGTH: 5
<212> TYPE: PRT
<213> ORGANISM: Artificial Sequence
<220> FEATURE:
<223> OTHER INFORMATION: INTEGRIN-BINDING PEPTIDE

<400> SEQUENCE: 1075

Cys Asn Gly Arg Cys
1               5

<210> SEQ ID NO 1076
<211> LENGTH: 9
<212> TYPE: PRT
<213> ORGANISM: Artificial Sequence
<220> FEATURE:
<223> OTHER INFORMATION: INTEGRIN-BINDING PEPTIDE

<400> SEQUENCE: 1076

Cys Asp Cys Arg Gly Asp Cys Phe Cys
1               5

<210> SEQ ID NO 1077
<211> LENGTH: 7
<212> TYPE: PRT
<213> ORGANISM: Artificial Sequence
<220> FEATURE:
<223> OTHER INFORMATION: INTEGRIN-BINDING PEPTIDE

<400> SEQUENCE: 1077

Cys Gly Ser Leu Val Arg Cys
1               5

<210> SEQ ID NO 1078
<211> LENGTH: 8
<212> TYPE: PRT
<213> ORGANISM: Artificial Sequence
<220> FEATURE:
<223> OTHER INFORMATION: INTEGRIN-BINDING PEPTIDE

<400> SEQUENCE: 1078

Arg Thr Asp Leu Asp Ser Leu Arg
1               5
```

```
<210> SEQ ID NO 1079
<211> LENGTH: 12
<212> TYPE: PRT
<213> ORGANISM: Artificial Sequence
<220> FEATURE:
<223> OTHER INFORMATION: INTEGRIN-BINDING PEPTIDE

<400> SEQUENCE: 1079

Gly Asp Leu Asp Leu Leu Lys Leu Arg Leu Thr Leu
1               5                   10

<210> SEQ ID NO 1080
<211> LENGTH: 12
<212> TYPE: PRT
<213> ORGANISM: Artificial Sequence
<220> FEATURE:
<223> OTHER INFORMATION: INTEGRIN-BINDING PEPTIDE

<400> SEQUENCE: 1080

Gly Asp Leu His Ser Leu Arg Gln Leu Leu Ser Arg
1               5                   10

<210> SEQ ID NO 1081
<211> LENGTH: 12
<212> TYPE: PRT
<213> ORGANISM: Artificial Sequence
<220> FEATURE:
<223> OTHER INFORMATION: INTEGRIN-BINDING PEPTIDE

<400> SEQUENCE: 1081

Arg Asp Asp Leu His Met Leu Arg Leu Gln Leu Trp
1               5                   10

<210> SEQ ID NO 1082
<211> LENGTH: 12
<212> TYPE: PRT
<213> ORGANISM: Artificial Sequence
<220> FEATURE:
<223> OTHER INFORMATION: INTEGRIN-BINDING PEPTIDE

<400> SEQUENCE: 1082

Ser Ser Asp Leu His Ala Leu Lys Lys Arg Tyr Gly
1               5                   10

<210> SEQ ID NO 1083
<211> LENGTH: 12
<212> TYPE: PRT
<213> ORGANISM: Artificial Sequence
<220> FEATURE:
<223> OTHER INFORMATION: INTEGRIN-BINDING PEPTIDE

<400> SEQUENCE: 1083

Arg Gly Asp Leu Lys Gln Leu Ser Glu Leu Thr Trp
1               5                   10

<210> SEQ ID NO 1084
<211> LENGTH: 12
<212> TYPE: PRT
<213> ORGANISM: Artificial Sequence
<220> FEATURE:
<223> OTHER INFORMATION: INTEGRIN-BINDING PEPTIDE

<400> SEQUENCE: 1084

Arg Gly Asp Leu Ala Ala Leu Ser Ala Pro Pro Val
1               5                   10
```

<210> SEQ ID NO 1085
<211> LENGTH: 20
<212> TYPE: PRT
<213> ORGANISM: Artificial Sequence
<220> FEATURE:
<223> OTHER INFORMATION: VEGF-ANTAGONIST

<400> SEQUENCE: 1085

Arg Gly Trp Val Glu Ile Cys Val Ala Asp Asp Asn Gly Met Cys Val
1               5                   10                  15

Thr Glu Ala Gln
            20

<210> SEQ ID NO 1086
<211> LENGTH: 19
<212> TYPE: PRT
<213> ORGANISM: Artificial Sequence
<220> FEATURE:
<223> OTHER INFORMATION: VEGF-ANTAGONIST

<400> SEQUENCE: 1086

Gly Trp Asp Glu Cys Asp Val Ala Arg Met Trp Glu Trp Glu Cys Phe
1               5                   10                  15

Ala Gly Val

<210> SEQ ID NO 1087
<211> LENGTH: 16
<212> TYPE: PRT
<213> ORGANISM: Artificial Sequence
<220> FEATURE:
<223> OTHER INFORMATION: VEGF-ANTAGONIST

<400> SEQUENCE: 1087

Arg Gly Trp Val Glu Ile Cys Glu Ser Asp Val Trp Gly Arg Cys Leu
1               5                   10                  15

<210> SEQ ID NO 1088
<211> LENGTH: 16
<212> TYPE: PRT
<213> ORGANISM: Artificial Sequence
<220> FEATURE:
<223> OTHER INFORMATION: VEGF-ANTAGONIST

<400> SEQUENCE: 1088

Arg Gly Trp Val Glu Ile Cys Glu Ser Asp Val Trp Gly Arg Cys Leu
1               5                   10                  15

<210> SEQ ID NO 1089
<211> LENGTH: 19
<212> TYPE: PRT
<213> ORGANISM: Artificial Sequence
<220> FEATURE:
<223> OTHER INFORMATION: VEGF-ANTAGONIST

<400> SEQUENCE: 1089

Gly Gly Asn Glu Cys Asp Ile Ala Arg Met Trp Glu Trp Glu Cys Phe
1               5                   10                  15

Glu Arg Leu

<210> SEQ ID NO 1090
<211> LENGTH: 16
<212> TYPE: PRT
<213> ORGANISM: Artificial Sequence
<220> FEATURE:
<223> OTHER INFORMATION: VEGF-ANTAGONIST

```
<400> SEQUENCE: 1090

Arg Gly Trp Val Glu Ile Cys Ala Ala Asp Asp Tyr Gly Arg Cys Leu
1               5                   10                  15

<210> SEQ ID NO 1091
<211> LENGTH: 8
<212> TYPE: PRT
<213> ORGANISM: Artificial Sequence
<220> FEATURE:
<223> OTHER INFORMATION: MMP INHIBITOR
<220> FEATURE:
<221> NAME/KEY: misc_feature
<222> LOCATION: (6)..(6)
<223> OTHER INFORMATION: Xaa = any amino acid

<400> SEQUENCE: 1091

Cys Leu Arg Ser Gly Xaa Gly Cys
1               5

<210> SEQ ID NO 1092
<211> LENGTH: 10
<212> TYPE: PRT
<213> ORGANISM: Artificial Sequence
<220> FEATURE:
<223> OTHER INFORMATION: MMP INHIBITOR
<220> FEATURE:
<221> NAME/KEY: misc_feature
<222> LOCATION: (2, 3, 8)..(9)
<223> OTHER INFORMATION: Xaa = any amino acid.

<400> SEQUENCE: 1092

Cys Xaa Xaa His Trp Gly Phe Xaa Xaa Cys
1               5                   10

<210> SEQ ID NO 1093
<211> LENGTH: 5
<212> TYPE: PRT
<213> ORGANISM: Artificial Sequence
<220> FEATURE:
<223> OTHER INFORMATION: MMP INHIBITOR
<220> FEATURE:
<221> NAME/KEY: misc_feature
<222> LOCATION: (2)..(4)
<223> OTHER INFORMATION: Xaa = any amino acid

<400> SEQUENCE: 1093

Cys Xaa Pro Xaa Cys
1               5

<210> SEQ ID NO 1094
<211> LENGTH: 10
<212> TYPE: PRT
<213> ORGANISM: Artificial Sequence
<220> FEATURE:
<223> OTHER INFORMATION: MMP INHIBITOR

<400> SEQUENCE: 1094

Cys Arg Arg His Trp Gly Phe Glu Phe Cys
1               5                   10

<210> SEQ ID NO 1095
<211> LENGTH: 10
<212> TYPE: PRT
<213> ORGANISM: Artificial Sequence
<220> FEATURE:
<223> OTHER INFORMATION: MMP INHIBITOR

<400> SEQUENCE: 1095
```

```
Ser Thr Thr His Trp Gly Phe Thr Leu Ser
1               5                   10
```

<210> SEQ ID NO 1096
<211> LENGTH: 10
<212> TYPE: PRT
<213> ORGANISM: Artificial Sequence
<220> FEATURE:
<223> OTHER INFORMATION: CTLA4-MIMETIC

<400> SEQUENCE: 1096

```
Cys Ser Leu His Trp Gly Phe Trp Trp Cys
1               5                   10
```

<210> SEQ ID NO 1097
<211> LENGTH: 15
<212> TYPE: PRT
<213> ORGANISM: Artificial Sequence
<220> FEATURE:
<223> OTHER INFORMATION: CARBOHYDRATE (GD1 ALPHA) MIMETIC

<400> SEQUENCE: 1097

```
Trp His Trp Arg His Arg Ile Pro Leu Gln Leu Ala Ala Gly Arg
1               5                   10                  15
```

<210> SEQ ID NO 1098
<211> LENGTH: 6
<212> TYPE: PRT
<213> ORGANISM: Artificial Sequence
<220> FEATURE:
<223> OTHER INFORMATION: BETA2GPI AB BINDING

<400> SEQUENCE: 1098

```
Leu Lys Thr Pro Arg Val
1               5
```

<210> SEQ ID NO 1099
<211> LENGTH: 8
<212> TYPE: PRT
<213> ORGANISM: Artificial Sequence
<220> FEATURE:
<223> OTHER INFORMATION: BETA2GPI AB BINDING

<400> SEQUENCE: 1099

```
Asn Thr Leu Lys Thr Pro Arg Val
1               5
```

<210> SEQ ID NO 1100
<211> LENGTH: 11
<212> TYPE: PRT
<213> ORGANISM: Artificial Sequence
<220> FEATURE:
<223> OTHER INFORMATION: BETA2GPI AB BINDING

<400> SEQUENCE: 1100

```
Asn Thr Leu Lys Thr Pro Arg Val Gly Gly Cys
1               5                   10
```

<210> SEQ ID NO 1101
<211> LENGTH: 6
<212> TYPE: PRT
<213> ORGANISM: Artificial Sequence
<220> FEATURE:
<223> OTHER INFORMATION: BETA2GPI AB BINDING

<400> SEQUENCE: 1101

Lys Asp Lys Ala Thr Phe

<210> SEQ ID NO 1102
<211> LENGTH: 10
<212> TYPE: PRT
<213> ORGANISM: Artificial Sequence
<220> FEATURE:
<223> OTHER INFORMATION: BETA2GPI AB BINDING

<400> SEQUENCE: 1102

Lys Asp Lys Ala Thr Phe Gly Cys His Asp
1               5                   10

<210> SEQ ID NO 1103
<211> LENGTH: 12
<212> TYPE: PRT
<213> ORGANISM: Artificial Sequence
<220> FEATURE:
<223> OTHER INFORMATION: BETA2GPI AB BINDING

<400> SEQUENCE: 1103

Lys Asp Lys Ala Thr Phe Gly Cys His Asp Gly Cys
1               5                   10

<210> SEQ ID NO 1104
<211> LENGTH: 6
<212> TYPE: PRT
<213> ORGANISM: Artificial Sequence
<220> FEATURE:
<223> OTHER INFORMATION: BETA2GPI AB BINDING

<400> SEQUENCE: 1104

Thr Leu Arg Val Tyr Lys
1               5

<210> SEQ ID NO 1105
<211> LENGTH: 9
<212> TYPE: PRT
<213> ORGANISM: Artificial Sequence
<220> FEATURE:
<223> OTHER INFORMATION: BETA2GPI AB BINDING

<400> SEQUENCE: 1105

Ala Thr Leu Arg Val Tyr Lys Gly Gly
1               5

<210> SEQ ID NO 1106
<211> LENGTH: 10
<212> TYPE: PRT
<213> ORGANISM: Artificial Sequence
<220> FEATURE:
<223> OTHER INFORMATION: BETA2GPI AB BINDING

<400> SEQUENCE: 1106

Cys Ala Thr Leu Arg Val Tyr Lys Gly Gly
1               5                   10

<210> SEQ ID NO 1107
<211> LENGTH: 14
<212> TYPE: PRT
<213> ORGANISM: Artificial Sequence
<220> FEATURE:
<223> OTHER INFORMATION: MEMBRANE-TRANSPORTING

<400> SEQUENCE: 1107

Ile Asn Leu Lys Ala Leu Ala Ala Leu Ala Lys Lys Ile Leu
1               5                   10

<210> SEQ ID NO 1108
<211> LENGTH: 12
<212> TYPE: PRT
<213> ORGANISM: Artificial Sequence
<220> FEATURE:
<223> OTHER INFORMATION: MEMBRANE-TRANSPORTING

<400> SEQUENCE: 1108

Gly Trp Thr Leu Asn Ser Ala Gly Tyr Leu Leu Gly
1               5                   10

<210> SEQ ID NO 1109
<211> LENGTH: 27
<212> TYPE: PRT
<213> ORGANISM: Artificial Sequence
<220> FEATURE:
<223> OTHER INFORMATION: MEMBRANE-TRANSPORTING

<400> SEQUENCE: 1109

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 1110
<211> LENGTH: 57
<212> TYPE: DNA
<213> ORGANISM: Artificial Sequence
<220> FEATURE:
<223> OTHER INFORMATION: Fc VEGF ANTAGONIST

<400> SEQUENCE: 1110
gttgaaccga actgtgacat ccatgttatg tgggaatggg aatgttttga acgtctg        57

<210> SEQ ID NO 1111
<211> LENGTH: 57
<212> TYPE: DNA
<213> ORGANISM: Artificial Sequence
<220> FEATURE:
<223> OTHER INFORMATION: Fc VEGF ANTAGONIST

<400> SEQUENCE: 1111
cagacgttca aaacattccc attcccacat aacatggatg tcacagttcg gttcaac        57

<210> SEQ ID NO 1112
<211> LENGTH: 81
<212> TYPE: DNA
<213> ORGANISM: Artificial Sequence
<220> FEATURE:
<223> OTHER INFORMATION: Fc-TNA-ALPHA INHIBITORS

<400> SEQUENCE: 1112
ccgcggatcc attacggacg gtgacccaga gaggtgtttt tgtagtgcgg caggaagtca     60
ccaccacctc caccttttacc c                                              81

<210> SEQ ID NO 1113
<211> LENGTH: 57
<212> TYPE: DNA
<213> ORGANISM: Artificial Sequence
<220> FEATURE:
<223> OTHER INFORMATION: Fc VEGF ANTAGONIST
<220> FEATURE:
<221> NAME/KEY: CDS
<222> LOCATION: (1)..(57)
<223> OTHER INFORMATION:

-continued

```
<400> SEQUENCE: 1113 gtt gaa ccg aac tgt gac atc cat gtt atg tgg gaa tgg gaa tgt ttt      48
Val Glu Pro Asn Cys Asp Ile His Val Met Trp Glu Trp Glu Cys Phe
1               5                   10                  15 gaa cgt ctg                                                          57
Glu Arg Leu <210> SEQ ID NO 1114
<211> LENGTH: 19
<212> TYPE: PRT
<213> ORGANISM: Artificial Sequence
<220> FEATURE:
<223> OTHER INFORMATION: Fc VEGF ANTAGONIST

<400> SEQUENCE: 1114

Val Glu Pro Asn Cys Asp Ile His Val Met Trp Glu Trp Glu Cys Phe
1               5                   10                  15

Glu Arg Leu

<210> SEQ ID NO 1115
<211> LENGTH: 66
<212> TYPE: DNA
<213> ORGANISM: Artificial Sequence
<220> FEATURE:
<223> OTHER INFORMATION: Fc MMP INHIBITOR

<400> SEQUENCE: 1115
ccgcggatcc attagcacag ggtgaaaccc cagtgggtgg tgcaaccacc acctccacct    60
ttaccc                                                               66

<210> SEQ ID NO 1116
<211> LENGTH: 63
<212> TYPE: DNA
<213> ORGANISM: Artificial Sequence
<220> FEATURE:
<223> OTHER INFORMATION: MMP INHIBITOR Fc

<400> SEQUENCE: 1116
gaataacata tgtgcaccac ccactggggt ttcaccctgt gcggtggagg cggtggggac    60
aaa                                                                  63

<210> SEQ ID NO 1117
<211> LENGTH: 81
<212> TYPE: DNA
<213> ORGANISM: Artificial Sequence
<220> FEATURE:
<223> OTHER INFORMATION: TNF-ALPHA INHIBITOR Fc

<400> SEQUENCE: 1117
gaataacata tggacttcct gccgcactac aaaaacacct ctctgggtca ccgtccgggt    60
ggaggcggtg gggacaaaac t                                              81

<210> SEQ ID NO 1118
<211> LENGTH: 81
<212> TYPE: DNA
<213> ORGANISM: Artificial Sequence
<220> FEATURE:
<223> OTHER INFORMATION: Fc IL-1 ANTAGONIST

<400> SEQUENCE: 1118
ccgcggatcc attacagcgg cagagcgtac ggctgccagt aacccggggt ccattcgaaa    60
```

```
ccaccacctc caccttaccc c                                          81
```

<210> SEQ ID NO 1119
<211> LENGTH: 81
<212> TYPE: DNA
<213> ORGANISM: Artificial Sequence
<220> FEATURE:
<223> OTHER INFORMATION: IL-1 ANTAGONIST Fc

<400> SEQUENCE: 1119

```
gaataacata tgttcgaatg gaccccgggt tactggcagc cgtacgctct gccgctgggt    60
ggaggcggtg gggacaaaac t                                              81
```

<210> SEQ ID NO 1120
<211> LENGTH: 48
<212> TYPE: DNA
<213> ORGANISM: Artificial Sequence
<220> FEATURE:
<223> OTHER INFORMATION: Fc VEGF ANTAGONIST

<400> SEQUENCE: 1120

```
atttgattct agaaggagga ataacatatg gacaaaactc acacatgt                 48
```

<210> SEQ ID NO 1121
<211> LENGTH: 51
<212> TYPE: DNA
<213> ORGANISM: Artificial Sequence
<220> FEATURE:
<223> OTHER INFORMATION: Fc VEGF ANTAGONIST

<400> SEQUENCE: 1121

```
gtcacagttc ggttcaacac caccaccacc acctttaccc ggagacaggg a             51
```

<210> SEQ ID NO 1122
<211> LENGTH: 54
<212> TYPE: DNA
<213> ORGANISM: Artificial Sequence
<220> FEATURE:
<223> OTHER INFORMATION: Fc VEGF ANTAGONIST

<400> SEQUENCE: 1122

```
tccctgtctc cgggtaaagg tggtggtggt ggtgttgaac cgaactgtga catc          54
```

<210> SEQ ID NO 1123
<211> LENGTH: 39
<212> TYPE: DNA
<213> ORGANISM: Artificial Sequence
<220> FEATURE:
<223> OTHER INFORMATION: Fc VEGF ANTAGONIST

<400> SEQUENCE: 1123

```
ccgcggatcc tcgagttaca gacgttcaaa acattccca                           39
```

<210> SEQ ID NO 1124
<211> LENGTH: 48
<212> TYPE: DNA
<213> ORGANISM: Artificial Sequence
<220> FEATURE:
<223> OTHER INFORMATION: VEGF ANTAGONIST Fc

<400> SEQUENCE: 1124

```
atttgattct agaaggagga ataacatatg gttgaaccga actgtgac                 48
```

<210> SEQ ID NO 1125
<211> LENGTH: 51

```
<212> TYPE: DNA
<213> ORGANISM: Artificial Sequence
<220> FEATURE:
<223> OTHER INFORMATION: VEGF ANTAGONIST Fc
<220> FEATURE:
<221> NAME/KEY: misc_feature
<222> LOCATION: (2)..(2)
<223> OTHER INFORMATION: Position 2, Xaa is L-lys, D-lys, or an ornithyl
      residue
<220> FEATURE:
<221> NAME/KEY: misc_feature
<222> LOCATION: (3)..(3)
<223> OTHER INFORMATION: Position 3, Xaa is L-tyr, D-ytr, phe, trp, or a
      p-aminophenylalanyl residue
<220> FEATURE:
<221> NAME/KEY: misc_feature
<222> LOCATION: (4)..(4)
<223> OTHER INFORMATION: Position 4, Xaa is a hydropholic aliphatic
      amino acid residue
<220> FEATURE:
<221> NAME/KEY: misc_feature
<222> LOCATION: (4)..(4)
<223> OTHER INFORMATION: Position 4, optional attachment to leu,
      norleucyl, D-ala, Asn-Ser, asn-ser-ile, asn-ser-tyr, asn-ser-ile-
      leu, asn-ser-tyr-leu, or asn-ser-tyr-leu-asn

<400> SEQUENCE: 1125
acatgtgtga gttttgtcac caccaccacc acccagacgt tcaaaacatt c            51

<210> SEQ ID NO 1126
<211> LENGTH: 51
<212> TYPE: DNA
<213> ORGANISM: Artificial Sequence
<220> FEATURE:
<223> OTHER INFORMATION: VEGF ANTAGONIST Fc

<400> SEQUENCE: 1126
gaatgttttg aacgtctggg tggtggtggt ggtgacaaaa ctcacacatg t            51

<210> SEQ ID NO 1127
<211> LENGTH: 39
<212> TYPE: DNA
<213> ORGANISM: Artificial Sequence
<220> FEATURE:
<223> OTHER INFORMATION: VEGF ANTAGONIST Fc

<400> SEQUENCE: 1127
ccgcggatcc tcgagttatt tacccggaga cagggagag                          39

<210> SEQ ID NO 1128
<211> LENGTH: 36
<212> TYPE: PRT
<213> ORGANISM: Artificial Sequence
<220> FEATURE:
<223> OTHER INFORMATION: SYNTHETIC SCHEME FOR PREPARATION OF PEGYLATED
      PEPTIDE
<220> FEATURE:
<221> NAME/KEY: misc_feature
<222> LOCATION: (1)..(1)
<223> OTHER INFORMATION: Butoxycarbonyl group attached to the amino
      terminus.
<220> FEATURE:
<221> NAME/KEY: misc_feature
<222> LOCATION: (2, 5, 24 and)..(27)
<223> OTHER INFORMATION: Tert-butyl group attached to the sidechain.
<220> FEATURE:
<221> NAME/KEY: misc_feature
<222> LOCATION: (7, 13, 29 and)..(35)
<223> OTHER INFORMATION: 2,2,4,6,7-pendamethyldihydrobenzofuran-5-
      sulfonyl group attached to the sidechain.
<220> FEATURE:
<221> NAME/KEY: misc_feature
<222> LOCATION: (8 and)..(30)
```

```
<223> OTHER INFORMATION: Trityl group attached to the sidechain.
<220> FEATURE:
<221> NAME/KEY: misc_feature
<222> LOCATION: (9 and)..(31)
<223> OTHER INFORMATION: Butoxycarbonyl group attached to the sidechain.
<220> FEATURE:
<221> NAME/KEY: misc_feature
<222> LOCATION: (18)..(18)
<223> OTHER INFORMATION: 1-(4,4-dimethyl-2,6-dioxo-cyclohexylidene)ethyl
      group attached to the sidechain.
<220> FEATURE:
<221> NAME/KEY: misc_feature
<222> LOCATION: (36)..(36)
<223> OTHER INFORMATION: Methoxy resin attached to the carboxyl
      terminus.

<400> SEQUENCE: 1128

Ile Glu Gly Pro Thr Leu Arg Gln Trp Leu Ala Ala Arg Ala Gly Gly
1               5                   10                  15

Gly Lys Gly Gly Gly Gly Ile Glu Gly Pro Thr Leu Arg Gln Trp Leu
            20                  25                  30

Ala Ala Arg Ala
            35

<210> SEQ ID NO 1129
<211> LENGTH: 36
<212> TYPE: PRT
<213> ORGANISM: Artificial Sequence
<220> FEATURE:
<223> OTHER INFORMATION: SYNTHETIC SCHEME FOR PREPARATION OF PEGYLATED
      PEPTIDE
<220> FEATURE:
<221> NAME/KEY: misc_feature
<222> LOCATION: (1)..(1)
<223> OTHER INFORMATION: Butoxycarbonyl group attached to the amino
      terminus.
<220> FEATURE:
<221> NAME/KEY: misc_feature
<222> LOCATION: (2, 5, 24 and)..(27)
<223> OTHER INFORMATION: Tert-butyl group attached to the sidechain.
<220> FEATURE:
<221> NAME/KEY: misc_feature
<222> LOCATION: (7, 12, 29 and)..(35)
<223> OTHER INFORMATION: 2,2,4,6,7-pendamethyldihydrobenzofuran-5-
      sulfonyl group attached to the sidechain.
<220> FEATURE:
<221> NAME/KEY: misc_feature
<222> LOCATION: (8 and)..(30)
<223> OTHER INFORMATION: Trityl group attached to the sidechain.
<220> FEATURE:
<221> NAME/KEY: misc_feature
<222> LOCATION: (9 and)..(31)
<223> OTHER INFORMATION: Butoxycarbonyl group attached to the sidechain.
<220> FEATURE:
<221> NAME/KEY: misc_feature
<222> LOCATION: (36)..(36)
<223> OTHER INFORMATION: Methoxy resin attached to the carboxyl terminus.

<400> SEQUENCE: 1129

Ile Glu Gly Pro Thr Leu Arg Gln Trp Leu Ala Ala Arg Ala Gly Gly
1               5                   10                  15

Gly Lys Gly Gly Gly Gly Ile Glu Gly Pro Thr Leu Arg Gln Trp Leu
            20                  25                  30

Ala Ala Arg Ala
            35

<210> SEQ ID NO 1130
<211> LENGTH: 36
<212> TYPE: PRT
<213> ORGANISM: Artificial Sequence
<220> FEATURE:
```

```
<223> OTHER INFORMATION: SYNTHETIC SCHEME FOR PREPARATION OF PEGYLATED
      PEPTIDE
<220> FEATURE:
<221> NAME/KEY: misc_feature
<222> LOCATION: (1)..(1)
<223> OTHER INFORMATION: Butoxycarbonyl group attached to the amino
      terminus.
<220> FEATURE:
<221> NAME/KEY: misc_feature
<222> LOCATION: (2, 5, 24 and)..(27)
<223> OTHER INFORMATION: Tert-butyl group attached to the sidechain.
<220> FEATURE:
<221> NAME/KEY: misc_feature
<222> LOCATION: (7, 13, 29 and)..(35)
<223> OTHER INFORMATION: 2,2,4,6,7-pendamethyldihydrobenzofuran-5-
      sulfonyl group attached to the sidechain.
<220> FEATURE:
<221> NAME/KEY: misc_feature
<222> LOCATION: (8 and)..(30)
<223> OTHER INFORMATION: Trityl group attached to the sidechain.
<220> FEATURE:
<221> NAME/KEY: misc_feature
<222> LOCATION: (9 and)..(31)
<223> OTHER INFORMATION: Butoxycarbonyl group attached to the sidechain.
<220> FEATURE:
<221> NAME/KEY: misc_feature
<222> LOCATION: (18)..(18)
<223> OTHER INFORMATION: Bromoacetyl group attached to the sidechain.
<220> FEATURE:
<221> NAME/KEY: misc_feature
<222> LOCATION: (36)..(36)
<223> OTHER INFORMATION: Methoxy resin attached to the carboxyl
      terminus.

<400> SEQUENCE: 1130

Ile Glu Gly Pro Thr Leu Arg Gln Trp Leu Ala Ala Arg Ala Gly Gly
1               5                   10                  15

Gly Lys Gly Gly Gly Gly Ile Glu Gly Pro Thr Leu Arg Gln Trp Leu
            20                  25                  30

Ala Ala Arg Ala
            35

<210> SEQ ID NO 1131
<211> LENGTH: 36
<212> TYPE: PRT
<213> ORGANISM: Artificial Sequence
<220> FEATURE:
<223> OTHER INFORMATION: SYNTHETIC SCHEME FOR PREPARATION OF PEGYLATED
      PEPTIDE
<220> FEATURE:
<221> NAME/KEY: misc_feature
<222> LOCATION: (18)..(18)
<223> OTHER INFORMATION: Bromoacetyl group attached to the sidechain.

<400> SEQUENCE: 1131

Ile Glu Gly Pro Thr Leu Arg Gln Trp Leu Ala Ala Arg Ala Gly Gly
1               5                   10                  15

Gly Lys Gly Gly Gly Gly Ile Glu Gly Pro Thr Leu Arg Gln Trp Leu
            20                  25                  30

Ala Ala Arg Ala
            35

<210> SEQ ID NO 1132
<211> LENGTH: 36
<212> TYPE: PRT
<213> ORGANISM: Artificial Sequence
<220> FEATURE:
<223> OTHER INFORMATION: SYNTHETIC SCHEME FOR PREPARATION OF PEGYLATED
      PEPTIDE
<220> FEATURE:
<221> NAME/KEY: misc_feature
```

-continued

```
<222> LOCATION: (2, 5, 24 and)..(27)
<223> OTHER INFORMATION: Tert-butyl group attached to the sidechain.
<220> FEATURE:
<221> NAME/KEY: misc_feature
<222> LOCATION: (7, 13, 29 and)..(35)
<223> OTHER INFORMATION: 2,2,4,6,7-pendamethyldihydrobenzofuran-5-
      sulfonyl group attached to the sidechain.
<220> FEATURE:
<221> NAME/KEY: misc_feature
<222> LOCATION: (8, 18 and)..(30)
<223> OTHER INFORMATION: Trityl group attached to the sidechain.
<220> FEATURE:
<221> NAME/KEY: misc_feature
<222> LOCATION: (9 and)..(31)
<223> OTHER INFORMATION: Butoxycarbonyl group attached to the sidechain.
<220> FEATURE:
<221> NAME/KEY: misc_feature
<222> LOCATION: (36)..(36)
<223> OTHER INFORMATION: Methoxy resin attached to the carboxyl terminus.

<400> SEQUENCE: 1132

Ile Glu Gly Pro Thr Leu Arg Gln Trp Leu Ala Ala Arg Ala Gly Gly
1               5                   10                  15

Gly Cys Gly Gly Gly Gly Ile Glu Gly Pro Thr Leu Arg Gln Trp Leu
            20                  25                  30

Ala Ala Arg Ala
        35

<210> SEQ ID NO 1133
<211> LENGTH: 36
<212> TYPE: PRT
<213> ORGANISM: Artificial Sequence
<220> FEATURE:
<223> OTHER INFORMATION: SYNTHETIC SCHEME FOR PREPARATION OF PEGYLATED
      PEPTIDE

<400> SEQUENCE: 1133

Ile Glu Gly Pro Thr Leu Arg Gln Trp Leu Ala Ala Arg Ala Gly Gly
1               5                   10                  15

Gly Cys Gly Gly Gly Gly Ile Glu Gly Pro Thr Leu Arg Gln Trp Leu
            20                  25                  30

Ala Ala Arg Ala
        35
```

What is claimed is:

1. A composition of matter of the formula $(X^1)_a\text{-}F^1\text{-}(X^2)_b$ and multimers thereof, wherein:

$F^1$ is an Fc domain;

$X^1$ and $X^2$ are each independently selected from $\text{-}(L^1)_c\text{-}P^1$, $\text{-}(L^1)_c\text{-}P^1\text{-}(L^2)_d\text{-}P^2$, $\text{-}(L^1)_c\text{-}P^1\text{-}(L^2)_d\text{-}P^2\text{-}(L^3)_e\text{-}P^3$, and $\text{-}(L^1)_c\text{-}P^1\text{-}(L^2)_d\text{-}P^2\text{-}(L^3)_e\text{-}P^3\text{-}(L^4)_f\text{-}P^4$ $P^1$, $P^2$, $P^3$, and $P^4$ are each independently randomized EPO-mimetic peptide sequences;

$L^1$, $L^2$, $L^3$, and $L^4$ are each independently linkers; and a, b, c, d, e, and f are each independently 0 or 1, provided that at least one of a and b is 1 and wherein "peptide" refers to molecules 2 to 40 amino acid and wherein neither X1 nor X2 is a native protein.

2. The composition of matter of claim 1 of the formulae $X^1\text{-}F^1$ or $F^1\text{-}X^2$.

3. The composition of matter of claim 1 of the formula $F^1\text{-}(L^1)_c\text{-}P^1$.

4. The composition of matter of claim 1 of the formula $F^1\text{-}(L^1)_c\text{-}P^1\text{-}(L^2)_d\text{-}P^2$.

5. The composition of matter of claim 1 wherein $F^1$ is an IgG Fc domain.

6. The composition of matter of claim 1 wherein $F^1$ is an IgG1 Fc domain.

7. The composition of matter of claim 1 wherein $F^1$ comprises the sequence of SEQ ID NO: 2.

8. The composition of matter of claim 1 wherein the EPO mimetic peptide sequence is selected from Table 5.

9. The composition of matter of claim 8 wherein $F^1$ comprises the sequence of SEQ ID NO: 2.

10. The composition of matter of claim 1 comprising a sequence selected from SEQ ID NOS: 83, 84, 85, 124, 419, 420, 421, and 41.

11. The composition of matter of claim 1 comprising a sequence selected from SEQ ID NOS: 339 and 340.

* * * * *